United States Patent
Kuroita et al.

(10) Patent No.: US 8,664,380 B2
(45) Date of Patent: *Mar. 4, 2014

(54) HETEROCYCLIC COMPOUND AND USE THEREOF

(75) Inventors: Takanobu Kuroita, Kanagawa (JP);
Yasuhiro Imaeda, Kanagawa (JP);
Kouichi Iwanaga, Kanagawa i (JP);
Naohiro Taya, Kanagawa (JP);
Hidekazu Tokuhara, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 734 days.

This patent is subject to a terminal disclaimer.

(21) Appl. No.: 12/457,646

(22) Filed: Jun. 17, 2009

(65) Prior Publication Data

US 2010/0137587 A1  Jun. 3, 2010

(30) Foreign Application Priority Data

Jun. 19, 2008  (JP) .................................. 2008-161049
Jan. 13, 2009  (JP) .................................. 2009-004882

(51) Int. Cl.
*C07D 413/14* (2006.01)

(52) U.S. Cl.
USPC ....................................................... 544/130

(58) Field of Classification Search
USPC ....................................................... 544/130
See application file for complete search history.

(56) References Cited

U.S. PATENT DOCUMENTS

| | | | |
|---|---|---|---|
| 7,618,984 B2 | 11/2009 | Yamada et al. | |
| 2004/0138286 A1 | 7/2004 | Imazaki et al. | |
| 2004/0204455 A1 | 10/2004 | Cody et al. | |
| 2006/0111355 A1 | 5/2006 | Garrick et al. | |
| 2006/0135523 A1 | 6/2006 | Cheng et al. | |
| 2007/0179127 A1 | 8/2007 | Yamada et al. | |
| 2009/0131666 A1 | 5/2009 | Kontani et al. | |
| 2010/0056497 A1 | 3/2010 | Nakahira et al. | |
| 2010/0240644 A1 | 9/2010 | Akatsuka et al. | |

FOREIGN PATENT DOCUMENTS

| | | |
|---|---|---|
| EP | 0 520 423 | 12/1992 |
| EP | 0 826 673 | 3/1998 |
| EP | 2 168 952 A1 | 3/2010 |
| EP | 2 202 228 | 6/2010 |
| EP | 2 243 779 | 10/2010 |
| GE | P2005 3470 | 2/2005 |
| JP | 2006-522793 | 10/2006 |
| JP | 2008-285482 | 11/2008 |
| JP | 2011-513272 | 4/2011 |
| RU | 2 168 510 | 4/1999 |
| RU | 2 159 613 | 11/2000 |
| RU | 2 160 256 | 12/2000 |
| RU | 2 374 236 | 4/2005 |
| RU | 2 440 993 | 11/2008 |
| WO | 96/39385 | 12/1996 |
| WO | 96/40681 | 12/1996 |
| WO | 97/09308 | 3/1997 |
| WO | 2007/026664 | 3/2000 |
| WO | 02/100833 | 12/2002 |
| WO | 03/000677 | 1/2003 |
| WO | 03/037274 | 5/2003 |
| WO | 03/055482 | 7/2003 |
| WO | 03/079973 | 10/2003 |
| WO | 2004/037171 | 5/2004 |
| WO | 2004/089903 | 10/2004 |
| WO | 2004/111033 | 12/2004 |
| WO | 2005/018547 | 3/2005 |
| WO | 2005/019206 | 3/2005 |
| WO | 2005/047251 | 5/2005 |
| WO | 2005/061457 | 7/2005 |

(Continued)

OTHER PUBLICATIONS

International Search Report issued Mar. 30, 2010 in corresponding International (PCT) Application No. PCT/JP2009/061438.
Written Opinion of the International Searching Authority issued Mar. 30, 2010 in corresponding International (PCT) Application No. PCT/JP2009/061438.
J. Rahuel et al., "Structure-based drug design: the discovery of novel nonpeptide orally active inhibitors of human rennin", Chem. & Biol., Jun. 16, 2000, vol. 7, No. 7, pp. 493-504.

(Continued)

*Primary Examiner* — Rebecca Anderson
(74) *Attorney, Agent, or Firm* — Wenderoth, Lind & Ponack, L.L.P.

(57) ABSTRACT

Compounds represented by the formulas

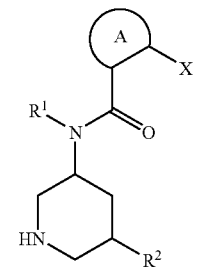

(I)

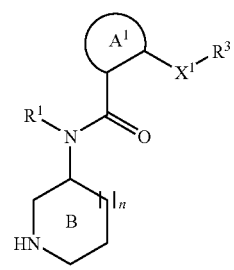

(II)

wherein each symbol is as defined in the specification, and a prodrug thereof have a superior renin inhibitory activity, and are useful as agents for the prophylaxis or treatment of hypertension, various organ damages attributable to hypertension and the like.

1 Claim, No Drawings

(56) References Cited

FOREIGN PATENT DOCUMENTS

| | | |
|---|---|---|
| WO | 2006/005741 | 1/2006 |
| WO | 2006/020598 | 2/2006 |
| WO | 2006/042150 | 4/2006 |
| WO | 2006/069788 | 7/2006 |
| WO | 2006/101780 | 9/2006 |
| WO | 2006/128659 | 12/2006 |
| WO | 2007/006534 | 1/2007 |
| WO | 2007/034035 | 3/2007 |
| WO | 2007/071621 | 6/2007 |
| WO | 2007/077005 | 7/2007 |
| WO | 2007/082907 | 7/2007 |
| WO | 2007/094513 | 8/2007 |
| WO | 2007/111227 | 10/2007 |
| WO | 2008/093737 | 8/2008 |
| WO | 2008/136457 | 11/2008 |
| WO | 2008/139941 | 11/2008 |
| WO | 2008/153135 | 12/2008 |
| WO | 2008/153182 | 12/2008 |
| WO | 2009/001915 | 12/2008 |
| WO | 2009/005002 | 1/2009 |
| WO | 2009/014217 | 1/2009 |
| WO | 2009/051112 | 4/2009 |
| WO | 2009/072649 | 6/2009 |
| WO | 2009/078481 | 6/2009 |
| WO | 2009/106531 | 9/2009 |
| WO | 2009/112490 | 9/2009 |
| WO | 2010/126002 | 11/2010 |

OTHER PUBLICATIONS

Alice Stanton et al., "Blood Pressure Lowering in Essential Hypertension With an Oral Renin Inhibitor, Aliskiren", Hypertension, Dec. 2003, vol. 42, pp. 1137-1143.

Jeanette M. Wood et al., "Aliskiren, a novel, orally effective rennin inhibitor, lowers blood pressure in marmosets and spontaneously hypertensive rats", Journal of Hypertension, 2005, vol. 23, No. 2, pp. 417-426.

John R. Proudfoot et al., "Novel Non-nucleoside Inhibitors of HIV-1 Reverse Transcriptase. 3. Dipyrido[2,3-b:2',3-e] diazepinones", Journal of Medicinal Chemistry, 1995, vol. 38, No. 8, pp. 1406-1410.

Search Report issued Sep. 24, 2012 in corresponding Taiwanese Application No. 098120213.

Georgian Search Report dated Mar. 16, 2012 in corresponding Georgian Application No. AP 2009 012066.

Oppostion filed in corresponding Costa Rican Patent Application No. 2011-0001 on Jun. 24, 2013 with English translataion.

Columbian Office Action issued Jun. 13, 2013 in corresponding Columbia Patent Application No. 11.005.108.

Notice of Reasons for Refusal mailed Nov. 5, 2013 in corresponding Japanese Application No. 086570/2011 (with partial English translation).

Chinese Search Report issued Oct. 10, 2013 in corresponding Chinese Application No. 200980132372.7.

Aurelio Orjales et al.; "Benzimidazole-2-carboxylic acid amides and esters: a new structural class of 5-HT$_3$ ligands"; Eur. J. Med. Chem.; vol. 34, Issue 5; May 1999; pp. 415-422.

Costa Rican Opposition issued Jan. 6, 2014 in corresponding Costa Rican Application No. 2013-0360.

HETEROCYCLIC COMPOUND AND USE THEREOF

TECHNICAL FIELD OF THE INVENTION

The present invention relates to a heterocyclic compound and the like, which has a superior renin inhibitory activity and is useful as an agent for the prophylaxis or treatment of hypertension, various organ damages attributable to hypertension, and the like.

BACKGROUND OF THE INVENTION

Hypertension is one of representative lifestyle-related diseases. Hypertension which is left untreated for long time lays a heavy burden on the cardiovascular system and results is in arteriosclerosis to progress, thus causing various disorders in important organs, such as cerebral hemorrhage, cerebral infarction, cardiac failure, angina pectoris, myocardial infarction, renal failure and the like. Accordingly, the purpose of treating hypertension lies not only in lowering the blood pressure, but also in improving and/or preventing disorders in important organs including brain, heart and kidney, by controlling the blood pressure. As a method of treating hypertension, there are available fundamental treatments based on improvement in the lifestyle, such as dietetic therapy, exercise therapy and the like, as well as an attempt to control the blood pressure by positive pharmaceutical intervention.

The renin-angiotensin (RA) system is a system of biosynthesis of angiotensin II (AII), which is a major vasopressor factor, and takes an important role in the control of the blood pressure and the amount of body fluid. AII exhibits a strong vasoconstrictive effect brought by the intervention of AII receptors on the cellular membrane, thus raising the blood pressure, and also promotes cellular propagation or production of extracellular matrix by directly acting on the AII receptors in the cardiac cells or renal cells. Therefore, drugs inhibiting increase in the activity of the RA system can be expected to have a blood pressure lowering action as well as a powerful organ protecting action, and thus active researches on such drugs have been conducted so far.

The method of inhibiting the AII action is broadly classified into methods of inhibiting the biosynthesis of AII and methods of inhibiting the binding of AII to AII receptors. For the drugs inhibiting the biosynthesis of AII, angiotensin converting enzyme (ACE) inhibitory drugs have been already put to practical use and are being confirmed to have a blood pressure lowering action as well as an effect for protecting various organs. However, since ACE is an enzyme identical to kininase II, which is a bradykinin degrading enzyme, ACE inhibitory drug inhibits the biosynthesis of AII as well as the degradation of bradykinin. As a result, ACE inhibitory drugs are believed to induce side effects such as dry cough, angioedema and the like, which are considered to be caused by accumulation of bradykinin.

As the drugs inhibiting the binding of AII to AII receptors, AII type 1 receptor blockers (ARB) have been developed. ARB has a merit in that it can inhibit, at the receptor level, the action of AII that is biosynthesized by not only ACE but also an enzyme other than ACE, such as chymase and the like. It is known that administration of ACE inhibitors and ARB increases the plasma renin activity (PRA) as a compensatory feedback effect, since these drugs act on a more peripheral region of the RA system.

Renin is an enzyme occupying a position at the uppermost stream of the RA system, and converts angiotensinogen to angiotensin I. A renin inhibitory drug inhibits the RA system by inhibiting the biosynthesis of AII in the same manner as the ACE inhibitory drugs do, and thus can be expected to have a blood pressure lowering action or an effect of protecting various organs. Since the renin inhibitory drug does not have influence on the metabolism of bradykinin, it is believed to have no risk of side effects such as dry cough and the like, that are observed with the ACE inhibitory drugs. Furthermore, while the ACE inhibitory drugs or ARB increase the PRA level, the renin inhibitory drugs are the only drugs that can reduce PRA.

As renin inhibitors, orally administrable Aliskiren has been reported (Chem. Biol., 2000, vol. 7, pages 493-504; Hypertension, 2003, vol. 42, pages 1137-1143; J. Hypertens., 2005, vol. 23, pages 417-426 etc.).

As other renin inhibitors, the following compounds have been reported.

(1) A compound represented by the formula

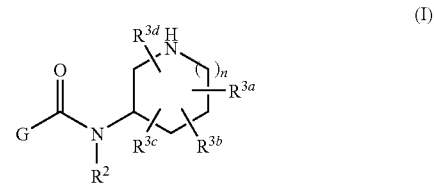

wherein G is any one of groups represented by the following formulas (a) to (c)

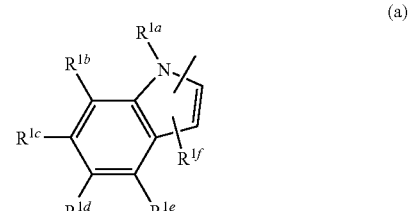

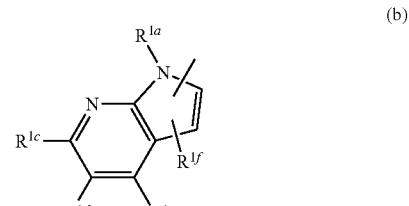

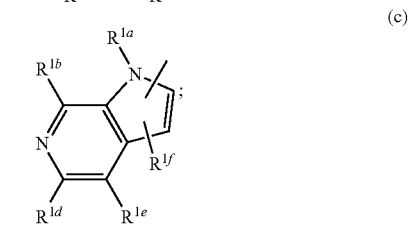

$R^{1a}$ is an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group or an optionally substituted 5-membered to 10-membered monocyclic or polycyclic heteroaryl-$C_{1-4}$ alkyl group;

$R^{1b}$, $R^{1c}$, $R^{1d}$ and $R^{1e}$ are the same or different and each independently is a hydrogen atom, a halogen atom, a hydroxyl group, a formyl group, a carboxy group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group, an optionally substituted saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{6-10}$ arylthio group, an optionally substituted $C_{6-10}$ arylsulfinyl group, an optionally substituted $C_{6-10}$ arylsulfonyl group, an optionally substituted $C_{1-6}$ alkoxy group, an optionally substituted $C_{3-6}$ alkynyloxy group, an optionally substituted $C_{3-6}$ cycloalkyloxy group, an optionally substituted $C_{6-10}$ aryloxy group, an optionally substituted $C_{7-14}$ aralkyloxy group, an optionally substituted 5-membered to 10-membered monocyclic or polycyclic heteroaryloxy group, an optionally substituted 5-membered to 10-membered monocyclic or polycyclic heteroaryl $C_{1-4}$ alkyloxy group, an optionally substituted amino group, an optionally substituted aminocarbonyl group, an optionally substituted aminocarbonyloxy group, an optionally substituted aminosulfonyl group, an optionally substituted $C_{1-6}$ alkoxycarbonyl group, an optionally substituted $C_{3-6}$ cycloalkyloxycarbonyl group, an optionally substituted $C_{1-4}$ alkylcarbonyl group, an optionally substituted $C_{3-6}$ cycloalkylcarbonyl group, an optionally substituted $C_{6-10}$ arylcarbonyl group or an optionally substituted 5-membered to 10-membered monocyclic or polycyclic heteroarylcarbonyl group;

$R^{1f}$ is a hydrogen atom, a halogen atom, a hydroxyl group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group, an optionally substituted saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{1-6}$ alkoxy group, an optionally substituted $C_{3-6}$ alkynyloxy group, an optionally substituted $C_{3-6}$ cycloalkyloxy group, an optionally substituted $C_{6-10}$ aryloxy group, an optionally substituted $C_{7-14}$ aralkyloxy group, an optionally substituted 5-membered to 10-membered monocyclic or polycyclic heteroaryl $C_{1-4}$ alkyloxy group, an optionally substituted amino group, an optionally substituted aminocarbonyl group, an optionally substituted aminosulfonyl group, an optionally substituted $C_{1-4}$ alkoxycarbonyl group, an optionally substituted $C_{3-6}$ cycloalkyloxycarbonyl group, an optionally substituted $C_{1-4}$ alkylcarbonyl group, an optionally substituted $C_{3-6}$ cycloalkylcarbonyl group, an optionally substituted $C_{6-10}$ arylcarbonyl group or an optionally substituted 5-membered to 10-membered monocyclic or polycyclic heteroarylcarbonyl group;

$R^2$ is an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, an optionally substituted $C_{5-6}$ cycloalkenyl group, an optionally substituted $C_{6-10}$ aryl group, an optionally substituted $C_{7-14}$ aralkyl group or an optionally substituted 5-membered to 10-membered monocyclic or polycyclic heteroaryl group;

$R^{3a}$, $R^{3b}$, $R^{3c}$ and $R^{3d}$ are the same or different and each independently is a halogen atom, a cyano group or a group: -A-B (wherein A is a single bond, —$(CH_2)_sO$—, —$(CH_2)_sN(R^4)$—, —$(CH_2)_sSO_2$—, —$(CH_2)_sCO$—, —$(CH_2)_sCOO$—, —$(CH_2)_sN(R^4)CO$—, —$(CH_2)_sN(R^4)SO_2$—, —$(CH_2)_sN(R^4)COO$—, —$(CH_2)_sOCON(R^4)$—, —$(CH_2)_sO$—CO—, —$(CH_2)_sON(R^4)$—, —$(CH_2)_sN(R^4)CON(R^4)$— or —$(CH_2)_sSO_2N(R^4)$—, B is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group or an optionally substituted 5-membered or 6-membered saturated heterocyclic group (when A is —$(CH_2)_sN(R^4)$—, —$(CH_2)_sO$-CON($R^4$)—, —$(CH_2)_sCON(R^4)$—, —$(CH_2)_sN(R^4)CON(R^4)$— or —$(CH_2)_sSO_2N(R^4)$—, $R^4$ and B may be bonded to each other to form a ring)), or two of $R^{3a}$, $R^{3b}$, $R^{3c}$ and $R^{3d}$ are hydrogen atoms, and the other two are bonded to each other to form a bridged ring together with the hetero ring;

$R^4$ is a hydrogen atom, an optionally substituted $C_{1-6}$ alkyl group, an optionally substituted $C_{3-6}$ cycloalkyl group, an optionally substituted $C_{6-10}$ aryl group, an optionally substituted $C_{7-14}$ aralkyl group or an optionally substituted 5-membered to 10-membered monocyclic or polycyclic heteroaryl group;

s is 0, 1 or 2 (when A is —$(CH_2)_sN(R^4)$—, s is 0 or 2, and when A is —$(CH_2)_sCON(R^4)$—, s is 1 or 2); and n is 0, 1 or 2, or a salt thereof (see WO2009/14217).

(2) A compound represented by the formula

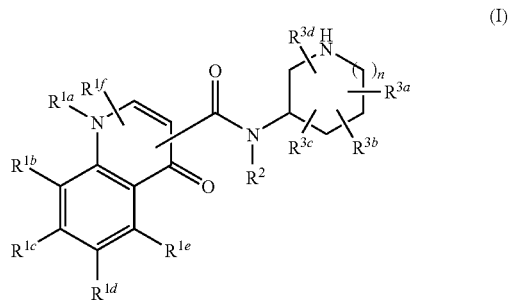

(I)

wherein $R^{1a}$ is an optionally substituted $C_{1-6}$ alkyl group, an optionally substituted $C_{2-10}$ alkenyl group, an optionally substituted $C_{2-6}$ alkynyl group, an optionally substituted $C_{3-6}$ cycloalkyl group, an optionally substituted $C_{5-6}$ cycloalkenyl group, an optionally substituted $C_{1-6}$ alkylsulfinyl group, an optionally substituted $C_{1-6}$ alkylsulfonyl group, an optionally substituted aminocarbonyl group, an optionally substituted $C_{1-4}$ alkoxycarbonyl group or an optionally substituted $C_{1-4}$ alkylcarbonyl group;

$R^{1b}$ and $R^{1e}$ are the same or different and each independently is a hydrogen atom, a halogen atom, a cyano group, an optionally substituted $C_{1-6}$ alkyl group, an optionally substituted $C_{1-6}$ alkoxy group, an optionally substituted $C_{3-6}$ cycloalkyloxy group or an optionally substituted aminocarbonyl group;

$R^{1c}$ and $R^{1d}$ are the same or different and each independently is a hydrogen atom, a halogen atom, a hydroxyl group, a formyl group, a carboxy group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group, an optionally substituted saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{6-10}$ arylthio group, an optionally substituted $C_{6-10}$ arylsulfinyl group, an optionally substituted $C_{6-10}$ arylsulfonyl group, an optionally substituted $C_{1-6}$ alkoxy group, an optionally substituted $C_{3-6}$ alkynyloxy group, an optionally substituted $C_{3-10}$ cycloalkyloxy group, an optionally substituted $C_{6-10}$ aryloxy group, an optionally substituted $C_{7-14}$ aralkyloxy group, an optionally substituted 5-membered to 10-membered monocyclic or polycyclic heteroaryloxy group, an optionally substituted 5-membered to 10-membered monocyclic or polycyclic heteroaryl $C_{1-4}$ alkyloxy group, an optionally substituted amino group, an optionally substituted aminocarbonyl group, an optionally substituted aminosulfonyl group, an optionally substituted $C_{1-4}$ alkoxycarbonyl group, an optionally substituted $C_{3-6}$ cycloalkyloxycarbonyl group, an optionally substituted $C_{1-4}$ alkylcarbonyl group, an optionally substituted $C_{3-6}$ cycloalkylcarbonyl group, an optionally substituted $C_{6-10}$ arylcarbonyl group or an optionally substituted 5-membered to 10-membered monocyclic or polycyclic heteroarylcarbonyl group;

$R^{1f}$ are the same or different and each independently is a hydrogen atom, a halogen atom, a cyano group, an optionally substituted $C_{1-6}$ alkyl group, an optionally substituted $C_{1-6}$ alkoxy group, an optionally substituted $C_{3-10}$ cycloalkyl group, an optionally substituted $C_{2-6}$ alkenyl group, an optionally substituted $C_{2-6}$ alkenyloxy group, an optionally substituted $C_{3-6}$ alkynyl group, an optionally substituted $C_{3-6}$ alkynyloxy group or an optionally substituted $C_{3-10}$ cycloalkyloxy group;

$R^2$ is an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group or an optionally substituted 5-membered to 10-membered monocyclic or polycyclic heteroaryl group;

$R^{3a}$, $R^{3b}$, $R^{3c}$ and $R^{3d}$ are the same or different and each independently is a halogen atom, a cyano group or a group: -A-B (wherein A is a single bond, —$(CH_2)_sO$—, —$(CH_2)_sN(R^4)$—, —$(CH_2)_sSO_2$—, —$(CH_2)_sCO$—, —$(CH_2)_sCOO$—, —$(CH_2)_sN(R^4)CO$—, —$(CH_2)_sN(R^4)SO_2$—, —$(CH_2)_sN(R^4)COO$—, —$(CH_2)_sOCON(R^4)$—, —$(CH_2)_sO$—$CO$—, —$(CH_2)_sON(R^4)$—, —$(CH_2)_sN(R^4)CON(R^4)$— or —$(CH_2)_sSO_2N(R^4)$—, B is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group or an optionally substituted saturated heterocyclic group (when A is —$(CH_2)_sN(R^4)$—, —$(CH_2)_sOCON(R^4)$—, —$(CH_2)_sCON(R^4)$—, —$(CH_2)_sN(R^4)CON(R^4)$— or —$(CH_2)_sSO_2N(R^4)$—, $R^4$ and B may be bonded to each other to form a ring)), or two of $R^{3a}$, $R^{3b}$, $R^{3c}$ and $R^{3d}$ are hydrogen atoms, and the other two are bonded to each other to form a bridged ring together with the hetero ring;

$R^4$ is a hydrogen atom, an optionally substituted $C_{1-6}$ alkyl group, an optionally substituted $C_{3-6}$ cycloalkyl group, an optionally substituted $C_{6-10}$ aryl group, an optionally substituted $C_{7-14}$ aralkyl group or an optionally substituted 5-membered to 10-membered monocyclic or a polycyclic heteroaryl group;

s is 0, 1 or 2 (when A is —$(CH_2)_sN(R^4)$—, s is 0 or 2, and when A is —$(CH_2)_sCON(R^4)$—, s is 1 or 2); and n is 0, 1 or 2, or a salt thereof (see WO2009/05002).

(3) A compound represented by the formula

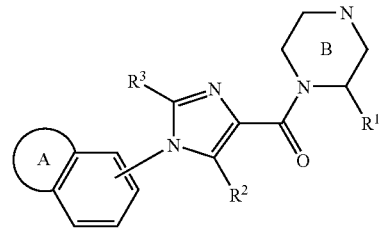

wherein
$R^1$ is a substituent;
$R^2$ is a cyclic group optionally having substituent(s), a $C_{1-10}$ alkyl optionally having substituent(s), a $C_{2-10}$ alkenyl optionally having substituent(s) or a $C_{2-10}$ alkynyl optionally having substituent(s);
$R^3$ is a hydrogen atom, a halogen atom, a $C_{1-6}$ alkyl or $C_{1-6}$ alkoxy;
ring A is a nitrogen-containing heterocycle optionally having substituent(s); and
ring B is a piperazine optionally further having substituent(s) besides $R^1$, or a salt thereof (see WO2009/001915).

(4) A compound represented by the formula

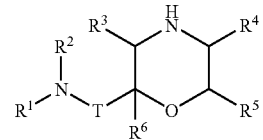

wherein $R^1$ is A) an alkyl group substituted by the group selected from 1) an optionally substituted alkoxy group, 2) a hydroxyl group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrochromenyl group, 11) an optionally substituted dihydrobenzofuranyl group, 12) an optionally substituted indazolyl group, 13) an optionally substituted pyrrolopyridinyl group, 14) an optionally substituted benzoxazinyl group, 15) an optionally substituted xanthenyl group, 16) an optionally substituted indolinyl group and 17) an optionally substituted imidazopyridinyl group, B) an optionally substituted aryl group, C) an optionally substituted heterocyclic group, D) a cycloalkyl group or E) an alkyl group, $R^2$ is A) an alkyl group substituted by the group selected from 1) an optionally substituted alkoxy group, 2) a hydroxyl group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrochromenyl group, 11) an optionally substituted dihydrobenzofuranyl group, 12) an optionally substituted indazolyl group, 13) an optionally substituted pyrrolopyridinyl group, 14) an optionally substituted benzoxazinyl group, 15) an optionally substituted xanthenyl group, 16) an optionally substituted indolinyl group and 17) an optionally substituted imidazopyridinyl group, B) an optionally substituted aryl group, C) an optionally substituted heterocyclic group, D) an optionally substituted alkylcarbonyl group, E) an optionally substituted arylcarbonyl group, F) an optionally substituted heterocyclic group-substituted carbonyl group or G) a cycloalkylcarbonyl group, T is a methylene group or a carbonyl group, and $R^3$, $R^4$, $R^5$ and $R^6$ are the same or different and each is a hydrogen atom, an optionally substituted carbamoyl group or an optionally a substituted alkyl group, or a salt thereof (see WO2008/153182).

(5) A compound represented by the formula

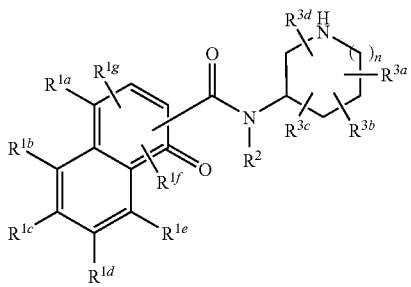

wherein $R^{1a}$ is an optionally substituted $C_{1-6}$ alkyl group, a $C_{3-6}$ cycloalkyl group substituted by $C_{1-4}$ alkoxy, an optionally substituted $C_{2-6}$ alkenyl group, an optionally substituted $C_{2-6}$ alkenyloxy group, an optionally substituted $C_{3-6}$ alkynyl group, an optionally substituted $C_{3-6}$ alkynyloxy group, an optionally substituted $C_{1-6}$ alkylsulfinyl group, an optionally substituted $C_{1-6}$ alkylsulfonyl group, an optionally substituted $C_{1-6}$ alkoxy group, an optionally substituted amino group, an optionally substituted aminocarbonyl group, an optionally substituted $C_{1-4}$ alkoxycarbonyl group or an optionally substituted $C_{1-4}$ alkylcarbonyl group;

$R^{1b}$ and $R^{1e}$ are each a hydrogen atom, a halogen atom, a cyano group, an optionally substituted $C_{1-6}$ alkyl group, an optionally substituted $C_{1-6}$ alkoxy group, an optionally substituted $C_{3-6}$ cycloalkyloxy group or an optionally substituted aminocarbonyl group;

$R^{1c}$ and $R^{1d}$ are the same or different and each independently is a hydrogen atom, a halogen atom, a hydroxyl group, a formyl group, a carboxy group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group, an optionally substituted saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{6-10}$ arylthio group, an optionally substituted $C_{6-10}$ arylsulfinyl group, an optionally substituted $C_{6-10}$ arylsulfonyl group, an optionally substituted $C_{1-6}$ alkoxy group, an optionally substituted $C_{3-6}$ alkynyloxy group, an optionally substituted $C_{3-10}$ cycloalkyloxy group, an optionally substituted $C_{6-10}$ aryloxy group, an optionally substituted $C_{7-14}$ aralkyloxy group, an optionally substituted 5-membered to 10-membered monocyclic or polycyclic heteroaryloxy group, an optionally substituted 5-membered to 10-membered monocyclic or polycyclic heteroaryl $C_{1-4}$ alkyloxy group, an optionally substituted amino group, an optionally substituted aminocarbonyl group, an optionally substituted aminosulfonyl group, an optionally substituted $C_{1-4}$ alkoxycarbonyl group, an optionally substituted $C_{3-10}$ cycloalkyloxycarbonyl group, an optionally substituted $C_{1-4}$ alkylcarbonyl group, an optionally substituted $C_{3-10}$ cycloalkylcarbonyl group, an optionally substituted $C_{6-10}$ arylcarbonyl group or an optionally substituted 5-membered to 10-membered monocyclic or polycyclic heteroarylcarbonyl group;

$R^{1f}$ and $R^{1g}$ are the same or different and each independently is a hydrogen atom, a halogen atom, a cyano group, an optionally substituted $C_{1-6}$ alkyl group, an optionally substituted $C_{1-6}$ alkoxy group, an optionally substituted $C_{3-10}$ cycloalkyl group, an optionally substituted $C_{2-6}$ alkenyl group, an optionally substituted $C_{2-6}$ alkenyloxy group, an optionally substituted $C_{3-6}$ alkynyl group, an optionally substituted $C_{3-6}$ alkynyloxy group or an optionally substituted $C_{3-10}$ cycloalkyloxy group;

$R^2$ is an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group or an optionally substituted 5-membered to 10-membered monocyclic or polycyclic heteroaryl group;

$R^{3a}$, $R^{3b}$, $R^{3c}$ and $R^{3d}$ are the same or different and each independently is a halogen atom, a cyano group or a group: -A-B (wherein A is a single bond, $-(CH_2)_sO-$, $-(CH_2)_sN(R^4)-$, $-(CH_2)_sSO_2-$, $-(CH_2)_sCO-$, $-(CH_2)_sCOO-$, $-(CH_2)_sN(R^4)CO-$, $-(CH_2)_sN(R^4)SO_2-$, $-(CH_2)_sN(R^4)COO-$, $-(CH_2)_sOCON(R^4)-$, $-(CH_2)_sO-CO-$, $-(CH_2)_sON(R^4)-$, $-(CH_2)_sN(R^4)CON(R^4)-$ or $-(CH_2)_sSO_2N(R^4)-$, B is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group or an optionally substituted saturated heterocyclic group (when A is —$(CH_2)_sN(R^4)$—, —$(CH_2)_sOCON(R^4)$—, —$(CH_2)_sCON(R^4)$—, —$(CH_2)_sN(R^4)CON(R^4)$— or —$(CH_2)_sSO_2N(R^4)$—, $R^4$ and B may be bonded to each other to form a ring)), or two of $R^{3a}$, $R^{3b}$, $R^{3c}$ and $R^{3d}$ are hydrogen atoms, and the other two are bonded to each other to form a bridged ring together with the hetero ring;

$R^4$ is a hydrogen atom, an optionally substituted $C_{1-6}$ alkyl group, an optionally substituted $C_{3-6}$ cycloalkyl group, an optionally substituted $C_{6-10}$ aryl group, an optionally substituted $C_{7-14}$ aralkyl group or an optionally substituted 5-membered to 10-membered monocyclic or a polycyclic heteroaryl group;

s is 0, 1 or 2 (when A is —$(CH_2)_sN(R^4)$—, s is 0 or 2, and when A is —$(CH_2)_sCON(R^4)$—, s is 1 or 2); and n is 0, 1 or 2, or a salt thereof (see WO2008/153135).

(6) A compound represented by the formula

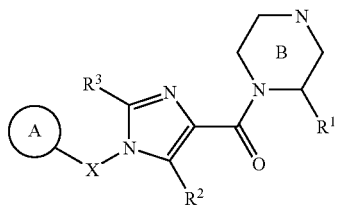

wherein
$R^1$ is a substituent,
$R^2$ is a cyclic group optionally having substituent(s), $C_{1-10}$ alkyl optionally having substituent(s) $C_{2-10}$ alkenyl optionally having substituent(s) or $C_{2-10}$ alkynyl optionally having substituent(s),
$R^3$ is a hydrogen atom, a halogen atom, $C_{1-6}$ alkyl or $C_{1-6}$ alkoxy,
X is a bond or a spacer having 1 to 6 atoms in the main chain,
ring A is a $C_{5-7}$ cycloalkane optionally having substituent(s), and
ring B is a piperazine optionally further having substituent(s) besides $R^1$, or a salt thereof (see WO2008/139941).

(7) A compound represented by the formula

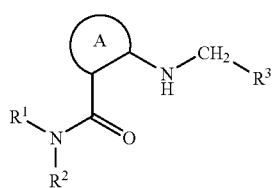

wherein $R^1$ and $R^2$ are each a hydrocarbon group optionally having substituent(s) or a heterocyclic group optionally having substituent(s), or $R^1$ and $R^2$ may form, together with the nitrogen atom bonded thereto, a nitrogen-containing heterocycle optionally having substituent(s),
$R^3$ is a substituent,
ring A is a homocycle optionally having substituent(s) or a heterocycle optionally having substituent(s), or a salt thereof (see WO2009/051112).

(8) A compound represented by the formula

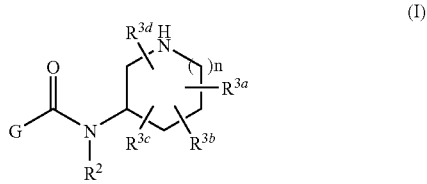

(I)

wherein G is one group selected from the group consisting of the following formulas (a) to (d)

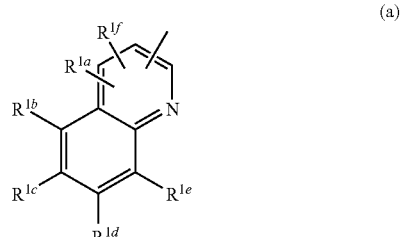

(a)

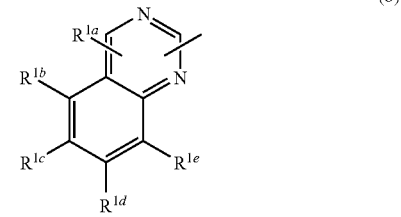

(b)

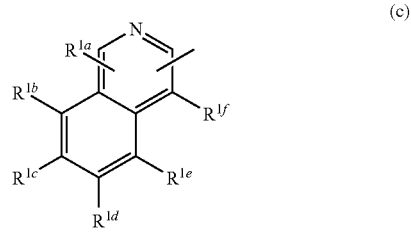

(c)

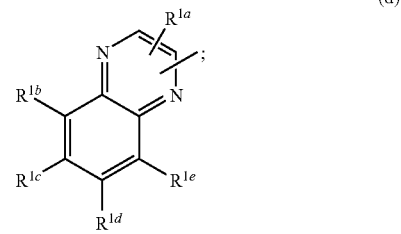

(d)

wherein $R^{1a}$ is an optionally substituted $C_{1-6}$ alkyl group, a $C_{3-6}$ cycloalkoxy group substituted by $C_{1-4}$ alkoxy, an optionally substituted $C_{2-6}$ alkenyl group, an optionally substituted $C_{2-6}$ alkenyloxy group, an optionally substituted $C_{3-6}$ alkynyl group, an optionally substituted $C_{3-6}$ alkynyloxy group, an optionally substituted $C_{1-6}$ alkylsulfinyl group, an optionally substituted $C_{1-6}$ alkylsulfonyl group, an optionally substituted $C_{1-6}$ alkoxy group, an optionally substituted amino group, an optionally substituted aminocarbonyl group, an optionally substituted $C_{1-4}$ alkoxycarbonyl group or an optionally substituted $C_{1-4}$ alkylcarbonyl group;

$R^{1b}$ and $R^{1e}$ are the same or different and each independently is a hydrogen atom, a cyano group, an optionally substituted $C_{1-8}$ alkyl group, an optionally substituted $C_{1-6}$ alkoxy group, an optionally substituted $C_{2-6}$ alkenyl group, $C_{1-6}$ alkylsulfonyl group, or a halogen atom;

$R^{1c}$ and $R^{1d}$ are the same or different and each independently is a hydrogen atom, a halogen atom, a hydroxyl group, a formyl group, a carboxy group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered or 6-membered saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{6-10}$ arylthio group, an optionally substituted $C_{6-10}$ arylsulfinyl group, an optionally substituted $C_{6-10}$ arylsulfonyl group, an optionally substituted $C_{1-6}$ alkoxy group, an optionally substituted $C_{3-6}$ alkynyloxy group, an optionally substituted $C_{3-10}$ cycloalkyloxy group, an optionally substituted $C_{6-10}$ aryloxy group, an optionally substituted $C_{7-14}$ aralkyloxy group, an optionally substituted 5-membered to 10-membered monocyclic or polycyclic heteroaryloxy group, an optionally substituted amino group, an optionally substituted aminocarbonyl group, an optionally substituted aminosulfonyl group, an optionally substituted $C_{1-4}$ alkoxycarbonyl group, an optionally substituted $C_{3-10}$ cycloalkyloxycarbonyl group, an optionally substituted $C_{1-4}$ alkylcarbonyl group, an optionally substituted $C_{3-10}$ cycloalkylcarbonyl group, an optionally substituted $C_{6-10}$ arylcarbonyl group or an optionally substituted 5-membered to 10-membered monocyclic or polycyclic heteroarylcarbonyl group;

$R^{1f}$ is a hydrogen atom, a halogen atom, a cyano group, an optionally substituted $C_{3-6}$ cycloalkyl group, an optionally substituted $C_{2-6}$ alkenyl group, an optionally substituted $C_{2-6}$ alkenyloxy group, an optionally substituted $C_{3-6}$ alkynyl group, an optionally substituted $C_{3-6}$ alkynyloxy group, an optionally substituted $C_{3-10}$ cycloalkyloxy group, an optionally substituted $C_{1-6}$ alkoxy group or an optionally substituted $C_{1-6}$ alkyl group;

$R^2$ is an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group or an optionally substituted 5-membered to 10-membered monocyclic or polycyclic heteroaryl group;

$R^{3a}$, $R^{3b}$, $R^{3c}$ and $R^{3d}$ are the same or different and each independently is a halogen atom, a hydroxyl group, a formyl group, a carboxy group, a cyano group or a group: -A-B (wherein A is a single bond, —$(CH_2)_sO$—, —$(CH_2)_sN(R^4)$—, —$(CH_2)_sSO_2$—, —$(CH_2)_sCO$—, —$(CH_2)_sCOO$—, —$(CH_2)_sN(R^4)CO$—, —$(CH_2)_sN(R^4)SO_2$—, —$(CH_2)_sN(R^4)COO$—, —$(CH_2)_sOCON(R^4)$—, —$(CH_2)_sO$—$CO$—, —$(CH_2)_sON(R^4)$—, —$(CH_2)_sN(R^4)CON(R^4)$— or —$(CH_2)_sSO_2N(R^4)$—, B is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group or an optionally substituted 5-membered or 6-membered saturated heterocyclic group (when A is —$(CH_2)_sN(R^4)$—, —$(CH_2)_sOCON(R^4)$—, —$(CH_2)_sCON(R^4)$—, —$(CH_2)_sN(R^4)CON(R^4)$— or —$(CH_2)_sSO_2N(R^4)$—, $R^4$ and B may be bonded to each other to form a ring)), or two of $R^{3a}$, $R^{3b}$, $R^{3c}$ and $R^{3d}$ are hydrogen atoms, and the other two are bonded to each other to form a bridged ring together with the hetero ring;

$R^4$ is a hydrogen atom, an optionally substituted $C_{1-6}$ alkyl group, an optionally substituted $C_{3-6}$ cycloalkyl group, an optionally substituted $C_{6-10}$ aryl group, an optionally substituted $C_{7-14}$ aralkyl group or an optionally substituted 5-membered to 10-membered monocyclic or polycyclic heteroaryl group;

s is 0, 1 or 2 (when A is —$(CH_2)_sN(R^4)$—, s is 0 or 2, and when A is —$(CH_2)_sCON(R^4)$—, s is 1 or 2); and n is 0, 1 or 2, or a salt thereof (see 2008/136457).

(9) A compound represented by the formula

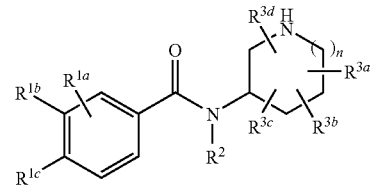

wherein $R^{1a}$ is a hydrogen atom, a halogen atom, a hydroxyl group, a formyl group, a carboxy group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, a $C_{1-6}$ alkylthio group, a $C_{1-6}$ alkylsulfonyl group, a $C_{1-6}$ alkoxy group optionally substituted by a halogen atom, $C_{1-4}$ alkoxy or $C_{3-6}$ cycloalkyl, an optionally substituted $C_{3-6}$ cycloalkoxy group, an optionally substituted amino group, aminocarbonyl group, $C_{1-4}$ alkoxycarbonyl group, a $C_{1-4}$ alkylcarbonyl group, an optionally substituted $C_{6-10}$ aryl group, an optionally substituted $C_{6-10}$ aryloxy group or an optionally substituted $C_{7-14}$ aralkyloxy group;

$R^{1b}$ is a $C_{1-6}$ alkyl group substituted by mono-$C_{1-6}$ alkoxycarbonylamino, an optionally substituted $C_{1-6}$ alkylsulfinyl group, an optionally substituted $C_{1-6}$ alkylsulfonyl group, a substituted $C_{1-6}$ alkoxy group, an optionally substituted amino group, an optionally substituted aminocarbonyl group, an optionally substituted $C_{1-4}$ alkoxycarbonyl group or an optionally substituted $C_{1-4}$ alkylcarbonyl group (wherein the substituted $C_{1-6}$ alkoxy group is substituted by one group selected from the group consisting of hydroxy, $C_{1-4}$ alkoxy, $C_{3-6}$ cycloalkoxy, trifluoromethyl, trifluoromethoxy, difluoromethoxy, carboxy, mono-$C_{1-6}$ alkylcarbonylamino and mono-$C_{1-6}$ alkoxycarbonylamino), $R^{1c}$ is a hydrogen atom, a halogen atom, a hydroxyl group, a formyl group, a carboxy group, a cyano group, an optionally substituted $C_{1-6}$ alkyl group, an optionally substituted $C_{3-6}$ cycloalkyl group, an optionally substituted $C_{5-6}$ cycloalkenyl group, an optionally substituted 5-membered or 6-membered saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{6-10}$ arylthio group, an optionally substituted $C_{6-10}$ arylsulfinyl group, an optionally substituted $C_{6-10}$ arylsulfonyl group, an optionally substituted $C_{1-6}$ alkoxy group, an optionally substituted $C_{3-6}$ cycloalkyloxy group, an optionally substituted $C_{6-10}$ aryloxy group, an optionally substituted $C_{7-14}$ aralkyloxy group, an optionally substituted amino group, an optionally substituted aminocarbonyl group, an optionally substituted $C_{1-4}$ alkoxycarbonyl group, an optionally substituted $C_{3-6}$ cycloalkyloxycarbonyl group, an optionally substituted $C_{1-4}$ alkylcarbonyl group, an optionally substituted $C_{3-6}$ cycloalkylcarbonyl group, an optionally substituted $C_{6-10}$ arylcarbonyl group, an optionally substituted $C_{7-14}$ aralkyl group or an optionally substituted 5-membered to 10-membered monocyclic or polycyclic heteroarylcarbonyl group, or $R^{1a}$ is a hydrogen atom; $R^{1b}$ and $R^{1c}$ in combination form a fused ring together with the hetero ring, which contains at least one hetero atom;

$R^2$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group or an optionally substituted 5-membered to 10-membered monocyclic or polycyclic heteroaryl group (when $R^{1a}$ is a $C_{1-6}$ alkoxy group substituted by a halogen atom, $R^2$ is not a hydrogen atom);

$R^{3a}$, $R^{3b}$, $R^{3c}$ and $R^{3d}$ are the same or different and each independently is a halogen atom, a cyano group or a group: -A-B (wherein A is a single bond, —$(CH_2)_sO$—, —$(CH_2)_sN(R^4)$—, —$(CH_2)_sSO_2$—, —$(CH_2)_sCO$—, —$(CH_2)_sCOO$—, —$(CH_2)_sN(R^4)CO$—, —$(CH_2)_sN(R^4)SO_2$—, —$(CH_2)_sN(R^4)COO$—, —$(CH_2)_sOCON(R^4)$—, —$(CH_2)_sO$—CO—, —$(CH_2)_sCON(R^4)$—, —$(CH_2)_sN(R^4)CON(R^4)$— or —$(CH_2)_sSO_2N(R^4)$—, B is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group or an optionally substituted saturated heterocyclic group (when A is —$(CH_2)_sN(R^4)$—, —$(CH_2)_sOCON(R^4)$—, —$(CH_2)_sCON(R^4)$—, —$(CH_2)_sN(R^4)CON(R^4)$— or —$(CH_2)_sSO_2N(R^4)$—, $R^4$ and B may be bonded to each other to form a ring)), or two of $R^{3a}$, $R^{3b}$, $R^{3c}$ and $R^{3d}$ are hydrogen atoms, and the other two are bonded to each other to form a bridged ring together with the hetero ring;

$R^4$ is a hydrogen atom, optionally substituted $C_{1-6}$ alkyl group, an optionally substituted $C_{3-10}$ cycloalkyl group, an optionally substituted $C_{6-10}$ aryl group, an optionally substituted $C_{7-14}$ aralkyl group or an optionally substituted 5-membered to 10-membered monocyclic or polycyclic heteroaryl group;

s is 0, 1 or 2 (when A is —$(CH_2)_sN(R^4)$—, s is 0 or 2, and when A is —$(CH_2)_sCON(R^4)$—, s is 1 or 2); and n is 0, 1 or 2, or a salt thereof (see WO2008/093737).

(10) A compound represented by the formula

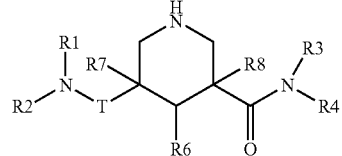

wherein R1 is hydrogen, unsubstituted or substituted alky!, unsubstituted or substituted alkenyl, unsubstituted or substituted alkynyl, unsubstituted or substituted aryl, unsubstituted or substituted heterocyclyl or unsubstituted or substituted cycloalkyl;

R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;

R3 is hydrogen, unsubstituted or substituted aryl or unsubstituted or substituted alkyl;

R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;

or R3 and R4 may form together a 3 to 7 membered nitrogen containing saturated hydrocarbon ring which can be unsubstituted or substituted;

R6 is hydrogen, halo, unsubstituted alkyl or unsubstituted alkoxy;

R7 and R8 are independently of each other hydrogen or halo; and

T is methylene or carbonyl; or a salt thereof (see WO2007/077005).

(11) A compound represented by the formula

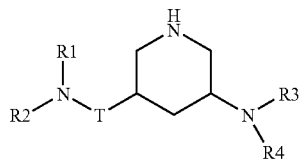

wherein R1 is hydrogen, unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl;

R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;

R3 is hydrogen, unsubstituted or substituted aryl or unsubstituted or substituted alkyl, R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;

or R3 and R4 may form together a 3 to 7 membered nitrogen containing saturated hydrocarbon ring which can be unsubstituted or substituted; and T is methylene or carbonyl; or a salt thereof (see WO2007/006534).

(12) A compound represented by the formula

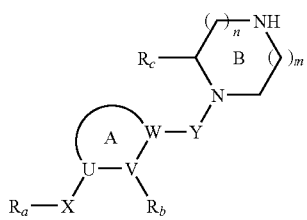

wherein ring A is a 5- or 6-membered aromatic heterocycle optionally having substituent(s);

U, V and W are each independently C or N, provided that when any one of U, V and W is N, then the others should be C;

Ra and Rb are each independently a cyclic group optionally having substituent(s), a $C_{1-10}$ alkyl group optionally having substituent(s), a $C_{2-10}$ alkenyl group optionally having substituent(s), or a $C_{2-10}$ alkynyl group optionally having substituent(s);

X is a bond, or a spacer having 1 to 6 atoms in the main chain;

Y is a spacer having 1 to 6 atoms in the main chain;

Rc is a hydrocarbon group optionally containing heteroatom(s) as the constituting atom(s), which optionally has substituent(s);

m and n are each independently 1 or 2; and ring B optionally further has substituent(s), or a salt thereof (see WO2007/094513).

On the other hand, as heterocyclic compounds, the following compounds have been reported.

(13) In WO2007/111227, for example, a compound having the following formula is reported as a CCR4 inhibitor.

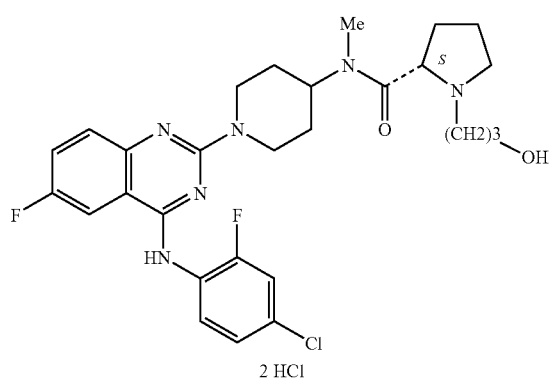

(14) In WO2006/101780, for example, a compound having the following formula is reported as a kinesin inhibitor.

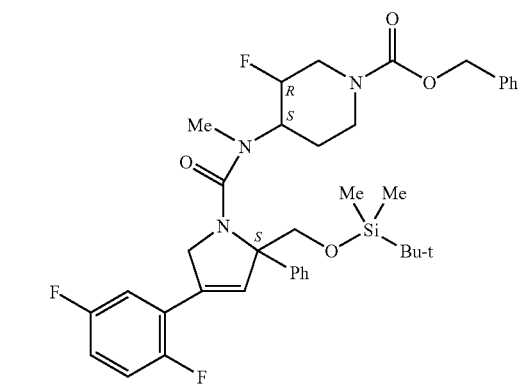

(15) In WO2005/047251, for example, a compound having the following formula is reported as a melanocortin receptor agonist.

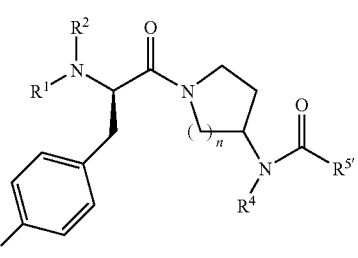

(16) In WO2005/019206, for example, a compound having the following formula is reported as a kinesin inhibitor.

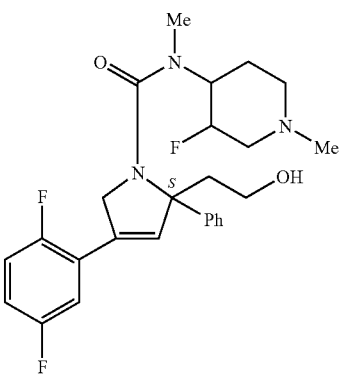

(17) In WO2005/018547, for example, a compound having the following formula is reported as a kinesin inhibitor.

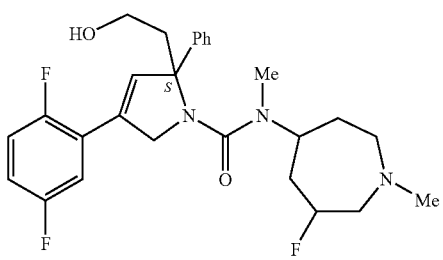

(18) In WO2004/037171, for example, a compound having the following formula is reported as a kinesin inhibitor.

(19) In WO2003/079973, for example, a compound having the following formula is reported as a kinesin inhibitor.

(20) In WO2003/037274, for example, a compound having the following formula is reported as a Na$^+$ channel inhibitor.

(21) In WO97/09308, for example, a compound having the following formula is reported as a NPY receptor antagonist.

(22) In WO2003/000677, for example, a compound having the following formula is reported as an ORL-1 receptor ligand.

However, these reports do not describe a renin inhibitory activity.

patent document 1: WO2009/14217
patent document 2: WO2009/05002
patent document 3: WO2009/001915
patent document 4: WO2008/153182
patent document 5: WO2008/153135
patent document 6: WO2008/139941
patent document 7: WO2008/136457
patent document 8: WO2009/051112
patent document 9: WO2008/093737
patent document 10: WO2007/077005
patent document 11: WO2007/006534
patent document 12: WO2007/094513
patent document 13: WO2007/111227
patent document 14: WO2006/101780
patent document 15: WO2005/047251
patent document 16: WO2005/019206
patent document 17: WO2005/018547
patent document 18: WO2004/037171
patent document 19: WO2003/079973
patent document 20: WO2003/037274
patent document 21: WO97/09308
patent document 22: WO2003/000677
non-patent document 1: Chem. Biol., 2000, vol. 7, page 493-504
non-patent document 2: Hypertension, 2003, vol. 42, page 1137-1143
non-patent document 3: J. Hypertens., 2005, vol. 23, page 417-426
non-patent document 4: Journal of Medicinal Chemistry, 1995, vol. 38, page 1406-1410

SUMMARY OF THE INVENTION

There is a demand on the development of a compound having a superior renin inhibitory activity, which is useful as a medicament (e.g., agent for the prophylaxis or treatment of hypertension, various organ damages attributable to hypertension, and the like) and a novel renin inhibitor.

The present inventors have conducted various studies, and as a result, first succeeded in the creation of novel compounds represented by the following formulas (I) and (II), and a salt thereof, and found that the compound and a salt thereof unexpectedly have a superior renin inhibitory activity, and are useful as medicaments such as renin inhibitor and the like, which resulted in the completion of the present invention.

The present invention relates to

[1] a compound represented by the formula (I):

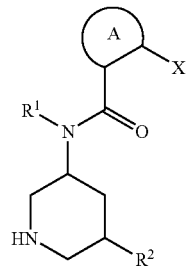

wherein

R¹ is a hydrogen atom, an alkyl group optionally having substituent(s), an alkenyl group optionally having substituent(s) or a cycloalkyl group optionally having substituent(s);

R² is a halogen atom, a hydroxy group, a cyano (nitrile) group, an amino group optionally having substituent(s), a mercapto group optionally having a substituent (the mercapto group is optionally oxidized), an alkyl group optionally having substituent(s) other than a substituted amino group, an alkoxy group optionally having substituent(s), a 3- to 10-membered cyclic hydrocarbon group optionally having substituent(s), a 3- to 10-membered heterocyclic group optionally having substituent(s) or an acyl group (wherein when the acyl group is —CONR'R", then R' and R" are both hydrogen atoms or form, together with the nitrogen atom bonded thereto, a nitrogen-containing heterocycle optionally having substituent(s));

X is absent, or a hydrogen atom, an alkyl group optionally substituted by group(s) other than a heterospiro ring optionally having substituent(s) or a cycloalkyl group optionally having substituent(s); and ring A is a heterocycle optionally having substituent(s), which is other than

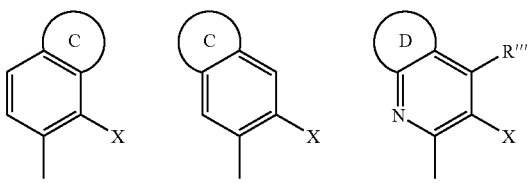

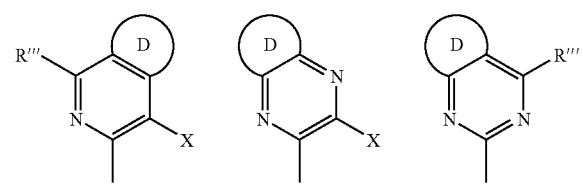

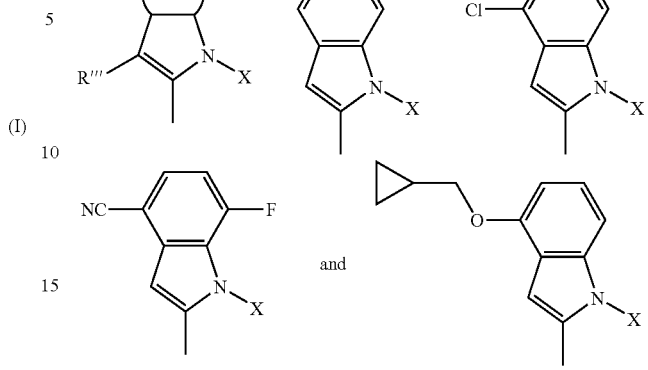

wherein ring C is a heterocycle optionally having substituent(s), ring D is a benzene ring optionally having substituent(s), R''' is a substituted alkyl group or a substituted alkoxy group, R'''' is a substituent, and X is as defined above), or a salt thereof;

[2] a compound represented by the formula (II):

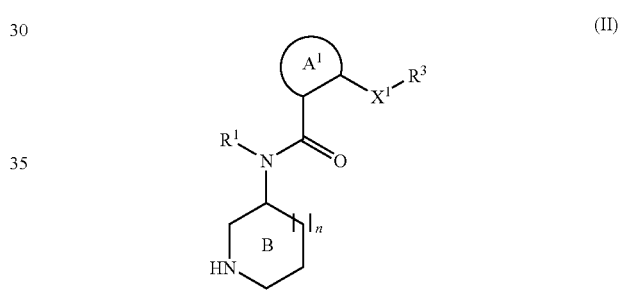

wherein

R¹ is a hydrogen atom, an alkyl group optionally having substituent(s), an alkenyl group optionally having substituent(s) or a cycloalkyl group optionally having substituent(s);

R³ is an alkyl group optionally substituted by group(s) other than a heterospiro ring optionally having substituent(s), an alkenyl group optionally having substituent(s), a cycloalkyl group optionally having substituent(s), an alkylthio group optionally having substituent(s), an alkylsulfinyl group optionally having substituent(s), an alkylsulfonyl group optionally having substituent(s), an alkoxy group optionally having substituent(s), an aryl group optionally having substituent(s) or a heteroaryl group optionally having substituent(s);

X¹ is a $C_{1-6}$ alkylene group optionally substituted by group(s) other than a heterospiro ring optionally having substituent(s);

ring A¹ is a fused heterocycle optionally having substituent(s);

ring B is a 5- to 7-membered nitrogen-containing heterocycle optionally having substituent(s); and n is 0, 1 or 2, or a salt thereof;

[3] a compound represented by the formula (II):

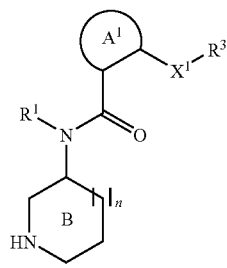

(II)

wherein
R¹ is a hydrogen atom, an alkyl group optionally having substituent(s), an alkenyl group optionally having substituent(s) or a cycloalkyl group optionally having substituent(s);
R³ is an alkyl group optionally substituted by group(s) other than a heterospiro ring optionally having substituent(s), an alkenyl group optionally having substituent(s), a cycloalkyl group optionally having substituent(s), an alkylthio group optionally having substituent(s), an alkylsulfinyl group optionally having substituent(s), an alkylsulfonyl group optionally having substituent(s), an alkoxy group optionally having substituent(s), an aryl group optionally having substituent(s) or a heteroaryl group optionally having substituent(s);
X¹ is a $C_{1-6}$ alkylene group optionally substituted by group(s) other than a heterospiro ring optionally having substituent(s);
ring A¹ is a fused heterocycle optionally having substituent(s);
ring B is a 5- to 7-membered nitrogen-containing heterocycle optionally having substituent(s); and
n is 0, 1 or 2, provided that ring A¹ is other than

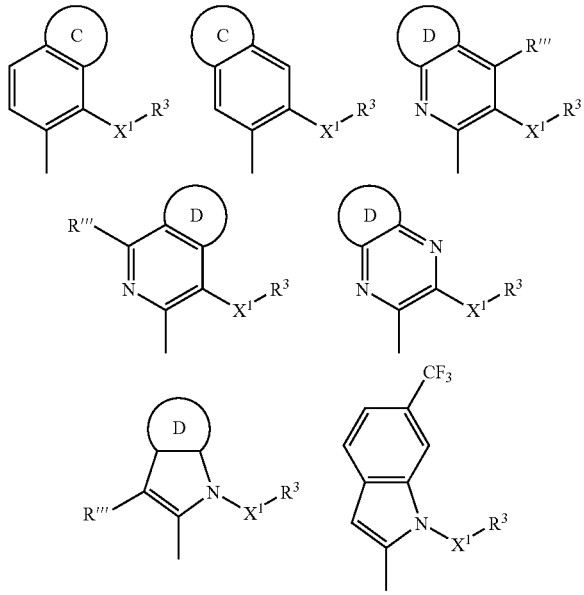

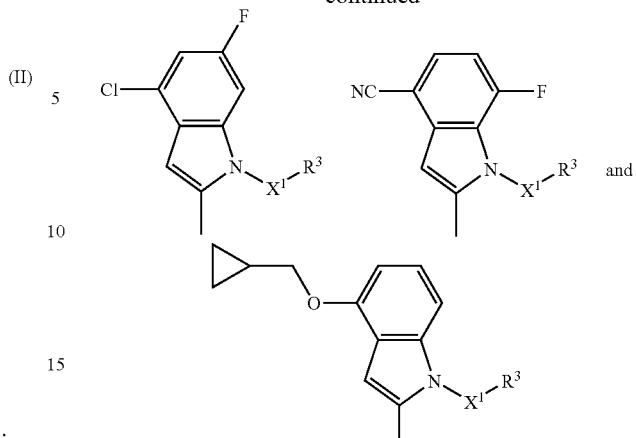

wherein ring C is a heterocycle optionally having substituent(s), ring D is a benzene ring optionally having substituent(s), R''' is a substituted alkyl group or a substituted alkoxy group, R'''' is a substituent, and other symbols are as defined above,
or a salt thereof;
[4] a compound represented by the formula (II):

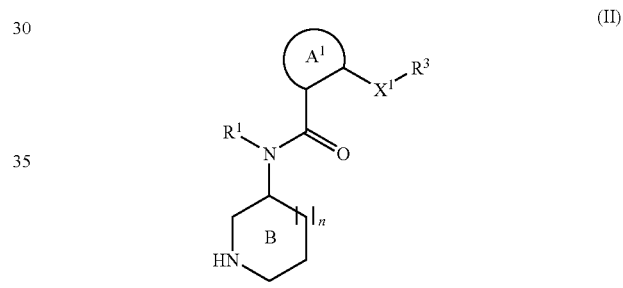

(II)

wherein
R¹ is a hydrogen atom, an alkyl group optionally having substituent(s), an alkenyl group optionally having substituent(s) or a cycloalkyl group optionally having substituent(s);
R³ is an alkyl group optionally substituted by group(s) other than a heterospiro ring optionally having substituent(s), an alkenyl group optionally having substituent(s), a cycloalkyl group optionally having substituent(s), an alkylthio group optionally having substituent(s), an alkylsulfinyl group optionally having substituent(s), an alkylsulfonyl group optionally having substituent(s), an alkoxy group optionally having substituent(s), an aryl group optionally having substituent(s) or a heteroaryl group optionally having substituent(s);
X¹ is a $C_{1-6}$ alkylene group optionally substituted by group(s) other than a heterospiro ring optionally having substituent(s);
ring A¹ is a fused heterocycle optionally having substituent(s);
ring B is a 5- to 7-membered nitrogen-containing heterocycle optionally substituted by substituent(s) selected from a halogen atom, a hydroxy group, a cyano (nitrile) group, an amino group optionally having substituent(s), a mercapto group optionally having a substituent (the mercapto group is optionally oxidized), an alkyl group optionally having substituent(s) other than a substituted amino group, an alkoxy group optionally having substituent(s), a 3- to 10-membered cyclic hydrocarbon group optionally having substituent(s), a 3- to 10-membered heterocyclic group optionally having substituent(s), and an acyl group (wherein when the acyl group is —CONR'R", then R' and R" are both hydrogen atoms or form, together with the nitrogen atom bonded thereto, a nitrogen-containing heterocycle optionally having substituent(s)); and n is 0, 1 or 2, or a salt thereof;

[5] a compound represented by the formula (II):

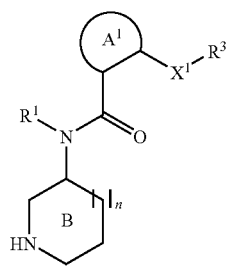

(II)

wherein $R^1$ is a hydrogen atom, an alkyl group optionally having substituent(s), an alkenyl group optionally having substituent(s) or a cycloalkyl group optionally having substituent(s);

$R^3$ is an alkyl group optionally substituted by group(s) other than a-heterospiro ring optionally having substituent(s), an alkenyl group optionally having substituent(s), a cycloalkyl group optionally having substituent(s), an alkylthio group optionally having substituent(s), an alkylsulfinyl group optionally having substituent(s), an alkylsulfonyl group optionally having substituent(s), an alkoxy group optionally having substituent(s), an aryl group optionally having substituent(s) or a heteroaryl group optionally having substituent(s);

$X^1$ is a $C_{1-6}$ alkylene group optionally substituted by group(s) other than a heterospiro ring optionally having substituent(s);

ring $A^1$ is a fused heterocycle optionally having substituent(s);

ring B is a 5- to 7-membered nitrogen-containing heterocycle optionally substituted by substituent(s) selected from a m halogen atom, a hydroxy group, a cyano (nitrile) group, an amino group optionally having substituent(s), a mercapto group optionally having a substituent (the mercapto group is optionally oxidized), an alkyl group optionally having substituent(s) other than a substituted amino group, an alkoxy group optionally having substituent(s), a 3- to 10-membered cyclic hydrocarbon group optionally having substituent(s), a 3- to 10-membered heterocyclic group optionally having substituent(s), and an acyl group (wherein when the acyl group is —CONR'R", then R' and R" are both hydrogen atoms or form, together with the nitrogen atom bonded thereto, a nitrogen-containing heterocycle optionally having substituent(s)); and n is 0, 1 or 2, provided ring $A^1$ is other than

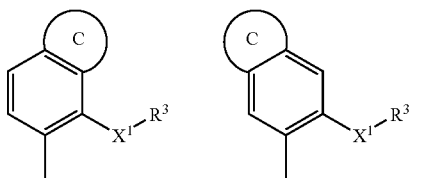

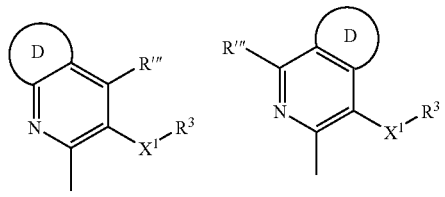

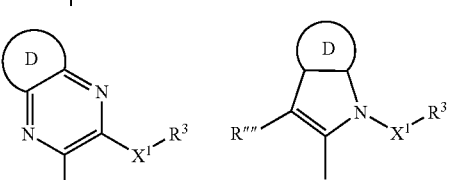

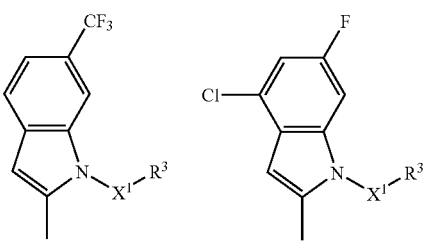

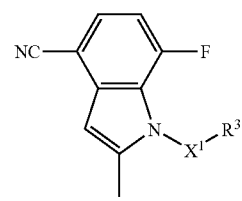

and

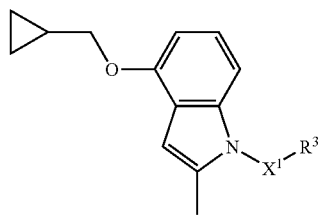

wherein ring C is a heterocycle optionally having substituent(s), ring D is a benzene ring optionally having substituent(s), R'" is a substituted alkyl group or a substituted alkoxy group, R"" is a substituent, and other symbols are as defined above, or a salt thereof;

[6] the compound of any of the above-mentioned [1] to [5], wherein ring A and ring $A^1$ are each a ring represented by the formula

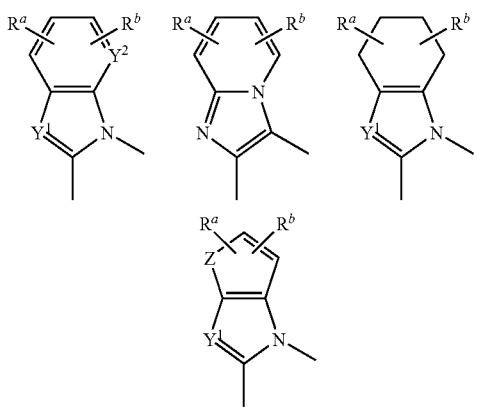

wherein
- $R^a$ and $R^b$ are each independently a hydrogen atom, a halogen atom, an alkyl group optionally having substituent(s), an alkoxy group optionally having substituent(s) or an acyl group;
- $R^c$ is a hydrogen atom, a halogen atom, =O, =S, an alkyl group optionally having substituent(s), an alkoxy group optionally having substituent(s) or an acyl group;
- $Y^1$ and $Y^2$ are each independently CH or N; and
- Z is $CH_2$, NH, O or S;

[7] the compound of any of the above-mentioned [1] to [5], wherein ring A and ring $A^1$ are each a ring represented by the formula

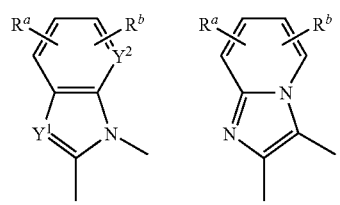

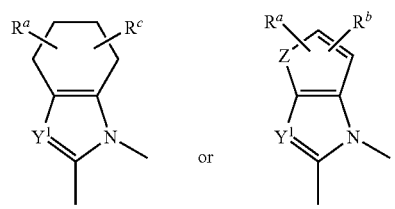

wherein
- $R^a$ and $R^b$ are each a hydrogen atom;
- $R^c$ is a hydrogen atom, a halogen atom, =O, =S, an alkyl group optionally having substituent(s), an alkoxy group optionally having substituent(s) or an acyl group;
- $Y^1$ and $Y^2$ are each independently CH or N; and
- Z is $CH_2$, NH, O or S;

[8] the compound of any of the above-mentioned [1] to [5], wherein ring A or ring $A^1$ is a ring represented by the formula

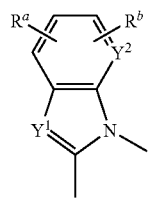

wherein $Y^1$, $Y^2$, $R^a$ and $R^b$ are as defined in the above-mentioned [7];

[9] the compound of any of the above-mentioned [1] to [5], wherein ring A or ring $A^1$ is a ring represented by the formula

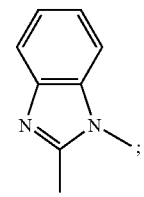

[10] the compound of any of the above-mentioned [2] to [5], wherein ring B is a ring represented by the formula

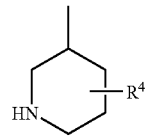

wherein
- $R^4$ is a hydrogen atom, a halogen atom, a hydroxy group, a cyano (nitrile) group, an amino group optionally having substituent(s), a mercapto group optionally having a substituent (the mercapto group is optionally oxidized), an alkyl group optionally having substituent(s) other than a substituted amino group, an alkoxy group optionally having substituent(s), a 3- to 10-membered cyclic hydrocarbon group optionally having substituent(s), a 3- to 10-membered heterocyclic group optionally having substituent(s) or an acyl group (wherein when the acyl group is —CONR'R", then R' and R" are both hydrogen atoms or form, together with the nitrogen atom bonded thereto, a nitrogen-containing heterocycle optionally having substituent(s));

[11] the compound of any of the above-mentioned [2] to [5], wherein ring B is a ring represented by the formula

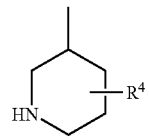

wherein $R^4$ is
(1) a hydrogen atom,
(2) a cyano(nitrile) group,
(3) a $C_{1-6}$ alkyl group optionally having 1 to 3 substituents selected from
(a) a hydroxy group,
(b) a $C_{1-6}$ alkoxy group, (c) a $C_{1-6}$ alkyl-carbonyloxy group,
(d) an aromatic heterocyclic group optionally having 1 to 3 halogen atoms,
(e) a $C_{3-10}$ cycloalkyl group, and
(f) a cyclic amino group optionally having an oxo group,
(4) a 3- to 10-membered heterocyclic group optionally having 1 to 3 substituents selected from a $C_{1-6}$ alkyl group and an oxo group,
(5) a carboxy group,
(6) a $C_{1-6}$ alkoxy-carbonyl group optionally having 1 to 3 substituents selected from a nonaromatic heterocyclic group optionally having 1 to 3 substituents selected from a $C_{1-6}$ alkyl group and an oxo group or
(7) a group represented by the formula: —CO—NR'R" wherein R' and R" are each a hydrogen atom, or R' and R" form, together with the nitrogen atom bonded thereto, a nitrogen-containing heterocycle optionally having 1 to 3 substituents selected from halogen atom(s);
[12] the compound of any of the above-mentioned [2] to [5], wherein ring B is a ring represented by

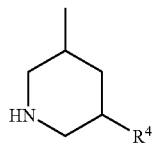

wherein $R^4$ is
(1) a cyano(nitrile) group,
(2) a $C_{1-6}$ alkyl group optionally having 1 to 3 substituents selected from
(a) a hydroxy group,
(b) a $C_{1-6}$ alkoxy group,
(c) a $C_{1-6}$ alkyl-carbonyloxy group,
(d) an aromatic heterocyclic group optionally having 1 to 3 halogen atoms,
(e) a $C_{3-10}$ cycloalkyl group, and
(f) a cyclic amino group optionally having an oxo group,
(3) a 3- to 10-membered heterocyclic group optionally having 1 to 3 substituents selected from a $C_{1-6}$ alkyl group and an oxo group,
(4) a carboxy group,
(5) a $C_{1-6}$ alkoxy-carbonyl group optionally having 1 to 3 substituents selected from a nonaromatic heterocyclic group optionally having 1 to 3 substituents selected from a $C_{1-6}$ alkyl group and an oxo group or
(6) a group represented by the formula: —CO—NR'R" wherein R' and R" are each a hydrogen atom, or
R' and R" form, together with the nitrogen atom bonded thereto, a nitrogen-containing heterocycle optionally having 1 to 3 substituents selected from halogen atom(s);
[13] the compound of any of the above-mentioned [2] to [5], wherein ring B is a ring represented by

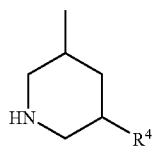

wherein $R^4$ is —CO—NR'R" wherein R' and R" are each a hydrogen atom, or R' and R" form, together with the nitrogen atom bonded thereto, a nitrogen-containing heterocycle optionally having 1 to 3 substituents selected from halogen atom(s);
[14] the compound of any of the above-mentioned [1] to [5], wherein $R^1$ is a $C_{1-6}$ alkyl group optionally having substituent(s);
[15] the compound of the above-mentioned [1], wherein $R^2$ is an acyl group (wherein when the acyl group is —CONR'R", then R' and R" are both hydrogen atoms or form, together with the nitrogen atom bonded thereto, a nitrogen-containing heterocycle optionally having substituent(s));
[16] the compound of the above-mentioned [1], wherein X is a $C_{1-6}$ alkyl group optionally substituted by a $C_{1-6}$ alkoxy group;
[17] the compound of any of the above-mentioned [2] to [5], wherein $X^1$ is a $C_{1-6}$ alkylene group optionally substituted by group(s) other than a heterospiro ring optionally having substituent(s) and an oxo group;
[18] the compound of any of the above-mentioned [2] to [5], wherein $X^1$ is a $C_{1-6}$ alkylene group;
[19] the compound of any of the above-mentioned [2] to [5], wherein $R^3$ is a $C_{1-6}$ alkoxy group optionally having substituent(s);
[20] the compound of the above-mentioned [1], wherein $R^1$ is a $C_{1-6}$ alkyl group optionally having substituent(s), $R^2$ is an acyl group (wherein when the acyl group is —CONR'R", then R' and R" are both hydrogen atoms or form, together with the nitrogen atom bonded thereto, a nitrogen-containing heterocycle optionally having substituent(s)),
Ring A is a Ring Represented by the Formula

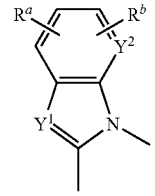

wherein $Y^1$, $Y^2$, $R^a$ and $R^b$ are as defined in the above-mentioned [7], and
X is a $C_{1-6}$ alkyl group optionally substituted by a $C_{1-6}$ alkoxy group;
[21] the compound of any of the above-mentioned [2] to [5], wherein $R^1$ is a $C_{1-6}$ alkyl group optionally having substituent(s),
$R^3$ is a $C_{1-6}$ alkoxy group optionally having substituent(s), ring $A^1$ is a ring represented by the formula

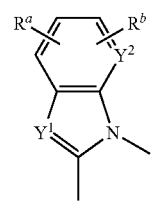

wherein $Y^1$, $Y^2$, $R^a$ and $R^b$ are as defined in the above-mentioned [7],
$X^1$ is a $C_{1-6}$ alkylene group, and Ring B is a Ring Represented by the Formula

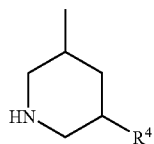

wherein R⁴ is —CO—NR'R" wherein R' and R" are each a hydrogen atom, or R' and R" form, together with the nitrogen atom bonded thereto, a nitrogen-containing heterocycle optionally having 1 to 3 substituents selected from halogen atom(s);

[22] N-[(3S,5R)-5-carbamoylpiperidin-3-yl]-1-(4-methoxybutyl)-N-(2-methylpropyl)-1H-benzimidazole-2-carboxamide or a salt thereof;

[23] N-{(3S,5R)-5-[1-hydroxyethyl]piperidin-5-yl}-1-(4-methoxybutyl)-N-(2-methylpropyl)-1H-benzimidazole-2-carboxamide or a salt thereof;

[24] 1-(4-methoxybutyl)-N-(2-methylpropyl)-N-[(3S,5R)-5-(morpholin-4-ylcarbonyl)piperidin-3-yl]-1H-benzimidazole-2-carboxamide or a salt thereof;

[25] 1-(4-hydroxybutyl)-N-(2-methylpropyl)-N-[(3S,5R)-5-(morpholin-4-ylcarbonyl)piperidin-3-yl]-1H-benzimidazole-2-carboxamide or a salt thereof;

[26] 1-(2-fluorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide or a salt thereof;

[27] 1-(4-methoxybutyl)-N-[(3S,5R)-5-(morpholin-4-ylcarbonyl)piperidin-3-yl]-N-propyl-1H-benzimidazole-2-carboxamide or a salt thereof;

[28] a prodrug of the compound of any of the above-mentioned [1] to [5];

[29] a medicament comprising the compound of any of the above-mentioned [1] to [5], or a prodrug thereof as an active ingredient;

[30] the medicament of the above-mentioned [29], which is a renin inhibitor;

[31] the medicament of the above-mentioned [29], which is a prophylactic or therapeutic agent of a circulatory disease;

[32] the medicament of the above-mentioned [29], which is a prophylactic or therapeutic agent of hypertension and/or various organ damages attributable to hypertension;

[33] a method for the prophylaxis or treatment of a circulatory disease in a mammal comprising administering the compound of any of the above-mentioned [1] to [5] or a prodrug thereof to the mammal;

[34] a method for the prophylaxis or treatment of hypertension and/or various organ damages attributable to hypertension in a mammal comprising administering the compound of any of the above-mentioned [1] to [5] or a prodrug thereof to the mammal;

[35] use of the compound of any of the above-mentioned [1] to [5] or a prodrug thereof for the production of a prophylactic or therapeutic agent for a circulatory disease;

[36] use of the compound of any of the above-mentioned [1] to [5] or a prodrug thereof for the production of a prophylactic or therapeutic agent for hypertension and/or various organ damages attributable to hypertension, and the like.

Compound (I) has a superior renin inhibitory activity, and thus it is useful as an agent for the prophylaxis or treatment of hypertension, various organ damages attributable to hypertension, and the like.

DETAILED DESCRIPTION OF THE INVENTION

Examples of the "halogen atom" in the present specification include fluorine, chlorine, bromine and iodine.

Examples of the "$C_{1-4}$ alkylenedioxy group" in the present specification include methylenedioxy, ethylenedioxy, trimethylenedioxy and the like.

Examples of the "alkyl group" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like. Among these, a $C_{1-6}$ alkyl group is preferable.

Examples of the "alkenyl group" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like. Among these, a $C_{2-6}$ alkenyl group is preferable.

Examples of the "alkynyl group" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Among these, a $C_{2-6}$ alkynyl group is preferable.

Examples of the "cycloalkyl group" in the present specification include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like. Among these, a $C_{3-10}$ cycloalkyl group is preferable.

Examples of the "alkylthio group" in the present specification include methylthio, ethylthio, propylthio, isopropylthio, butylthio, isobutylthio, sec-butylthio, tert-butylthio, pentylthio, isopentylthio, neopentylthio, 1-ethylpropylthio, hexylthio, isohexylthio, 1,1-dimethylbutylthio, 2,2-dimethylbutylthio, 3,3-dimethylbutylthio, 2-ethylbutylthio and the like. Among these, a $C_{1-6}$ alkylthio group is preferable.

Examples of the "alkylsulfinyl group" in the present specification include methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, 1-ethylpropylsulfinyl, hexylsulfinyl, isohexylsulfinyl, 1,1-dimethylbutylsulfinyl, 2,2-dimethylbutylsulfinyl, 3,3-dimethylbutylsulfinyl, 2-ethylbutylsulfinyl and the like. Among these, a $C_{1-6}$ alkylsulfinyl group is preferable.

Examples of the "alkylsulfonyl group" in the present specification include methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, 1-ethylpropylsulfonyl, hexylsulfonyl, isohexylsulfonyl, 1,1-dimethylbutylsulfonyl, 2,2-dimethylbutylsulfonyl, 3,3-dimethylbutylsulfonyl, 2-ethylbutylsulfonyl and the like. Among these, a $C_{1-6}$ alkylsulfonyl group is preferable.

Examples of the "alkoxy group" in the present specification include methoxy, ethoxy, propoxy, isopropoxy, butoxy, isobutoxy, sec-butoxy, tert-butoxy, pentyloxy, isopentyloxy, neopentyloxy, 1-ethylpropyloxy, hexyloxy, isohexyloxy, 1,1-dimethylbutyloxy, 2,2-dimethylbutyloxy, 3,3-dimethylbutyloxy, 2-ethylbutyloxy and the like. Among these, a $C_{1-6}$ alkoxy group is preferable.

Examples of the "$C_{1-6}$ alkoxy-carbonyl group" in the present specification include methoxycarbonyl, ethoxycarbonyl, propoxycarbonyl, tert-butoxycarbonyl and the like.

Examples of the "$C_{1-6}$ alkyl-carbonyl group" in the present specification include acetyl, propanoyl, butanoyl, isobutanoyl, pentanoyl, isopentanoyl, hexanoyl and the like.

The "optionally halogenated" in the present specification means being optionally substituted by 1 to 5, preferably 1 to 3, halogen atoms.

Examples of the "$C_{1-6}$ alkylene group" in the present specification include methylene, ethylene, trimethylen, tetramethylene, pentamethylene, hexamethylene, —CH(CH$_3$)—, —C(CH$_3$)$_2$—, —CH(CH$_2$CH$_3$)—, —C(CH$_2$CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—, —CH(CH$_3$)—(CH$_2$)$_2$, —CH$_2$—CH(CH$_3$)—CH$_2$—, —(CH$_2$)$_2$—CH(CH$_3$)—, —C(CH$_3$)$_2$—(CH$_2$)$_2$—, —CH$_2$—C(CH$_3$)$_2$—CH$_2$—, —(CH$_2$)$_2$—C(CH$_3$)$_2$— and the like.

Examples of the "hydrocarbon group" of the "hydrocarbon group optionally having substituent(s)" in the present specification include alkyl group, alkenyl group, alkynyl group, alkylidene group, cycloalkyl group, cycloalkenyl group, cycloalkadienyl group, aryl group, aralkyl group, arylalkenyl group, cycloalkylalkyl group and the like. Preferably, $C_{1-10}$ alkyl group, $C_{2-10}$ alkenyl group, $C_{2-10}$ alkynyl group, $C_{1-3}$ alkylidene group, $C_{3-10}$ cycloalkyl group, $C_{3-10}$ cycloalkenyl group, $C_{4-10}$ cycloalkadienyl group, $C_{6-14}$ aryl group, $C_{7-16}$ aralkyl group, $C_{8-13}$ arylalkenyl group, $C_{3-10}$ cycloalkyl-$C_{1-6}$ alkyl group and the like. The above-mentioned $C_{3-10}$ cycloalkyl group, $C_{3-10}$ cycloalkenyl group and $C_{4-10}$ cycloalkadienyl group may be each condensed with a benzene ring.

Examples of the "$C_{1-10}$ alkyl group" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Among these, a $C_{1-6}$ alkyl group is preferable.

Examples of the "$C_{2-10}$ alkenyl group" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Among these, a $C_{2-6}$ alkenyl group is preferable.

Examples of the "$C_{2-10}$ alkynyl group" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Among these, a $C_{2-6}$ alkynyl group is preferable.

Examples of the "$C_{1-3}$ alkylidene group" in the present specification include methylidene, ethylidene, propylidene, isopropylidene and the like.

Examples of the "$C_{3-10}$ cycloalkyl group" in the present specification include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like. Among these, a $C_{3-6}$ cycloalkyl group is preferable. The above-mentioned $C_{3-10}$ cycloalkyl may be condensed with a benzene ring, and examples of the fused group include indanyl, tetrahydronaphthyl, fluorenyl and the like.

Examples of the "$C_{3-10}$ cycloalkenyl group" in the present specification include 2-cyclopenten-1-yl, 3-cyclopenten-1-yl, 2-cyclohexen-1-yl, 3-cyclohexen-1-yl and the like. The above-mentioned $C_{3-10}$ cycloalkenyl may be condensed with a benzene ring, and examples of the fused group include indenyl and the like.

Examples of the "$C_{4-10}$ cycloalkadienyl group" in the present specification include 2,4-cyclopentadien-1-yl, 2,4-cyclohexadien-1-yl, 2,5-cyclohexadien-1-yl and the like. The above-mentioned $C_{4-10}$ cycloalkadienyl may be condensed with a benzene ring.

Examples of the "$C_{6-14}$ aryl group" in the present specification include phenyl, 1-naphthyl, 2-naphthyl, biphenylyl, 2-anthryl and the like. Among these, a $C_{6-10}$ aryl group is preferable, and phenyl is more preferable. The above-mentioned $C_{6-14}$ aryl may be condensed with $C_{3-10}$ cycloalkane (examples of the $C_{3-10}$ cycloalkane include a ring corresponding to the above-mentioned $C_{3-10}$ cycloalkyl group), and examples of the fused group include tetrahydronaphthyl, indanyl and the like.

Examples of the "$C_{7-16}$ aralkyl group" in the present specification include benzyl, phenethyl, naphthylmethyl, biphenylylmethyl and the like.

Examples of the "$C_{8-13}$ arylalkenyl group" in the present specification include styryl and the like.

Examples of the "$C_{3-10}$ cycloalkyl-$C_{1-6}$ alkyl group" in the present specification include cyclopropylmethyl, cyclohexylmethyl and the like.

The "hydrocarbon group" of the "hydrocarbon group optionally having substituent(s)" optionally has substituent(s) (e.g., 1 to 5, preferably 1 to 3 substituents) at substitutable position(s). When the number of the substituents is two or more, respective substituents may be the same or different.

Examples of the "substituent" of the "hydrocarbon group optionally having substituent(s)" include the following substituents (hereinafter to be referred to as substituent group A).
(1) a halogen atom;
(2) a nitro group;
(3) a cyano (nitrile) group;
(4) a hydroxy group;
(5) an alkoxy group optionally having substituent(s);
(6) an amino group optionally having substituent(s);
(7) =O (oxo group);
(8) =S (thioxo group);
(9) a mercapto group optionally having a substituent (the mercapto group is optionally oxidized);
(10) a $C_{1-4}$ alkylenedioxy group;
(11) an alkyl group optionally having substituent(s);
(12) a $C_{7-16}$ aralkyl group;
(13) an acyl group;
(14) a 3- to 10-membered cyclic hydrocarbon group optionally having substituent(s);
(15) a 3- to 10-membered heterocyclic group optionally having substituent(s) and the like.

Examples of the "3- to 10-membered cyclic hydrocarbon group" of the "3- to 10-membered cyclic hydrocarbon group optionally having substituent(s)" for substituent group A include $C_{3-10}$ cycloalkyl group, $C_{3-10}$ cycloalkenyl group, $C_{4-10}$ cycloalkadienyl group, $C_{6-10}$ aryl group and the like. Examples of the $C_{3-10}$ cycloalkyl group, $C_{3-10}$ cycloalkenyl group, $C_{4-10}$ cycloalkadienyl group and $C_{6-10}$ aryl group include those similar to the $C_{3-10}$ cycloalkyl group, $C_{3-10}$ cycloalkenyl group, $C_{4-10}$ cycloalkadienyl group and $C_{6-10}$ aryl group exemplified as the "hydrocarbon group" of the "hydrocarbon group optionally having substituent(s)".

Examples of the "3- to 10-membered heterocyclic group" of the "3- to 10-membered heterocyclic group optionally having substituent(s)" for substituent group A include a 3- to 10-membered ring from the "heterocyclic group" of the "heterocyclic group optionally having substituent(s)" to be mentioned later.

Examples of the "substituent" of the "$C_{1-6}$ alkyl group optionally having substituent(s)" and "$C_{1-6}$ alkoxy group optionally having substituent(s)", "3- to 10-membered cyclic hydrocarbon group optionally having substituent(s)" and "3- to 10-membered heterocyclic group optionally having substituent(s)" for substituent group A include 1 to 5, preferably 1 to 3 selected from the following substituents (hereinafter to be referred to as substituent group B). When the number of the substituents is two or more, the respective substituents may be the same or different.

(1) a halogen atom;
(2) a nitro group;
(3) a cyano (nitrile) group;
(4) a hydroxy group;
(5) a $C_{1-6}$ alkoxy group optionally having 1 to 3 halogen atoms;
(6) an amino group;
(7) a mono- or di-$C_{1-6}$ alkylamino group;
(8) a $C_{7-16}$ aralkylamino group;
(9) a $C_{1-6}$ alkoxy-carbonylamino group;
(10) a $C_{1-6}$ alkyl-carbonylamino group;
(11) a $C_{1-6}$ alkyl-carbonyloxy group;
(12) a $C_{1-6}$ alkyl-carbonyl group;
(13) a carboxy group;
(14) a $C_{1-6}$ alkoxy-carbonyl group;
(15) a carbamoyl group;
(16) a mono- or di-$C_{1-6}$ alkylcarbamoyl group;
(17) =O (oxo group);
(18) =S (thioxo group);
(19) a mercapto group;
(20) a $C_{1-6}$ alkylthio group;
(21) a $C_{1-6}$ alkylsulfinyl group;
(22) a $C_{1-6}$ alkylsulfonyl group;
(23) a $C_{1-4}$ alkylenedioxy group;
(24) a $C_{1-6}$ alkyl group optionally having 1 to 3 substituents selected from
  (a) a halogen atom,
  (b) a hydroxy group,
  (c) a $C_{1-6}$ alkoxy group,
  (d) a $C_{6-14}$ aryl group,
  (e) an amino group,
  (f) a mono- or di-$C_{1-6}$ alkylamino group,
  (g) a $C_{7-16}$ aralkylamino group, and
  (h) a $C_{1-6}$ alkoxy-carbonylamino group;
(25) an aryl group optionally having 1 to 3 halogen atoms;
(26) an aromatic heterocyclic group (e.g., pyridyl, pyrazolyl, triazolyl) optionally having 1 to 3 halogen atoms;
(27) a nonaromatic heterocyclic group (e.g., dioxolyl) is optionally having 1 to 3 substituents selected from a $C_{1-6}$ alkyl group and an oxo group;
(28) a $C_{7-16}$ aralkyl group;
(29) a $C_{3-10}$ cycloalkyl group;
(30) a cyclic amino group (e.g., pyrrolidinyl, piperidino, morpholino, thiomorpholino, piperazinyl, imidazolidin-1-yl, pyrazolidin-1-yl etc.) optionally having an oxo group and the like.

Examples of the "substituent" of the "amino group optionally having substituent(s)" for substituent group A include 1 or 2 selected from substituent group B. When the number of the substituents is two or more, the respective substituents may be the same or different.

Examples of the "substituent" of the "mercapto group optionally having a substituent" for substituent group A include substituent group B. The mercapto group may be oxidized by 1 or 2 oxygens.

Examples of the "heterocyclic group" of the "heterocyclic group optionally having substituent(s)" in the present specification include an aromatic heterocyclic group and a nonaromatic heterocyclic group.

Examples of the "aromatic heterocyclic group" include a 4- to 10-membered (preferably 5- or 6-membered) monocyclic aromatic heterocyclic group containing, as a ring-constituting atom besides carbon atoms, 1 to 4 heteroatoms selected from an oxygen atom, a sulfur atom and a nitrogen atom, and a fused aromatic heterocyclic group. Examples of the fused aromatic heterocyclic group include a group derived from a fused ring wherein a ring corresponding to such 4- to 10-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed, and the like.

Examples of the "aromatic heterocyclic group" include 4- to 7-membered (preferably 5- or 6-membered) monocyclic aromatic heterocyclic groups such as furyl (e.g., 2-furyl, 3-furyl), thienyl (e.g., 2-thienyl, 3-thienyl), pyridyl 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, isoxazolyl), oxadiazolyl (e.g., 1,2,4-oxadiazol-5-yl, 1,3,4-oxadiazol-2-yl), thiadiazolyl (e.g., 1,2,4-thiadiazol-5-yl, 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,3,5-triazin-2-yl, 1,3,5-triazin-4-yl, 1,2,3-triazin-4-yl, 1,2,4-triazin-3-yl) and the like;

fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

Examples of the "non-aromatic heterocyclic group" include a 3- to 10-membered (preferably 5- or 6-membered) monocyclic non-aromatic heterocyclic group containing, as a ring-constituting atom besides carbon atoms, 1 to 4 heteroatoms selected from an oxygen atom, a sulfur atom and a nitrogen atom, and a fused non-aromatic heterocyclic group. Examples of the fused non-aromatic heterocyclic group include a group derived from a fused ring wherein a ring corresponding to such 3- to 10-membered monocyclic non-aromatic heterocyclic group, and 1 or 2 rings selected from a 5- or 6-membered heterocycle containing 1 or 2 nitrogen atoms, a 5-membered heterocycle containing one sulfur atom and a benzene ring are condensed, and the like.

Examples of the "non-aromatic heterocyclic group" include 4- to 7-membered (preferably 5- or 6-membered) monocyclic non-aromatic heterocyclic groups such as pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), hexahydropyrimidinyl (e.g., hexahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;

fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydrobenzofuran-5-yl), dihydrobenzodioxinyl (e.g., 2,3- dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydrobenzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like;

and the like.

The above-mentioned "heterocyclic group" optionally has substituent(s) (e.g., 1 to 5, preferably 1 to 3 substituents) at substitutable position(s). When the number of the substituents is two or more, the respective substituents may be the same or different.

Examples of the "substituent" of the "heterocyclic group optionally having substituents" include the groups exemplified as the aforementioned substituent group A and the like.

Examples of the "acyl group" in the present specification include groups represented by the formulas: —COR$^A$, —CO—OR$^A$, —SO$_2$R$^A$, —SOR$^A$, —CO—NR'R", —CS—NR'R" wherein R$^A$ is a hydrogen atom, a hydroxy group, a hydrocarbon group optionally having substituent(s), an amino group optionally having substituent(s) or a heterocyclic group optionally having substituent(s). R' and R" are each a hydrogen atom, a hydrocarbon group optionally having substituent(s) or a heterocyclic group optionally having substituent(s), or R' and R" form, together with the nitrogen atom bonded thereto, a nitrogen-containing heterocycle optionally having substituent(s), and the like.

Examples of the "hydrocarbon group" of the "hydrocarbon group optionally having substituent(s)" for R$^A$, R' or R" include those similar to the "hydrocarbon group" of the aforementioned "hydrocarbon group optionally having substituent(s)".

Examples of the "heterocyclic group" of the "heterocyclic group optionally having substituent(s)" for R$^A$, R' or R" include those similar to the "heterocyclic group" of the aforementioned "heterocyclic group optionally having substituent(s)".

Examples of the "amino group optionally having substituent(s)" for R$^A$ include those similar to the "amino group optionally having substituent(s)" of the aforementioned substituent group A.

Examples of the substituent of the "hydrocarbon group optionally having substituent(s)" and "heterocyclic group optionally having substituent(s)" for R$^A$, R' or R" include 1 to 5, preferably 1 to 3, selected from the aforementioned substituent group A. When the number of the substituents is two or more, the respective substituents may be the same or different.

Examples of the "nitrogen-containing heterocycle" of the "nitrogen-containing heterocycle optionally having substituent(s)" formed by R' and R" together with the nitrogen atom bonded thereto include a 4- to 7-membered nonaromatic nitrogen-containing heterocycle containing, as a ring-constituting atom besides carbon atom, one nitrogen atom, and optionally further containing 1 or 2 hetero atoms selected from an oxygen atom, a sulfur atom and a nitrogen atom. The nonaromatic nitrogen-containing heterocycle may be condensed with a benzene ring.

Examples of the nitrogen-containing heterocycle include azetidine, pyrrolidine, imidazolidine, pyrazolidine, piperidine, homopiperidine, piperazine, homopiperazine, morpholine, homomorpholine, thiomorpholine, thiohomomorpholine, dihydrobenzoxazine (e.g., 3,4-dihydro-2H-1,4-benzoxazine), 1,2,3,4-tetrahydroquinoline, 7-aza-bicyclo [2.2.1]heptane and the like.

The "nitrogen-containing heterocycle" optionally has (preferably 1 to 3, more preferably 1 or 2) substituent(s) at substitutable position(s). Examples of the substituent include substituent group B and the like. When the number of the substituents is two or more, the respective substituents may be the same or different.

Preferable examples of the "acyl" include
(1) a formyl group;
(2) a carboxy group;
(3) a C$_{1-6}$ alkyl-carbonyl group;
(4) a C$_{1-6}$ alkoxy-carbonyl group (e.g., methoxycarbonyl, ethoxycarbonyl, propoxycarbonyl, tert-butoxycarbonyl) optionally having 1 to 3 substituents selected from the substituent group B;
(5) a group represented by the formula: —CO—NR'R" wherein R' and R" are each a hydrogen atom, a hydrocarbon group optionally having 1 to 3 substituents selected from the aforementioned substituent group B or a heterocyclic group optionally having 1 to 3 substituents selected from the aforementioned substituent group B, or R' and R" optionally form, together with the nitrogen atom bonded thereto, a nitrogen-containing heterocycle optionally having 1 to 3 substituents selected from the aforementioned substituent group B, and the like.

Examples of the "aryl group" in the present specification include $C_{6-14}$ aryl such as phenyl, 1-naphthyl, 2-naphthyl, biphenylyl, 2-anthryl and the like. Among these, $C_{6-10}$ aryl is preferable and phenyl is more preferable. The above-mentioned aryl may be condensed with $C_{3-10}$ cycloalkane (examples of the $C_{3-10}$ cycloalkane include a ring corresponding to the above-mentioned $C_{3-10}$ cycloalkyl), and examples of the fused group include tetrahydronaphthyl, indanyl and the like.

Examples of the "heteroaryl group" in the present specification include a monocyclic aromatic heterocyclic group and a fused aromatic heterocyclic group from the "heterocyclic group" of the aforementioned "heterocycle optionally having substituent(s)".

Examples of the "heterocycle" in the present specification include monocyclic heterocycle and fused heterocycle.

Examples of the "monocyclic heterocycle" include monocyclic aromatic heterocycle and monocyclic non-aromatic heterocycle.

Examples of the "monocyclic aromatic heterocycle" include a 4- to 10-membered (preferably 5- or 6-membered) monocyclic aromatic heterocycle containing, as a ring-constituting atom besides carbon atoms, 1 to 4 heteroatoms selected from an oxygen atom, a sulfur atom and a nitrogen atom.

Examples of the "monocyclic aromatic heterocycle" include a 4- to 7-membered (preferably 5- or 6-membered) monocyclic aromatic heterocycle such as furan, thiophene, pyridine, pyrimidine, pyridazine, pyrazine, pyrrole, imidazole, pyrazole, thiazole, isothiazole, oxazole, isoxazole, oxadiazolyl (e.g., 1,2,4-oxadiazole, 1,3,4-oxadiazole), thiadiazole (e.g., 1,2,4-thiadiazole, 1,3,4-thiadiazole), triazole (e.g., 1,2,4-triazole, 1,2,3-triazole), tetrazole, triazine (e.g., 1,3,5-triazine, 1,2,3-triazine, 1,2,4-triazine) and the like.

Examples of the "monocyclic non-aromatic heterocycle" include a 3- to 10-membered (preferably 5- or 6-membered) monocyclic non-aromatic heterocycle containing, as a ring-constituting atom besides carbon atoms, 1 to 4 heteroatoms selected from an oxygen atom, a sulfur atom and a nitrogen atom.

Examples of the "monocyclic non-aromatic heterocycle" include a 4- to 7-membered (preferably 5- or 6-membered) monocyclic non-aromatic heterocycle such as pyrrolidine, piperidine, morpholine, thiomorpholine, piperazine, hexamethylenimine, oxazolidine, thiazolidine, imidazolidine, oxazoline, thiazoline, imidazoline, dioxole, dioxolane, dihydrooxadiazole (e.g., 4,5-dihydro-1,2,4-oxadiazole), 2-thioxo-1,3-oxazolidine, pyran, tetrahydropyran, thiopyran, tetrahydrothiopyran, 1-oxidetetrahydrothiopyran, 1,1-dioxidetetrahydrothiopyran, tetrahydrofuran, pyrazolidine, pyrazoline, tetrahydropyrimidine, dihydrotriazole, tetrahydrotriazole (e.g., 2,3,4,5-tetrahydro-1H-1,2,3-triazole) and the like.

Examples of the "fused heterocycle" include fused aromatic heterocycle and fused non-aromatic heterocycle.

Examples of the "fused aromatic heterocycle" include a ring wherein a 4- to 7-membered (preferably 5- or 6-membered) monocyclic aromatic heterocycle containing, as a ring-constituting atom besides carbon atoms, 1 to 4 heteroatoms selected from an oxygen atom, a sulfur atom and a nitrogen atom, and 1 or 2 rings selected from a 5- or 6-membered aromatic heterocycle containing 1 or 2 nitrogen atoms, a 5-membered aromatic heterocycle containing one sulfur atom and a benzene ring are condensed and the like.

Examples of the "fused aromatic heterocycle" include quinoline, isoquinoline, quinazoline, quinoxaline, benzofuran, benzothiophene, benzoxazole, benzisoxazole, benzothiazole, benzimidazole, benzotriazole, indole, indazole, pyrrolopyrazine (e.g., 1H-pyrrolo[2,3-b]pyrazine), imidazopyridine (e.g., 3H-imidazo[4,5-b]pyridine, 1H-imidazo[5,4-b]pyridine, 1H-imidazo[4,5-c]pyridine, imidazo[1,2-a]pyridine), imidazopyrazine (e.g., 1H-imidazo[4,5-b]pyrazine, imidazo[1,2-a]pyrazine), imidazopyrimidine (e.g., imidazo[1,2-a]pyrimidine, imidazo[1,2-c]pyrimidine), imidazopyridazine (e.g., imidazo[1,2-b]pyridazine), pyrazolopyridine (e.g., 1H-pyrazolo[4,3-c]pyridine), thienopyrrole (e.g., 4H-thieno[3,2-b]pyrrole), pyrazolothiophene (e.g., 2H-pyrazolo[3,4-b]thiophene), pyrazolotriazine (e.g., pyrazolo[5,1-c][1,2,4]triazine), pyrrolopyridine (e.g., 1H-pyrrolo[1,2-b]pyridine), 1,4-dihydropyrrolo[3,2-b]pyrrole, 4H-furo[3,2-b]pyrrole, 4H-thieno[3,2-b]pyrrole, 1H-furo[2,3-d]imidazole, 1H-thieno[2,3-d]imidazole and the like.

Examples of the "fused non-aromatic heterocycle" include a ring wherein a 4- to 7-membered (preferably 5- or 6-membered) monocyclic non-aromatic heterocycle containing, as a ring-constituting atom besides carbon atoms, 1 to 4 heteroatoms selected from an oxygen atom, a sulfur atom and a nitrogen atom, and 1 or 2 rings selected from a 5- or 6-membered aromatic heterocycle containing 1 or 2 nitrogen atoms, a 5-membered aromatic heterocycle containing one sulfur atom and a benzene ring are condensed, and the like.

Examples of the "fused non-aromatic heterocycle" include dihydroindole (e.g., 1,2-dihydroindole), tetrahydroindole (e.g., 4,5,6,7-tetrahydro-1H-indole), dihydroisoindole, tetrahydroisoindole (e.g., 4,5,6,7-tetrahydroisoindole), dihydrobenzofuran, dihydrobenzodioxine (e.g., 2,3-dihydro-1,4-benzodioxine), dihydrobenzodioxepine (e.g., 3,4-dihydro-2H-1,5-benzodioxepine), tetrahydrobenzimidazole (e.g., 4,5,6,7-tetrahydro-1H-benzimidazole), tetrahydrobenzofuran (e.g., 4,5,6,7-tetrahydrobenzofuran), chromene (e.g., 4H-chromene, 2H-chromene), dihydroquinoline (e.g., 1,2-dihydroquinoline), tetrahydroquinoline (e.g., 1,2,3,4-tetrahydroquinoline), dihydroisoquinoline (e.g., 1,2-dihydroisoquinoline), tetrahydroisoquinoline (e.g., 1,2,3,4-tetrahydroisoquinoline), dihydrophthalazine (e.g., 1,4-dihydrophthalazine), 1,4-dihydrocyclopenta[b]pyrrole, 1,4-dihydrocyclopentaimidazole, 1,4-dihydropyrrolo[2,3-d]imidazole and the like.

Examples of the "5- to 7-membered nitrogen-containing heterocycle" in the present specification include pyrrolidine, piperidine and homopiperidine.

Each symbol in the formulas (I) and (II) is defined in detail in the following.

$R^1$

In the formulas (I) and (II), $R^1$ is a hydrogen atom, an alkyl group optionally having substituent(s), an alkenyl group optionally having substituent(s) or a cycloalkyl group optionally having substituent(s).

Examples of the substituent of the "alkyl group optionally having substituent(s)", "alkenyl group optionally having substituent(s)" and "cycloalkyl group optionally having substituent(s)" for $R^1$ include 1 to 5, preferably 1 to 3 selected from the aforementioned substituent group A. When the number of the substituents is two or more, the respective substituents may be the same or different.

$R^1$ is preferably a hydrogen atom or a $C_{1-6}$ alkyl group optionally having substituent(s), more preferably a $C_{1-6}$ alkyl group (e.g., methyl group, ethyl group, propyl group, isopropyl group, isobutyl group etc.) optionally having 1 to 3 substituents selected from halogen atom(s), a cyano group, a hydroxy group, a $C_{3-10}$ cycloalkyl (e.g., cyclopropyl) and the like, and still more preferably, a $C_{1-6}$ alkyl group (particularly, isobutyl).

$R^2$

In the formula (I), $R^2$ is a halogen atom, a hydroxy group, a cyano (nitrile) group, an amino group optionally having substituent(s), a mercapto group optionally having a substituent (the mercapto group is optionally oxidized), an alkyl group optionally having substituent(s) other than a substituted amino group, an alkoxy group optionally having substituent(s), a 3- to 10-membered cyclic hydrocarbon group optionally having substituent(s), a 3- to 10-membered heterocyclic group optionally having substituent(s), or an acyl group (wherein when the acyl group is —CONR'R", then R' and R" are both hydrogen atoms or form, together with the nitrogen atom bonded thereto, a nitrogen-containing heterocycle optionally having substituent(s)).

The "amino group" of the "amino group optionally having substituent(s)" for $R^2$ optionally has 1 or 2 substituents at substitutable position(s). When the number of the substituents is two, the respective substituents may be the same or different. Examples of the substituent include the aforementioned substituent group B.

The "mercapto group" of the "mercapto group optionally having a substituent" for $R^2$ optionally has a substituent and optionally oxidized by 1 or 2 oxygens. Examples of the substituent include the aforementioned substituent group B.

The "alkyl group" of the "alkyl group optionally having substituent(s) other than a substituted amino group" for $R^2$ optionally has (for example, 1 to 5, preferably 1 to 3) substituent(s) other than a substituted amino group at substitutable position(s). When the number of the substituents is two or more, the respective substituents may be the same or different. Examples of the substituent include substituent group B (except mono- or di-$C_{1-6}$ alkylamino group, $C_{7-16}$ aralkylamino group, $C_{1-6}$ alkoxy-carbonylamino group and $C_{1-6}$ alkyl-carbonylamino group). Examples of the "substituent" of the "substituted amino group" include unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl or acyl (e.g., $C_{1-6}$ cycloalkyl group or $C_{1-6}$ alkyl group substituted by heterocycle) and the like.

The "alkoxy group" of the "alkoxy group optionally having substituent(s)" for $R^2$ optionally has (for example, 1 to 5, preferably 1 to 3) substituent(s). When the number of the substituents is two or more, the respective substituents may be the same or different. Examples of the substituent include the aforementioned substituent group B.

The "cyclic hydrocarbon group" of the "3- to 10-membered cyclic hydrocarbon group optionally having substituent(s)" and the "heterocyclic group" of the "3- to 10-membered heterocyclic group optionally having substituent(s)" for $R^2$ optionally has (for example, 1 to 5, preferably 1 to 3) substituent(s). When the number of the substituents is two or more, the respective substituents may be the same or different. Examples of the substituent include the aforementioned substituent group B.

Examples of the "cyclic hydrocarbon group" of the "3- to 10-membered cyclic hydrocarbon group optionally having substituent(s)" for $R^2$ include those similar to the "3- to 10-membered cyclic hydrocarbon group" of the "3- to 10-membered cyclic hydrocarbon group optionally having substituent(s)" of the aforementioned substituent group A.

Examples of the "heterocyclic group" of the "3- to 10-membered heterocyclic group optionally having substituent(s)" for $R^2$ include those similar to the "heterocyclic group" of the "3- to 10-membered heterocyclic group optionally having substituent(s)" of the aforementioned substituent group A.

When the "acyl group" for $R^2$ is —CO—NR'R", R' and R" are both hydrogen atoms or form, together with the nitrogen atom bonded thereto, a nitrogen-containing heterocycle optionally having substituent(s). Examples of the nitrogen-containing heterocycle include those mentioned above, and morpholine is particularly preferable.

Examples of the substituent of the "nitrogen-containing heterocycle optionally having substituent(s)" formed by R' and R" together with the nitrogen atom bonded thereto include 1 to 5, preferably 1 to 3, selected from the aforementioned substituent group B. When the number of the above-mentioned substituents is two or more, the respective substituents may be the same or different.

$R^2$ is preferably a $C_{1-6}$ alkyl group (e.g., methyl, ethyl, propyl, isopropyl, butyl, isobutyl, pentyl) optionally having substituent(s) other than a substituted amino group, a 3- to 10-membered heterocyclic group optionally having substituent(s) or an acyl group (wherein when the acyl group is —CONR'R", R' and R" are both hydrogen atoms or form, together with the nitrogen atom bonded thereto, a nitrogen-containing heterocycle (e.g., morpholine) optionally having substituent(s)), more preferably (1) a $C_{1-6}$ alkyl group (e.g., methyl, ethyl, propyl, isopropyl, butyl, isobutyl, pentyl) optionally having 1 to 3 substituents selected from
(a) a hydroxy group,
(b) a halogen atom (e.g., fluorine atom),
(c) a $C_{1-6}$ alkoxy group (e.g., methoxy, ethoxy),
(d) a $C_{1-6}$ alkyl-carbonyloxy group (e.g., acetyloxy),
(e) an aromatic heterocyclic group (e.g., pyridyl) optionally having 1 to 3 halogen atoms,
(f) a $C_{3-10}$ cycloalkyl group (e.g., cyclopropyl), and
(g) a cyclic amino group (e.g., pyrrolidinyl, piperidino, morpholino, thiomorpholino, piperazinyl, imidazolidin-1-yl, pyrazolidin-1-yl etc.) optionally having an oxo group,
(2) a 3- to 10-membered heterocyclic group (1,2,4-triazolyl, 1,3,4-oxadiazolyl, 1,2,4-oxadiazolyl, 4,5-dihydro-1,2,4-oxadiazolyl, tetrazolyl, tetrahydropyrimidinyl, oxazolyl, piperidinyl, pyrrolidinyl, hexahydropyrimidinyl) optionally having 1 to 3 substituents selected from a $C_{1-6}$ alkyl group and an oxo group,
(3) a carboxy group,
(4) a $C_{1-6}$ alkoxy-carbonyl group (e.g., methoxycarbonyl, ethoxycarbonyl, propoxycarbonyl, tert-butoxycarbonyl) optionally having 1 to 3 substituents selected from a non-aromatic heterocyclic group (e.g., dioxolyl) optionally having 1 to 3 substituents selected from a $C_{1-6}$ alkyl group (e.g., methyl) and oxo group,
(5) a $C_{1-6}$ alkyl-carbonyl group (e.g., acetyl), or
(6) the formula: —CO—NR'R"
wherein R' and R" are each a hydrogen atom, or R' and R" form, together with the nitrogen atom bonded thereto, a nitrogen-containing heterocycle (e.g., azetidine, morpholine, pyrrolidine, piperidine, 7-aza-bicyclo[2.2.1]heptane, homomorpholine, dihydrobenzoxazin (e.g., 3,4-dihydro-2H-1,4-benzoxazin)) optionally having 1 to 3 substituents selected from halogen atom(s) (e.g., fluorine atom).

$R^3$

In the formula (II), $R^3$ is an alkyl group optionally substituted by group(s) other than a heterospiro ring optionally having substituent(s), an alkenyl group optionally having substituent(s), a cycloalkyl group optionally having substituent(s), an alkylthio group optionally having substituent(s), an alkylsulfinyl group optionally having substituent(s), an alkylsulfonyl group optionally having substituent(s), an alkoxy group optionally having substituent(s), an aryl group optionally having substituent(s) or a heteroaryl group optionally having substituent(s).

Examples of the "heterospiro ring" of the "alkyl group optionally substituted by group(s) other than a heterospiro ring optionally having substituent(s)" for $R^3$ include a Spiro ring formed from a 4- to 7-membered (preferably 5- or 6-membered) monocyclic non-aromatic heterocycle containing, as a ring constituting atom besides carbon atom, 1 to 4 hetero atoms selected from an oxygen atom, a sulfur atom and a nitrogen atom and a $C_{3-10}$ cycloalkane (as the $C_{3-10}$ cycloalkane, a ring corresponding to the above-mentioned $C_{3-10}$ cycloalkyl can be mentioned, which is optionally condensed with a benzene ring), a Spiro ring formed from the monocyclic non-aromatic heterocycles, and the like.

Examples of the "heterospiro ring" include a spiro ring formed from a 4- to 7-membered (preferably 5- or 6-membered) monocyclic non-aromatic heterocycle such as pyrrolidine, piperidine, morpholine, thiomorpholine, piperazine, hexamethylenimine, oxazolidine, thiazolidine, imidazolidine, oxazoline, thiazoline, imidazoline, dioxole (e.g., 1,3-dioxole), dioxolane (e.g., 1,3-dioxolane), dihydrooxadiazole (e.g., 4,5-dihydro-1,2,4-oxadiazole), 2-thioxo-1,3-oxazolidine, pyran, tetrahydropyran, thiopyran, tetrahydrothiopyran, 1-oxidetetrahydrothiopyran, 1,1-dioxidetetrahydrothiopyran, tetrahydrofuran, pyrazolidine, pyrazoline, tetrahydropyrimidine, dihydrotriazole (e.g., 2,3-dihydro-1H-1,2,3-triazole), tetrahydrotriazole (e.g., 2,3,4,5-tetrahydro-1H-1,2,3-triazole) and the like, and a $C_{3-10}$ cycloalkane such as cyclopropane, cyclobutane, cyclopentane, cyclohexane, cycloheptane, cyclooctane and the like or a fused ring (e.g., indane, tetrahydronaphthalene, fluorene etc.) formed from the $C_{3-10}$ cycloalkane and benzene ring; or a spiro ring formed from the monocyclic non-aromatic heterocycles, a Spiro ring formed from pyrrolidine, piperidine, morpholine, thiomorpholine, piperazine and the like and, cyclopropane, cyclobutane, cyclopentane, cyclohexane, indane, tetrahydronaphthalene and the like is preferable.

As the "heterospiro ring", spiro[indane-1,4'-piperidine] and the like can be specifically mentioned.

As the substituent of the "heterospiro ring", 1 to 5, preferably 1 to 3, selected from the aforementioned substituent group A can be mentioned. When the number of the substituents is two or more, the respective substituents may be the same or different.

The "alkyl group" of the "alkyl group optionally substituted by group(s) other than a heterospiro ring optionally having substituent(s)" for $R^3$ optionally has (for example, 1 to 5, preferably 1 to 3) substituent(s) other than the "heterospiro ring optionally having substituent(s)" at substitutable position(s). When the number of the substituents is two or more, the respective substituents may be the same or different. Examples of the substituent include the aforementioned substituent group A.

Examples of the substituent of the "alkenyl group optionally having substituent(s)", "cycloalkyl group optionally having substituent(s)", "alkylthio group optionally having substituent(s)", "alkylsulfinyl group optionally having substituent(s)", "alkylsulfonyl group optionally having substituent(s)", "alkoxy group optionally having substituent(s)", "aryl group optionally having substituent(s)" and "heteroaryl group optionally having substituent(s)" for $R^3$ include 1 to 5, preferably 1 to 3, selected from the aforementioned substituent group A. When the number of the substituents is two or more, the respective substituents may be the same or different.

$R^3$ is preferably a $C_{1-6}$ alkoxy group (e.g., methoxy, ethoxy) optionally having substituent(s), a $C_{1-6}$ alkylthio group (e.g., methylthio) optionally having substituent(s), a $C_{3-10}$ cycloalkyl group (e.g., cyclopropyl) optionally having substituent(s), an aryl (e.g., phenyl) group optionally having substituent(s), or a heteroaryl group (e.g., thienyl) optionally having substituent(s), more preferably, a $C_{1-6}$ alkoxy group (e.g., methoxy, ethoxy) optionally substituted by a $C_{1-6}$ alkoxy group (e.g., methoxy, ethoxy) or a halogen atom (e.g., fluorine atom), a $C_{1-6}$ alkylthio group (e.g., methylthio), a $C_{3-10}$ cycloalkyl group (e.g., cyclopropyl) optionally substituted by a $C_{1-6}$ alkyl group (e.g., methyl), an aryl group (e.g., phenyl) or a heteroaryl group (e.g., thienyl, thiazolyl, pyridyl, pyrazolyl, imidazolyl, 1,3,4-oxadiazolyl, 1,2,4-oxadiazolyl) optionally substituted by a $C_{1-6}$ alkyl group (e.g., methyl), more preferably, a $C_{1-6}$ alkoxy group (e.g., methoxy, ethoxy) optionally having substituent(s).

X

In the formula (I), X is absent or a hydrogen atom, an alkyl group optionally substituted by group(s) other than a heterospiro ring optionally having substituent(s) or a cycloalkyl group optionally having substituent(s).

Examples of the "heterospiro ring optionally having substituent(s)" of the "alkyl group optionally substituted by group(s) other than a heterospiro ring optionally having substituent(s)" for X include those similar to the "heterospiro ring optionally having substituent(s)" of the aforementioned "$C_{1-6}$ alkyl group optionally substituted by group(s) other than a heterospiro ring optionally having substituent(s)" for $R^3$.

The "alkyl group" of the "alkyl group optionally substituted by group(s) other than a heterospiro ring optionally having substituent(s)" for X optionally has (for example, 1 to 5, preferably 1 to 3) substituent(s) other than the heterospiro ring optionally having substituent(s) at substitutable position(s). When the number of the substituents is two or more, the respective substituents may be the same or different. Examples of the substituent include a halogen atom, a hydroxy group, an alkenyl group optionally having substituent(s), an alkynyl group optionally having substituent(s), a cycloalkyl group optionally having substituent(s), a cycloalkyloxy group optionally having substituent(s), an alkylthio group optionally having substituent(s), an alkylsulfinyl group optionally having substituent(s), an alkylsulfonyl group optionally having substituent(s), an alkoxy group optionally having substituent(s), an aryl group optionally having substituent(s), a heteroaryl group optionally having substituent(s), an aryloxy group optionally having substituent(s), and an acyl group.

Examples of the substituent of the "alkenyl group optionally having substituent(s)", "alkynyl group optionally having substituent(s)", "cycloalkyl group optionally having substituent(s)", "cycloalkyloxy group optionally having substituent(s)", "alkylthio group optionally having substituent(s)", "alkylsulfinyl group optionally having substituent(s)", "alkylsulfonyl group optionally having substituent(s)", "alkoxy group optionally having substituent(s)", "aryl group optionally having substituent(s)", "heteroaryl group optionally having substituent(s)" and "aryloxy group optionally having substituent(s)" exemplified as the "substituent" of the "alkyl group optionally substituted by group(s) other than a heterospiro ring optionally having substituent(s)" for X include 1 to 5, preferably 1 to 3, selected from the aforementioned substituent group A. When the number of the substituents is two or more, the respective substituents may be the same or different.

Examples of the substituent of the "cycloalkyl group optionally having substituent(s)" for X include 1 to 5, preferably 1 to 3, selected from the aforementioned substituent group A. When the number of the substituents is two or more, the respective substituents may be the same or different.

X is Preferably (1) a hydrogen atom;

(2) a $C_{1-6}$ alkyl group (e.g., methyl, ethyl, propyl, isopropyl, butyl, hexyl) optionally substituted by 1 to 3 substituents selected from (a) a halogen atom (e.g., fluorine atom), (b) a hydroxy group, (c) a $C_{1-6}$ alkoxy group (e.g., methoxy, ethoxy) optionally having a $C_{1-6}$ alkoxy group (e.g., methoxy) or a halogen atom (e.g., fluorine atom), (d) a $C_{1-6}$ alkylthio group (e.g., methylthio), (e) an aryl group (e.g., phenyl), (f) a aryloxy group (e.g., phenyloxy) optionally having a $C_{1-6}$ alkoxy group (e.g., methoxy) or a halogen atom (e.g., fluorine atom), and (g) a heteroaryl group (e.g., thienyl, thiazolyl); or (3) a $C_{3-10}$ cycloalkyl group (e.g., cyclopropyl), more preferably, a $C_{1-6}$ alkyl group (e.g., methyl, ethyl, propyl, isopropyl, butyl) optionally substituted by a $C_{1-6}$ alkoxy group (e.g., methoxy, ethoxy).

$X^1$

In the formula (II), $X^1$ is a $C_{1-6}$ alkylene group optionally substituted by group(s) other than a heterospiro ring optionally having substituent(s).

Examples of the "heterospiro ring optionally having substituent(s)" of the "$C_{1-6}$ alkylene group optionally substituted by group(s) other than a heterospiro ring optionally having substituent(s)" for $X^1$ include those similar to the "heterospiro ring optionally having substituent(s)" of the aforementioned "$C_{1-6}$ alkyl group optionally substituted by group(s) other than a heterospiro ring optionally having substituent(s)" for $R^3$.

The "$C_{1-6}$ alkylene group" of the "$C_{1-6}$ alkylene group optionally substituted by group(s) other than a heterospiro ring optionally having substituent(s)" for $X^1$ optionally has (for example, 1 to 5, preferably 1 to 3) substituent(s) other than a heterospiro ring optionally having substituent(s) at substitutable position(s). When the number of the substituents is two or more, the respective substituents may be the same or different. Examples of the substituent include the aforementioned substituent group A.

$X^1$ is preferably a "$C_{1-6}$ alkylene group optionally substituted by group(s) other than a heterospiro ring optionally having substituent(s) and an oxo group", more preferably, a $C_{1-6}$ alkylene group (e.g., methylene, ethylene, trimethylene, tetramethylene).

Ring A and Ring $A^1$

In the formula (I), ring A is a heterocycle optionally having substituent(s), and in the formula (II), ring $A^1$ is a fused heterocycle optionally having substituent(s). However, ring A is not

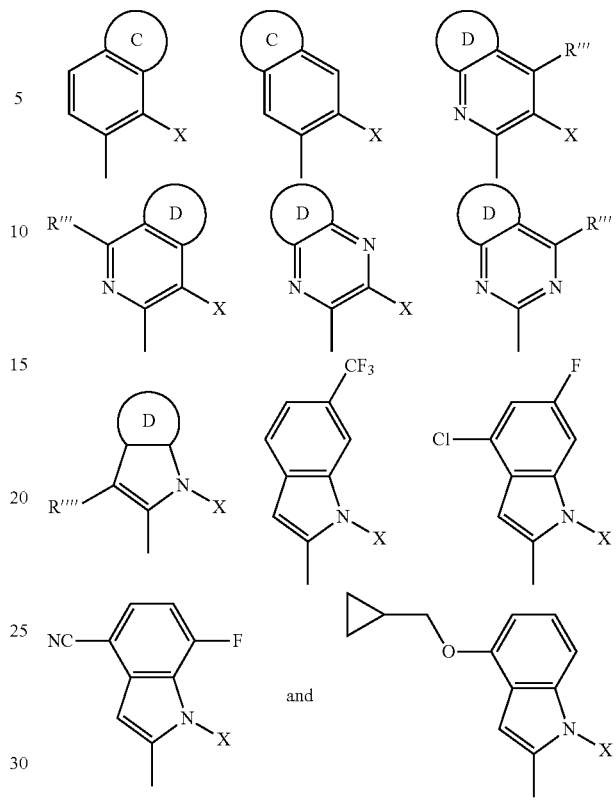

wherein —X is as defined above, ring C is a heterocycle optionally having substituent(s), ring D is a benzene ring optionally having substituent(s), R''' is a substituted alkyl group or a substituted alkoxy group and R'''' is a substituent, and ring $A^1$ is not

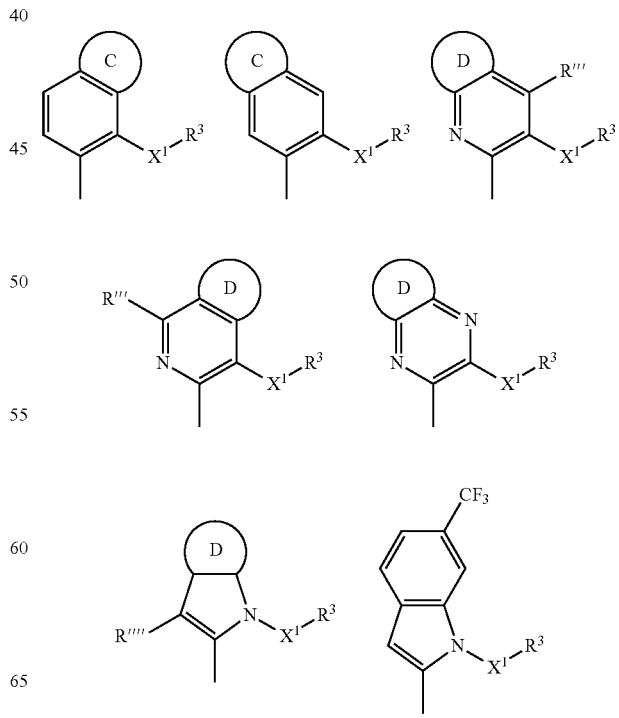

-continued

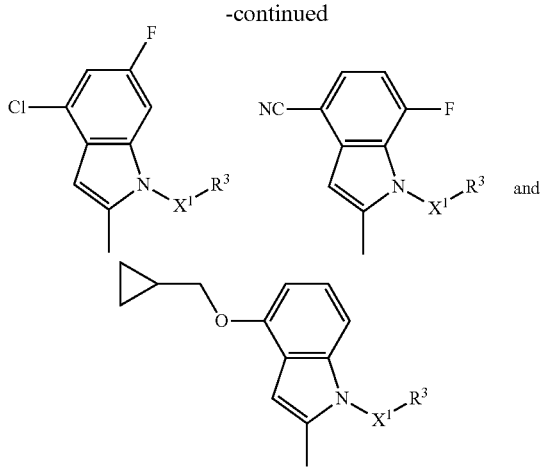

wherein ring C is a heterocycle optionally having substituent(s), ring D is a benzene ring optionally having substituent(s), R''' is a substituted alkyl group or a substituted alkoxy group, R'''' is a substituent, and other symbols are as defined above.

More preferably, the "heterocycle" of the "heterocycle optionally having substituent(s)" for ring A and the "fused heterocycle" of the "fused heterocycle optionally having substituent(s)" for ring $A^1$ are not the following rings.

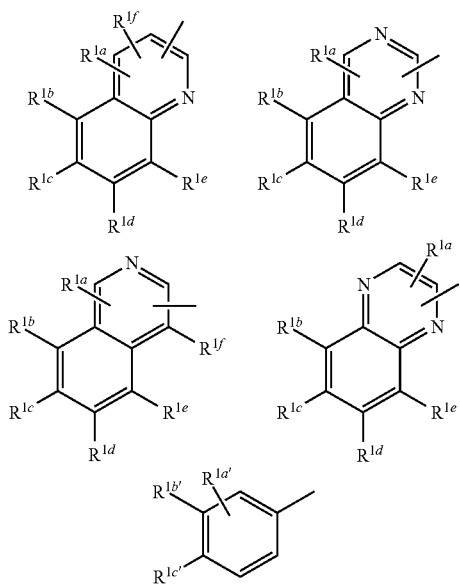

wherein
$R^{1a}$ is an optionally substituted $C_{1-6}$ alkyl group, a $C_{3-6}$ cycloalkoxy group substituted by $C_{1-4}$ alkoxy, an optionally substituted $C_{2-6}$ alkenyl group, an optionally substituted $C_{2-6}$ alkenyloxy group, an optionally substituted $C_{3-6}$ alkynyl group, an optionally substituted $C_{3-6}$ alkynyloxy group, an optionally substituted $C_{1-6}$ alkylsulfinyl group, an optionally substituted $C_{1-6}$ alkylsulfonyl group, an optionally substituted $C_{1-6}$ alkoxy group, an optionally substituted amino group, an optionally substituted aminocarbonyl group, an optionally substituted $C_{1-4}$ alkoxycarbonyl group or an optionally substituted $C_{1-4}$ alkylcarbonyl group;

$R^{1b}$ and $R^{1e}$ are the same or different and each independently is a hydrogen atom, a cyano group, an optionally substituted $C_{1-8}$ alkyl group, an optionally substituted $C_{1-6}$ alkoxy group, an optionally substituted $C_{2-6}$ alkenyl group, $C_{1-6}$ alkylsulfonyl group, or a halogen atom;

$R^{1c}$ and $R^{1d}$ are the same or different and each independently is a hydrogen atom, a halogen atom, a hydroxyl group, a formyl group, a carboxy group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered or 6-membered saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{6-10}$ arylthio group, an optionally substituted $C_{6-10}$ arylsulfinyl group, an optionally substituted $C_{6-10}$ arylsulfonyl group, an optionally substituted $C_{1-6}$ alkoxy group, an optionally substituted $C_{3-6}$ alkynyloxy group, an optionally substituted $C_{3-10}$ cycloalkyloxy group, an optionally substituted $C_{6-10}$ aryloxy group, an optionally substituted $C_{7-14}$ aralkyloxy group, an optionally substituted 5-membered to 10-membered monocyclic or polycyclic heteroaryloxy group, an optionally substituted amino group, an optionally substituted aminocarbonyl group, an optionally substituted aminosulfonyl group, an optionally substituted $C_{1-4}$ alkoxycarbonyl group, an optionally substituted $C_{3-10}$ cycloalkyloxycarbonyl group, an optionally substituted $C_{1-4}$ alkylcarbonyl group, an optionally substituted $C_{3-10}$ cycloalkylcarbonyl group, an optionally substituted $C_{6-10}$ arylcarbonyl group or an optionally substituted 5-membered to 10-membered monocyclic or polycyclic heteroarylcarbonyl group;

$R^{1f}$ is a hydrogen atom, a halogen atom, a cyano group, an optionally substituted $C_{3-6}$ cycloalkyl group, an optionally substituted $C_{2-6}$ alkenyl group, an optionally substituted $C_{2-6}$ alkenyloxy group, an optionally substituted $C_{3-6}$ alkynyl group, an optionally substituted $C_{3-6}$ alkynyloxy group, an optionally substituted $C_{3-10}$ cycloalkyloxy group, an optionally substituted $C_{1-6}$ alkoxy group or an optionally substituted $C_{1-6}$ alkyl group;

$R^{1a'}$ is a hydrogen atom, a halogen atom, a hydroxyl group, a formyl group, a carboxy group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-6}$ cycloalkyl group, a $C_{1-6}$ alkylthio group, $C_{1-6}$ alkylsulfonyl group, a $C_{1-6}$ alkoxy group optionally substituted by a halogen atom, $C_{1-4}$ alkoxy or $C_{3-6}$ cycloalkyl, an optionally substituted $C_{3-6}$ cycloalkoxy group, an optionally substituted amino group, an aminocarbonyl group, a $C_{1-4}$ alkoxycarbonyl group, a $C_{1-4}$ alkylcarbonyl group, an optionally substituted $C_{6-10}$ aryl group, an optionally substituted $C_{6-10}$ aryloxy group or an optionally substituted $C_{7-14}$ aralkyloxy group;

or $R^{1a'}$ is a hydrogen atom; $R^{1b'}$ and $R^{1c'}$ in combination form a fused ring with a benzene ring, which contains at least one hetero atom

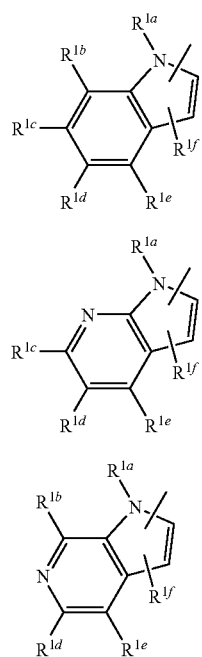

(a)

(b)

(c)

wherein $R^{1a}$ is an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group or an optionally substituted 5-membered to 10-membered monocyclic or polycyclic heteroaryl-$C_{1-4}$ alkyl group;

$R^{1b}$, $R^{1c}$, $R^{1d}$ and $R^{1e}$ are the same or different and each independently is a hydrogen atom, a halogen atom, a hydroxyl group, a formyl group, a carboxy group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group, an optionally substituted saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{6-10}$ arylthio group, an optionally substituted $C_{6-10}$ arylsulfinyl group, an optionally substituted $C_{6-10}$ arylsulfonyl group, an optionally substituted $C_{1-6}$ alkoxy group, an optionally substituted $C_{3-6}$ alkynyloxy group, an optionally substituted $C_{3-6}$ cycloalkyloxy group, an optionally substituted $C_{6-10}$ aryloxy group, an optionally substituted $C_{7-14}$ aralkyloxy group, an optionally substituted 5-membered to 10-membered monocyclic or polycyclic heteroaryloxy group, an optionally substituted 5-membered to 10-membered monocyclic or polycyclic heteroaryl $C_{1-4}$ alkyloxy group, an optionally substituted amino group, an optionally substituted aminocarbonyl group, an optionally substituted aminocarbonyloxy group, an optionally substituted aminosulfonyl group, an optionally substituted $C_{1-6}$ alkoxycarbonyl group, an optionally substituted $C_{3-6}$ cycloalkyloxycarbonyl group, an optionally substituted $C_{1-4}$ alkylcarbonyl group, an optionally substituted $C_{3-6}$ cycloalkylcarbonyl group, an optionally substituted $C_{6-10}$ arylcarbonyl group or an optionally substituted 5-membered to 10-membered monocyclic or polycyclic heteroarylcarbonyl group;

$R^{1f}$ is a hydrogen atom, a halogen atom, a hydroxyl group, a cyano group, an optionally substituted $C_{1-6}$ alkyl group, an optionally substituted $C_{2-6}$ alkenyl group, an optionally substituted $C_{2-6}$ alkynyl group, an optionally substituted $C_{3-10}$ cycloalkyl group, an optionally substituted $C_{5-6}$ cycloalkenyl group, an optionally substituted $C_{6-10}$ aryl group, an optionally substituted $C_{7-14}$ aralkyl group, an optionally substituted 5-membered to 10-membered monocyclic or polycyclic heteroaryl group, an optionally substituted 5-membered to 10-membered monocyclic or polycyclic heteroaryl $C_{1-4}$ alkyl group, an optionally substituted saturated heterocyclic group, an optionally substituted $C_{1-6}$ alkylthio group, an optionally substituted $C_{1-6}$ alkylsulfinyl group, an optionally substituted $C_{1-6}$ alkylsulfonyl group, an optionally substituted $C_{1-6}$ alkoxy group, an optionally substituted $C_{3-6}$ alkynyloxy group, an optionally substituted $C_{3-6}$ cycloalkyloxy group, an optionally substituted $C_{6-10}$ aryloxy group, an optionally substituted $C_{7-14}$ aralkyloxy group, an optionally substituted 5-membered to 10-membered monocyclic or polycyclic heteroaryl $C_{1-4}$ alkyloxy group, an optionally substituted amino group, an optionally substituted aminocarbonyl group, an optionally substituted aminosulfonyl group, an optionally substituted $C_{1-4}$ alkoxycarbonyl group, an optionally substituted $C_{3-6}$ cycloalkyloxycarbonyl group, an optionally substituted $C_{1-4}$ alkylcarbonyl group, an optionally substituted $C_{3-6}$ cycloalkylcarbonyl group, an optionally substituted $C_{6-10}$ arylcarbonyl group or an optionally substituted 5-membered to 10-membered monocyclic or polycyclic heteroarylcarbonyl group.

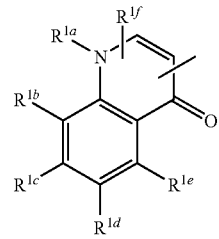

wherein $R^{1a}$ is an optionally substituted $C_{1-6}$ alkyl group, an optionally substituted $C_{2-10}$ alkenyl group, an optionally substituted $C_{2-6}$ alkynyl group, an optionally substituted $C_{3-6}$ cycloalkyl group, an optionally substituted $C_{5-6}$ cycloalkenyl group, an optionally substituted $C_{1-6}$ alkylsulfinyl group, an optionally substituted $C_{1-6}$ alkylsulfonyl group, an optionally substituted aminocarbonyl group, an optionally substituted $C_{1-4}$ alkoxycarbonyl group or an optionally substituted $C_{1-4}$ alkylcarbonyl group;

$R^{1b}$ and $R^{1e}$ are the same or different and each independently is a hydrogen atom, a halogen atom, a cyano group, an optionally substituted $C_{1-6}$ alkyl group, an optionally substituted $C_{1-6}$ alkoxy group, an optionally substituted $C_{3-6}$ cycloalkyloxy group or an optionally substituted aminocarbonyl group;

$R^{1c}$ and $R^{1d}$ are the same or different and each independently is a hydrogen atom, a halogen atom, a hydroxyl group, a formyl group, a carboxy group, a cyano group, an optionally substituted C₁₋₆ alkyl group, an optionally substituted C₂₋₆ alkenyl group, an optionally substituted C₂₋₆ alkynyl group, an optionally substituted C₃₋₁₀ cycloalkyl group, an optionally substituted C₅₋₆ cycloalkenyl group, an optionally substituted C₆₋₁₀ aryl group, an optionally substituted C₇₋₁₄ aralkyl group, an optionally substituted 5-membered to 10-membered monocyclic or polycyclic heteroaryl group, an optionally substituted 5-membered to 10-membered monocyclic or polycyclic heteroaryl C₁₋₄ alkyl group, an optionally substituted saturated heterocyclic group, an optionally substituted C₁₋₆ alkylthio group, an optionally substituted C₁₋₆ alkylsulfinyl group, an optionally substituted C₁₋₆ alkylsulfonyl group, an optionally substituted C₆₋₁₀ arylthio group, an optionally substituted C₆₋₁₀ arylsulfinyl group, an optionally substituted C₆₋₁₀ arylsulfonyl group, an optionally substituted C₁₋₆ alkoxy group, an optionally substituted C₃₋₆ alkynyloxy group, an optionally substituted C₃₋₁₀ cycloalkyloxy group, an optionally substituted C₆₋₁₀ aryloxy group, an optionally substituted C₇₋₁₄ aralkyloxy group, an optionally substituted 5-membered to 10-membered monocyclic or polycyclic heteroaryloxy group, an optionally substituted 5-membered to 10-membered monocyclic or polycyclic heteroaryl C₁₋₄ alkyloxy group, an optionally substituted amino group, an optionally substituted aminocarbonyl group, an optionally substituted aminosulfonyl group, an optionally substituted C₁₋₄ alkoxycarbonyl group, an optionally substituted C₃₋₆ cycloalkyloxycarbonyl group, an optionally substituted C₁₋₄ alkylcarbonyl group, an optionally substituted C₃₋₆ cycloalkylcarbonyl group, an optionally substituted C₆₋₁₀ arylcarbonyl group or an optionally substituted 5-membered to 10-membered monocyclic or polycyclic heteroarylcarbonyl group;

$R^{1f}$ is a hydrogen atom, a halogen atom, a cyano group, an optionally substituted C₁₋₆ alkyl group, an optionally substituted C₁₋₆ alkoxy group, an optionally substituted C₃₋₁₀ cycloalkyl group, an optionally substituted C₂₋₆ alkenyl group, an optionally substituted C₂₋₆ alkenyloxy group, an optionally substituted C₃₋₆ alkynyl group, an optionally substituted C₃₋₆ alkynyloxy group or an optionally substituted C₃₋₁₀ cycloalkyloxy group.

Examples of the substituent of the "heterocycle optionally having substituent(s)" for ring A and the "fused heterocycle optionally having substituent(s)" for ring A¹ include 1 to 5, preferably 1 to 3, selected from the aforementioned substituent group A. When the number of the substituents is two or more, the respective substituents may be the same or different.

Ring A is preferably a monocyclic heterocycle such as pyrimidine, pyrrole, imidazole, pyrazole or triazole(1,2,3-triazole, 1,2,4-triazole) and the like; or a fused heterocycle such as indole, benzimidazole, 1H-pyrrolo[1,2-b]pyridine, 3H-imidazo[4,5-b]pyridine, imidazo[1,2-a]pyridine, 5,6,7,8-tetrahydroimidazo[1,2-a]pyridine, 4,5,6,7-tetrahydro-1H-indole, 4,5,6,7-tetrahydro-1H-benzimidazole, 1,4-dihydrocyclopenta[b]pyrrole, 1,4-dihydropyrrolo[3,2-b]pyrrole, 4H-furo[3,2-b]pyrrole, 4H-thieno[3,2-b]pyrrole, 1,4-dihydrocyclopentaimidazole, 1,4-dihydropyrrolo[2,3-d]imidazole, 1H-furo[2,3-d]imidazole or 1H-thieno[2,3-d]imidazole, imidazo[1,2-a]pyrimidine, imidazo[1,2-a]pyrazine, imidazo[1,2-c]pyrimidine, imidazo[1,2-b]pyridazine, benzofuran, benzothiophene, benzothiazole, quinoline, isoquinoline and the like, each of which optionally has 1 to 5, preferably 1 to 3, substituent(s) selected from substituent group A.

Preferable ring A¹ is a fused heterocycle selected from ring A.

Each of ring A and ring A¹ is more preferably a ring represented by any of the formulas

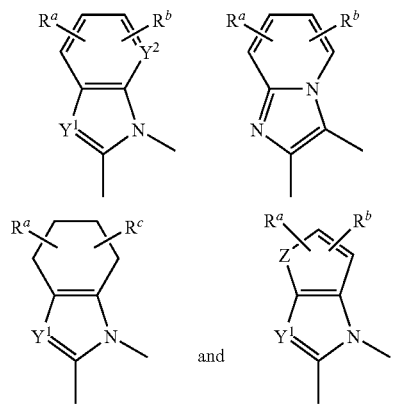

and wherein $R^a$ and $R^b$ are each independently a hydrogen atom, a halogen atom (e.g., fluorine atom, chlorine atom), an alkyl group optionally having substituent(s), an alkoxy group (e.g., methoxy) optionally having substituent(s), or an acyl group (e.g., C₁₋₆ alkoxy-carbonyl) (particularly preferably a hydrogen atom);

$R^c$ is a hydrogen atom, a halogen atom (e.g., fluorine atom, chlorine atom), =O, =S, an alkyl group optionally having substituent(s), an alkoxy (e.g., methoxy) group optionally having substituent(s), or an acyl group (e.g., C₁₋₆ alkoxy-carbonyl);

$Y^1$ and $Y^2$ are each independently CH or N; and

Z is CH₂, NH, O or S, more preferably a ring represented by

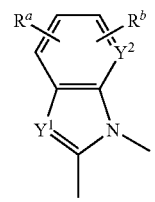

wherein $Y^1$, $Y^2$, $R^a$ and $R^b$ are as defined above.

Examples of the substituent of the "alkyl group optionally having substituent(s)" and "alkoxy group optionally having substituent(s)" for $R^a$, $R^b$ or $R^c$ include 1 to 5, preferably 1 to 3, selected from the aforementioned substituent group B. When the number of the substituents is two or more, the respective substituents may be the same or different.

Each of ring A and ring A¹ is more preferably a ring represented by any of the formulas

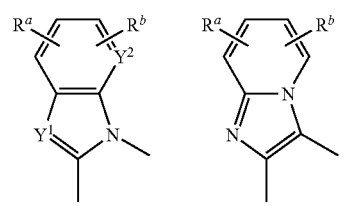

-continued

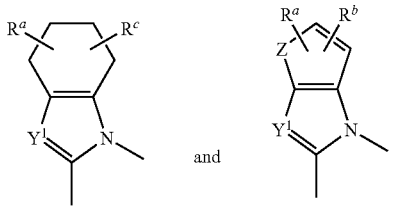 and 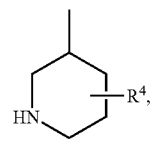

wherein $R^a$ and $R^b$ are each independently a hydrogen atom, a halogen atom (e.g., fluorine atom, chlorine atom), a $C_{1-6}$ alkoxy group (e.g., methoxy), or a $C_{1-6}$ alkoxy-carbonyl group (e.g., methoxycarbonyl) (particularly preferably a hydrogen atom);

$R^c$ is a hydrogen atom or =O;

$Y^1$ and $Y^2$ are each independently CH or N; and

Z is S, more preferably, a ring represented by

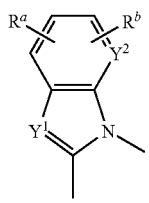

wherein $R^a$ and $R^b$ are each independently a hydrogen atom, a halogen atom (e.g., fluorine atom, chlorine atom), a $C_{1-6}$ alkoxy group (e.g., methoxy), or a $C_{1-6}$ alkoxy-carbonyl group (e.g., methoxycarbonyl) (particularly preferably a hydrogen atom); and $Y^1$ and $Y^2$ are each independently CH or N, more preferably,

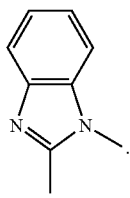

Ring B

In the formula (II), ring B is a 5- to 7-membered nitrogen-containing heterocycle optionally having substituent(s), n is 0, 1 or 2 and NH constituting ring B is unsubstituted.

Examples of the substituent of the "5- to 7-membered nitrogen-containing heterocycle optionally having substituent(s)" for ring B include 1 to 5, preferably 1 to 3, selected from the aforementioned substituent group A or two substituents bonded to the carbon atoms adjacent to ring B may be bonded to form $C_{3-10}$ cycloalkane (e.g., cyclopentane, cyclohexane) to be condensed with ring B. When the number of the substituents is two or more, the respective substituents may be the same or different.

Ring B is preferably a 6-membered (n=1) nitrogen-containing heterocycle optionally having 1 to 5, preferably 1 to 3, substituents selected from substituent group A, more preferably, the formula more preferably, a ring represented by the formula wherein $R^4$ is
a hydrogen atom,
a halogen atom,
a hydroxy group,
a cyano (nitrile) group,
an amino group optionally having substituent(s),
a mercapto group optionally having a substituent (the mercapto group is optionally oxidized)
an alkyl group optionally having substituent(s) other than a substituted amino group,
an alkoxy group optionally having substituent(s),
a 3- to 10-membered cyclic hydrocarbon group optionally having substituent(s),
a 3- to 10-membered heterocyclic group optionally having substituent(s) or
an acyl group (wherein when the acyl group is —CONR'R", then R' and R" are both hydrogen atoms or form, together with the nitrogen atom bonded thereto, a nitrogen-containing heterocycle optionally having substituent(s)).

The "alkyl group" of the "alkyl group optionally having substituent(s) other than a substituted amino group" for $R^4$ optionally has (for example, 1 to 5, preferably 1 to 3) substituent(s) other than the substituted amino group at substitutable position(s). When the number of the substituents is two or more, the respective substituents may be the same or different. Examples of the substituent include substituent group B (except mono- or di-$C_{1-6}$ alkylamino group, $C_{7-16}$ aralkylamino group, $C_{1-6}$ alkoxy-carbonylamino group and $C_{1-6}$ alkyl-carbonylamino group). Examples of the "substituent" of the "substituted amino group" include unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl or acyl (e.g., $C_{1-6}$ alkyl group substituted by $C_{1-6}$ cycloalkyl group or heterocycle) and the like.

Examples of the substituent of the "alkoxy group optionally having substituent(s)", "3- to 10-membered cyclic hydrocarbon group optionally having substituent(s)" and "3- to 10-membered heterocyclic group optionally having substituent(s)" for $R^4$ include 1 to 5, preferably 1 to 3, selected from the aforementioned substituent group B. When the number of the substituents is two or more, the respective substituents may be the same or different.

Examples of the "substituent" of the "amino group optionally having substituent(s)" for $R^4$ include 1 or 2 selected from the aforementioned substituent group B. When the number of the substituents is two, the respective substituents may be the same or different.

Examples of the "substituent" of the "mercapto group optionally having a substituent" for $R^4$ include the aforementioned substituent group B. The mercapto group may be oxidized by 1 or 2 oxygens.

Examples of the substituent of the "nitrogen-containing heterocycle optionally having substituent(s)" formed by R' and R", together with the nitrogen atom include 1 to 5, preferably 1 to 3, selected from the aforementioned substituent group B. When the number of the above-mentioned substituents is two or more, the respective substituents may be the same or different.

Ring B is more preferably a ring represented by the formula

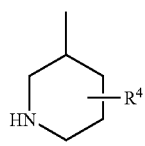

wherein $R^4$ is
a hydrogen atom,
a halogen atom,
a hydroxy group,
a cyano (nitrile) group,
an amino group optionally having 1 or 2 substituents selected from the substituent group B,
a mercapto group optionally having a substituent selected from the substituent group B (the mercapto group is optionally oxidized)
a $C_{1-6}$ alkyl group optionally having 1 or 2 substituents selected from the substituent group B,
a $C_{1-6}$ alkoxy group optionally having a substituent selected from the substituent group B,
a 3- to 10-membered cyclic hydrocarbon group optionally having 1 to 3 substituents selected from the substituent group B,
a 3- to 10-membered heterocyclic group optionally having 1 to 3 substituents selected from the substituent group B,
a carboxy group,
a $C_{1-6}$ alkoxy-carbonyl group (e.g., methoxycarbonyl, ethoxycarbonyl, propoxycarbonyl, tert-butoxycarbonyl) optionally having 1 to 3 substituents selected from the substituent group B, or
a group represented by the formula: —CONR'R"
wherein R' and R" are each a hydrogen atom, or R' and R" form, together with the nitrogen atom bonded thereto, a nitrogen-containing heterocycle optionally having 1 to 3 substituents selected from the aforementioned substituent group B.

Ring B is more preferably a ring represented by

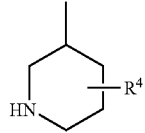

wherein $R^4$ is
(1) a hydrogen atom,
(2) a cyano (nitrile) group,
(3) a $C_{1-6}$ alkyl group (e.g., methyl, ethyl, propyl, isopropyl, butyl, isobutyl, pentyl) optionally having 1 to 3 substituents selected from (a) a hydroxy group,
(b) a $C_{1-6}$ alkoxy group (e.g., methoxy, ethoxy),
(c) a $C_{1-6}$ alkyl-carbonyloxy group (e.g., acetyloxy),
(d) an aromatic heterocyclic group (e.g., pyridyl, pyrazolyl, triazolyl) optionally having 1 to 3 halogen atoms,
(e) a $C_{3-10}$ cycloalkyl group (e.g., cyclopropyl), and
(f) a cyclic amino group (e.g., pyrrolidinyl, piperidino, morpholino, thiomorpholino, piperazinyl, imidazolidin-1-yl, pyrazolidin-1-yl etc.) optionally having an oxo group,
(4) a 3- to 10-membered heterocyclic group (1,2,4-triazolyl, 1,3,4-oxadiazolyl, 1,2,4-oxadiazolyl, 4,5-dihydro-1,2,4-oxadiazolyl, tetrazolyl, tetrahydropyrimidinyl, oxazolyl, piperidinyl, pyrrolidinyl, hexahydropyrimidinyl) optionally having 1 to 3 substituents selected from a $C_{1-6}$ alkyl group and an oxo group,
(5) a carboxy group,
(6) a $C_{1-6}$ alkoxy-carbonyl group (e.g., methoxycarbonyl, ethoxycarbonyl, propoxycarbonyl, tert-butoxycarbonyl) optionally having 1 to 3 substituents selected from a non-aromatic heterocyclic group (e.g., dioxolyl) optionally having 1 to 3 substituents selected from a $C_{1-6}$ alkyl group (e.g., methyl) and oxo group, or
(7) a group represented by the formula: —CO—NR'R"
wherein R' and R" are each a hydrogen atom, or form, together with the nitrogen atom bonded thereto, a nitrogen-containing heterocycle (e.g., azetidine, morpholine, pyrrolidine, piperidine, 7-aza-bicyclo[2.2.1]heptane, homomorpholine, dihydrobenzoxazine (e.g., 3,4-dihydro-2H-1,4-benzoxazine)) optionally having 1 to 3 substituents selected from halogen atom(s) (e.g., fluorine atom).

Preferable examples of compound (I) include the following.

[Compound I-1]
A compound represented by the formula (I) wherein ring A is a ring represented by

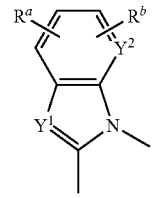

wherein $R^a$ and $R^b$ are each independently a hydrogen atom, a halogen atom, an alkyl group optionally having substituent(s), an alkoxy group optionally having substituent(s) or an acyl group (particularly preferably a hydrogen atom);
$Y^1$ and $Y^2$ are each independently CH or N,
$R^1$ is a $C_{1-6}$ alkyl group optionally having substituent(s),
$R^2$ is a $C_{1-6}$ alkyl group (e.g., methyl, ethyl, propyl, isopropyl, butyl, isobutyl, pentyl) optionally having substituent(s) other than a substituted amino group or an acyl group (wherein when the acyl group is —CONR'R", then R' and R" are both hydrogen atoms or form, together with the nitrogen atom bonded thereto, a nitrogen-containing heterocycle (e.g., morpholine) optionally having substituent (s)), and
X is a $C_{1-6}$ alkyl group optionally substituted by an alkoxy group (e.g., methoxy, ethoxy), or a salt thereof.

Here, examples of the substituent of the "$C_{1-6}$ alkyl group optionally having substituent(s)" for $R^1$ include 1 to 5, preferably 1 to 3, selected from the aforementioned substituent group A.

Examples of the substituent of the "$C_{1-6}$ alkyl group optionally having substituent(s)" and "$C_{1-6}$ alkoxy group optionally having substituent(s)" for $R^a$ or $R^b$ include 1 to 5, preferably 1 to 3, selected from the aforementioned substituent group B.

Examples of the substituent of the "$C_{1-6}$ alkyl group optionally having substituent(s) other than a substituted amino group" for $R^2$ include 1 to 5, preferably 1 to 3, selected from the aforementioned substituent group B.

Examples of the substituent of the "nitrogen-containing heterocycle optionally having substituent(s)" formed by R' and R" together with the nitrogen atom bonded thereto include 1 to 5, preferably 1 to 3, selected from the aforementioned substituent group B. When the number of the above-mentioned substituents is two or more, the respective substituents may be the same or different.

[Compound I-2]

A compound represented by the formula (II) wherein ring $A^1$ is a ring represented by

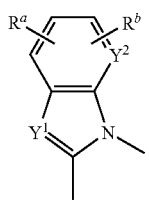

wherein $R^a$ and $R^b$ are each independently a hydrogen atom, a halogen atom, an alkyl group optionally having substituent(s), an alkoxy group optionally having substituent(s), or an acyl group (particularly preferably a hydrogen atom);
$Y^1$ and $Y^2$ are each independently CH or N,
Ring B is a Ring Represented by

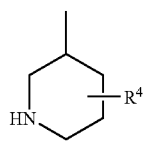

wherein $R^4$ is
a hydrogen atom,
a halogen atom,
a hydroxy group,
a cyano (nitrile) group,
an amino group optionally having substituent(s),
a mercapto group optionally having a substituent (the mercapto group is optionally oxidized),
an alkyl group optionally having substituent(s),
an alkoxy group optionally having substituent(s),
a 3- to 10-membered cyclic hydrocarbon group optionally having substituent(s),
a 3- to 10-membered heterocyclic group optionally having substituent(s), or
an acyl group,
$R^1$ is a $C_{1-6}$ alkyl group optionally having substituent(s),
$R^3$ is a $C_{1-6}$ alkoxy group optionally having substituent(s), and
$X^1$ is a $C_{1-6}$ alkylene group, or a salt thereof.

Here, examples of the substituent of the "$C_{1-6}$ alkyl group optionally having substituent(s)" for $R^1$ and the "$C_{1-6}$ alkoxy group optionally having substituent(s)" for $R^3$ include 1 to 5, preferably 1 to 3, selected from the aforementioned substituent group A.

Examples of the substituent of the "$C_{1-6}$ alkyl group optionally having substituent(s)" and "$C_{1-6}$ alkoxy group optionally having substituent(s)" for $R^a$ or $R^b$ include 1 to 5, preferably 1 to 3, selected from the aforementioned substituent group B.

Examples of the substituent of the "$C_{1-6}$ alkyl group optionally having substituent(s)", "$C_{1-6}$ alkoxy group optionally having substituent(s)", "3- to 10-membered cyclic hydrocarbon group optionally having substituent(s)" and "3- to 10-membered heterocyclic group optionally having substituent(s)" for $R^4$ include 1 to 5, preferably 1 to 3, selected from the aforementioned substituent group B. When the number of the above-mentioned substituents is two or more, the respective substituents may be the same or different.

Examples of the "substituent" of the "amino group optionally having substituent(s)" for $R^4$ include 1 or 2 selected from the aforementioned substituent group B. When the number of the above-mentioned substituents is two, the respective substituents may be the same or different.

Examples of the "substituent" of the "mercapto group optionally having a substituent" for $R^4$ include the aforementioned substituent group B. The mercapto group may be oxidized by 1 or 2 oxygens.

[Compound I-3]

A compound represented by the formula (II) wherein ring $A^1$ is a ring represented by

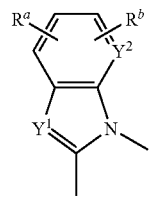

wherein $R^a$ and $R^b$ are each independently a hydrogen atom, a halogen atom, an alkyl group optionally having substituent(s), an alkoxy group optionally having substituent(s) or an acyl group (particularly preferably a hydrogen atom);
$Y^1$ and $Y^2$ are each independently CH or N,
Ring B is a Ring Represented by

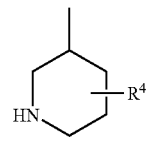

wherein $R^4$ is
a hydrogen atom,
a halogen atom,
m a hydroxy group,
a cyano (nitrile) group,
an amino group optionally having substituent(s),
a mercapto group optionally having a substituent (the mercapto group is optionally oxidized),
an alkyl group optionally having substituent(s) other than a substituted amino group,
an alkoxy group optionally having substituent(s), a 3- to 10-membered cyclic hydrocarbon group optionally having substituent(s), a 3- to 10-membered heterocyclic group optionally having substituent(s), or an acyl group (wherein when the acyl group is —CONR'R", then R' and R" are both hydrogen atoms or form, together with the nitrogen atom bonded thereto, a nitrogen-containing heterocycle optionally having substituent(s)), $R^1$ is a $C_{1-6}$ alkyl group optionally having substituent(s), $R^3$ is a $C_{1-6}$ alkoxy group optionally having substituent(s), and $X^1$ is a $C_{1-6}$ alkylene group, or a salt thereof.

Here, Examples of the substituent of the "$C_{1-6}$ alkyl group optionally having substituent(s)" for $R^1$ and the "$C_{1-6}$ alkoxy group optionally having substituent(s)" for $R^3$ include 1 to 5, preferably 1 to 3, selected from the aforementioned substituent group A.

Examples of the substituent of the "$C_{1-6}$ alkyl group optionally having substituent(s)" and "$C_{1-6}$ alkoxy group optionally having substituent(s)" for $R^a$ or $R^b$ include 1 to 5, preferably 1 to 3, selected from the aforementioned substituent group B.

Examples of the substituent of the "$C_{1-6}$ alkyl group optionally having substituent(s) other than a substituted amino group", "$C_{1-6}$ alkoxy group optionally having substituent(s)", "3- to 10-membered cyclic hydrocarbon group optionally having substituent(s)" and "3- to 10-membered heterocyclic group optionally having substituent(s)" for $R^4$ include 1 to 5, preferably 1 to 3, selected from the aforementioned substituent group B.

Examples of the substituent of the "nitrogen-containing heterocycle optionally having substituent(s)" formed by R' and R" together with the nitrogen atom bonded thereto include 1 to 5, preferably 1 to 3, selected from the aforementioned substituent group B. When the number of the above-mentioned substituents is two or more, the respective substituents may be the same or different.

Examples of the "substituent" of the "amino group optionally having substituent(s)" for $R^4$ include 1 or 2 selected from the aforementioned substituent group B. When the number of the above-mentioned substituents is two, the respective substituents may be the same or different.

Examples of the "substituent" of the "mercapto group optionally having a substituent" for $R^4$ include the aforementioned substituent group B. The mercapto group may be oxidized by 1 or 2 oxygens.

[Compound I-4]

A compound represented by the formula (II) wherein ring $A^1$ is a ring represented by any one of

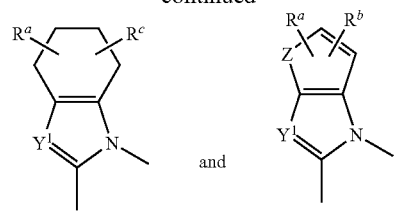

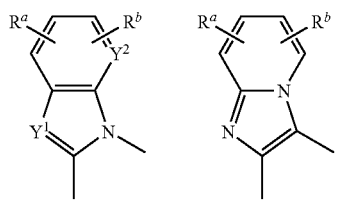

wherein $R^a$ and $R^b$ are each independently a hydrogen atom, a halogen atom (e.g., fluorine atom, chlorine atom), a $C_{1-6}$ alkoxy group (e.g., methoxy), or $C_{1-6}$ alkoxy-carbonyl group (e.g., methoxycarbonyl) (particularly preferably a hydrogen atom);

$R^c$ is a hydrogen atom, or =O;

$Y^1$ and $Y^2$ are each independently CH or N;

Z is S,

Ring B is a Ring Represented by

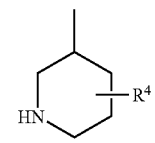

wherein $R^4$ is (1) a hydrogen atom, (2) a cyano (nitrile) group, (3) a $C_{1-6}$ alkyl group (e.g., methyl, ethyl, propyl, isopropyl, butyl, isobutyl, pentyl) optionally having 1 to 3 substituents selected from (a) a hydroxy group, (b) a $C_{1-6}$ alkoxy group (e.g., methoxy, ethoxy), (c) a $C_{1-6}$ alkyl-carbonyloxy group (e.g., acetyloxy), (d) an aromatic heterocyclic group (e.g., pyridyl, pyrazolyl, triazolyl) optionally having 1 to 3 halogen atoms, (e) a $C_{3-10}$ cycloalkyl group (e.g., cyclopropyl), and (f) a cyclic amino group (e.g., pyrrolidinyl, piperidino, morpholino, thiomorpholino, piperazinyl, imidazolidin-1-yl, pyrazolidin-1-yl etc.) optionally having an oxo group, (4) a 3- to 10-membered heterocyclic group (1,2,4-triazolyl, 1,3,4-oxadiazolyl, 1,2,4-oxadiazolyl, 4,5-dihydro-1,2,4-oxadiazolyl, tetrazolyl, tetrahydropyrimidinyl, oxazolyl, piperidinyl, pyrrolidinyl, hexahydropyrimidinyl) optionally having 1 to 3 substituents selected from a $C_{1-6}$ alkyl group and an oxo group, (5) a carboxy group, (6) a $C_{1-6}$ alkoxy-carbonyl group (e.g., methoxycarbonyl, ethoxycarbonyl, propoxycarbonyl, tert-butoxycarbonyl) optionally having 1 to 3 substituents selected from a non-aromatic heterocyclic group (e.g., dioxolyl) optionally having 1 to 3 substituents selected from a $C_{1-6}$ alkyl group (e.g., methyl) and oxo group or (7) a group represented by the formula: —CO—NR'R" wherein R' and R" are each a hydrogen atom, or R' and R" form, together with the nitrogen atom bonded thereto, a nitrogen-containing heterocycle (e.g., azetidine, morpholine, pyrrolidine, piperidine, 7-aza-bicyclo[2.2.1]heptane, homomorpholine, dihydrobenzoxazin (e.g., 3,4-dihydro-2H-1,4-benzoxazin)) optionally having 1 to 3 substituents selected from halogen atom(s) (e.g., fluorine atom), $R^3$ is a $C_{1-6}$ alkoxy group (e.g., methoxy, ethoxy) optionally substituted by a $C_{1-6}$ alkoxy group (e.g., methoxy, ethoxy) or a halogen atom (e.g., fluorine atom), a $C_{1-6}$ alkylthio group (e.g., methylthio), a $C_{3-10}$ cycloalkyl group (e.g., cyclopropyl) optionally substituted by a $C_{1-6}$ alkyl group (e.g., methyl), an aryl group (e.g., phenyl) or a heteroaryl group (e.g., thienyl, thiazolyl, pyridyl, pyrazolyl, imidazolyl, 1,3,4-oxadiazolyl, 1,2,4-oxadiazolyl) optionally substituted by a $C_{1-6}$ alkyl group (e.g., methyl), and $X^1$ is a $C_{1-6}$ alkylene group (e.g., methylene, ethylene, trimethylene, tetramethylene), or a salt thereof.

[Compound I-5]

A compound represented by the formula (I) wherein ring A is a pyrimidine optionally having substituent(s), a pyrrole optionally having substituent(s), an imidazole optionally having substituent(s), a pyrazole optionally having substituent(s) or a triazole (e.g., 1,2,3-triazole, 1,2,4-triazole) optionally having substituent(s), $R^2$ is (1) a $C_{1-6}$ alkyl group (e.g., methyl, ethyl, propyl, isopropyl, butyl, isobutyl, pentyl) optionally having 1 to 3 substituents selected from
(a) a hydroxy group,
(b) a halogen atom (e.g., fluorine atom),
(c) a $C_{1-6}$ alkoxy group (e.g., methoxy, ethoxy),
(d) a $C_{1-6}$ alkyl-carbonyloxy group (e.g., acetyloxy),
(e) an aromatic heterocyclic group (e.g., pyridyl) optionally having 1 to 3 halogen atoms,
(f) a $C_{3-10}$ cycloalkyl group (e.g., cyclopropyl), and
(g) a cyclic amino group (e.g., pyrrolidinyl, piperidino, morpholino, thiomorpholino, piperazinyl, imidazolidin-1-yl, pyrazolidin-1-yl etc.) optionally having an oxo group, (2) a 3- to 10-membered heterocyclic group (1,2,4-triazolyl, 1,3,4-oxadiazolyl, 1,2,4-oxadiazolyl, 4,5-dihydro-1,2,4-oxadiazolyl, tetrazolyl, tetrahydropyrimidinyl, oxazolyl, piperidinyl, pyrrolidinyl, hexahydropyrimidinyl) optionally as having 1 to 3 substituents selected from a $C_{1-6}$ alkyl group and an oxo group, (3) a carboxy group, (4) a $C_{1-6}$ alkoxy-carbonyl group (e.g., methoxycarbonyl, ethoxycarbonyl, propoxycarbonyl, tert-butoxycarbonyl) optionally having 1 to 3 substituents selected from a non-aromatic heterocyclic group (e.g., dioxolyl) optionally having 1 to 3 substituents selected from a $C_{1-6}$ alkyl group (e.g., methyl) and oxo group, (5) a $C_{1-6}$ alkyl-carbonyl group (e.g., acetyl), or (6) a group represented by the formula: —CO—NR'R" wherein R' and R" are each a hydrogen atom, or R' and R" form, together with the nitrogen atom bonded thereto, a nitrogen-containing heterocycle (e.g., azetidine, morpholine, pyrrolidine, piperidine, 7-aza-bicyclo[2.2.1] heptane, homomorpholine, dihydrobenzoxazin (e.g., 3,4-dihydro-2H-1,4-benzoxazin)) optionally having 1 to 3 substituents selected from halogen atom(s) (e.g., fluorine atom), $R^1$ is a $C_{1-6}$ alkyl group (e.g., isobutyl), and X is (1) a hydrogen atom;

(2) a $C_{1-6}$ alkyl group (e.g., methyl, ethyl, propyl, isopropyl, butyl, hexyl) optionally substituted by 1 to 3 substituents selected from
(a) a halogen atom (e.g., fluorine atom),
(b) a hydroxy group,
(c) a $C_{1-6}$ alkoxy group (e.g., methoxy, ethoxy) optionally having a $C_{1-6}$ alkoxy group (e.g., methoxy) or a halogen atom (e.g., fluorine atom),
(d) a $C_{1-6}$ alkylthio group (e.g., methylthio),
(e) an aryl group (e.g., phenyl),
(f) an aryloxy group (e.g., phenyloxy) optionally having a $C_{1-6}$ alkoxy group (e.g., methoxy) or a halogen atom (e.g., fluorine atom), and
(g) a heteroaryl group (e.g., thienyl, thiazolyl); or (3) a $C_{3-10}$ cycloalkyl group (e.g., cyclopropyl), or a salt thereof.

Here, examples of the substituent of the "pyrimidine" of "pyrimidine optionally having substituent(s)", "pyrrole" of "pyrrole optionally having substituent(s)", "imidazole" of "imidazole optionally having substituent(s)", "pyrazole" of "pyrazole optionally having substituent(s)" and "triazole" of "triazole optionally having substituent(s)" for ring A include 1 to 3 selected from the aforementioned substituent group A.

[Compound I-6]

A compound represented by the formula (I) wherein $R^1$ is a $C_{1-6}$ alkyl-group optionally having substituent(s); $R^2$ is an acyl group (wherein when the acyl group is —CONR'R", then R' and R" are both hydrogen atoms or form, together with the nitrogen atom bonded thereto, a nitrogen-containing heterocycle optionally having substituent(s)); ring A is a ring represented by the formula

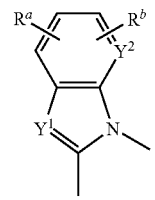

wherein $R^a$ and $R^b$ are each a hydrogen atom; and $Y^1$ and $Y^2$ are each independently CH or N, and X is a $C_{1-6}$ alkyl group optionally substituted by a $C_{1-6}$ alkoxy group, or a salt thereof.

[Compound I-7]

A compound represented by the formula (II) wherein $R^1$ is a $C_{1-6}$ alkyl group optionally having substituent(s), $R^3$ is a $C_{1-6}$ alkoxy group optionally having substituent(s), ring $A^1$ is a ring represented by the formula

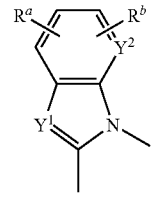

wherein $R^a$ and $R^b$ are each a hydrogen atom; and $Y^1$ and $Y^2$ are each independently CH or N, $X^1$ is a $C_{1-6}$ alkylene group, and Ring B is

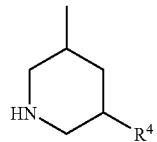

wherein $R^4$ is —CO—NR'R" wherein R' and R" are each a hydrogen atom, or R' and R" form, together with the nitrogen atom bonded thereto, a nitrogen-containing heterocycle optionally having 1 to 3 substituents selected from halogen atom(s), or a salt thereof.

Examples of the salts of compound (I) and compound (II) include metal salts, ammonium salts, salts with organic bases, salts with inorganic acids, salts with organic acids, salts with basic or acidic amino acids, and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N-dibenzylethylenediamine or the like.

Preferable examples of the salt with inorganic acid include a salt with hydrochloric acid, hydrobromic acid, nitric acid, sulfuric acid, phosphoric acid or the like.

Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid or the like.

Preferable examples of the salt with basic amino acid include a salt with arginine, lysine, ornithine or the like.

Preferable examples of the salt with acidic amino acid include a salt with aspartic acid, glutamic acid or the like.

Of these, a pharmaceutically acceptable salt is preferable. When the compound has an acidic functional group, examples thereof include inorganic salts such as alkali metal salts (e.g., sodium salt, potassium salt, etc.), alkaline earth metal salts (e.g., calcium salt, magnesium salt, barium salt, etc.) and the like, ammonium salts, and the like. When the compound has a basic functional group, examples thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

The production methods of compound (I) and compound (II) are shown in the following.

Compound (I) compound (II) are obtained by, for example, methods shown in the following reaction schemes or a method analogous thereto, or the like.

Each of compounds (II)-(XXXXI) shown in the reaction schemes may form a salt. Examples of the salt include salts similar to the salts of compound (I) and compound (II).

The compound obtained in each step can also be used for the next reaction directly as the reaction mixture or as a crude product. In addition, it can also be isolated from the reaction mixture according to a conventional method, and can be isolated and purified by a known method such as phase transfer, concentration, solvent extraction, fractional distillation, pH conversion, crystallization, recrystallization, chromatography and the like.

The reaction schemes thereof are shown in the following.

Each symbol of the compounds in the schemes is as defined above. R is a $C_{1-4}$ alkyl group, E is a carboxyl group, an alkali metal salt of carboxyl group, a chlorocarbonyl group, an acid anhydride, a trichloromethyl group, a trichloromethylcarbonyl group or an ester group, Q is a hydrogen atom or an alkali metal atom, W is a hydrogen atom or any substituent, V is a hydrogen atom, an alkyl group or an alkali metal atom, LG is a leaving group (e.g., chloro group, bromo group, iodo group, methanesulfonate group etc.) or a hydroxyl group, and PG is an N-protecting group (e.g., benzyl group, tert-butoxycarbonyl group, benzyloxycarbonyl group etc.).

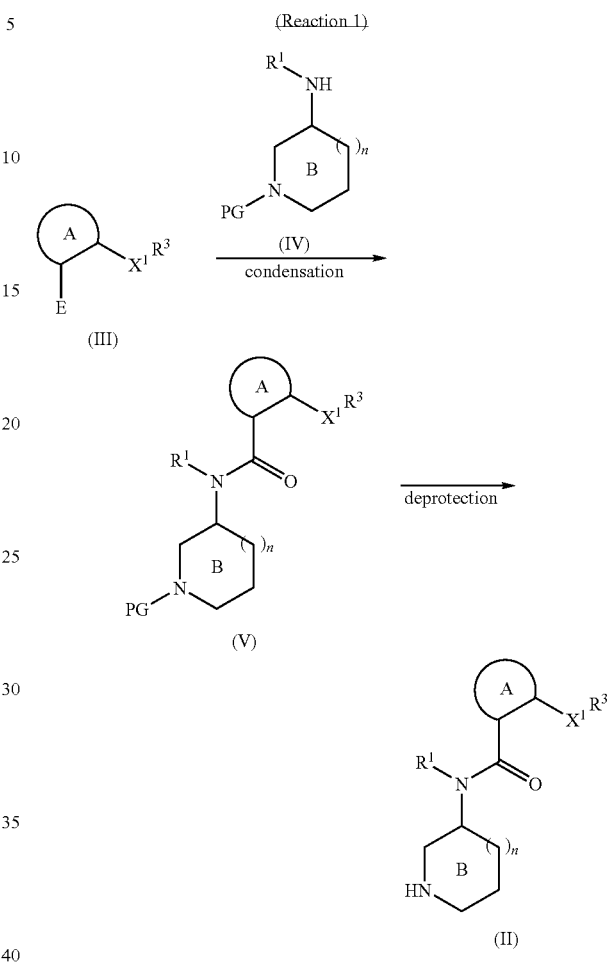

Compound (V) can be produced by a condensation reaction of compound (III) and compound (IV).

Compound (III) can be produced according to a method known per se, for example, the method described in Bioorganic and Medicinal Chemistry (Bioorg. Med. Chem.), 2001, vol. 9, page 1045-1057 and the like, or a method analogous thereto.

Compound (IV) may be a commercially available product, or can be produced according to a method known per se, for example, the method described in Bioorganic and Medicinal Chemistry Letters (Bioorg. Med. Chem. Lett.), 2005, vol. 15, page 833-838 or EP1757582 and the like, or a method analogous thereto.

When E is a carboxyl group, the condensation reaction is performed according to a conventional peptide synthesis technique, for example, an acid chloride method, an acid anhydride method, a mixed anhydride method, a method of using N,N'-dicyclohexylcarbodiimide (DCC), an active ester method, a method of using N,N'-carbonyldiimidazole (CDI), a method of using diethyl cyanophosphate (DEPC), a method of using N-ethyl-N'-(3-dimethylaminopropyl)carbodiimide hydrochloride (WSC•HCl) and 1-hydroxybenzotriazole (HOBt), or the like. Compound (IV) is used in a proportion of about 1 to 2 mol, preferably about 1.0 to 1.1 mol, per 1 mol of compound (III). The reagent used in the above-mentioned method is used in a proportion of about 1 mol to large excess, preferably about 1.1 to 5 mol, per 1 mol of compound (III). The reaction temperature is generally −10 to 80° C., preferably 0 to 30° C.

When E is an alkali metal salt of a carboxyl group, the condensation reaction is advantageously performed according to a method using WSC•HCl and HOBt. Compound (IV) is used in an amount of about 1 to 2 mol, preferably about 1.0 to 1.1 mol, per 1 mol of compound (III). WSC•HCl is used in an amount of about 1 to 4 mol, preferably about 1.5 to 2.5 mol, per 1 mol of compound (III). HOBt is used in an amount of about 1 to 8 mol, preferably about 2.5 to 5.0 mol, per 1 mol of compound (III). The reaction temperature is generally −10 to 100° C., preferably 40 to 70° C.

In both cases, the condensation reaction is preferably performed in a solvent. Examples of the usable solvent include halogenated hydrocarbons such as dichloromethane, chloroform, carbon tetrachloride, 1,2-dichloroethane and the like, ethers such as diethyl ether, tetrahydrofuran, dioxane and the like, amides such as N,N-dimethylformamide, N,N-dimethylacetamide and the like, dimethyl sulfoxide, pyridine, acetonitrile and a mixed solvent thereof.

While the reaction time varies depending on the reagent or solvent to be used, it is generally 30 min to 3 days, preferably 30 min to 15 hr.

Compound (V) can also be produced by further carrying out the above-mentioned reaction in combination with one or more of known hydrolysis reaction, acylation reaction, alkylation reaction, amination reaction, oxidation-reduction reaction, cyclization reaction, carbon chain extension reaction, substituent exchange reaction and the like, as desired.

Compound (II) can be produced by removing the N-protecting group PG of compound (VI). In addition, in each of the aforementioned reactions, when the starting compound has an amino group, a carboxyl group or a hydroxy group as a substituent, a protecting group generally used in peptide chemistry and the like may be introduced into these groups. By removing the protecting group as necessary after the reaction, the objective compound can be obtained. Introduction or removal of these protective groups may be carried out according to a method known per se, for example, the method disclosed in Theodora W. Greene and Peter G. M. Wuts, "Protective Groups in Organic Synthesis, 3$^{rd}$ Ed.", Wiley-Interscience (1999), or the like.

Examples of the amino-protecting group include formyl group; $C_{1-6}$ alkyl-carbonyl group, phenylcarbonyl group, $C_{1-6}$ alkoxy-carbonyl group, allyloxycarbonyl (Alloc) group, phenyloxycarbonyl group, fluorenylmethyloxycarbonyl (Fmoc) group, $C_{7-10}$ aralkyl-carbonyl group (e.g., benzylcarbonyl etc.), $C_{7-10}$ aralkyloxy-carbonyl group (e.g., benzyloxycarbonyl (Cbz) etc.), $C_{7-10}$ aralkyl group (e.g., benzyl etc.), trityl group, phthaloyl group, dithiasuccinyl group, N,N-dimethylaminomethylene group, each of which optionally has substituent(s) and the like. Examples of the substituent include phenyl group, halogen atom, $C_{1-6}$ alkyl-carbonyl group, $C_{1-6}$ alkoxy group (e.g., methoxy, ethoxy, trifluoromethoxy etc.) optionally substituted by halogen atom, nitro group and the like, and the number of the substituents is 1 to 3.

Examples of the protecting group for carboxyl group include $C_{1-6}$ alkyl group, allyl group, benzyl group, phenyl group, trityl group, trialkylsilyl group, each of which optionally has substituent(s), and the like. Examples of the substituent include halogen atom, a formyl group, $C_{1-6}$ alkyl-carbonyl group, $C_{1-6}$ alkoxy group (e.g., methoxy, ethoxy, trifluoromethoxy etc.) optionally substituted by halogen atom, nitro group and the like, and the number of the substituents is 1 to 3.

Examples of the protecting group for hydroxy group include $C_{1-6}$ alkyl group, $C_{7-20}$ aralkyl group (e.g., benzyl, trityl etc.), a formyl group, $C_{1-6}$ alkyl-carbonyl group, benzoyl group, $C_{7-10}$ aralkyl-carbonyl group (e.g., benzylcarbonyl etc.), 2-tetrahydropyranyl group, tetrahydrofuranyl group, trialkylsilyl group (e.g., trimethylsilyl, tert-butyldimethylsilyl, diisopropylethylsilyl etc.), each of which optionally has substituent(s), and the like. Examples of the substituent include halogen atom, $C_{1-6}$ alkyl group, phenyl group, $C_{7-10}$ aralkyl group (e.g., benzyl etc.), $C_{1-6}$ alkoxy group, nitro group and the like, and the number of the substituents is 1 to 4.

When compound (II) is obtained as a free compound, it can be converted to an object salt by a method known per se or a method analogous thereto, and when it is obtained as a salt, it can be converted to a free form or other object salt by a method known per se or a method analogous thereto.

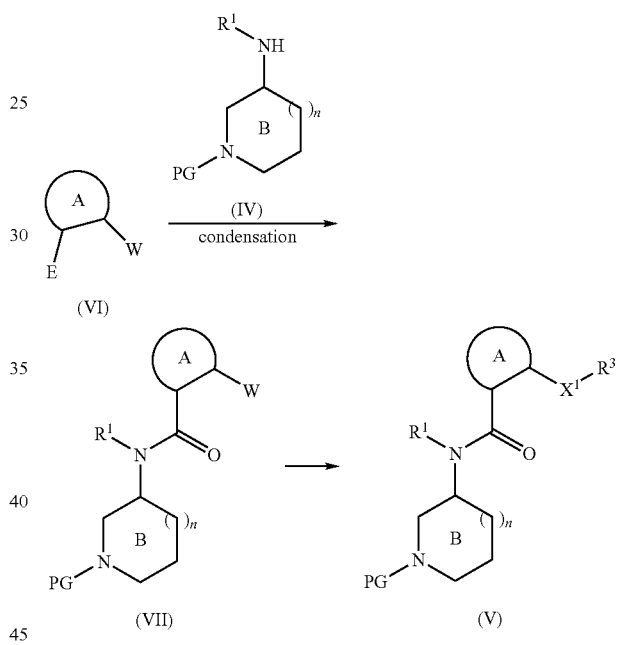

Compound (VII) can be produced by a reaction of compound (VI) with compound (IV).

Compound (VI) may be a commercially available product, or can be produced according to a method known per se, for example, the method described in Journal of Organic Chemistry (J. Org. Chem.), 2002, vol. 67, page 9276-9287 and the like, or a method analogous thereto.

The condensation reaction of compound (VI) and compound (IV) can be performed under the conditions of the method used for the aforementioned production of compound (V).

Compound (V) can be produced from compound (VII).

The reaction from compound (VII) to compound (V) can be performed according to a method known per se, for example, the method described in Bioorganic and Medicinal Chemistry Letters (Bioorg. Med. Chem. Lett.), 2000, vol. 10, page 957-961 or Journal of Medicinal Chemistry (J. Med. Chem.), 1996, vol. 39, page 2856-2859 and the like, or a method analogous thereto.

Compound (V) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 3)

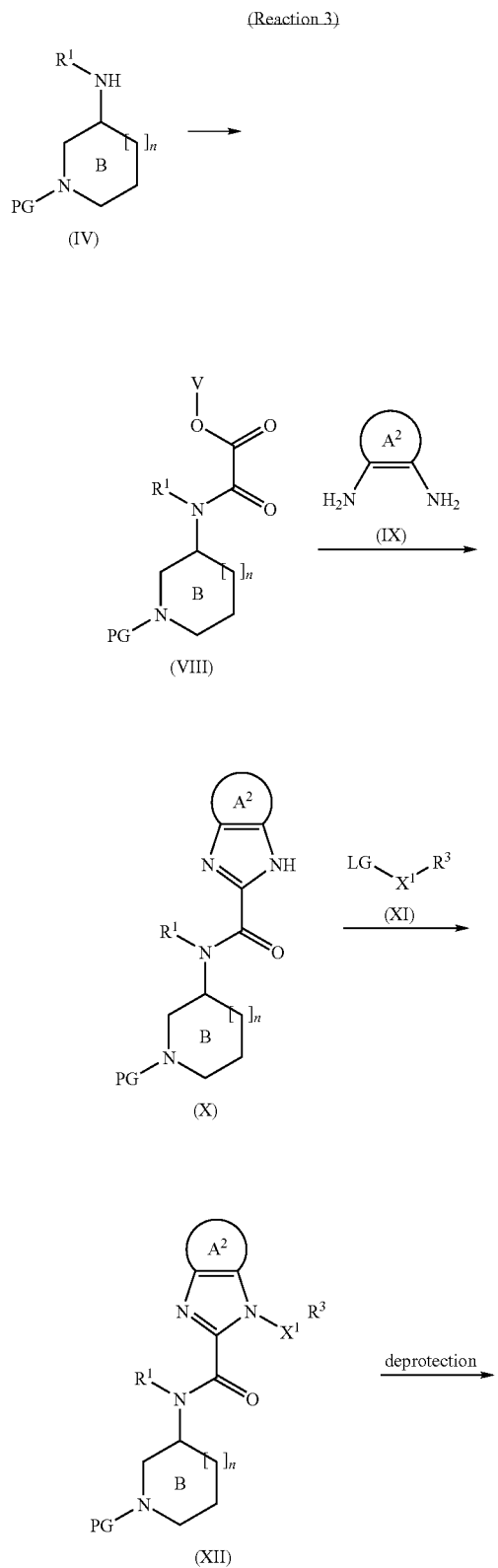

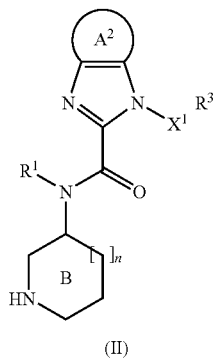

This method is used for the production of compound (II) wherein ring $A^1$ is a fused imidazole ring.

Compound (VIII) can be produced from compound (IV).

Compound (VIII) can be produced using compound (IV) and according to a known method, for example, the method described in Tetrahedron, 1993, vol. 49, page 4015-4034 and the like, or a method analogous thereto.

Compound (IX) may be a commercially available product, or can be produced according to a method known per se, for example, the method described in Journal of Medicinal Chemistry (J. Med. Chem.), 1995, vol. 38, page 4906-4916 or Journal of American Chemical Society (J. Am. Chem. Soc.), 2006, vol. 128, page 8569-8574 or Bioorganic and Medicinal Chemistry (Bio. Med. Chem.), 1998, vol. 6, page 163-172 and the like or a method analogous thereto.

Compound (X) can be produced from compound (VIII) and compound (IX) according to a known method, for example, the method described in Journal of Chemical Society Perkin transaction 2 (J. Chem. Soc. Perkin Trans. 2), 2001, page 1817-1823 or Bioorganic and Medicinal Chemistry Letters (Bioorg. Med. Chem. Lett.), 2006, vol. 16, page 4638-4640, and the like, or a method analogous thereto.

When LG is a substitutable leaving group, compound (XI) may be a commercially available product, or can be produced according to a method known per se, for example, the method described in WO2005003122 and the like, or a method analogous thereto.

When LG is a hydroxyl group, compound (XI) may be a commercially available product, or can be produced according to a method known per se, for example, the method described in WO2005003122 and the like, or a method analogous thereto.

Compound (XII) can be produced from compound (X) and compound (XI) according to a known method, for example, the method described in EP1479676 or Bioorganic and Medicinal Chemistry Letters (Bioorg. Med. Chem. Lett.), 2006, vol. 16, page 4638-4640 or Bioorganic and Medicinal Chemistry Letters (Bioorg. Med. Chem. Lett.), 1997, vol. 7, page 2819-2824, and the like, or a method analogous thereto.

Compound (XII) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

Compound (II) can be produced by removing N-protecting group PG from compound (XII). In each of the above-mentioned reactions, when the starting compound has an amino group, a carboxyl group or a hydroxyl group as a substituent, these groups may be protected with a protecting group generally used in peptide chemistry and the like. In this case, the object compound can be obtained by removing the protecting group as necessary after the reaction. These protecting groups can be introduced or removed according to a method known per se, for example, the method described in Theodora W. Greene and Peter G. M. Wuts, "Protective Groups in Organic Synthesis, 3rd Ed.", Wiley-Interscience (1999) and the like.

When compound (II) is obtained as a free compound, it can be converted to an object salt by a method known per se or a method analogous thereto, and when it is obtained as a salt, it can be converted to a free form or other object salt by a method known per se or a method analogous thereto.

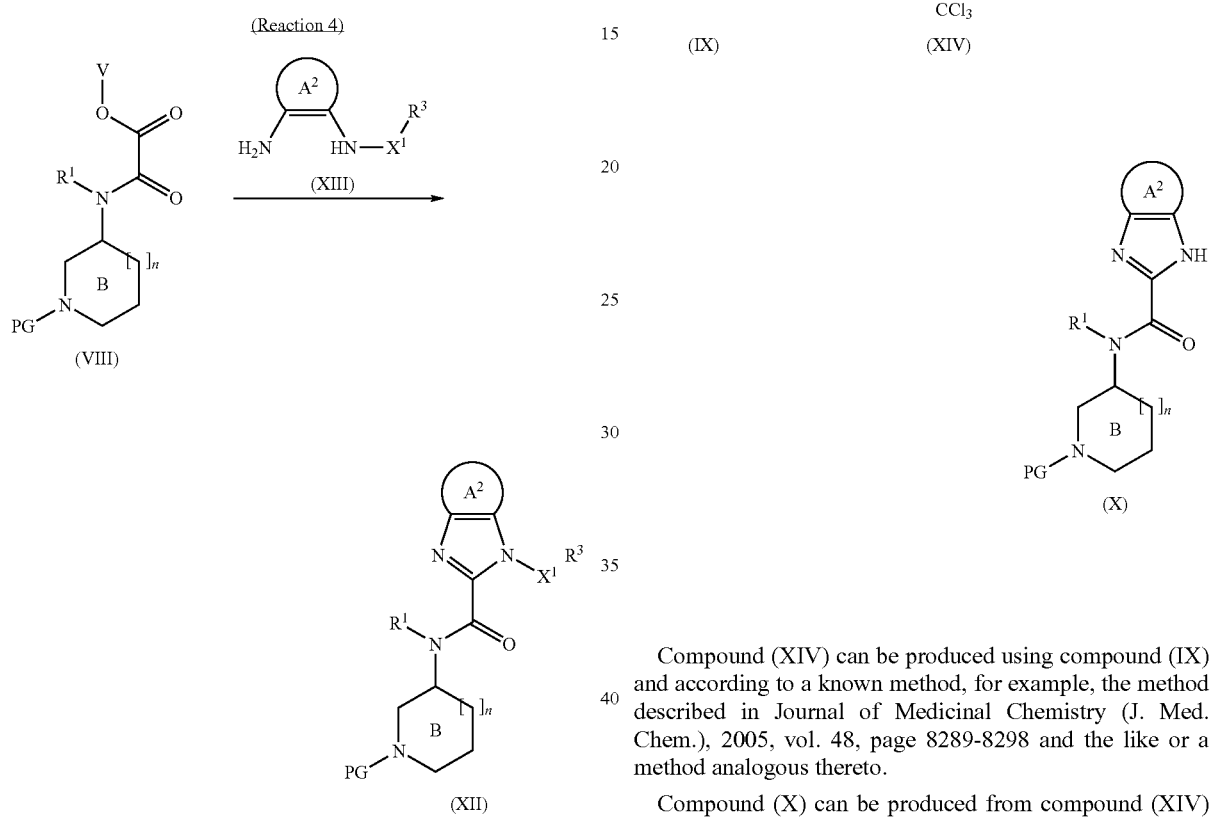

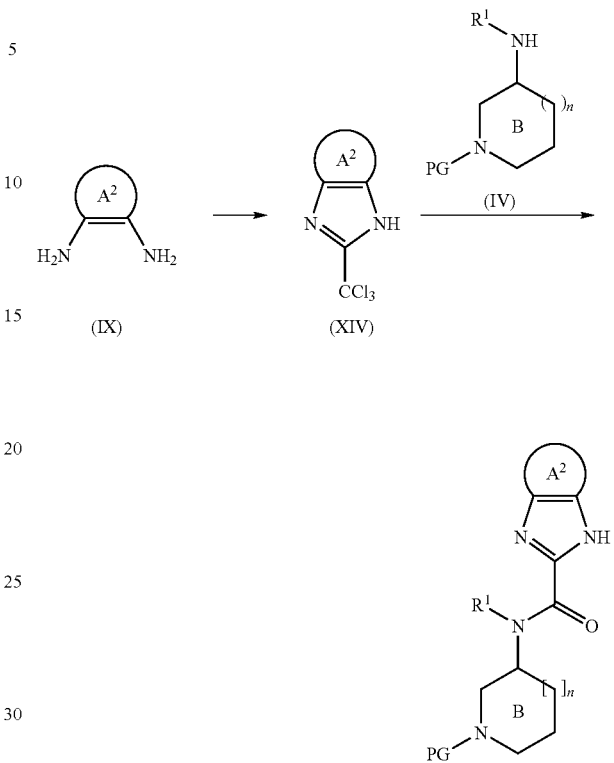

Compound (XII) can also be produced from compound (VIII) and compound (XIII).

Compound (XIII) may be a commercially available product, or can be produced according to a method known per se, for example, the method described in Heterocycles (Heterocycles), 1998, vol. 48, page 1347-1364 and the like, or a method analogous thereto.

The reaction to produce compound (XII) from compound (VIII) and compound (XIII) can be performed under the conditions employed for the production of compound (X).

Compound (XII) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

Compound (XIV) can be produced using compound (IX) and according to a known method, for example, the method described in Journal of Medicinal Chemistry (J. Med. Chem.), 2005, vol. 48, page 8289-8298 and the like or a method analogous thereto.

Compound (X) can be produced from compound (XIV) and compound (IV) according to a known method, for example, the method described in Journal of Medicinal Chemistry (J. Med. Chem.), 2005, vol. 48, page 8289-8298 page and the like or a method analogous thereto.

Compound (X) can also be produced by performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 6)

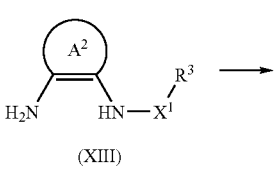

-continued

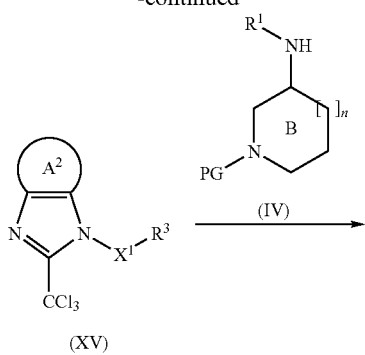

(XV)

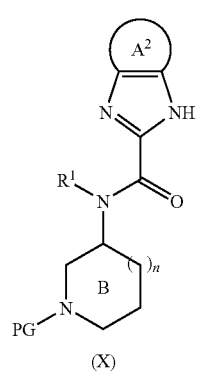

(X)

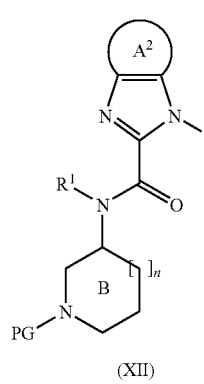

(XII)

Compound (XV) may be a commercially available product, or can be produced according to a method known per se, for example, the method described in Heterocycles (Heterocycles), 2006, vol. 67, page 769-775 and the like, or a method analogous thereto.

Compound (X) can be produced from compound (XV) and compound (IV) according to a known method, for example, the method described in Bioorganic and Medicinal Chemistry Letters (Bioorg. Med. Chem. Lett.), 1997, vol. 7, page 1863-1868, and the like, or a method analogous thereto.

Compound (X) can also be produced by performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

Compound (XV) can be produced using compound (XIII) and according to a known method, for example, the method described in Journal of Medicinal Chemistry (J. Med. Chem.), 2005, vol. 48, page 8289-8298 and the like or a method analogous thereto.

Compound (XII) can be produced from compound (XV) and compound (IV) according to a known method, for example, the method described in Journal of Medicinal Chemistry (J. Med. Chem.), 2005, vol. 48, page 8289-8298 and the like or a method analogous thereto.

Compound (XII) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 8)

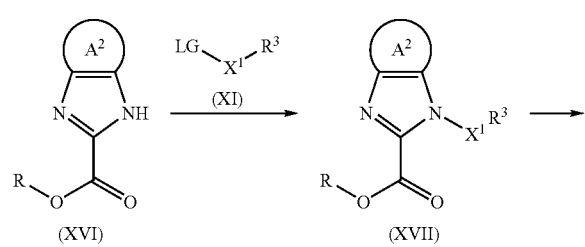

(Reaction 7)

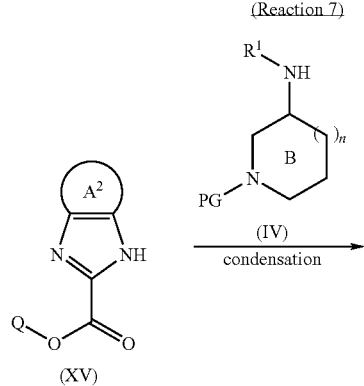

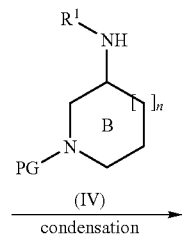

(XVIII)

-continued

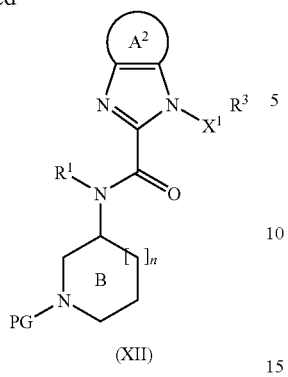

(XII)

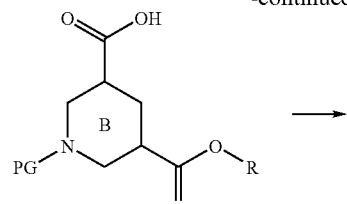

(XXI) or (XXII)

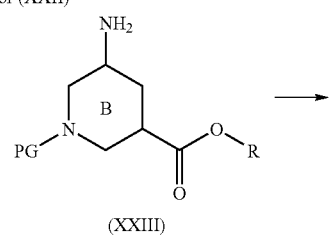

(XXIII)

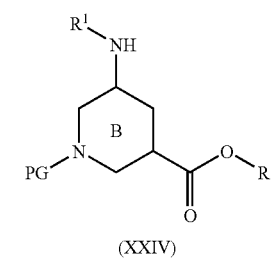

(XXIV)

Compound (XVI) may be a commercially available product, or can be produced according to a method known per se, for example, the method described in Journal of Organic Chemistry (J. Org. Chem.), 2002, vol. 69, page 2626-2629 and the like, or a method analogous thereto.

Compound (XVII) can be produced from compound (XVI) and compound (XI) according to a known method, for example, the method described in EP1479676 or Bioorganic and Medicinal Chemistry Letters (Bioorg. Med. Chem. Lett.), 2006, vol. 16, page 4638-4640 or Bioorganic and Medicinal Chemistry Letters (Bioorg. Med. Chem. Lett.), 1997, vol. 7, page 2819-2824, and the like or a method analogous thereto.

Compound (XVIII) can be produced by subjecting compound (XVII) to known hydrolysis, for example, alkali hydrolysis or acid hydrolysis.

Compound (XII) can be produced from compound (XVIII) and compound (IV) according to a known method, for example, the method described in Bioorganic and Medicinal Chemistry Letters (Bioorg. Med. Chem. Lett.), 1997, vol. 7, page 1863-1868, and the like or a method analogous thereto.

Compound (XII) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 9)

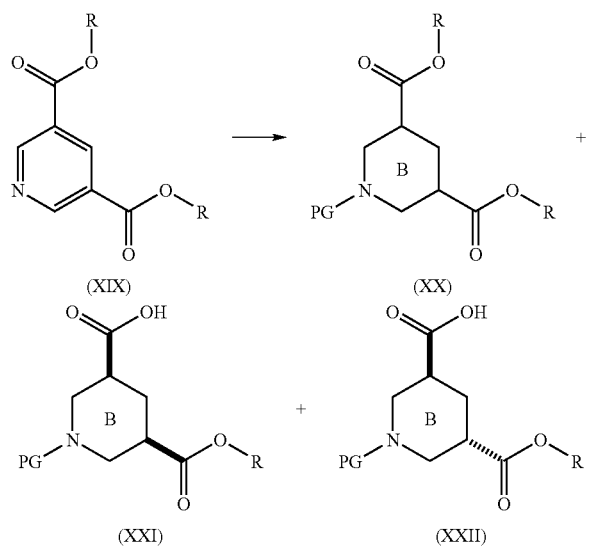

This method is used for the production of a compound wherein compound (IV) is a structure shown by compound (XXIV).

Compound (XIX) can be produced according to a method known per se, for example, U.S. Pat. No. 6,018,046 etc. or a method analogous thereto.

Compounds (XX), (XXI) and (XXII) can be each produced by subjecting compound (XIX) to a known reduction reaction, for example, a hydrogenation reaction in the presence of a metal catalyst and the like, and then introducing a PG group (a protecting group) by known reactions.

The hydrogenation reaction and the subsequent introduction of the protecting group (PG group) can be performed according to a known method, for example, the method described in Tetrahedron Letters (Tetrahedron Lett.), 1994, vol. 35, page 4515-4518 or Tetrahedron: Asymmetry (Tetrahedron: Asymmetry.), 2003, vol. 14, page 1541-1545 or Tetrahedron Letters (Tetrahedron Lett.), 2003, vol. 44, page 1611-1614 and the like, or a method analogous thereto.

The hydrogenation reaction is more advantageously performed under acidic conditions. Preferable examples of the acid for this step include mineral acids such as mineral acid, hydrochloric acid and the like, organic acids such as acetic acid and the like, and the like. The amount of the acid to be used is about 1 mol to large excess per 1 mol of compound (XIX).

As the metal catalyst used for the hydrogenation reaction, for example, rhodium carbon, platinum oxide, palladium carbon, rhodium-platinum oxide alloy and the like are preferable. The amount of the catalyst to be used is about 0.01 g to 1 g, preferably about 0.05 g to 0.3 g, per 1 g of compound (XIX).

The hydrogenation reaction is advantageously performed using a solvent inert to the reaction. The solvent is not particularly limited as long as the reaction proceeds, for example, organic acid such as acetic acid and the like, mineral acid such as hydrochloric acid and the like, alcohols such as methanol, ethanol, propanol and the like, hydrocarbons such as benzene, toluene, cyclohexane, hexane and the like, ethers such as diethyl ether, tetrahydrofuran, dioxane and the like, esters such as ethyl acetate and the like, highly-polar solvent such as N,N-dimethylformamide or N-methylpyrrolidone and the like or a mixed solvent thereof and the like are preferable.

While the reaction time varies depending on the reagents and solvents to be used, it is generally 30 min to 60 hr, preferably 30 min to 30 hr.

The reaction temperature is generally 0 to 150° C., preferably 20 to 70° C.

After the reduction reaction, the reaction mixture is neutralized by adding an inorganic base (e.g., sodium hydroxide, potassium carbonate etc.), an organic base (e.g., triethylamine etc.) and the like and concentrated or, the reaction mixture is directly concentrated and the concentrate is neutralized by adding an inorganic base (e.g., sodium hydroxide, potassium carbonate etc.), an organic base (e.g., triethylamine etc.) and the like, and the protecting group (PG group) is introduced thereinto to give compounds (XX), (XXI) and (XXII). The protecting group (PG group) can be introduced according to a method known per se, for example, the method described in Theodora W. Greene and Peter G. M. Wuts, "Protective Groups in Organic Synthesis, 3$^{rd}$ Ed.", Wiley-Interscience (1999), and the like.

Compounds (XX), (XXI) and (XXII) can be isolated from the mixture of compounds (XX), (XXI) and (XXII), respectively, by a known purification method, for example, silica gel column chromatography, recrystallization, high-pressure liquid chromatography and the like.

Compound (XXI) can also be produced according to a method known per se, for example, the method described in WO97/18813 and the like, or a method analogous thereto.

Compound (XXIII) can be produced by a rearrangement reaction (e.g., Curtius rearrangement and the like) of compound (XXI) or compound (XXII).

Compound (XXIII) can be produced according to a method known per se, for example, the method described in U.S. Pat. No. 5,817,678 and the like, or a method analogous thereto.

Compound (XXIV) can be produced by a reaction to introduce substituent R$^1$ into the amino group of compound (XXIII) (e.g., reductive alkylation).

Compound (XXIV) can be produced according to a known method, for example, Bioorganic and Medicinal Chemistry Letters (Bioorg. Med. Chem. Lett.), 2005, vol. 15, page 833-838 or a method analogous thereto.

(Reaction 10)

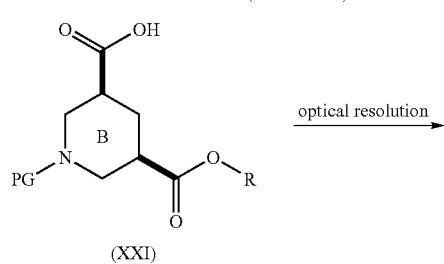

(XXI)

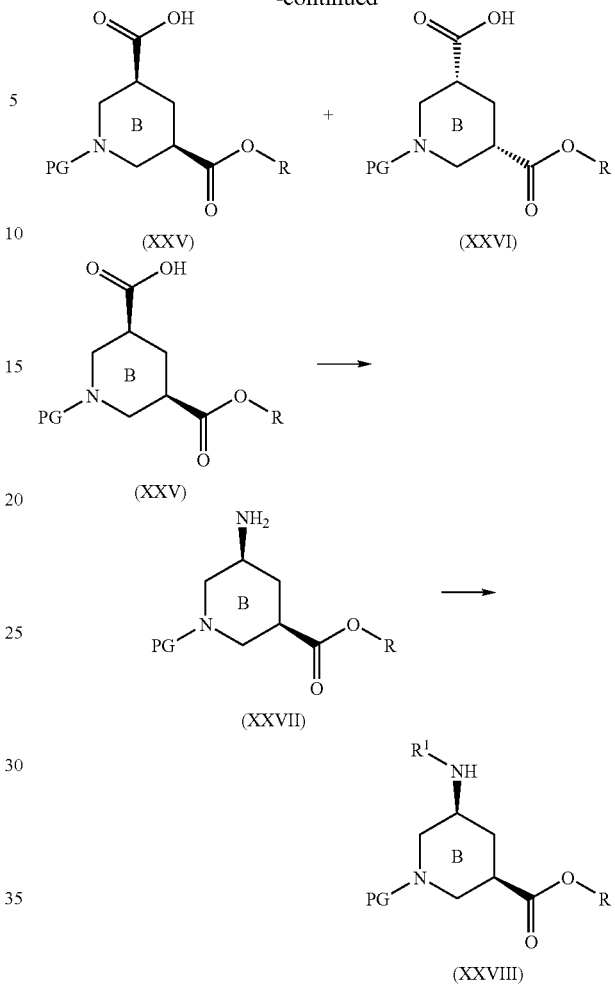

This method is used for the production of a compound wherein compound (IV) is a structure shown by compound (XXVIII).

Compound (XXV) can be separated from compound (XXI), which is a mixture of compounds (XXV) and (XXVI), by a known purification method, for example, diastereomer salt method, optically active column chromatography and the like.

Compound (XXV) can also be produced according to a method known per se, for example, the method described in Tetrahedron Letters, 2003, vol. 44, page 1611-1614 and the like, or a method analogous thereto.

Compound (XXVII) can be produced by a rearrangement reaction (e.g., Curtius rearrangement and the like) of compound (XXV).

Compound (XXVII) can be produced according to a known method, for example, the method described in Tetrahedron Letters, 2003, vol. 44, page 1611-1614 and the like, or a method analogous thereto.

Compound (XXVIII) can be produced by a reaction to introduce substituent R$^1$ into the amino group of compound (XXVII) (e.g., reductive alkylation).

Compound (XXVIII) can be produced according to a known method, for example, Bioorganic and Medicinal Chemistry Letters (Bioorg. Med. Chem. Lett.), 2005, vol. 15, page 833-838 or a method analogous thereto.

(Reaction 11)

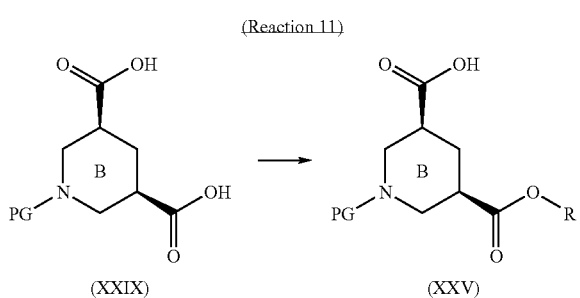

Compound (XXIX) can also be produced according to a method known per se, for example, the method described in Tetrahedron Letters, 2003, vol. 44, page 1611-1614 and the like, or a method analogous thereto.

Compound (XXV) can be produced by a known asymmetric esterification reaction and using compound (XXIX).

Compound (XXV) can also be produced according to a known method, for example, the method described in Journal of American Chemical Society (J. Am. Chem. Soc.), 2000, vol. 122, page 9542-9543 and the like or a method analogous thereto.

(Reaction 12)

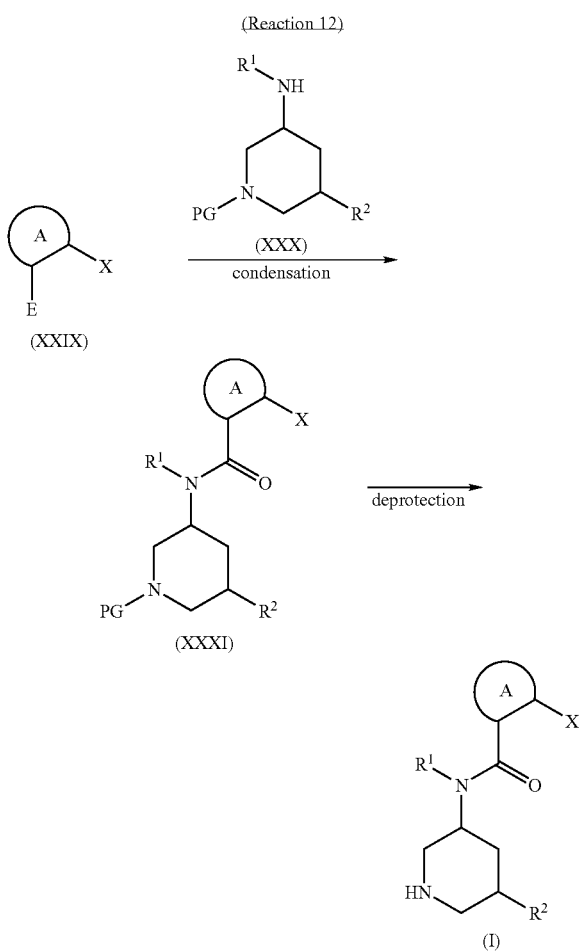

Compound (XXXI) can be produced by a condensation reaction of compound (XXIX) and compound (XXX).

Compound (XXIX) can be produced according to a method known per se, for example, the method described in Bioorganic and Medicinal Chemistry (Bioorg. Med. Chem.), 2001, vol. 9, page 1045-1057 and the like or Journal of Medicinal Chemistry (J. Med. Chem.), 1995, vol. 38, page 86-97 or Organic and Biomolecular Chemistry, 2003, vol. 1, page 2103-2110 or Chemistry of Heterocyclic Compounds (Chemistry of Heterocyclic Compounds), 1982, vol. 18, page 758-761 or WO2007094513 or EP1867331, or a method analogous thereto.

Compound (XXX) may be a commercially available product, or can be produced according to a method known per se, for example, the method described in Bioorganic and Medicinal Chemistry Letters (Bioorg. Med. Chem. Lett.), 2005, vol. 15, page 833-838 or EP1757582 and the like, the method described for the synthesis of compound (XXVIII), or a method analogous thereto.

When E is a carboxyl group, the condensation reaction is performed by a general method of peptide synthesis, for example, acid chloride method, acid anhydride method, mixed acid anhydride method, a method using N,N'-dicyclohexylcarbodiimide (DCC), activity ester method, a method using N,N'-carbonyldiimidazole (CDI), a method using diethyl cyanophosphate (DEPC), a method using N-ethyl-N'-(3-dimethylaminopropyl)carbodiimide hydrochloride (WSC.HCl) and 1-hydroxybenzotriazole (HOBt) and the like. Compound (XXX) is used in a proportion of about 1 to 2 mol, preferably about 1.0 to 1.1 mol, per 1 mol of compound (XXIX). The reagent used in the above-mentioned method is used in a proportion of about 1 mol to large excess, preferably about 1.1 to 5 mol, per 1 mol of compound (XXIX). The reaction temperature is generally −10 to 80° C., preferably 0 to 30° C.

When E is an alkali metal salt of a carboxyl group, the condensation reaction is advantageously performed by a method using WSC.HCl and HOBt. Compound (XXX) is used in a proportion of about 1 to 2 mol, preferably about 1.0 to 1.1 mol, per 1 mol of compound (XXIX). WSC.HCl is used in a proportion of about 1 to 4 mol, preferably about 1.5 to 2.5 mol, per 1 mol of compound (XXIX). HOBt is used in a proportion of about 1 to 8 mol, preferably about 2.5 to 5.0 mol, per 1 mol of compound (XXIX). The reaction temperature is generally −10 to 100° C., preferably 40 to 70° C.

In any case, the condensation reaction is preferably performed in a solvent, and examples of the solvent include halogenated hydrocarbons such as dichloromethane, chloroform, carbon tetrachloride, 1,2-dichloroethane and the like, ethers such as diethyl ether, tetrahydrofuran, dioxane and the like, amides such as N,N-dimethylformamide, N,N-dimethylacetamide and the like, dimethyl sulfoxide, pyridine, acetonitrile and a mixed solvent thereof.

While the reaction time varies depending on the reagents and solvents to be used, it is generally 30 min to 3 days, preferably 30 min to 15 hr.

Compound (XXXI) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

Compound (I) can be produced by removing N-protecting group PG from compound (XXXI). In each of the above-mentioned reactions, when the starting compound has an amino group, a carboxyl group or a hydroxyl group as a substituent, these groups may be protected with a protecting group generally used in peptide chemistry and the like. In this case, the object compound can be obtained by removing the protecting group as necessary after the reaction. These protecting groups can be introduced or removed according to a method known per se, for example, the method described in Theodora W. Greene and Peter G. M. Wuts, "Protective Groups in Organic Synthesis, 3$^{rd}$ Ed.", Wiley-Interscience (1999) and the like, or a method analogous thereto.

As the amino-protecting group, for example, a formyl group; $C_{1-6}$ alkyl-carbonyl group, phenylcarbonyl group, $C_{1-6}$ alkoxy-carbonyl group, allyloxycarbonyl (Alloc) group, phenyloxycarbonyl group, fluorenylmethyloxycarbonyl (Fmoc) group, $C_{7-10}$ aralkyl-carbonyl group (e.g., benzylcarbonyl and the like), $C_{7-10}$ aralkyloxy-carbonyl group (e.g., benzyloxycarbonyl (Cbz) and the like), $C_{7-10}$ aralkyl group (e.g., benzyl and the like), trityl group, phthaloyl group, dithiasuccinoyl group, N,N-dimethylaminomethylene group, each optionally having substituent(s), and the like can be mentioned. As the substituent(s), for example, phenyl group, a halogen atom, $C_{1-6}$ alkyl-carbonyl group, $C_{1-6}$ alkoxy group optionally substituted by halogen atom(s) (e.g., methoxy, ethoxy, trifluoromethoxy and the like), nitro group and the like can be used. The number of the substituents is 1 to 3.

As the carboxyl-protecting group, for example, $C_{1-6}$ alkyl group, allyl group, benzyl group, phenyl group, trityl group, trialkylsilyl group, each optionally having substituent(s), and the like can be mentioned. As the substituent(s), for example, a halogen atom, a formyl group, $C_{1-6}$ alkyl-carbonyl group, $C_{1-6}$ alkoxy group optionally substituted by halogen atom(s) (e.g., methoxy, ethoxy, trifluoromethoxy and the like), nitro group and the like can be used. The number of the substituents is 1 to 3.

As the hydroxy-protecting group, for example, $C_{1-6}$ alkyl group, $C_{7-20}$ aralkyl group (e.g., benzyl, trityl and the like), a formyl group, $C_{1-6}$ alkyl-carbonyl group, benzoyl group, $C_{7-10}$ aralkyl-carbonyl group (e.g., benzylcarbonyl and the like), 2-tetrahydropyranyl group, tetrahydrofuranyl group, trialkylsilyl group (e.g., trimethylsilyl, tert-butyldimethylsilyl, diisopropylethylsilyl and the like), each optionally having substituent(s), and the like can be mentioned. As the substituent(s), for example, a halogen atom, $C_{1-6}$ alkyl group, phenyl group, $C_{7-10}$ aralkyl group (e.g., benzyl and the like), $C_{1-6}$ alkoxy group, nitro group and the like can be used. The number of the substituents is 1 to 4.

When compound (I) is obtained as a free compound, it can be converted to the object salt according to a method known per se or a method analogous thereto, and when it is obtained as a salt, it can be converted to a free compound or other object salt according to a method known per se or a method analogous thereto.

(Reaction 13)

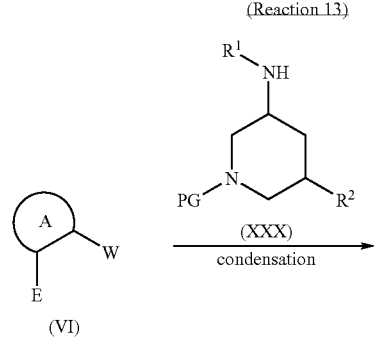

(VI)

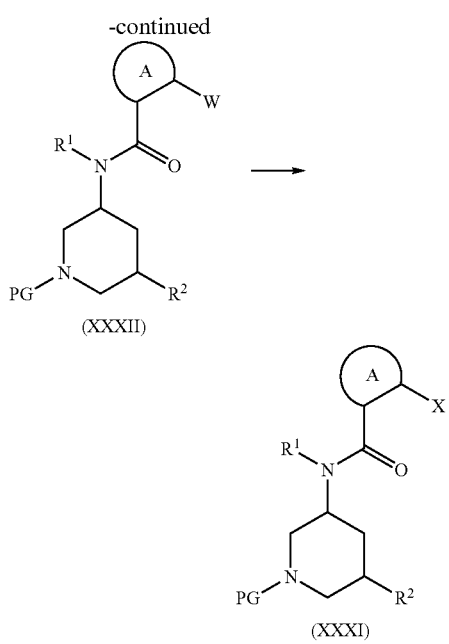

Compound (XXXII) can be produced by reacting compound (VI) with compound (XXX).

Compound (VI) may be a commercially available product, or can be produced according to a method known per se, for example, the method described in Journal of Organic Chemistry (J. Org. Chem.), 2002, vol. 67, page 9276-9287 and the like, or a method analogous thereto.

The condensation reaction of compound (VI) and compound (XXX) can be performed under the conditions employed for the production of the aforementioned compound (V).

Compound (XXXI) can be produced from compound (XXXII).

The reaction from compound (XXXII) to compound (XXXI) can be performed according to a method known per se, for example, the method described in Bioorganic and Medicinal Chemistry Letters (Bioorg. Med. Chem. Lett.), 2000, vol. 10, page 957-961 or Journal of Medicinal Chemistry (J. Med. Chem.), 1996, vol. 39, page 2856-2859 and the like or a method analogous thereto.

Compound (XXXI) can also be produced by performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 14)

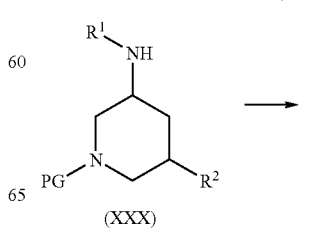

(XXX)

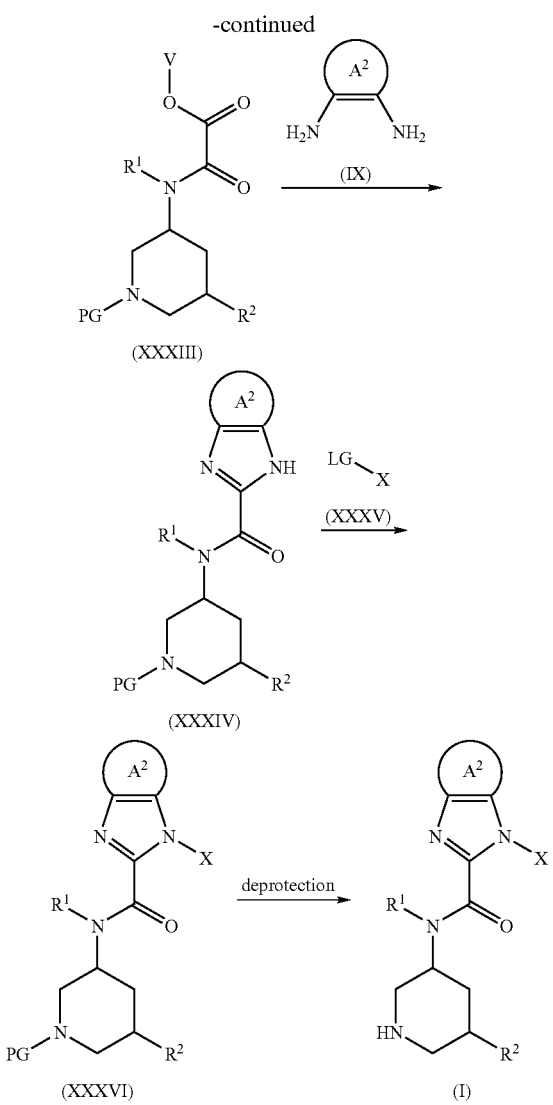

This method can be used for the production of compound (I) wherein ring A is a fused imidazole ring.

Compound (XXXIII) can be produced from compound (XXX).

Compound (XXXIII) can be produced using compound (XXX) and according to a known method, for example, the method described in Tetrahedron (Tetrahedron), 1993, vol. 49, page 4015-4034 and the like or a method analogous thereto.

Compound (IX) may be a commercially available product, or can be produced according to a method known per se, for example, the method described in Journal of Organic Chemistry (J. Org. Chem.), 1995, vol. 38, page 4906-4916 or Journal of American Chemical Society (J. Am. Chem. Soc.), 2006, vol. 128, page 8569-8574, or Bioorganic and Medicinal Chemistry (Bio. Med. Chem.), 1998, vol. 6, page 163-172 and the like, or a method analogous thereto.

Compound (XXXIV) can be produced from compound (XXXIII) and compound (IX) according to a known method, for example, the method described in Journal of Chemical Society Perkin transaction 2 (J. Chem. Soc. Perkin Trans. 2), 2001, page 1817-1823 or Bioorganic and Medicinal Chemistry Letters (Bioorg. Med. Chem. Lett.), 2006, vol. 16, page 4638-4640, and the like or a method analogous thereto.

Compound (XXXIV) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

When LG is a substitutable leaving group, compound (XXXV) may be a commercially available product, or can be produced according to a method known per se, for example, the method described in WO2005003122 and the like, or a method analogous thereto.

When LG is a hydroxyl group, compound (XXXV) may be a commercially available product, or can be produced according to a method known per se, for example, the method described in WO2005003122 and the like, or a method analogous thereto.

Compound (XXXVI) can be produced from compound (XXXIV) and compound (XXXV) according to a known method, for example, the method described in EP1479676 or Bioorganic and Medicinal Chemistry Letters (Bioorg. Med. Chem. Lett.), 2006, vol. 16, page 4638-4640 or Bioorganic and Medicinal Chemistry Letters (Bioorg. Med. Chem. Lett.), 1997, vol. 7, page 2819-2824, and the like or a method analogous thereto.

Compound (XXXVI) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

Compound (I) can be produced by removing N-protecting group PG from compound (XXXVI). In each of the above-mentioned reactions, when the starting compound has an amino group, a carboxyl group or a hydroxyl group as a substituent, these groups may be protected with a protecting group generally used in peptide chemistry and the like. In this case, the object compound can be obtained by removing the protecting group as necessary after the reaction. These protecting groups can be introduced or removed according to a method known per se, for example, a method analogous to the method described in Theodora W. Greene and Peter G. M. Wuts, "Protective Groups in Organic Synthesis, $3^{rd}$ Ed.", Wiley-Interscience (1999) and the like.

When X of compound (I) is a hydrogen atom, the compound can be produced by removing N-protecting group PG from compound (XXXIV). In each of the above-mentioned reactions, when the starting compound has an amino group, a carboxyl group or a hydroxyl group as a substituent, these groups may be protected with a protecting group generally used in peptide chemistry and the like. In this case, the object compound can be obtained by removing the protecting group as necessary after the reaction. These protecting groups can be introduced or removed according to a method known per se, for example, a method analogous to the method described in Theodora W. Greene and Peter G. M. Wuts, "Protective Groups in Organic Synthesis, $3^{rd}$ Ed.", Wiley-Interscience (1999) and the like.

When compound (I) is obtained as a free compound, it can be converted to an object salt by a method known per se or a method analogous thereto, and when it is obtained as a salt, it can be converted to a free form or other object salt by a method known per se or a method analogous thereto.

(Reaction 15)

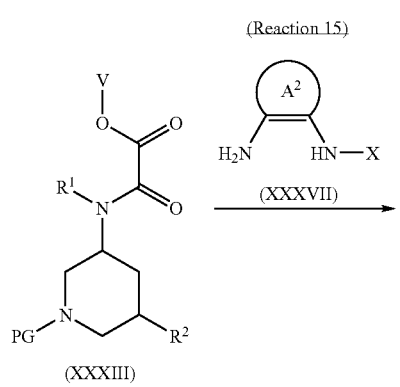

(XXXIII)

Compound (XXXVI) can also be produced from compound (XXXIII) and compound (XXXVII).

Compound (XXXVII) may be a commercially available product, or can be produced according to a method known per se, for example, the method described in Heterocycles (Heterocycles), 1998, vol. 48, page 1347-1364 and the like, or a method analogous thereto.

The reaction to produce compound (XXXVI) from compound (XXXIII) and compound (XXXVII) can be performed under the conditions employed for the production of compound (XXXIV).

Compound (XXXVI) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 16)

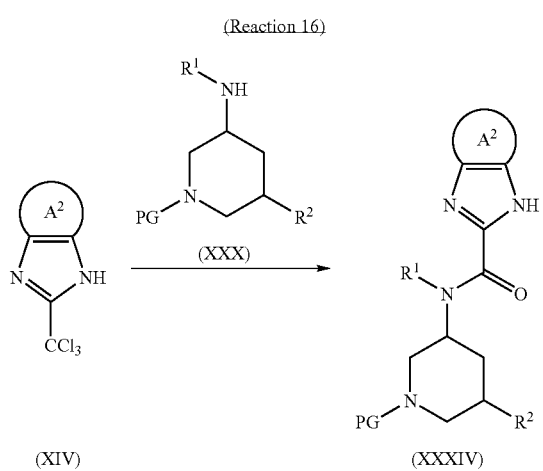

Compound (XXXIV) can be produced from compound (XIV) and compound (XXX) according to a known method, for example, the method described in Journal of Medicinal Chemistry (J. Med. Chem.), 2005, vol. 48, page 8289-8298 and the like or a method analogous thereto.

Compound (XXXIV) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 17)

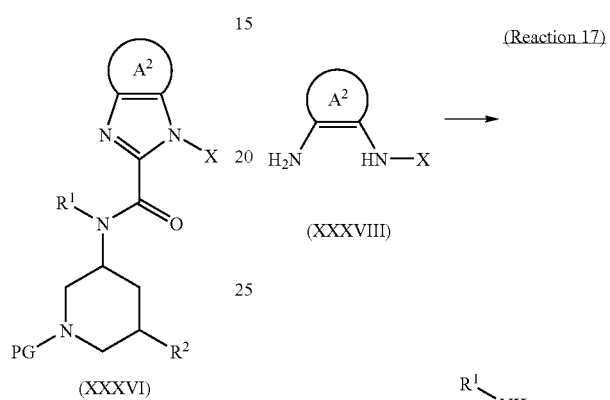

(XXXVIII)

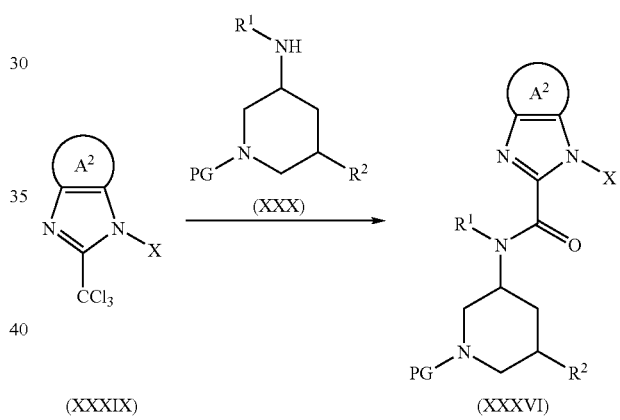

Compound (XXXIX) can be produced using compound (XXXVIII) and according to a known method, for example, the method described in Journal of Medicinal Chemistry (J. Med. Chem.), 2005, vol. 48, page 8289-8298 and the like or a method analogous thereto.

Compound (XXXVI) can be produced from compound (XXXIX) and compound (XXX) according to a known method, for example, the method described in Journal of Medicinal Chemistry (J. Med. Chem.), 2005, vol. 48, page 8289-8298 and the like or a method analogous thereto.

Compound (XXXVI) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 18)

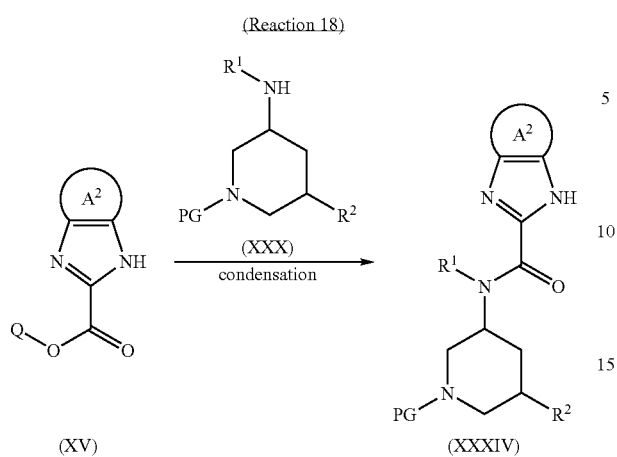

Compound (XV) may be a commercially available product, or can be produced according to a method known per se, for example, the method described in Heterocycles, 2006, vol. 67, page 769-775 and the like, or a method analogous thereto.

Compound (XXXIV) can be produced from compound (XV) and compound (XXX) according to a known method, for example, the method described in Bioorganic and Medicinal Chemistry Letters (Bioorg. Med. Chem. Lett.), 1997, vol. 7, page 1863-1868, and the like or a method analogous thereto.

Compound (XXXIV) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

(Reaction 19)

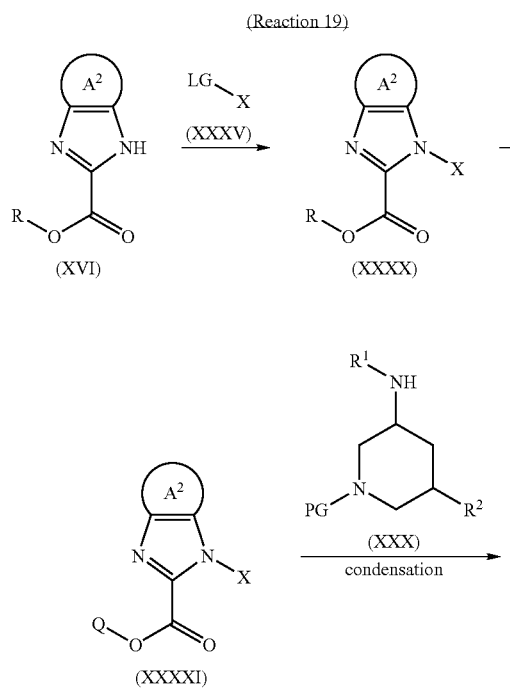

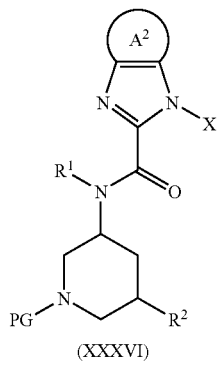

Compound (XVI) may be a commercially available product, or can be produced according to a method known per se, for example, the method described in Journal of Organic Chemistry (J. Org. Chem.), 2004, vol. 69, page 2626-2629 and the like, or a method analogous thereto.

Compound (XXXX) can be produced from compound (XVI) and compound (XXXV) according to a known method, for example, the method described in EP1479676 or Bioorganic and Medicinal Chemistry Letters (Bioorg. Med. Chem. Lett.), 2006, vol. 16, page 4638-4640 or Bioorganic and Medicinal Chemistry Letters (Bioorg. Med. Chem. Lett.), 1997, vol. 7, page 2819-2824, and the like or a method analogous thereto.

Compound (XXXXI) can be produced by a known hydrolysis, for example, alkali hydrolysis or acid hydrolysis.

Compound (XXXVI) can be produced from compound (XXXXI) and compound (XXX) according to a known method, for example, the method described in Bioorganic and Medicinal Chemistry Letters (Bioorg. Med. Chem. Lett.), 1997, vol. 7, page 1863-1868, and the like or a method analogous thereto.

Compound (XXXVI) can also be produced by further performing the above-mentioned reaction in combination with one or more of known hydrolysis, acylation reaction, alkylation reaction, amination reaction, oxidation reduction reaction, cyclization reaction, carbon chain extension reaction, substituent exchange reaction and the like, as desired.

Compound (I) and compound (II) may be used as prodrugs. A prodrug of compound (I) or compound (II) means a compound which is converted to compound (I) or compound (II) with a reaction due to an enzyme, an gastric acid, etc. under the physiological condition in the living body, that is a compound which is converted to compound (I) or compound (II) with oxidation, reduction, hydrolysis, etc. according to an enzyme; a compound which is converted to compound (I) or compound (II) by hydrolysis etc. due to gastric acid, etc.

Examples of a prodrug of compound (I) or compound (II) include a compound wherein an amino group of compound (I) or compound (II) is acylated, alkylated or phosphorylated (e.g., compound wherein amino group of compound (I) or compound (II) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like); a compound wherein a hydroxy group of compound (I) or compound (II) is acylated, alkylated, phosphorylated or borated (e.g., a compound wherein a hydroxy group of compound (I) or compound (II) is acetylated, palmitoylated, propanoylated, pivaloylated, succinylated, fumarylated, alanylated or dimethylaminomethylcarbonylated, and the like); a compound wherein a carboxyl group of compound (I) or compound (II) is esterified or amidated (e.g., a compound wherein a carboxyl group of compound (I) or compound (II) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated, and the like) and the like. These compounds can be produced from compound (I) by a method known per se.

A prodrug of compound (I) and compound (II) may also be one which is converted into compound (I) or compound (II) under a physiological condition, such as those described in IYAKUHIN no KAIHATSU (Development of Pharmaceuticals), Vol. 7, Design of Molecules, p. 163-198, Published by HIROKAWA SHOTEN (1990).

When compound (I) and compound (II) has an isomer such as optical isomer, stereoisomer, positional isomer, rotational isomer and the like, any isomers and a mixture thereof are encompassed in compound (I) or compound (II). For example, when compound (I) or compound (II) has an optical isomer, an optical isomer resolved from a racemate is also encompassed in compound (I) and compound (II). Such isomer can be obtained as a single product by a synthesis method, a separation method (e.g., concentration, solvent extraction, column chromatography, recrystallization etc.), optical resolution method (e.g., fractional recrystallization, chiral column method, diastereomer method etc.) and the like known per se.

Compound (I) and compound (II) may be a crystal, and both a single crystal and crystal mixtures are encompassed in compound (I) and compound (II). Crystals can be produced by crystallization according to crystallization methods known per se.

Compound (I) and compound (II) may be a solvate (e.g., hydrate etc.) or a non-solvate (e.g., non-hydrate etc.), both of which are encompassed in compound (I) and compound (II).

A compound labeled with an isotope (e.g., $^3$H, $^{14}$C, $^{35}$S, $^{125}$I and the like) and the like is also encompassed in compound (I) and compound (II).

Deuterium-converted compound wherein $^1$H has been converted to $^2$H(D) are also encompassed in the compound (I) and compound (II).

Compound (I) or compound (II) or its prodrug, or salts thereof (hereinafter, sometimes to be abbreviated to as a compound of the present invention) exhibit superior renin inhibitory activity. They have low toxicity (e.g., acute toxicity, chronic toxicity, genetic toxicity, reproductive toxicity, cardiac toxicity, drug interaction, carcinogenicity, etc.) and high water-solubility, and are excellent in the aspects of stability, pharmacokinetics (absorbability, distribution, metabolism, excretion, etc.) and efficacy, thus being useful as medicine.

The compound of the present invention acts as a renin inhibitory drug in mammals (e.g., mouse, rat, hamster, rabbit, cat, dog, cattle, sheep, monkey, human, etc.), and is useful as a drug inhibiting the RA system by inhibiting the biosynthesis of AII, and is useful as an agent for the prophylaxis or treatment of various diseases caused by the RA system.

Examples of such diseases include hypertension (e.g., essential hypertension, renal vascular hypertension, renoparenchymal hypertension, primary aldosteronism, Cushing's syndrome etc.), blood pressure circadian rhythm abnormality, heart diseases (e.g., cardiac hypertrophy, acute heart failure, chronic heart failure including congestive heart failure, failure of expansion, cardiac myopathy, angina pectoris, myocarditis, atrial fibrillation, arrhythmia, tachycardia, cardiac infraction etc.), cerebrovascular disorders (e.g., asymptomatic cerebrovascular disorder, transient cerebral ischemia, cerebrovascular dementia, hypertensive encephalopathy, cerebral infarction etc.), cerebral edema, cerebral circulatory disorder, recurrence and sequela of cerebrovascular disorders (e.g., neurotic symptom, psychic symptom, subjective symptom, disorder in daily living activities etc.), ischemic peripheral circulation disorder, myocardial ischemia, venous insufficiency, progression of cardiac insufficiency after myocardial infarction, renal diseases (e.g., nephritis, glomerulonephritis, glomerulosclerosis, renal failure, nephrotic syndrome, thrombotic vasculopathy, complication of dialysis, organ damage including nephropathy by radiation irradiation etc.), arteriosclerosis including atherosclerosis (e.g., aneurysm, coronary arteriosclerosis, cerebral arteriosclerosis, peripheral arteriosclerosis etc.), vascular hypertrophy, vascular hypertrophy or obliteration and organ damages after intervention (e.g., percutaneous transluminal coronary angioplasty, stenting, coronary angioscopy, intravascular ultrasound, dounce thrombolytic therapy etc.), vascular re-obliteration and restenosis after bypass, polycythemia, hypertension, organ damage and vascular hypertrophy after transplantation, rejection after transplantation, ocular diseases (e.g., glaucoma, ocular hypertension etc.), thrombosis, multiple organ disorder, endothelial dysfunction, hypertensive tinnitus, other cardiovascular diseases (e.g., deep vein thrombosis, obstructive peripheral circulatory disorder, arteriosclerosis obliterans, thromboangiitis obliterans, ischemic cerebral circulatory disorder, Raynaud's disease, Berger disease etc.), metabolic and/or nutritional disorders (e.g., diabetes, impaired glucose tolerance, insulin resistance, hyperinsulinemia, diabetic nephropathy, diabetic retinopathy, diabetic neuropathy, obesity, hyperlipidemia, hypercholesterolemia, hyperuricacidemia, hyperkalemia, hypernatremia etc.), metabolic syndrome, nonalcoholic steatohepatitis (NASH), nonalcoholic fatty liver disease (NAFLD), nerve degeneration diseases (e.g., Alzheimer's disease, Parkinson's disease, Creutzfeldt-Jakob disease, multiple sclerosis, amyotrophic lateral sclerosis, AIDS encephalopathy etc.), central nervous system disorders (e.g., damages such as cerebral hemorrhage and cerebral infarction, and sequela and complication thereof, head injury, spinal injury, cerebral edema, sensory malfunction, sensory functional disorder, autonomic nervous system disorder, autonomic nervous system malfunction etc.), dementia, migraine, defects of memory, disorder of consciousness, amnesia, anxiety symptom, catatonic symptom, discomfort mental state, sleep disorder, agrypnia, sychopathies (e.g., depression, epilepsy, alcoholism etc.), inflammatory diseases (e.g., arthritis such as rheumatoid arthritis, osteoarthritis, rheumatoid myelitis, periostitis etc.; inflammation after operation or injury; remission of swelling; pharyngitis; cystitis; pneumonia; atopic dermatitis; inflammatory intestinal diseases such as Crohn's disease, ulcerative colitis etc.; meningitis; inflammatory ocular disease; inflammatory pulmonary disease such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, pneumocytis carinni pneumonia, collagen diseases (e.g., systemic lupus erythematodes, scleroderma, polyarteritis etc.), hepatic diseases (e.g., hepatitis including chronic hepatitis, hepatic cirrhosis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or myelopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, bone Paget's disease, sclerosing myelitis, rheumatoid arthritis, joint tissue dysfunction and the like caused by osteoarthritis of the knee and diseases similar to these), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, pheochromocytoma etc.), urinary organ and/or male genital diseases (e.g., cystitis, prostatic hypertrophy, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared or laser beam, altitude sickness etc.), respiratory diseases (e.g., cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, Hemangioma, psoriasis etc.), eye disease (e.g., cataract, glaucoma etc.), intradialytic hypotension, myasthenia gravis, systemic diseases such as chronic fatigue syndrome and the like.

The compound of the present invention can be used in combination with an existing hypertension therapeutic drug such as an ACE inhibitor (captopril, enalapril maleate, alacepril, delapril hydrochloride, imidapril hydrochloride, quinapril hydrochloride, cilazapril, temocapril hydrochloride, trandolapril, benazepril hydrochloride, perindopril, lisinopril, etc.), ARB (losartan potassium, candesartan cilexetil, valsartan, TAK-536, TAK-491, TAK-591, irbesartan, telmisartan, eprosartan, olmesartan medoxomil, etc.), an aldosterone receptor antagonist (spironolactone, eplerenone, etc.), a Ca-ion channel inhibitor (verapamil hydrochloride, diltiazem hydrochloride, nifedipine, amlodipine besilate, azelnidipine, aranidipine, efonidipine hydrochloride, cilnidipine, nicardipine hydrochloride, nisoldipine, nitrendipine, nilvadipine, barnidipine hydrochloride, felodipine, benidipine hydrochloride, manidipine hydrochloride, etc.), diuretic (trichlormethiazide, hydrochlorothiazide, benzylhydrochlorothiazide, indapamide, tripamide, meticrane, mefruside, furosemide, triamterene, chlorthalidon etc.), a β-blocker (propranolol hydrochloride, atenolol, metoprolol tartrate, bisoprolol fumarate, etc.), an α,β-blocker (carvedilol, etc.), and the like.

Moreover, the compound of the present invention can be also used in combination with an antithrombotic drug such as heparin sodium, heparin calcium, warfarin calcium (Warfarin), a blood coagulation factor Xa inhibitor, drug having a function of balance correction in the coagulation-fibrinolysis system, an oral thrombin inhibitor (aragatroban, dabigatran, etc.), a thrombolytic drug (tPA, urokinase, etc.), an antiplatelet drug [aspirin, sulfinpyrazone (Anturane), dipyridamol (Persantine), ticlopidine hydrochloride (Panaldine), clopidogrel, cilostazol (Pletal), GPIIb/IIIa antagonist (abciximab, tirofiban, etc.)], and the like. Also, the compound can be used in combination with a lipid lowering drug or a cholesterol lowering drug. Examples thereof include a squalene synthase inhibitor (lapaquistat acetate etc.), fibrates (clofibrate, benzafibrate, gemfibrozil, etc.), nicotinic acid, its derivatives and analogs (acipimox, probucol, etc.), a bile acid binding resin (cholestyramine, colestipol, etc.), an omega-3 polyunsaturated fatty acid (EPA (eicosapentaenoic acid), DHA (docosahexaenoic acid), or a mixture thereof etc.), a compound inhibiting cholesterol absorption (sitosterol, neomycin, etc.), and a squalene epoxidase inhibitor (NB-598 and its analogs, etc.). Furthermore, other possible combination components are an oxidosqualene-lanosterol cyclase, for example, a decalin derivative, an azadecalin derivative, an indane derivative and the like. Combination with a HMG-CoA reductase (3-hydroxy-3-methylglutaryl coenzyme A reductase) inhibitor (atorvastatin calcium hydrate, pravastatin sodium, simvastatin, itavastatin, lovastatin, fluvastatin, etc.) is also possible.

The compound of the present invention can also be used in combination with a therapeutic drug for diabetes or a therapeutic drug for diabetic complications. For example, the compound of the present invention can be used in combination with an insulin preparation, an insulin sensitivity improving drug [pioglitazone hydrochloride, rosiglitazone, etc.], an α-glucosidase inhibitor [voglibose, acarbose, miglitol, emiglitate etc.], biguanide [phenformin, metformin, buformine etc.], insulin secretagogue [tolbutamide, glibenclamide, gliclazide, nateglinide, mitiglinide, glimepiride etc.], a dipeptidylpeptidase IV inhibitor [Alogliptin benzoate, Vidagliptin (LAF237), P32/98, Saxagliptin (BMS-477118) etc.], glucose sensitivity insulin secretagogue (TAK-875 etc.), GPR40 agonist, GK activator, SGLT inhibitor (dapagliflozin, remogliflozin etc.), Kinedak, Penfill, Humulin, Euglucon, Glimicron, Daonil, Novolin, Monotard, Glucobay, Dimelin, Rastinon, Bacilcon, Deamelin S, Iszilin family, or the like.

In addition, the compound can be also used together with other pharmaceutical components, including a bone disease medicine, a myocardial protective drug, a coronary artery disease medicine, a chronic cardiac failure medicine, a hypothyroidism medicine, a nephrotic syndrome medicine, a chronic renal failure medicine, a gynecological disease medicine, an infection medicine, or the like.

The administration mode may be exemplified by (1) administration of a single preparation obtained by simultaneously formulating the compound of the present invention and the combination drug, (2) simultaneous administration through the same administration route of two preparations obtained by separately formulating the compound of the present invention and the combination drug, (3) administration with a time interval through the same administration route of two preparations obtained by separately formulating the compound of the present invention and the combination drug, (4) simultaneous administration through different administration routes of two preparations obtained by separately formulating the compound of the present invention and the combination drug, (5) administration with a time interval through different administration routes of two preparations obtained by separately formulating the compound of the present invention and the combination drug (e.g., administration in order of the compound of the present invention and then the combination drug, or administration in the reverse order), or the like. The amount of the combination drug to be administered can be appropriately selected with reference to the clinically used dosage. The mixing ratio of the compound of the present invention and the combination drug can be appropriately selected in accordance with the subject of administration, administration route, disease to be treated, symptoms, combination, and the like.

The compound of the present invention can be also used in combination with, for example, gene therapy involving VEGF, TNFα or the like, or therapeutic methods involving various antibody medicines or the like.

The compound of the present invention can be safely administered individually, or according to ordinary methods (e.g., methods described in the Japanese Pharmacopeia, etc.), as a pharmaceutical composition mixed with pharmaceutically acceptable carriers, for example, a tablet (including a sugar-coated tablet and a film-coated tablet), a film, a powder, a granule, a capsule, a liquid, an emulsion, a suspension, an injectable preparation, a suppository, a sustained release preparation, a patch and the like, either orally or parenterally (e.g., topical, rectal, intravenous administration, etc.).

The dosage form of the aforementioned pharmaceutical preparation may be exemplified by oral preparations such as a tablet (including a sublingual tablet and a buccal disintegration tablet), a film (including a buccal disintegration film), a capsule (including a soft capsule and a microcapsule), a granule, a powder, a troche, a syrup, an emulsion, a suspension and the like; and parenteral preparations such as an injectable preparation (e.g., a subcutaneous injectable preparation, an intravenous injectable preparation, intramuscular injectable preparation, intraperitoneal injectable preparation, a drip infusion), external preparation (e.g., a percutaneous preparation, an ointment), a suppository (e.g., a rectal suppository, a vaginal suppository), a pellet, a transnasal preparation, a transpulmonary preparation (inhalant), an eye drop and the like.

These preparations may be controlled release preparations such as a rapid release preparation, a sustained release preparation and the like (e.g., a sustained release microcapsule).

The content of the compound of the present invention in the pharmaceutical composition is about 0.01 to 100% by weight of the entire composition.

The amount of administration of the compound of the present invention may vary depending on the subject of administration, administration route, subject disease or the like; however, in the case of administering orally to an adult as a hypertension medicine, the amount of administration is about 0.0005 to 2 mg/kg of body weight, preferably about 0.001 to 1 mg/kg of body weight, and more preferably about 0.001 to 0.5 mg/kg of body weight, in terms of compound (I) or (II), the active ingredient, possibly once to several times a day.

The aforementioned pharmaceutically acceptable carrier may be exemplified by various organic or inorganic carrier materials that are conventionally used as preparation materials, for example, excipient, gliding agent, binding agent and disintegrant for solid preparations; or solvent, solution aid, suspending agent, isotonic agent, buffering agent, soothing agent and the like for liquid preparations. Further, if necessary, additives such as preservative, antioxidant, colorant, sweetening agent, adsorbing agent, wetting agent and the like can be also used.

Examples of the excipient include lactose, white sugar, D-mannitol, starch, corn starch, crystalline cellulose, light anhydrous silicic acid and the like.

Examples of the gliding agent include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoic acid esters, chlorobutanol, benzyl alcohol, phenethyl alcohol, dehydroacetic acid, sorbic acid and the like.

Examples of the antioxidant include sulfites, ascorbic acid, α-tocopherol and the like.

Examples of the colorant include water-soluble Food coal tar dyes (e.g., Food dyes such as Food Red No. 2 and No. 3, Food Yellow No. 4 and No. 5, Food Blue No. 1 and No. 2, and the like), water-insoluble lake dyes (e.g., aluminum salts of the aforementioned water-soluble Food coal tar dyes), natural dyes (e.g., β-carotene, chlorophyll, red iron oxide) and the like.

Examples of the sweetening agent include saccharin sodium, dipotassium glycyrrhizinate, aspartame, stevia and the like.

EXAMPLES

The present invention is explained in detail in the following by referring to Reference Examples, Examples, Preparation Examples and Experimental Examples, which are not to be construed as limitative. Of the synthesis starting materials used in Reference Examples and Examples, synthesis methods of known compounds are omitted.

"Room temperature" in the following Reference Examples and Examples represents a temperature of about 10° C. to about 35° C., and "%" represents weight% unless otherwise stated. Provided that, yield represents mol/mol %.

$^1$H-NMR spectra were measured with a Varian MERCURY 300 (300 MHz) spectrometer or a BRUKER ADVANCE 300 spectrometer (300 MHz) using tetramethylsilane as an internal standard. All of the δ values are represented in ppm.

LC/MS spectra were measured under the following conditions (condition 1 or 2).

Condition 1: Equipment: Agilent 1100 HPLC (Gilson 215 autosampler)/Waters ZQ, or Waters 2795/ZQ Column: CapcellPak C18UG120 (1.5 mmID×35 mmL, S-3 μm), manufactured by Shiseido Co., Ltd.

solvent: SOLUTION A (0.05% trifluoroacetic acid-containing water), SOLUTION B (0.04% trifluoroacetic acid-containing water)

gradient cycle: 0.00 min (A/B=90/10), 2.00 min (A/B=5/95), 2.75 min (A/B=5/95), 2.76 min (A/B=90/10), 3.45 min (A/B=90/10)

flow rate: 0.5 ml/min detection: UV (220 nm)

Mass spectrum: electrospray method (ESI)

condition 2: Measurement instrument: LC-MS system, Waters Corporation

HPLC part: HP1100, Agilent Technologies, Inc.

MS part: Micromass ZMD

HPLC Conditions
Column: CAPCELL PAK C18UG120, S-3 µm, 1.5×35 mm (Shiseido Co., Ltd.)
Solvent: Solution A; 0.05% trifluoroacetic acid-containing water, Solution B; 0.04% trifluoroacetic acid-containing acetonitrile
Gradient cycle: 0.00 min (Solution A/Solution B=90/10), 2.00 min (Solution A/Solution B=5/95), 2.75 min (Solution A/Solution B=5/95), 2.76 min (Solution A/Solution B=90/10), 3.60 min (Solution A/Solution B=90/10)
Injection volume: 2 µL, Flow rate: 0.5 mL/min,
Detection method: UV 220 nm
MS Conditions
Ionization method: ESI
For reversed-phase preparative HPLC, Gilson Inc. UniPoint System equipped with YMC CombiPrep ODS-A (20 mmID×50 mmL, S-5 µm) column was used, and elution was performed using 0.1% trifluoroacetic acid-containing acetonitrile-water (10:90-100:0) at flow rate of 25 ml/min. Alternatively, the reversed-phase preparative HPLC was performed under the following conditions.
Equipment: Gilson Inc., High Throughput Purification System
Column: YMC Combi Prep Hydro Sphere S-5 µm, 19×50 mm
Solvent: Solution A; 0.1% trifluoroacetic acid-containing water, Solution B; 0.1% trifluoroacetic acid-containing acetonitrile
Gradient cycle: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5)
Flow rate: 20 mL/min, Detection method: UV 220 nm
The microwave reactor used was Discover of CEM.
Other symbols used in the present text indicate the following.
s: singlet, d: doublet, t: triplet, q: quartet, dd: double doublet, dt: double triplet, td: triple doublet, dq: double quartet, tq: triple quartet, ddd: double double doublet, m: multiplet, br: broad, quin: quintet.
DMF: N,N-dimethylformamide, DMA: N,N-dimethylacetamide, DMSO: dimethyl sulfoxide, THF: tetrahydrofuran.
HOBt: 1-hydroxybenzotriazole monohydrate, WSC.HCl: 1-ethyl-3-[3-(dimethylamino)propyl]carbodiimide hydrochloride.
TFA: trifluoroacetic acid.
MSA: methanesulfonic acid, DIEA: N-ethyldiisopropylamine, M: mole concentration.

Reference Example 1 dimethyl pyridine-3,5-dicarboxylate

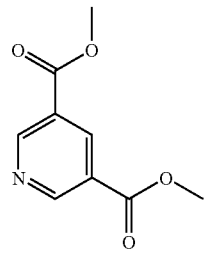

Pyridine-3,5-dicarboxylic acid (25.5 g) was suspended in methanol (184 ml), and thionyl chloride (33.8 ml) was added dropwise at room temperature. The reaction mixture was stirred with heating under reflux for 3 hr, and the mixture was allowed to cool to room temperature and concentrated under reduced pressure. The residue was diluted with water, and the mixture was extracted with ethyl acetate. The aqueous layer was neutralized with 8M aqueous sodium hydroxide solution, and extracted with ethyl acetate. The extract was washed successively with saturated aqueous sodium hydrogen carbonate solution and saturated brine, and dried over anhydrous sodium sulfate. The solvent was evaporated under reduced pressure to give the object product (27.9 g) as a powder.
$^1$H-NMR (CDCl$_3$) δ 4.00 (6H, s), 8.88(1H, t), 9.37(2H, d)

Reference Example 2

(3RS,5SR)-1-(tert-butoxycarbonyl)-5-(methoxycarbonyl)piperidine-3-carboxylic acid and (3RS,5RS)-1-(tert-butoxycarbonyl)-5-(methoxycarbonyl)piperidine-3-carboxylic acid and 1-tert-butyl 3,5-dimethyl piperidine-1,3,5-tricarboxylate

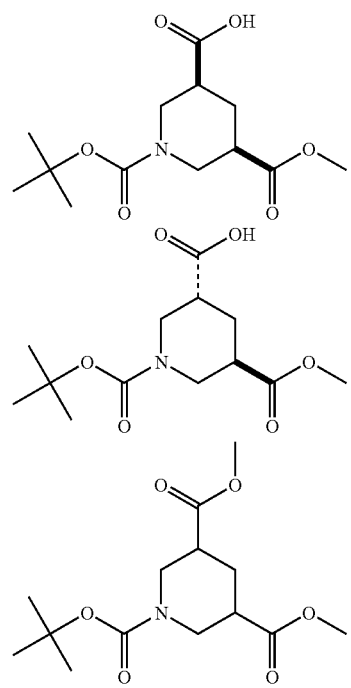

Dimethyl pyridine-3,5-dicarboxylate (15 g) was dissolved in methanol (150 ml), and 6M hydrochloric acid (19 ml) and rhodium-carbon (1.5 g) were added. The reaction mixture was stirred under hydrogen pressurization (5 atm) at 50° C. for 25 hr. The mixture was allowed to cool to room temperature, the rhodium catalyst was filtered off and the filtrate was concentrated under reduced pressure. The residue was dissolved in ethanol (100 ml), and triethylamine (16 ml) and di-tert-butyl bicarbonate (18.5 g) were successively added under ice-cooling. The reaction mixture was stirred at room temperature for 15 hr, and concentrated under reduced pressure. The residue was dissolved in 0.5M hydrochloric acid and the mixture was extracted with ethyl acetate. The extract was washed with saturated brine, and dried over anhydrous sodium sulfate. The solvent was evaporated under reduced pressure. The residue was subjected to silica gel column chromatography, and fractions eluted with hexane-ethyl acetate (7:1-1:4) were obtained. A less polar fraction was concentrated under reduced pressure to give 1-tert-butyl 3,5-dimethyl piperidine-1,3,5-tricarboxylate (15.2 g). A highly-polar fraction was concentrated under reduced pressure, and the residue was diluted with ethyl acetate. The precipitate was collected by filtration and washed with ethyl acetate to give (3RS,5SR)-1-(tert-butoxycarbonyl)-5-(methoxycarbonyl)piperidine-3-carboxylic acid (2.1 g) as a powder. The filtrate was concentrated under reduced pressure to give a mixture (4.2 g) of (3RS,5SR)-1-(tert-butoxycarbonyl)-5-(methoxycarbonyl)piperidine-3-carboxylic acid and (3RS,5RS)-1-(tert-butoxycarbonyl)-5-(methoxycarbonyl)piperidine-3-carboxylic acid.

(3RS,5SR)-1-(tert-butoxycarbonyl)-5-(methoxycarbonyl)piperidine-3-carboxylic acid $^1$H-NMR (CDCl$_3$) δ 1.47 (9H, s), 1.72 (1H, d), 2.41-2.63 (3H, m), 2.72 (2H, br s), 3.71 (3H, s), 4.38 (2H, d)

mixture of (3RS,5SR)-1-(tert-butoxycarbonyl)-5-(methoxycarbonyl)piperidine-3-carboxylic acid and (3RS,5RS)-1-(tert-butoxycarbonyl)-5-(methoxycarbonyl)piperidine-3-carboxylic acid $^1$H-NMR (CDCl$_3$) δ 1.44-1.47 (9H, m), 1.60-1.82 (1H, m), 2.10 (1H, br s), 2.38-2.61 (3H, m), 2.72 (2H, br s), 3.71 (3H, s), 4.38 (2H, br s)

1-tert-butyl 3,5-dimethyl piperidine-1,3,5-tricarboxylate $^1$H-NMR (CDCl$_3$) δ 1.45-1.49 (9H, m), 1.63-1.76 (1H, m), 2.07 (1H, br s), 2.38-2.55 (2H, m), 2.61-2.89 (2H, m), 3.70 (6H, s), 4.35 (2H, br s)

Reference Example 3

(3S,5R)-1-(tert-butoxycarbonyl)-5-(methoxycarbonyl)piperidine-3-carboxylic acid

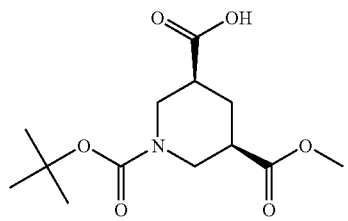 [SMILES: COC(=O)[C@@H]1C[C@H](C(=O)O)CN(C(=O)OC(C)(C)C)C1]

A mixture of (3RS,5SR)-1-(tert-butoxycarbonyl)-5-(methoxycarbonyl)piperidine-3-carboxylic acid (6.16 g), (R)-(+)-1-phenylethylamine (2.60 g) and ethanol (24 ml) was dissolved by heating to 70° C., and recrystallized. The precipitated crystals were collected by filtration, dissolved in ethanol (7 ml) again and recrystallized. The precipitated crystals were collected by filtration, the obtained crystals were suspended in water, acidified by adding saturated aqueous potassium hydrogen sulfate solution, and the mixture was extracted 3 times with ethyl acetate. The extract was washed with saturated brine, and dried over anhydrous magnesium sulfate. The solvent was evaporated under reduced pressure to give the object product (915 mg) as a powder.

specific optical rotation [α]20D: −6.2° (after drying, 20.12 mg, methanol, 2 ml, 100 mm)

$^1$H-NMR (DMSO-d$_6$) δ 1.39 (9H, s), 1.52 (1H, q), 2.18-2.54 (3H, m), 2.55-2.78 (2H, m), 3.63 (3H, s), 4.03-4.23 (2H, m), 12.51 (1H, br s)

Reference Example 4

(3R,5S)-1-(tert-butoxycarbonyl)piperidine-3,5-dicarboxylic acid

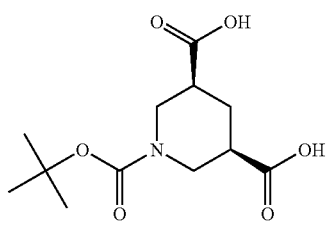 [SMILES: CC(C)(C)OC(=O)N1C[C@H](C(=O)O)C[C@H](C(=O)O)C1]

Dimethyl pyridine-3,5-dicarboxylate (62.8 g) was dissolved in acetic acid (300 mL), 5% rhodium-carbon (6 g) was added and the mixture was stirred under hydrogen pressurization (5 atm) at 50° C. for 20 hr. The reaction mixture was allowed to cool to room temperature, the rhodium catalyst was filtered off, and the filtrate was concentrated under reduced pressure. The residue was dissolved in methanol (300 mL), and triethylamine (180 mL) and di-tert-butyl bicarbonate (105 g) were successively added under ice-cooling. The reaction mixture was stirred at room temperature for 15 hr, and concentrated under reduced pressure. The residue was dissolved in water, and the mixture was adjusted to pH 3 with 6M hydrochloric acid and extracted with ethyl acetate. The ethyl acetate extraction layer was washed with saturated brine, and dried over anhydrous sodium sulfate. The solvent was evaporated under reduced pressure. The residue was dissolved in methanol (300 mL), and 8N aqueous sodium hydroxide solution (161 mL) was added dropwise at room temperature. The reaction mixture was stirred at room temperature for 20 hr, and methanol was evaporated under reduced pressure. The concentrate was diluted with saturated aqueous sodium hydrogen carbonate solution (100 ml) and washed twice with diethyl ether. The basic aqueous layer was acidified (pH 3) with 6M hydrochloric acid. The precipitated powder was collected by filtration, washed with water and air-dried to give the object product (80.5 g) as a powder.

$^1$H-NMR (DMSO-d$_6$) δ 1.34-1.43 (9H, m), 1.48 (1H, m), 2.15-2.42 (3H, m), 2.59-2.72 (2H, m), 4.13 (2H, d)

Reference Example 5

(3S,5R)-1-(tert-butoxycarbonyl)-5-(methoxycarbonyl)piperidine-3-carboxylic acid

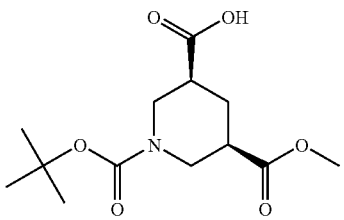 [SMILES: COC(=O)[C@@H]1C[C@H](C(=O)O)CN(C(=O)OC(C)(C)C)C1]

(3R,5S)-1-(tert-Butoxycarbonyl)piperidine-3,5-dicarboxylic acid (113 g) was suspended in acetic anhydride (1000 ml), and the mixture was heated under reflux for 3 hr and concentrated under reduced pressure. Toluene (100 ml) was added to the residue and the mixture was concentrated under reduced pressure. Toluene (100 ml) was added again and the mixture was concentrated under reduced pressure. A similar reaction was repeated twice to give a residue (209 g). The obtained residue (51 g) and quinidine (71 g) were dissolved in THF (900 ml), and the mixture was cooled to −40° C. A solution of methanol (81 ml) in THF (100 ml) was added dropwise over 30 min, and the mixture was stirred at the same temperature for 6 hr. THF (about 700 ml) was evaporated under reduced pressure, ethyl acetate was added and the mixture was washed with 2N hydrochloric acid. The aqueous layer was extracted with ethyl acetate, and the organic layers were combined, washed successively with 2N hydrochloric acid and saturated brine, and dried over anhydrous magnesium sulfate. The solvent was concentrated under reduced pressure. A similar reaction was repeated 3 times and the obtained residue (216 g) was suspended in ethanol (835 ml). (R)-(+)-1-Phenylethylamine (91 g) was added and dissolved by heating the mixture to 70° C. The hot ethanol solution was quickly filtered, and the filtrate was stood still at room temperature for 12 hr. The precipitated colorless crystals were collected by filtration, washed successively with ethyl acetate-hexane and hexane, and air dried. The obtained solid was suspended in water, saturated aqueous potassium hydrogen sulfate solution was added and the mixture was extracted 3 times with ethyl acetate. The organic layer was washed with saturated brine, dried over anhydrous magnesium sulfate and concentrated to dryness to give the object product (148 g) as a solid.

$^1$H-NMR (DMSO-$d_6$) δ 1.39 (9H, s), 1.52 (1H, q), 2.18-2.54 (3H, m), 2.55-2.78 (2H, m), 3.63 (3H, s), 4.03-4.23 (2H, m), 12.51 (1H, br s)

Reference Example 6

1-tert-butyl 3-methyl (3R,5S)-5-aminopiperidine-1,3-dicarboxylate

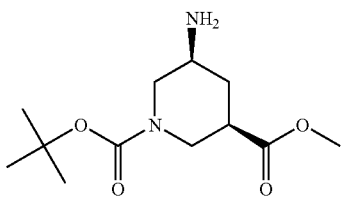 [SMILES: COC(=O)[C@@H]1C[C@H](N)CN(C(=O)OC(C)(C)C)C1]

(3S,5R)-1-(tert-Butoxycarbonyl)-5-(methoxycarbonyl)piperidine-3-carboxylic acid (2.83 g) was suspended in toluene (36 ml), diphenylphosphoryl azide (2.60 ml) and triethylamine (1.70 ml) were added, and the mixture was stirred at 100° C. for 1 hr. The reaction mixture was cooled to room temperature, benzyl alcohol (1.53 ml) and triethylamine (7.00 ml) were added and the mixture was stirred at 80° C. for 3 hr. The reaction mixture was concentrated, the residue was dissolved in ethyl acetate, and the solution was washed with water, 0.5M hydrochloric acid, and saturated brine in this order, and dried over anhydrous magnesium sulfate. The solvent was evaporated under reduced pressure. The residue was subjected to silica gel column chromatography, and a fraction eluted with ethyl acetate-hexane (1:3-3:1) was concentrated under reduced pressure. The obtained residue was dissolved in methanol (60 ml), 10% palladium carbon (50% in water) (150 mg) was added and the mixture was stirred under a hydrogen pressurization (5 atom) at ambient temperature for 5 hr. The catalyst was filtered off, and the filtrate was concentrated under reduced pressure to give the object product (1.83 g) as an oil.

$^1$H-NMR (CDCl$_3$) δ 1.22-1.43 (4H, m), 1.46 (9H, s), 2.27-2.79 (4H, m), 3.70 (3H, s), 4.13 (2H, br s)

In the same manner as in the method shown in Reference Example 6, the following compound (Reference Example 7) was obtained.

Reference Example 7

1-tert-butyl 3-methyl 5-aminopiperidine-1,3-dicarboxylate

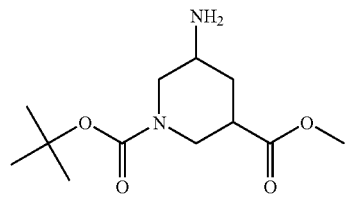 [SMILES: COC(=O)C1CC(N)CN(C(=O)OC(C)(C)C)C1]

$^1$H-NMR (CDCl$_3$) δ 1.19-1.41 (3H, m), 1.46-1.50 (9H, m), 1.82-2.78 (4H, m), 3.49 (1H, m), 3.64-3.73 (3H, m), 4.15 (2H, br s)

Reference Example 8

1-tert-butyl 3-methyl (3R,5S)-5-[(2-methylpropyl)amino]piperidine-1,3-dicarboxylate

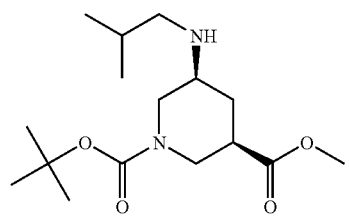 [SMILES: COC(=O)[C@@H]1C[C@H](NCC(C)C)CN(C(=O)OC(C)(C)C)C1]

1-tert-Butyl 3-methyl (3R,5S)-5-aminopiperidine-1,3-dicarboxylate (1.83 g), isobutyraldehyde (0.78 ml) and acetic acid (0.49 ml) were dissolved in methanol (50 ml), and the mixture was stirred at room temperature for 30 min. Sodium triacetoxyborohydride (3.80 g) was added to the reaction mixture, and the mixture was stirred at room temperature for 7 hr. The reaction mixture was concentrated under reduced pressure, the concentrate was basified with aqueous sodium bicarbonate, and extracted with ethyl acetate. The extract was washed with water and saturated brine, and dried over anhydrous magnesium sulfate. The solvent was evaporated under reduced pressure. The residue was subjected to silica gel column chromatography, and a fraction eluted with ethyl acetate-hexane (1:1)-ethyl acetate 100%-ethyl acetate-methanol (9:1) was concentrated under reduced pressure to give the object product (1.42 g) as an oil.

$^1$H-NMR (CDCl$_3$) δ 0.90 (6H, d), 1.22-1.38 (3H, m), 1.46 (9H, s), 1.69 (1H, dt), 2.23-2.39 (2H, m), 2.44-2.59 (1H, m), 2.47 (2H, d), 2.74 (1H, br s), 3.69 (3H, s), 4.18-4.34 (2H, m)

In the same manner as in the method shown in Reference Example 8, the following compound (Reference Example 9) was obtained.

Reference Example 9

1-tert-butyl 3-methyl 5-[(2-methylpropyl)amino]piperidine-1,3-dicarboxylate

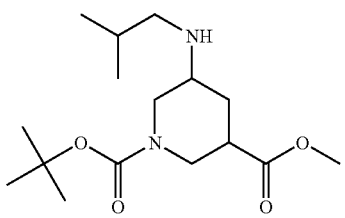 [SMILES: COC(=O)C1CC(NCC(C)C)CN(C(=O)OC(C)(C)C)C1]

$^1$H-NMR (CDCl$_3$) δ 0.93-1.09 (2H, m), 1.02 (4H, d), 1.45 (9H, d), 2.05 (3H, s), 2.65-2.79 (2H, m), 2.83-2.98 (1H, m), 3.25 (1H, dd), 3.49 (2H, s), 3.58-3.75 (3H, m), 3.94 (1H, d)

Reference Example 10 ethyl 1-(4-methoxybutyl)-7-oxo-4,5,6,7-tetrahydro-1H-indole-2-carboxylate

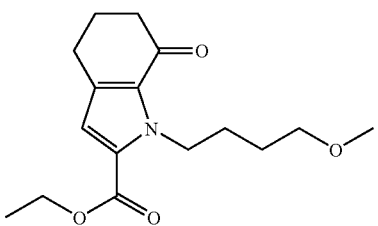 [SMILES: CCOC(=O)c1cc2c(n1CCCCOC)C(=O)CCC2]

A solution of ethyl 7-oxo-4,5,6,7-tetrahydro-1H-indole-2-carboxylate (207 mg), 4-methoxybutyl methanesulfonate (273 mg) and cesium carbonate (652 mg) in N,N-dimethylacetamide (10 ml) was stirred at 60° C. for 15 hr. After cooling to room temperature, the reaction mixture was diluted with water and extracted with ethyl acetate (10 ml×2). The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-3:7) was concentrated under reduced pressure to give the object product (250 mg).

MS (ESI+, m/e) 294 (M+1)

Reference Example 11

1-(4-methoxybutyl)-7-oxo-4,5,6,7-tetrahydro-1H-indole-2-carboxylic acid

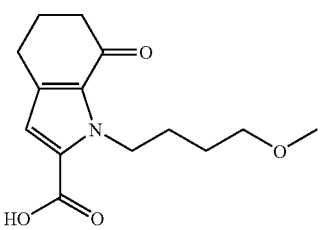 [SMILES: COCCCCn1c(C(=O)O)cc2c1C(=O)CCC2]

Ethyl 1-(4-methoxybutyl)-7-oxo-4,5,6,7-tetrahydro-1H-indole-2-carboxylate (250 mg) and lithium hydroxide monohydrate (54 mg) were dissolved in ethanol (4 ml) and water (2 ml), and the mixture was stirred at 60° C. for 3 hr. The solvent was concentrated under reduced pressure, and the residue was neutralized with 1N hydrochloric acid, extracted with ethyl acetate (10 ml×2), and dried over anhydrous magnesium sulfate. The solvent was evaporated under reduced pressure. The residue was subjected to silica gel column chromatography, and a fraction eluted with ethyl acetate-hexane (5:95-3:7) was concentrated under reduced pressure to give the object product (215 mg).

MS (ESI+, m/e) 266 (M+1)

Reference Example 12

4-methoxybutyl 1-(4-methoxybutyl)-4,5,6,7-tetrahydro-1H-indole-2-carboxylate

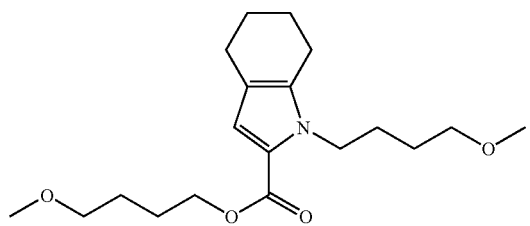

A solution of 4,5,6,7-tetrahydro-1H-indole-2-carboxylic acid (280 mg), 4-methoxybutyl methanesulfonate (775 mg) and cesium carbonate (2.77 g) in N,N-dimethylacetamide (25 ml) was stirred at 65° C. for 15 hr. After cooling to room temperature, the reaction mixture was diluted with water and extracted with ethyl acetate (20 ml×2). The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-3:7) was concentrated under reduced pressure to give the object product (375 mg).

MS (ESI+, m/e) 338 (M+1)

In the same manner as in Reference Example 11, the following compound (Reference Example 13) was obtained.

Reference Example 13

1-(4-methoxybutyl)-4,5,6,7-tetrahydro-1H-indole-2-carboxylic acid

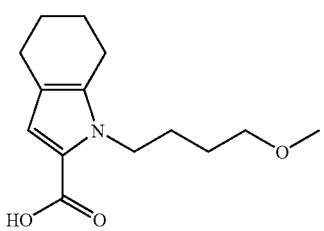

MS (ESI+, m/e) 252 (M+1)

Reference Example 14

1-(4-methoxybutyl)-1H-indole-2-carboxylic acid

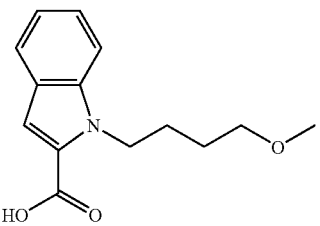 [SMILES: COCCCCn1c(C(=O)O)cc2ccccc21]

Methyl 1H-indole-2-carboxylate (0.67 g), cesium carbonate (1.9 g) and 4-methoxybutyl methanesulfonate (0.70 g) were suspended in DMA (20 ml), and the suspension was stirred at 60° C. for 4 hr. The reaction mixture was concentrated under reduced pressure, the residue was diluted with water, and the mixture was extracted with ethyl acetate. The extract was washed with saturated brine, dried over anhydrous magnesium sulfate and concentrated under reduced pressure. The obtained residue was subjected to silica gel chromatography, and a fraction eluted with ethyl acetate-hexane (0:10-4:6) was concentrated under reduced pressure. The obtained residue was dissolved in methanol (10 ml), 4N aqueous sodium hydroxide solution (5 ml) was added, and the mixture was heated at 80° C. for 2 hr. The mixture was allowed to cool to room temperature, acidified with 1N aqueous hydrochloric acid and extracted with ethyl acetate. The extract was washed with saturated brine, dried over anhydrous magnesium sulfate and concentrated under reduced pressure to give the object product (0.77 g).

$^1$H-NMR (DMSO-$d_6$) δ 1.32-1.53 (2H, m), 1.63-1.79 (2H, m), 3.18 (3H, s), 3.28 (2H, t), 4.59 (2H, t), 7.11 (1H, s), 7.23 (1H, d), 7.32 (1H, s), 7.58 (1H, dd), 7.67 (1H, d)

MS (ESI+, m/e) 248 (M+1)

Reference Example 15 tert-butyl (3S,5R)-3-[{[1-(4-methoxybutyl)-1H-indol-2-yl]carbonyl}(2-methylpropyl)amino]-5-(morpholin-4-ylcarbonyl)piperidine-1-carboxylate

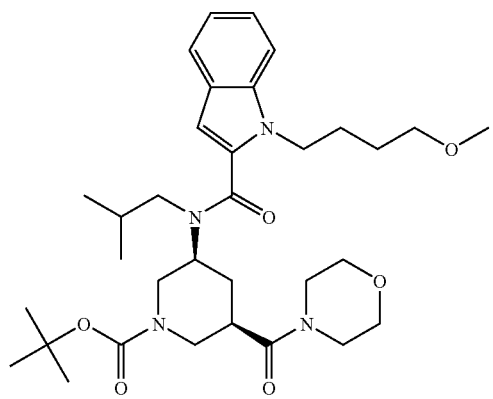 [SMILES: COCCCCn1c(C(=O)N(CC(C)C)[C@H]2C[C@@H](C(=O)N3CCOCC3)CN(C(=O)OC(C)(C)C)C2)cc2ccccc21]

1-(4-Methoxybutyl)-1H-indole-2-carboxylic acid (210 mg), tert-butyl (3S,5R)-3-[(2-methylpropyl)amino]-5-(morpholin-4-ylcarbonyl)piperidine-1-carboxylate (270 mg) and N,N-diisopropylethylamine (560 μl) were dissolved in 1,2-dichloroethane (10 ml), chloro-N,N,N',N'-tetramethylformamidinium hexafluorophosphate (360 mg) was added, and the mixture was stirred at room temperature for 2 hr. The reaction mixture was concentrated, and the residue was subjected to silica gel column chromatography, and a fraction eluted with ethyl acetate-hexane (0:10-10:0) was concentrated under reduced pressure to give the object product (83 mg).

MS (ESI+, m/e) 599 (M+1)

Reference Example 16 methyl 2-[(tert-butoxycarbonyl)(4-methoxybutyl)amino]-3-nitrobenzoate

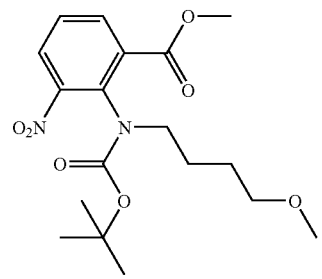 [SMILES: COCCCCN(C(=O)OC(C)(C)C)c1c(C(=O)OC)cccc1[N+](=O)[O-]]

Methyl 2-[(tert-butoxycarbonyl)amino]-3-nitrobenzoate (3.0 g), 4-methoxybutyl methanesulfonate (2.0 g) and potassium carbonate (2.1 g) were dissolved in DMF (30 ml), and the mixture was stirred at 60° C. overnight. The reaction mixture was concentrated, aqueous potassium carbonate solution was added, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (0:10→8:2) was concentrated under reduced pressure to give the object product (2.9 g).

$^1$H-NMR (CDCl$_3$) δ 1.28-1.34 (9H, m), 1.47-1.61 (6H, m), 3.28 (3H, s), 3.30-3.40 (2H, m), 3.90-3.95 (3H, m), 7.49 (1H, s), 7.91-8.02 (1H, m), 8.04-8.16 (1H, m)

Reference Example 17 methyl 1-(4-methoxybutyl)-2-(trichloromethyl)-1H-benzimidazole-7-carboxylate

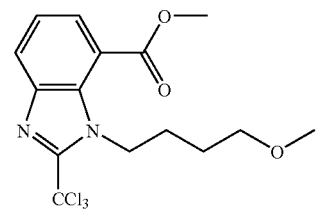

Methyl 2-[(tert-butoxycarbonyl)(4-methoxybutyl)amino]-3-nitrobenzoate (2.9 g) was dissolved in methanol (30 ml), palladium-carbon (5%, 500 mg) was added, and the mixture was stirred for 3 hr under a hydrogen atmosphere. The reaction mixture was filtered through celite, and the filtrate was concentrated under reduced pressure. The residue (1.8 g) was dissolved in acetic acid (40 ml), methyl 2,2,2-trichloroethanimidate (0.88 ml) was added, and the mixture was stirred at 50° C. for 6 hr. The reaction mixture was poured into water, and the mixture was extracted with ethyl acetate. The extract was washed with saturated brine, and dried over anhydrous magnesium sulfate. The solvent was evaporated under reduced pressure to give the object product (2.6 g).

$^1$H-NMR (CDCl$_3$) δ 1.71 (4H, br s), 3.31 (3H, s), 3.37 (2H, t), 4.00 (3H, s), 4.91 (1H, dd), 4.92 (1H, d), 7.36 (1H, t), 7.83 (1H, dd), 8.06 (1H, dd)

Reference Example 18 methyl 3-[(2-methoxyethoxy)methyl]imidazo[1,2-a]pyridine-2-carboxylate

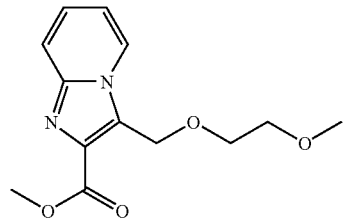

To a solution of methyl 3-(hydroxymethyl)imidazo[1,2-a]pyridine-2-carboxylate (0.30 g) in DMF (5 ml) was added sodium hydride (60 mg) under ice-cooling. The mixture was stirred at room temperature for 30 min, 2-methoxyethyl bromide (220 mg) was added under ice-cooling, and the mixture was stirred at 60° C. for 3 hr. The reaction mixture was concentrated under reduced pressure, and the residue was diluted with aqueous potassium carbonate, and the mixture was extracted with ethyl acetate. The extract was washed with saturated brine, dried over anhydrous sodium sulfate, and concentrated under reduced pressure. The obtained residue was subjected to silica gel chromatography, and a fraction eluted with ethyl acetate-hexane (0:10-10:0) was concentrated under reduced pressure to give the object product (0.16 g).

$^1$H NMR (CDCl$_3$) δ 3.42 (3H, s), 3.48-3.57 (2H, m), 3.65 (2H, dd), 3.95-4.00 (3H, m), 5.31 (2H, d), 6.88 (1H, dd), 7.26 (1H, dd), 7.66 (1H, dt), 8.07-8.20 (1H, m)

MS (ESI+, m/e) 265 (M+1)

Reference Example 19

1-tert-butyl 3-methyl (3R,5S)-5-{[(benzyloxy)carbonyl]amino}piperidine-1,3-dicarboxylate

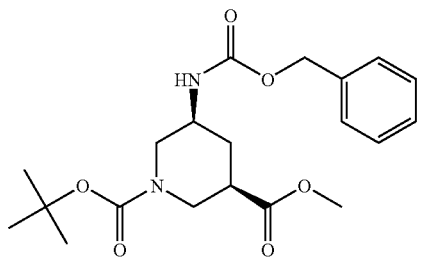 [SMILES: COC(=O)[C@@H]1C[C@H](NC(=O)OCc2ccccc2)CN(C(=O)OC(C)(C)C)C1]

(3S,5R)-1-(tert-Butoxycarbonyl)-5-(methoxycarbonyl)piperidine-3-carboxylic acid (2.83 g) was suspended in toluene (36 ml), diphenylphosphoryl azide (2.60 ml) and triethylamine (1.70 ml) were added and the mixture was stirred at 100° C. for 1 hr. The reaction mixture was cooled to room temperature, benzyl alcohol (1.53 ml) and triethylamine (7.00 ml) were added and the mixture was stirred at 80° C. for 3 hr. The reaction mixture was concentrated, the residue was dissolved in ethyl acetate, washed with water, 0.5M hydrochloric acid and saturated brine in this order, and dried over anhydrous magnesium sulfate. The solvent was evaporated under reduced pressure. The residue was subjected to silica gel column chromatography, and a fraction eluted with ethyl acetate-hexane (1:3-3:1) was concentrated under reduced pressure to give the object product (2.79 g) as an oil.

MS (ESI+, m/e) 393 (M+1)

Reference Example 20

(3R,5S)-5-{[(benzyloxy)carbonyl]amino}-1-(tert-butoxycarbonyl)piperidine-3-carboxylic acid

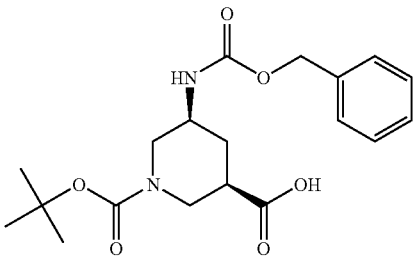 [SMILES: CC(C)(C)OC(=O)N1C[C@@H](NC(=O)OCc2ccccc2)C[C@@H](C(=O)O)C1]

To a solution (700 ml) of 1-tert-butyl 3-methyl (3R,5S)-5-{[(benzyloxy)carbonyl]amino}piperidine-1,3-dicarboxylate (115 g) in methanol was added 1M aqueous sodium hydroxide solution (350 ml) under ice-cooling, and the mixture was stirred at room temperature for 12 hr. The reaction mixture was concentrated under reduced pressure to about 1/3 volume, and the residual aqueous solution was washed with ethyl acetate-hexane (1:1, 600 ml). The aqueous layer was neutralized with 1M hydrochloric acid and the mixture was extracted with ethyl acetate. The extract was washed with saturated brine, and dried over anhydrous magnesium sulfate. The solvent was evaporated under reduced pressure to give the object product (98.5 g).

$^1$H-NMR (DMSO-d$_6$) δ: 1.33 (1H, br s), 1.40 (9H, s), 2.09 (1H, d), 2.36-2.52 (3H, m), 3.93-4.09 (2H, m), 5.03 (2H, s), 7.28-7.43 (5H, m), 12.52 (1H, br s).

Reference Example 21 tert-butyl (3S,5R)-3-{[(benzyloxy)carbonyl]amino}-5-(morpholin-4-ylcarbonyl)piperidine-1-carboxylate

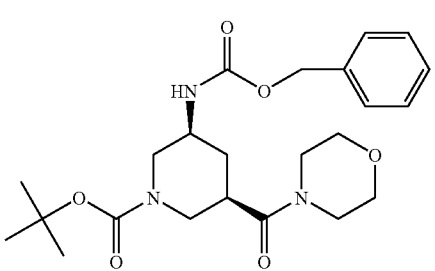 [SMILES: CC(C)(C)OC(=O)N1C[C@@H](NC(=O)OCc2ccccc2)C[C@@H](C(=O)N2CCOCC2)C1]

(3R,5S)-5-{[(Benzyloxy)carbonyl]amino}-1-(tert-butoxycarbonyl)piperidine-3-carboxylic acid (49.2 g), morpholine (11.4 ml), 1H-benzotriazol-1-ol (10.0 g) and triethylamine (40 ml) were dissolved in DMF (250 ml), WSC.HCl (30.0 g) was added, and the mixture was stirred at room temperature for 4 days. The reaction mixture was poured into water, and the mixture was extracted with ethyl acetate. The extract was washed successively with saturated aqueous sodium hydrogen carbonate solution and saturated brine, and dried over anhydrous magnesium sulfate. The solvent was evaporated under reduced pressure to give the object product (62.9 g).

$^1$H-NMR (CDCl$_3$) δ: 1.46 (9H, s), 1.69 (2H, br s), 2.04 (1H, s), 2.73 (2H, br s), 2.79-2.96 (1H, m), 3.52-3.65 (6H, m), 3.69 (2H, d), 3.67 (1H, br s), 4.04 (1H, d), 5.09 (2H, s), 5.40 (1H, br s), 7.25-7.41 (5H, m).

Reference Example 22 tert-butyl (3S,5R)-3-[(2-methylpropyl)amino]-5-(morpholin-4-ylcarbonyl)piperidine-1-carboxylate

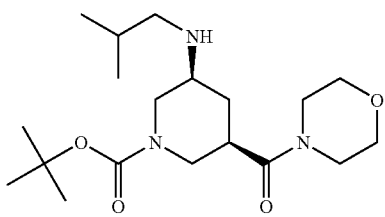 [SMILES: CC(C)CN[C@H]1C[C@@H](C(=O)N2CCOCC2)CN(C(=O)OC(C)(C)C)C1]

tert-Butyl (3S,5R)-3-{[(benzyloxy)carbonyl]amino}-5-(morpholin-4-ylcarbonyl)piperidine-1-carboxylate (58 g) and palladium(II) hydroxide-carbon (5 g) were suspended in methanol (400 ml) and the mixture was stirred under a hydrogen atmosphere (1 atom) at room temperature for 16 hr. The palladium catalyst was filtered off, and the filtrate was concentrated under reduced pressure. The obtained residue and acetic acid (8.8 ml) were dissolved in methanol (400 ml), 2-methylpropanal (14.0 ml) was added, and the mixture was stirred at room temperature for 1 hr. Sodium triacetoxyborohydride (40.4 g) was added to the reaction mixture, and the mixture was stirred at room temperature for 2 hr. The reaction mixture was concentrated under reduced pressure, and the concentrate was basified with 3.5M aqueous potassium carbonate solution, and the mixture was extracted with ethyl acetate. The extract was washed with saturated brine, and dried over anhydrous magnesium sulfate. The solvent was evaporated under reduced pressure. The residue was subjected to basic silica gel column chromatography, and a fraction eluted with ethyl acetate-hexane (1:5)-ethyl acetate-hexane (1:1) was concentrated under reduced pressure to give the object product (33.3 g).

$^1$H-NMR (CDCl$_3$) δ: 0.90 (6H, d), 1.46 (9H, s), 1.54 (1H, d), 1.69 (1H, dt), 1.96-2.12 (2H, m), 2.23-2.37 (1H, m), 2.47 (3H, d), 2.66 (1H, d), 3.61 (1H, br s), 3.55 (2H, d), 3.69 (5H, ddd), 4.01-4.46 (2H, m).

Reference Example 23 tert-butyl (3S,5R)-3-[{[1-(4-methoxybutyl)-7-oxo-4,5,6,7-tetrahydro-1H-indol-2-yl]carbonyl}(2-methylpropyl)amino]-5-(morpholin-4-ylcarbonyl)piperidine-1-carboxylate

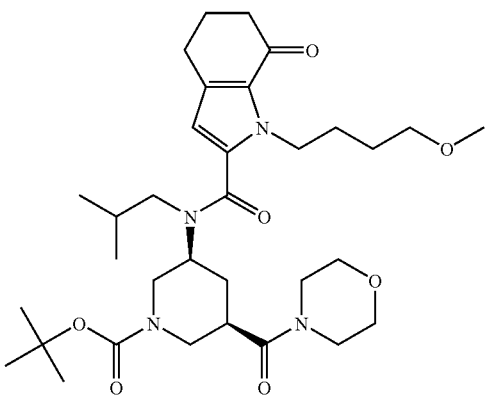 [SMILES: COCCCCn1c(C(=O)N(CC(C)C)[C@H]2C[C@@H](C(=O)N3CCOCC3)CN(C(=O)OC(C)(C)C)C2)cc2c1C(=O)CCC2]

1-(4-Methoxybutyl)-7-oxo-4,5,6,7-tetrahydro-1H-indole-2-carboxylic acid (210 mg), tert-butyl (3S,5R)-3-[(2-methylpropyl)amino]-5-(morpholin-4-ylcarbonyl)piperidine-1-carboxylate (292 mg) and N,N-diisopropylethylamine (550 μl) were dissolved in 1,2-dichloroethane (10 ml), chloro-N,N,N',N'-tetramethylformamidinium hexafluorophosphate (244 mg) was added, and the mixture was stirred at room temperature for 15 hr. The reaction mixture was diluted with saturated aqueous sodium hydrogen carbonate solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (245 mg).

MS (ESI+, m/e) 617 (M+1)

In the same manner as in Reference Example 23, the following compound (Reference Example 24) was obtained.

Reference Example 24 tert-butyl (3S,5R)-3-[{[1-(4-methoxybutyl)-4,5,6,7-tetrahydro-1H-indol-2-yl]carbonyl}(2-methylpropyl)amino]-5-(morpholin-4-ylcarbonyl)piperidine-1-carboxylate

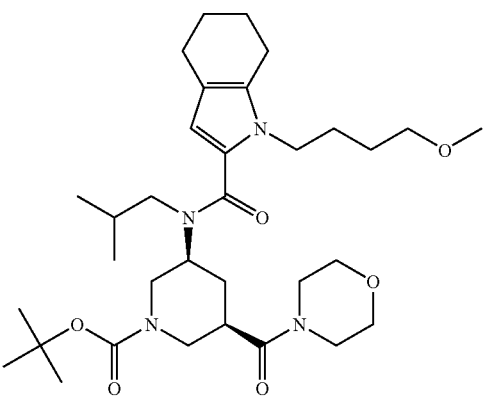

MS (ESI+, m/e) 603 (M+1)

Example 1

1-(4-methoxybutyl)-N-(2-methylpropyl)-N-[(3S,5R)-5-(morpholin-4-ylcarbonyl)piperidin-3-yl]-4,5,6,7-tetrahydro-1H-indole-2-carboxamide

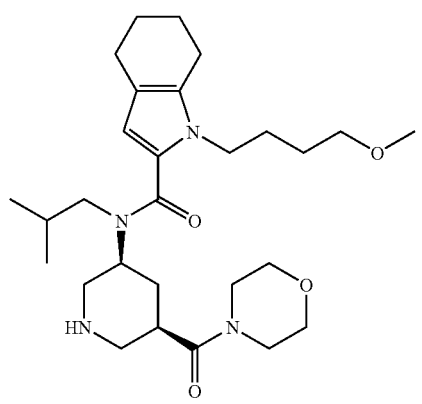 [SMILES: COCCCCn1c(C(=O)N(CC(C)C)[C@@H]2CNC[C@H](C(=O)N3CCOCC3)C2)cc2c1CCCC2]

tert-Butyl (3S,5R)-3-[{[1-(4-methoxybutyl)-4,5,6,7-tetrahydro-1H-indol-2-yl]carbonyl}(2-methylpropyl)amino]-5-(morpholin-4-ylcarbonyl)piperidine-1-carboxylate (100 mg) was dissolved in dichloromethane (0.5 ml), TFA (0.5 ml) was added, and the mixture was stirred at room temperature for 15 min. The solvent was evaporated under reduced pressure, and the residue was neutralized with saturated aqueous sodium hydrogen carbonate. The mixture was extracted with ethyl acetate (10 ml×2), and dried over anhydrous magnesium sulfate. The solvent was evaporated under reduced pressure. The residue was dried under reduced pressure to give the object product (45 mg).
MS (ESI+, m/e) 503 (M+1)

Example 2

1-(4-methoxybutyl)-N-(2-methylpropyl)-N-[(3S,5R)-5-(morpholin-4-ylcarbonyl)piperidin-3-yl]-7-oxo-4,5,6,7-tetrahydro-1H-indole-2-carboxamide monohydrochloride

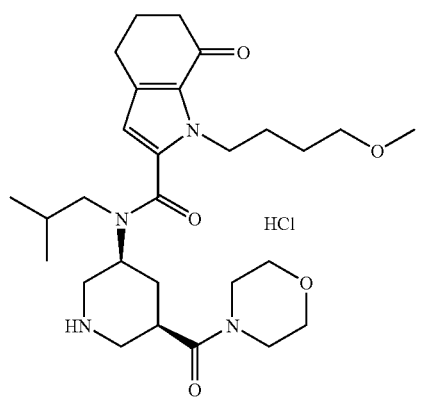 [SMILES: COCCCCn1c(C(=O)N(CC(C)C)[C@@H]2CNC[C@H](C(=O)N3CCOCC3)C2)cc2c1C(=O)CCC2 ; Cl]

tert-Butyl (3S,5R)-3-[{[1-(4-methoxybutyl)-7-oxo-4,5,6,7-tetrahydro-1H-indol-2-yl]carbonyl}(2-methylpropyl)amino]-5-(morpholin-4-ylcarbonyl)piperidine-1-carboxylate (100 mg) was dissolved in ethyl acetate (1 ml), 4N hydrogen chloride-ethyl acetate solution (1 ml) was added, and the mixture was stirred at room temperature for 1 hr. The solvent was evaporated under reduced pressure, and the residue was dried under reduced pressure to give the object product (52 mg).
MS (ESI+, m/e) 517 (M+1)

Example 3

1-(4-methoxybutyl)-N-(2-methylpropyl)-N-[(3S,5R)-5-(morpholin-4-ylcarbonyl)piperidin-3-yl]-1H-indole-2-carboxamide hydrochloride

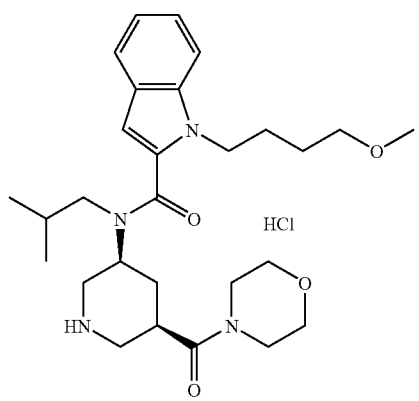 [SMILES: COCCCCn1c(C(=O)N(CC(C)C)[C@@H]2CNC[C@H](C(=O)N3CCOCC3)C2)cc2ccccc21 ; Cl]

tert-Butyl (3S,5R)-3-[{[1-(4-methoxybutyl)-1H-indol-2-yl]carbonyl}(2-methylpropyl)amino]-5-(morpholin-4-ylcarbonyl)piperidine-1-carboxylate (83.4 mg) was dissolved in 4N hydrogen chloride-ethyl acetate (3 ml), and the mixture was stirred at room temperature for 1.5 hr. The reaction mixture was concentrated to give the object product (67 mg).
MS (ESI+, m/e) 499 (M+1)

Example 4

3-[(2-methoxyethoxy)methyl]-N-(2-methylpropyl)-N-[(3S,5R)-5-(morpholin-4-ylcarbonyl)piperidin-3-yl]imidazo[1,2-a]pyridine-2-carboxamide dihydrochloride

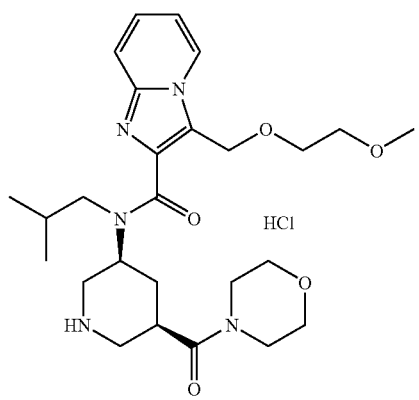 [SMILES: COCCOCc1c(C(=O)N(CC(C)C)[C@@H]2CNC[C@H](C(=O)N3CCOCC3)C2)nc2ccccn12 ; Cl]

Methyl 3-[(2-methoxyethoxy)methyl]imidazo[1,2-a]pyridine-2-carboxylate (160 mg) and lithium hydroxide (76 mg) were dissolved in water (10 ml) and methanol (2 ml), and the mixture was stirred at 70° C. for 6 hr. The mixture was allowed to cool to room temperature, acidified with 1N aqueous hydrochloric acid and extracted with ethyl acetate. The extract was washed with saturated brine, dried over anhydrous magnesium sulfate and concentrated under reduced pressure. The residue, tert-butyl (3S,5R)-3-[(2-methylpropyl)amino]-5-(morpholin-4-ylcarbonyl)piperidine-1-carboxylate (130 mg) and N,N-diisopropylethylamine (340 μg) were dissolved in 1,2-dichloroethane (10 ml), chloro-N,N,N',N'-tetramethylformamidinium hexafluorophosphate (220 mg) was added, and the mixture was stirred at room temperature for 3 hr. The reaction mixture was concentrated, diluted with aqueous calcium carbonate solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (0:10-10:0) was concentrated under reduced pressure. The residue was dissolved in 4N hydrogen chloride-ethyl acetate (1 ml), and the mixture was stirred at room temperature for 1.5 hr. The reaction mixture was concentrated to give the object product (65 mg).

MS (ESI+, m/e) 502 (M+1)

Example 5

4-(4-methoxybutyl)-N-(2-methylpropyl)-N-[(3S,5R)-5-(morpholin-4-ylcarbonyl)piperidin-3-yl]-4H-thieno[3,2-b]pyrrole-5-carboxamide

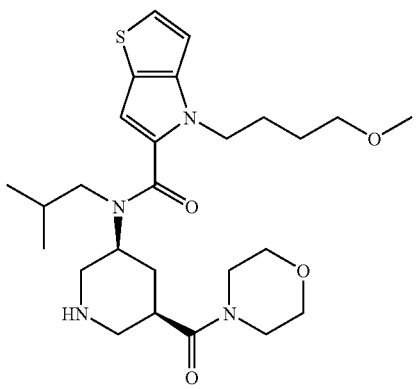 [SMILES: COCCCCn1c(C(=O)N(CC(C)C)[C@@H]2CNC[C@H](C(=O)N3CCOCC3)C2)cc2sccc21]

4H-Thieno[3,2-b]pyrrole-5-carboxylic acid (160 mg), tert-butyl (3S,5R)-3-[(2-methylpropyl)amino]-5-(morpholin-4-ylcarbonyl)piperidine-1-carboxylate (250 mg) and N,N-diisopropylethylamine (630 μl) were dissolved in 1,2-dichloroethane (10 ml), chloro-N,N,N',N'-tetramethylformamidinium hexafluorophosphate (410 mg) was added, and the mixture was stirred at room temperature for 3 hr. The reaction mixture was concentrated, diluted with aqueous calcium carbonate solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (0:10-10:0) was concentrated under reduced pressure. The residue was dissolved in DMA (10 ml), cesium carbonate (790 mg) and 4-methoxybutyl methanesulfonate (230 mg) were added, and the mixture was stirred at 70° C. overnight. The reaction mixture was concentrated under reduced pressure, the residue was diluted with water, and the mixture was extracted with ethyl acetate. The extract was washed with saturated brine, dried over anhydrous magnesium sulfate and concentrated under reduced pressure. The residue was dissolved in TFA (1.0 ml), and the mixture was stirred at room temperature for 30 min and concentrated under reduced pressure. This was purified by HPLC, and the object fraction was concentrated, diluted with aqueous calcium carbonate solution and the mixture was extracted with ethyl acetate. The extract was washed with saturated brine, and dried over anhydrous magnesium sulfate. The solvent was evaporated under reduced pressure to give the object product (52 mg).

MS (ESI+, m/e) 505 (M+1)

Example 6 methyl 2-{(2-methylpropyl)[(3S,5R)-5-(morpholin-4-ylcarbonyl)piperidin-3-yl]carbamoyl}-1-(4-methoxybutyl)-3H-benzimidazole-7-carboxylate dihydrochloride

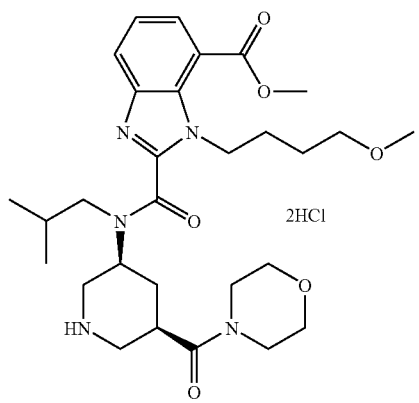 [SMILES: COCCCCn1c(C(=O)N(CC(C)C)[C@@H]2CNC[C@H](C(=O)N3CCOCC3)C2)nc2cccc(C(=O)OC)c21 ; "2HCl"]

Methyl 1-(4-methoxybutyl)-2-(trichloromethyl)-1H-benzimidazole-7-carboxylate (0.44 g) and tert-butyl (3S,5R)-3-[(2-methylpropyl)amino]-5-(morpholin-4-ylcarbonyl)piperidine-1-carboxylate (0.3 g) were dissolved in acetonitrile (5.0 ml) and water (5.0 ml), potassium carbonate (2.4 g) was added, and the mixture was stirred at 60° C. overnight. The reaction mixture was cooled to room temperature, and the mixture was extracted with ethyl acetate. The extract was washed successively with 10% aqueous citric acid solution, aqueous sodium bicarbonate and saturated brine, and dried over anhydrous magnesium sulfate. The solvent was evaporated under reduced pressure. The residue was subjected to silica gel column chromatography, and a fraction eluted with ethyl acetate-hexane (0:10→10:0) was concentrated under reduced pressure, and a fraction eluted with ethyl acetate was concentrated under reduced pressure. The residue was dissolved in 4N hydrochloric acid-ethyl acetate solution, and the mixture was stirred for 30 min. The reaction mixture was concentrated, purified by HPLC, and the object fraction was concentrated, diluted with aqueous calcium carbonate solution and the mixture was extracted with ethyl acetate. The extract was washed with saturated brine, and dried over anhydrous magnesium sulfate. The solvent was evaporated under reduced pressure, and converted to hydrochloride with 4N hydrochloric acid-ethyl acetate solution to give the object product (9.3 mg).

MS (ESI+, m/e) 558 (M+1)

Example 7

(5-methyl-2-oxo-1,3-dioxol-4-yl)methyl (3R,5S)-5-[{[1-(4-methoxybutyl)-1H-benzimidazol-2-yl]carbonyl}(2-methylpropyl)amino]piperidine-3-carboxylate dihydrochloride

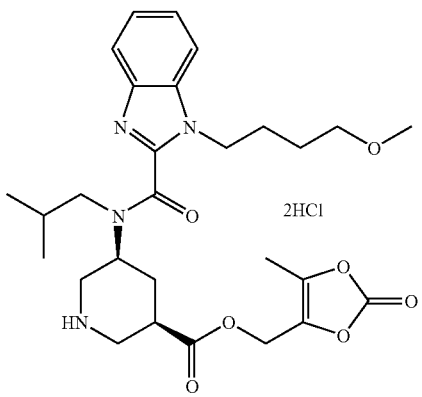 [SMILES: COCCCCn1c(C(=O)N(CC(C)C)[C@@H]2CNC[C@H](C(=O)OCc3oc(=O)oc3C)C2)nc2ccccc21 ; "2HCl"]

(3R,5S)-1-(tert-Butoxycarbonyl)-5-[{[1-(4-methoxybutyl)-1H-benzimidazol-2-yl]carbonyl}(2-methylpropyl)amino]piperidine-3-carboxylic acid (0.3 g) and 4-(hydroxymethyl)-5-methyl-1,3-dioxol-2-one (0.09 g) were dissolved in DMA (3.0 ml), toluenesulfonyl chloride (0.13 g), DMAP (0.014 g) and potassium carbonate (0.1 g) were added with stirring under ice-cooling, and the mixture was stirred for 6 hr under ice-cooling, and further at room temperature overnight. The reaction mixture was neutralized with 1N aqueous hydrochloric acid and extracted with ethyl acetate. The extract was washed successively with aqueous sodium bicarbonate and saturated brine, and dried over anhydrous magnesium sulfate. The solvent was evaporated under reduced pressure. The residue was subjected to silica gel column chromatography, and a fraction eluted with ethyl acetate-hexane (0:10→1:1) was concentrated under reduced pressure, and a fraction eluted with ethyl acetate was concentrated under reduced pressure. The residue was dissolved in 2N hydrochloric acid-ethyl acetate solution, and the mixture was stirred at room temperature for 1 hr. The reaction mixture was concentrated to give the object product (186 mg).

MS (ESI+, m/e) 543 (M+1)

Example 8 methyl (3R,5S)-5-[{[1-(4-methoxybutyl)-1H-indol-2-yl]carbonyl}(2-methylpropyl)amino]piperidine-3-carboxylate

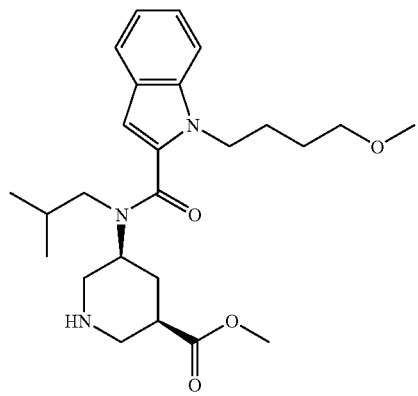 [SMILES: COCCCCn1c(C(=O)N(CC(C)C)[C@@H]2CNC[C@H](C(=O)OC)C2)cc2ccccc21]

1-(4-Methoxybutyl)-1H-indole-2-carboxylic acid (247 mg), 1-tert-butyl 3-methyl (3R,5S)-5-[(2-methylpropyl)amino]piperidine-1,3-dicarboxylate (314 mg) and diisopropylethylamine (862 µl) were dissolved in methylene chloride (5 ml), chloro-N,N,N',N'-tetramethylformamidinium hexafluorophosphate (337 mg) was added, and the mixture was stirred at room temperature for 15 hr. The reaction mixture was subjected to silica gel column chromatography, and a fraction eluted with ethyl acetate-hexane (3:7) was concentrated under reduced pressure to give 1-tert-butyl 3-methyl (3R,5S)-5-[{[1-(4-methoxybutyl)-1H-indol-2-yl]carbonyl}(2-methylpropyl)amino]piperidine-1,3-dicarboxylate (40 mg) as an oil. The obtained 1-tert-butyl 3-methyl (3R,5S)-5-[{[1-(4-methoxybutyl)-1H-indol-2-yl]carbonyl}(2-methylpropyl)amino]piperidine-1,3-dicarboxylate (40 mg) was dissolved in methanol (2 ml), 4M hydrogen chloride-ethyl acetate (2 ml) was added, and the mixture was stirred at room temperature for 15 hr. The reaction mixture was concentrated, and the residue was purified by reversed-phase preparative HPLC, and the object fraction was concentrated under reduced pressure. An aqueous sodium bicarbonate solution was added to the residue, and the mixture was extracted with ethyl acetate. The extract was washed with saturated brine, dried over anhydrous magnesium sulfate, and concentrated to give the object product (13 mg).

MS (ESI+, m/e) 444 (M+1)

Reference Example 25 methyl 1-(2-phenylethyl)-1H-indole-2-carboxylate

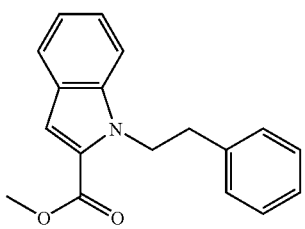 [SMILES: COC(=O)c1cc2ccccc2n1CCc1ccccc1]

Methyl 1H-indole-2-carboxylate (526 mg) and (2-bromoethyl)benzene (1.11 g) were dissolved in DMA (15 ml), cesium carbonate (2.93 g) was added, and the mixture was stirred at 60° C. for 15 hr. The reaction mixture was concentrated, and the residue was diluted with aqueous sodium bicarbonate, and the mixture was extracted with ethyl acetate. The extract was washed with saturated brine, dried over anhydrous magnesium sulfate, and concentrated. The residue was subjected to silica gel column chromatography, and a fraction eluted with ethyl acetate-hexane (3:7) was concentrated under reduced pressure to give the object product (318 mg) as an oil.

MS (ESI+, m/e) 280 (M+1)

Reference Example 26 tert-butyl (3S,5R)-3-[(2-methylpropyl){[1-(2-phenyl-ethyl)-1H-indol-2-yl]carbonyl}amino]-5-(morpho-lin-4-ylcarbonyl)piperidine-1-carboxylate

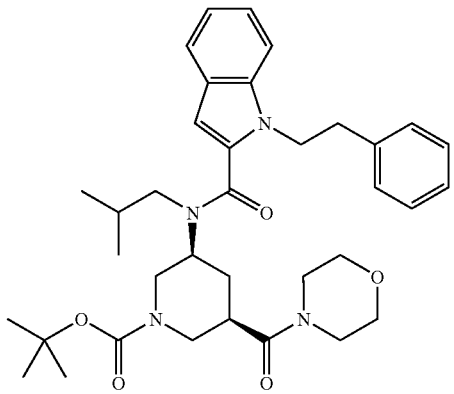 [SMILES: CC(C)CN(C(=O)c1cc2ccccc2n1CCc1ccccc1)[C@H]1C[C@@H](C(=O)N2CCOCC2)CN(C(=O)OC(C)(C)C)C1]

Methyl 1-(2-phenylethyl)-1H-indole-2-carboxylate (318 mg) was dissolved in methanol (5 ml), 2M aqueous sodium hydroxide solution (1.14 ml) was added, and the mixture was stirred at room temperature for 17 hr. The aqueous layer was adjusted to pH 7 with 1M hydrochloric acid, saturated brine was added, and the mixture was extracted with ethyl acetate. The extract was washed with saturated brine, and dried over anhydrous sodium sulfate. The solvent was evaporated under reduced pressure to give 1-(2-phenylethyl)-1H-indole-2-carboxylic acid (300 mg). The obtained 1-(2-phenylethyl)-1H-indole-2-carboxylic acid (300 mg), 1-tert-butyl 3-methyl (3R,5S)-5-[(2-methylpropyl)amino]piperidine-1,3-dicarboxylate (185 mg) and diisopropylethylamine (431 μl) were dissolved in methylene chloride (5 ml), chloro-N,N,N',N'-tetramethylformamidinium hexafluorophosphate (168 mg) was added, and the mixture was stirred at room temperature for 15 hr. Aqueous sodium bicarbonate was added to the reaction mixture, and the mixture was extracted with ethyl acetate. The extract was washed with saturated brine, and dried over anhydrous sodium sulfate. The solvent was evaporated under reduced pressure, and the residue was subjected to silica gel column chromatography, and a fraction eluted with ethyl acetate was concentrated under reduced pressure to give the object product (83 mg).
MS (ESI+, m/e) 617 (M+1)

Example 9

N-(2-methylpropyl)-N-[(3S,5R)-5-(morpholin-4-ylcarbonyl)piperidin-3-yl]-1-(2-phenylethyl)-1H-indole-2-carboxamide hydrochloride

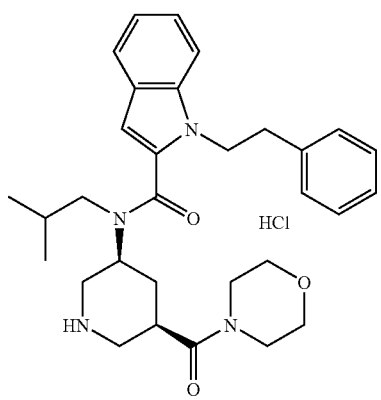 [SMILES: CC(C)CN(C(=O)c1cc2ccccc2n1CCc1ccccc1)[C@@H]1CNC[C@H](C(=O)N2CCOCC2)C1 ; Cl]

tert-Butyl (3S,5R)-3-[(2-methylpropyl){[1-(2-phenyl-ethyl)-1H-indol-2-yl]carbonyl}amino]-5-(morpholin-4-yl-carbonyl)piperidine-1-carboxylate (83 mg) was dissolved in 4M hydrogen chloride-ethyl acetate (2 ml), and the mixture was stirred at room temperature for 15 hr. The reaction mixture was concentrated to give the object product (75 mg).
MS (ESI+, m/e) 517 (M+1)

Reference Example 27

N-(4-methoxybutyl)benzene-1,2-diamine

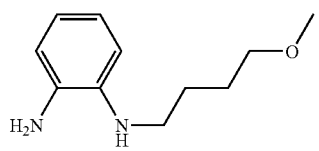

To a solution of phenylenediamine (10.8 g) and 4-methoxybutyl methanesulfonate (9.11 g) in acetonitrile (100 ml) was added potassium carbonate (20.7 g), and the mixture was stirred heated under reflux for 15 hr. Water was added to the reaction mixture, and the mixture was extracted twice with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (35:65) was concentrated under reduced pressure to give the object product (5.44 g).
$^1$H-NMR (CDCl$_3$) δ 1.67-1.82 (4H, m), 3.13 (2H, t), 3.24-3.39 (6H, m), 3.38-3.50 (2H, m), 6.62-6.74 (3H, m), 6.81 (1H, m).
MS (ESI+, m/e) 195 (M+1)

Reference Example 28 tert-butyl (3S,5R)-3-{[ethoxy(oxo)acetyl](2-methyl-propyl)amino}-5-(morpholin-4-ylcarbonyl)piperi-dine-1-carboxylate

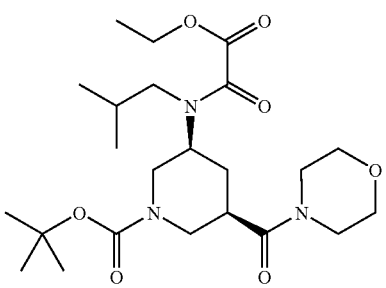 [SMILES: CCOC(=O)C(=O)N(CC(C)C)[C@H]1C[C@@H](C(=O)N2CCOCC2)CN(C(=O)OC(C)(C)C)C1]

To a solution of tert-butyl (3S,5R)-3-[(2-methylpropyl)amino]-5-(morpholin-4-ylcarbonyl)piperidine-1-carboxylate (9.24 g) and diisopropylethylamine (10.5 ml) in DMA (100 ml) was added dropwise ethyl chloroglyoxylate (3.4 ml) at 0° C. The reaction mixture was stirred at room temperature for 15 hr, and the reaction mixture was concentrated. An aqueous sodium bicarbonate solution was added to the residue, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate was concentrated under reduced pressure to give the object product (10.3 g).

$^1$H-NMR (CDCl$_3$) δ 0.84-1.00 (6H, m), 1.37 (3H, q), 1.42-1.53 (9H, m), 1.80-2.19 (3H, m), 2.26-2.42 (1H, m), 2.59-2.96 (1H, m), 2.97-3.30 (3H, m), 3.37-3.92 (9H, m), 4.01-4.26 (2H, m), 4.26-4.40 (2H, m).

MS (ESI+, m/e) 470 (M+1)

Reference Example 29

{[(3S,5R)-1-(tert-butoxycarbonyl)-5-(morpholin-4-ylcarbonyl)piperidin-3-yl](2-methylpropyl)amino} (oxo)acetic acid

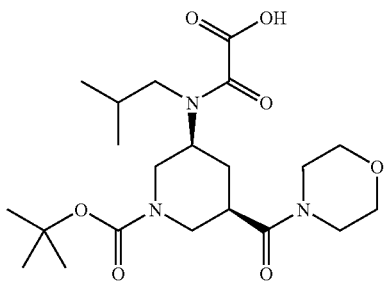 [SMILES: CC(C)CN(C(=O)C(=O)O)[C@H]1C[C@@H](C(=O)N2CCOCC2)CN(C(=O)OC(C)(C)C)C1]

To a solution of tert-butyl (3S,5R)-3-{[ethoxy(oxo)acetyl](2-methylpropyl)amino}-5-(morpholin-4-ylcarbonyl)piperidine-1-carboxylate (10.3 g) in ethanol (40 ml) was added 2M aqueous sodium hydroxide solution (22 ml), and the mixture was stirred at room temperature for 6 hr. The reaction mixture was adjusted to pH 7 with 1M hydrochloric acid, and extracted with ethyl acetate. The extract was washed with saturated brine, and dried over anhydrous magnesium sulfate. The solvent was evaporated under reduced pressure to give the object product (10.3 g).

$^1$H-NMR (CDCl$_3$) δ 0.78-0.99 (6H, m), 1.37-1.52 (9H, m), 1.79-2.16 (3H, m), 2.38-3.86 (14H, m), 3.93-4.43 (2H, m).

MS (ESI+, m/e) 442 (M+1)

Reference Example 30 tert-butyl (3S,5R)-3-{[({2-[(4-methoxybutyl)amino]phenyl}amino)(oxo)acetyl](2-methylpropyl)amino}-5-(morpholin-4-ylcarbonyl)piperidine-1-carboxylate

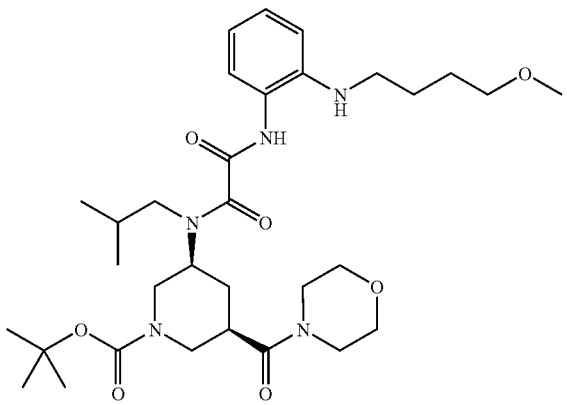 [SMILES: COCCCCNc1ccccc1NC(=O)C(=O)N(CC(C)C)[C@H]1C[C@@H](C(=O)N2CCOCC2)CN(C(=O)OC(C)(C)C)C1]

{[(3S,5R)-1-(tert-Butoxycarbonyl)-5-(morpholin-4-ylcarbonyl)piperidin-3-yl](2-methylpropyl)amino}(oxo)acetic acid (10.3 g), HOBt (4.13 g) and WSC.HCl (6.28 g) were dissolved in DMF (50 ml), N-(4-methoxybutyl)benzene-1,2-diamine (4.67 g) and diisopropylethylamine (11.3 ml) were added, and the mixture was stirred at room temperature for 15 hr and at 60° C. for 2 hr. The reaction mixture was concentrated, and the residue was diluted with aqueous sodium bicarbonate, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate was concentrated under reduced pressure to give the object product (9.11 g).

$^1$H-NMR (CDCl$_3$) δ 0.86-1.03 (6H, m), 1.37-1.53 (9H, m), 1.70 (4H, d), 1.86-2.26 (3H, m), 2.37-2.97 (3H, m), 3.09-3.22 (3H, m), 3.25-3.48 (6H, m), 3.48-3.98 (10H, m), 4.01-4.97 (2H, m), 6.70-6.84 (2H, m), 7.10-7.21 (1H, m), 7.35 (1H, dd), 8.47-8.80 (1H, m).

MS (ESI+, m/e) 618 (M+1)

Reference Example 31 tert-butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate and 1-(4-methoxybutyl)-N-(2-methylpropyl)-N-[(3S,5R)-5-(morpholin-4-ylcarbonyl)piperidin-3-yl]-1H-benzimidazole-2-carboxamide

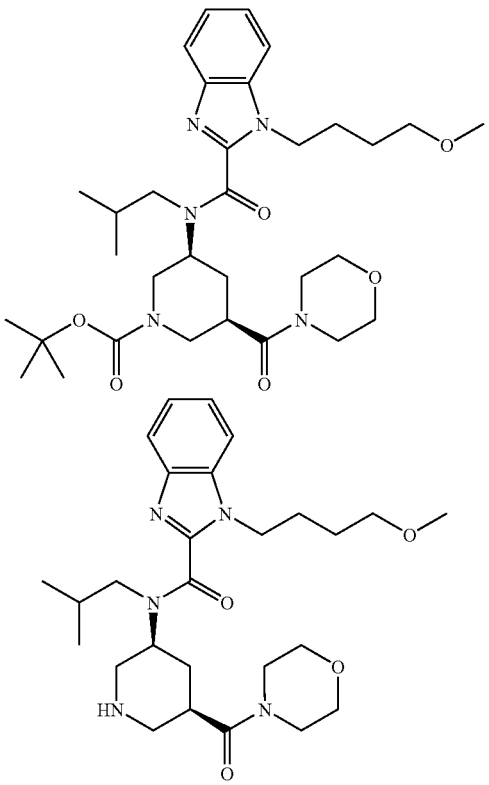

tert-Butyl (3S,5R)-3-{[({2-[(4-methoxybutyl)amino]phenyl}amino)(oxo)acetyl](2-methylpropyl)amino}-5-(morpholin-4-ylcarbonyl)piperidine-1-carboxylate (9.11 g) was dissolved in acetic acid (50 ml), and the mixture was stirred at 80° C. for 15 hr. The reaction mixture was cooled to room temperature and concentrated under reduced pressure, the residue was diluted with aqueous sodium bicarbonate, and the mixture was extracted with ethyl acetate. The extract was washed with saturated brine, and dried over anhydrous magnesium sulfate. The solvent was evaporated under reduced pressure. The residue was subjected to basic silica gel column chromatography, and a fraction eluted with ethyl acetate was concentrated under reduced pressure to give tert-butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate (5.85 g), and a fraction eluted with ethyl acetate-methanol (85:15) was concentrated under reduced pressure to give 1-(4-methoxybutyl)-N-(2-methylpropyl)-N-[(3S,5R)-5-(morpholin-4-ylcarbonyl)piperidin-3-yl]-1H-benzimidazole-2-carboxamide (580 mg).

tert-butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate $^1$H-NMR (CDCl$_3$) δ 0.63-0.80 (2H, m), 0.89-1.07 (4H, m), 1.41-1.59 (9H, m), 1.59-1.80 (2H, m), 1.87-2.23 (4H, m), 2.30-2.98 (3H, m), 3.21-3.46 (6H, m), 3.49-3.91 (10H, m), 3.95-4.47 (5H, m), 7.18-7.51 (3H, m), 7.56-7.84 (1H, m).

MS (ESI+, m/e) 600 (M+1)

1-(4-methoxybutyl)-N-(2-methylpropyl)-N-[(3S,5R)-5-(morpholin-4-ylcarbonyl)piperidin-3-yl]-1H-benzimidazole-2-carboxamide $^1$H-NMR (CDCl$_3$) δ 0.64-0.74 (2H, m), 0.95-1.07 (4H, m), 1.43-1.74 (3H, m), 1.84-2.41 (4H, m), 2.48-2.67 (1H, m), 2.67-3.01 (3H, m), 3.03-3.44 (8H, m), 3.47-3.78 (9H, m), 4.06-4.46 (3H, m), 7.28-7.47 (3H, m), 7.62-7.81 (1H, m).

MS (ESI+, m/e) 500 (M+1)

Example 10

1-(4-methoxybutyl)-N-(2-methylpropyl)-N-[(3S,5R)-5-(morpholin-4-ylcarbonyl)piperidin-3-yl]-1H-benzimidazole-2-carboxamide dihydrochloride

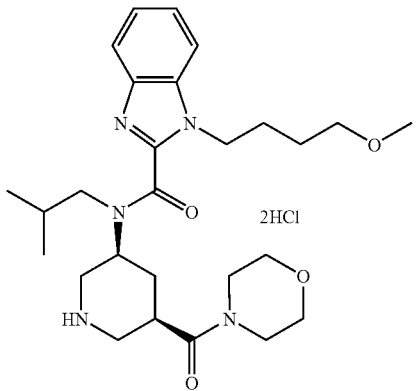 [SMILES: COCCCCn1c(C(=O)N(CC(C)C)[C@@H]2CNC[C@H](C(=O)N3CCOCC3)C2)nc2ccccc21 ; "2HCl"]

tert-Butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate (5.85 g) was dissolved in methanol (20 ml), 4M hydrogen chloride-ethyl acetate (20 ml) was added, and the mixture was stirred at room temperature for 15 hr. The reaction mixture was concentrated, and the residue was diluted with aqueous sodium bicarbonate, and the mixture was extracted with ethyl acetate. The extract was washed with saturated brine, and dried over anhydrous magnesium sulfate. The solvent was evaporated under reduced pressure. The residue was subjected to basic silica gel column chromatography, and a fraction eluted with ethyl acetate-methanol (9:1) was concentrated under reduced pressure to give 1-(4-methoxybutyl)-N-(2-methylpropyl)-N-[(3S,5R)-5-(morpholin-4-ylcarbonyl)piperidin-3-yl]-1H-benzimidazole-2-carboxamide (4.40 g). The obtained 1-(4-methoxybutyl)-N-(2-methylpropyl)-N-[(3S,5R)-5-(morpholin-4-ylcarbonyl)piperidin-3-yl]-1H-benzimidazole-2-carboxamide (2.20 g) was dissolved in ethyl acetate (20 ml), 4M hydrogen chloride-ethyl acetate (5 ml) and methanol (20 ml) were added, and the mixture was stirred at room temperature for 5 min. The reaction mixture was concentrated under reduced pressure to give the object product (2.52 g).

$^1$H-NMR (DMSO-d$_6$) δ 0.63-0.76 (2H, m), 0.85-1.00 (4H, m), 1.40-1.60 (2H, m), 1.68-1.89 (2H, m), 1.93-2.17 (2H, m), 2.20-2.44 (2H, m), 2.81-3.81 (20H, m), 4.19-4.39 (3H, m), 7.23-7.46 (2H, m), 7.57-7.81 (2H, m), 8.38-9.77 (2H, m).

MS (ESI+, m/e) 500 (M+1)

Reference Example 32

5-fluoro-N-(4-methoxybutyl)-2-nitroaniline

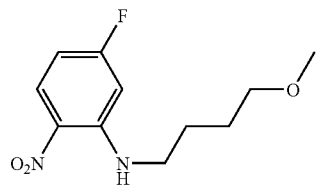 [SMILES: COCCCCNc1cc(F)ccc1[N+](=O)[O-]]

5-Fluoro-2-nitroaniline (1.0 g) was dissolved in THF (20 ml), sodium hydride (60% in oil, 384 mg) was added, and the mixture was stirred at room temperature for 30 min. 4-Methoxybutyl methanesulfonate (1.28 g) was added, and the mixture was heated under reflux with stirring for 15 hr. The reaction mixture was cooled to room temperature and saturated brine was added, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (30:70) was concentrated under reduced pressure to give the object product (494 mg).

$^1$H-NMR (CDCl$_3$) δ 1.66-1.77 (2H, m), 1.78-1.89 (2H, m), 3.25-3.34 (2H, m), 3.36 (3H, s), 3.45 (2H, t), 6.36 (1H, ddd), 6.49 (1H, dd), 8.16-8.27 (2H, m).

MS (ESI+, m/e) 243 (M+1)

Reference Example 33

4-fluoro-2-(4-methoxybutylamino)aniline

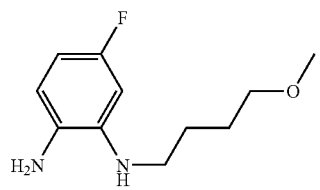

5-Fluoro-N-(4-methoxybutyl)-2-nitroaniline (494 mg) was dissolved in methanol (20 ml), 10% palladium carbon (50% in water, 100 mg) was added, and the mixture was stirred under a hydrogen stream at ambient temperature and normal pressure for 15 hr. The catalyst was filtered off, and the filtrate was concentrated under reduced pressure to give the object product (451 mg) as an oil.

$^1$H-NMR (CDCl$_3$) δ 1.63 (2H, br s), 1.67-1.81 (4H, m), 3.08 (1H, br s), 3.10 (2H, t), 3.36 (3H, s), 3.39-3.47 (2H, m), 6.26-6.38 (2H, m), 6.61 (1H, dd).

MS (ESI+, m/e) 213 (M+1)

Reference Example 34 tert-butyl (3S,5R)-3-{[({4-fluoro-2-[(4-methoxybutyl)amino]phenyl}amino)(oxo)acetyl](2-methylpropyl)amino}-5-(morpholin-4-ylcarbonyl)piperidine-1-carboxylate

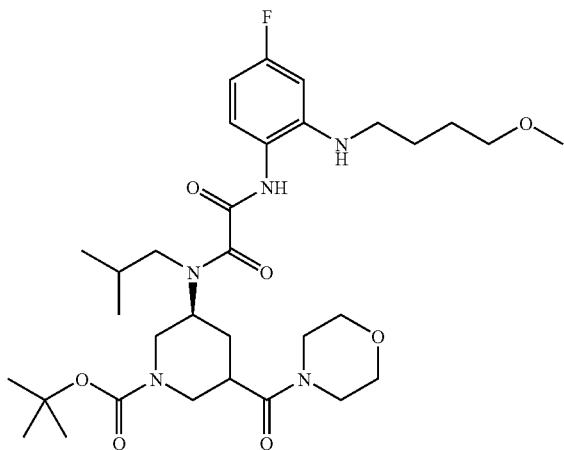 [SMILES: COCCCCNc1cc(F)ccc1NC(=O)C(=O)N(CC(C)C)[C@H]1CC(C(=O)N2CCOCC2)CN(C(=O)OC(C)(C)C)C1]

{[(3S,5R)-1-(tert-Butoxycarbonyl)-5-(morpholin-4-ylcarbonyl)piperidin-3-yl](2-methylpropyl)amino}(oxo)acetic acid (221 mg), HOBt (95 mg) and WSC.HCl (144 mg) were dissolved in DMF (5 ml), 4-fluoro-2-(4-methoxybutylamino)aniline (106 mg) and diisopropylethylamine (97 μl) were added, and the mixture was stirred at room temperature for 15 hr and at 60° C. for 2 hr. The reaction mixture was cooled to room temperature, and concentrated under reduced pressure. The residue was diluted with aqueous sodium bicarbonate and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (9.11 mg).

$^1$H-NMR (CDCl$_3$) δ 0.89-1.01 (6H, m), 1.39-1.53 (9H, m), 1.61-1.79 (4H, m), 1.88-2.19 (2H, m), 3.05-3.21 (4H, m), 3.30-3.37 (5H, m), 3.38-3.49 (3H, m), 3.48-3.79 (12H, m), 3.95-4.22 (1H, m), 6.35-6.48 (2H, m), 7.11-7.21 (1H, m), 8.52 (1H, s).

MS (ESI+, m/e) 636 (M+1)

Example 11

6-fluoro-1-(4-methoxybutyl)-N-(2-methylpropyl)-N-[(3S,5R)-5-(morpholin-4-ylcarbonyl)piperidin-3-yl]-1H-benzimidazole-2-carboxamide dihydrochloride

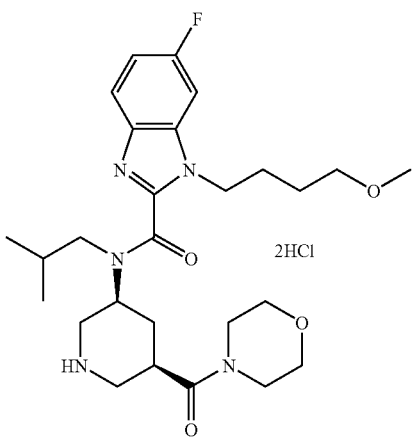 [SMILES: COCCCCn1c(C(=O)N(CC(C)C)[C@@H]2CNC[C@H](C(=O)N3CCOCC3)C2)nc2ccc(F)cc21 ; "2HCl"]

tert-Butyl (3S,5R)-3-{[({4-fluoro-2-[(4-methoxybutyl)amino]phenyl}amino)(oxo)acetyl](2-methylpropyl)amino}-5-(morpholin-4-ylcarbonyl)piperidine-1-carboxylate (294 mg) was dissolved in acetic acid (5 ml), and the mixture was stirred at 80° C. for 3 days. The reaction mixture was cooled to room temperature, 4M hydrogen chloride-ethyl acetate (5 ml) was added to the reaction mixture, and the mixture was stirred at room temperature for 2 hr. The reaction mixture was concentrated, and the residue was diluted with aqueous sodium bicarbonate, and extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate-methanol (85:15) was concentrated under reduced pressure. The residue was dissolved in ethyl acetate, 4M hydrogen chloride-ethyl acetate (1 ml) was added, and the mixture was concentrated again to give the object product (113 mg).

$^1$H-NMR (DMSO-d$_6$) δ 0.64-0.79 (2H, m), 0.83-1.01 (4H, m), 1.37-1.60 (2H, m), 1.66-1.89 (2H, m), 1.91-2.18 (2H, m), 2.15-2.44 (1H, m), 2.85-3.85 (20H, m), 4.30 (3H, t), 7.09-7.25 (1H, m), 7.57-7.79 (2H, m), 8.57 (1H, br s), 9.20-9.42 (1H, m), 9.46-9.81 (1H, m).

MS (ESI+, m/e) 518 (M+1)

Reference Example 35

6-fluoro-1-(4-methoxybutyl)-2-(trichloromethyl)-1H-benzimidazole

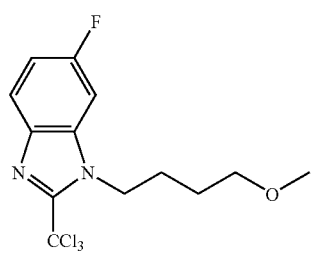

4-Fluoro-2-(4-methoxybutylamino)aniline (4.28 g) was dissolved in acetic acid (100 ml), methyl 2,2,2-trichloroethanimidate (2.49 ml) was added dropwise, and the mixture was stirred at room temperature for 2 hr. The reaction mixture was concentrated under reduced pressure, and the residue was azeotroped with toluene. The residue was subjected to silica gel column chromatography, and a fraction eluted with ethyl acetate was concentrated under reduced pressure to give the object product (6.53 g).

$^1$H-NMR (CDCl$_3$) δ 1.71-1.84 (2H, m), 2.00-2.14 (2H, m), 3.38 (3H, s), 3.48 (2H, t), 4.46-4.59 (2H, m), 7.03-7.16 (2H, m), 7.81 (1H, dd).

MS (ESI+, m/e) 339 (M+1)

Reference Example 36 tert-butyl (3S,5R)-3-[{[6-fluoro-1-(4-methoxybutyl)-1H-benzimidazol-2-yl]carbonyl}(2-methylpropyl)amino]-5-(morpholin-4-ylcarbonyl)piperidine-1-carboxylate

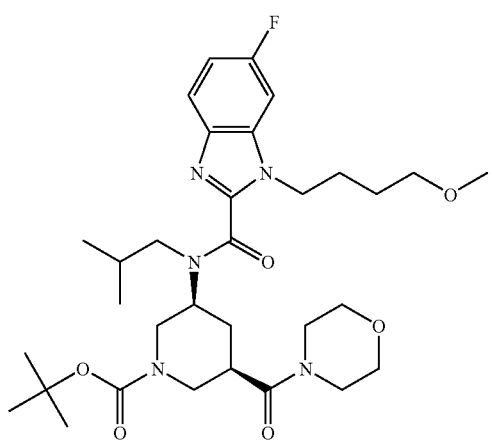 [SMILES: COCCCCn1c(C(=O)N(CC(C)C)[C@H]2C[C@@H](C(=O)N3CCOCC3)CN(C(=O)OC(C)(C)C)C2)nc2ccc(F)cc21]

6-Fluoro-1-(4-methoxybutyl)-2-(trichloromethyl)-1H-benzimidazole (1.02 g) and tert-butyl (3S,5R)-3-[(2-methylpropyl)amino]-5-(morpholin-4-ylcarbonyl)piperidine-1-carboxylate (1.11 g) were dissolved in acetonitrile (50 ml) and water (25 ml), potassium carbonate (4.15 g) was added, and the mixture was stirred at 60° C. for 17 hr. The reaction mixture was cooled to room temperature, and the mixture was extracted with ethyl acetate. The extract was washed successively with 10% aqueous citric acid solution, aqueous sodium bicarbonate and saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (595 mg).

$^1$H-NMR (CDCl$_3$) δ 0.64-0.82 (3H, m), 0.89-1.05 (3H, m), 1.41-1.60 (9H, m), 1.59-1.78 (2H, m), 1.83-2.24 (3H, m), 2.28-2.99 (3H, m), 3.33 (17H, d), 3.96-4.43 (5H, m), 7.00-7.17 (2H, m), 7.49-7.75 (1H, m).

MS (ESI+, m/e) 618 (M+1)

Example 12

6-fluoro-1-(4-methoxybutyl)-N-(2-methylpropyl)-N-[(3S,5R)-5-(morpholin-4-ylcarbonyl)piperidin-3-yl]-1H-benzimidazole-2-carboxamide dihydrochloride

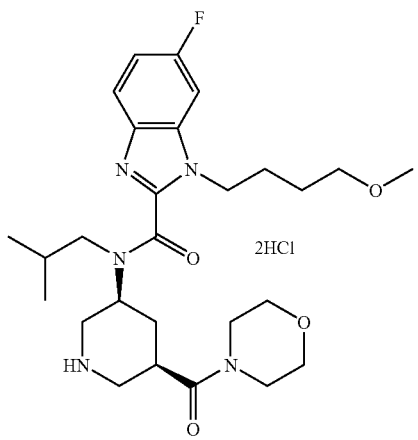 [SMILES: COCCCCn1c(C(=O)N(CC(C)C)[C@@H]2CNC[C@H](C(=O)N3CCOCC3)C2)nc2ccc(F)cc21 ; "2HCl"]

tert-Butyl (3S,5R)-3-[{[6-fluoro-1-(4-methoxybutyl)-1H-benzimidazol-2-yl]carbonyl}(2-methylpropyl)amino]-5-(morpholin-4-ylcarbonyl)piperidine-1-carboxylate was dissolved in 4M hydrogen chloride-ethyl acetate (5 ml), and the mixture was stirred at room temperature for 4 hr. The reaction mixture was concentrated to give the object product (567 mg).

$^1$H-NMR (DMSO-d$_6$) δ 0.64-0.79 (2H, m), 0.83-1.01 (4H, m), 1.37-1.60 (2H, m), 1.66-1.89 (2H, m), 1.91-2.18 (2H, m), 2.15-2.44 (1H, m), 2.85-3.85 (20H, m), 4.30 (3H, t), 7.09-7.25 (1H, m), 7.57-7.79 (2H, m), 8.57 (1H, br s), 9.20-9.42 (1H, m), 9.46-9.81 (1H, m).

MS (ESI+, m/e) 518 (M+1)

Reference Example 37

1-tert-butyl 3-methyl (3R,5S)-5-[{[6-fluoro-1-(4-methoxybutyl)-1H-benzimidazol-2-yl]carbonyl}(2-methylpropyl)amino]piperidine-1,3-dicarboxylate and (3R,5S)-1-(tert-butoxycarbonyl)-5-[{[6-fluoro-1-(4-methoxybutyl)-1H-benzimidazol-2-yl]carbonyl}(2-methylpropyl)amino]piperidine-3-carboxylic acid

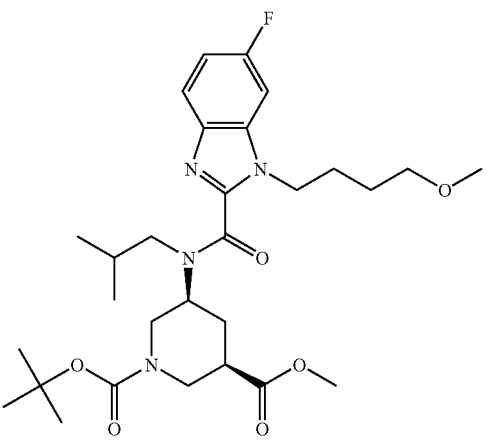

-continued

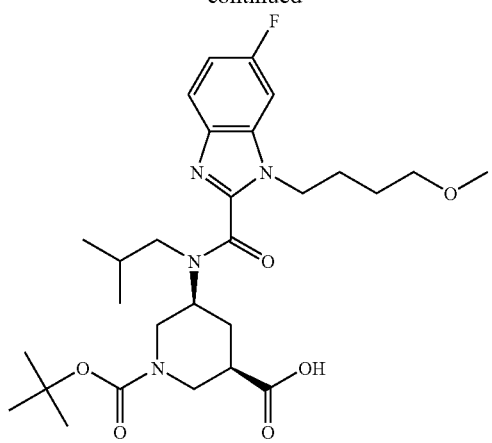

6-Fluoro-1-(4-methoxybutyl)-2-(trichloromethyl)-1H-benzimidazole (3.40 g) and 1-tert-butyl 3-methyl (3R,5S)-5-[(2-methylpropyl)amino]piperidine-1,3-dicarboxylate (3.14 g) were dissolved in acetonitrile (100 ml) and water (50 ml), cesium carbonate (32.6 g) was added, and the mixture was stirred at 60° C. for 17 hr. The reaction mixture was cooled to room temperature, adjusted to pH 7 with 1M hydrochloric acid, and extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (1:1) was concentrated under reduced pressure to give 1-tert-butyl 3-methyl (3R,5S)-5-[{[6-fluoro-1-(4-methoxybutyl)-1H-benzimidazol-2-yl]carbonyl}(2-methylpropyl)amino]piperidine-1,3-dicarboxylate (1.60 g), and a fraction eluted with ethyl acetate was concentrated under reduced pressure to give (3R,5S)-1-(tert-butoxycarbonyl)-5-[{[6-fluoro-1-(4-methoxybutyl)-1H-benzimidazol-2-yl]carbonyl}(2-methylpropyl)amino]piperidine-3-carboxylic acid (1.36 g).

1-tert-butyl 3-methyl (3R,5S)-5-[{[6-fluoro-1-(4-methoxybutyl)-1H-benzimidazol-2-yl]carbonyl}(2-methylpropyl)amino]piperidine-1,3-dicarboxylate $^1$H-NMR (CDCl$_3$) δ 0.70-0.82 (4H, m), 1.00 (2H, d), 1.29-1.36 (3H, m), 1.44-1.52 (6H, m), 1.58-1.72 (2H, m), 1.72-2.04 (3H, m), 2.12-2.37 (1H, m), 2.42-2.93 (3H, m), 3.28-3.80 (12H, m), 4.15-4.51 (4H, m), 7.00-7.14 (2H, m), 7.59-7.77 (1H, m).

MS (ESI+, m/e) 563 (M+1)

(3R,5S)-1-(tert-butoxycarbonyl)-5-[{[6-fluoro-1-(4-methoxybutyl)-1H-benzimidazol-2-yl]carbonyl}(2-methylpropyl)amino]piperidine-3-carboxylic acid $^1$H-NMR (CDCl$_3$) δ 0.69-0.83 (4H, m), 0.95-1.07 (2H, m), 1.16-1.30 (3H, m), 1.42-1.55 (6H, m), 1.60-1.73 (3H, m), 1.75-2.10 (5H, m), 2.40-2.94 (2H, m), 3.29-3.68 (10H, m), 4.15-4.36 (2H, m), 7.02-7.18 (2H, m), 7.86-8.07 (1H, m).

MS (ESI+, m/e) 549 (M+1)

Reference Example 38

(3R,5S)-1-(tert-butoxycarbonyl)-5-[{[6-fluoro-1-(4-methoxybutyl)-1H-benzimidazol-2-yl]carbonyl}(2-methylpropyl)amino]piperidine-3-carboxylic acid

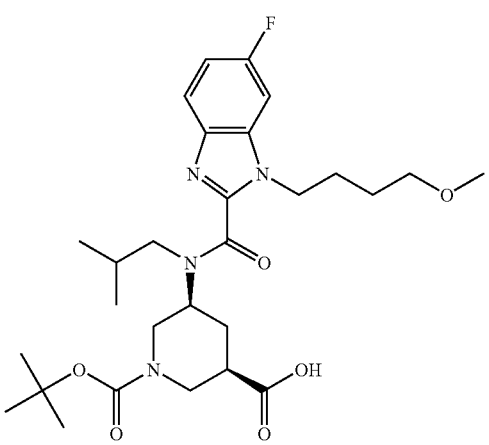 [SMILES: COCCCCn1c(C(=O)N(CC(C)C)[C@H]2C[C@@H](C(=O)O)CN(C(=O)OC(C)(C)C)C2)nc2ccc(F)cc21]

1-tert-Butyl 3-methyl (3R,5S)-5-[{[6-fluoro-1-(4-methoxybutyl)-1H-benzimidazol-2-yl]carbonyl}(2-methylpropyl)amino]piperidine-1,3-dicarboxylate (1.6 g) was dissolved in ethanol (100 ml), 2M aqueous sodium hydroxide solution (14.2 ml) was added, and the mixture was stirred at 50° C. for 5 hr. The reaction mixture was cooled to room temperature, adjusted to pH 7 with 1M hydrochloric acid, and extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (1.55 g).

$^1$H-NMR (CDCl$_3$) δ 0.69-0.83 (4H, m), 0.95-1.07 (2H, m), 1.16-1.30 (3H, m), 1.42-1.55 (6H, m), 1.60-1.73 (3H, m), 1.75-2.10 (5H, m), 2.40-2.94 (2H, m), 3.29-3.68 (10H, m), 4.15-4.36 (2H, m), 7.02-7.18 (2H, m), 7.86-8.07 (1H, m).

MS (ESI+, m/e) 549 (M+1)

Reference Example 39 tert-butyl (3S,5R)-3-[{[6-fluoro-1-(4-methoxybutyl)-1H-benzimidazol-2-yl]carbonyl}(2-methylpropyl)amino]-5-(morpholin-4-ylcarbonyl)piperidine-1-carboxylate

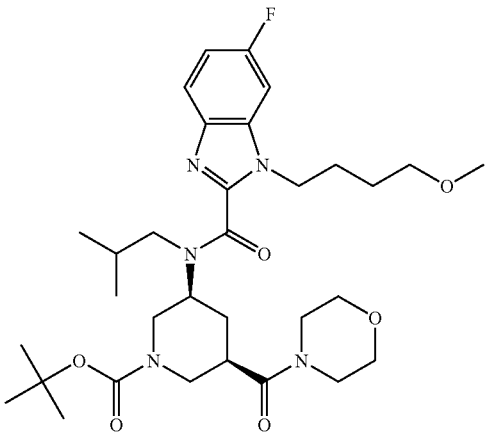 [SMILES: COCCCCn1c(C(=O)N(CC(C)C)[C@H]2C[C@@H](C(=O)N3CCOCC3)CN(C(=O)OC(C)(C)C)C2)nc2ccc(F)cc21]

(3R,5S)-1-(tert-Butoxycarbonyl)-5-[{[6-fluoro-1-(4-methoxybutyl)-1H-benzimidazol-2-yl]carbonyl}(2-methylpropyl)amino]piperidine-3-carboxylic acid (1.05 g), HOBt (361 mg) and WSC.HCl (549 mg) were dissolved in DMF (50 ml), morpholine (332 μl) and diisopropylethylamine (780 μl) were added, and the mixture was stirred at 60° C. for 4 hr. The reaction mixture was cooled to room temperature, concentrated under reduced pressure, and the residue was diluted with aqueous sodium bicarbonate. The mixture was extracted with ethyl acetate, and the extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (1.14 g).

$^1$H-NMR (CDCl$_3$) δ 0.64-0.82 (3H, m), 0.89-1.05 (3H, m), 1.41-1.60 (9H, m), 1.59-1.78 (2H, m), 1.83-2.24 (3H, m), 2.28-2.99 (3H, m), 3.33 (17H, d), 3.96-4.43 (5H, m), 7.00-7.17 (2H, m), 7.49-7.75 (1H, m).

MS (ESI+, m/e) 618 (M+1)

In the same manner as in Reference Example 32, the following compound (Reference Example 40) was obtained.

Reference Example 40

4-fluoro-N-(4-methoxybutyl)-2-nitroaniline

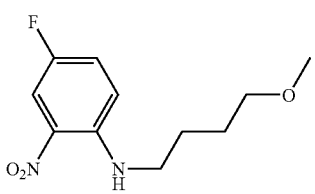 [SMILES: COCCCCNc1ccc(F)cc1[N+](=O)[O-]]

$^1$H-NMR (CDCl$_3$) δ 1.66-1.89 (4H, m), 3.25-3.40 (5H, m), 3.44 (2H, t), 6.84 (1H, dd), 7.21-7.30 (1H, m), 7.84-8.05 (2H, m).

In the same manner as in Reference Example 33, the following compound (Reference Example 41) was obtained.

Reference Example 41

5-fluoro-2-(4-methoxybutylamino)aniline

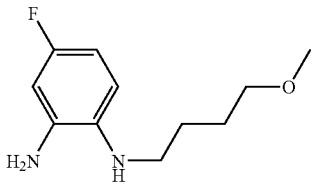

$^1$H-NMR (CDCl$_3$) δ 1.66-1.78 (4H, m), 3.12 (1H, br s), 3.04-3.11 (2H, m), 3.35 (3H, s), 3.39-3.46 (2H, m), 3.58 (2H, br s), 6.42-6.51 (2H, m), 6.53-6.60 (1H, m).

In the same manner as in Reference Example 34, the following compound (Reference Example 42) was obtained.

Reference Example 42 tert-butyl (3S,5R)-3-{[({5-fluoro-2-[(4-methoxybutyl)amino]phenyl}amino)(oxo)acetyl](2-methylpropyl)amino}-5-(morpholin-4-ylcarbonyl)piperidine-1-carboxylate

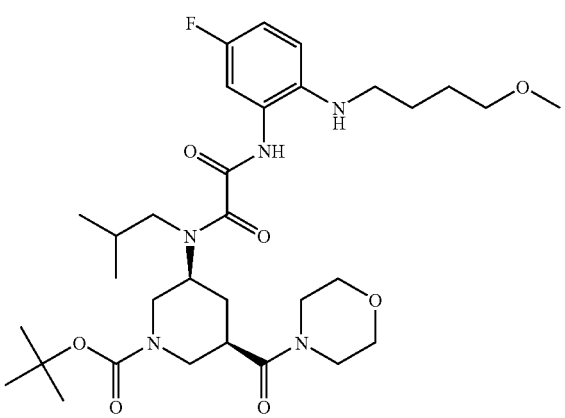 [SMILES: COCCCCNc1ccc(F)cc1NC(=O)C(=O)N(CC(C)C)[C@H]1C[C@@H](C(=O)N2CCOCC2)CN(C(=O)OC(C)(C)C)C1]

MS (ESI+, m/e) 636 (M+1)

In the same manner as in Example 11, the following compound (Example 13) was obtained.

Example 13

5-fluoro-1-(4-methoxybutyl)-N-(2-methylpropyl)-N-[(3S,5R)-5-(morpholin-4-ylcarbonyl)piperidin-3-yl]-1H-benzimidazole-2-carboxamide dihydrochloride

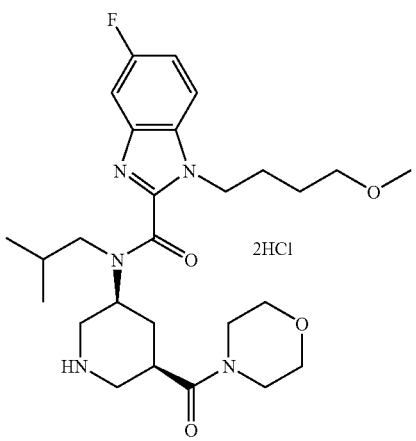 [SMILES: COCCCCn1c(C(=O)N(CC(C)C)[C@@H]2CNC[C@H](C(=O)N3CCOCC3)C2)nc2cc(F)ccc21 ; "2HCl"]

MS (ESI+, m/e) 518 (M+1)

In the same manner as in Reference Example 35, the following compound (Reference Example 43) was obtained.

Reference Example 43

5-fluoro-1-(4-methoxybutyl)-2-(trichloromethyl)-1H-benzimidazole

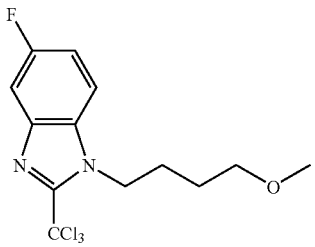

MS (ESI+, m/e) 339 (M+1)

In the same manner as in Reference Example 37, the following compound (Reference Example 44) was obtained.

Reference Example 44

1-tert-butyl 3-methyl (3R,5S)-5-[{[5-fluoro-1-(4-methoxybutyl)-1H-benzimidazol-2-yl]carbonyl}(2-methylpropyl)amino]piperidine-1,3-dicarboxylate

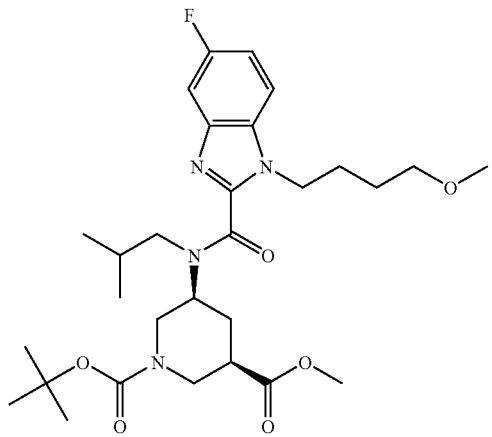 [SMILES: COCCCCn1c(C(=O)N(CC(C)C)[C@H]2C[C@@H](C(=O)OC)CN(C(=O)OC(C)(C)C)C2)nc2cc(F)ccc21]

MS (ESI+, m/e) 563 (M+1)

In the same manner as in Reference Example 38, the following compound (Reference Example 45) was obtained.

Reference Example 45

(3R,5S)-1-(tert-butoxycarbonyl)-5-[{[5-fluoro-1-(4-methoxybutyl)-1H-benzimidazol-2-yl]carbonyl}(2-methylpropyl)amino]piperidine-3-carboxylic acid

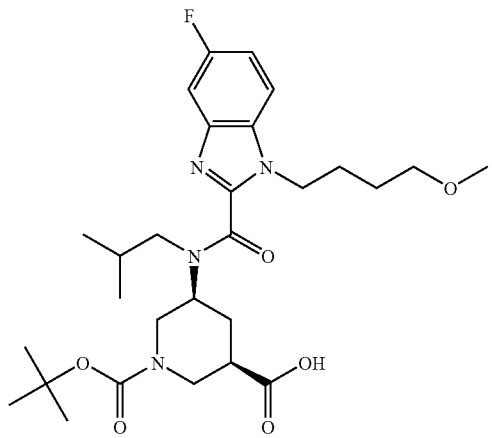

MS (ESI+, m/e) 549 (M+1)

Reference Example 46 tert-butyl (3S)-3-[(2-methylpropyl)amino]piperidine-1-carboxylate

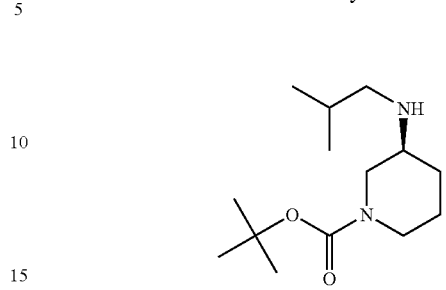

tert-Butyl (3S)-3-aminopiperidine-1-carboxylate (5.0 g), isobutylaldehyde (2.66 ml) and acetic acid (1.72 ml) were dissolved in methanol (100 ml), and the mixture was stirred at room temperature for 10 min. Sodium triacetoxyborohydride (13.2 g) was added to the reaction mixture, and the mixture was stirred at room temperature for 30 min. The reaction mixture was basified with aqueous sodium bicarbonate, and extracted with ethyl acetate. The extract was washed with saturated brine, and dried over anhydrous magnesium sulfate. The solvent was evaporated under reduced pressure. A part of the residue was subjected to silica gel column chromatography, and a fraction eluted with ethyl acetate-hexane (35:65) was concentrated under reduced pressure to give the object product (3.04 g) as an oil.

$^1$H-NMR (CDCl$_3$) δ 0.79-1.15 (8H, m), 1.16-1.36 (1H, m), 1.36-1.56 (11H, m), 1.58-1.80 (2H, m), 1.80-2.00 (1H, m), 2.35-2.60 (3H, m), 2.74-2.99 (1H, m), 3.68-3.91 (1H, m).

MS (ESI+, m/e) 257 (M+1)

Reference Example 47 tert-butyl (3S)-3-[{[1-(4-methoxybutyl)-1H-benzimidazol-2-yl]carbonyl}(2-methylpropyl)amino]piperidine-1-carboxylate

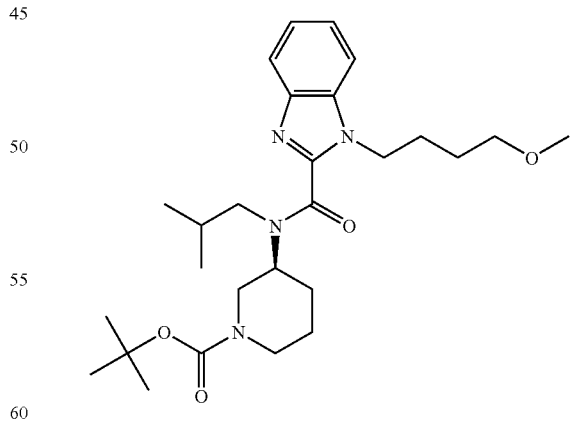

1-(4-Methoxybutyl)-2-(trichloromethyl)-1H-benzimidazole (470 mg) and tert-butyl (3S)-3-[(2-methylpropyl)amino]piperidine-1-carboxylate (400 mg) were dissolved in acetonitrile (30 ml) and water (15 ml), potassium carbonate (2.02 g) was added, and the mixture was stirred at 80° C. for 15 hr. The reaction mixture was cooled to room temperature and diluted with saturated brine. The mixture was extracted with ethyl acetate, and the extract was washed with saturated brine and dried over anhydrous sodium sulfate. The solvent was evaporated under reduced pressure. The residue was subjected to silica gel column chromatography, and a fraction eluted with ethyl acetate-hexane (60:40) was concentrated under reduced pressure to give the object product (446 mg).

MS (ESI+, m/e) 487 (M+1)

In the same manner as in Example 12, the following compound (Example 14) was obtained.

Example 14

1-(4-methoxybutyl)-N-(2-methylpropyl)-N-[(3S)-piperidin-3-yl]-1H-benzimidazole-2-carboxamide dihydrochloride

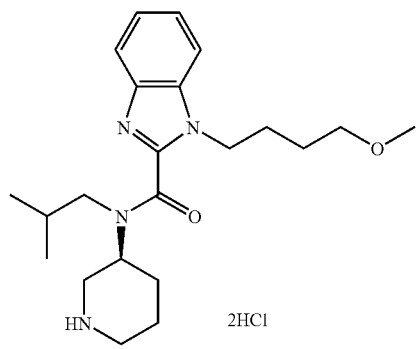 [SMILES: COCCCCn1c(C(=O)N(CC(C)C)[C@H]2CCCNC2)nc2ccccc21 ; "2HCl"]

MS (ESI+, m/e) 387 (M+1)

Reference Example 48

N-(4-methoxybutyl)-3-nitropyridin-2-amine

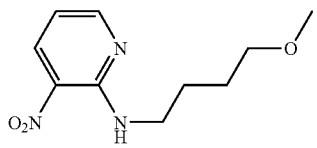

2-Chloro-3-nitropyridine (3.54 g) and 4-methoxybutan-1-amine hydrochloride (3.12 g) were suspended in 2-propanol (100 ml), diisopropylethylamine (11.6 μl) was added and the mixture was heated under reflux with stirring for 4 days. The reaction mixture was cooled to room temperature, and concentrated under reduced pressure. The residue was subjected to silica gel column chromatography, and a fraction eluted with ethyl acetate-hexane (3:7) was concentrated under reduced pressure to give the object product (4.26 g).

$^1$H-NMR (CDCl$_3$) δ 1.63-1.85 (4H, m), 3.35 (3H, s), 3.44 (2H, t), 3.61-3.72 (2H, m), 6.57-6.67 (1H, m), 8.31 (1H, br s), 8.36-8.51 (2H, m).

In the same manner as in Reference Example 33, the following compound (Reference Example 49) was obtained.

Reference Example 49

2-(4-methoxybutylamino)-3-aminopyridine

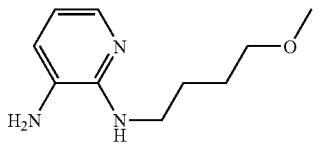 [SMILES: COCCCCNc1ncccc1[N+](=O)[O-]]

$^1$H-NMR (CDCl$_3$) δ 1.66-1.83 (4H, m), 3.36 (3H, s), 3.42-3.55 (4H, m), 3.69 (2H, br s), 5.05 (1H, br s), 6.52 (1H, dd), 6.85 (1H, dd), 7.67 (1H, dd).

In the same manner as in Reference Example 35, the following compound (Reference Example 50) was obtained.

Reference Example 50

3-(4-methoxybutyl)-2-(trichloromethyl)-3H-imidazo[4,5-b]pyridine

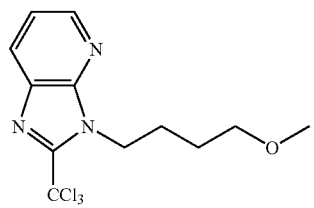

MS (ESI+, m/e) 322 (M+1)

In the same manner as in Reference Example 47, the following compound (Reference Example 51) was obtained.

Reference Example 51 tert-butyl (3S)-3-[{[3-(4-methoxybutyl)-3H-imidazo[4,5-b]pyridin-2-yl]carbonyl}(2-methylpropyl)amino]piperidine-1-carboxylate

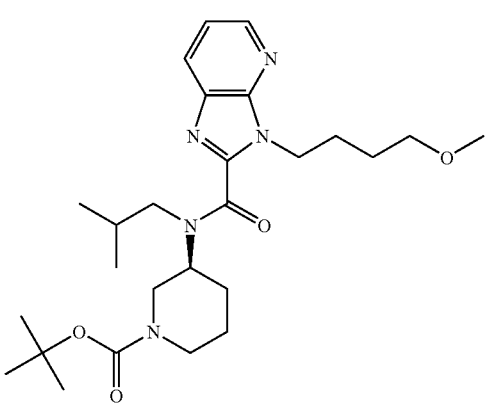 [SMILES: COCCCCn1c(C(=O)N(CC(C)C)[C@H]2CCCN(C(=O)OC(C)(C)C)C2)nc2cccnc21]

MS (ESI+, m/e) 488 (M+1)

In the same manner as in Example 12, the following compound (Example 15) was obtained.

Example 15

3-(4-methoxybutyl)-N-(2-methylpropyl)-N-[(3S)-piperidin-3-yl]-3H-imidazo[4,5-b]pyridine-2-carboxamide dihydrochloride

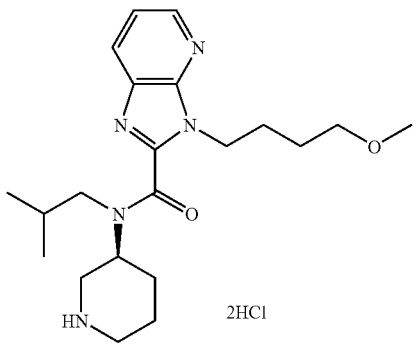 [SMILES: COCCCCn1c(C(=O)N(CC(C)C)[C@H]2CCCNC2)nc2cccnc21 ; "2HCl"]

MS (ESI+, m/e) 388 (M+1)

Reference Example 52

1-(4-methoxybutyl)-4,5,6,7-tetrahydro-1H-benzimidazole

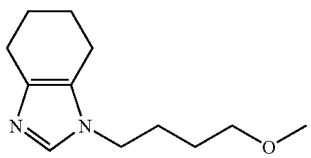

4,5,6,7-Tetrahydro-1H-benzimidazole (2.45 g) was dissolved in DMF (20 ml), sodium hydride (60% in oil, 880 mg) was added, and the mixture was stirred at room temperature for 30 min. 4-Methoxybutyl methanesulfonate (1.28 g) was added, and the mixture was stirred at room temperature for 15 hr. The reaction mixture was concentrated under reduced pressure, water was added and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (2.90 g).
MS (ESI+, m/e) 209 (M+1)

Reference Example 53 methyl 1-(4-methoxybutyl)-4,5,6,7-tetrahydro-1H-benzimidazole-2-carboxylate

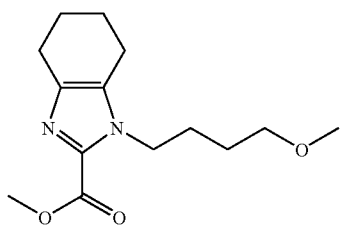

1-(4-Methoxybutyl)-4,5,6,7-tetrahydro-1H-benzimidazole (625 mg) was dissolved in acetonitrile (5 ml), and the mixture was cooled to −15° C. Triethylamine (1.25 ml) and methyl chlorocarbonate (691 μl) were added dropwise. The reaction mixture was heated to room temperature and stirred for 12 hr. The reaction mixture was again cooled to −15° C., triethylamine (1.25 ml) and methyl chlorocarbonate (691 μl) were added dropwise, heated to room temperature and stirred for 12 hr. This operation was further repeated 3 times, aqueous sodium bicarbonate was added to the reaction mixture, and the mixture was extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate was concentrated under reduced pressure to give the object product (225 mg).
MS (ESI+, m/e) 267 (M+1)

Reference Example 54 tert-butyl (3S,5R)-3-[{[1-(4-methoxybutyl)-4,5,6,7-tetrahydro-1H-benzimidazol-2-yl]carbonyl}(2-methylpropyl)amino]-5-(morpholin-4-ylcarbonyl)piperidine-1-carboxylate

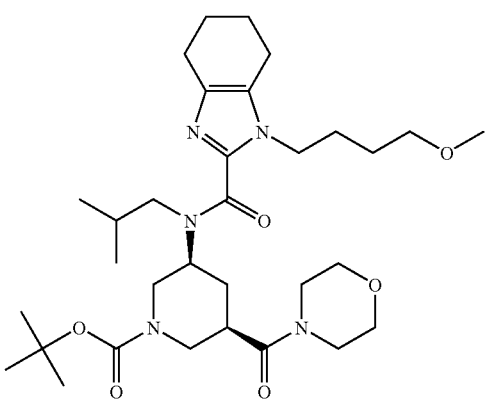 [SMILES: COCCCCn1c(C(=O)N(CC(C)C)[C@H]2C[C@@H](C(=O)N3CCOCC3)CN(C(=O)OC(C)(C)C)C2)nc2c1CCCC2]

Methyl 1-(4-methoxybutyl)-4,5,6,7-tetrahydro-1H-benzimidazole-2-carboxylate (225 mg) was dissolved in ethanol (10 ml) and water (5 ml), lithium hydroxide monohydrate (53 mg) was added, and the mixture was stirred at room temperature for 15 hr. The reaction mixture was concentrated under reduced pressure, and the residue was azeotroped with toluene. The residue was dissolved in 1,2-dichloroethane, tert-butyl (3S,5R)-3-[(2-methylpropyl)amino]-5-(morpholin-4-ylcarbonyl)piperidine-1-carboxylate (314 mg), diisopropylethylamine (732 μl) and chloro-N,N,N',N'-tetramethylformamidinium hexafluorophosphate (168 mg) were added, and the mixture was stirred at room temperature for 15 hr. Aqueous sodium bicarbonate was added to the reaction mixture, and the mixture was extracted with ethyl acetate. The extract was washed with saturated brine, and dried over anhydrous sodium sulfate. The solvent was evaporated under reduced pressure, and the residue was subjected to basic silica gel column chromatography, and a fraction eluted with ethyl acetate-hexane (6:4) was concentrated under reduced pressure to give the object product (178 mg).
MS (ESI+, m/e) 604 (M+1)

In the same manner as in Example 12, the following compound (Example 16) was obtained.

Example 16

1-(4-methoxybutyl)-N-(2-methylpropyl)-N-[(3S,5R)-5-(morpholin-4-ylcarbonyl)piperidin-3-yl]-4,5,6,7-tetrahydro-1H-benzimidazole-2-carboxamide dihydrochloride

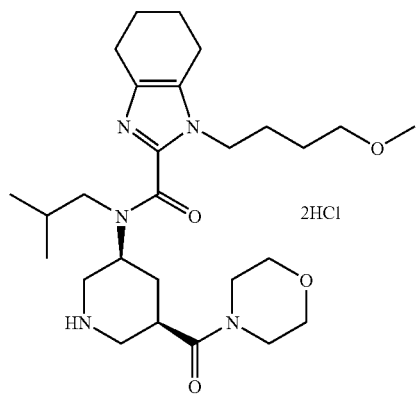 [SMILES: COCCCCn1c(C(=O)N(CC(C)C)[C@@H]2CNC[C@H](C(=O)N3CCOCC3)C2)nc2c1CCCC2 ; "2HCl"]

MS (ESI+, m/e) 504 (M+1)

Reference Example 55 tert-butyl (3R,5S)-3-carbamoyl-5-[{[5-fluoro-1-(4-methoxybutyl)-1H-benzimidazol-2-yl]carbonyl}(2-methylpropyl)amino]piperidine-1-carboxylate

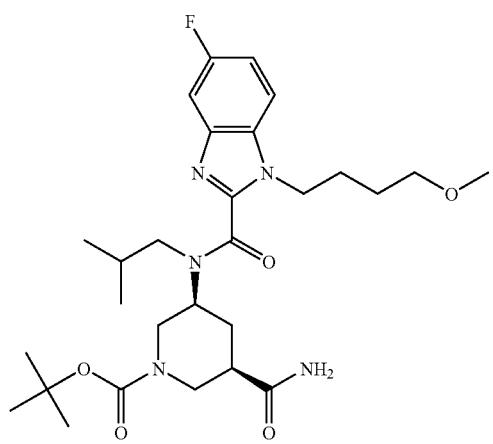 [SMILES: COCCCCn1c(C(=O)N(CC(C)C)[C@H]2C[C@@H](C(N)=O)CN(C(=O)OC(C)(C)C)C2)nc2cc(F)ccc21]

(3R,5S)-1-(tert-Butoxycarbonyl)-5-[{[5-fluoro-1-(4-methoxybutyl)-1H-benzimidazol-2-yl]carbonyl}(2-methylpropyl)amino]piperidine-3-carboxylic acid (549 mg), 1H-1,2,3-benzotriazol-1-ol ammonium salt (304 mg) and WSC.HCl (288 mg) were dissolved in DMF (5 ml), diisopropylethylamine (517 μl) was added, and the mixture was stirred at 60° C. for 3 hr. The reaction mixture was cooled to room temperature, concentrated under reduced pressure, and the residue was diluted with aqueous sodium bicarbonate and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (1.14 g).

MS (ESI+, m/e) 548 (M+1)

In the same manner as in Reference Example 55, the following compound (Reference Example 56) was obtained.

Reference Example 56 tert-butyl (3R,5S)-3-carbamoyl-5-[{[6-fluoro-1-(4-methoxybutyl)-1H-benzimidazol-2-yl]carbonyl}(2-methylpropyl)amino]piperidine-1-carboxylate

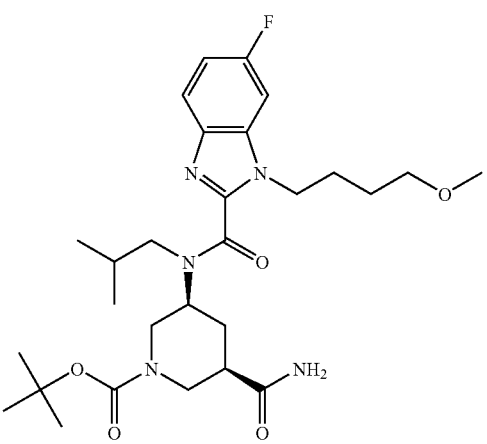 [SMILES: COCCCCn1c(C(=O)N(CC(C)C)[C@H]2C[C@@H](C(N)=O)CN(C(=O)OC(C)(C)C)C2)nc2ccc(F)cc21]

MS (ESI+, m/e) 548 (M+1)

In the same manner as in Reference Example 39, the following compounds (Reference Examples 57-59) were obtained.

Reference Example 57 tert-butyl (3S,5R)-3-[{[5-fluoro-1-(4-methoxybutyl)-1H-benzimidazol-2-yl]carbonyl}(2-methylpropyl)amino]-5-(pyrrolidin-1-ylcarbonyl)piperidine-1-carboxylate

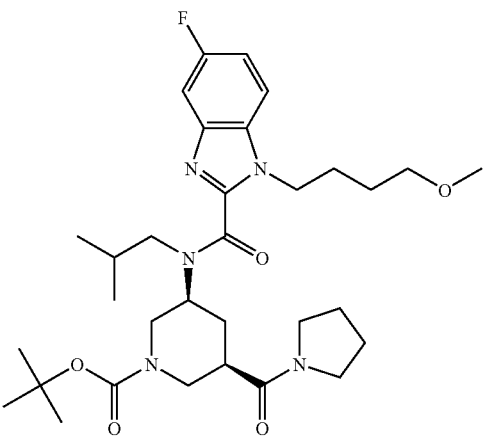 [SMILES: COCCCCn1c(C(=O)N(CC(C)C)[C@H]2C[C@@H](C(=O)N3CCCC3)CN(C(=O)OC(C)(C)C)C2)nc2cc(F)ccc21]

MS (ESI+, m/e) 602 (M+1)

Reference Example 58 tert-butyl (3R,5S)-3-(azetidin-1-ylcarbonyl)-5-[{[5-fluoro-1-(4-methoxybutyl)-1H-benzimidazol-2-yl]carbonyl}(2-methylpropyl)amino]piperidine-1-carboxylate

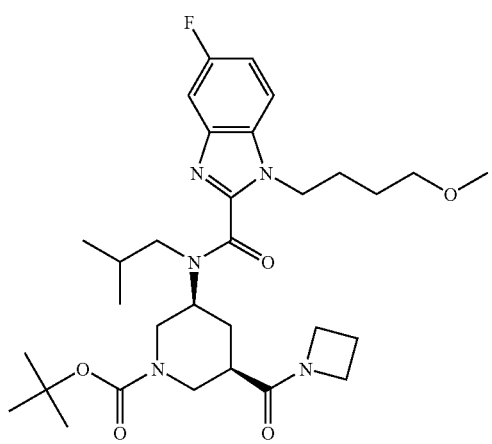 [SMILES: COCCCCn1c(C(=O)N(CC(C)C)[C@H]2C[C@@H](C(=O)N3CCC3)CN(C(=O)OC(C)(C)C)C2)nc2cc(F)ccc21]

MS (ESI+, m/e) 558 (M+1)

Reference Example 59 tert-butyl (3S,5R)-3-[{[1-(4-methoxybutyl)-1H-benzimidazol-2-yl]carbonyl}(2-methylpropyl)amino]-5-(piperidin-1-ylcarbonyl)piperidine-1-carboxylate

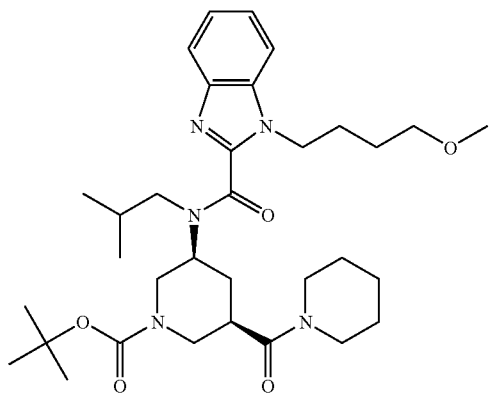

MS (ESI+, m/e) 598 (M+1)

In the same manner as in Example 12, the following compounds (Examples 17-22) were obtained.

Example 17

(3R,5S)-5-[{[6-fluoro-1-(4-methoxybutyl)-1H-benzimidazol-2-yl]carbonyl}(2-methylpropyl)amino]piperidine-3-carboxylic acid dihydrochloride

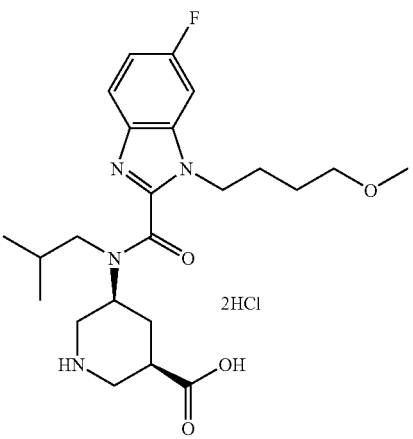 [SMILES: COCCCCn1c(C(=O)N(CC(C)C)[C@@H]2CNC[C@H](C(=O)O)C2)nc2ccc(F)cc21 ; "2HCl"]

MS (ESI+, m/e) 449 (M+1)

Example 18

5-fluoro-1-(4-methoxybutyl)-N-(2-methylpropyl)-N-[(3S,5R)-5-(pyrrolidin-1-ylcarbonyl)piperidin-3-yl]-1H-benzimidazole-2-carboxamide dihydrochloride

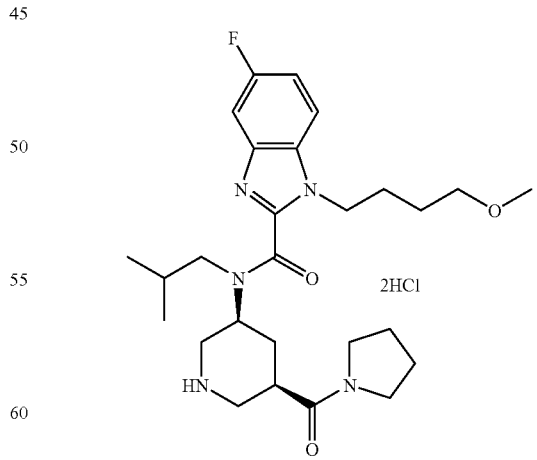

MS (ESI+, m/e) 502 (M+1)

Example 19

N-[(3S,5R)-5-carbamoylpiperidin-3-yl]-5-fluoro-1-(4-methoxybutyl)-N-(2-methylpropyl)-1H-benzimidazole-2-carboxamide dihydrochloride

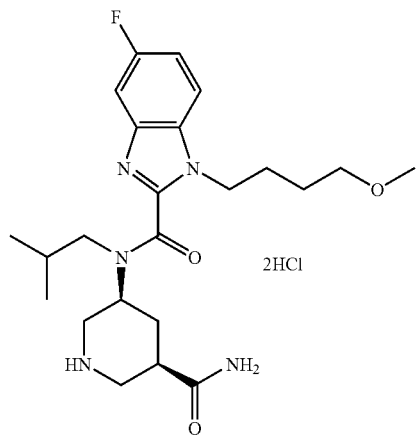 [SMILES: COCCCCn1c(C(=O)N(CC(C)C)[C@@H]2CNC[C@H](C(N)=O)C2)nc2cc(F)ccc21 ; "2HCl"]

MS (ESI+, m/e) 448 (M+1)

Example 20

N-[(3S,5R)-5-carbamoylpiperidin-3-yl]-6-fluoro-1-(4-methoxybutyl)-N-(2-methylpropyl)-1H-benzimidazole-2-carboxamide dihydrochloride

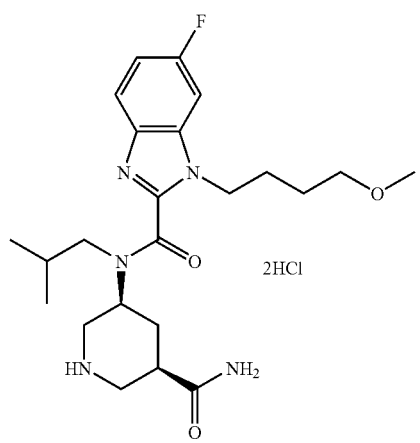 [SMILES: COCCCCn1c(C(=O)N(CC(C)C)[C@@H]2CNC[C@H](C(N)=O)C2)nc2ccc(F)cc21 ; "2HCl"]

MS (ESI+, m/e) 448 (M+1)

Example 21

1-(4-methoxybutyl)-N-(2-methylpropyl)-N-[(3S,5R)-5-(piperidin-1-ylcarbonyl)piperidin-3-yl]-1H-benzimidazole-2-carboxamide dihydrochloride

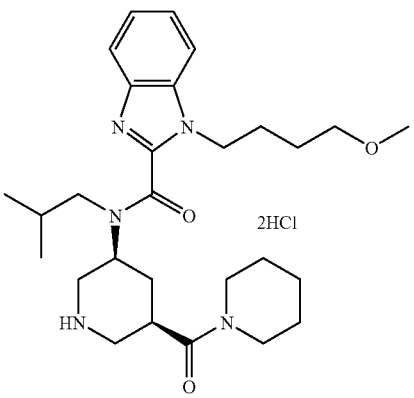

MS (ESI+, m/e) 498 (M+1)

Example 22

5-fluoro-1-(4-methoxybutyl)-N-(2-methylpropyl)-N-[(3S,5R)-5-(4H-1,2,4-triazol-3-yl)piperidin-3-yl]-1H-benzimidazole-2-carboxamide dihydrochloride

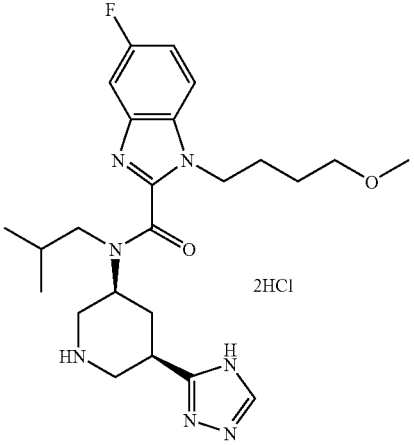 [SMILES: COCCCCn1c(C(=O)N(CC(C)C)[C@@H]2CNC[C@H](c3nnc[nH]3)C2)nc2cc(F)ccc21 ; "2HCl"]

MS (ESI+, m/e) 472 (M+1)

Example 23

N-[(3S,5R)-5-(azetidin-1-ylcarbonyl)piperidin-3-yl]-5-fluoro-1-(4-methoxybutyl)-N-(2-methylpropyl)-1H-benzimidazole-2-carboxamide

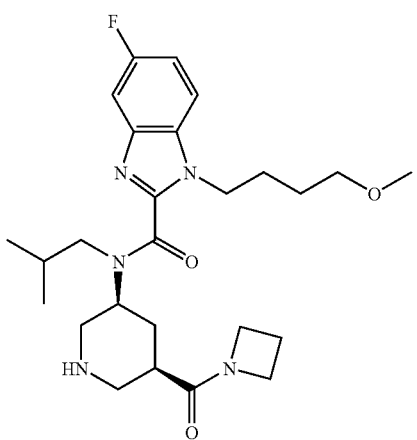 [SMILES: COCCCCn1c(C(=O)N(CC(C)C)[C@@H]2CNC[C@H](C(=O)N3CCC3)C2)nc2cc(F)ccc21]

tert-Butyl (3R,5S)-3-(azetidin-1-ylcarbonyl)-5-[{[5-fluoro-1-(4-methoxybutyl)-1H-benzimidazol-2-yl]carbonyl}(2-methylpropyl)amino]piperidine-1-carboxylate (80 mg) was dissolved in trifluoroacetic acid (3 ml), and the mixture was stirred at room temperature for 1 hr. Aqueous sodium bicarbonate was added to the reaction mixture, and the mixture was extracted with ethyl acetate. The extract was washed with saturated brine, and dried over anhydrous sodium sulfate. The solvent was evaporated under reduced pressure to give the object product (42 mg).

MS (ESI+, m/e) 488 (M+1)

Reference Example 60 tert-butyl (3S,5R)-3-[{[6-fluoro-1-(4-methoxybutyl)-1H-benzimidazol-2-yl]carbonyl}(2-methylpropyl)amino]-5-(hydroxymethyl)piperidine-1-carboxylate

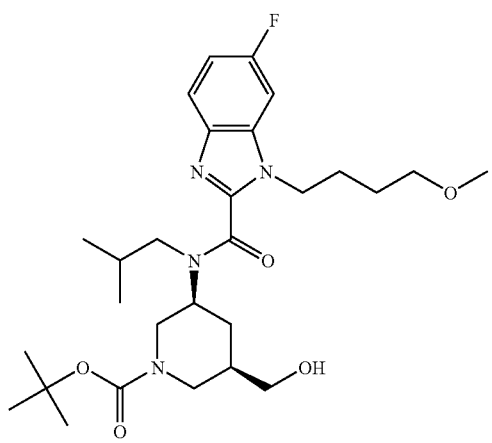 [SMILES: COCCCCn1c(C(=O)N(CC(C)C)[C@H]2C[C@@H](CO)CN(C(=O)OC(C)(C)C)C2)nc2ccc(F)cc21]

To a solution of (3R,5S)-1-(tert-butoxycarbonyl)-5-[{[6-fluoro-1-(4-methoxybutyl)-1H-benzimidazol-2-yl]carbonyl}(2-methylpropyl)amino]piperidine-3-carboxylic acid (274 mg) and 4-methylmorpholine (66 μl) in THF (5 ml) was added dropwise ethyl chlorocarbonate (57 μl) at 0° C., and the mixture was stirred at the same temperature for 1 hr. Sodium borohydride (57 mg) and methanol (1 ml) were added to the reaction mixture, and the mixture was stirred at 0° C. for 1 hr. The reaction mixture was diluted with aqueous sodium bicarbonate, and the mixture was extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate was concentrated under reduced pressure to give the object product (182 mg).

MS (ESI+, m/e) 535 (M+1)

Example 24

6-fluoro-N-[(3S,5R)-5-(hydroxymethyl)piperidin-3-yl]-1-(4-methoxybutyl)-N-(2-methylpropyl)-1H-benzimidazole-2-carboxamide dihydrochloride

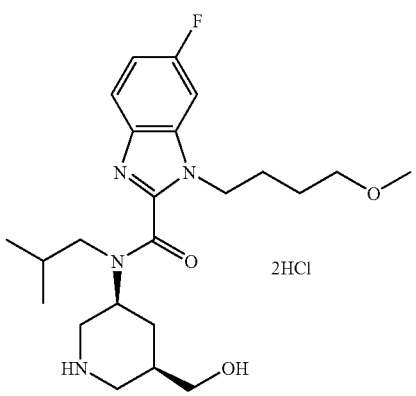 [SMILES: COCCCCn1c(C(=O)N(CC(C)C)[C@@H]2CNC[C@H](CO)C2)nc2ccc(F)cc21 ; "2HCl"]

tert-Butyl (3S,5R)-3-[{[6-fluoro-1-(4-methoxybutyl)-1H-benzimidazol-2-yl]carbonyl}(2-methylpropyl)amino]-5-(hydroxymethyl)piperidine-1-carboxylate (182 mg) was dissolved in 10-20% hydrogen chloride-methanol (5 ml), and the mixture was stirred at room temperature for 3 days. The reaction mixture was concentrated to give the object product (169 mg).

MS (ESI+, m/e) 435 (M+1)

Reference Example 61

2-(trichloromethyl)-1H-benzimidazole

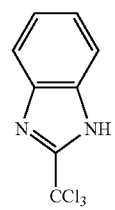

O-Phenylenediamine (25 g) was dissolved in acetic acid (750 ml), and methyl 2,2,2-trichloroacetimidate (28.5 ml) was added dropwise over 15 min. After stirring at room temperature for 1 hr, the reaction mixture was concentrated to about 150 ml, and poured into water (1500 ml). The precipitated crystals were collected by filtration, washed with water (1000 ml) and suspended in toluene (500 ml). The solvent was evaporated under reduced pressure. The residue was again suspended in toluene (500 ml) and the solvent was evaporated under reduced pressure. The residue was dried under reduced pressure to give the object product (51.8 g).

$^1$H-NMR (CDCl$_3$) δ 7.31-7.45 (2H, m), 7.49-7.55 (1H, m), 7.89 (1H, d), 9.74 (1H, br s)

In the same manner as in Reference Example 61, the following compounds (Reference Examples 62-63) were obtained.

Reference Example 62

5,6-difluoro-2-(trichloromethyl)-1H-benzimidazole

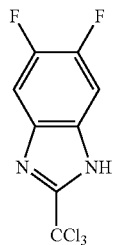

$^1$H-NMR (CDCl$_3$) δ 7.10-7.83 (2H, m), 10.10 (1H, br s)

Reference Example 63

4-chloro-2-(trichloromethyl)-1H-benzimidazole

$^1$H-NMR (CDCl$_3$) δ 7.14-7.51 (3H, m), 9.59-10.26 (1H, m)

Reference Example 64

1-tert-butyl 3-methyl (3R,5S)-5-[(1H-benzimidazol-2-ylcarbonyl)(2-methylpropyl)amino]piperidine-1,3-dicarboxylate

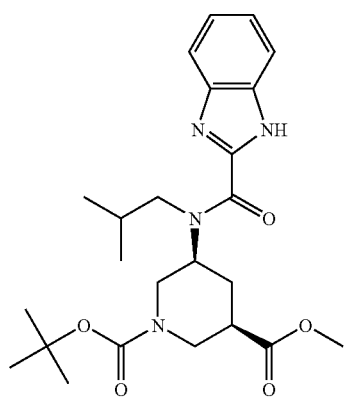 [SMILES: COC(=O)[C@@H]1C[C@H](N(CC(C)C)C(=O)c2nc3ccccc3[nH]2)CN(C(=O)OC(C)(C)C)C1]

2-(Trichloromethyl)-1H-benzimidazole (19 g) and 1-tert-butyl 3-methyl (3R,5S)-5-[(2-methylpropyl)amino]piperidine-1,3-dicarboxylate (25 g) were dissolved in THF (1200 ml), sodium hydrogen carbonate (67 g) and water (600 ml) were added, and the mixture was stirred at room temperature for 1 hr and at 50° C. for 1 hr. After evaporation of the solvent, the residue was extracted 3 times with ethyl acetate (700 ml). The extract was washed successively with 10%-aqueous citric acid solution (500 ml) and brine, and dried over anhydrous sodium sulfate. The solvent was evaporated under reduced pressure. The residue was dissolved in ethyl acetate (1000 ml), subjected to basic silica gel column chromatography, and a fraction eluted with ethyl acetate was concentrated under reduced pressure to give the object product (30.6 g).

$^1$H-NMR (CDCl$_3$) δ 0.78-1.09 (6 H, m), 1.17-1.55 (9 H, m), 1.77-2.95 (5 H, m), 3.11-3.79 (6 H, m), 3.99-4.73 (4 H, m), 7.24-7.41 (2 H, m), 7.45-7.59 (1 H, m), 7.72-7.88 (1 H, m), 10.66-10.98 (1 H, m)

MS (ESI+, m/e) 459 (M+1)

Reference Example 65 tert-butyl (3S,5R)-3-{[(5,6-difluoro-1H-benzimidazol-2-yl)carbonyl](2-methylpropyl)amino}-5-(morpholin-4-ylcarbonyl)piperidine-1-carboxylate

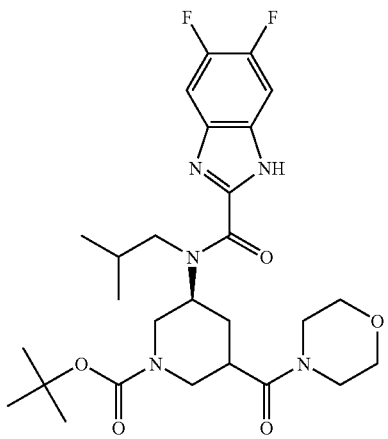 [SMILES: CC(C)CN(C(=O)c1nc2cc(F)c(F)cc2[nH]1)[C@H]1CC(C(=O)N2CCOCC2)CN(C(=O)OC(C)(C)C)C1]

To a solution of 5,6-difluoro-2-(trichloromethyl)-1H-benzimidazole (500 mg) and tert-butyl (3S,5R)-3-[(2-methylpropyl)amino]-5-(morpholin-4-ylcarbonyl)piperidine-1-carboxylate (680 mg) in THF (50 ml) were added sodium hydrogen carbonate (1.3 g) and water (20 ml), and the mixture was stirred at room temperature for 1 hr and extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (710 mg).

MS (ESI+, m/e) 550 (M+1)

In the same manner as in Reference Example 65, the following compounds (Reference Examples 66-68) were obtained.

Reference Example 66

1-tert-butyl 3-methyl (3R,5S)-5-{[(5,6-difluoro-1H-benzimidazol-2-yl)carbonyl](2-methylpropyl)amino}piperidine-1,3-dicarboxylate

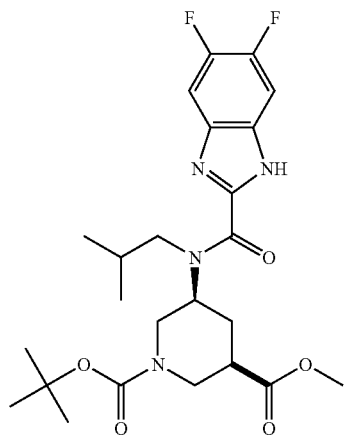

MS (ESI+, m/e) 495 (M+1)

Reference Example 67

1-tert-butyl 3-methyl (3R,5S)-5-{[(4-chloro-1H-benzimidazol-2-yl)carbonyl](2-methylpropyl)amino}piperidine-1,3-dicarboxylate

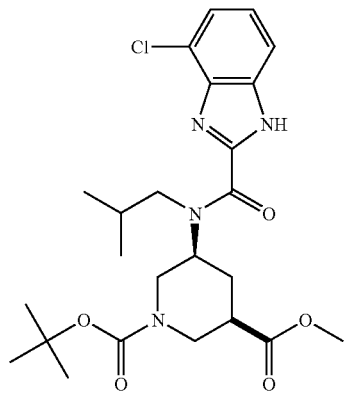

MS (ESI+, m/e) 493 (M+1)

Reference Example 68

1-tert-butyl 3-methyl 5-[(1H-benzimidazol-2-ylcarbonyl)(2-methylpropyl)amino]piperidine-1,3-dicarboxylate

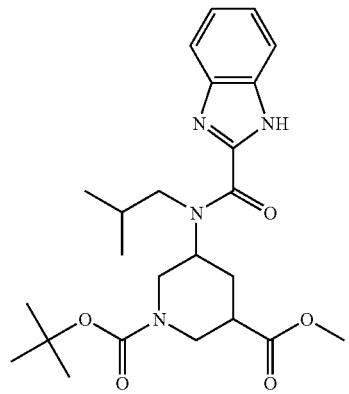 [SMILES: COC(=O)C1CC(N(CC(C)C)C(=O)c2nc3ccccc3[nH]2)CN(C(=O)OC(C)(C)C)C1]

MS (ESI+, m/e) 459 (M+1)

Reference Example 69

1-tert-butyl 3-methyl (3R,5S)-5-[{[1-(4-methoxybutyl)-1H-benzimidazol-2-yl]carbonyl}(2-methylpropyl)amino]piperidine-1,3-dicarboxylate

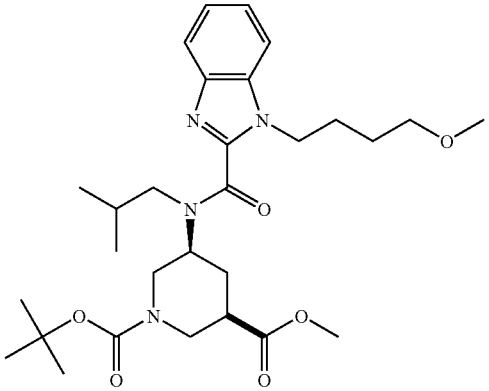

1-tert-Butyl 3-methyl (3R,5S)-5-[(1H-benzimidazol-2-ylcarbonyl)(2-methylpropyl)amino]piperidine-1,3-dicarboxylate (30 g) and 4-methoxybutyl methanesulfonate (12.5 g) were dissolved in DMA (600 ml), cesium carbonate (32 g) was added, and the mixture was stirred at 70° C. for 12 hr. The reaction mixture was poured into ice water (1000 ml), and the mixture was extracted twice with ethyl acetate (1000 ml). The extract was washed with brine, and dried over anhydrous sodium sulfate. The solvent was evaporated under reduced pressure. The residue was subjected to silica gel column chromatography, and a fraction eluted with ethyl acetate-hexane (1:4-1:1) was concentrated under reduced pressure to give the object product (28.7 g).

$^1$H-NMR (CDCl$_3$) δ 0.76 (4H, d), 1.01 (2H, d), 1.30-1.52 (9H, m), 1.58-2.07 (4H, m), 2.10-2.93 (4H, m), 3.27-3.75 (12H, m), 4.06-4.57 (5H, m), 7.26-7.48 (3H, m), 7.79 (1H, d)
MS (ESI+, m/e) 545 (M+1)

In the same manner as in Reference Example 69, the following compounds (Reference Examples 70-72) were obtained.

Reference Example 70 tert-butyl (3S,5R)-3-{[(5,6-difluoro-1-(4-methoxybutyl)-1H-benzimidazol-2-yl)carbonyl](2-methylpropyl)amino}-5-(morpholin-4-ylcarbonyl)piperidine-1-carboxylate

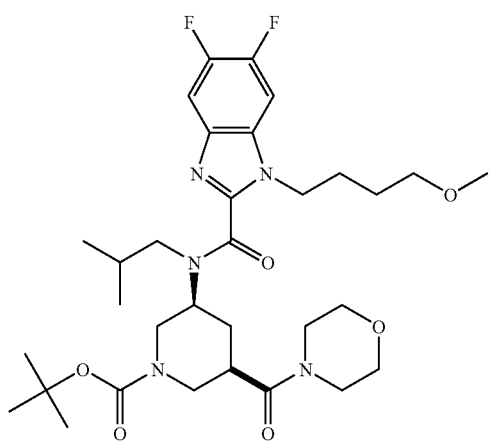

MS (ESI+, m/e) 636 (M+1)

Reference Example 71

1-tert-butyl 3-methyl (3R,5S)-5-[{[5,6-difluoro-1-(4-methoxybutyl)-1H-benzimidazol-2-yl]carbonyl}(2-methylpropyl)amino]piperidine-1,3-dicarboxylate

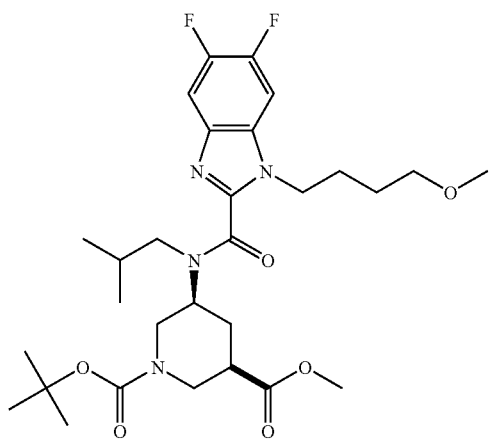

MS (ESI+, m/e) 495 (M+1)

Reference Example 72

1-tert-butyl 3-methyl 5-[{[1-(4-methoxybutyl)-1H-benzimidazol-2-yl]carbonyl}(2-methylpropyl)amino]piperidine-1,3-dicarboxylate

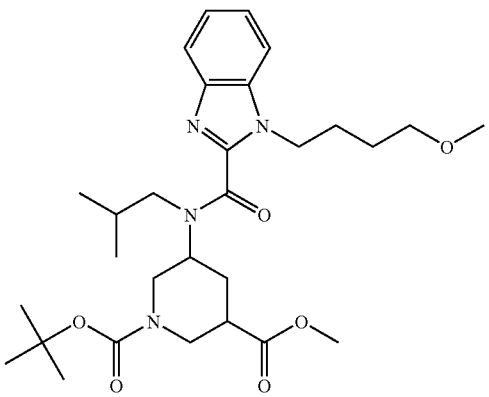 [SMILES: COCCCCn1c(C(=O)N(CC(C)C)C2CC(C(=O)OC)CN(C(=O)OC(C)(C)C)C2)nc2ccccc21]

MS (ESI+, m/e) 545 (M+1)

Reference Example 73

1-tert-butyl 3-methyl (3R,5S)-5-[{[7-chloro-1-(4-methoxybutyl)-1H-benzimidazol-2-yl]carbonyl}(2-methylpropyl)amino]piperidine-1,3-dicarboxylate and 1-tert-butyl 3-methyl (3R,5S)-5-[{[4-chloro-1-(4-methoxybutyl)-1H-benzimidazol-2-yl]carbonyl}(2-methylpropyl)amino]piperidine-1,3-dicarboxylate

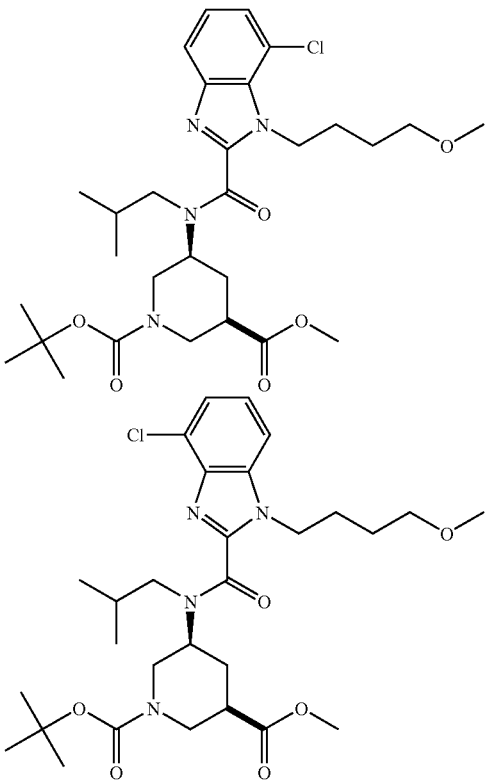

1-tert-Butyl 3-methyl (3R,5S)-5-{[(4-chloro-1H-benzimidazol-2-yl)carbonyl](2-methylpropyl)amino}piperidine-1,3-dicarboxylate (1.7 g) and 4-methoxybutyl methanesulfonate (754 mg) were dissolved in DMA (50 ml), cesium carbonate (1.7 g) was added, and the mixture was stirred at 70° C. for 12 hr. The reaction mixture was poured into ice water (100 ml), and the mixture was extracted twice with ethyl acetate (100 ml). The extract was washed with brine, and dried over anhydrous sodium sulfate. The solvent was evaporated under reduced pressure. The residue was subjected to silica gel column chromatography, and a less polar fraction eluted with ethyl acetate-hexane (1:4-1:1) was concentrated under reduced is pressure to give 1-tert-butyl 3-methyl (3R,5S)-5-[{[7-chloro-1-(4-methoxybutyl)-1H-benzimidazol-2-yl]carbonyl}(2-methylpropyl)amino]piperidine-1,3-dicarboxylate (200 mg).

MS (ESI+, m/e) 580 (M+1)

A highly-polar fraction was concentrated to give 1-tert-butyl 3-methyl (3R,5S)-5-[{[4-chloro-1-(4-methoxybutyl)-1H-benzimidazol-2-yl]carbonyl}(2-methylpropyl)amino]piperidine-1,3-dicarboxylate (1.4 g).

MS (ESI+, m/e) 580 (M+1)

Reference Example 74

(3R,5S)-1-(tert-butoxycarbonyl)-5-[{[1-(4-methoxybutyl)-1H-benzimidazol-2-yl]carbonyl}(2-methylpropyl)amino]piperidine-3-carboxylic acid

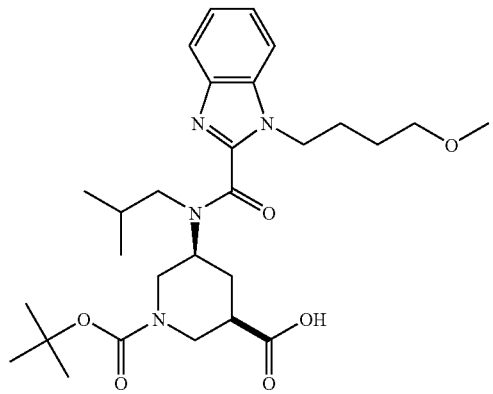

1-tert-Butyl 3-methyl (3R,5S)-5-[{[1-(4-methoxybutyl)-1H-benzimidazol-2-yl]carbonyl}(2-methylpropyl)amino]piperidine-1,3-dicarboxylate (15 g) was dissolved in methanol (150 ml), 4N-aqueous sodium hydroxide solution (250 ml) was added, and the mixture was stirred at 50° C. for 1 hr. The solvent was evaporated under reduced pressure, and the residue was ice-cooled, neutralized with 2N hydrochloric acid, and extracted twice ethyl acetate (500 ml). The extract was washed with brine, and dried over anhydrous sodium sulfate. The solvent was evaporated under reduced pressure. The residue was dried under reduced pressure to give the object product (15.0 g).

In the same manner as in Reference Example 74, the following compounds (Reference Examples 75-78) were obtained.

Reference Example 75

(3R,5S)-1-(tert-butoxycarbonyl)-5-[{[5,6-difluoro-1-(4-methoxybutyl)-1H-benzimidazol-2-yl]carbonyl}(2-methylpropyl)amino]piperidine-3-carboxylic acid

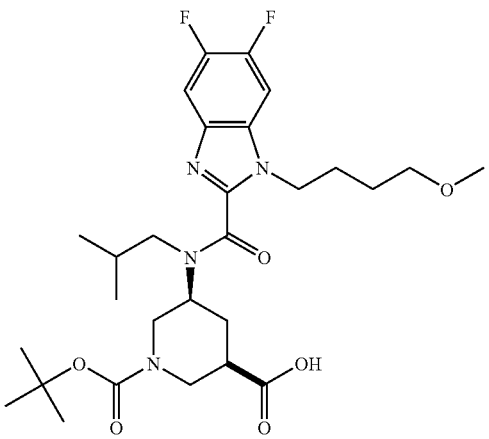

MS (ESI+, m/e) 567 (M+1)

Reference Example 76

(3R,5S)-1-(tert-butoxycarbonyl)-5-[{[7-chloro-1-(4-methoxybutyl)-1H-benzimidazol-2-yl]carbonyl}(2-methylpropyl)amino]piperidine-3-carboxylic acid

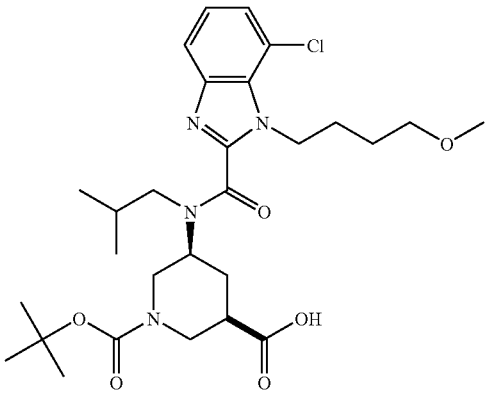

MS (ESI+, m/e) 565 (M+1)

Reference Example 77

(3R,5S)-1-(tert-butoxycarbonyl)-5-[{[4-chloro-1-(4-methoxybutyl)-1H-benzimidazol-2-yl]carbonyl}(2-methylpropyl)amino]piperidine-3-carboxylic acid

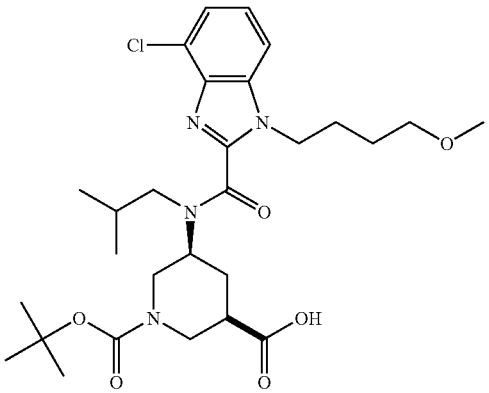

MS (ESI+, m/e) 565 (M+1)

Reference Example 78

1-(tert-butoxycarbonyl)-5-[{[1-(4-methoxybutyl)-1H-benzimidazol-2-yl]carbonyl}(2-methylpropyl)amino]piperidine-3-carboxylic acid

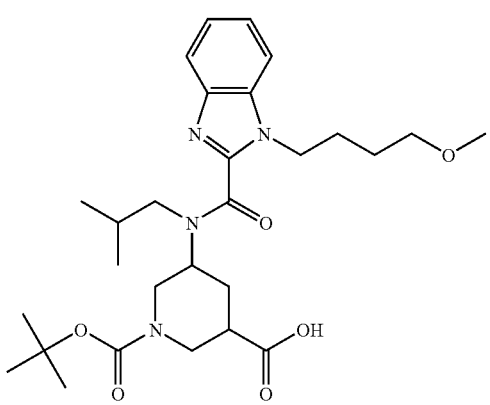 [SMILES: COCCCCn1c(C(=O)N(CC(C)C)C2CC(C(=O)O)CN(C(=O)OC(C)(C)C)C2)nc2ccccc21]

MS (ESI+, m/e) 531 (M+1)

Reference Example 79 tert-butyl (3R,5S)-3-(hydroxymethyl)-5-[{[1-(4-methoxybutyl)-1H-benzimidazol-2-yl]carbonyl}(2-methylpropyl)amino]piperidine-1-carboxylate

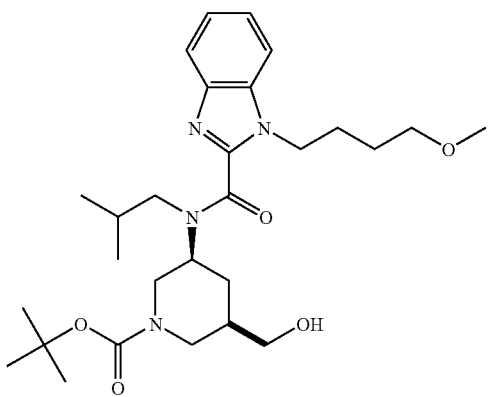

Sodium borohydride (4.45 g) was suspended in THF (25 ml)-ethanol (75 ml), and calcium chloride (6.5 g) was added. After stirring at 0° C. for 1 hr, a solution of 1-tert-butyl 3-methyl (3R,5S)-5-[{[1-(4-methoxybutyl)-1H-benzimidazol-2-yl]carbonyl}(2-methylpropyl)amino]piperidine-1,3-dicarboxylate (4.0 g) in THF (50 ml) was added. After stirring at room temperature for 12 hr, ethyl acetate (150 ml) and water (50 ml) were slowly added in this order, and the mixture was filtered. The organic layer of the filtrate was partitioned, washed with brine, and dried over anhydrous sodium sulfate. The solvent was evaporated under reduced pressure. The residue was dried under reduced pressure to give the object product (1.8 g).

$^1$H-NMR (CDCl$_3$) δ 0.77 (4H, d), 1.02 (2H, d), 1.31-1.51 (9H, m), 1.56-2.88 (9H, m), 3.24-3.73 (11H, m), 3.98-4.48 (5H, m), 7.28-7.53 (3H, m), 7.79 (1H, dd)
MS (ESI+, m/e) 517 (M+1)

Reference Example 80 tert-butyl (3R,5S)-3-carbamoyl-5-[{[1-(4-methoxybutyl)-1H-benzimidazol-2-yl]carbonyl}(2-methylpropyl)amino]piperidine-1-carboxylate

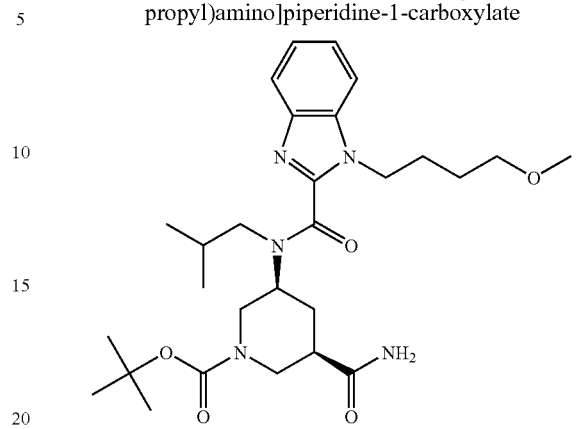

A solution of (3R,5S)-1-(tert-butoxycarbonyl)-5-[{[1-(4-methoxybutyl)-1H-benzimidazol-2-yl]carbonyl}(2-methylpropyl)amino]piperidine-3-carboxylic acid (540 mg), 1H-1,2,3-benzotriazol-1-ol ammonium salt (345 mg) and WSC.HCl (383 mg) in DMF (10 ml) was stirred at room temperature for 24 hr, and the mixture was poured into water and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (1:9-1:0) was concentrated under reduced pressure to give the object product (270 mg).

$^1$H-NMR (CDCl$_3$) δ 0.77 (3H, d) 0.93-1.07 (3H, m), 1.21-1.55 (9H, m), 1.55-3.01 (9H, m), 3.24-4.60 (12H, m), 5.45 (1H, d), 5.66-6.06 (1H, m), 7.23-7.52 (3H, m), 7.79 (1H, d)
MS (ESI+, m/e) 430 (M+1)

In the same manner as in Reference Example 80, the following compound (Reference Example 81) was obtained.

Reference Example 81 tert-butyl (3R,5S)-3-carbamoyl-5-[{[5,6-difluoro-1-(4-methoxybutyl)-1H-benzimidazol-2-yl]carbonyl}(2-methylpropyl)amino]piperidine-1-carboxylate

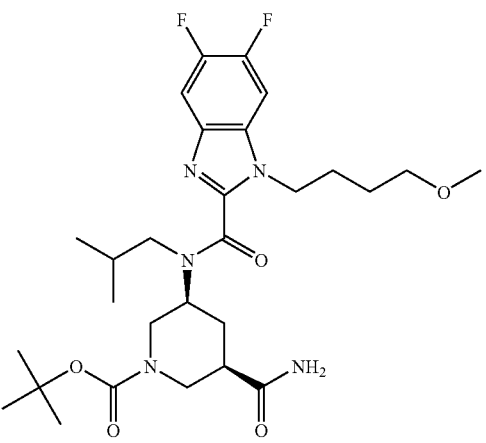 [SMILES: COCCCCn1c(C(=O)N(CC(C)C)[C@H]2C[C@@H](C(N)=O)CN(C(=O)OC(C)(C)C)C2)nc2cc(F)c(F)cc21]

MS (ESI+, m/e) 566 (M+1)

Reference Example 82 tert-butyl (3S,5R)-3-[{[1-(4-methoxybutyl)-1H-benzimidazol-2-yl]carbonyl}(2-methylpropyl)amino]-5-(pyrrolidin-1-ylcarbonyl)piperidine-1-carboxylate

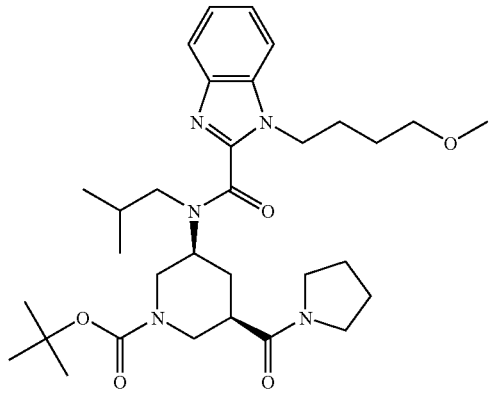 [SMILES: COCCCCn1c(C(=O)N(CC(C)C)[C@H]2C[C@@H](C(=O)N3CCCC3)CN(C(=O)OC(C)(C)C)C2)nc2ccccc21]

(3R,5S)-1-(tert-Butoxycarbonyl)-5-[{[1-(4-methoxybutyl)-1H-benzimidazol-2-yl]carbonyl}(2-methylpropyl)amino]piperidine-3-carboxylic acid (400 mg) and pyrrolidine (59 mg) were dissolved in DMF (10 ml), WSC.HCL (217 mg) and HOBt (150 mg) were added, and the mixture was stirred at 50° C. for 12 hr. The reaction mixture was poured into 10% aqueous sodium bicarbonate, and the mixture was extracted with ethyl acetate. The extracts were combined and washed with brine and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (420 mg).

MS (ESI+, m/e) 584 (M+1)

In the same manner as in Reference Example 82, the following compounds (Reference Examples 83-91) were obtained.

Reference Example 83 tert-butyl (3RS,5RS)-3-[{[1-(4-methoxybutyl)-1H-benzimidazol-2-yl]carbonyl}(2-methylpropyl)amino]-5-(morpholin-4-ylcarbonyl)piperidine-1-carboxylate

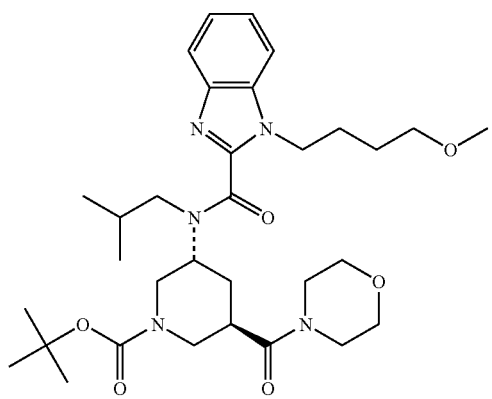

MS (ESI+, m/e) 600 (M+1)

Reference Example 84

(3R,5S)-3-(azetidin-1-ylcarbonyl)-5-[{[1-(4-methoxybutyl)-1H-benzimidazol-2-yl]carbonyl}(2-methylpropyl)amino]piperidine-1-carboxylate

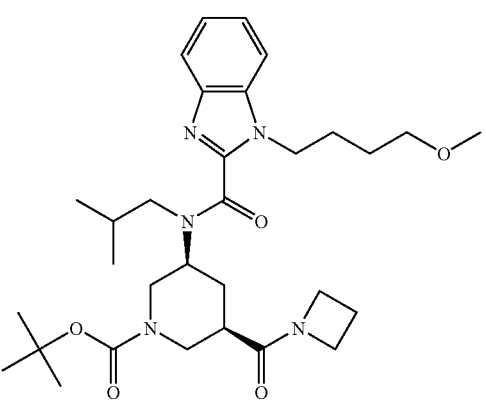 [SMILES: COCCCCn1c(C(=O)N(CC(C)C)[C@H]2C[C@@H](C(=O)N3CCC3)CN(C(=O)OC(C)(C)C)C2)nc2ccccc21]

MS (ESI+, m/e) 570(M+1)

Reference Example 85 tert-butyl (3R,5S)-3-[(4,4-difluoropiperidin-1-yl)carbonyl]-5-[{[1-(4-methoxybutyl)-1H-benzimidazol-2-yl]carbonyl}(2-methylpropyl)amino]piperidine-1-carboxylate

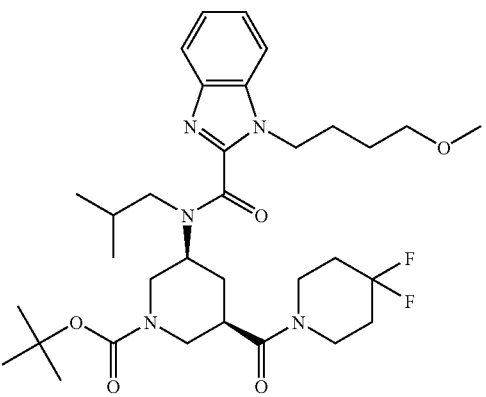 [SMILES: COCCCCn1c(C(=O)N(CC(C)C)[C@H]2C[C@@H](C(=O)N3CCC(F)(F)CC3)CN(C(=O)OC(C)(C)C)C2)nc2ccccc21]

MS (ESI+, m/e) 634 (M+1)

Reference Example 86 tert-butyl (3R,5S)-3-(7-azabicyclo[2.2.1]hepta-7-ylcarbonyl)-5-[{[1-(4-methoxybutyl)-1H-benzimidazol-2-yl]carbonyl}(2-methylpropyl)amino]piperidine-1-carboxylate

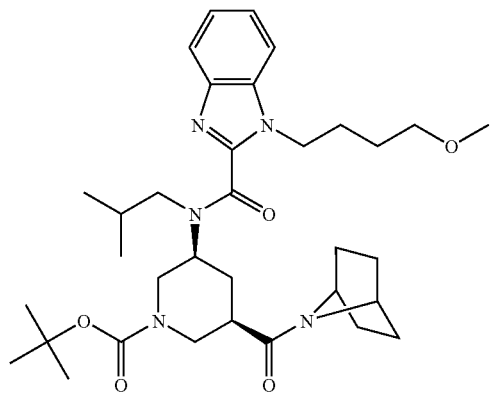 [SMILES: COCCCCn1c(C(=O)N(CC(C)C)[C@H]2C[C@@H](C(=O)N3C4CCC3CC4)CN(C(=O)OC(C)(C)C)C2)nc2ccccc21]

MS (ESI+, m/e) 610 (M+1)

Reference Example 87 tert-butyl (3S,5R)-3-[{[1-(4-methoxybutyl)-1H-benzimidazol-2-yl]carbonyl}(2-methylpropyl)amino]-5-(1,4-oxazepan-4-ylcarbonyl)piperidine-1-carboxylate

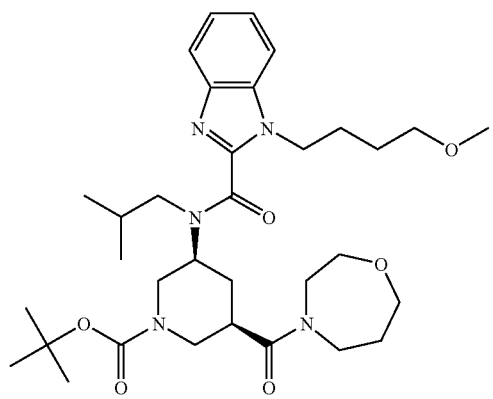 [SMILES: COCCCCn1c(C(=O)N(CC(C)C)[C@H]2C[C@@H](C(=O)N3CCCOCC3)CN(C(=O)OC(C)(C)C)C2)nc2ccccc21]

MS (ESI+, m/e) 614 (M+1)

Reference Example 88 tert-butyl (3R,5S)-3-(2,3-dihydro-4H-1,4-benzoxazin-4-ylcarbonyl)-5-[{[1-(4-methoxybutyl)-1H-benzimidazol-2-yl]carbonyl}(2-methylpropyl)amino]piperidine-1-carboxylate

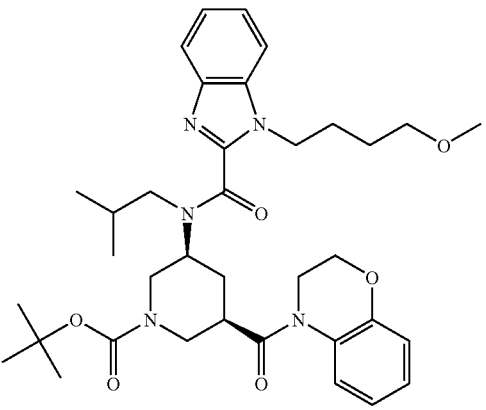 [SMILES: COCCCCn1c(C(=O)N(CC(C)C)[C@H]2C[C@@H](C(=O)N3CCOc4ccccc43)CN(C(=O)OC(C)(C)C)C2)nc2ccccc21]

MS (ESI+, m/e) 648 (M+1)

Reference Example 89 tert-butyl (3R,5S)-3-(azetidin-1-ylcarbonyl)-5-[{[5,6-difluoro-1-(4-methoxybutyl)-1H-benzimidazol-2-yl]carbonyl}(2-methylpropyl)amino]piperidine-1-carboxylate

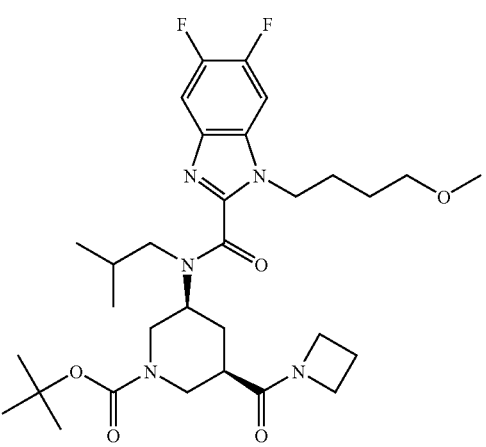 [SMILES: COCCCCn1c(C(=O)N(CC(C)C)[C@H]2C[C@@H](C(=O)N3CCC3)CN(C(=O)OC(C)(C)C)C2)nc2cc(F)c(F)cc21]

MS (ESI+, m/e) 606 (M+1)

Reference Example 90 tert-butyl (3S,5R)-3-[{[7-chloro-1-(4-methoxybutyl)-1H-benzimidazol-2-yl]carbonyl}(2-methylpropyl)amino]-5-(morpholin-4-ylcarbonyl)piperidine-1-carboxylate

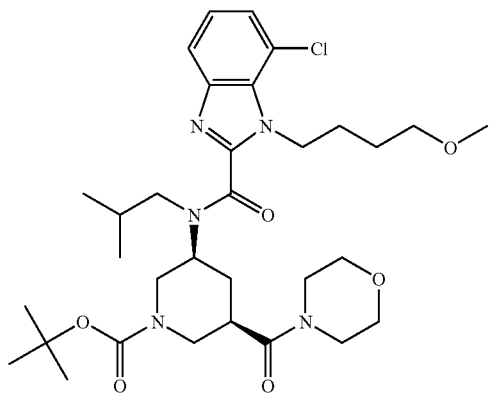 [SMILES: COCCCCn1c(C(=O)N(CC(C)C)[C@H]2C[C@@H](C(=O)N3CCOCC3)CN(C(=O)OC(C)(C)C)C2)nc2cccc(Cl)c21]

MS (ESI+, m/e) 634 (M+1)

Reference Example 91 tert-butyl (3S,5R)-3-[{[4-chloro-1-(4-methoxybutyl)-1H-benzimidazol-2-yl]carbonyl}(2-methylpropyl)amino]-5-(morpholin-4-ylcarbonyl)piperidine-1-carboxylate

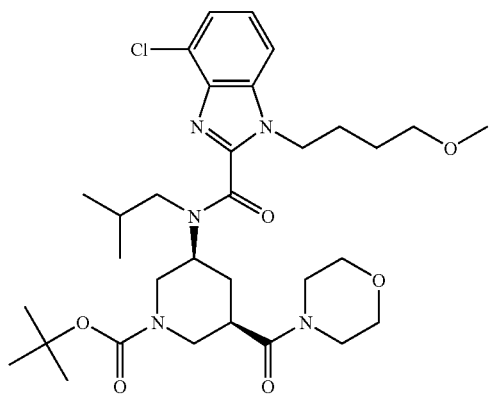 [SMILES: COCCCCn1c(C(=O)N(CC(C)C)[C@H]2C[C@@H](C(=O)N3CCOCC3)CN(C(=O)OC(C)(C)C)C2)nc2c(Cl)cccc21]

MS (ESI+, m/e) 634 (M+1)

Reference Example 92 tert-butyl (3R,5S)-3-(1-hydroxy-1-methylethyl)-5-[{[1-(4-methoxybutyl)-1H-benzimidazol-2-yl]carbonyl}(2-methylpropyl)amino]piperidine-1-carboxylate

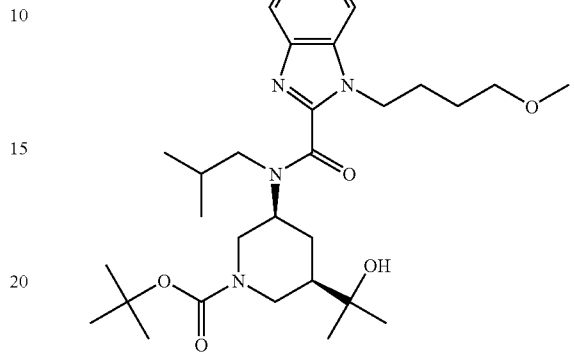

A solution of 1-tert-butyl 3-methyl (3R,5S)-5-[{[1-(4-methoxybutyl)-1H-benzimidazol-2-yl]carbonyl}(2-methylpropyl)amino]piperidine-1,3-dicarboxylate (330 mg) in THF (5 ml) was cooled to −40° C., a solution (1 ml) of 3M-methyl magnesium bromide in ether was added and the mixture was stirred at room temperature for 1 hr. The reaction mixture was poured into saturated aqueous ammonium chloride solution, and the mixture was extracted with ethyl acetate. The extract was dried over anhydrous sodium sulfate and the solvent was evaporated under reduced pressure. The residue was subjected to silica gel column chromatography, and a fraction eluted with ethyl acetate-hexane (1:1-1:0) was concentrated under reduced pressure to give the object product (180 mg).
MS (ESI+, m/e) 545 (M+1)

In the same manner as in Reference Example 92, the following compound (Reference Example 93) was obtained.

Reference Example 93 tert-butyl (3S,5R)-3-[{[5,6-difluoro-1-(4-methoxybutyl)-1H-benzimidazol-2-yl]carbonyl}(2-methylpropyl)amino]-5-(1-hydroxy-1-methylethyl)piperidine-1-carboxylate

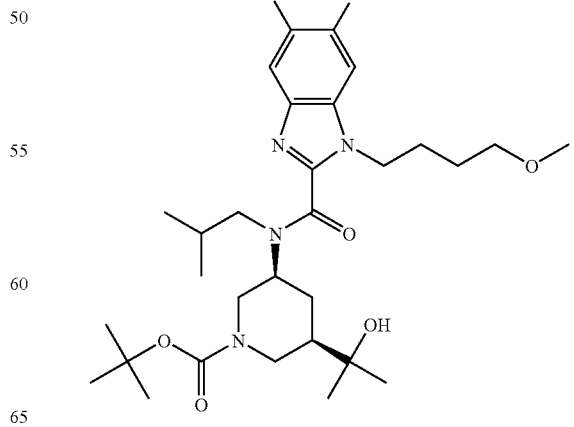

MS (ESI+, m/e) 581 (M+1)

Reference Example 94 tert-butyl (3R,5S)-3-formyl-5-[{[1-(4-methoxybutyl)-1H-benzimidazol-2-yl]carbonyl}(2-methylpropyl)amino]piperidine-1-carboxylate

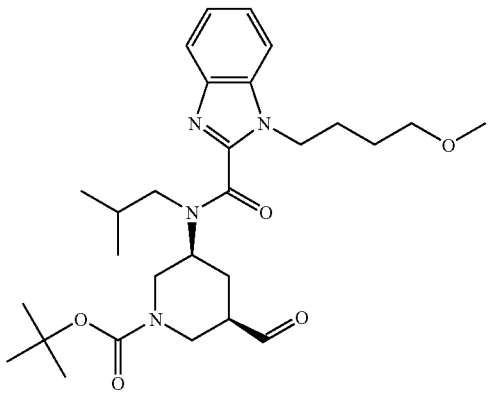 [SMILES: COCCCCn1c(C(=O)N(CC(C)C)[C@H]2C[C@@H](C=O)CN(C(=O)OC(C)(C)C)C2)nc2ccccc21]

To a solution of tert-butyl (3R,5S)-3-(hydroxymethyl)-5-[{[1-(4-methoxybutyl)-1H-benzimidazol-2-yl]carbonyl}(2-methylpropyl)amino]piperidine-1-carboxylate (1.0 g) in acetonitrile (20 ml) was added 1,1,1-tris(acetyloxy)-1,1-dihydro-1,2-benziodoxol-3-(1H)-one (0.98 g), and the mixture was stirred at room temperature for 3 hr. 10% Aqueous sodium thiosulfate solution was added to the reaction mixture, and the mixture was stirred for 30 min. After partitioning, the organic layer was washed with saturated aqueous sodium hydrogen carbonate and brine, and dried over anhydrous sodium sulfate. The solvent was evaporated under reduced pressure. The residue was subjected to silica gel column chromatography, and a fraction eluted with ethyl acetate-hexane (1:1) was concentrated under reduced pressure to give the object product (1.0 g).

MS (ESI+, m/e) 515 (M+1)

Reference Example 95 tert-butyl (3R,5S)-3-(1-hydroxyethyl)-5-[{[1-(4-methoxybutyl)-1H-benzimidazol-2-yl]carbonyl}(2-methylpropyl)amino]piperidine-1-carboxylate

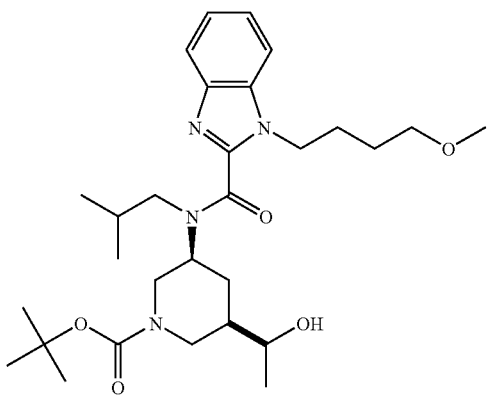 [SMILES: COCCCCn1c(C(=O)N(CC(C)C)[C@H]2CC([C@H](C)O)CN(C(=O)OC(C)(C)C)C2)nc2ccccc21]

To a solution of tert-butyl (3R,5S)-3-formyl-5-[{[1-(4-methoxybutyl)-1H-benzimidazol-2-yl]carbonyl}(2-methylpropyl)amino]piperidine-1-carboxylate (150 mg) in THF (10 ml) was added 3M-methyl magnesium bromide-ether solution (0.3 ml), and the mixture was stirred at room temperature for 1 hr. The reaction mixture was poured into saturated aqueous ammonium chloride solution, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (100 mg).

MS (ESI+, m/e) 531 (M+1)

In the same manner as in Reference Example 95, the following compound (Reference Example 96) was obtained.

Reference Example 96 tert-butyl (3R,5S)-3-[cyclopropyl(hydroxy)methyl]-5-[{[1-(4-methoxybutyl)-1H-benzimidazol-2-yl]carbonyl}(2-methylpropyl)amino]piperidine-1-carboxylate

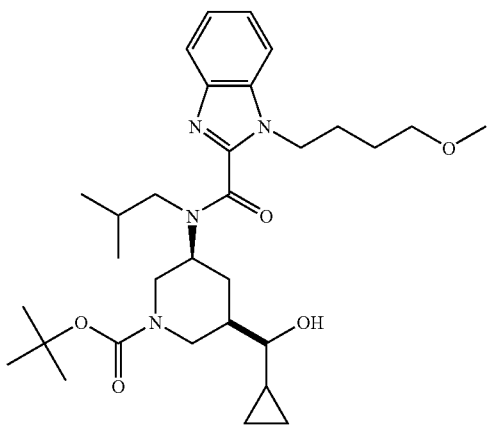 [SMILES: COCCCCn1c(C(=O)N(CC(C)C)[C@H]2CC([C@@H](O)C3CC3)CN(C(=O)OC(C)(C)C)C2)nc2ccccc21]

MS (ESI+, m/e) 557 (M+1)

Reference Example 97 tert-butyl (3R,5S)-3-[hydroxy(pyridin-2-yl)methyl]-5-[{[1-(4-methoxybutyl)-1H-benzimidazol-2-yl)carbonyl }(2-methylpropyl)amino)piperidine-1-carboxylate

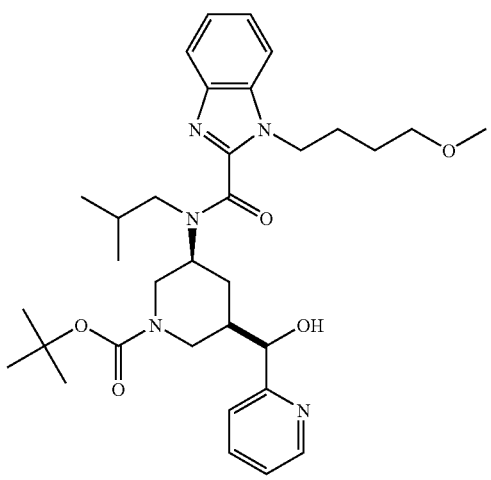 [SMILES: COCCCCn1c(C(=O)N(CC(C)C)[C@H]2CC([C@@H](O)c3ccccn3)CN(C(=O)OC(C)(C)C)C2)nc2ccccc21]

To a solution of bromopyridine (0.058 ml) cooled to −78° C. in THF (5 ml) was added 1.6M-butyllithium hexane solution (0.33 ml) and the mixture was stirred for 30 min. A solution of tert-butyl (3R,5S)-3-formyl-5-[{[1-(4-methoxybutyl)-1H-benzimidazol-2-yl]carbonyl}(2-methylpropyl)amino]piperidine-1-carboxylate (257 mg) in THF (5 ml) was added and the mixture was stirred at −20° C. for 2 hr. The reaction mixture was poured into saturated aqueous ammonium chloride solution, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (100 mg).

MS (ESI+, m/e) 594 (M+1)

Reference Example 98 tert-butyl (3S,5R)-3-[{[1-(4-methoxybutyl)-1H-benzimidazol-2-yl]carbonyl}(2-methylpropyl)amino]-5-(oxiran-2-yl)piperidine-1-carboxylate

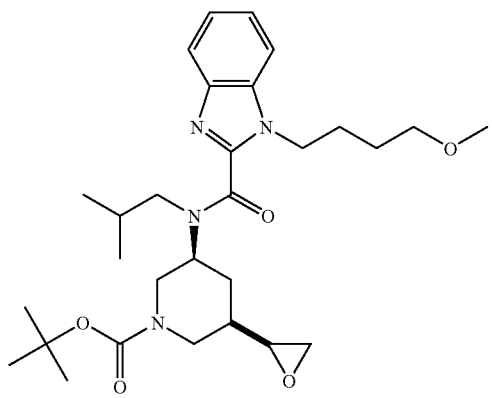 [SMILES: COCCCCn1c(C(=O)N(CC(C)C)[C@H]2CC([C@H]3CO3)CN(C(=O)OC(C)(C)C)C2)nc2ccccc21]

Trimethylsulfoxonium iodide (240 mg) was dissolved in DMSO (5 ml), sodium hydride (60% in oil, 45 mg) was added, and the mixture was stirred at room temperature for 30 min. A solution of tert-butyl (3R,5S)-3-formyl-5-[{[1-(4-methoxybutyl)-1H-benzimidazol-2-yl]carbonyl}(2-methylpropyl)amino]piperidine-1-carboxylate (450 mg) in DMSO (10 ml) was added and the mixture was stirred at room temperature for 30 min. The reaction mixture was poured into saturated aqueous ammonium chloride solution and the mixture was extracted with ethyl acetate. The extract was dried over anhydrous sodium sulfate and the solvent was evaporated under reduced pressure. The residue was subjected to silica gel column chromatography, and a fraction eluted with ethyl acetate was concentrated under reduced pressure to give the object product (230 mg).

MS (ESI+, m/e) 529 (M+1)

Reference Example 99 tert-butyl (3R,5S)-3-(1-hydroxy-2-methoxyethyl)-5-[{[1-(4-methoxybutyl)-1H-benzimidazol-2-yl]carbonyl}(2-methylpropyl)amino]piperidine-1-carboxylate

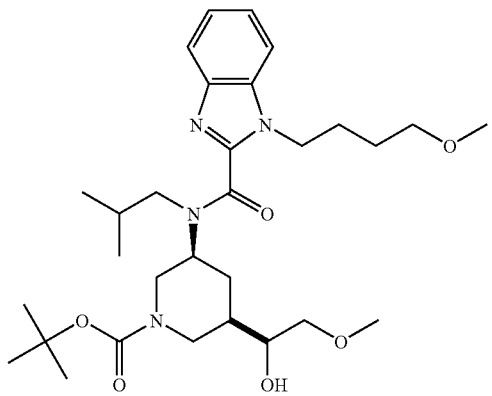 [SMILES: COCCCCn1c(C(=O)N(CC(C)C)[C@H]2CC([C@H](O)COC)CN(C(=O)OC(C)(C)C)C2)nc2ccccc21]

tert-Butyl (3S,5R)-3-[{[1-(4-methoxybutyl)-1H-benzimidazol-2-yl]carbonyl}(2-methylpropyl)amino]-5-oxirane-2-ylpiperidine-1-carboxylate (200 mg) was dissolved in methanol (5 ml), 28% sodium methylate-methanol solution was added, and the mixture was stirred at 70° C. for 6 hr. The solvent was evaporated under reduced pressure, and the residue was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (157 mg). MS (ESI+, m/e) 561(M+1)

Reference Example 100 tert-butyl (3S,5R)-3-[{[1-(4-methoxybutyl)-1H-benzimidazol-2-yl]carbonyl}(2-methylpropyl)amino]-5-(5-methyl-1,3,4-oxadiazol-2-yl)piperidine-1-carboxylate

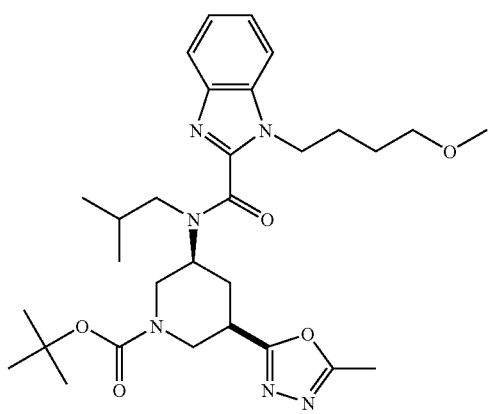

Methyltetrazole (63 mg) and (3R,5S)-1-(tert-butoxycarbonyl)-5-[{[1-(4-methoxybutyl)-1H-benzimidazol-2-yl]carbonyl}(2-methylpropyl)amino]piperidine-3-carboxylic acid (265 mg) were dissolved in toluene (5 ml), DCC (155 mg) was added and the mixture was stirred at 100° C. for 12 hr. The reaction mixture was diluted with ethyl acetate, filtered and the solvent of the mother liquor was evaporated under reduced pressure. The residue was subjected to silica gel column chromatography, and a fraction eluted with ethyl acetate-hexane (1:1-1:0) was concentrated under reduced pressure to give the object product (100 mg).

MS (ESI+, m/e) 569 (M+1)

Example 25

N-[(3S,5R)-5-carbamoylpiperidin-3-yl]-1-(4-methoxybutyl)-N-(2-methylpropyl)-1H-benzimidazole-2-carboxamide dihydrochloride

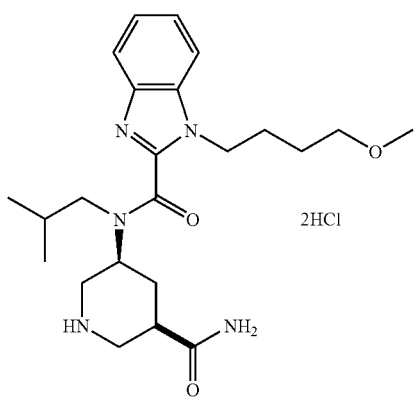

tert-Butyl (3R,5S)-3-carbamoyl-5-[{[1-(4-methoxybutyl)-1H-benzimidazol-2-yl]carbonyl}(2-methylpropyl)amino]piperidine-1-carboxylate (260 mg) was dissolved in ethyl acetate (3 ml), 4N hydrogen chloride-ethyl acetate (5 ml) was added, and the mixture was stirred for 1 hr. The solvent was evaporated under reduced pressure to give the object product (220 mg).

$^1$H-NMR (DMSO-$d_6$) δ 0.61-0.79 (3H, m) 0.88-0.99 (3H, m), 1.45-1.60 (2H, m), 1.74-1.88 (2H, m), 2.07-2.41 (2H, m), 2.70-3.01 (1H, m), 3.10-3.63 (9H, m), 4.21-4.41 (3H, m), 7.12 (1H, br s), 7.28-7.48 (2H, m), 7.53-7.84 (3H, m), 8.98 (2H, br s), 9.54-9.95 (2H, m)

MS (ESI+, m/e) 430 (M+1)

In the same manner as in Example 25, the following compounds (Examples 26-39) were obtained.

Example 26

1-(4-methoxybutyl)-N-(2-methylpropyl)-N-[(3RS,5RS)-5-(morpholin-4-ylcarbonyl)piperidin-3-yl]-1H-benzimidazole-2-carboxamide dihydrochloride

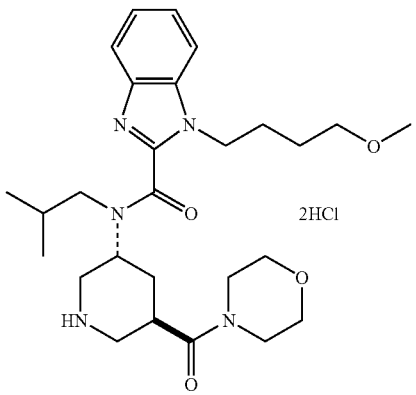

MS (ESI+, m/e) 500 (M+1)

Example 27

1-(4-methoxybutyl)-N-(2-methylpropyl)-N-[(3S,5R)-5-(pyrrolidin-1-ylcarbonyl)piperidin-3-yl]-1H-benzimidazole-2-carboxamide dihydrochloride

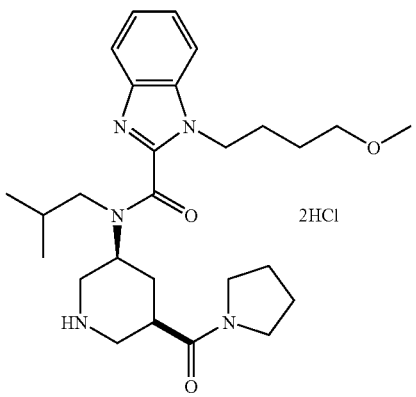

MS (ESI+, m/e) 484 (M+1)

Example 28

N-{(3S,5R)-5-[(4,4-difluoropiperidin-1-yl)carbonyl]piperidin-3-yl}-1-(4-methoxybutyl)-N-(2-methylpropyl)-1H-benzimidazole-2-carboxamide dihydrochloride

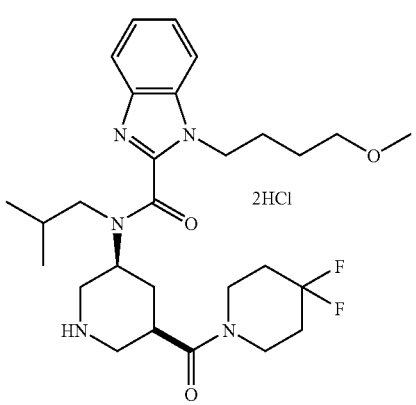

MS (ESI+, m/e) 534 (M+1)

Example 29

N-[(3S,5R)-5-(7-azabicyclo[2.2.1]hept-7-ylcarbonyl)piperidin-3-yl]-1-(4-methoxybutyl)-N-(2-methylpropyl)-1H-benzimidazole-2-carboxamide dihydrochloride

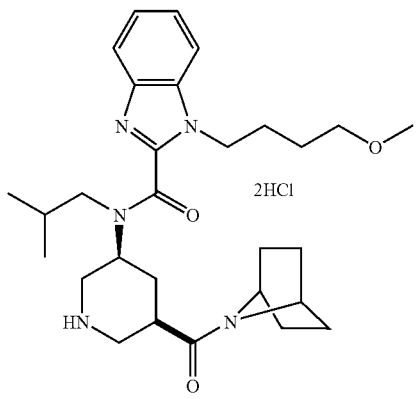

MS (ESI+, m/e) 510 (M+1)

Example 30

1-(4-methoxybutyl)-N-(2-methylpropyl)-N-[(3S,5R)-5-(1,4-oxazepan-4-ylcarbonyl)piperidin-3-yl]-1H-benzimidazole-2-carboxamide dihydrochloride

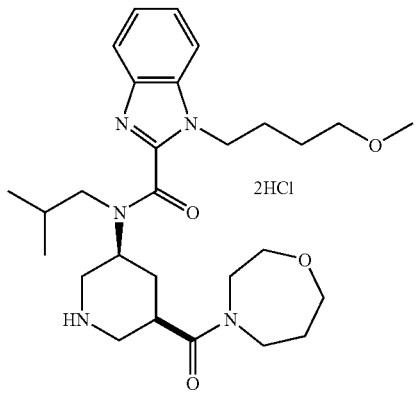

MS (ESI+, m/e) 514 (M+1)

Example 31

N-[(3S,5R)-5-(2,3-dihydro-4H-1,4-benzoxazin-4-ylcarbonyl)piperidin-3-yl]-1-(4-methoxybutyl)-N-(2-methylpropyl)-1H-benzimidazole-2-carboxamide dihydrochloride

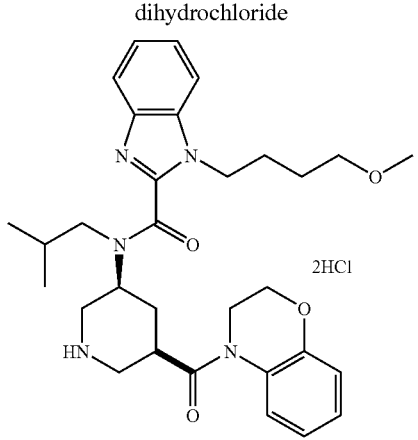

MS (ESI+, m/e) 548 (M+1)

Example 32 methyl (3R,5S)-5-[{[1-(4-methoxybutyl)-1H-benzimidazol-2-yl]carbonyl}(2-methylpropyl)amino]piperidine-3-carboxylate dihydrochloride

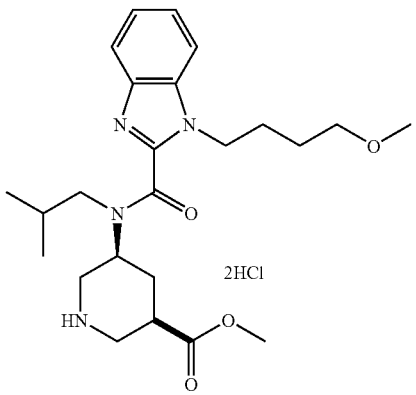

Example 33

(3R,5S)-5-[{[1-(4-methoxybutyl)-1H-benzimidazol-2-yl]carbonyl}(2-methylpropyl)amino]piperidine-3-carboxylic acid dihydrochloride

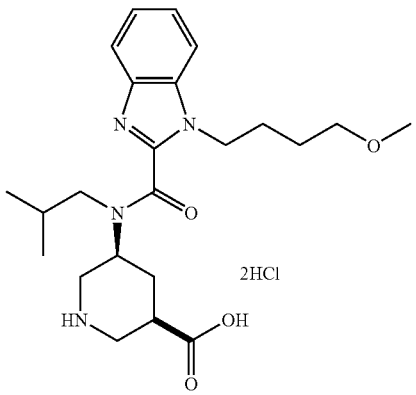

MS (ESI+, m/e) 431 (M+1)

Example 34

5,6-difluoro-1-(4-methoxybutyl)-N-(2-methylpropyl)-N-[(3S,5R)-5-(morpholin-4-ylcarbonyl)piperidin-3-yl]-1H-benzimidazole-2-carboxamide dihydrochloride

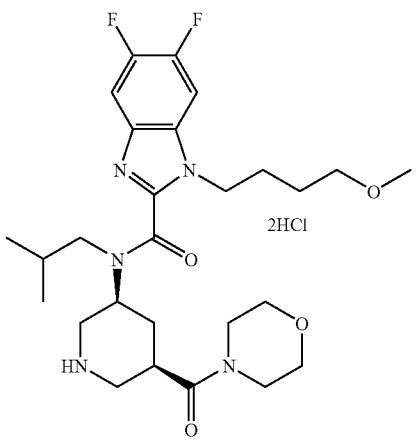 [SMILES: COCCCCn1c(C(=O)N(CC(C)C)[C@@H]2CNC[C@H](C(=O)N3CCOCC3)C2)nc2cc(F)c(F)cc21 ; "2HCl"]

MS (ESI+, m/e) 536 (M+1)

Example 35

N-[(3S,5R)-5-carbamoylpiperidin-3-yl]-5,6-difluoro-1-(4-methoxybutyl)-N-(2-methylpropyl)-1H-benzimidazole-2-carboxamide dihydrochloride

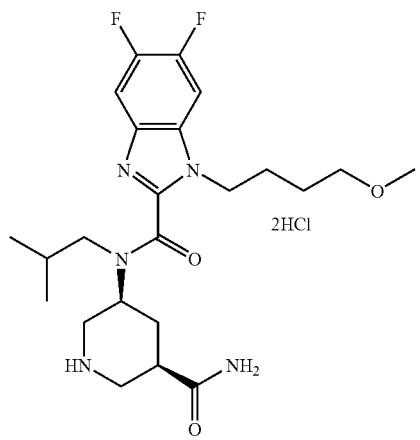 [SMILES: COCCCCn1c(C(=O)N(CC(C)C)[C@@H]2CNC[C@H](C(N)=O)C2)nc2cc(F)c(F)cc21 ; "2HCl"]

MS (ESI+, m/e) 466 (M+1)

Example 36

7-chloro-1-(4-methoxybutyl)-N-(2-methylpropyl)-N-[(3S,5R)-5-(morpholin-4-ylcarbonyl)piperidin-3-yl]-1H-benzimidazole-2-carboxamide dihydrochloride

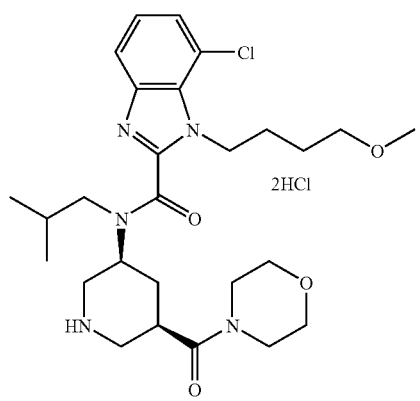 [SMILES: COCCCCn1c(C(=O)N(CC(C)C)[C@@H]2CNC[C@H](C(=O)N3CCOCC3)C2)nc2cccc(Cl)c21 ; "2HCl"]

MS (ESI+, m/e) 534 (M+1)

Example 37

4-chloro-1-(4-methoxybutyl)-N-(2-methylpropyl)-N-[(3S,5R)-5-(morpholin-4-ylcarbonyl)piperidin-3-yl]-1H-benzimidazole-2-carboxamide dihydrochloride

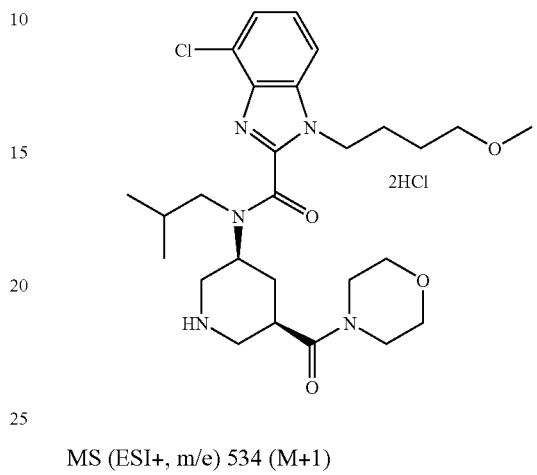

MS (ESI+, m/e) 534 (M+1)

Example 38

N-[(3S,5R)-5-(1-hydroxy-1-methylethyl)piperidin-3-yl]-1-(4-methoxybutyl)-N-(2-methylpropyl)-1H-benzimidazole-2-carboxamide dihydrochloride

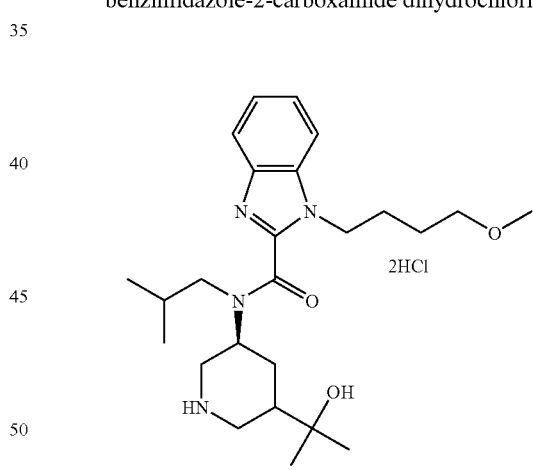

tert-Butyl (3R,5S)-3-(1-hydroxy-1-methylethyl)-5-[{[1-(4-methoxybutyl)-1H-benzimidazol-2-yl]carbonyl}(2-methylpropyl)amino]piperidine-1-carboxylate (180 mg) was dissolved in ethyl acetate (2 ml), 4N hydrogen chloride-ethyl acetate (4 ml) was added, and the mixture was stirred for 1 hr. The solvent was evaporated under reduced pressure to give the object product (130 mg).

$^1$H-NMR (DMSO-$d_6$) δ 0.64-0.75 (2H, m), 0.86-0.98 (4H, m), 1.40-1.58 (2H, m), 1.65-1.88 (2H, m), 1.88-2.36 (4H, m), 2.69-3.63 (9H, m), 3.79-3.95 (3H, m), 4.07-4.40 (5H, m), 4.99 (2H, br s), 7.22-7.44 (2H, m), 7.62-7.79 (2H, m), 8.41 (1H, br s), 8.67-8.87 (1H, m), 9.14 (1H, br s)

MS (ESI+, m/e) 445 (M+1)

Example 39

5,6-difluoro-N-[(3S,5R)-5-(1-hydroxy-1-methyl-ethyl)piperidin-3-yl]-1-(4-methoxybutyl)-N-(2-methylpropyl)-1H-benzimidazole-2-carboxamide dihydrochloride

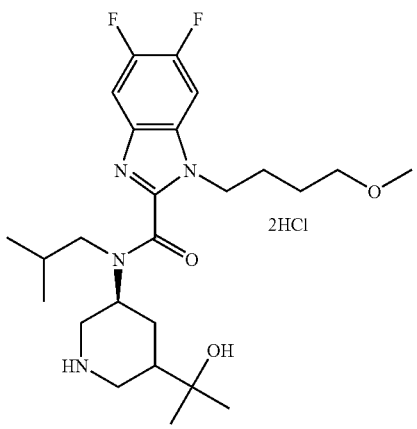 [SMILES: COCCCCn1c(C(=O)N(CC(C)C)[C@@H]2CNCC(C(C)(C)O)C2)nc2cc(F)c(F)cc21 ; "2HCl"]

MS (ESI+, m/e) 481 (M+1)

Example 40

N-[(3S,5R)-5-(hydroxymethyl)piperidin-3-yl]-1-(4-methoxybutyl)-N-(2-methylpropyl)-1H-benzimidazole-2-carboxamide dihydrochloride

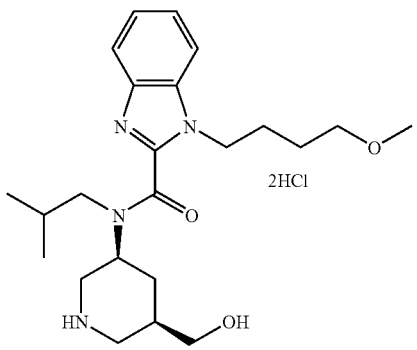 [SMILES: COCCCCn1c(C(=O)N(CC(C)C)[C@@H]2CNC[C@H](CO)C2)nc2ccccc21 ; "2HCl"]

To tert-butyl (3R,5S)-3-(hydroxymethyl)-5-[{[1-(4-methoxybutyl)-1H-benzimidazol-2-yl]carbonyl}(2-methylpropyl)amino]piperidine-1-carboxylate (150 mg) in THF (2 ml) was added TFA (5 ml) and the mixture was stirred at room temperature for 1 hr. The solvent was evaporated under reduced pressure, and the residue was subjected to reversed-phase preparative HPLC and the eluted fraction was concentrated under reduced pressure. The residual aqueous layer was neutralized with saturated aqueous sodium hydrogen carbonate and extracted with ethyl acetate. The extract was dried over anhydrous sodium sulfate, 10-20% hydrogen chloride-methanol was added, and the solvent was evaporated under reduced pressure to give the object product (75 mg).

$^1$H-NMR (DMSO-$d_6$) δ 0.67-0.76 (3H, m) 0.90-0.99 (3H, m), 1.37-1.58 (2H, m), 1.63-1.88 (2H, m), 1.86-2.21 (2H, m), 2.50 (2H, dt), 3.02-4.92 (16H, m), 7.37 (2H, d), 7.63-7.84 (2H, m), 8.65 (1H, br s), 9.05-9.74 (1H, m)

MS (ESI+, m/e) 417 (M+1)

In the same manner as in Example 40, the following compounds (Examples 41-44) were obtained.

Example 41

1-(4-methoxybutyl)-N-[(3S,5R)-5-(5-methyl-1,3,4-oxadiazol-2-yl)piperidin-3-yl]-N-(2-methylpropyl)-1H-benzimidazole-2-carboxamide dihydrochloride

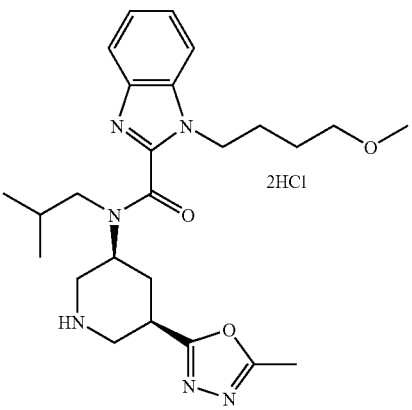 [SMILES: COCCCCn1c(C(=O)N(CC(C)C)[C@@H]2CNC[C@H](c3nnc(C)o3)C2)nc2ccccc21 ; "2HCl"]

MS (ESI+, m/e) 469 (M+1)

Example 42

N-[(3S,5R)-5-(1-hydroxyethyl)piperidin-3-yl]-1-(4-methoxybutyl)-N-(2-methylpropyl)-1H-benzimidazole-2-carboxamide dihydrochloride

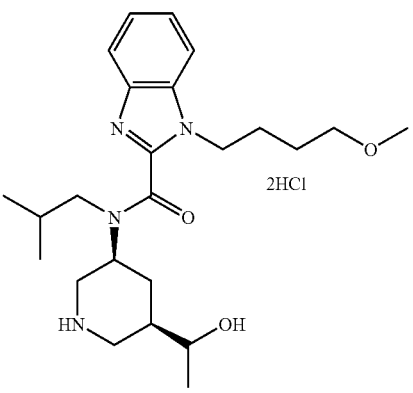 [SMILES: COCCCCn1c(C(=O)N(CC(C)C)[C@@H]2CNC[C@H](C(C)O)C2)nc2ccccc21 ; "2HCl"]

MS (ESI+, m/e) 431 (M+1)

Example 43

N-{(3S,5R)-5-[cyclopropyl(hydroxy)methyl]piperidin-3-yl}-1-(4-methoxybutyl)-N-(2-methylpropyl)-1H-benzimidazole-2-carboxamide dihydrochloride

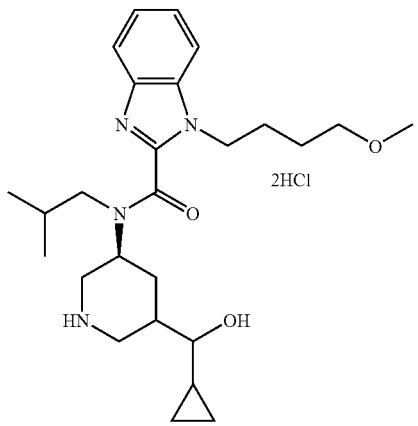 [SMILES: COCCCCn1c(C(=O)N(CC(C)C)[C@@H]2CNCC(C(O)C3CC3)C2)nc2ccccc21 ; "2HCl"]

MS (ESI+, m/e) 457 (M+1)

Example 44

N-{(3S,5R)-5-[hydroxy(pyridin-2-yl)methyl]piperidin-3-yl}-1-(4-methoxybutyl)-N-(2-methylpropyl)-1H-benzimidazole-2-carboxamide trihydrochloride

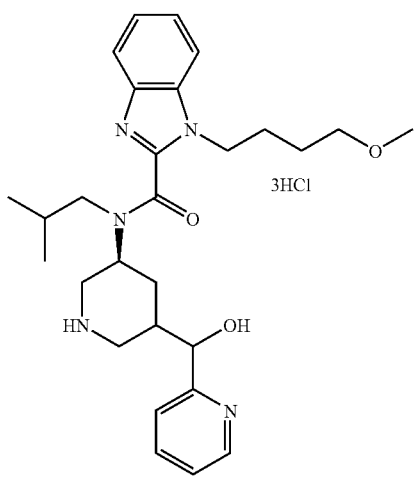 [SMILES: COCCCCn1c(C(=O)N(CC(C)C)[C@@H]2CNCC(C(O)c3ccccn3)C2)nc2ccccc21 ; "3HCl"]

MS (ESI+, m/e) 494 (M+1)

Example 45

N-[(3S,5R)-5-(azetidin-1-ylcarbonyl)piperidin-3-yl]-1-(4-methoxybutyl)-N-(2-methylpropyl)-1H-benzimidazole-2-carboxamide

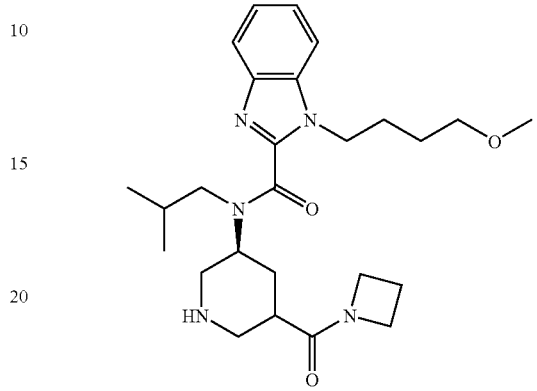

To tert-butyl (3R,5S)-3-(azetidin-1-ylcarbonyl)-5-[{[1-(4-methoxybutyl)-1H-benzimidazol-2-yl]carbonyl}(2-methylpropyl)amino]piperidine-1-carboxylate (230 mg) in 1,2-dichloroethane (3 ml) was added TFA (3 ml) and the mixture was stirred at room temperature for 1 hr. The solvent was evaporated under reduced pressure, and the residue was dissolved in ethyl acetate-water, and neutralized with saturated aqueous sodium hydrogen carbonate. The organic layer was dried over anhydrous sodium sulfate and the solvent was evaporated under reduced pressure to give the object product (100 mg).

MS (ESI+, m/e) 470 (M+1)

Example 46

N-[(3S,5R)-5-(azetidin-1-ylcarbonyl)piperidin-3-yl]-5,6-difluoro-1-(4-methoxybutyl)-N-(2-methylpropyl)-1H-benzimidazole-2-carboxamide 1/2 fumarate

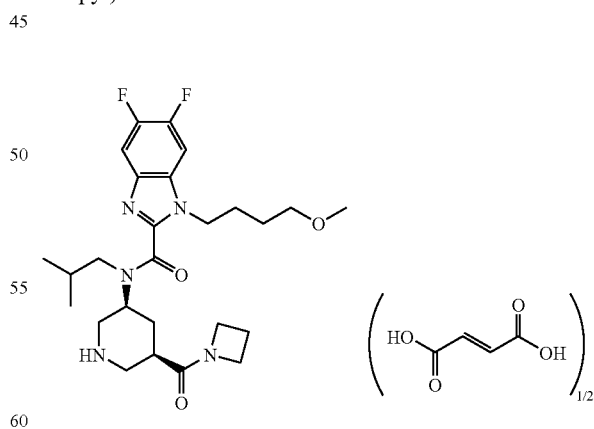

To tert-butyl (3R,5S)-3-(azetidin-1-ylcarbonyl)-5-[{[5,6-difluoro-1-(4-methoxybutyl)-1H-benzimidazol-2-yl]carbonyl}(2-methylpropyl)amino]piperidine-1-carboxylate (270 mg) in 1,2-dichloroethane (3 ml) was added TFA (5 ml) and the mixture was stirred at room temperature for 1 hr. The solvent was evaporated under reduced pressure, and the residue was dissolved in ethyl acetate-water, and neutralized with saturated aqueous sodium hydrogen carbonate. The organic layer was dried over anhydrous sodium sulfate, fumaric acid (23 mg) was added, and the solvent was evaporated under reduced pressure to give the object product (210 mg).

MS (ESI+, m/e) 506 (M+1)

Example 47

{(3R,5S)-5-[{[1-(4-methoxybutyl)-1H-benzimidazol-2-yl]carbonyl}(2-methylpropyl)amino]piperidin-3-yl}methyl acetate dihydrochloride

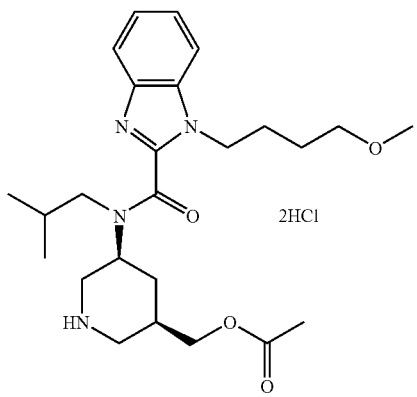 [SMILES: COCCCCn1c(C(=O)N(CC(C)C)[C@@H]2CNC[C@H](COC(C)=O)C2)nc2ccccc21 ; "2HCl"]

tert-Butyl (3R,5S)-3-(hydroxymethyl)-5-[{[1-(4-methoxybutyl)-1H-benzimidazol-2-yl]carbonyl}(2-methylpropyl)amino]piperidine-1-carboxylate (200 mg) was dissolved in ethyl acetate (2 ml), 4N hydrogen chloride-ethyl acetate (5 ml) was added, and the mixture was stirred for 1 hr. The solvent was evaporated under reduced pressure to give the object product (200 mg).

MS (ESI+, m/e) 459 (M+1)

Example 48

N-[(3S,5R)-5-(1-hydroxy-2-methoxyethyl)piperidin-3-yl]-1-(4-methoxybutyl)-N-(2-methylpropyl)-1H-benzimidazole-2-carboxamide dihydrochloride

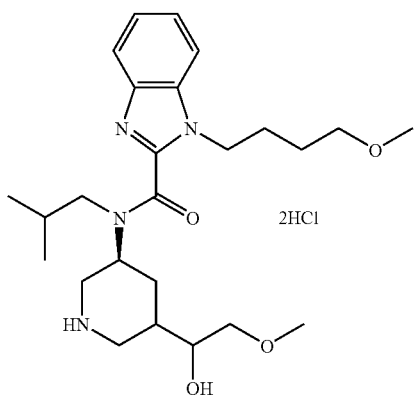 [SMILES: COCCCCn1c(C(=O)N(CC(C)C)[C@@H]2CNCC(C(O)COC)C2)nc2ccccc21 ; "2HCl"]

tert-Butyl (5S)-3-(1-hydroxy-2-methoxyethyl)-5-[{[1-(4-methoxybutyl)-1H-benzimidazol-2-yl]carbonyl}(2-methylpropyl)amino]piperidine-1-carboxylate (150 mg) was dissolved in 10-20%-hydrogen chloride methanol solution (10 ml), and the mixture was stirred at room temperature for 3 hr. The solvent was evaporated under reduced pressure to give the object product (140 mg).

MS (ESI+, m/e) 461 (M+1)

Example 49

1-(4-methoxybutyl)-N-(2-methylpropyl)-N-[(3S,5R)-5-(morpholin-4-ylcarbonyl)piperidin-3-yl]-1H-benzimidazole-2-carboxamide methanesulfonate

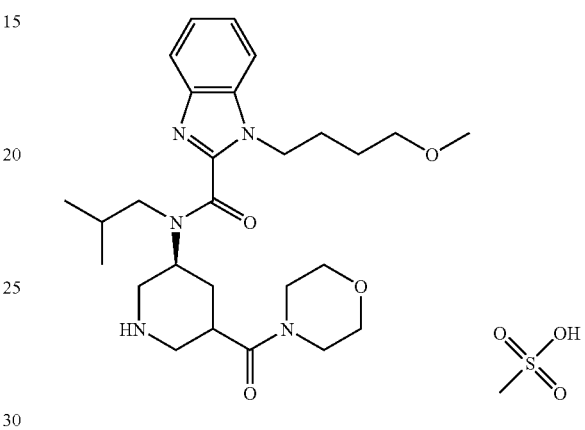

tert-Butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate (10.2 g) was dissolved in ethyl acetate (17 ml) and methanol (5 ml), 4N hydrogen chloride-ethyl acetate (34 ml) was added, and the mixture was stirred for 1 hr. The reaction mixture was poured into 10%-aqueous sodium hydrogen carbonate solution (125 ml), and the mixture was extracted with ethyl acetate. The extract was washed with brine, and dried over anhydrous sodium sulfate. The solvent was evaporated under reduced pressure. A part (7.8 g) of the residue (8.1 g) was dissolved in ethyl acetate (60 ml), and dissolved in methanesulfonic acid (1.5 g) by heating (90° C.). This was stood at room temperature for 4 days, and the precipitated crystals were collected by filtration to give the object product as crude crystals (7.3 g).

MS (ESI+, m/e) 500 (M+1)

Reference Example 101

2-fluoro-N-(4-methoxybutyl)-6-nitroaniline

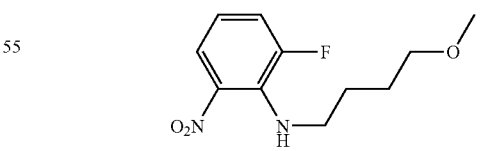

To a solution of 1,2-difluoro-3-nitrobenzene (5.15 g) and 4-methoxybutan-1-amine hydrochloride (5.42 g) in acetonitrile (100 ml) was added diisopropylethylamine (17 µl), and the mixture was stirred at 60° C. for 12 hr. 4-Methoxybutan-1-amine hydrochloride (1.00 g) was further added, and the mixture was stirred at 70° C. for 5 hr. The reaction mixture was concentrated under reduced pressure, saturated aqueous

Reference Example 102

3-fluoro-2-(4-methoxybutylamino)aniline

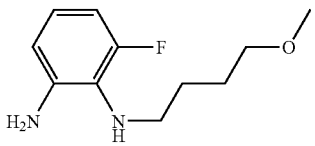 [SMILES: COCCCCNc1c(F)cccc1[N+](=O)[O-]]

2-Fluoro-N-(4-methoxybutyl)-6-nitroaniline (3.54 g) was dissolved in methanol (50 ml), palladium-carbon (5%, 140 mg) was added, and the mixture was stirred for 3.5 hr under a hydrogen atmosphere. The reaction mixture was filtered through celite, and the filtrate was concentrated under reduced pressure to give the object product (3.05 g).

$^1$H-NMR (CDCl$_3$) δ 1.49-1.76 (4 H, m), 2.89-3.12 (1 H, m), 2.98 (2 H, t), 3.34 (3 H, s), 3.40 (2 H, t), 3.91 (2 H, br s), 6.43-6.52 (2 H, m), 6.78 (1 H, td)

Reference Example 103

(3R,5S)-1-(tert-butoxycarbonyl)-5-[{[7-fluoro-1-(4-methoxybutyl)-1H-benzimidazol-2-yl]carbonyl}(2-methylpropyl)amino]piperidine-3-carboxylic acid

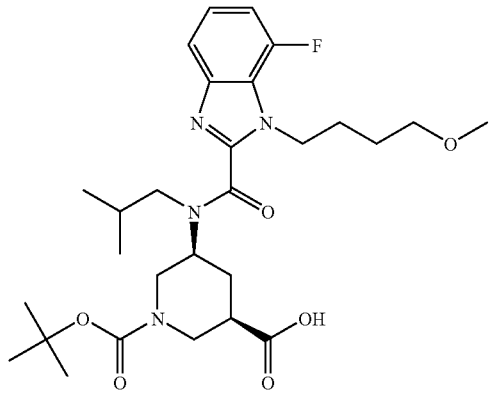 [SMILES: COCCCCn1c(C(=O)N(CC(C)C)[C@H]2C[C@@H](C(=O)O)CN(C(=O)OC(C)(C)C)C2)nc2cccc(F)c21]

3-Fluoro-2-(4-methoxybutylamino)aniline (3.05 g) was dissolved in acetic acid (80 ml), methyl 2,2,2-trichloroethanimidate (1.92 ml) was added, and the mixture was stirred for 1.5 hr. The reaction mixture was concentrated under reduced pressure, and the residue was diluted with diisopropyl ether, and washed with water. The organic layer was dried over anhydrous magnesium sulfate, and concentrated under reduced pressure. The residue was immediately dissolved in acetonitrile-water (2:1, 225 ml), and 1-tert-butyl 3-methyl (3R,5S)-5-{(2-methylpropyl)amino}piperidine-1,3-dicarboxylate (3.58 g) was added. Potassium carbonate (16 g) was added, and the mixture was stirred at 80° C. for 19 hr. The reaction mixture was concentrated under reduced pressure, diluted with saturated aqueous ammonium chloride solution, and the mixture was extracted with ethyl acetate. The extract was dried over anhydrous magnesium sulfate, and concentrated under reduced pressure. The residue was subjected to silica gel chromatography, and a fraction eluted with ethyl acetate-hexane (5:95)-ethyl acetate-ethyl acetate-methanol (85:15) was concentrated under reduced pressure to give the object product (1.65 g).

MS (ESI+, m/e) 549 (M+1)

Reference Example 104 tert-butyl (3S,5R)-3-{{{7-fluoro-1-(4-methoxybutyl)-1H-benzimidazol-2-yl}carbonyl}(2-methylpropyl)amino}-5-(morpholin-4-ylcarbonyl)piperidine-1-carboxylate

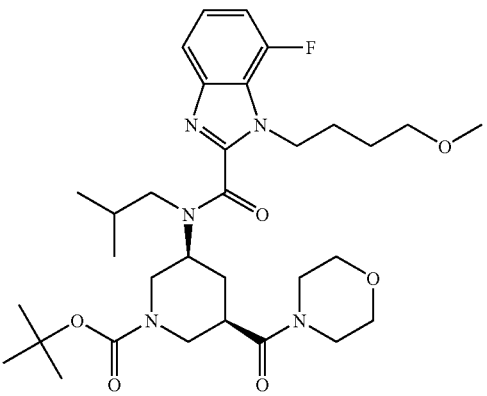 [SMILES: COCCCCn1c(C(=O)N(CC(C)C)[C@H]2C[C@@H](C(=O)N3CCOCC3)CN(C(=O)OC(C)(C)C)C2)nc2cccc(F)c21]

(3R,5S)-1-(tert-Butoxycarbonyl)-5-[{[7-fluoro-1-(4-methoxybutyl)-1H-benzimidazol-2-yl]carbonyl}(2-methylpropyl)amino]piperidine-3-carboxylic acid (207 mg), morpholine (87 μl), HOBt (40 mg) and triethylamine (210 μl) were dissolved in DMF (10 ml), WSC.HCl (180 mg) was added, and the mixture was stirred at 50° C. for 1 hr. The reaction mixture was concentrated under reduced pressure, diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and a fraction eluted with ethyl acetate-hexane (1:9)-ethyl acetate was concentrated under reduced pressure to give the object product (160 mg).

MS (ESI+, m/e) 618 (M+1)

Reference Example 105 tert-butyl (3R,5S)-3-carbamoyl-5-{{{7-fluoro-1-(4-methoxybutyl)-1H-benzimidazol-2-yl}carbonyl}(2-methylpropyl)amino}piperidine-1-carboxylate

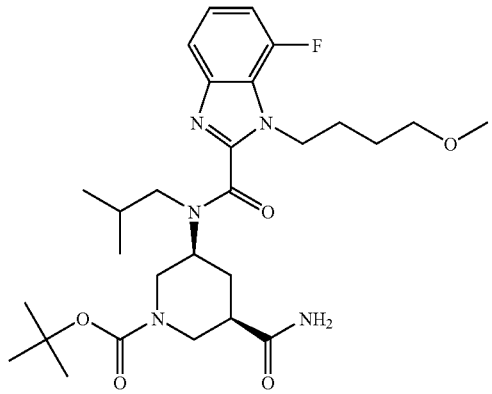 [SMILES: COCCCCn1c(C(=O)N(CC(C)C)[C@H]2C[C@@H](C(N)=O)CN(C(=O)OC(C)(C)C)C2)nc2cccc(F)c21]

(3R,5S)-1-(tert-Butoxycarbonyl)-5-[{[7-fluoro-1-(4-methoxybutyl)-1H-benzimidazol-2-yl]carbonyl}(2-methylpropyl)amino]piperidine-3-carboxylic acid (360 mg), 1H-1,2,3-benzotriazol-1-ol ammonium salt (250 mg) and triethylamine (360 μl) were dissolved in DMF (10 ml), WSC.HCl (315 mg) was added, and the mixture was stirred at 50° C. for 1 hr. The reaction mixture was concentrated under reduced pressure, diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and a fraction eluted with ethyl acetate-hexane (3:7)-ethyl acetate-ethyl acetate-methanol (9:1) was concentrated under reduced pressure to give the object product (263 mg).

MS (ESI+, m/e) 548 (M+1)

Reference Example 106 tert-butyl (3S,5R)-3-{{{7-fluoro-1-(4-methoxybutyl)-1H-benzimidazol-2-yl}carbonyl}(2-methylpropyl)amino}-5-(4H-1,2,4-triazol-3-yl)piperidine-1-carboxylate

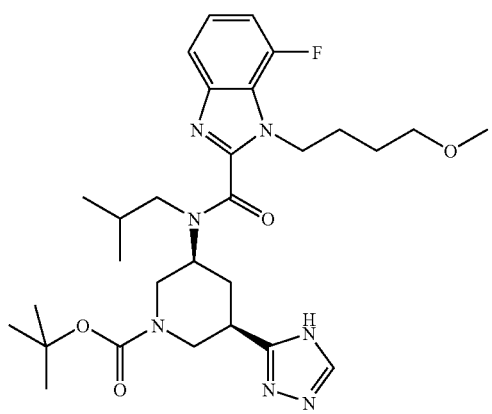 [SMILES: COCCCCn1c(C(=O)N(CC(C)C)[C@H]2C[C@@H](c3nnc[nH]3)CN(C(=O)OC(C)(C)C)C2)nc2cccc(F)c21]

tert-Butyl (3R,5S)-3-carbamoyl-5-{{{7-fluoro-1-(4-methoxybutyl)-1H-benzimidazol-2-yl}carbonyl}(2-methylpropyl)amino}piperidine-1-carboxylate (115 mg) was dissolved in dimethylformamide dimethylacetal (5 ml), and the mixture was stirred at 100° C. for 15 hr. The reaction mixture was concentrated under reduced pressure, and the residue was dissolved in acetic acid (7 ml). Hydrazine monohydrate (48 μl) was added and the mixture was stirred at 80° C. for 3 hr. The reaction mixture was concentrated under reduced pressure, diluted with 0.5M aqueous sodium hydroxide solution, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-ethyl acetate-methanol (9:1) was concentrated under reduced pressure to give the object product (130 mg).

MS (ESI+, m/e) 572 (M+1)

Reference Example 107 tert-butyl (3S,5R)-3-{{{7-fluoro-1-(4-methoxybutyl)-1H-benzimidazol-2-yl}carbonyl}(2-methylpropyl)amino}-5-(pyrrolidin-1-ylcarbonyl)piperidine-1-carboxylate

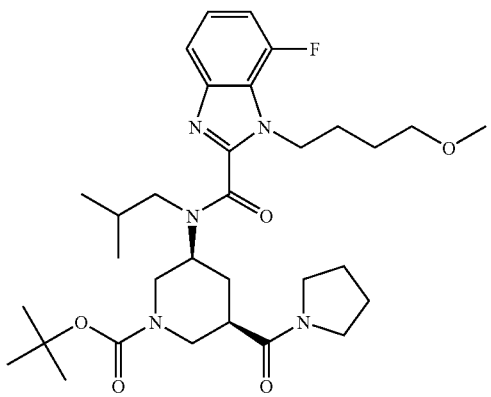 [SMILES: COCCCCn1c(C(=O)N(CC(C)C)[C@H]2C[C@@H](C(=O)N3CCCC3)CN(C(=O)OC(C)(C)C)C2)nc2cccc(F)c21]

(3R,5S)-1-(tert-Butoxycarbonyl)-5-[{[7-fluoro-1-(4-methoxybutyl)-1H-benzimidazol-2-yl]carbonyl}(2-methylpropyl)amino]piperidine-3-carboxylic acid (1.65 g), pyrrolidine (500 μl), HOBt (270 mg) and triethylamine (1.27 ml) were dissolved in DMF (50 ml), WSC.HCl (1.15 g) was added, and the mixture was stirred at 50° C. for 1 hr. The reaction mixture was concentrated under reduced pressure, diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and a fraction eluted with ethyl acetate-hexane (5:95)-ethyl acetate-ethyl acetate-methanol (9:1) was concentrated under reduced pressure to give the object product (170 mg).

MS (ESI+, m/e) 602 (M+1)

Example 50

7-fluoro-1-(4-methoxybutyl)-N-(2-methylpropyl)-N-{(3S,5R)-5-(morpholin-4-ylcarbonyl)piperidin-3-yl}-1H-benzimidazole-2-carboxamide dihydrochloride

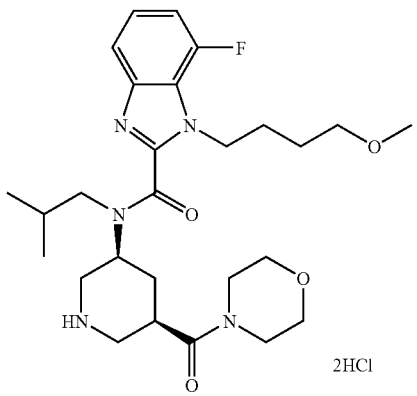 [SMILES: COCCCCn1c(C(=O)N(CC(C)C)[C@@H]2CNC[C@H](C(=O)N3CCOCC3)C2)nc2cccc(F)c21 ; "2HCl"]

2HCl tert-Butyl (3S,5R)-3-{{{7-fluoro-1-(4-methoxybutyl)-1H-benzimidazol-2-yl}carbonyl}(2-methylpropyl)amino}-5-(morpholin-4-ylcarbonyl)piperidine-1-carboxylate (160 mg) was dissolved in 2M hydrogen chloride-ethyl acetate (3 ml), and the mixture was stirred at room temperature for 10 hr. The reaction mixture was concentrated under reduced pressure. The residue was subjected to reversed-phase preparative HPLC, and a fraction eluted with water-acetonitrile (9:1-6:4) was collected, basified (pH 10) with saturated aqueous potassium carbonate solution, and extracted with ethyl acetate. The extract was dried over anhydrous magnesium sulfate, and concentrated under reduced pressure. The residue was dissolved in 1M hydrogen chloride-ethyl acetate (1 ml), and the reaction mixture was concentrated under reduced pressure to give the object product (104 mg).

MS (ESI+, m/e) 518 (M+1)

In the same manner as in Example 50, the following compounds (Examples 51-52) were obtained.

Example 51

N-{(3S,5R)-5-carbamoylpiperidin-3-yl}-7-fluoro-1-(4-methoxybutyl)-N-(2-methylpropyl)-1H-benzimidazole-2-carboxamide dihydrochloride

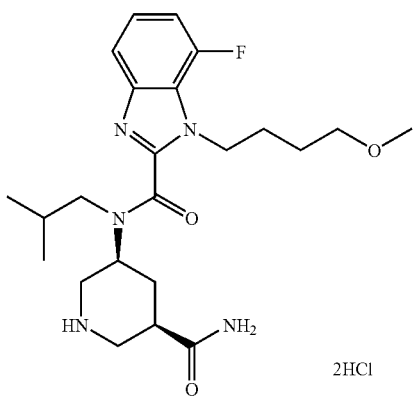 [SMILES: COCCCCn1c(C(=O)N(CC(C)C)[C@@H]2CNC[C@H](C(N)=O)C2)nc2cccc(F)c21 ; "2HCl"]

2HCl

MS (ESI+, m/e) 448 (M+1)

Example 52

7-fluoro-1-(4-methoxybutyl)-N-(2-methylpropyl)-N-{(3S,5R)-5-(pyrrolidin-1-ylcarbonyl)piperidin-3-yl}-1H-benzimidazole-2-carboxamide dihydrochloride

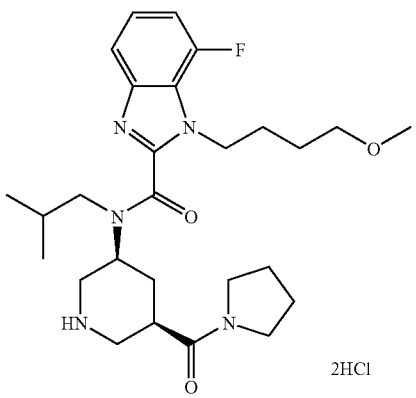 [SMILES: COCCCCn1c(C(=O)N(CC(C)C)[C@@H]2CNC[C@H](C(=O)N3CCCC3)C2)nc2cccc(F)c21 ; "2HCl"]

2HCl

MS (ESI+, m/e) 502 (M+1)

Example 53 2-carboxamide 1/2 fumarate 7-fluoro-1-(4-methoxybutyl)-N-(2-methylpropyl)-N-{(3S,5R)-5-(4H-1,2,4-triazol-3-yl)piperidin-3-yl}-1H-benzimidazole-2-carboxamide dihydrochloride

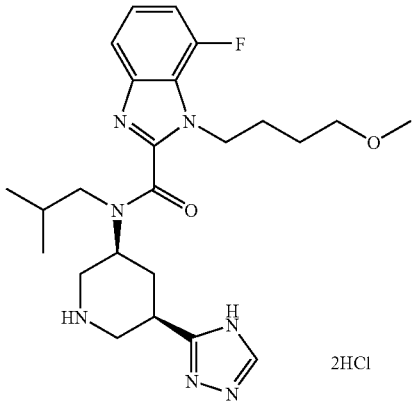 [SMILES: COCCCCn1c(C(=O)N(CC(C)C)[C@@H]2CNC[C@H](c3nnc[nH]3)C2)nc2cccc(F)c21 ; "2HCl"]

2HCl tert-Butyl (3S,5R)-3-{{{7-fluoro-1-(4-methoxybutyl)-1H-benzimidazol-2-yl}carbonyl}(2-methylpropyl)amino}-5-(4H-1,2,4-triazol-3-yl)piperidine-1-carboxylate (130 mg) was dissolved in 2M hydrogen chloride-ethyl acetate (3 ml), and the mixture was stirred at room temperature for 12 hr. The reaction mixture was concentrated to give the object product (91 mg).

MS (ESI+, m/e) 472 (M+1)

Reference Example 108

3-fluoro-N-(4-methoxybutyl)-2-nitroaniline

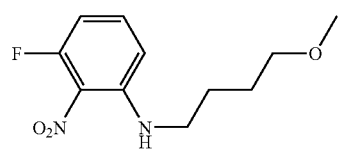 [SMILES: COCCCCNc1cccc(F)c1[N+](=O)[O-]]

To a solution of 1,3-difluoro-2-nitrobenzene (3.00 g) and diisopropylethylamine (7 μl) in acetonitrile (30 ml) was added a solution of 4-methoxybutan-1-amine hydrochloride (2.51 g) in acetonitrile (10 ml), and the mixture was stirred at room temperature for 90 hr. The reaction mixture was concentrated under reduced pressure, and the residue was subjected to silica gel column chromatography, and a fraction eluted with ethyl acetate-hexane (2:98-25:75) was concentrated under reduced pressure to give the object product (2.90 g).

$^1$H-NMR (CDCl$_3$) δ 1.65-1.84 (4H, m), 3.28 (2H, ddd), 3.35 (3H, s), 3.43 (2H, t), 6.41 (1H, ddd), 6.58 (1H, d), 7.22-7.32 (2H, m)

Reference Example 109

6-fluoro-2-(4-methoxybutylamino)aniline

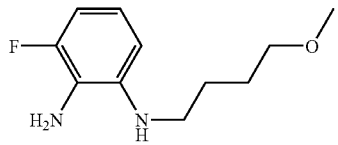

3-Fluoro-N-(4-methoxybutyl)-2-nitroaniline (2.90 g) was dissolved in methanol (50 ml), palladium-carbon (5%, 230 mg) was added, and the mixture was stirred for 3 hr under a hydrogen atmosphere. The reaction mixture was filtered through celite, and the filtrate was concentrated under reduced pressure to give the object product (2.54 g).

$^1$H-NMR (CDCl$_3$) δ 1.64-1.79 (4H, m), 3.14 (2H, t), 3.18-3.32 (2H, m), 3.35 (3H, s), 3.43 (2H, t), 3.53 (1H, br s), 6.42 (1H, d), 6.51 (1H, ddd), 6.73 (1H, td)

Reference Example 110

1-tert-butyl 3-methyl (3R,5S)-5-{{{4-fluoro-1-(4-methoxybutyl)-1H-benzimidazol-2-yl}carbonyl}(2-methylpropyl)amino}piperidine-1,3-dicarboxylate

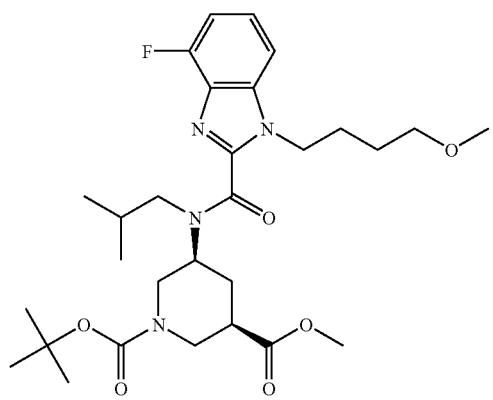 [SMILES: COCCCCn1c(C(=O)N(CC(C)C)[C@H]2C[C@@H](C(=O)OC)CN(C(=O)OC(C)(C)C)C2)nc2c(F)cccc21]

6-Fluoro-2-(4-methoxybutylamino)aniline (2.54 g) was dissolved in acetic acid (90 ml), methyl 2,2,2-trichloroethanimidate (1.48 ml) was added, and the mixture was stirred for 1.5 hr. The reaction mixture was concentrated under reduced pressure, and the residue was suspended in toluene (50 ml) and concentrated under reduced pressure. This operation was repeated twice. The residue was immediately dissolved in acetonitrile-water (3:1, 200 ml), 1-tert-butyl 3-methyl (3R, 5S)-5-{(2-methylpropyl)amino}piperidine-1,3-dicarboxylate (3.70 g) was added, and potassium carbonate (16.5 g) was added and the mixture was stirred at 80° C. for 19 hr. The reaction mixture was concentrated under reduced pressure, diluted with saturated aqueous ammonium chloride solution, and extracted with ethyl acetate. The extract was dried over anhydrous magnesium sulfate, and concentrated under reduced pressure. The residue was subjected to silica gel chromatography, and a fraction eluted with ethyl acetate-hexane (5:95-1:1) was concentrated under reduced pressure to give the object product (195 mg).

MS (ESI+, m/e) 563(M+1)

Reference Example 111

(3R,5S)-1-(tert-butoxycarbonyl)-5-{{{4-fluoro-1-(4-methoxybutyl)-1H-benzimidazol-2-yl}carbonyl}(2-methylpropyl)amino}piperidine-3-carboxylic acid

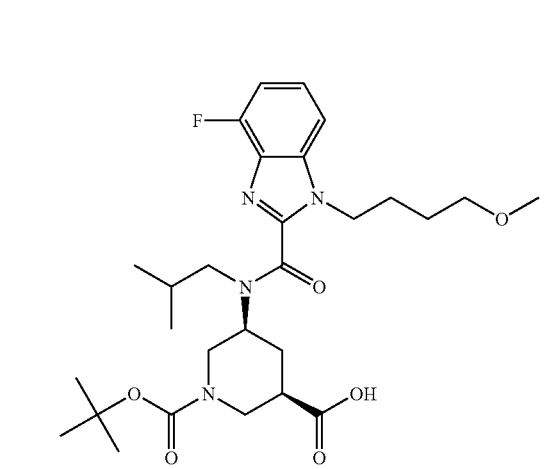 [SMILES: COCCCCn1c(C(=O)N(CC(C)C)[C@H]2C[C@@H](C(=O)O)CN(C(=O)OC(C)(C)C)C2)nc2c(F)cccc21]

1-tert-Butyl 3-methyl (3R,5S)-5-{{{4-fluoro-1-(4-methoxybutyl)-1H-benzimidazol-2-yl}carbonyl}(2-methylpropyl)amino}piperidine-1,3-dicarboxylate (195 mg) was dissolved in tetrahydrofuran-methanol (1:2, 15 ml), 2M aqueous sodium hydroxide solution (1 ml) was added, and the mixture was stirred at 45° C. for 4 hr. The reaction mixture was concentrated under reduced pressure, neutralized with saturated aqueous ammonium chloride solution and extracted with ethyl acetate. The extract was dried over anhydrous magnesium sulfate, concentration under reduced pressure to give the object product (180 mg).

MS (ESI+, m/e) 549(M+1)

In the same manner as in Reference Example 104, the following compound (Reference Example 112) was obtained.

Reference Example 112 tert-butyl (3S,5R)-3-{{{4-fluoro-1-(4-methoxybutyl)-1H-benzimidazol-2-yl}carbonyl}(2-methylpropyl)amino}-5-(morpholin-4-ylcarbonyl)piperidine-1-carboxylate

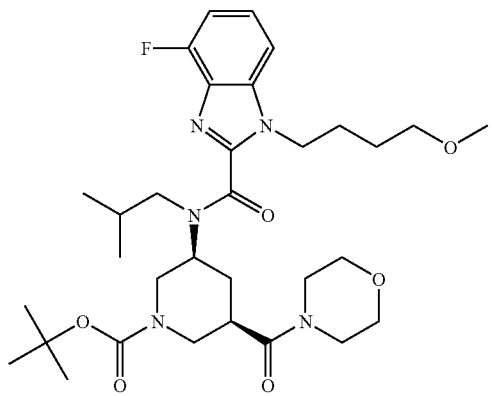 [SMILES: COCCCCn1c(C(=O)N(CC(C)C)[C@H]2C[C@@H](C(=O)N3CCOCC3)CN(C(=O)OC(C)(C)C)C2)nc2c(F)cccc21]

MS (ESI+, m/e) 618 (M+1)

Example 54

4-fluoro-1-(4-methoxybutyl)-N-(2-methylpropyl)-N-{(3S,5R)-5l-(morpholin-4-ylcarbonyl)piperidin-3-yl}-1H-benzimidazole-2-carboxamide dihydrochloride

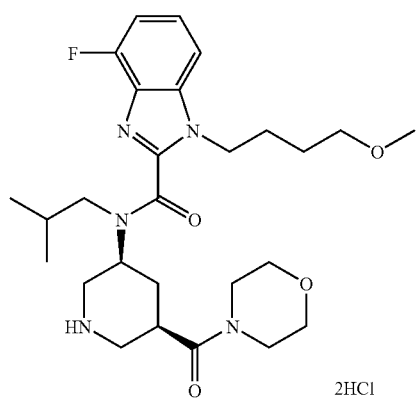 [SMILES: COCCCCn1c(C(=O)N(CC(C)C)[C@@H]2CNC[C@H](C(=O)N3CCOCC3)C2)nc2c(F)cccc21 ; "2HCl"]

tert-Butyl (3S,5R)-3-{{{4-fluoro-1-(4-methoxybutyl)-1H-benzimidazol-2-yl}carbonyl}(2-methylpropyl)amino}-5-(morpholin-4-ylcarbonyl)piperidine-1-carboxylate (75 mg) was dissolved in 3M hydrogen chloride-ethyl acetate (2 ml), and the mixture was stirred at room temperature for 30 min and concentrated to give the object product (67 mg).

MS (ESI+, m/e) 518 (M+1)

Reference Example 113 tert-butyl (3-methoxy-2-nitrophenyl)carbamate

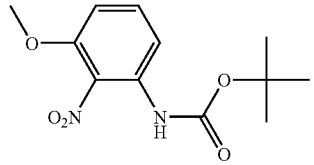 [SMILES: COc1cccc(NC(=O)OC(C)(C)C)c1[N+](=O)[O-]]

3-Methoxy-2-nitrobenzoic acid (10.25 g) was suspended in toluene (200 ml), and triethylamine (8.65 ml) and diphenylphosphoryl azide (13.4 ml) were added dropwise at room temperature. The mixture was stirred at 90° C. for 1.5 hr, triethylamine (29 ml) and 2-methylpropan-2-ol (15 ml) were added, and the mixture was further stirred at 90° C. for 2 hr. The reaction mixture was concentrated under reduced pressure, diluted, with ethyl acetate, 0.5M hydrochloric acid (200 ml) was added, and the mixture was filtered through celite. The organic layer of the filtrate was collected, washed with saturated aqueous sodium hydrogen carbonate, dried over anhydrous magnesium sulfate, and concentrated under reduced pressure. The residue was subjected to silica gel chromatography, and a fraction eluted with ethyl acetate-hexane (5:95-1:1) was concentrated under reduced pressure to give the object product (10.18 g).

$^1$H-NMR (CDCl$_3$) δ 1.50 (8 H, s), 3.90 (3 H, s), 6.71 (1 H, d), 7.39 (2 H, t), 7.55 (1 H, br s), 7.77 (1 H, d)

Reference Example 114 tert-butyl (4-methoxybutyl)(3-methoxy-2-nitrophenyl)carbamate

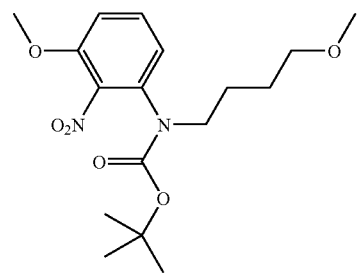

tert-Butyl (3-methoxy-2-nitrophenyl)carbamate (3.00 g) and 4-methoxybutyl methanesulfonate (3.06 g) were dissolved in dimethylformamide (40 ml), cesium carbonate (7.30 g) was added, and the mixture was stirred at 65° C. for 4 hr. The reaction mixture was concentrated under reduced pressure, diluted with water, and the mixture was extracted with ethyl acetate. The extract was washed with saturated brine, and dried over s anhydrous magnesium sulfate and concentrated under reduced pressure. The residue was subjected to silica gel chromatography, and a fraction eluted with ethyl acetate-hexane (5:95-7:3) was concentrated under reduced pressure to give the object product (2.11 g).

$^1$H-NMR (CDCl$_3$) δ 1.36 (9 H, br s), 1.47-1.71 (6 H, m), 3.30 (3 H, s), 3.37 (2 H, t), 3.91 (3 H, s), 6.86 (1 H, d), 6.98 (1 H, d), 7.40 (1 H, t)

Reference Example 115

3-methoxy-N-(4-methoxybutyl)-2-nitroaniline

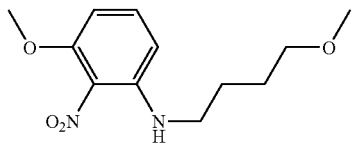

tert-Butyl (4-methoxybutyl) (3-methoxy-2-nitrophenyl)carbamate (2.11 g) was dissolved in ethyl acetate (30 ml), 4M hydrogen chloride-ethyl acetate (15 ml) was added, and the mixture was stirred for 12 hr. The reaction mixture was concentrated under reduced pressure, diluted with saturated aqueous sodium hydrogen carbonate, and the mixture was extracted with ethyl acetate. The extract was dried over anhydrous magnesium sulfate, concentration under reduced pressure to give the object product (1.50 g).

$^1$H-NMR (CDCl$_3$) δ 1.60-1.80 (4 H, m), 3.21 (2 H, ddd), 3.34 (3 H, s), 3.41 (2 H, t), 3.87 (3 H, s), 6.17 (1 H, br s), 6.25 (1 H, d), 6.37 (1 H, d), 7.22 (1 H, t)

Reference Example 116

6-methoxy-2-(4-methoxybutylamino)aniline

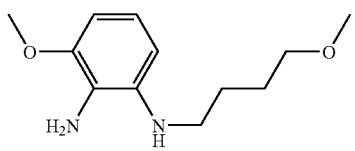

3-Methoxy-N-(4-methoxybutyl)-2-nitroaniline (230 mg) was dissolved in methanol (30 ml), palladium-carbon (5%, 90 mg) was added, and the mixture was stirred for 2 hr under a hydrogen atmosphere. The reaction mixture was filtered through celite, and the filtrate was concentrated under reduced pressure to give the object product (210 mg).

$^1$H-NMR (CDCl$_3$) δ 1.67-1.78 (4 H, m), 3.10-3.20 (2 H, m), 3.31-3.47 (5 H, m), 3.35 (3 H, s), 3.84 (3 H, s), 6.37 (1 H, dd), 6.40 (1 H, dd), 6.77 (1 H, t)

Reference Example 117 tert-butyl (3S,5R)-3-{{({2-methoxy-6-{(4-methoxybutyl)amino}phenyl}amino)(oxo)acetyl}(2-methylpropyl)amino}-5-(morpholin-4-ylcarbonyl)piperidine-1-carboxylate

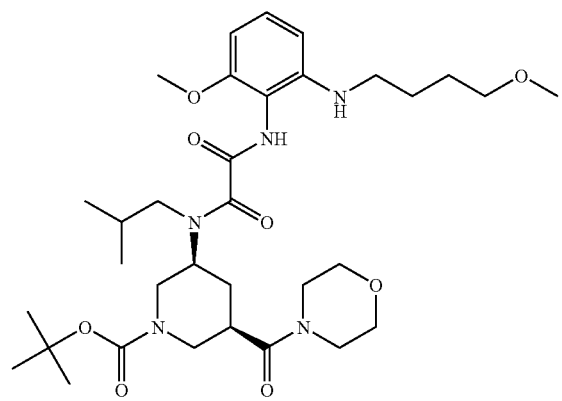 [SMILES: COCCCCNc1cccc(OC)c1NC(=O)C(=O)N(CC(C)C)[C@H]1C[C@@H](C(=O)N2CCOCC2)CN(C(=O)OC(C)(C)C)C1]

6-Methoxy-2-(4-methoxybutylamino)aniline (210 mg), {{(3S,5R)-1-(tert-butoxycarbonyl)-5-(morpholin-4-ylcarbonyl)piperidin-3-yl}(2-methylpropyl)amino}(oxo)acetic acid (308 mg), HOBt (97 mg) and triethylamine (370 µl) were dissolved in 1,2-dichloroethane (15 ml), WSC.HCl (430 mg) was added, and the mixture was stirred at 60° C. for 2 hr. The reaction mixture was concentrated under reduced pressure, diluted with saturated aqueous sodium hydrogen carbonate, and the mixture was extracted with ethyl acetate. The extract was dried over anhydrous magnesium sulfate and the solvent was evaporated under reduced pressure. The residue was subjected to silica gel column chromatography, and a fraction eluted with ethyl acetate-hexane (2:8)-ethyl acetate was concentrated under reduced pressure to give the object product (240 mg).

MS (ESI+, m/e) 648 (M+1)

In the same manner as in Reference Example 103, the following compound (Reference Example 118) was obtained.

Reference Example 118

(3R,5S)-1-(tert-butoxycarbonyl)-5-{{{4-methoxy-1-(4-methoxybutyl)-1H-benzimidazol-2-yl}carbonyl}(2-methylpropyl)amino}piperidine-3-carboxylic acid

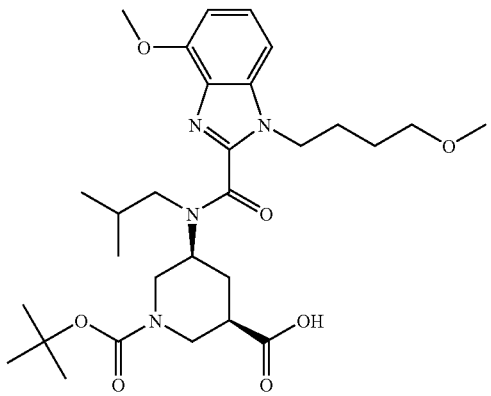 [SMILES: COCCCCn1c(C(=O)N(CC(C)C)[C@H]2C[C@@H](C(=O)O)CN(C(=O)OC(C)(C)C)C2)nc2c(OC)cccc21]

MS (ESI+, m/e) 561 (M+1)

In the same manner as in Reference Example 105, the following compound (Reference Example 119) was obtained.

Reference Example 119 tert-butyl (3R,5S)-3-carbamoyl-5-{{{4-methoxy-1-(4-methoxybutyl)-1H-benzimidazol-2-yl}carbonyl}(2-methylpropyl)amino}piperidine-1-carboxylate

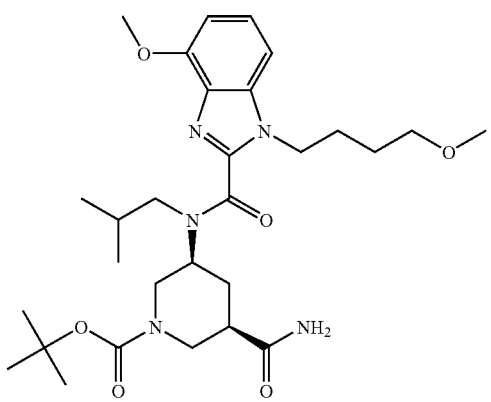 [SMILES: COCCCCn1c(C(=O)N(CC(C)C)[C@H]2C[C@@H](C(N)=O)CN(C(=O)OC(C)(C)C)C2)nc2c(OC)cccc21]

MS (ESI+, m/e) 560 (M+1)

In the same manner as in Reference Example 106, the following compound (Reference Example 120) was obtained.

Reference Example 120 tert-butyl (3S,5R)-3-{{{4-methoxy-1-(4-methoxybutyl)-1H-benzimidazol-2-yl}carbonyl}(2-methylpropyl)amino}-5-(4H-1,2,4-triazol-3-yl)piperidine-1-carboxylate

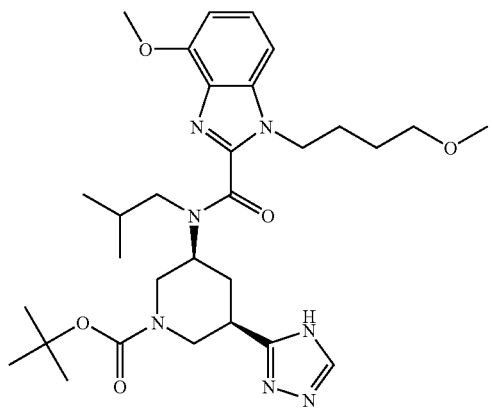 [SMILES: COCCCCn1c(C(=O)N(CC(C)C)[C@H]2C[C@@H](c3nnc[nH]3)CN(C(=O)OC(C)(C)C)C2)nc2c(OC)cccc21]

MS (ESI+, m/e) 584 (M+1)

In the same manner as in Reference Example 107, the following compound (Reference Example 121) was obtained.

Reference Example 121 tert-butyl (3S,5R)-3-{{{4-methoxy-1-(4-methoxybutyl)-1H-benzimidazol-2-yl}carbonyl}(2-methylpropyl)amino}-5-(pyrrolidin-1-ylcarbonyl)piperidine-1-carboxylate

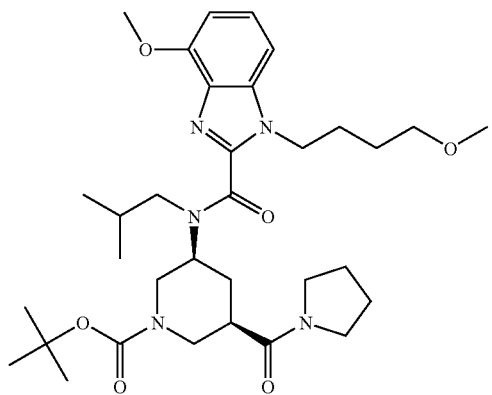 [SMILES: COCCCCn1c(C(=O)N(CC(C)C)[C@H]2C[C@@H](C(=O)N3CCCC3)CN(C(=O)OC(C)(C)C)C2)nc2c(OC)cccc21]

MS (ESI+, m/e) 614 (M+1)

Reference Example 122 tert-butyl (3S,5R)-3-{{{4-methoxy-1-(4-methoxybutyl)-1H-benzimidazol-2-yl}carbonyl}(2-methylpropyl)amino}-5-(piperidin-1-ylcarbonyl)piperidine-1-carboxylate

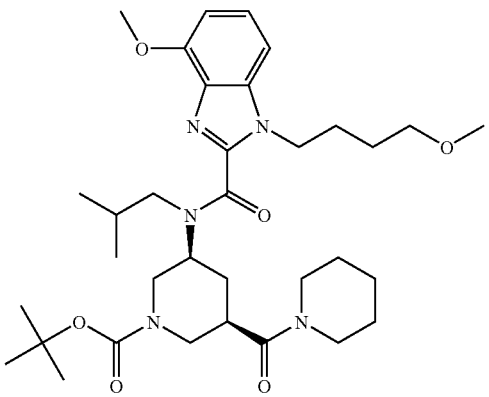 [SMILES: COCCCCn1c(C(=O)N(CC(C)C)[C@H]2C[C@@H](C(=O)N3CCCCC3)CN(C(=O)OC(C)(C)C)C2)nc2c(OC)cccc21]

(3R,5S)-1-(tert-Butoxycarbonyl)-5-{{{4-methoxy-1-(4-methoxybutyl)-1H-benzimidazol-2-yl}carbonyl}(2-methylpropyl)amino}piperidine-3-carboxylic acid (205 mg), piperidine (69 μl), HOBt (40 mg) and triethylamine (140 μl) were dissolved in DMF (10 ml), WSC.HCl (134 mg) was added, and the mixture was stirred at 50° C. for 1 hr. The reaction mixture was concentrated under reduced pressure, diluted with saturated aqueous sodium hydrogen carbonate, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (1:9)-ethyl acetate was concentrated under reduced pressure to give the object product (65 mg).

MS (ESI+, m/e) 628 (M+1)

Example 55

4-methoxy-1-(4-methoxybutyl)-N-(2-methylpropyl)-N-{(3S, 5R)-5-(morpholin-4-ylcarbonyl)piperidin-3-yl}-1H-benzimidazole-2-carboxamide dihydrochloride

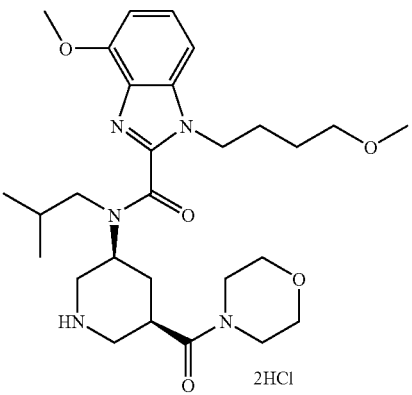 [SMILES: COCCCCn1c(C(=O)N(CC(C)C)[C@@H]2CNC[C@H](C(=O)N3CCOCC3)C2)nc2c(OC)cccc21 ; "2HCl"]

tert-Butyl (3S,5R)-3-{{({2-methoxy-6-{(4-methoxybutyl)amino}phenyl}amino)(oxo)acetyl}(2-methylpropyl)amino}-5-(morpholin-4-ylcarbonyl)piperidine-1-carboxylate (240 mg) was dissolved in acetic acid (5 ml), and the mixture was stirred at 80° C. for 14 hr. The reaction mixture was concentrated under reduced pressure, the residue was dissolved in 2M hydrogen chloride-ethyl acetate (3 ml), and the mixture was stirred at room temperature for 2 hr and concentrated under reduced pressure. The residue was subjected to reversed-phase preparative HPLC, and a fraction eluted with water-acetonitrile (9:1-6:4) was collected, basified (pH 10) with saturated aqueous potassium carbonate solution, and extracted with ethyl acetate. The extract was dried over anhydrous magnesium sulfate, and concentrated under reduced pressure. The residue was dissolved in 0.7M hydrogen chloride-ethyl acetate (1.2 ml), and the mixture was concentrated under reduced pressure to give the object product (79 mg).

MS (ESI+, m/e) 530 (M+1)

In the same manner as in Example 50 or Example 53, the following compounds (Examples 56-59) were obtained.

Example 56

N-{(3S,5R)-5-carbamoylpiperidin-3-yl}-4-methoxy-1-(4-methoxybutyl)-N-(2-methylpropyl)-1H-benzimidazole-2-carboxamide dihydrochloride

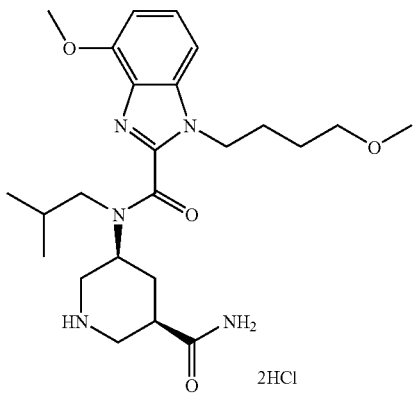 [SMILES: COCCCCn1c(C(=O)N(CC(C)C)[C@@H]2CNC[C@H](C(N)=O)C2)nc2c(OC)cccc21 ; "2HCl"]

MS (ESI+, m/e) 460 (M+1)

Example 57

4-methoxy-1-(4-methoxybutyl)-N-(2-methylpropyl)-N-{(3S,5R)-5-(4H-1,2,4-triazol-3-yl)piperidin-3-yl}-1H-benzimidazole-2-carboxamide dihydrochloride

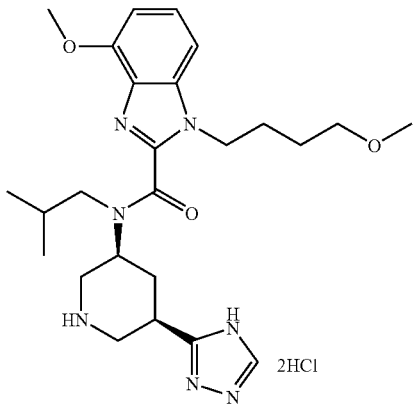 [SMILES: COCCCCn1c(C(=O)N(CC(C)C)[C@@H]2CNC[C@H](c3nnc[nH]3)C2)nc2c(OC)cccc21 ; "2HCl"]

MS (ESI+, m/e) 484 (M+1)

Example 58

4-methoxy-1-(4-methoxybutyl)-N-(2-methylpropyl)-N-{(3S,5R)-5-(pyrrolidin-1-ylcarbonyl)piperidin-3-yl}-1H-benzimidazole-2-carboxamide dihydrochloride

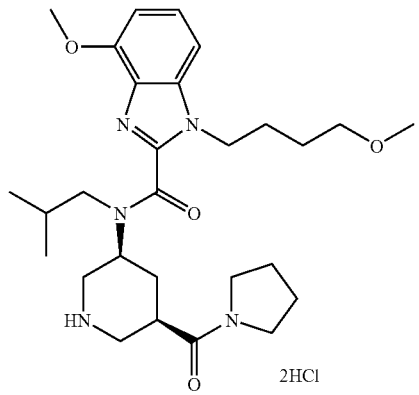 [SMILES: COCCCCn1c(C(=O)N(CC(C)C)[C@@H]2CNC[C@H](C(=O)N3CCCC3)C2)nc2c(OC)cccc21 ; "2HCl"]

MS (ESI+, m/e) 514 (M+1)

Example 59

4-methoxy-1-(4-methoxybutyl)-N-(2-methylpropyl)-N-{(3S,5R)-5-(piperidin-1-ylcarbonyl)piperidin-3-yl}-1H-benzimidazole-2-carboxamide dihydrochloride

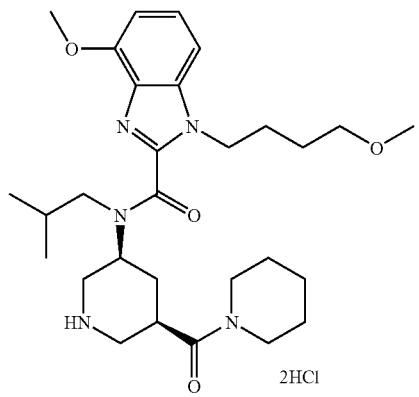 [SMILES: COCCCCn1c(C(=O)N(CC(C)C)[C@@H]2CNC[C@H](C(=O)N3CCCCC3)C2)nc2c(OC)cccc21 ; "2HCl"]

MS (ESI+, m/e) 528 (M+1)

Reference Example 123 tert-butyl (5-methoxy-2-nitrophenyl)carbamate

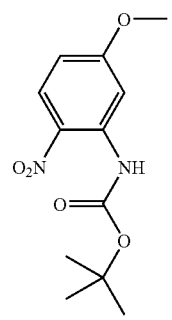 [SMILES: COc1ccc([N+](=O)[O-])c(NC(=O)OC(C)(C)C)c1]

5-Methoxy-2-nitrobenzoic acid (10.30 g) was suspended in toluene (200 ml), triethylamine (9 ml) and diphenylphosphoryl azide (14 ml) were added dropwise at room temperature, and the mixture was stirred at 95° C. for 1.5 hr. Triethylamine (29 ml) and 2-methylpropan-2-ol (15 ml) were added, and the mixture was further stirred at 95° C. for 3 hr. The reaction mixture was concentrated under reduced pressure, and diluted with ethyl acetate. 0.5M Hydrochloric acid (200 ml) was added, and the mixture was filtered through celite. The organic layer of the filtrate was collected, washed with saturated aqueous sodium hydrogen carbonate, dried over anhydrous magnesium sulfate, and concentrated under reduced pressure. The residue was subjected to silica gel chromatography, and a fraction eluted with ethyl acetate-hexane (5:95-1:1) was concentrated under reduced pressure to give the object product (13.28 g).

$^1$H-NMR (CDCl$_3$) δ 1.55 (9 H, s), 3.92 (3 H, s), 6.58 (1 H, dd), 8.16 (1 H, s), 8.18 (1 H, d), 10.10 (1 H, br s)

In the same manner as in Reference Example 114, the following compound (Reference Example 124) was obtained.

Reference Example 124 tert-butyl (4-methoxybutyl)(5-methoxy-2-nitrophenyl)carbamate

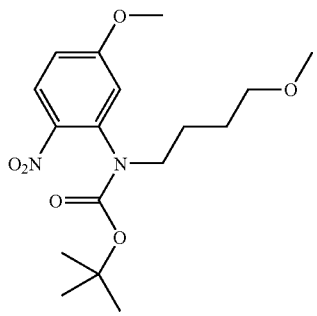 [SMILES: COCCCCN(C(=O)OC(C)(C)C)c1cc(OC)ccc1[N+](=O)[O-]]

$^1$H-NMR (CDCl$_3$) δ 1.25-1.54 (9 H, m), 1.54-1.81 (4 H, m), 3.30 (3 H, s), 3.34-3.44 (2 H, m), 3.56-3.79 (2 H, m), 3.89 (3 H, s), 6.72-6.89 (2 H, m), 7.96-8.09 (1 H, m)

In the same manner as in Reference Example 115, the following compound (Reference Example 125) was obtained.

Reference Example 125

5-methoxy-N-(4-methoxybutyl)-2-nitroaniline

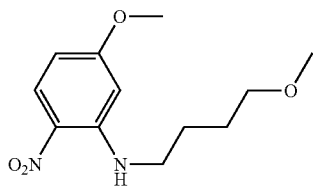

$^1$H-NMR (CDCl$_3$) δ 1.68-1.88 (4 H, m), 3.27-3.35 (2 H, m), 3.35 (3 H, s), 3.45 (2 H, t), 3.87 (3 H, s), 6.15 (1 H, d), 6.23 (1 H, dd), 8.14 (1 H, d), 8.32 (1 H, br s)

In the same manner as in Reference Example 116, the following compound (Reference Example 126) was obtained.

Reference Example 126

4-methoxy-2-(4-methoxybutylamino)aniline

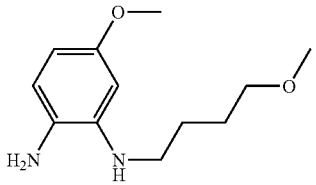 [SMILES: COCCCCNc1cc(OC)ccc1[N+](=O)[O-]]

$^1$H-NMR (CDCl$_3$) δ 1.65-1.81 (4 H, m), 2.99 (2 H, br s), 3.06-3.16 (2 H, m), 3.35 (3 H, s), 3.38-3.47 (2 H, m), 3.75 (3 H, s), 3.70 (1 H, br s), 6.17 (1 H, dd), 6.25 (1 H, d), 6.64 (1 H,

Reference Example 127

6-methoxy-1-(4-methoxybutyl)-2-(trichloromethyl)-1H-benzimidazole

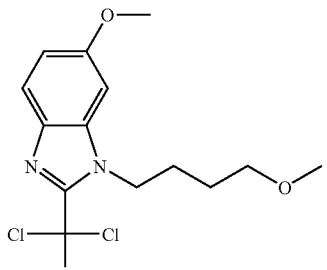

4-Methoxy-2-(4-methoxybutylamino)aniline (2.50 g) was dissolved in acetic acid (30 ml), methyl 2,2,2-trichloroethanimidate (1.62 ml) was added, and the mixture was stirred for 1.5 hr. The reaction mixture was concentrated under reduced pressure, and the residue was diluted with diisopropyl ether, and washed with water. The organic layer was dried over anhydrous magnesium sulfate, and concentrated under reduced pressure to give the object product (1.75 g). MS (ESI+, m/e) 351 (M+1)

Reference Example 128 tert-butyl (3S,5R)-3-{{{6-methoxy-1-(4-methoxybutyl)-1H-benzimidazol-2-yl}carbonyl}(2-methylpropyl)amino}-5-(morpholin-4-ylcarbonyl)piperidine-1-carboxylate

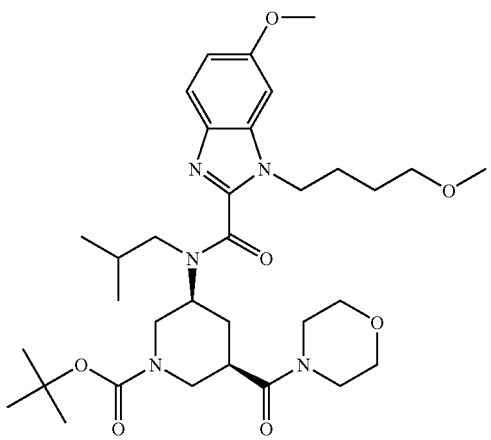 [SMILES: COCCCCn1c(C(=O)N(CC(C)C)[C@H]2C[C@@H](C(=O)N3CCOCC3)CN(C(=O)OC(C)(C)C)C2)nc2ccc(OC)cc21]

6-Methoxy-1-(4-methoxybutyl)-2-(trichloromethyl)-1H-benzimidazole (330 mg) was dissolved in acetonitrile-water (2:1, 50 ml), and tert-butyl (3S,5R)-3-{(2-methylpropyl)amino}-5-(morpholin-4-ylcarbonyl)piperidine-1-carboxylate (350 mg) was added. Potassium carbonate (1.3 g) was added, and the mixture was stirred at 80° C. for 5 hr. The reaction mixture was concentrated under reduced pressure, acidified (pH 3) with 6M hydrochloric acid, and the mixture was extracted with ethyl acetate. The extract was dried over anhydrous magnesium sulfate, and concentrated under reduced pressure. The residue was subjected to silica gel chromatography, and a fraction eluted with ethyl acetate-hexane (3:7)-ethyl acetate was concentrated under reduced pressure. The residue was further subjected to reversed-phase preparative HPLC, and a fraction eluted with water-acetonitrile (9:1-6:4) was collected, basified (pH 10) with saturated aqueous potassium carbonate solution, and extracted with ethyl acetate. The extract was dried over anhydrous magnesium sulfate, and concentrated under reduced pressure to give the object product (82 mg).

MS (ESI+, m/e) 630 (M+1)

Reference Example 129

(3R,5S)-1-(tert-butoxycarbonyl)-5-{{{6-methoxy-1-(4-methoxybutyl)-1H-benzimidazol-2-yl}carbonyl}(2-methylpropyl)amino}piperidine-3-carboxylic acid

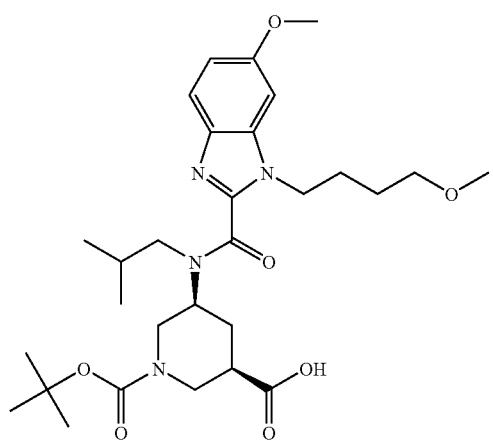 [SMILES: COCCCCn1c(C(=O)N(CC(C)C)[C@H]2C[C@@H](C(=O)O)CN(C(=O)OC(C)(C)C)C2)nc2ccc(OC)cc21]

6-Methoxy-1-(4-methoxybutyl)-2-(trichloromethyl)-1H-benzimidazole (1.42 g) was dissolved in acetonitrile-water (2:1, 150 ml), 1-tert-butyl 3-methyl (3R,5S)-5-{(2-methylpropyl)amino}piperidine-1,3-dicarboxylate (1.02 g) was added, potassium carbonate (5.5 g) was added and the mixture was stirred at 80° C. for 19 hr. The reaction mixture was concentrated under reduced pressure, acidified (pH3) with 6M hydrochloric acid, and extracted with ethyl acetate. The extract was dried over anhydrous magnesium sulfate, and concentrated under reduced pressure. The residue was subjected to silica gel chromatography, and a fraction eluted with ethyl acetate-hexane (5:95)-ethyl acetate-ethyl acetate-methanol (85:15) was concentrated under reduced pressure. The residue was subjected to reversed-phase preparative HPLC, and a fraction eluted with water-acetonitrile (9:1-6:4) was collected, basified (pH 10) with saturated aqueous potassium carbonate solution, and extracted with ethyl acetate. The extract was dried over anhydrous magnesium sulfate, and concentrated under reduced pressure to give the object product (460 mg).

MS (ESI+, m/e) 561 (M+1)

In the same manner as in Reference Example 105, the following compound (Reference Example 130) was obtained.

Reference Example 130 tert-butyl (3R,5S)-3-carbamoyl-5-{{{6-methoxy-1-(4-methoxybutyl)-1H-benzimidazol-2-yl}carbonyl}(2-methylpropyl)amino}piperidine-1-carboxylate

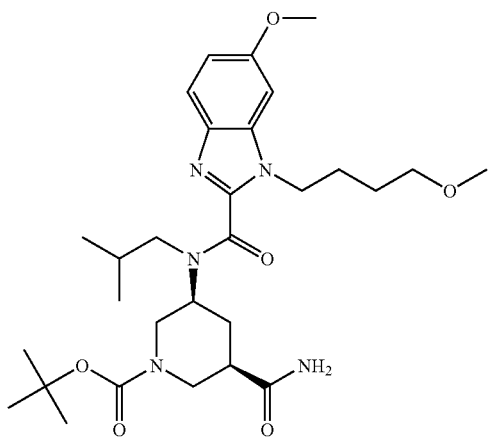 [SMILES: COCCCCn1c(C(=O)N(CC(C)C)[C@H]2C[C@@H](C(N)=O)CN(C(=O)OC(C)(C)C)C2)nc2ccc(OC)cc21]

MS (ESI+, m/e) 560 (M+1)

In the same manner as in Reference Example 107, the following compound (Reference Example 131) was obtained.

Reference Example 131 tert-butyl (3S,5R)-3-{{{6-methoxy-1-(4-methoxybutyl)-1H-benzimidazol-2-yl}carbonyl}(2-methylpropyl)amino}-5-(pyrrolidin-1-ylcarbonyl)piperidine-1-carboxylate

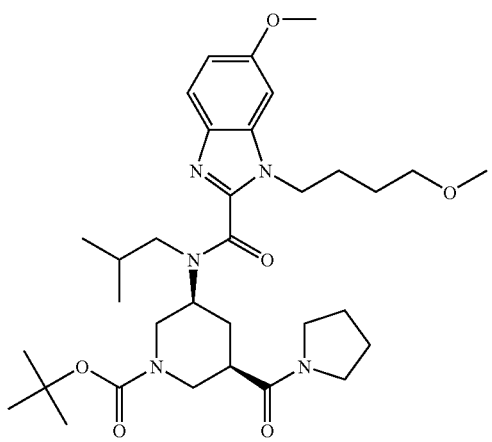 [SMILES: COCCCCn1c(C(=O)N(CC(C)C)[C@H]2C[C@@H](C(=O)N3CCCC3)CN(C(=O)OC(C)(C)C)C2)nc2ccc(OC)cc21]

MS (ESI+, m/e) 614 (M+1)

Example 60

6-methoxy-1-(4-methoxybutyl)-N-(2-methylpropyl)-N-{(3S,5R)-5-(morpholin-4-ylcarbonyl)piperidin-3-yl}-1H-benzimidazole-2-carboxamide dihydrochloride

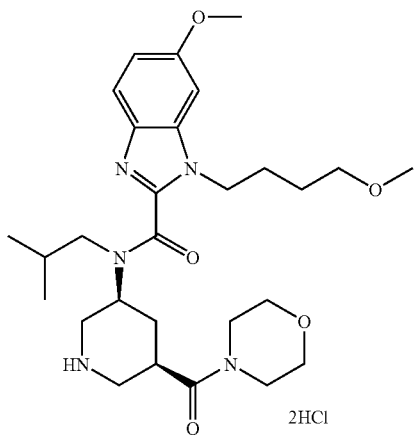 [SMILES: COCCCCn1c(C(=O)N(CC(C)C)[C@@H]2CNC[C@H](C(=O)N3CCOCC3)C2)nc2ccc(OC)cc21 ; "2HCl"]

tert-Butyl (3S,5R)-3-{{{6-methoxy-1-(4-methoxybutyl)-1H-benzimidazol-2-yl}carbonyl}(2-methylpropyl)amino}-5-(morpholin-4-ylcarbonyl)piperidine-1-carboxylate (82 mg) was dissolved in 2M hydrogen chloride-ethyl acetate (3 ml), and the mixture was stirred at room temperature for 1 hr and concentrated to give the object product (78 mg).

MS (ESI+, m/e) 530 (M+1)

In the same manner as in Example 60, the following compounds (Examples 61-62) were obtained.

Example 61

N-{(3S,5R)-5-carbamoylpiperidin-3-yl}-6-methoxy-1-(4-methoxybutyl)-N-(2-methylpropyl)-1H-benzimidazole-2-carboxamide dihydrochloride

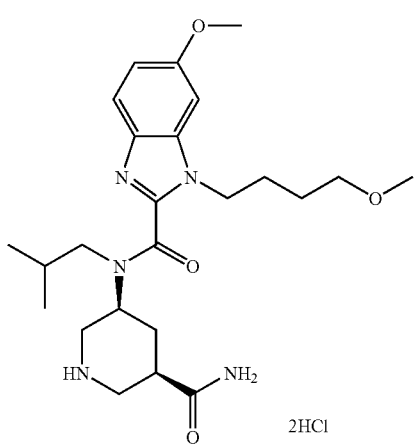 [SMILES: COCCCCn1c(C(=O)N(CC(C)C)[C@@H]2CNC[C@H](C(N)=O)C2)nc2ccc(OC)cc21 ; "2HCl"]

MS (ESI+, m/e) 460 (M+1)

Example 62

6-methoxy-1-(4-methoxybutyl)-N-(2-methylpropyl)-N-{(3S,5R)-5-(pyrrolidin-1-ylcarbonyl)piperidin-3-yl}-1H-benzimidazole-2-carboxamide dihydrochloride

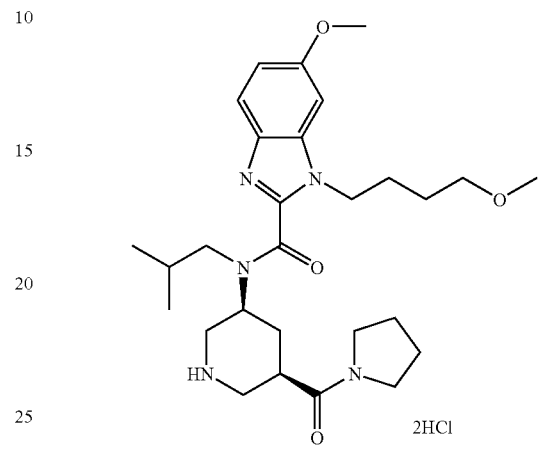

MS (ESI+, m/e) 514 (M+1)

Reference Example 132 tert-butyl (3S,5R)-3-{(1H-benzimidazol-2-ylcarbonyl)(2-methylpropyl)amino}-5-(morpholin-4-ylcarbonyl)piperidine-1-carboxylate

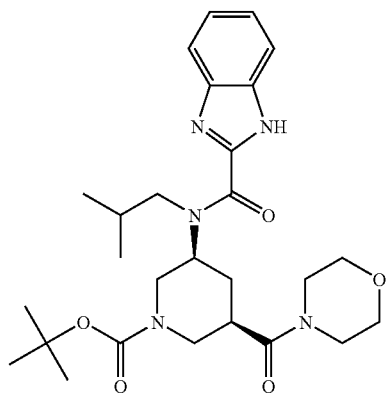 [SMILES: CC(C)CN(C(=O)c1nc2ccccc2[nH]1)[C@H]1C[C@@H](C(=O)N2CCOCC2)CN(C(=O)OC(C)(C)C)C1]

2-(Trichloromethyl)-1H-benzimidazole (2.00 g) and tert-butyl (3S,5R)-3-{(2-methylpropyl)amino}-5-(morpholin-4-ylcarbonyl)piperidine-1-carboxylate (2.84 g) were dissolved in tetrahydrofuran-water (3:2, 150 ml), sodium hydrogen carbonate (6.45 g) was added and the mixture was stirred at room temperature for 1 hr. The reaction mixture was concentrated under reduced pressure, diluted with water, and the mixture was extracted with ethyl acetate. The extract was washed with saturated brine, dried over anhydrous magnesium sulfate, and concentrated under reduced pressure. The precipitated white solid was collected by filtration, washed with ethyl acetate-hexane (1:1) and dried to give the object product (3.03 g).

$^1$H-NMR (CDCl$_3$) δ 0.86-1.01 (6H, m), 1.30-1.50 (9H, m), 1.89-2.64 (3H, m), 2.68-3.08 (2H, m), 3.22-4.01 (10H, m), 4.07-4.44 (3H, m), 5.53-6.12 (1H, m), 7.27-7.42 (2H, m), 7.52 (1H, t), 7.61-7.86 (1H, m), 10.15-10.52 (1H, m)
MS (ESI+, m/e) 514 (M+1)

Reference Example 133 tert-butyl (3S,5R)-3-{(2-methylpropyl){{1-(2-phenylethyl)-1H-benzimidazol-2-yl}carbonyl}amino}-5-(morpholin-4-ylcarbonyl)piperidine-1-carboxylate

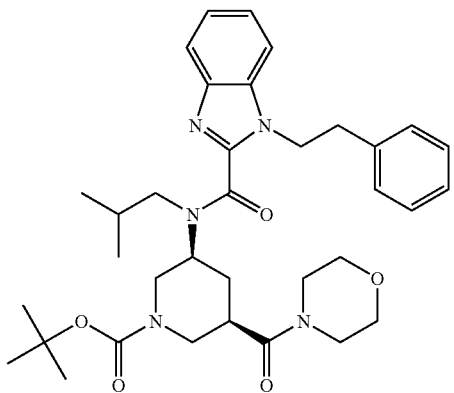 [SMILES: CC(C)CN(C(=O)c1nc2ccccc2n1CCc1ccccc1)[C@H]1C[C@@H](C(=O)N2CCOCC2)CN(C(=O)OC(C)(C)C)C1]

tert-Butyl (3S,5R)-3-{(1H-benzimidazol-2-ylcarbonyl)(2-methylpropyl)amino}-5-(morpholin-4-ylcarbonyl)piperidine-1-carboxylate (147 mg) was dissolved in dimethylformamide (12 ml), (2-bromoethyl)benzene (58 µl) and cesium carbonate (200 mg) were added and the mixture was stirred at 65° C. for 3 hr. (2-Bromoethyl)benzene (58 µl) was added, and the mixture was further stirred for 2 hr. The reaction mixture was concentrated under reduced pressure, diluted with water, and extracted with ethyl acetate. The extract was washed with saturated brine, dried over anhydrous magnesium sulfate, and concentrated under reduced pressure. The residue was subjected to silica gel chromatography, and a fraction eluted with ethyl acetate-hexane (1:9)-ethyl acetate was concentrated under reduced pressure to give the object product (164 mg). MS (ESI+, m/e) 618 (M+1)

Reference Example 134

2-(thiophen-2-yl)ethyl methanesulfonate

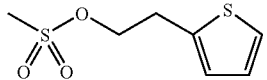

2-(Thiophen-2-yl)ethanol (1.05 g) was dissolved in tetrahydrofuran (25 ml), triethylamine (1.63 ml) and methanesulfonyl chloride (725 µl) were added and the mixture was stirred for 20 min. Saturated aqueous sodium hydrogen carbonate (50 ml) was added to the reaction mixture, and the mixture was extracted with diisopropyl ether. The extract was washed with saturated brine, dried over anhydrous magnesium sulfate, and concentrated under reduced pressure to give the object product (1.62 g).
$^1$H-NMR (CDCl$_3$) δ 2.93 (3 H, s), 3.28 (2 H, ddd), 4.42 (2 H, t), 6.90-6.93 (1 H, m), 6.96 (1 H, dd), 7.20 (1 H, dd)

Reference Example 135 tert-butyl (3S,5R)-3-{(2-methylpropyl){{1-(2-(thiophen-2-yl)ethyl)-1H-benzimidazol-2-yl}carbonyl}amino}-5-(morpholin-4-ylcarbonyl)piperidine-1-carboxylate

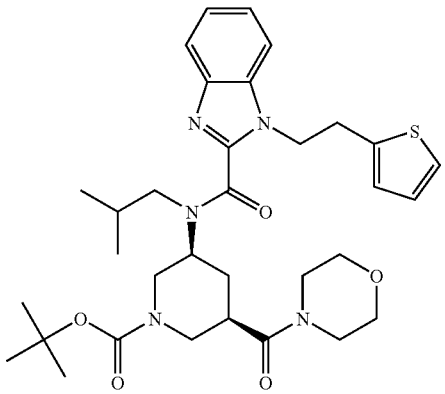 [SMILES: CC(C)CN(C(=O)c1nc2ccccc2n1CCc1cccs1)[C@H]1C[C@@H](C(=O)N2CCOCC2)CN(C(=O)OC(C)(C)C)C1]

tert-Butyl (3S,5R)-3-{(1H-benzimidazol-2-ylcarbonyl)(2-methylpropyl)amino}-5-(morpholin-4-ylcarbonyl)piperidine-1-carboxylate (150 mg) was dissolved in dimethylformamide (10 ml), 2-(thiophen-2-yl)ethyl methanesulfonate (90 mg) and cesium carbonate (190 mg) were added and the mixture was stirred at 65° C. for 30 min. 2-Thiophen-2-ylethyl methanesulfonate (90 mg) was added, and the mixture was further stirred for 1 hr. The reaction mixture was concentrated under reduced pressure, diluted with water, and extracted with ethyl acetate. The extract was washed with saturated brine, dried over anhydrous magnesium sulfate, and concentrated under reduced pressure. The residue was subjected to silica gel chromatography, and a fraction eluted with ethyl acetate-hexane (1:9)-ethyl acetate was concentrated under reduced pressure to give the object product (156 mg).
MS (ESI+, m/e) 624 (M+1)

In the same manner as in Example 60, the following compounds (Examples 63-64) were obtained.

Example 63

N-(2-methylpropyl)-N-{(3S,5R)-5-(morpholin-4-ylcarbonyl)piperidin-3-yl}-1-(2-phenylethyl)-1H-benzimidazole-2-carboxamide dihydrochloride

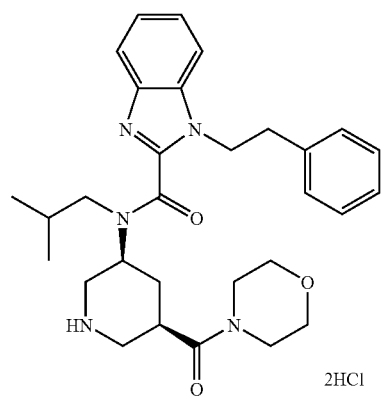 [SMILES: CC(C)CN(C(=O)c1nc2ccccc2n1CCc1ccccc1)[C@@H]1CNC[C@H](C(=O)N2CCOCC2)C1 ; "2HCl"]

MS (ESI+, m/e) 518 (M+1)

Example 64

N-(2-methylpropyl)-N-{(3S,5R)-5-(morpholin-4-ylcarbonyl)piperidin-3-yl}-1-(2-(thiophen-2-yl)ethyl)-1H-benzimidazole-2-carboxamide dihydrochloride

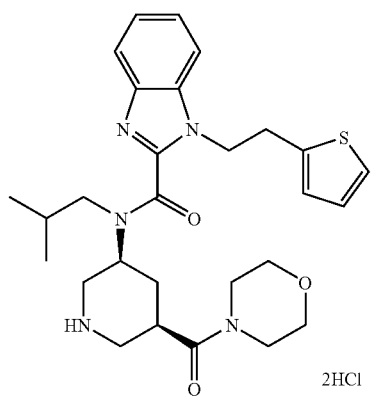 [SMILES: CC(C)CN(C(=O)c1nc2ccccc2n1CCc1cccs1)[C@@H]1CNC[C@H](C(=O)N2CCOCC2)C1 ; "2HCl"]

MS (ESI+, m/e) 524 (M+1)

In the same manner as in the method shown in Reference Example 106, the compound described in the following Reference Example 136 was obtained.

Reference Example 136 tert-butyl (3S,5R)-3-{{{1-(4-methoxybutyl)-1H-benzimidazol-2-yl}carbonyl}(2-methylpropyl)amino}-5-(4H-1,2,4-triazol-3-yl)piperidine-1-carboxylate

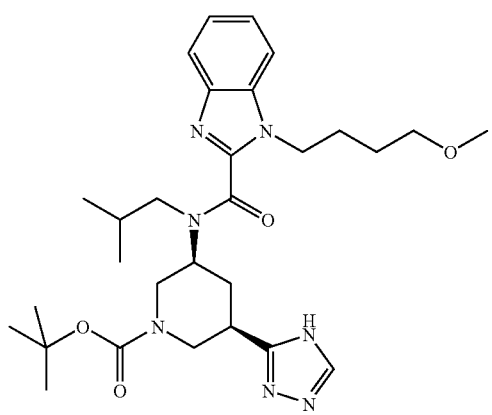 [SMILES: COCCCCn1c(C(=O)N(CC(C)C)[C@H]2C[C@@H](c3nnc[nH]3)CN(C(=O)OC(C)(C)C)C2)nc2ccccc21]

MS (ESI+, m/e) 454 (M+1)

Reference Example 137 tert-butyl (3R,5S)-3-cyano-5-{{{1-(4-methoxybutyl)-1H-benzimidazol-2-yl}carbonyl}(2-methylpropyl)amino}piperidine-1-carboxylate

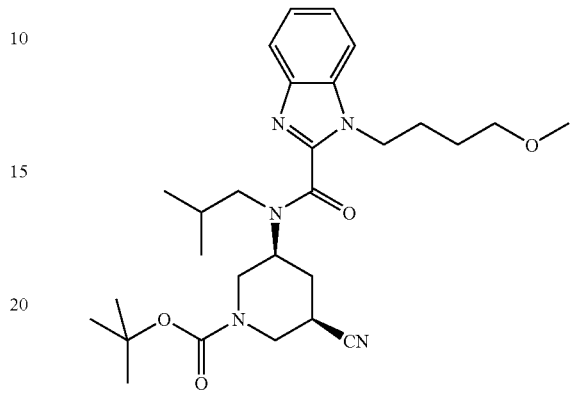

tert-Butyl (3R,5S)-3-carbamoyl-5-{{{1-(4-methoxybutyl)-1H-benzimidazol-2-yl}carbonyl}(2-methylpropyl)amino}piperidine-1-carboxylate (1.01 g) was dissolved in pyridine (10 ml), trifluoroacetic anhydride (570 μl) was added at 0° C., and the mixture was stirred at room temperature for 2 hr. The reaction mixture was concentrated under reduced pressure, and diluted with ethyl acetate. 1M Hydrochloric acid was added, and the mixture was extracted with ethyl acetate. The extract was washed with saturated brine, dried over anhydrous magnesium sulfate, and concentrated under reduced pressure. The residue was subjected m to silica gel chromatography, and a fraction eluted with ethyl acetate-hexane (5:95)-ethyl acetate was concentrated under reduced pressure to give the object product (1.01 g).

MS (ESI+, m/e) 512 (M+1)

Reference Example 138 tert-butyl (3S,5R)-3-{{{1-(4-methoxybutyl)-1H-benzimidazol-2-yl}carbonyl}(2-methylpropyl)amino}-5-(1,2,4-oxadiazol-3-yl)piperidine-1-carboxylate

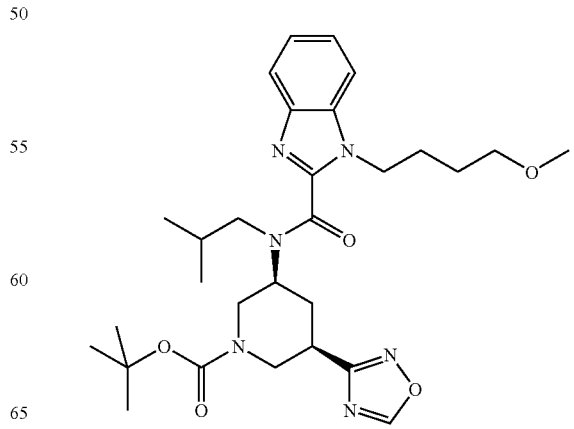

Hydroxylamine hydrochloride (383 mg) was dissolved in dimethyl sulfoxide (10 ml), and the mixture was stirred at 40° C. for 30 min. Sodium hydrogen carbonate (463 mg) was added, and the mixture was stirred at 50° C. for 1 hr. A solution of tert-butyl (3R,5S)-3-cyano-5-{{{1-(4-methoxybutyl)-1H-benzimidazol-2-yl}carbonyl}(2-methylpropyl)amino}piperidine-1-carboxylate (282 mg) in dimethyl sulfoxide (10 ml) was further added, and the mixture was stirred at 90° C. for 3 hr. The reaction mixture was allowed to cool to room temperature, diluted with water, and extracted with ethyl acetate. The extract was dried over anhydrous magnesium sulfate, and concentrated under reduced pressure. The residue was dissolved in trimethyl orthoformate (5 ml) and the mixture was stirred at 100° C. for 4 hr. The reaction mixture was concentrated under reduced pressure, and the residue was subjected to silica gel chromatography, and a fraction eluted with ethyl acetate-hexane (5:95-3:7) was concentrated under reduced pressure to give the object product (230 mg).

MS (ESI+, m/e) 555 (M+1)

Reference Example 139 tert-butyl (3S, 5R)-3-{{{1-(4-methoxybutyl)-1H-benzimidazol-2-yl}carbonyl}(2-methylpropyl)amino}-5-(5-oxo-4,5-dihydro-1,2,4-oxadiazol-3-yl)piperidine-1-carboxylate

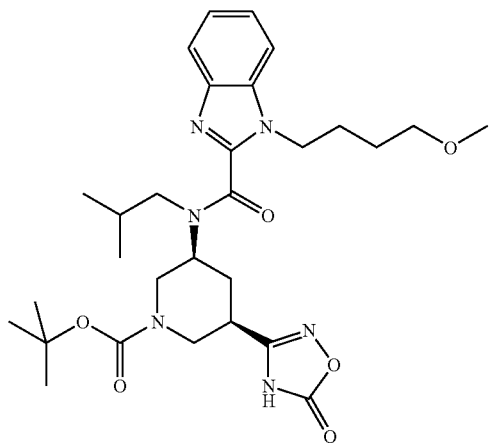 [SMILES: COCCCCn1c(C(=O)N(CC(C)C)[C@H]2C[C@@H](c3noc(=O)[nH]3)CN(C(=O)OC(C)(C)C)C2)nc2ccccc21]

Hydroxylamine hydrochloride (418 mg) was dissolved in dimethyl sulfoxide (10 ml), and the mixture was stirred at 40° C. for 30 min. Sodium hydrogen carbonate (506 mg) was added, and the mixture was stirred at 50° C. for 1 hr. A solution of tert-butyl (3R,5S)-3-cyano-5-{{{1-(4-methoxybutyl)-1H-benzimidazol-2-yl}carbonyl}(2-methylpropyl)amino}piperidine-1-carboxylate (308 mg) in dimethyl sulfoxide (10 ml) was further added, and the mixture was stirred at 90° C. for 3 hr. The reaction mixture was allowed to cool to room temperature, diluted with water, and the mixture was extracted with ethyl acetate. The extract was dried over anhydrous magnesium sulfate, concentrated under reduced pressure, and the residue was dissolved in tetrahydrofuran (15 ml). 1,1'-Carbonylbis(1H-imidazole) (490 mg) and 1,8-diazabicyclo{5.4.0}undec-7-ene (450 µl) were added and the mixture was stirred at room temperature for 1 hr. The reaction mixture was concentrated under reduced pressure, and the residue was diluted with ethyl acetate. The mixture was washed with 0.5M hydrochloric acid and saturated brine, dried over anhydrous magnesium sulfate, and concentrated under reduced pressure. The residue was subjected to silica gel chromatography, and a fraction eluted with ethyl acetate-hexane (5:95)-ethyl acetate was concentrated under reduced pressure to give the object product (256 mg).

MS (ESI+, m/e) 571 (M+1)

Reference Example 140 tert-butyl (3S,5R)-3-{{{1-(4-methoxybutyl)-1H-benzimidazol-2-yl}carbonyl}(2-methylpropyl)amino}-5-(1H-tetrazol-5-yl)piperidine-1-carboxylate

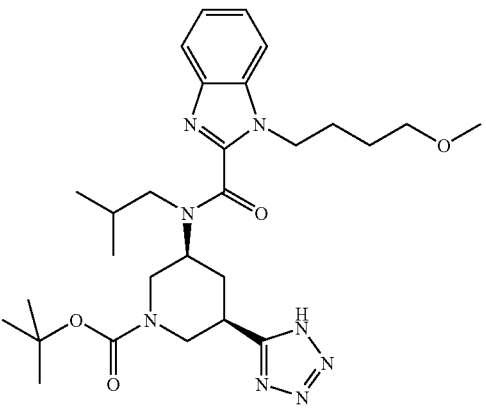 [SMILES: COCCCCn1c(C(=O)N(CC(C)C)[C@H]2C[C@@H](c3nnn[nH]3)CN(C(=O)OC(C)(C)C)C2)nc2ccccc21]

tert-Butyl (3R,5S)-3-cyano-5-{{{1-(4-methoxybutyl)-1H-benzimidazol-2-yl}carbonyl}(2-methylpropyl)amino}piperidine-1-carboxylate (320 mg) was dissolved in tetrahydrofuran (20 ml), azido(trimethyl)silane (1.5 ml) and dibutyl(oxo)stannane (100 mg) were added, and the mixture was heated under reflux with stirring for 43 hr. The reaction mixture was concentrated under reduced pressure, and the residue was subjected to silica gel chromatography, and a fraction eluted with ethyl acetate-ethyl acetate-methanol (8:2) was concentrated under reduced pressure to give the object product (304 mg).

MS (ESI+, m/e) 555 (M+1)

In the same manner as in Example 60, the following compounds (Examples 65-68) were obtained.

Example 65

1-(4-methoxybutyl)-N-(2-methylpropyl)-N-{(3S,5R)-5-(4H-1,2,4-triazol-3-yl)piperidin-3-yl}-1H-benzimidazole-2-carboxamide dihydrochloride

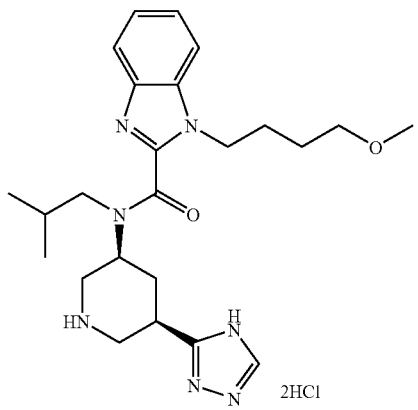 [SMILES: COCCCCn1c(C(=O)N(CC(C)C)[C@@H]2CNC[C@H](c3nnc[nH]3)C2)nc2ccccc21 ; "2HCl"]

MS (ESI+, m/e) 454 (M+1)

Example 66

N-{(3S,5R)-5-cyanopiperidin-3-yl}-1-(4-methoxybutyl)-N-(2-methylpropyl)-1H-benzimidazole-2-carboxamide dihydrochloride

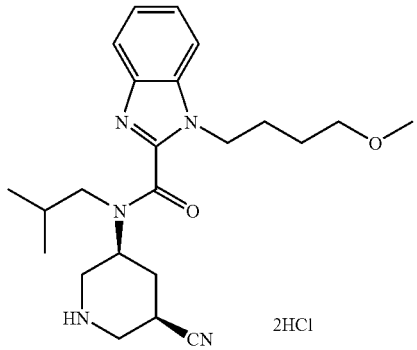

MS (ESI+, m/e) 412 (M+1)

Example 67

1-(4-methoxybutyl)-N-(2-methylpropyl)-N-{(3S,5R)-5-(1,2,4-oxadiazol-3-yl)piperidin-3-yl}-1H-benzimidazole-2-carboxamide dihydrochloride

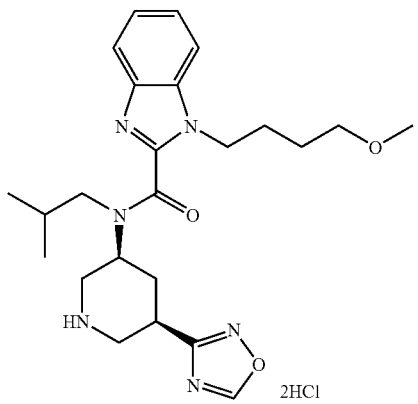 [SMILES: COCCCCn1c(C(=O)N(CC(C)C)[C@@H]2CNC[C@H](c3ncon3)C2)nc2ccccc21 ; "2HCl"]

MS (ESI+, m/e) 455 (M+1)

Example 68

1-(4-methoxybutyl)-N-(2-methylpropyl)-N-{(3S,5R)-5-(5-oxo-4,5-dihydro-1,2,4-oxadiazol-3-yl)piperidin-3-yl}-1H-benzimidazole-2-carboxamide dihydrochloride

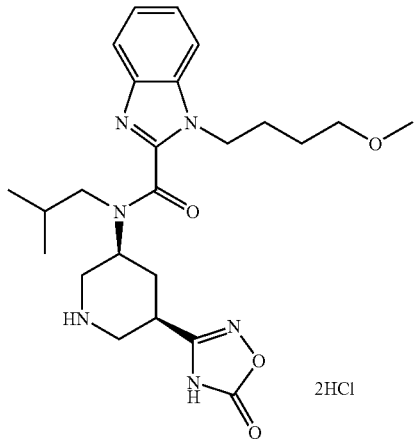 [SMILES: COCCCCn1c(C(=O)N(CC(C)C)[C@@H]2CNC[C@H](c3noc(=O)[nH]3)C2)nc2ccccc21 ; "2HCl"]

MS (ESI+, m/e) 471 (M+1)

Example 69

1-(4-methoxybutyl)-N-(2-methylpropyl)-N-{(3S,5R)-5-(1H-tetrazol-5-yl)piperidin-3-yl}-1H-benzimidazole-2-carboxamide dihydrochloride

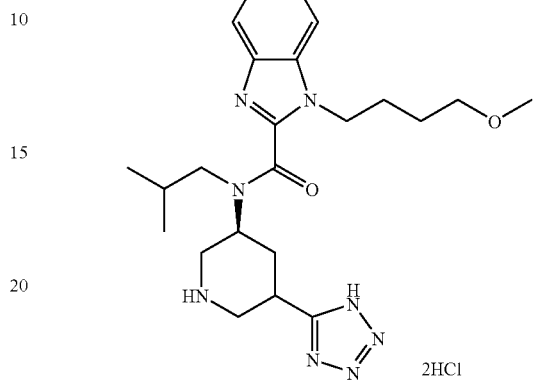

tert-Butyl (3S,5R)-3-{{{1-(4-methoxybutyl)-1H-benzimidazol-2-yl}carbonyl}(2-methylpropyl)amino}-5-(1H-tetrazol-5-yl)piperidine-1-carboxylate (304 mg) was dissolved in 2M hydrogen chloride-ethyl acetate (2 ml), and the mixture was stirred at room temperature for 1 hr. The reaction mixture was concentrated, and ethyl acetate-diisopropyl ether was added. The precipitate was collected by filtration, and washed with ethyl acetate-diisopropyl ether to give the object product (219 mg).

MS (ESI+, m/e) 455 (M+1)

In the same manner as in Reference Example 106, the following compound (Reference Example 141) was obtained.

Reference Example 141 tert-butyl (3S,5R)-3-[{[5-fluoro-1-(4-methoxybutyl)-1H-benzimidazol-2-yl]carbonyl}(2-methylpropyl)amino]-5-(4H-1,2,4-triazol-3-yl)piperidine-1-carboxylate

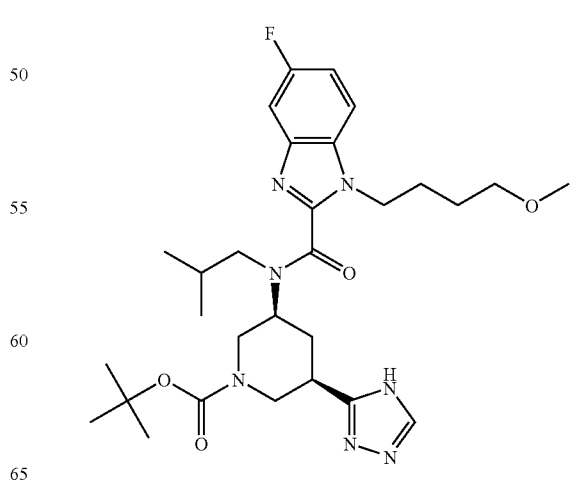

MS (ESI+, m/e) 572 (M+1)

Reference Example 142 tert-butyl (3S,5R)-3-{[(benzyloxy)carbonyl](2-methylpropyl)amino}-5-(hydroxymethyl)piperidine-1-carboxylate

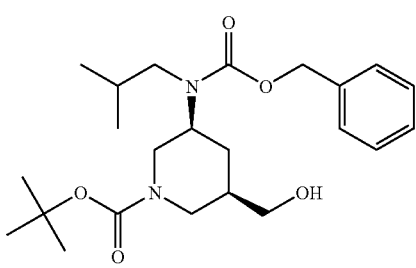 [SMILES: CC(C)CN(C(=O)OCc1ccccc1)[C@H]1C[C@@H](CO)CN(C(=O)OC(C)(C)C)C1]

Powder calcium chloride (0.49 g) was suspended in ethanol (10 ml), sodium borohydride (0.34 g) was added while cooling to 0° C., and the mixture was stirred at 0° C. for 30 min. A solution (10 ml) of 1-tert-butyl 3-methyl (3R,5S)-5-{[(benzyloxy)carbonyl](2-methylpropyl)amino}piperidine-1,3-dicarboxylate (1.00 g) in THF was added to the reaction suspension, and the mixture was stirred at 0° C. for 8 hr. 5% Aqueous sodium hydrogen sulfate solution was added to the reaction mixture for neutralization and the mixture was extracted with ethyl acetate. The extract was washed with saturated brine, and dried over anhydrous magnesium sulfate. The solvent was evaporated under reduced pressure to give the object product (0.88 g) as an oil.

$^1$H-NMR (CDCl$_3$) δ 0.90 (6H, d), 1.22-1.38 (3H, m), 1.46 (9H, s), 1.69 (1H, dt), 2.23-2.39 (2H, m), 2.44-2.59 (1H, m), 2.47 (2H, d), 2.74 (1H, br s), 3.69 (3H, s), 4.18-4.34 (2H, m)

Reference Example 143 tert-butyl (3S,5S)-3-[(2-methylpropyl)amino]-5-[(2-oxopyrrolidin-1-yl)methyl]piperidine-1-carboxylate

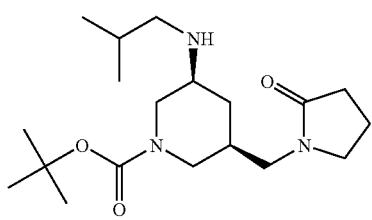 [SMILES: CC(C)CN[C@H]1C[C@@H](CN2CCCC2=O)CN(C(=O)OC(C)(C)C)C1]

To a solution of tert-butyl (3S,5R)-3-{[(benzyloxy)carbonyl](2-methylpropyl)amino}-5-(hydroxymethyl)piperidine-1-carboxylate (0.47 g) in THF (15 ml) were added phthalimide (0.40 g), diisopropyl azodicarboxylate (1.59 g) and triphenylphosphine (0.66 g) at room temperature, and the mixture was stirred at room temperature for 15 hr. The reaction mixture was concentrated under reduced pressure, the residue was diluted with water, and the mixture was extracted with ethyl acetate. The extract was washed with saturated brine, dried over anhydrous sodium sulfate, and concentrated under reduced pressure. The obtained residue was subjected to silica gel chromatography, and a fraction eluted with ethyl acetate-hexane (1:9-1:2) was concentrated under reduced pressure. The obtained residue was dissolved in ethanol (10 ml), hydrazine hydrate (95 µl) was added, and the mixture was heated under reflux for 3 hr. The mixture was allowed to cool to room temperature, the precipitate was filtered off, and the filtrate was concentrated under reduced pressure. The residue was dissolved in THF (5 ml), diisopropylethylamine (0.29 µl) and 4-bromobutyryl chloride (0.16 ml) were added at 0° C., and the mixture was stirred at 0° C. for 1 hr. The reaction mixture was diluted with water, and extracted with ethyl acetate. The extract was washed with saturated brine, dried over anhydrous sodium sulfate, and concentrated under reduced pressure. The residue was dissolved in THF (10 ml), potassium tert-butoxide (0.38 g) was added at 0° C., and the mixture was stirred at 0° C. for 1 hr. The reaction mixture was concentrated under reduced pressure, and the residue was diluted with water, and the mixture was extracted with ethyl acetate. The extract was washed with saturated brine, dried over anhydrous sodium sulfate, and concentrated under reduced pressure. The obtained residue was subjected to silica gel chromatography, and a fraction eluted with ethyl acetate-hexane (1:3-1:0) was concentrated under reduced pressure. The residue was dissolved in ethanol (10 ml), and 10% palladium-carbon (50% in water: 50 mg) was added. The reaction mixture was stirred under a hydrogen (normal pressure) at room temperature for 15 hr. The palladium catalyst was filtered off, and the filtrate was concentrated under reduced pressure to give the object product (0.30 g).

$^1$H-NMR (CDCl$_3$) δ 0.90 (6H, d), 1.45 (11H, s), 1.68 (1H, dt), 2.04 (2H, qd), 1.77-2.10 (2H, m), 2.21-2.54 (6H, m), 3.18 (2H, br s), 3.40 (2H, ddd), 4.02 (1H, br s), 4.26 (1H, br s)

In the same manner as in Reference Example 64, the following compound (Reference Example 144) was obtained.

Reference Example 144 tert-butyl (3S,5S)-3-[(1H-benzimidazol-2-ylcarbonyl)(2-methylpropyl)amino]-5-[(2-oxopyrrolidin-1-yl)methyl]piperidine-1-carboxylate

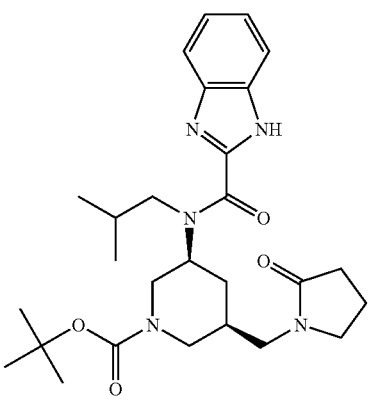 [SMILES: CC(C)CN(C(=O)c1nc2ccccc2[nH]1)[C@H]1C[C@@H](CN2CCCC2=O)CN(C(=O)OC(C)(C)C)C1]

MS (ESI+, m/e) 498 (M+1)

In the same manner as in Reference Example 69, the following compound (Reference Example 145) was obtained.

Reference Example 145 tert-butyl (3S,5S)-3-[{[1-(4-methoxybutyl)-1H-benzimidazol-2-yl]carbonyl}(2-methylpropyl)amino]-5-[(2-oxopyrrolidin-1-yl)methyl]piperidine-1-carboxylate

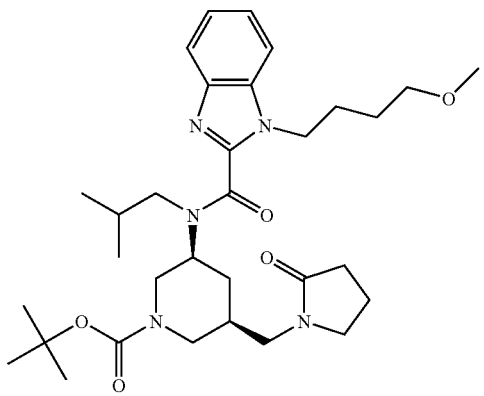 [SMILES: COCCCCn1c(C(=O)N(CC(C)C)[C@H]2C[C@@H](CN3CCCC3=O)CN(C(=O)OC(C)(C)C)C2)nc2ccccc21]

MS (ESI+, m/e) 584 (M+1)

In the same manner as in Example 60, the following compound (Example 70) was obtained.

Example 70

1-(4-methoxybutyl)-N-(2-methylpropyl)-N-{(3S,5R)-5-[(2-oxopyrrolidin-1-yl)methyl]piperidin-3-yl}-1H-benzimidazole-2-carboxamide dihydrochloride

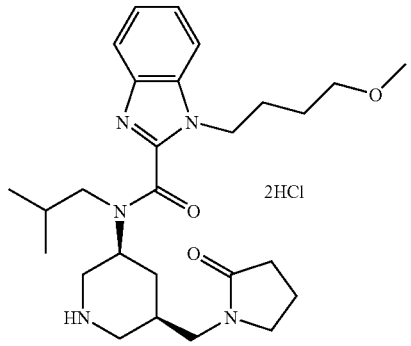 [SMILES: COCCCCn1c(C(=O)N(CC(C)C)[C@@H]2CNC[C@H](CN3CCCC3=O)C2)nc2ccccc21 ; "2HCl"]

MS (ESI+, m/e) 484 (M+1)

Reference Example 146 tert-butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate

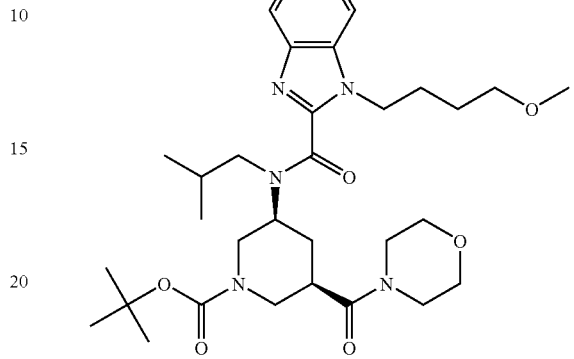

A solution of tert-butyl (3S,5R)-3-[(1H-benzimidazol-2-ylcarbonyl)(2-methylpropyl)amino]-5-(morpholin-4-ylcarbonyl)piperidine-1-carboxylate (200 mg), 4-methoxybutyl methanesulfonate (107 mg) and cesium carbonate (254 mg) in N,N-dimethylacetamide (5 ml) was stirred at 60° C. for 15 hr. After cooling to room temperature, the reaction mixture was diluted with water and extracted with ethyl acetate (10 ml×2). The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-3:7) was concentrated under reduced pressure to give the object product (190 mg).

Reference Example 147

1-(tert-butoxycarbonyl)-5-(methoxycarbonyl)piperidine-3-carboxylic acid

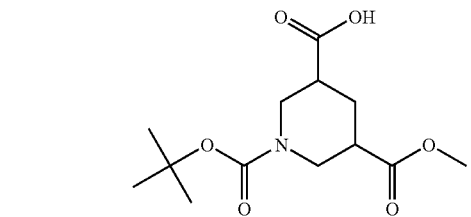 [SMILES: COC(=O)C1CC(C(=O)O)CN(C(=O)OC(C)(C)C)C1]

1-tert-Butyl 3,5-dimethyl piperidine-1,3,5-tricarboxylate (75 g) was dissolved in methanol (375 ml), and 2M aqueous sodium hydroxide solution (125 ml) was added dropwise at room temperature. The reaction mixture was stirred at room temperature for 14 hr, and methanol was evaporated under reduced pressure. The concentrate was diluted with saturated aqueous sodium hydrogen carbonate solution (100 ml) and washed twice with ethyl acetate. The basic aqueous layer was acidified (pH 2) with 6M hydrochloric acid, and the mixture was extracted with ethyl acetate. The extract was dried over anhydrous magnesium sulfate, and the solvent was evaporated under reduced pressure to give the object product (71 g).

$^1$H-NMR (CDCl$_3$) δ 1.33-1.50 (9H, m), 1.60-1.82 (1H, m), 1.96-2.22 (1H, m), 2.41-2.58 (2H, m), 2.62-2.91 (2H, m), 3.34-3.91 (1H, m), 3.71 (3H, s), 4.37 (1H, br s), 7.55-8.47 (1H, m)

Example 71

1-(4-methoxybutyl)-N-(2-methylpropyl)-N-[(3S,5R)-5-(morpholin-4-ylcarbonyl)piperidin-3-yl]-1H-benzimidazole-2-carboxamide

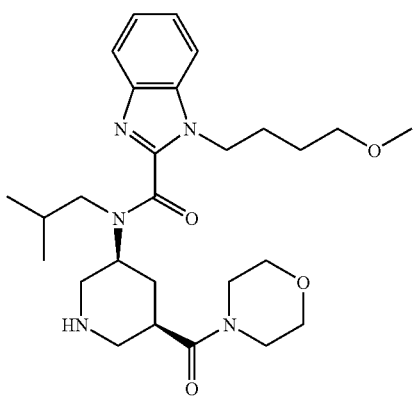 [SMILES: COCCCCn1c(C(=O)N(CC(C)C)[C@@H]2CNC[C@H](C(=O)N3CCOCC3)C2)nc2ccccc21]

tert-Butyl (3S,5R)-3-[{[1-(4-methoxybutyl)-1H-benzimidazol-2-yl]carbonyl}(2-methylpropyl)amino]-5-(morpholin-4-ylcarbonyl)piperidine-1-carboxylate (5.85 g) was dissolved in methanol (20 ml), 4M hydrogen chloride-ethyl acetate (20 ml) was added, and the mixture was stirred at room temperature for 15 hr. The reaction mixture was concentrated, the residue was diluted with aqueous sodium bicarbonate, and the mixture was extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate-methanol (9:1) was concentrated under reduced pressure to give the object product (4.40 g).

MS (ESI+, m/e) 500 (M+1)

Example 72

1-(4-methoxybutyl)-N-(2-methylpropyl)-N-[(3S,5R)-5-(morpholin-4-ylcarbonyl)piperidin-3-yl]-1H-benzimidazole-2-carboxamide methanesulfonate

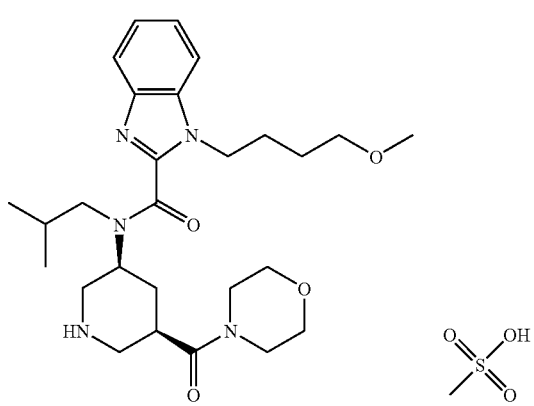

Crude crystals (163 g) of 1-(4-methoxybutyl)-N-(2-methylpropyl)-N-[(3S,5R)-5-(morpholin-4-ylcarbonyl)piperidin-3-yl]-1H-benzimidazole-2-carboxamide methanesulfonate were dissolved in 2-butanone (1600 ml) with heating (65° C.), and heptane (1600 ml) was added dropwise while keeping at 60° C. or above. The seed crystal was added, and the mixture was stirred at 50-55° C. for 1 hr and at room temperature for 12 hr and filtered. The crystals were washed with a small amount of 2-butanone-heptane (mixing ratio 1:2), and dried under reduced pressure to give the object product (155.6 g).

$^1$H-NMR (DMSO-d$_6$) δ 0.68-0.74 (2H, m), 0.89-0.99 (4H, m), 1.42-1.60 (2H, m), 1.70-1.87 (2H, m), 1.95-2.17 (2H, m), 2.15-2.39 (4H, m), 2.80-3.85 (20H, m), 4.15-4.40 (3H, m), 7.25-7.43 (2H, m), 7.62-7.75 (2H, m), 8.30 (1H, br s), 9.09 (1H, br s) MS (ESI+, m/e) 500 (M+1)

melting point : 137-138° C.

Reference Example 149 tert-butyl (3S,5R)-3-[{[1-(4-methoxybutyl)-1H-benzimidazol-2-yl]carbonyl}(2-methylpropyl)amino]-5-[methoxy(methyl)carbamoyl]piperidine-1-carboxylate

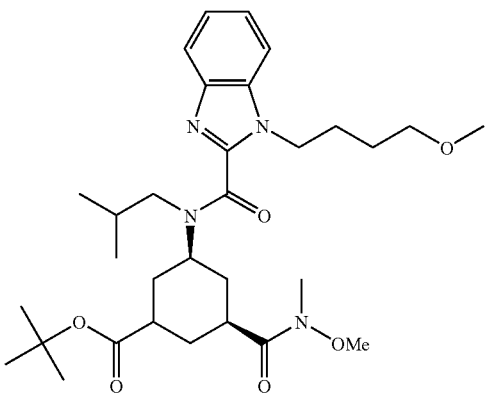 [SMILES: COCCCCn1c(C(=O)N(CC(C)C)[C@@H]2CC(C(=O)OC(C)(C)C)C[C@H](C(=O)N(C)OC)C2)nc2ccccc21]

(3R,5S)-1-(tert-Butoxycarbonyl)-5-[{[1-(4-methoxybutyl)-1H-benzimidazol-2-yl]carbonyl}(2-methylpropyl)amino]piperidine-3-carboxylic acid (7.5 g), WSC.HCL (4.06 g) and HOBt (3.25 g) were dissolved in DMF (50 ml), N-methoxymethylamine hydrochloride (1.38 g) and triethylamine (7.88 ml) were added and the mixture was stirred at room temperature for 15 hr. The reaction mixture was diluted with water, and the mixture was extracted with ethyl acetate. The extract was washed with water and brine, and dried over anhydrous sodium sulfate. The solvent was evaporated under reduced pressure. The residue was subjected to silica gel column chromatography, and a fraction eluted with ethyl acetate-hexane (1:4-9:1) was concentrated under reduced pressure to give the object product (4.76 g).

$^1$H-NMR (CDCl$_3$) δ 0.73 (3 H, d), 1.01 (3 H, dd), 1.30 (4 H, s), 1.48 (5 H, s), 1.67 (2 H, dt), 1.91-2.03 (2 H, m), 2.20 (1 H, t), 2.41 (1 H, q), 2.60-3.13 (5 H, m), 3.15-3.24 (3 H, m), 3.32 (3 H, d), 3.34-3.47 (3 H, m), 3.67-3.81 (3 H, m), 3.92-4.47 (5 H, m), 7.27-7.40 (2 H, m), 7.41-7.53 (1 H, m), 7.72 (1 H, dd), 7.84 (1 H, d)

MS (ESI+, m/e) 574 (M+1)

Reference Example 150 tert-butyl (3S,5R)-5-acetyl-3-[{[1-(4-methoxybutyl)-1H-benzimidazol-2-yl]carbonyl}(2-methylpropyl)amino]piperidine-1-carboxylate

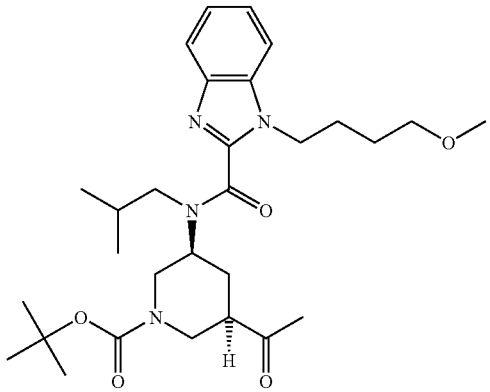

To a solution of tert-butyl (3S,5R)-3-[{[1-(4-methoxybutyl)-1H-benzimidazol-2-yl]carbonyl}(2-methylpropyl)amino]-5-[methoxy(methyl)carbamoyl]piperidine-1-carboxylate (1.06 g) in THF (20 ml) was added 1M-methyl magnesium bromide-THF solution (9.24 ml), and the mixture was stirred at room temperature for 5 hr. The reaction mixture was poured into saturated aqueous ammonium chloride solution, and the mixture was extracted with ethyl acetate. The extract was washed with water and saturated brine, and dried over anhydrous sodium sulfate. The solvent was evaporated under reduced pressure. The residue was subjected to silica gel column chromatography, and a fraction eluted with ethyl acetate-hexane (1:9-3:2) was concentrated under reduced pressure to give the object product (0.59 g).

$^1$H-NMR (CDCl$_3$) δ 0.76 (3 H, d), 1.01 (3 H, d), 1.31 (4 H, s), 1.49 (5 H, s), 1.79 (2 H, br s), 2.00 (2 H, br s), 2.21 (3 H, s), 2.27-2.47 (2 H, m), 2.56 (1 H, br s), 2.74 (2 H, d), 3.22-3.37 (3 H, m), 3.42 (3 H, t), 3.78 (2 H, br s), 4.31 (5 H, d), 7.28-7.41 (2 H, m), 7.45 (1 H, d), 7.79 (1 H, d) MS (ESI+, m/e) 529 (M+1)

Reference Example 151 tert-butyl (3R,5S)-3-(1-hydroxyethyl)-5-[{[1-(4-methoxybutyl)-1H-benzimidazol-2-yl]carbonyl}(2-methylpropyl)amino]piperidine-1-carboxylate

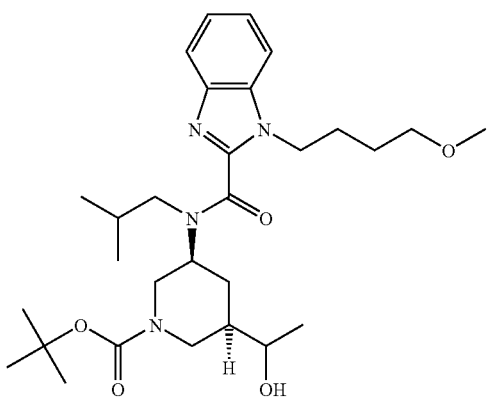

To a solution of tert-butyl (3R,5S)-3-acetyl-5-[{[1-(4-methoxybutyl)-1H-benzimidazol-2-yl]carbonyl}(2-methylpropyl)amino]piperidine-1-carboxylate (0.40 g) in ethanol (10 ml) was added sodium borohydride (29 mg), and the mixture was stirred at room temperature for 1 hr. The reaction mixture was concentrated under reduced pressure, and the residue was diluted with water. The mixture was acidified with 5% aqueous potassium hydrogen sulfate solution, and extracted with ethyl acetate. The extract was washed with water and saturated brine, and dried over anhydrous sodium sulfate. The solvent was evaporated under reduced pressure. The residue was subjected to silica gel column chromatography, and a fraction eluted with ethyl acetate-hexane (1:9-3:1) was concentrated under reduced pressure to give the object product (0.40 g).

$^1$H-NMR (CDCl$_3$) δ 0.77 (4 H, dd), 1.02 (2 H, d), 1.16-1.27 (3 H, m), 1.33 (4 H, d), 1.48 (7 H, s), 1.83 (1 H, br s), 1.98 (2 H, d), 2.11-2.90 (3 H, m), 3.30 (1 H, d), 3.33 (3 H, s), 3.35-3.46 (3 H, m), 3.66 (4 H, br s), 4.17-4.48 (4 H, m), 7.28-7.40 (2 H, m), 7.40-7.48 (1 H, m), 7.79 (1 H, d)

MS (ESI+, m/e) 531 (M+1)

Reference Example 152 tert-butyl (3S,5R)-3-[{[1-(4-methoxybutyl)-1H-benzimidazol-2-yl]carbonyl}(2-methylpropyl)amino]-5-propanoyl-piperidine-1-carboxylate

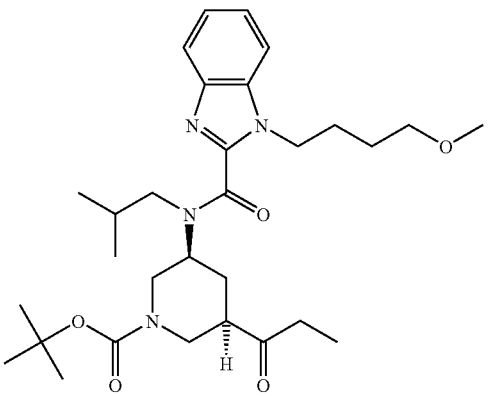

To a solution of tert-butyl (3S,5R)-3-[{[1-(4-methoxybutyl)-1H-benzimidazol-2-yl]carbonyl}(2-methylpropyl)amino]-5-[methoxy(methyl)carbamoyl]piperidine-1-carboxylate (22.7 g) in THF (20 ml) was added 1M-ethylmagnesium bromide-THF solution (119 ml) at room temperature, and the mixture was stirred at room temperature for 5 hr. The reaction mixture was poured into saturated aqueous ammonium chloride solution, and the mixture was extracted with ethyl acetate. The extract was washed with water and saturated brine, and dried over anhydrous sodium sulfate. The solvent was evaporated under reduced pressure. The residue was subjected to silica gel column chromatography, and a fraction eluted with ethyl acetate-hexane (1:9-3:2) was concentrated under reduced pressure to give the object product (14.96 g).

MS (ESI+, m/e) 543 (M+1)

Reference Example 153 tert-butyl (3R,5S)-3-(1-hydroxypropyl)-5-[{[1-(4-methoxybutyl)-1H-benzimidazol-2-yl]carbonyl}(2-methylpropyl)amino]piperidine-1-carboxylate

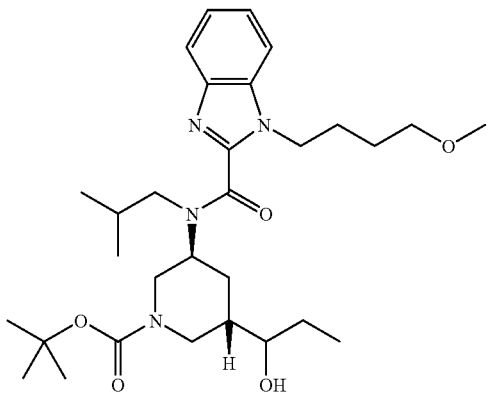

To a solution of tert-butyl (3S,5R)-3-[{[1-(4-methoxybutyl)-1H-benzimidazol-2-yl]carbonyl}(2-methylpropyl)amino]-5-propanoyl-piperidine-1-carboxylate (2.60 g) in ethanol (30 ml) was added sodium borohydride (181 mg), and the mixture was stirred at room temperature for 1 hr. The reaction mixture was concentrated under reduced pressure, and the residue was diluted with water, acidified with 5% aqueous potassium hydrogen sulfate solution, and extracted with ethyl acetate. The extract was washed with water and saturated brine, and dried over anhydrous sodium sulfate. The solvent was evaporated under reduced pressure. The residue was subjected to silica gel column chromatography, and a fraction eluted with ethyl acetate-hexane (1:9-1:1) was concentrated under reduced pressure to give the object product (2.02 g).

$^1$H-NMR (CDCl$_3$) δ 0.76 (4 H, d), 0.91-1.08 (5 H, m), 1.33 (3 H, d), 1.48 (6 H, s), 1.55 (2 H, d), 1.64-1.90 (5 H, m), 1.91-2.03 (2 H, m), 2.10-2.42 (2 H, m), 2.59 (1 H, d), 3.31 (1 H, d), 3.33 (2 H, s), 3.42 (4 H, t), 3.65 (2 H, br s), 4.17-4.46 (4 H, m), 7.27-7.39 (2 H, m), 7.39-7.51 (1 H, m), 7.69-7.85 (1 H, m)

MS (ESI+, m/e) 545 (M+1)

Example 73

N-{(3S,5R)-5-[(1R)-1-hydroxy-2-methoxyethyl]piperidin-3-yl}-1-(4-methoxybutyl)-N-(2-methylpropyl)-1H-benzimidazole-2-carboxamide dihydrochloride (Example 73-1) and N-{(3S,5R)-5-[(1S)-1-hydroxy-2-methoxyethyl]piperidin-3-yl}-1-(4-methoxybutyl)-N-(2-methylpropyl)-1H-benzimidazole-2-carboxamide dihydrochloride (Example 73-2)

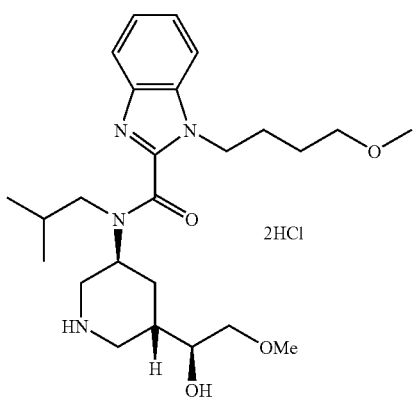

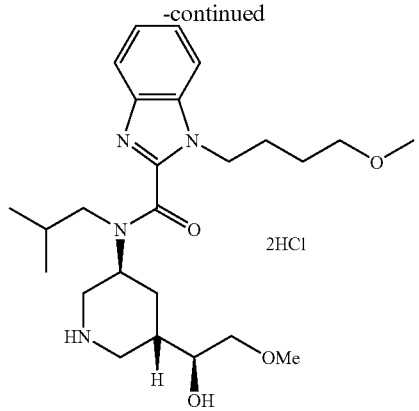

tert-Butyl (3R,5S)-3-(1-hydroxy-2-methoxyethyl)-5-[{[1-(4-methoxybutyl)-1H-benzimidazol-2-yl]carbonyl}(2-methylpropyl)amino]piperidine-1-carboxylate (1.34 g) was optically resolved by normal phase chiral HPLC under the following conditions to give a first elution component (598 mg) and a second elution component (549 mg).

column: CHIRALPAK IC 50 mm ID×500 mmL
mobile phase: hexane-ethanol (700:300)
flow rate: 60 ml/min
temperature: 30° C.
detection: UV (220 nm)
injection volume•concentration: 300 mg/load (5 mg/ml)

The obtained first elution component (495 mg) was dissolved in ethanol (1 ml), 12M hydrochloric acid (0.70 ml) was added and the mixture was stirred at room temperature for 1 hr. The reaction mixture was concentrated under reduced pressure, and the residue was dissolved in ethanol, and ethanol was evaporated under reduced pressure. This operation was repeated twice to give the object product (425 mg) of Example compound 73-1.

Example 73-1

Spectrum Data $^1$H-NMR (CDCl$_3$) δ 0.71 (2 H, dd), 0.95 (4 H, dd), 1.38-1.63 (2 H, m), 1.66-1.86 (3 H, m), 1.86-2.04 (1 H, m), 2.12 (2 H, dd), 2.59-2.91 (1 H, m), 3.02 (1 H, d), 3.09-3.22 (4 H, m), 3.24-3.39 (9 H, m), 3.50 (2 H, br s), 3.62 (1 H, br s), 4.15 (2 H, br s), 4.21-4.39 (2 H, m), 7.15-7.53 (2 H, m), 7.55-7.87 (2 H, m), 8.33-9.18 (1 H, m), 9.43 (1 H, br s)

MS (ESI+, m/e) 461 (M+1)

The obtained second elution component (447 mg) was dissolved in ethanol (1 ml), 12M hydrochloric acid (0.70 ml) was added at room temperature and the mixture was stirred for. 1 hr. The reaction mixture was concentrated under reduced pressure, the residue was dissolved in ethanol, and ethanol was evaporated under reduced pressure. This operation was repeated twice to give the object product (365 mg) of Example compound 73-2.

Example 73-2

Spectrum Data $^1$H-NMR (CDCl$_3$) δ 0.71 (2 H, dd), 0.81-1.12 (4 H, m), 1.31-1.61 (2 H, m), 1.62-1.98 (5 H, m), 1.98-2.23 (2 H, m), 2.57-2.87 (1 H, m), 3.14 (1 H, d), 3.18-3.23 (3 H, m), 3.23-

3.39 (10 H, m), 3.39-3.63 (3 H, m), 4.23-4.38 (3 H, m), 7.16-7.51 (2 H, m), 7.55-7.86 (2 H, m), 8.29-9.11 (1 H, m), 9.38 (1 H, br s)

MS (ESI+, m/e) 461 (M+1)

Example 74

N-{(3S,5R)-5-[(1S)-1-hydroxyethyl]piperidin-5-yl}-1-(4-methoxybutyl)-N-(2-methylpropyl)-1H-benzimidazole-2-carboxamide dihydrochloride (Example 74-1) and N-{(3S,5R)-5-[(1R)-1-hydroxyethyl]piperidin-5-yl}-1-(4-methoxybutyl)-N-(2-methylpropyl)-1H-benzimidazole-2-carboxamide carboxamide dihydrochloride (Example 74-2)

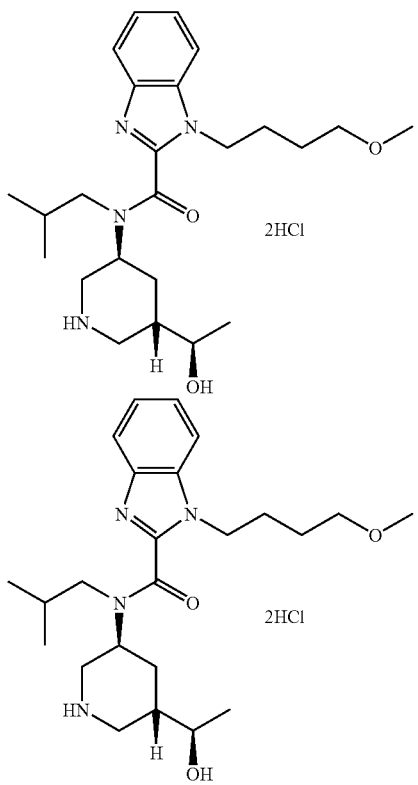

tert-Butyl (3R, 5S)-3-(1-hydroxyethyl)-5-[{[1-(4-methoxybutyl)-1H-benzimidazol-2-yl]carbonyl}(2-methylpropyl) amino]piperidine-1-carboxylate (3.2 g) was optically resolved by normal phase chiral HPLC under the following conditions to give a first elution component (1.31 g) and a second elution component (1.22 g).
column: CHIRALPAK IC 50 mm ID×500 mmL
mobile phase: hexane-ethanol (900:100)
flow rate: 80 ml/min
temperature: 30° C.
detection: UV (220 nm)
injection volume·concentration: 300 mg/load (5 mg/ml)

The obtained first elution component (1.1 g) was dissolved in 10% hydrogen chloride containing methanol solution (40 ml), and the mixture was stirred at room temperature for 15 hr. The reaction mixture was concentrated under reduced pressure, the residue was dissolved in ethanol, and ethanol was evaporated under reduced pressure. This operation was repeated twice to give the object product (0.90 g) of Example compound 74-1.

Example 74-1

Spectrum Data $^1$H-NMR (CDCl$_3$) δ 0.72 (3 H, dd), 0.84-1.18 (7 H, m), 1.45-1.66 (3 H, m), 1.67-1.98 (3 H, m), 2.00-2.19 (2 H, m), 2.54-2.81 (1 H, m), 2.92-3.23 (5 H, m), 3.25-3.40 (4 H, m), 3.40-3.70 (3 H, m), 4.07-4.47 (3 H, m), 7.23-7.51 (2 H, m), 7.54-7.91 (2 H, m), 8.56-9.55 (1 H, m), 9.86 (1 H, d)

MS (ESI+, m/e) 431 (M+1)

The obtained second elution component (1.0 g) was dissolved in 10% hydrogen chloride containing methanol solution (40 ml) was stirred at room temperature for 15 hr. The reaction mixture was concentrated under reduced pressure, the residue was dissolved in ethanol, and ethanol was evaporated under reduced pressure. This operation was repeated twice to give the object product (0.86 g) of Example compound 74-2.

Example 74-2

Spectrum Data $^1$H-NMR (CDCl$_3$) δ 0.71 (3 H, dd), 0.94 (3 H, d), 1.09 (3 H, dd), 1.27-1.64 (3 H, m), 1.70 (1 H, s), 1.74-2.00 (4 H, m), 2.00-2.29 (1 H, m), 2.54-2.76 (1 H, m), 3.11 (1 H, d), 3.20 (4 H, d), 3.24-3.62 (7 H, m), 4.32 (3 H, d), 7.16-7.54 (2 H, m), 7.72 (2 H, q), 8.27-9.22 (1 H, m), 9.36-9.56 (1 H, m)

MS (ESI+, m/e) 431 (M+1)

Example 75

N-{(3S, 5R)-5-[(1S)-1-hydroxypropyl]piperidin-5-yl}-1-(4-methoxybutyl)-N-(2-methylpropyl)-1H-benzimidazole-2-carboxamide dihydrochloride (Example 75-1) and N-{(3S, 5R)-5-[(1R)-1-hydroxypropyl]piperidin-5-yl}-1-(4-methoxybutyl)-N-(2-methylpropyl)-1H-benzimidazole-2-carboxamide dihydrochloride (Example 75-2)

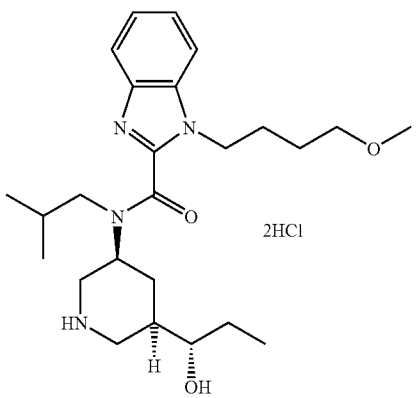

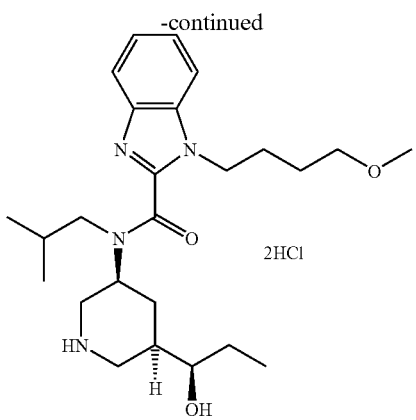

tert-Butyl (3R, 5S)-3-(1-hydroxypropyl)-5-[{[1-(4-methoxybutyl)-1H-benzimidazol-2-yl]carbonyl}(2-methylpropyl)amino]piperidine-1-carboxylate (2.11 g) was optically resolved by normal phase chiral HPLC under the following conditions to give a first elution component (1.26 g) and a second elution component (1.70 g).
column: CHIRALPAK IC 50 mm ID×500 mmL
mobile phase: hexane-ethanol (900:100)
flow rate: 80 ml/min
temperature: 30° C.
detection: UV (220 nm)
injection volume•concentration: 300 mg/load (5 mg/ml)

The obtained first elution component (1.03 g) was dissolved in ethanol (2 ml), 12M hydrochloric acid (1.5 ml) was added and the mixture was stirred at room temperature for 1 hr. The reaction mixture was concentrated under reduced pressure, the residue was dissolved in ethanol, and ethanol was evaporated under reduced pressure. This operation was repeated twice to give the object product (0.95 g) of Example compound 75-1.

Example 75-1

Spectrum Data $^1$H-NMR (CDCl$_3$) δ 0.71 (2 H, dd), 0.79-1.11 (7 H, m), 1.32-1.58 (4 H, m), 1.60-1.68 (1 H, m), 1.70-1.85 (3 H, m), 1.87-2.20 (2 H, m), 2.59-2.87 (1 H, m), 3.00 (1 H, d), 3.08-3.23 (4 H, m), 3.23-3.41 (6 H, m), 3.49 (1 H, d), 3.89-4.23 (2 H, m), 4.23-4.55 (2 H, m), 7.16-7.52 (2 H, m), 7.55-7.86 (2 H, m), 8.24-9.18 (1 H, m), 9.21-9.57 (1 H, m) MS (ESI+, m/e) 445 (M+1)

The obtained second elution component (0.85 g) was dissolved in ethanol (2 ml), 12M hydrochloric acid (1.5 ml) was added and the mixture was stirred at room temperature for 1 hr. The reaction mixture was concentrated under reduced pressure, the residue was dissolved in ethanol, and ethanol was evaporated under reduced pressure. This operation was repeated twice to give the object product (0.78 g) of Example compound 75-2.

Example 75-2

Spectrum Data $^1$H-NMR (CDCl$_3$) δ 0.71 (2 H, dd), 0.78-1.01 (7 H, m), 1.26-1.66 (4 H, m), 1.66-1.86 (4 H, m), 1.93 (1 H, d), 2.02-2.23 (1 H, m), 2.53-2.84 (1 H, m), 3.03-3.24 (5 H, m), 3.31 (5 H, q), 3.37-3.56 (2 H, m), 4.16 (2 H, br s), 4.22-4.44 (2 H, m), 7.16-7.54 (2 H, m), 7.54-7.87 (2 H, m), 8.16-9.27 (1 H, m), 9.36-9.84 (1 H, m)
MS (ESI+, m/e) 445 (M+1)

Example 76

N-[(3S, 5R)-5-(1-hydroxypropyl)piperidin-3-yl]-1-(4-methoxybutyl)-N-(2-methylpropyl)-1H-benzimidazole-2-carboxamide dihydrochloride

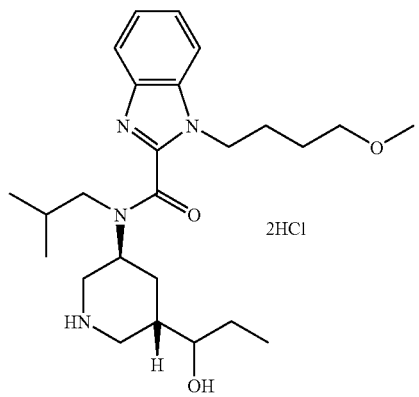

To a solution of tert-butyl (3R, 5S)-3-(1-hydroxypropyl)-5-[{[1-(4-methoxybutyl)-1H-benzimidazol-2-yl]carbonyl}(2-methylpropyl)amino]piperidine-1-carboxylate (200 mg) in ethanol (1 ml) was added 12M hydrochloric acid (0.30 ml), and the mixture was stirred at room temperature for 1 hr. The reaction mixture was concentrated under reduced pressure, the residue was dissolved in ethanol, and ethanol was evaporated under reduced pressure. This operation was repeated twice to give the object product (140 mg).
MS (ESI+, m/e) 445 (M+1)

Reference Example 154 tert-butyl (3S, 5R)-3-[{[1-(4-methoxybutyl)-1H-benzimidazol-2-yl]carbonyl}(2-methylpropyl)amino]-5-(1H-pyrazol-1-ylmethyl)piperidine-1-carboxylate

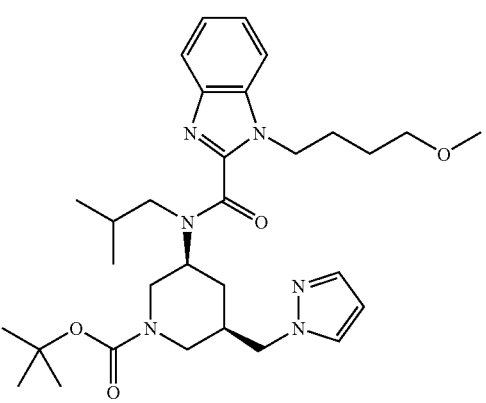 [SMILES: COCCCCn1c(C(=O)N(CC(C)C)[C@H]2C[C@@H](Cn3cccn3)CN(C(=O)OC(C)(C)C)C2)nc2ccccc21]

To a solution of tert-butyl (3R, 5S)-3-(hydroxymethyl)-5-[{[1-(4-methoxybutyl)-1H-benzimidazol-2-yl]carbonyl}(2-methylpropyl)amino]piperidine-1-carboxylate (517 mg) and triethylamine (0.21 ml) in ethyl acetate (20 ml) was added dropwise methanesulfonyl chloride (0.09 ml) at 0° C., and the mixture was stirred at 0° C. for 1 hr. The reaction mixture was washed with water and saturated brine, and dried over anhydrous sodium sulfate. The solvent was evaporated under reduced pressure. The residue was dissolved in DMF (5 ml), pyrazole (136 mg) and cesium carbonate (489 mg) were added and the mixture was stirred at 90° C. for 7 hr. The reaction mixture was cooled to room temperature, diluted with water and extracted with ethyl acetate. The extract was washed with water and brine, and dried over anhydrous sodium sulfate. The solvent was evaporated under reduced pressure. The residue was subjected to silica gel column chromatography, and a fraction eluted with ethyl acetate-hexane (1:9 to 1:0) was concentrated under reduced pressure to give the object product (105 mg). MS (ESI+, m/e) 567 (M+1)

Reference Example 155 tert-butyl (3S, 5R)-3-[{[1-(4-methoxybutyl)-1H-benzimidazol-2-yl]carbonyl}(2-methylpropyl) amino]-5-(1H-1,2,4-triazol-1-ylmethyl)piperidine-1-carboxylate

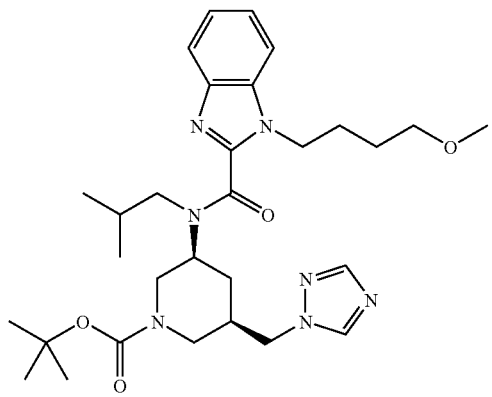 [SMILES: COCCCCn1c(C(=O)N(CC(C)C)[C@H]2C[C@@H](Cn3cncn3)CN(C(=O)OC(C)(C)C)C2)nc2ccccc21]

A solution of tert-butyl (3R, 5S)-3-(hydroxymethyl)-5-[[1-(4-methoxybutyl)-1H-benzimidazol-2-yl]carbonyl)(2-methylpropyl)amino]piperidine-1-carboxylate (208 mg), 1,3,4-triazole (52 mg), triphenylphosphine (262 mg) and diisopropyl azodicarboxylate (40% toluene solution, 632 mg) in THF (5 ml) was stirred at 50° C. for 15 hr. The reaction mixture was concentrated under reduced pressure, diluted with water and ethyl acetate, and the organic layer was separated. The organic layer was washed with saturated brine, and dried over anhydrous sodium sulfate. The solvent was evaporated under reduced pressure. The residue was subjected to silica gel column chromatography, and a fraction eluted with ethyl acetate-hexane (1:5-1:0) and ethyl acetate-methanol (1:0-9:1) was concentrated under reduced pressure. The residue was subjected to basic silica gel column chromatography, and a fraction eluted with ethyl acetate-hexane (1:9 to 3:1) was s concentrated under reduced pressure to give the object product (180 mg).

MS (ESI+, m/e) 568 (M+1)

In the same manner as in Example 60, the following compounds (Examples 77-79) were obtained.

Example 77

1-(4-methoxybutyl)-N-(2-methylpropyl)-N-[(3S, 5R)-5-(1H-pyrazol-1-ylmethyl)piperidin-3-yl]-1H-benzimidazole-2-carboxamide trihydrochloride

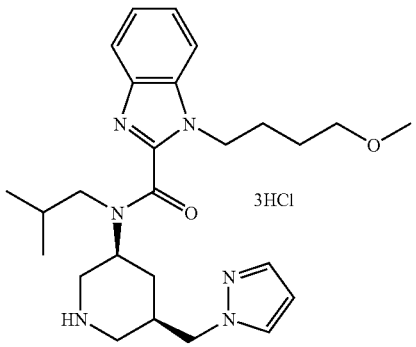 [SMILES: COCCCCn1c(C(=O)N(CC(C)C)[C@@H]2CNC[C@H](Cn3cccn3)C2)nc2ccccc21 ; "3HCl"]

MS (ESI+, m/e) 467 (M+1)

Example 78

1-(4-methoxybutyl)-N-(2-methylpropyl)-N-[(3S, 5R)-5-(1H-1,2,4-triazol-1-ylmethyl)piperidin-3-yl]-1H-benzimidazole-2-carboxamide dihydrochloride

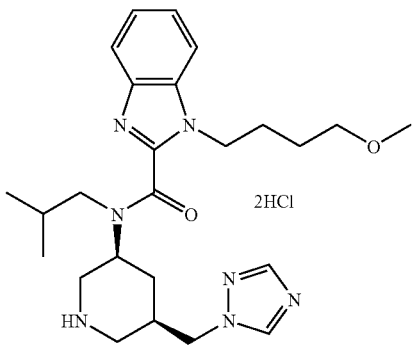 [SMILES: COCCCCn1c(C(=O)N(CC(C)C)[C@@H]2CNC[C@H](Cn3cncn3)C2)nc2ccccc21 ; "2HCl"]

MS (ESI+, m/e) 468 (M+1)

Example 79

N-[(3S, 5R)-5-acetylpiperidin-3-yl]-1-(4-methoxybutyl)-N-(2-methylpropyl)-1H-benzimidazole-2-carboxamide dihydrochloride

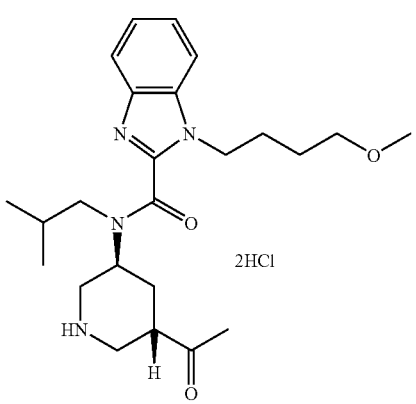

MS (ESI+, m/e) 429 (M+1)

In the same manner as in Reference Example 149, the following compound (Reference Example 156) was obtained.

Reference Example 156 tert-butyl (3S, 5R)-3-[{[6-fluoro-1-(4-methoxybutyl)-1H-benzimidazol-2-yl]carbonyl}(2-methylpropyl)amino]-5-[methoxy(methyl)carbamoyl]piperidine-1-carboxylate

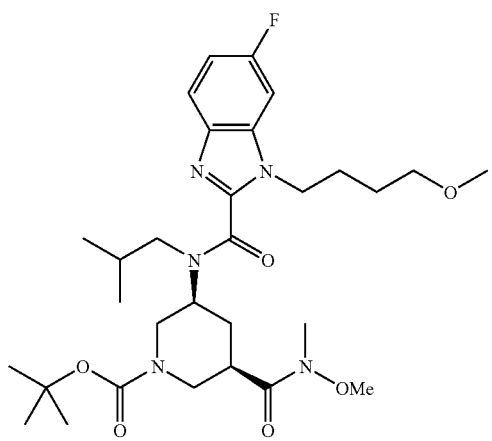 [SMILES: COCCCCn1c(C(=O)N(CC(C)C)[C@H]2C[C@@H](C(=O)N(C)OC)CN(C(=O)OC(C)(C)C)C2)nc2ccc(F)cc21]

MS (ESI+, m/e) 592 (M+1)

In the same manner as in Reference Example 150, the following compound (Reference Example 157) was obtained.

Reference Example 157 tert-butyl (3R, 5S)-3-acetyl-5-[{[6-fluoro-1-(4-methoxybutyl)-1H-benzimidazol-2-yl]carbonyl}(2-methylpropyl)amino]piperidine-1-carboxylate

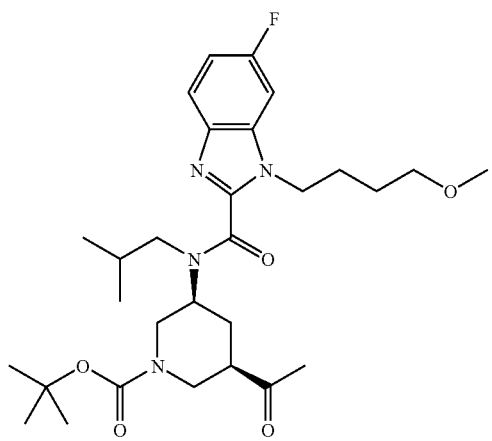 [SMILES: COCCCCn1c(C(=O)N(CC(C)C)[C@H]2C[C@@H](C(C)=O)CN(C(=O)OC(C)(C)C)C2)nc2ccc(F)cc21]

MS (ESI+, m/e) 547 (M+1)

In the same manner as in Reference Example 151, the following compound (Reference Example 158) was obtained.

Reference Example 158 tert-butyl (3S, 5R)-3-[{[6-fluoro-1-(4-methoxybutyl)-1H-benzimidazol-2-yl]carbonyl}(2-methylpropyl)amino]-5-(1-hydroxyethyl)piperidine-1-carboxylate

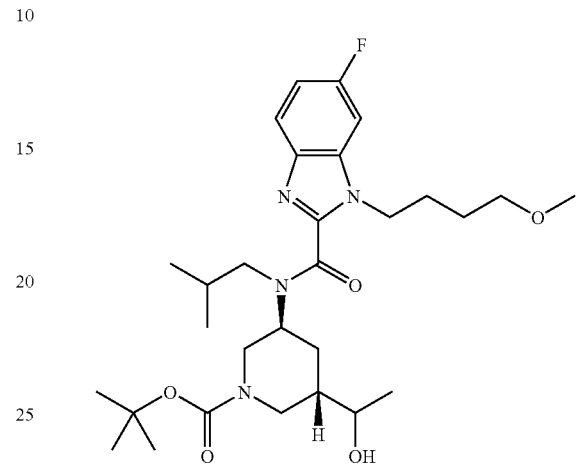

MS (ESI+, m/e) 549 (M+1)

In the same manner as in Example 76, the following compound (Example 80) was obtained.

Example 80

6-fluoro-N-[(3S, 5R)-5-(1-hydroxyethyl)piperidin-3-yl]-1-(4-methoxybutyl)-N-(2-methylpropyl)-1H-benzimidazole-2-carboxamide dihydrochloride

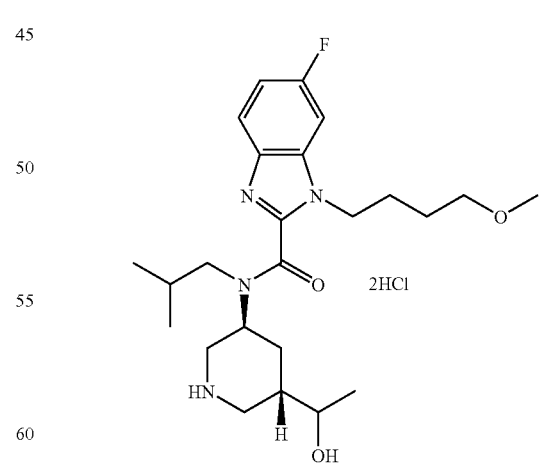

MS (ESI+, m/e) 449 (M+1)

In the same manner as in Reference Example 69, the following compounds (Reference Examples 159-160) were obtained.

Reference Example 159

1-tert-butyl 3-methyl (3R, 5S)-5-{[(1-ethyl-1H-benz-imidazol-2-yl)carbonyl](2-methylpropyl)amino}piperidine-1,3-dicarboxylate

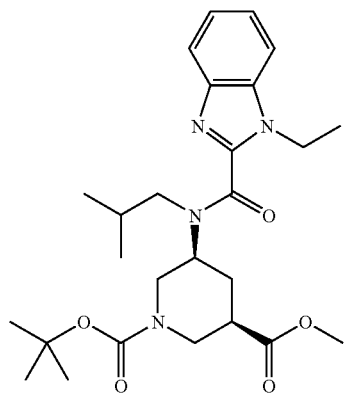 [SMILES: CCn1c(C(=O)N(CC(C)C)[C@H]2C[C@@H](C(=O)OC)CN(C(=O)OC(C)(C)C)C2)nc2ccccc21]

MS (ESI+, m/e) 487 (M+1)

Reference Example 160

1-tert-butyl 3-methyl (3R, 5S)-5-[{[1-(cyclopropyl-methyl)-1H-benzimidazol-2-yl]carbonyl}(2-methyl-propyl)amino]piperidine-1,3-dicarboxylate

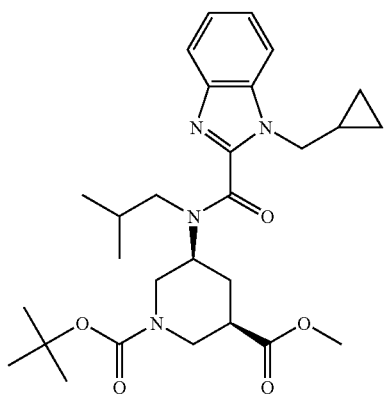 [SMILES: COC(=O)[C@@H]1C[C@H](N(CC(C)C)C(=O)c2nc3ccccc3n2CC2CC2)CN(C(=O)OC(C)(C)C)C1]

MS (ESI+, m/e) 513 (M+1)

In the same manner as in Reference Example 74, the following compounds (Reference Examples 161-162) were obtained.

Reference Example 161

(3R, 5S)-1-(tert-butoxycarbonyl)-5-{[(1-ethyl-1H-benzimidazol-2-yl)carbonyl](2-methylpropyl)amino}piperidine-3-carboxylic acid

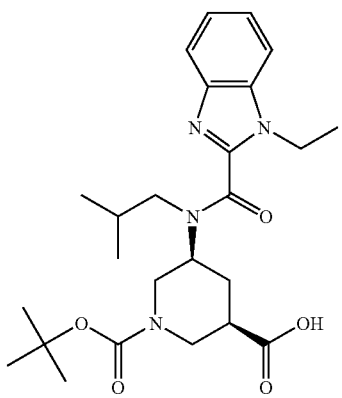 [SMILES: CCn1c(C(=O)N(CC(C)C)[C@H]2C[C@@H](C(=O)O)CN(C(=O)OC(C)(C)C)C2)nc2ccccc21]

MS (ESI+, m/e) 473 (M+1)

Reference Example 162

(3R, 5S)-1-(tert-butoxycarbonyl)-5-[{[1-(cyclopropylmethyl)-1H-benzimidazol-2-yl]carbonyl}(2-methylpropyl)amino]piperidine-3-carboxylic acid

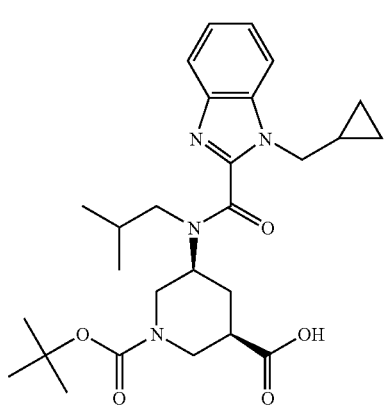 [SMILES: CC(C)CN(C(=O)c1nc2ccccc2n1CC1CC1)[C@H]1C[C@@H](C(=O)O)CN(C(=O)OC(C)(C)C)C1]

MS (ESI+, m/e) 499 (M+1)

Reference Example 163 tert-butyl (3S, 5R)-3-[{[1-(4-methoxybutyl)-1H-benzimidazol-2-yl]carbonyl}(2-methylpropyl)amino]-5-(morpholin-4-ylcarbonyl)piperidine-1-carboxylate

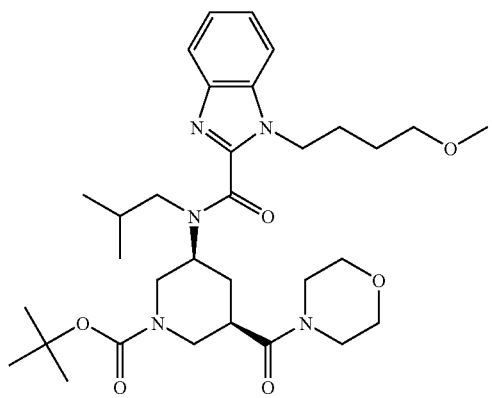 [SMILES: COCCCCn1c(C(=O)N(CC(C)C)[C@H]2C[C@@H](C(=O)N3CCOCC3)CN(C(=O)OC(C)(C)C)C2)nc2ccccc21]

(3R, 5S)-1-(tert-Butoxycarbonyl)-5-[{[1-(4-methoxybutyl)-1H-benzimidazol-2-yl]carbonyl}(2-methylpropyl)amino]piperidine-3-carboxylic acid (10 g) and morpholine (1.6 g) were dissolved in DMF (100 ml), WSC.HCL (4.8 g) and HOBt (3.1 g) were added, and the mixture was stirred at 50° C. for 12 hr. The reaction mixture was poured into 10% aqueous sodium bicarbonate, and the mixture was extracted with ethyl acetate. The extracts were combined, washed with brine, and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (8.9 g).

$^1$H-NMR (CDCl$_3$) δ 0.63-0.80 (2H, m), 0.89-1.07 (4H, m), 1.41-1.59 (9H, m), 1.59-1.80 (2H, m), 1.87-2.23 (4H, m), 2.30-2.98 (3H, m), 3.21-3.46 (6H, m), 3.49-3.91 (10H, m), 3.95-4.47 (5H, m), 7.18-7.51 (3H, m), 7.56-7.84 (1H, m).

MS (ESI+, m/e) 600 (M+1)

In the same manner as in Reference Example 163, the following compounds (Reference Examples 164-165) were obtained.

Reference Example 164 tert-butyl (3S, 5R)-3-{[(1-ethyl-1H-benzimidazol-2-yl)carbonyl](2-methylpropyl)amino}-5-(morpholin-4-ylcarbonyl)piperidine-1-carboxylate

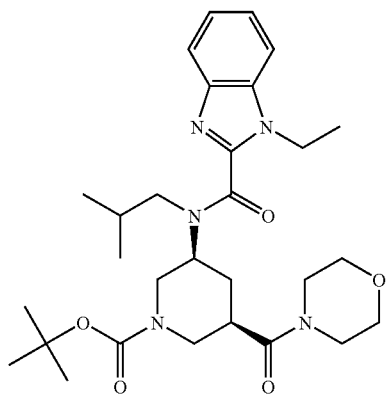 [SMILES: CCn1c(C(=O)N(CC(C)C)[C@H]2C[C@@H](C(=O)N3CCOCC3)CN(C(=O)OC(C)(C)C)C2)nc2ccccc21]

MS (ESI+, m/e) 542 (M+1)

Reference Example 165 tert-butyl (3S, 5R)-3-[{[1-(cyclopropylmethyl)-1H-benzimidazol-2-yl]carbonyl}(2-methylpropyl)amino]-5-(morpholin-4-ylcarbonyl)piperidine-1-carboxylate

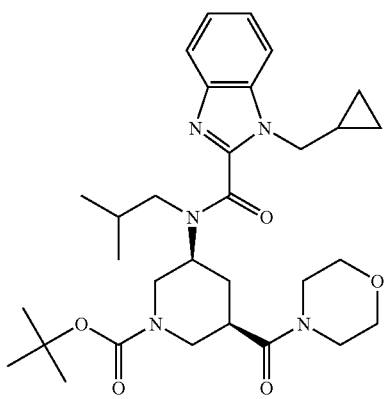 [SMILES: CC(C)CN(C(=O)c1nc2ccccc2n1CC1CC1)[C@H]1C[C@@H](C(=O)N2CCOCC2)CN(C(=O)OC(C)(C)C)C1]

MS (ESI+, m/e) 568 (M+1)

In the same manner as in Example 60, the following compounds (Examples 81-82) were obtained.

Example 81

1-ethyl-N-(2-methylpropyl)-N-[(3S, 5R)-5-(morpholin-4-ylcarbonyl)piperidin-3-yl]-1H-benzimidazole-2-carboxamide dihydrochloride

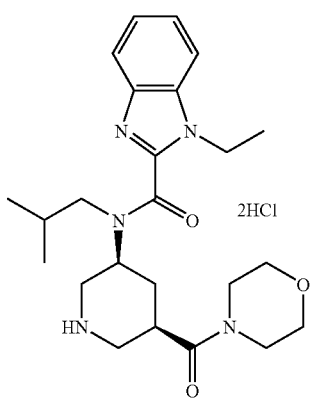 [SMILES: CCn1c(C(=O)N(CC(C)C)[C@@H]2CNC[C@H](C(=O)N3CCOCC3)C2)nc2ccccc21 ; "2HCl"]

MS (ESI+, m/e) 442 (M+1)

Example 82

1-(cyclopropylmethyl)-N-(2-methylpropyl)-N-[(3S,5R)-5-(morpholin-4-ylcarbonyl)piperidin-3-yl]-1H-benzimidazole-2-carboxamide dihydrochloride

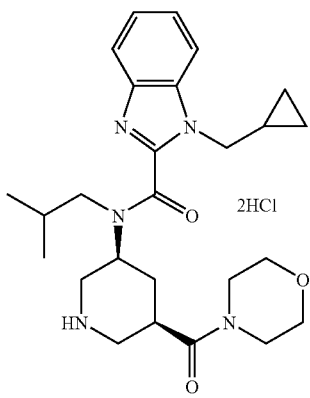 [SMILES: CC(C)CN(C(=O)c1nc2ccccc2n1CC1CC1)[C@@H]1CNC[C@H](C(=O)N2CCOCC2)C1 ; "2HCl"]

MS (ESI+, m/e) 468 (M+1)

In the same manner as in Reference Example 79, the following compound (Reference Example 166) was obtained.

Reference Example 166 tert-butyl (3S, 5R)-3-{[(1-ethyl-1H-benzimidazol-2-yl)carbonyl](2-methylpropyl)amino}-5-(hydroxymethyl)piperidine-1-carboxylate

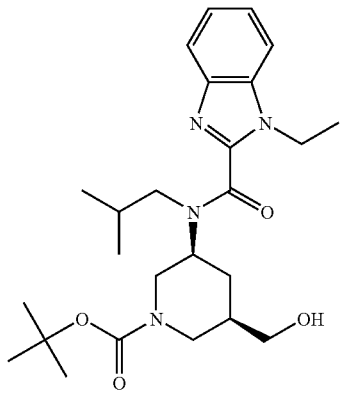 [SMILES: CCn1c(C(=O)N(CC(C)C)[C@H]2C[C@@H](CO)CN(C(=O)OC(C)(C)C)C2)nc2ccccc21]

MS (ESI+, m/e) 459 (M+1)

In the same manner as in Example 76, the following compound (Example 83) was obtained.

Example 83

1-ethyl-N-[(3S, 5R)-5-(hydroxymethyl)piperidin-3-yl]N-(2-methylpropyl)-1H-benzimidazole-2-carboxamide dihydrochloride

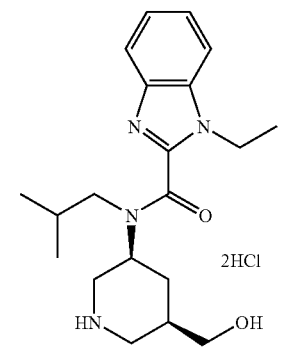 [SMILES: CCn1c(C(=O)N(CC(C)C)[C@@H]2CNC[C@H](CO)C2)nc2ccccc21 ; "2HCl"]

MS (ESI+, m/e) 359 (M+1)

Reference Example 167 tert-butyl (3S, 5R)-3-[(1,3-benzothiazol-2-ylcarbonyl)(2-methylpropyl)amino]-5-(morpholin-4-ylcarbonyl)piperidine-1-carboxylate

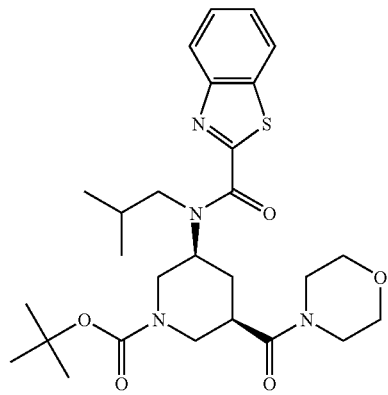 [SMILES: CC(C)CN(C(=O)c1nc2ccccc2s1)[C@H]1C[C@@H](C(=O)N2CCOCC2)CN(C(=O)OC(C)(C)C)C1]

1,3-Benzothiazole-2-carboxylic acid (29 mg), tert-butyl (3S, 5R)-3-[(2-methylpropyl)amino]-5-(morpholin-4-ylcarbonyl)piperidine-1-carboxylate (50 mg) and N,N-diisopropylethylamine (118 µl) were dissolved in acetonitrile (3 ml), chloro-N,N,N',N'-tetramethylformamidinium hexafluorophosphate (57 mg) was added at 0° C., and the mixture was stirred at room temperature for 2 hr. The reaction mixture was diluted with 10% aqueous sodium bicarbonate, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (58 mg).

MS (ESI+, m/e) 531 (M+1)

In the same manner as in Example 60, the following compound (Example 84) was obtained.

Example 84

N-(2-methylpropyl)-N-[(3S, 5R)-5-(morpholin-4-ylcarbonyl)piperidin-3-yl]-1,3-benzothiazole-2-carboxamide hydrochloride

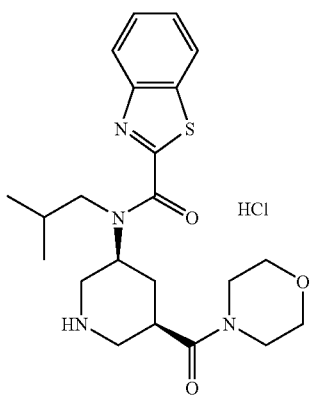 [SMILES: CC(C)CN(C(=O)c1nc2ccccc2s1)[C@@H]1CNC[C@H](C(=O)N2CCOCC2)C1 ; Cl]

MS (ESI+, m/e) 431 (M+1)

Example 85

1-(3-methoxypropyl)-N-(2-methylpropyl)-N-[(3S, 5R)-5-(morpholin-4-ylcarbonyl)piperidin-3-yl]-1H-benzimidazole-2-carboxamide 1/2 sulfate

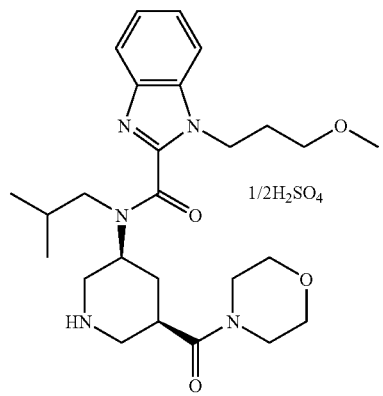 [SMILES: COCCCn1c(C(=O)N(CC(C)C)[C@@H]2CNC[C@H](C(=O)N3CCOCC3)C2)nc2ccccc21]

tert-Butyl (3S, 5R)-3-{(1H-benzimidazol-2-ylcarbonyl)(2-methylpropyl)amino}-5-(morpholin-4-ylcarbonyl)piperidine-1-carboxylate (700 mg), 3-methoxypropan-1-ol (123 mg) and triphenylphosphine (465 mg) were dissolved in THF (20 ml), diisopropyl azodicarboxylate (40% toluene solution: 896 mg) was added, and the mixture was stirred at room temperature for 60 hr. The reaction mixture was diluted with water, and the mixture was extracted with ethyl acetate. The extract was saturated aqueous sodium hydrogen carbonate and saturated washed with brine, and dried over anhydrous sodium sulfate. The solvent was evaporated under reduced pressure. The residue was subjected to silica gel column chromatography, and a fraction eluted with ethyl acetate-hexane (1:9-1:3) was concentrated under reduced pressure. The obtained substance was dissolved in ethyl acetate (3 ml), 4M hydrogen chloride-ethyl acetate (3 ml) was added, and the mixture was stirred at room temperature for 15 hr. The reaction mixture was basified with saturated aqueous sodium hydrogen carbonate, and extracted with ethyl acetate. The extract was dried over anhydrous sodium sulfate. The solvent was evaporated under reduced pressure. The residue was subjected to basic silica gel column chromatography, and a fraction eluted with ethyl acetate-hexane (1:9-1:0) and ethyl acetate-methanol (93:7) was concentrated under reduced pressure. The obtained substance was dissolved in ethyl acetate (10 ml), sulfuric acid (42 mg) was added, and the solvent was evaporated under reduced pressure. The residue was dissolved in ethanol (10 ml), and the solvent was evaporated under reduced pressure. The residue was crystallized from ethyl acetate-methanol to give the object product (180 mg) as crystals.

$^1$H-NMR (CDCl$_3$) δ 0.70 (2 H, d), 0.94 (4 H, dd), 1.69-2.28 (5 H, m), 2.60-2.85 (2 H, m), 2.85-3.15 (3 H, m), 3.15-3.25 (5 H, m), 3.41-3.74 (11 H, m), 3.86-4.20 (1 H, m), 4.20-4.52 (2 H, m), 7.18-7.48 (2 H, m), 7.53-7.84 (2 H, m)

MS (ESI+, m/e) 486 (M+1)

Example 86

1-(4-methoxybutyl)-N-(2-methylpropyl)-N-[(3S, 5R)-5-(morpholin-4-ylcarbonyl)piperidin-3-yl]-1H-benzimidazole-2-carboxamide 1/2 sulfate

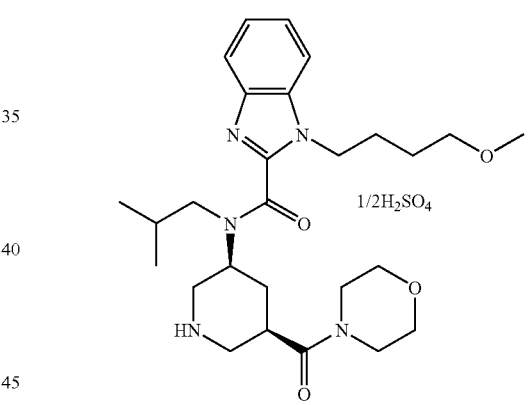

1-(4-Methoxybutyl)-N-(2-methylpropyl)-N-[(3S, 5R)-5-(morpholin-4-ylcarbonyl)piperidin-3-yl]-1H-benzimidazole-2-carboxamide (1 g) and sulfuric acid (0.055 ml) were dissolved in ethyl acetate (30 ml) and ethanol (1 ml) with heating (100° C.), and stood while gradually cooling to room temperature. The precipitate was collected by filtration, and washed with ethyl acetate. The obtained crude crystals (0.37 g) were dissolved in ethyl acetate (3.75 ml) and ethanol (1.5 ml) with heating (70° C.), and the seed crystal was added. The mixture was stood for 15 hr while gradually cooling to room temperature, and filtered. The crystals were washed with ethyl acetate, and dried under reduced pressure to give the object product (0.18 g) as crystals.

$^1$H-NMR (DMSO-d$_6$) δ 0.70 (2 H, d), 0.94 (4 H, dd), 1.30-1.61 (2 H, m), 1.78 (2 H, dd), 1.86-2.02 (1 H, m), 2.02-2.21 (1 H, m), 2.58-2.85 (2 H, m), 2.89-3.02 (1 H, m), 3.15-3.21 (3 H, m), 3.25-3.65 (17 H, m), 3.98 (1 H, br s), 4.19-4.53 (2 H, m), 7.23-7.56 (2 H, m), 7.62-8.00 (2 H, m)

MS (ESI+, m/e) 500 (M+1)

Reference Example 168 tert-butyl (3S, 5R)-3-[{[1-(2-methoxy-2-oxoethyl)-1H-benzimidazol-2-yl]carbonyl}(2-methylpropyl)amino]-5-(morpholin-4-ylcarbonyl)piperidine-1-carboxylate

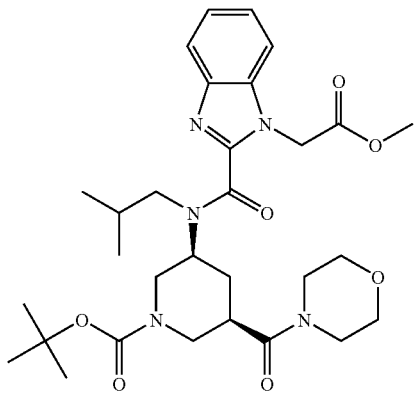 [SMILES: COC(=O)Cn1c(C(=O)N(CC(C)C)[C@H]2C[C@@H](C(=O)N3CCOCC3)CN(C(=O)OC(C)(C)C)C2)nc2ccccc21]

tert-Butyl (3S, 5R)-3-{(1H-benzimidazol-2-ylcarbonyl)(2-methylpropyl)amino}-5-(morpholin-4-ylcarbonyl)piperidine-1-carboxylate (1.06 g) was dissolved in dimethylformamide (20 ml), methyl bromoacetate (390 μl) and cesium carbonate (2.02 g) were added and the mixture was stirred at 55° C. for 1 hr. The reaction mixture was concentrated under reduced pressure, diluted with water, and the mixture was extracted with ethyl acetate. The extract was washed with saturated brine, dried over anhydrous magnesium sulfate, and concentrated under reduced pressure. The residue was subjected to silica gel chromatography, and a fraction eluted with ethyl acetate-hexane (1:9)-ethyl acetate was concentrated under reduced pressure to give the object product (1.19 g).

MS (ESI+, m/e) 586 (M+1)

Reference Example 169 tert-butyl (3S, 5R)-3-[[[1-(2-hydroxyethyl)-1H-benzimidazol-2-yl]carbonyl](2-methylpropyl)amino]-5-(morpholin-4-ylcarbonyl)piperidine-1-carboxylate

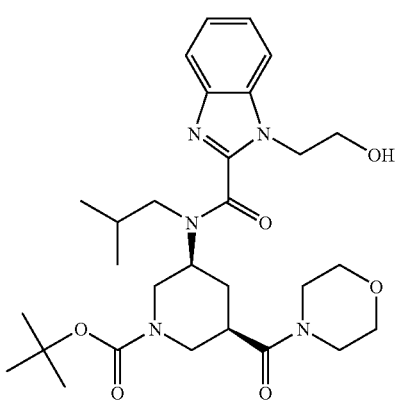 [SMILES: CC(C)CN(C(=O)c1nc2ccccc2n1CCO)[C@H]1C[C@@H](C(=O)N2CCOCC2)CN(C(=O)OC(C)(C)C)C1]

Calcium chloride (650 mg) was suspended in ethanol (80 ml) and sodium borohydride (740 mg) was added at 0° C. After stirring at 0° C. for 15 min, a solution of tert-butyl (3S, 5R)-3-[[[1-(2-methoxy-2-oxoethyl)-1H-benzimidazol-2-yl]carbonyl](2-methylpropyl)amino]-5-(morpholin-4-ylcarbonyl)piperidine-1-carboxylate (1.15 g) in THF (80 ml) was added dropwise. After stirring at room temperature for 2 hr, the reaction mixture was diluted with 10% aqueous citric acid solution, and the mixture was extracted with ethyl acetate. The extract was washed with saturated aqueous sodium hydrogen carbonate, and dried over anhydrous magnesium sulfate. The solvent was evaporated under reduced pressure. The residue was subjected to silica gel chromatography, and a fraction eluted with ethyl acetate-hexane (1:9-1:0)-ethyl acetate-methanol (85:15) was concentrated under reduced pressure to give the object product (849 mg).

MS (ESI+, m/e) 558 (M+1)

In the same manner as in the method shown in Example 60, the compound described in the following Example 87 was obtained.

Example 87 methyl (2-{(2-methylpropyl)[(3S, 5R)-5-(morpholin-4-ylcarbonyl)piperidin-3-yl]carbamoyl}-1H-benzimidazol-1-yl)acetate dihydrochloride

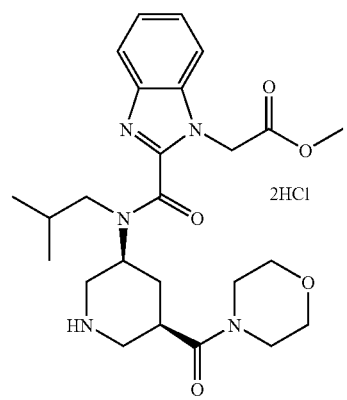 [SMILES: COC(=O)Cn1c(C(=O)N(CC(C)C)[C@@H]2CNC[C@H](C(=O)N3CCOCC3)C2)nc2ccccc21 ; "2HCl"]

MS (ESI+, m/e) 486 (M+1)

Example 88

1-(2-hydroxyethyl)-N-(2-methylpropyl)-N-[(3S, 5R)-5-(morpholin-4-ylcarbonyl)piperidin-3-yl]-1H-benzimidazole-2-carboxamide dihydrochloride

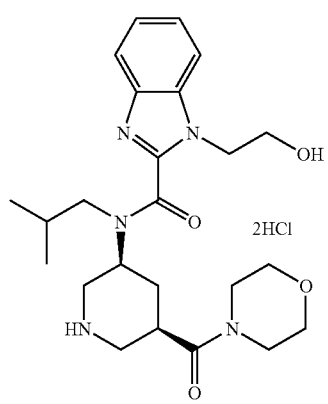 [SMILES: CC(C)CN(C(=O)c1nc2ccccc2n1CCO)[C@@H]1CNC[C@H](C(=O)N2CCOCC2)C1 ; "2HCl"]

tert-Butyl (3S, 5R)-3-[[[1-(2-hydroxyethyl)-1H-benzimidazol-2-yl]carbonyl](2-methylpropyl)amino]-5-(morpholin-4-ylcarbonyl)piperidine-1-carboxylate (51 mg) was dissolved in 10% hydrogen chloride-methanol (4 ml), and the mixture was stirred at room temperature for 41 hr and concentrated to give the object product (44 mg).

MS (ESI+, m/e) 458 (M+1)

Example 89

1-(2-cyclopropylethyl)-N-(2-methylpropyl)-N-[(3S, 5R)-5-(morpholin-4-ylcarbonyl)piperidin-3-yl]-1H-benzimidazole-2-carboxamide dihydrochloride

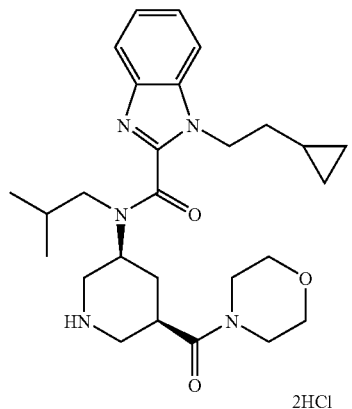 [SMILES: CC(C)CN(C(=O)c1nc2ccccc2n1CCC1CC1)[C@@H]1CNC[C@H](C(=O)N2CCOCC2)C1 ; "2HCl"]

2HCl

To a solution of tert-butyl (3S, 5R)-3-[(1H-benzimidazol-2-ylcarbonyl)(2-methylpropyl)amino]-5-(morpholin-4-ylcarbonyl)piperidine-1-carboxylate (257 mg), 2-cyclopropylethanol (86 mg) and triphenylphosphine (263 mg) in toluene (10 ml) was added diisopropyl azodicarboxylate (506 µl) at room temperature, and the mixture was stirred at the same temperature for 17 hr. The reaction mixture was diluted with aqueous sodium bicarbonate, and the mixture was extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate was concentrated under reduced pressure to give tert-butyl (3S, 5R)-3-[{[1-(2-cyclopropylethyl)-1H-benzimidazol-2-yl]carbonyl}(2-methylpropyl)amino]-5-(morpholin-4-ylcarbonyl)piperidine-1-carboxylate. The obtained tert-butyl (3S, 5R)-3-[{[1-(2-cyclopropylethyl)-1H-benzimidazol-2-yl]carbonyl}(2-methylpropyl)amino]-5-(morpholin-4-ylcarbonyl)piperidine-1-carboxylate was dissolved in 4M hydrogen chloride-ethyl acetate (5 ml), and the mixture was stirred at room temperature for 3 hr. The reaction mixture was concentrated, and the residue was subjected to reversed-phase preparative HPLC and the eluted fraction was concentrated under reduced pressure. The residue was diluted with aqueous sodium bicarbonate, and the mixture was extracted with ethyl acetate. The extract was washed with saturated brine, and dried over anhydrous sodium sulfate. 4M Hydrogen chloride-ethyl acetate (1 ml) was added and the mixture was stirred for 5 min. The solvent was evaporated under reduced pressure to give the object product (220 mg).

MS (ESI+, m/e) 482 (M+1)

Reference Example 170 tert-butyl (3R, 5S)-3-(1H-benzimidazol-2-yl)-5-[{[1-(4-methoxybutyl)-1H-benzimidazol-2-yl]carbonyl}(2-methylpropyl)amino]piperidine-1-carboxylate

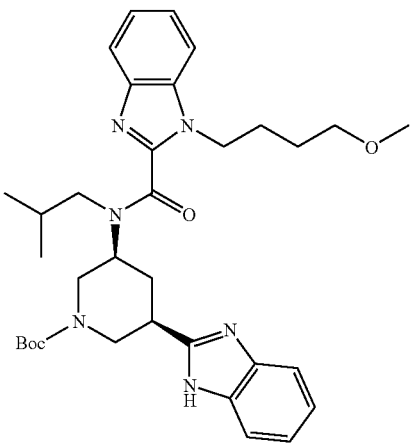 [SMILES: COCCCCn1c(C(=O)N(CC(C)C)[C@H]2C[C@@H](c3nc4ccccc4[nH]3)CN(C(=O)OC(C)(C)C)C2)nc2ccccc21]

(3R, 5S)-1-(tert-Butoxycarbonyl)-5-[{[1-(4-methoxybutyl)-1H-benzimidazol-2-yl]carbonyl}(2-methylpropyl)amino]piperidine-3-carboxylic acid (265 mg), phenylenediamine (54 mg), 1H-benzotriazol-1-ol (95 mg) and N,N-diisopropylethylamine (259 µl) were dissolved in DMF (5 ml), WSC.HCl (144 mg) was added and the mixture was stirred at room temperature for 15 hr. The reaction mixture was diluted with aqueous sodium bicarbonate, and extracted with ethyl acetate. The extract was washed successively with water and saturated brine, and dried over anhydrous magnesium sulfate. The solvent was evaporated under reduced pressure. The residue was dissolved in acetic acid (5 ml), and the mixture was stirred at 80° C. for 5 hr. The mixture was cooled to room temperature, and the reaction mixture was concentrated. To the residue was added aqueous sodium bicarbonate, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (115 mg).

MS (ESI+, m/e) 603 (M+1)

In the same manner as in Example 12, the following compound (Example 90) was obtained.

Example 90

N-[(3S, 5R)-5-(1H-benzimidazol-2-yl)piperidin-3-yl]-1-(4-methoxybutyl)-N-(2-methylpropyl)-1H-benzimidazole-2-carboxamide trihydrochloride

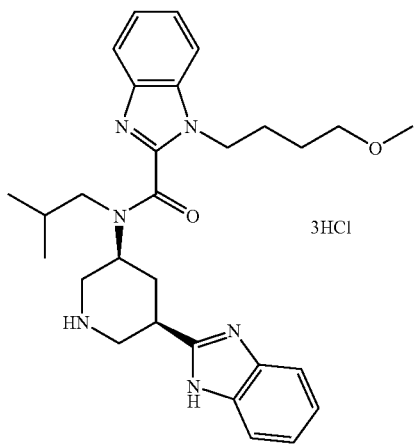 [SMILES: COCCCCn1c(C(=O)N(CC(C)C)[C@@H]2CNC[C@H](c3nc4ccccc4[nH]3)C2)nc2ccccc21 ; "3HCl"]

MS (ESI+, m/e) 503 (M+1)

Reference Example 171

1-tert-butyl 3-methyl (3R, 5S)-5-[(2-methylpropyl){[1-(2-phenylethyl)-1H-benzimidazol-2-yl]carbonyl}amino]piperidine-1,3-dicarboxylate

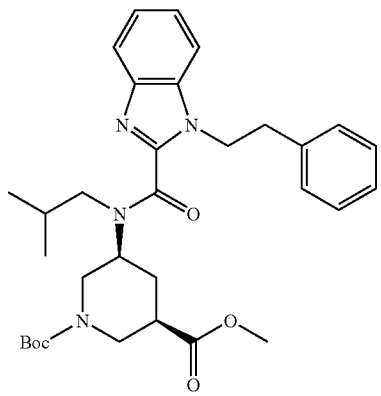 [SMILES: COC(=O)[C@@H]1C[C@H](N(CC(C)C)C(=O)c2nc3ccccc3n2CCc2ccccc2)CN(C(=O)OC(C)(C)C)C1]

To a solution of 1-tert-butyl 3-methyl (3R, 5S)-5-[(1H-benzimidazol-2-ylcarbonyl)(2-methylpropyl)amino]piperidine-1,3-dicarboxylate (1.38 g) and (2-bromoethyl)benzene (810 µl) in N,N-dimethylacetamide (30 ml) was added cesium carbonate (2.93 g), and the mixture was stirred at 65° C. for 15 hr. (2-Bromoethyl)benzene (810 µl) was added to the reaction mixture, and the mixture was further stirred at 65° C. for 5 hr. The reaction mixture was cooled to room temperature, diluted with water and extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (1:1) was concentrated under reduced pressure to give the object product (1.40 g).

MS (ESI+, m/e) 563 (M+1)

Reference Example 172

(3R, 5S)-1-(tert-butoxycarbonyl)-5-[(2-methylpropyl){[1-(2-phenylethyl)-1H-benzimidazol-2-yl]carbonyl}amino]piperidine-3-carboxylic acid

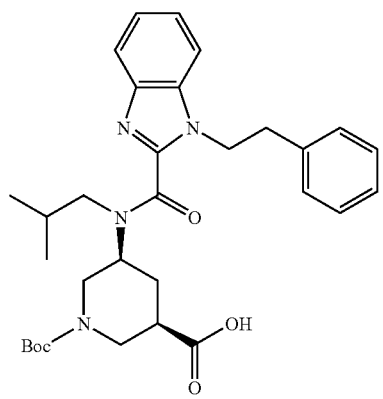 [SMILES: CC(C)CN(C(=O)c1nc2ccccc2n1CCc1ccccc1)[C@H]1C[C@@H](C(=O)O)CN(C(=O)OC(C)(C)C)C1]

1-tert-Butyl 3-methyl (3R, 5S)-5-[(2-methylpropyl){[1-(2-phenylethyl)-1H-benzimidazol-2-yl]carbonyl}amino]piperidine-1,3-dicarboxylate (1.12 g) was dissolved in methanol, 2M aqueous sodium hydroxide solution (10 ml) was added dropwise at room temperature. The reaction mixture was stirred at 50° C. for 3 hr. The reaction mixture was adjusted to pH 7 with 1M hydrochloric acid, and extracted with ethyl acetate. The extract was washed with saturated brine, and dried over anhydrous sodium sulfate. The solvent was evaporated under reduced pressure to give the object product (1.07 g).

MS (ESI+, m/e) 549 (M+1)

In the same manner as in Reference Example 55, the following compound (Reference Example 173) was obtained.

Reference Example 173 tert-butyl(3R, 5S)-3-carbamoyl-5-[(2-methylpropyl){[1-(2-phenylethyl)-1H-benzimidazol-2-yl]carbonyl}amino]piperidine-1-carboxylate

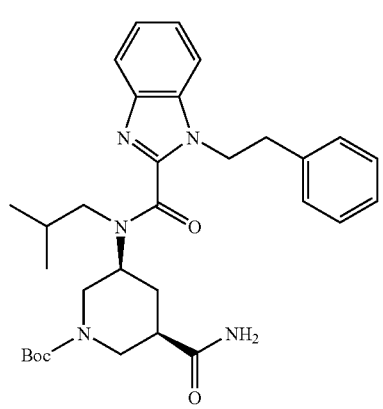

MS (ESI+, m/e) 548 (M+1)

In the same manner as in Example 12, the following compound (Example 91) was obtained.

Example 91

N-[(3S, 5R)-5-carbamoylpiperidin-3-yl]-N-(2-methylpropyl)-1-(2-phenylethyl)-1H-benzimidazole-2-carboxamide dihydrochloride

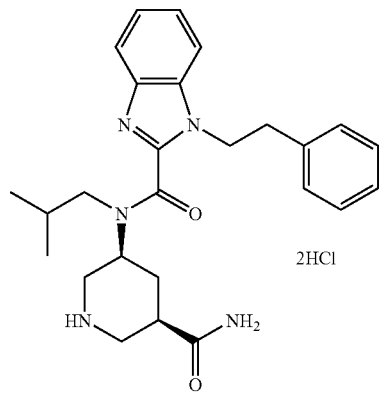 [SMILES: CC(C)CN(C(=O)c1nc2ccccc2n1CCc1ccccc1)[C@@H]1CNC[C@H](C(N)=O)C1 ; "2HCl"]

MS (ESI+, m/e) 448 (M+1)

In the same manner as in Reference Example 60, the following compound (Reference Example 174) was obtained.

Reference Example 174 tert-butyl(3R, 5S)-3-(hydroxymethyl)-5-[(2-methylpropyl){[1-(2-phenylethyl)-1H-benzimidazol-2-yl]carbonyl}amino]piperidine-1-carboxylate

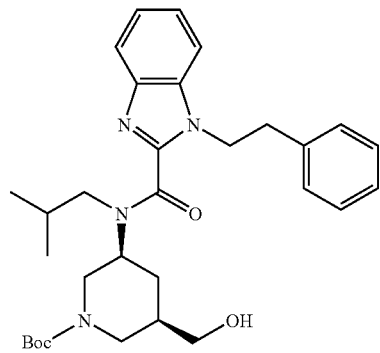 [SMILES: CC(C)CN(C(=O)c1nc2ccccc2n1CCc1ccccc1)[C@H]1C[C@@H](CO)CN(C(=O)OC(C)(C)C)C1]

MS (ESI+, m/e) 535 (M+1)

In the same manner as in Example 24, the following compound (Example 92) was obtained.

Example 92

N-[(3S, 5R)-5-(hydroxymethyl)piperidin-3-yl]-N-(2-methylpropyl)-1-(2-phenylethyl)-1H-benzimidazole-2-carboxamide dihydrochloride

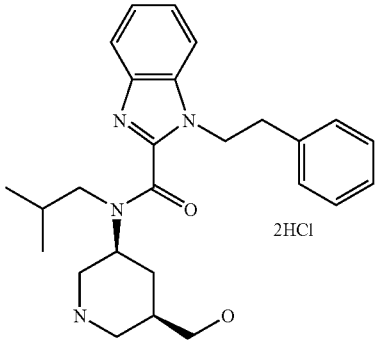 [SMILES: CC(C)CN(C(=O)c1nc2ccccc2n1CCc1ccccc1)[C@@H]1CNC[C@H](CO)C1 ; "2HCl"]

MS (ESI+, m/e) 435 (M+1)

Reference Example 175 tert-butyl(3S,5R)-3-{(2-methylpropyl)[(1-{2-[(methylsulfonyl)oxy]ethyl}-1H-benzimidazol-2-yl)carbonyl]amino}-5-(morpholin-4-ylcarbonyl)piperidine-1-carboxylate

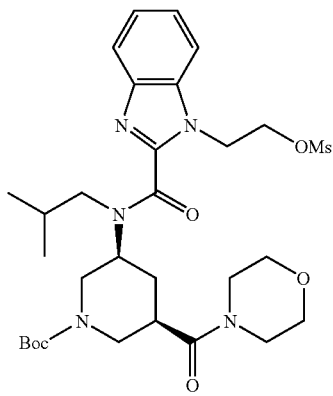 [SMILES: CC(C)CN(C(=O)c1nc2ccccc2n1CCOS(C)(=O)=O)[C@H]1C[C@@H](C(=O)N2CCOCC2)CN(C(=O)OC(C)(C)C)C1]

To a solution of tert-butyl(3S, 5R)-3-[[[1-(2-hydroxyethyl)-1H-benzimidazol-2-yl]carbonyl](2-methylpropyl)amino]-5-(morpholin-4-ylcarbonyl)piperidine-1-carboxylate (223 mg) and triethylamine (84 μl) in THF (5 ml) was added dropwise methanesulfonyl chloride (37 μl) at room temperature. The reaction mixture was stirred at room temperature for 3 hr, diluted with aqueous sodium bicarbonate, and extracted with ethyl acetate. The extract was washed with saturated brine, and dried over anhydrous sodium sulfate. The solvent was evaporated under reduced pressure to give the object product (288 mg).

MS (ESI+, m/e) 636 (M+1)

Reference Example 176 tert-butyl(3S, 5R)-3-[(2-methylpropyl)({1-[2-(1H-pyrazol-1-yl)ethyl]-1H-benzimidazol-2-yl}carbonyl)amino]-5-(morpholin-4-ylcarbonyl)piperidine-1-carboxylate

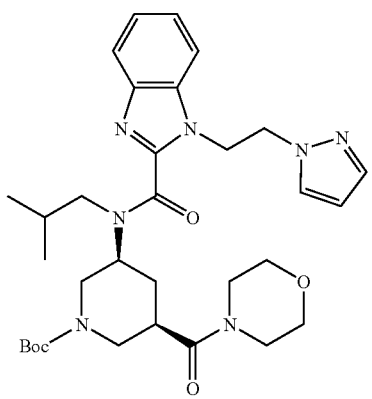 [SMILES: CC(C)CN(C(=O)c1nc2ccccc2n1CCn1cccn1)[C@H]1C[C@@H](C(=O)N2CCOCC2)CN(C(=O)OC(C)(C)C)C1]

To a solution of tert-butyl(3S, 5R)-3-{(2-methylpropyl)[(1-{2-[(methylsulfonyl)oxy]ethyl}-1H-benzimidazol-2-yl)carbonyl]amino}-5-(morpholin-4-ylcarbonyl)piperidine-1-carboxylate (127 mg) and pyrazole (41 mg) in N,N-dimethylacetamide (3 ml) was added cesium carbonate (326 mg), and the mixture was stirred at 60° C. for 3 days. The reaction mixture was diluted with water, and extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (72 mg).

MS (ESI+, m/e) 608 (M+1)

In the same manner as in Reference Example 176, the following compound (Reference Example 177) was obtained.

Reference Example 177 tert-butyl(3S, 5R)-3-[({1-[2-(1H-imidazol-1-yl)ethyl]-1H-benzimidazol-2-yl}carbonyl)(2-methylpropyl)amino]-5-(morpholin-4-ylcarbonyl)piperidine-1-carboxylate

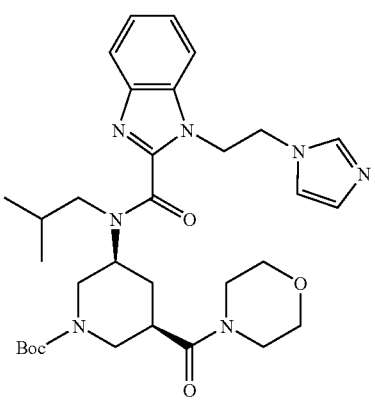 [SMILES: CC(C)CN(C(=O)c1nc2ccccc2n1CCn1ccnc1)[C@H]1C[C@@H](C(=O)N2CCOCC2)CN(C(=O)OC(C)(C)C)C1]

MS (ESI+, m/e) 608 (M+1)

In the same manner as in Example 12, the following compounds (Examples 93-94) were obtained.

Example 93

N-(2-methylpropyl)-N-[(3S, 5R)-5-(morpholin-4-ylcarbonyl)piperidin-3-yl]-1-[2-(1H-pyrazol-1-yl)ethyl]-1H-benzimidazole-2-carboxamide dihydrochloride

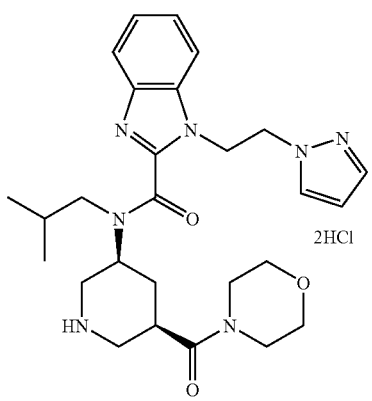 [SMILES: CC(C)CN(C(=O)c1nc2ccccc2n1CCn1cccn1)[C@@H]1CNC[C@H](C(=O)N2CCOCC2)C1 ; "2HCl"]

MS (ESI+, m/e) 508 (M+1)

Example 94

1-[2-(1H-imidazol-1-yl)ethyl]-N-(2-methylpropyl)-N-[(3S, 5R)-5-(morpholin-4-ylcarbonyl)piperidin-3-yl]-1H-benzimidazole-2-carboxamide trihydrochloride

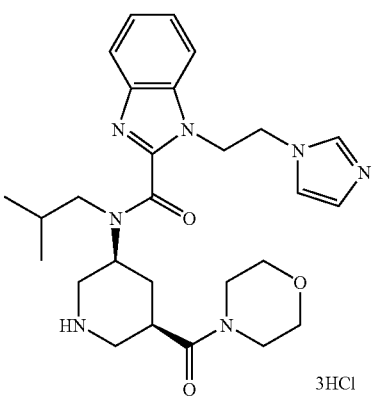 [SMILES: CC(C)CN(C(=O)c1nc2ccccc2n1CCn1ccnc1)[C@@H]1CNC[C@H](C(=O)N2CCOCC2)C1 ; "3HCl"]

MS (ESI+, m/e) 508 (M+1)

In the same manner as in Example 89, the following compound (Example 95) was obtained.

Example 95

1-(3-cyclopropylpropyl)-N-(2-methylpropyl)-N-[(3S, 5R)-5-(morpholin-4-ylcarbonyl)piperidin-3-yl]-1H-benzimidazole-2-carboxamide dihydrochloride

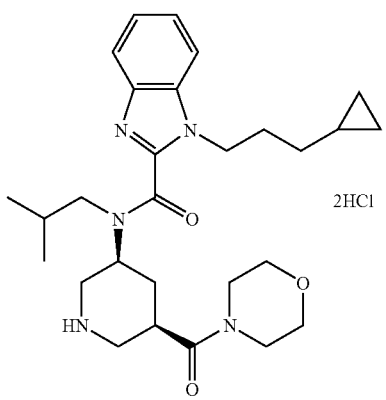 [SMILES: CC(C)CN(C(=O)c1nc2ccccc2n1CCCC1CC1)[C@@H]1CNC[C@H](C(=O)N2CCOCC2)C1 ; "2HCl"]

MS (ESI+, m/e) 496 (M+1)

Example 96

1-(3-hydroxypropyl)-N-(2-methylpropyl)-N-[(3S, 5R)-5-(morpholin-4-ylcarbonyl)piperidin-3-yl]-1H-benzimidazole-2-carboxamide dihydrochloride

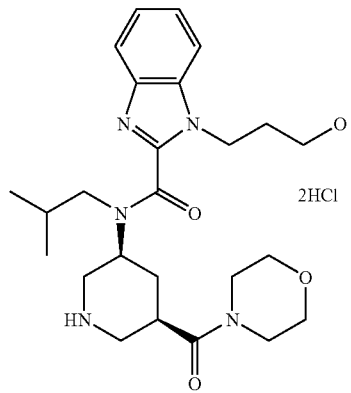 [SMILES: CC(C)CN(C(=O)c1nc2ccccc2n1CCCO)[C@@H]1CNC[C@H](C(=O)N2CCOCC2)C1 ; "2HCl"]

To a mixed solution of tert-butyl(3S, 5R)-3-[(1H-benzimidazol-2-ylcarbonyl)(2-methylpropyl)amino]-5-(morpholin-4-ylcarbonyl)piperidine-1-carboxylate (103 mg), propane-1,3-diol (152 mg) and triphenylphosphine (105 mg) in toluene (5 ml) and THF (5 ml) was added diisopropyl azodicarboxylate (202 μl) at room temperature, and the mixture was stirred at the same temperature for 15 hr. The reaction mixture was diluted with aqueous sodium bicarbonate, and extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate was concentrated under reduced pressure to give tert-butyl(3S, 5R)-3-[{[1-(3-hydroxypropyl)-1H-benzimidazol-2-yl]carbonyl}(2-methylpropyl)amino]-5-(morpholin-4-ylcarbonyl)piperidine-1-carboxylate. The obtained tert-butyl(3S, 5R)-3-[{[1-(3-hydroxypropyl)-1H-benzimidazol-2-yl]carbonyl}(2-methylpropyl)amino]-5-(morpholin-4-ylcarbonyl)piperidine-1-carboxylate was dissolved in 10-20% hydrogen chloride-methanol (3 ml), and the mixture was stirred at room temperature for 3 hr. The reaction mixture was concentrated to give the object product (22 mg).

MS (ESI+, m/e) 472 (M+1)

Reference Example 178 tert-butyl(3S, 5R)-3-[{[1-(3-ethoxy-3-oxopropyl)-1H-benzimidazol-2-yl]carbonyl}(2-methylpropyl)amino]-5-(morpholin-4-ylcarbonyl)piperidine-1-carboxylate

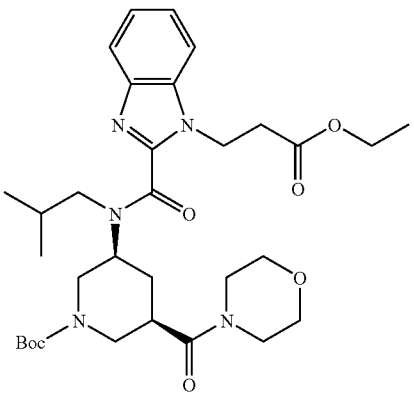 [SMILES: CCOC(=O)CCn1c(C(=O)N(CC(C)C)[C@H]2C[C@@H](C(=O)N3CCOCC3)CN(C(=O)OC(C)(C)C)C2)nc2ccccc21]

To a solution of tert-butyl(3S, 5R)-3-[(1H-benzimidazol-2-ylcarbonyl)(2-methylpropyl)amino]-5-(morpholin-4-ylcarbonyl)piperidine-1-carboxylate (257 mg) and ethyl 3-bromopropanoate (181 mg) in N,N-dimethylacetamide (5 ml) was added cesium carbonate (489 mg), and the mixture was stirred at 70° C. for 15 hr. Ethyl 3-bromopropanoate (181 mg) was added to the reaction mixture, and the mixture was further stirred at 70° C. for 5 hr. The reaction mixture was cooled to room temperature, diluted with water, and extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (6:4) was concentrated under reduced pressure to give the object product (225 mg).

MS (ESI+, m/e) 614 (M+1)

Reference Example 179 tert-butyl(3S, 5R)-3-[({1-[3-(2-acetylhydrazino)-3-oxopropyl]-1H-benzimidazol-2-yl}carbonyl)(2-methylpropyl)amino]-5-(morpholin-4-ylcarbonyl)piperidine-1-carboxylate

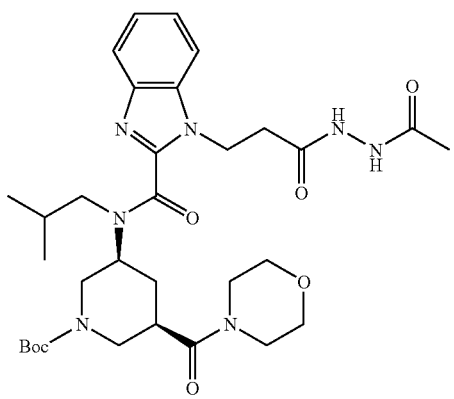 [SMILES: CC(=O)NNC(=O)CCn1c(C(=O)N(CC(C)C)[C@H]2C[C@@H](C(=O)N3CCOCC3)CN(C(=O)OC(C)(C)C)C2)nc2ccccc21]

tert-Butyl(3S, 5R)-3-[{[1-(3-ethoxy-3-oxopropyl)-1H-benzimidazol-2-yl]carbonyl}(2-methylpropyl)amino]-5-(morpholin-4-ylcarbonyl)piperidine-1-carboxylate (307 mg) was dissolved in ethanol (10 ml), hydrazine monohydrate (243 μl) was added and the mixture was heated under reflux for 6 hr with stirring. The reaction mixture was concentrated, ethyl acetate was added to the residue, and the mixture was washed with saturated brine, and dried over anhydrous sodium sulfate. The solvent was evaporated under reduced pressure. The residue was dissolved in THF (5 ml), and tri-ethylamine (209 μl) was added. The reaction mixture was cooled to 0° C., acetic anhydride (71 μl) was added dropwise and the mixture was stirred at room temperature for 15 hr. The reaction mixture was diluted with aqueous sodium bicarbonate, and extracted with ethyl acetate. The extract was washed with saturated brine, and dried over anhydrous sodium sulfate. The solvent was evaporated under reduced pressure to give the object product (292 mg).

MS (ESI+, m/e) 642 (M+1)

Reference Example 180 tert-butyl(3S, 5R)-3-[({1-[2-(5-methyl-1,3,4-oxadia-zol-2-yl)ethyl]-1H-benzimidazol-2-yl}carbonyl)(2-methylpropyl)amino]-5-(morpholin-4-ylcarbonyl)piperidine-1-carboxylate

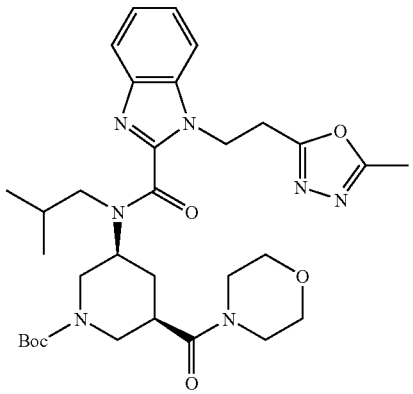 [SMILES: Cc1nnc(CCn2c(C(=O)N(CC(C)C)[C@H]3C[C@@H](C(=O)N4CCOCC4)CN(C(=O)OC(C)(C)C)C3)nc3ccccc32)o1]

tert-Butyl(3S, 5R)-3-[({1-[3-(2-acetylhydrazino)-3-oxo-propyl]-1H-benzimidazol-2-yl}carbonyl)(2-methylpropyl)amino]-5-(morpholin-4-ylcarbonyl)piperidine-1-carboxylate (292 mg) was dissolved in pyridine (5 ml), and trifluoromethanesulfonic anhydride (230 μl) was added dropwise at room temperature. The reaction mixture was stirred at room temperature for 15 hr, and concentrated. The residue was diluted with 10% aqueous citric acid solution, and the mixture was extracted with ethyl acetate. The extract was washed with aqueous sodium bicarbonate and saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (117 mg).

MS (ESI+, m/e) 624 (M+1)

In the same manner as in Example 23, the following compound (Example 97) was obtained.

Example 97

1-[2-(5-methyl-1,3,4-oxadiazol-2-yl)ethyl]-N-(2-methylpropyl)-N-[(3S, 5R)-5-(morpholin-4-ylcarbonyl)piperidin-3-yl]-1H-benzimidazole-2-carboxamide

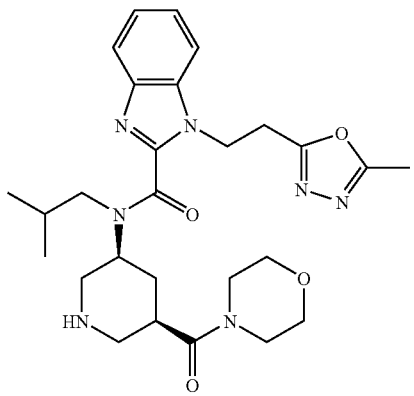 [SMILES: Cc1nnc(CCn2c(C(=O)N(CC(C)C)[C@@H]3CNC[C@H](C(=O)N4CCOCC4)C3)nc3ccccc32)o1]

MS (ESI+, m/e) 524 (M+1)

Reference Example 181

3-(2-{[(3S, 5R)-1-(tert-butoxycarbonyl)-5-(morpholin-4-ylcarbonyl)piperidin-3-yl](2-methylpropyl)carbamoyl}-1H-benzimidazol-1-yl)propanoic acid

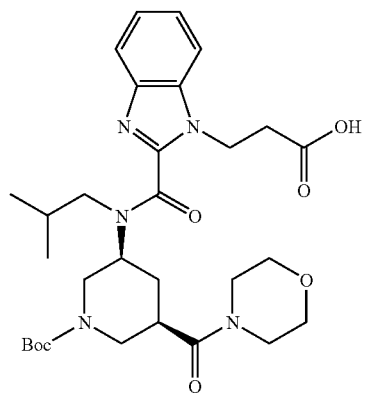 [SMILES: CC(C)CN(C(=O)c1nc2ccccc2n1CCC(=O)O)[C@H]1C[C@@H](C(=O)N2CCOCC2)CN(C(=O)OC(C)(C)C)C1]

To a solution of tert-butyl(3S, 5R)-3-[{[1-(3-ethoxy-3-oxopropyl)-1H-benzimidazol-2-yl]carbonyl}(2-methylpropyl)amino]-5-(morpholin-4-ylcarbonyl)piperidine-1-carboxylate (225 mg) in ethanol (5 ml) was added 2M aqueous sodium hydroxide solution, and the mixture was stirred at room temperature for 3 days. The reaction mixture was adjusted to pH 7 with 1M hydrochloric acid, and extracted with ethyl acetate. The extract was washed with saturated brine, and dried over anhydrous sodium sulfate. The solvent was evaporated under reduced pressure to give the object product (215 mg).

MS (ESI+, m/e) 586 (M+1)

Reference Example 182 tert-butyl(3S, 5R)-3-[{[1-(3-amino-3-oxopropyl)-1H-benzimidazol-2-yl]carbonyl}(2-methylpropyl)amino]-5-(morpholin-4-ylcarbonyl)piperidine-1-carboxylate

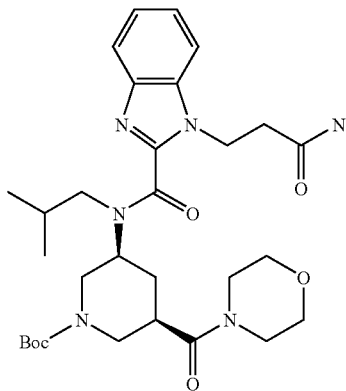 [SMILES: CC(C)CN(C(=O)c1nc2ccccc2n1CCC(N)=O)[C@H]1C[C@@H](C(=O)N2CCOCC2)CN(C(=O)OC(C)(C)C)C1]

3-(2-{[(3S, 5R)-1-(tert-Butoxycarbonyl)-5-(morpholin-4-ylcarbonyl)piperidin-3-yl](2-methylpropyl)carbamoyl}-1H-benzimidazol-1-yl)propanoic acid (215 mg) and 1H-1,2,3-benzotriazol-1-ol ammonium salt (84 mg) were dissolved in DMF (5 ml), WSC.HCl (142 mg) was added and the mixture was stirred at room temperature for 15 hr. The reaction mixture was concentrated under reduced pressure, and the residue was diluted with 10% aqueous citric acid solution and extracted with ethyl acetate. The extract was washed with aqueous sodium bicarbonate and saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (199 mg).
MS (ESI+, m/e) 585 (M+1)

Reference Example 183 tert-butyl(3S, 5R)-3-[{[1-(2-cyanoethyl)-1H-benzimidazol-2-yl]carbonyl}(2-methylpropyl)amino]-5-(morpholin-4-ylcarbonyl)piperidine-1-carboxylate

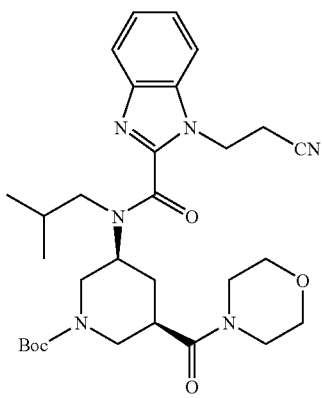 [SMILES: CC(C)CN(C(=O)c1nc2ccccc2n1CCC#N)[C@H]1C[C@@H](C(=O)N2CCOCC2)CN(C(=O)OC(C)(C)C)C1]

tert-Butyl(3S, 5R)-3-[{[1-(3-amino-3-oxopropyl)-1H-benzimidazol-2-yl]carbonyl}(2-methylpropyl)amino]-5-(morpholin-4-ylcarbonyl)piperidine-1-carboxylate (233 mg) was dissolved in pyridine (5 ml), trifluoroacetic anhydride (116 µl) was added at 0° C. and the mixture was stirred at room temperature for 2 hr. The reaction mixture was concentrated under reduced pressure, and diluted with ethyl acetate. 1M Hydrochloric acid was added, and the mixture was extracted with ethyl acetate. The extract was washed with aqueous sodium bicarbonate and saturated brine, dried over anhydrous magnesium sulfate, and concentrated under reduced pressure. The residue was subjected to silica gel chromatography, and a fraction eluted with ethyl acetate-hexane (7:3) was concentrated under reduced pressure to give the object product (197 mg).
MS (ESI+, m/e) 567 (M+1)

Example 98

N-(2-methylpropyl)-N-[(3S, 5R)-5-(morpholin-4-ylcarbonyl)piperidin-3-yl]-1-[2-(1,2,4-oxadiazol-3-yl)ethyl]-1H-benzimidazole-2-carboxamide dihydrochloride

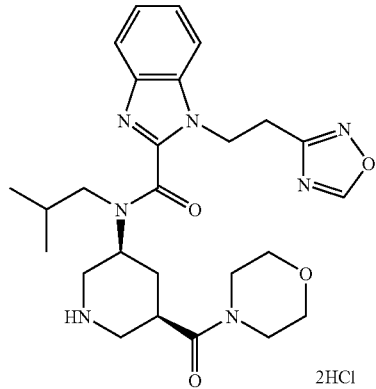 [SMILES: CC(C)CN(C(=O)c1nc2ccccc2n1CCc1ncon1)[C@@H]1CNC[C@H](C(=O)N2CCOCC2)C1 ; "2HCl"]

Hydroxylamine hydrochloride (125 mg) was dissolved in dimethyl sulfoxide (5 ml), sodium hydrogen carbonate (463 mg) was added and the mixture was stirred at 50° C. for 1 hr. A solution of tert-butyl(3S, 5R)-3-[{[1-(2-cyanoethyl)-1H-benzimidazol-2-yl]carbonyl}(2-methylpropyl)amino]-5-(morpholin-4-ylcarbonyl)piperidine-1-carboxylate (100 mg) in dimethyl sulfoxide (5 ml) was added to the reaction mixture, and the mixture was stirred at 90° C. for 3 hr. The reaction mixture was allowed to cool to room temperature, diluted with water, and extracted with ethyl acetate. The extract was washed with saturated brine, dried over anhydrous magnesium sulfate, and concentrated under reduced pressure. The residue was dissolved in trimethyl orthoformate (5 ml) and the mixture was stirred at 100° C. for 5 hr. The reaction mixture was concentrated under reduced pressure, and the residue was subjected to basic silica gel chromatography, and a fraction eluted with ethyl acetate was concentrated under reduced pressure to give tert-butyl(3S, 5R)-3-[(2-methylpropyl)({1-[2-(1,2,4-oxadiazol-3-yl)ethyl]-1H-benzimidazol-2-yl}carbonyl)amino]-5-(morpholin-4-ylcarbonyl)piperidine-1-carboxylate. The obtained tert-butyl (3S, 5R)-3-[(2-methylpropyl)({1-[2-(1,2,4-oxadiazol-3-yl)ethyl]-1H-benzimidazol-2-yl}carbonyl)amino]-5-(morpholin-4-ylcarbonyl)piperidine-1-carboxylate was dissolved in 4M hydrogen chloride-ethyl acetate (3 ml), and the mixture was stirred at room temperature for 2 hr. The reaction mixture was concentrated, and the residue was subjected to reversed-phase preparative HPLC and the eluted fraction was concentrated under reduced pressure. The residue was diluted with aqueous sodium bicarbonate, and the mixture was extracted with ethyl acetate. The extract was washed with saturated brine, and dried over anhydrous sodium sulfate. 4M Hydrogen chloride-ethyl acetate (1 ml) was added and the mixture was stirred for 5 min. The solvent was evaporated under reduced pressure to give the object product (35 mg).

MS (ESI+, m/e) 510 (M+1)

Reference Example 184 tert-butyl(3S, 5R)-3-[({1-[2-(ethenyloxy)ethyl]-1H-benzimidazol-2-yl}carbonyl)(2-methylpropyl)amino]-5-(morpholin-4-ylcarbonyl)piperidine-1-carboxylate

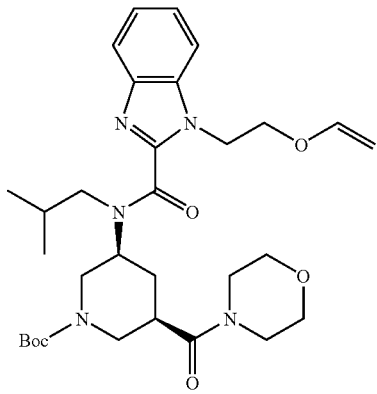 [SMILES: C=COCCn1c(C(=O)N(CC(C)C)[C@H]2C[C@@H](C(=O)N3CCOCC3)CN(C(=O)OC(C)(C)C)C2)nc2ccccc21]

To a solution of tert-butyl(3S, 5R)-3-{(1H-benzimidazol-2-ylcarbonyl)(2-methylpropyl)amino}-5-(morpholin-4-ylcarbonyl)piperidine-1-carboxylate (308 mg), (2-chloroethoxy)ethene (192 mg) and potassium iodide (5 mg) in N,N-dimethylacetamide (5 ml) was added cesium carbonate (586 mg), and the mixture was stirred at 60° C. for 15 hr. The reaction mixture was cooled to room temperature, diluted with water, and extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (6:4) was concentrated under reduced pressure to give the object product (323 mg).

MS (ESI+, m/e) 584 (M+1)

Example 99

1-[2-(cyclopropyloxy)ethyl]-N-(2-methylpropyl)-N-[(3S, 5R)-5-(morpholin-4-ylcarbonyl)piperidin-3-yl]-1H-benzimidazole-2-carboxamide dihydrochloride

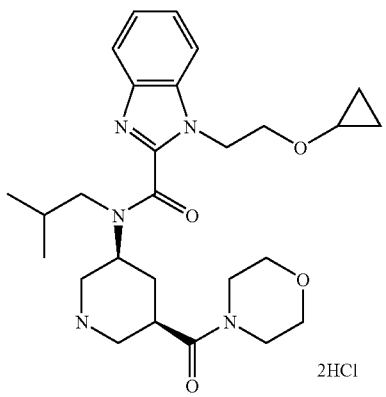 [SMILES: CC(C)CN(C(=O)c1nc2ccccc2n1CCOC1CC1)[C@@H]1CNC[C@H](C(=O)N2CCOCC2)C1 ; "2HCl"]

To a solution of tert-butyl(3S, 5R)-3-[({1-[2-(ethenyloxy)ethyl]-1H-benzimidazol-2-yl}carbonyl)(2-methylpropyl)amino]-5-(morpholin-4-ylcarbonyl)piperidine-1-carboxylate (323 mg) and 1M diethylzinc-hexane solution (2.5 ml) in dichloromethane (5 ml) was added dropwise diiodomethane (443 μl) at room temperature over 5 min, and the mixture was stirred at room temperature for 3 hr. The reaction mixture was diluted with 1M hydrochloric acid, and the mixture was extracted with ethyl acetate. The extract was washed with saturated brine, and dried over anhydrous sodium sulfate. The solvent was evaporated under reduced pressure. The residue was dissolved in methanol (5 ml), 4M hydrogen chloride-ethyl acetate (5 ml) was added and the mixture was stirred at room temperature for 5 hr. The reaction mixture was concentrated, and the residue was subjected to reversed-phase preparative HPLC and the eluted fraction was concentrated under reduced pressure. The residue was diluted with aqueous sodium bicarbonate, and the mixture was extracted with ethyl acetate. The extract was washed with saturated brine, and dried over anhydrous sodium sulfate. 4M Hydrogen chloride-ethyl acetate (1 ml) was added and the mixture was stirred for 5 min. The solvent was evaporated under reduced pressure to give the object product (35 mg).

MS (ESI+, m/e) 498 (M+1)

Reference Example 185 tert-butyl(3S, 5R)-3-[{[1-(5-hydroxypentyl)-1H-benzimidazol-2-yl]carbonyl}(2-methylpropyl)amino]-5-(morpholin-4-ylcarbonyl)piperidine-1-carboxylate

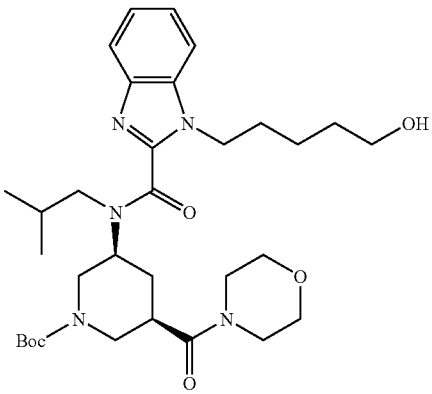 [SMILES: CC(C)CN(C(=O)c1nc2ccccc2n1CCCCCO)[C@H]1C[C@@H](C(=O)N2CCOCC2)CN(C(=O)OC(C)(C)C)C1]

To a mixed solution of tert-butyl(3S, 5R)-3-[(1H-benzimidazol-2-ylcarbonyl)(2-methylpropyl)amino]-5-(morpholin-4-ylcarbonyl)piperidine-1-carboxylate (308 mg), pentane-1,5-diol (1.25 g) and triphenylphosphine (472 mg) in toluene (10 ml)-THF (10 ml) was added diisopropyl azodicarboxylate (910 μl) at room temperature, and the mixture was stirred at the same temperature for 15 hr. The reaction mixture was diluted with aqueous sodium bicarbonate, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (250 mg).

MS (ESI+, m/e) 600 (M+1)

Example 100

1-(5-hydroxypentyl)-N-(2-methylpropyl)-N-[(3S,5R)-5-(morpholin-4-ylcarbonyl)piperidin-3-yl]-1H-benzimidazole-2-carboxamide dihydrochloride

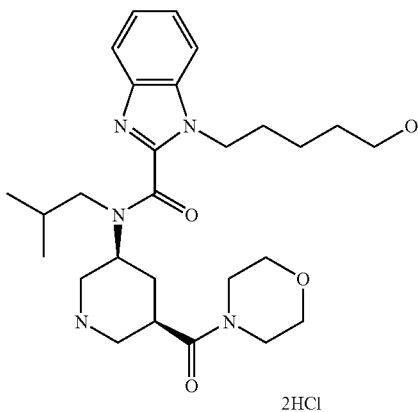 [SMILES: CC(C)CN(C(=O)c1nc2ccccc2n1CCCCCO)[C@@H]1CNC[C@H](C(=O)N2CCOCC2)C1 ; "2HCl"]

2HCl tert-Butyl(3S, 5R)-3-[{[1-(5-hydroxypentyl)-1H-benzimidazol-2-yl]carbonyl}(2-methylpropyl)amino]-5-(morpholin-4-ylcarbonyl)piperidine-1-carboxylate (100 mg) was dissolved in 10-20% hydrogen chloride-methanol (5 ml), and the mixture was stirred at room temperature for 15 hr. The reaction mixture was concentrated, and the residue was subjected to reversed-phase preparative HPLC and the eluted fraction was concentrated under reduced pressure. The residue was diluted with aqueous sodium bicarbonate, and the mixture was extracted with ethyl acetate. The extract was washed with saturated brine, and dried over anhydrous sodium sulfate. 10-20% Hydrogen chloride-methanol (3 ml) was added and the mixture was stirred for 5 min. The solvent was evaporated under reduced pressure to give the object product (34 mg).

MS (ESI+, m/e) 500 (M+1)

Reference Example 186 tert-butyl(3S, 5R)-3-[{[1-(5-methoxypentyl)-1H-benzimidazol-2-yl]carbonyl}(2-methylpropyl)amino]-5-(morpholin-4-ylcarbonyl)piperidine-1-carboxylate

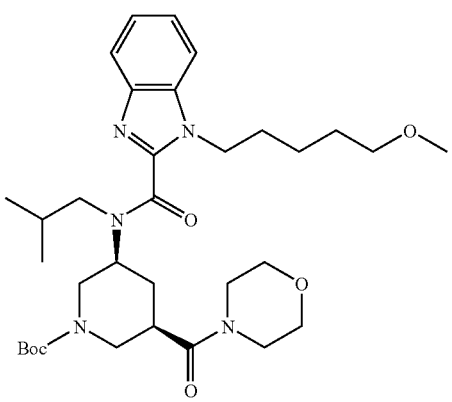 [SMILES: COCCCCCn1c(C(=O)N(CC(C)C)[C@H]2C[C@@H](C(=O)N3CCOCC3)CN(C(=O)OC(C)(C)C)C2)nc2ccccc21]

To a solution of tert-butyl(3S, 5R)-3-[{[1-(5-hydroxypentyl)-1H-benzimidazol-2-yl]carbonyl}(2-methylpropyl)amino]-5-(morpholin-4-ylcarbonyl)piperidine-1-carboxylate (150 mg) and triethylamine (70 µl) in tetrahydrofuran (5 ml) was added methanesulfonyl chloride (725 µl) at 0° C., and the mixture was stirred at room temperature for 2 hr. Aqueous sodium bicarbonate was added to the reaction mixture, and the mixture was extracted with ethyl acetate. The extract was washed with saturated brine, dried over anhydrous magnesium sulfate, and concentrated under reduced pressure. The residue was dissolved in methanol (5 ml), 28% sodium methoxide-methanol solution (482 mg) was added at room temperature and the mixture was stirred at 60° C. for 3 days. The reaction mixture was diluted with aqueous sodium bicarbonate, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (123 mg).

MS (ESI+, m/e) 614 (M+1)

Example 101

1-(5-methoxypentyl)-N-(2-methylpropyl)-N-[(3S,5R)-5-(morpholin-4-ylcarbonyl)piperidin-3-yl]-1H-benzimidazole-2-carboxamide dihydrochloride

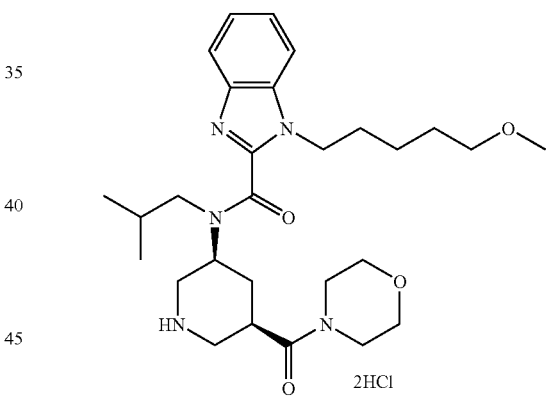

2HCl tert-Butyl(3S, 5R)-3-[{[1-(5-methoxypentyl)-1H-benzimidazol-2-yl]carbonyl}(2-methylpropyl)amino]-5-(morpholin-4-ylcarbonyl)piperidine-1-carboxylate (123 mg) was dissolved in 4M hydrogen chloride-ethyl acetate (5 ml), and the mixture was stirred at room temperature for 3 hr. The reaction mixture was concentrated, and the residue was subjected to reversed-phase preparative HPLC and the eluted fraction was concentrated under reduced pressure. The residue was diluted with aqueous sodium bicarbonate, and the mixture was extracted with ethyl acetate. The extract was washed with saturated brine, and dried over anhydrous sodium sulfate. 4M Hydrogen chloride-ethyl acetate (1 ml) was added and the mixture was stirred for 5 min. The solvent was evaporated under reduced pressure to give the object product (76 mg).

MS (ESI+, m/e) 514 (M+1)

In the same manner as in Reference Example 168, the following compound (Reference Example 187) was obtained.

Reference Example 187 tert-butyl(3S, 5R)-3-[{[1-(4-ethoxy-4-oxobutyl)-1H-benzimidazol-2-yl]carbonyl}(2-methylpropyl)amino]-5-(morpholin-4-ylcarbonyl)piperidine-1-carboxylate

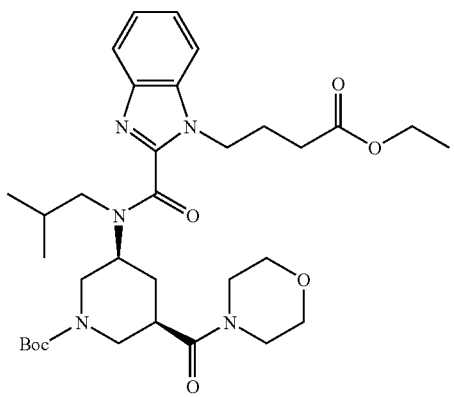 [SMILES: CCOC(=O)CCCn1c(C(=O)N(CC(C)C)[C@H]2C[C@@H](C(=O)N3CCOCC3)CN(C(=O)OC(C)(C)C)C2)nc2ccccc21]

MS (ESI+, m/e) 628 (M+1)

In the same manner as in Reference Example 169, the following compound (Reference Example 188) was obtained.

Reference Example 188 tert-butyl(3S, 5R)-3-[{[1-(4-hydroxybutyl)-1H-benzimidazol-2-yl]carbonyl}(2-methylpropyl)amino]-5-(morpholin-4-ylcarbonyl)piperidine-1-carboxylate

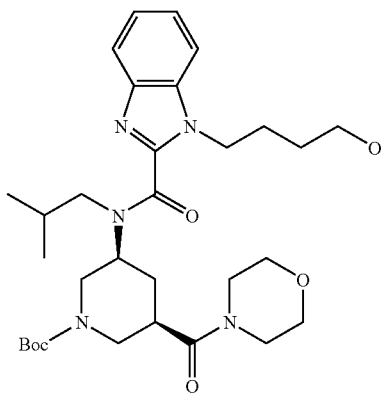 [SMILES: CC(C)CN(C(=O)c1nc2ccccc2n1CCCCO)[C@H]1C[C@@H](C(=O)N2CCOCC2)CN(C(=O)OC(C)(C)C)C1]

MS (ESI+, m/e) 586 (M+1)

In the same manner as in Example 100, the following compound (Example 102) was obtained.

Example 102

1-(4-hydroxybutyl)-N-(2-methylpropyl)-N-[(3S, 5R)-5-(morpholin-4-ylcarbonyl)piperidin-3-yl]-1H-benzimidazole-2-carboxamide dihydrochloride

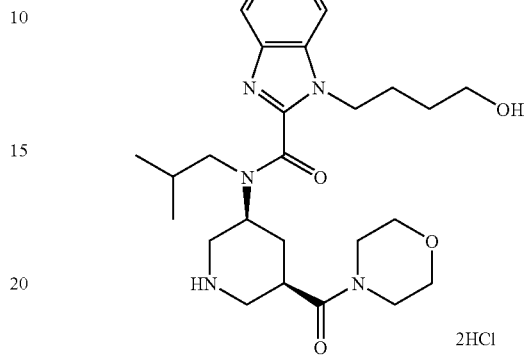

MS (ESI+, m/e) 486 (M+1)

Example 103

1-(4-methoxybutyl)-N-[(3S, 5R)-5-(3-methyl-1,2,4-oxadiazol-5-yl)piperidin-3-yl]-N-(2-methylpropyl)-1H-benzimidazole-2-carboxamide dihydrochloride

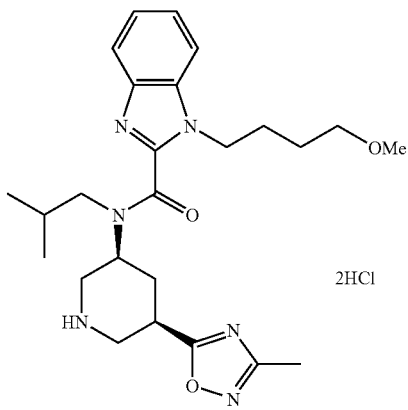 [SMILES: COCCCCn1c(C(=O)N(CC(C)C)[C@@H]2CNC[C@H](c3nc(C)no3)C2)nc2ccccc21 ; "2HCl"]

(3R, 5S)-1-(tert-Butoxycarbonyl)-5-[{[1-(4-methoxybutyl)-1H-benzimidazol-2-yl]carbonyl}(2-methylpropyl)amino]piperidine-3-carboxylic acid (265 mg), N-hydroxy acetamidine (56 mg), 1H-benzotriazol-1-ol (95 mg) and N,N-diisopropylethylamine (259 μl)) were dissolved in DMF (10 ml), WSC.HCl (144 mg) was added and the mixture was stirred at room temperature for 15 hr. The reaction mixture was concentrated under reduced pressure, and the mixture was extracted with ethyl acetate. The extract was washed with saturated brine, and dried over anhydrous magnesium sulfate. The solvent was evaporated under reduced pressure. The residue was dissolved in toluene (15 ml), and the mixture was refluxed under heating for 15 hr. The reaction mixture was cooled to room temperature, and concentrated under reduced pressure. The residue was subjected to silica gel column chromatography, and a fraction eluted with ethyl acetate-hexane (1:1) was concentrated under reduced pressure to give tert-butyl(3S, 5R)-3-[{[1-(4-methoxybutyl)-1H-benzimidazol-2-yl]carbonyl}(2-methylpropyl)amino]-5-(3-methyl-1,2,4-oxadiazol-5-yl)piperidine-1-carboxylate (324 mg). The obtained tert-butyl(3S, 5R)-3-[{[1-(4-methoxybutyl)-1H-benzimidazol-2-yl]carbonyl}(2-methylpropyl)amino]-5-(3-methyl-1,2,4-oxadiazol-5-yl)piperidine-1-carboxylate was dissolved in 4M hydrogen chloride-ethyl acetate (5 ml), and the mixture was stirred at room temperature for 3 hr. The reaction mixture was concentrated, and the residue was diluted with aqueous sodium bicarbonate, and extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate was concentrated under reduced pressure. The residue was dissolved in methanol (3 ml), 4M Hydrogen chloride-ethyl acetate (1 ml) was added and the mixture was stirred for 5 min. The solvent was evaporated under reduced pressure to give the object product (74 mg).

MS (ESI+, m/e) 469 (M+1)

In the same manner as in Example 12, the following compound (Example 104) was obtained.

Example 104

N-(2-methylpropyl)-N-[(3S, 5R)-5-(morpholin-4-ylcarbonyl)piperidin-3-yl]-1H-benzimidazole-2-carboxamide dihydrochloride

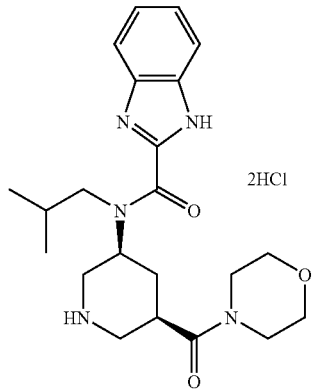 [SMILES: CC(C)CN(C(=O)c1nc2ccccc2[nH]1)[C@@H]1CNC[C@H](C(=O)N2CCOCC2)C1 ; "2HCl"]

MS (ESI+, m/e) 414 (M+1)

Reference Example 189 tert-butyl(3S, 5R)-3-{[(1-methyl-1H-benzimidazol-2-yl)carbonyl](2-methylpropyl)amino}-5-(morpholin-4-ylcarbonyl)piperidine-1-carboxylate

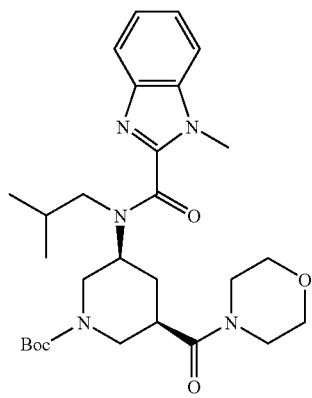 [SMILES: CC(C)CN(C(=O)c1nc2ccccc2n1C)[C@H]1C[C@@H](C(=O)N2CCOCC2)CN(C(=O)OC(C)(C)C)C1]

tert-Butyl(3S, 5R)-3-{(1H-benzimidazol-2-ylcarbonyl)(2-methylpropyl)amino}-5-(morpholin-4-ylcarbonyl)piperidine-1-carboxylate (205 mg) was dissolved in dimethylformamide (5 ml), methyl iodide (75 µl) and cesium carbonate (391 mg) were added and the mixture was stirred at room temperature for 2 hr. The reaction mixture was concentrated under reduced pressure, diluted with aqueous sodium bicarbonate, and the mixture was extracted with ethyl acetate. The extract was washed with saturated brine, dried over anhydrous magnesium sulfate, and concentrated under reduced pressure. The residue was subjected to silica gel chromatography, and a fraction eluted with ethyl acetate-hexane (6:4) was concentrated under reduced pressure to give the object product (184 mg).

MS (ESI+, m/e) 528 (M+1)

In the same manner as in Example 12, the following compound (Example 105) was obtained.

Example 105

1-methyl-N-(2-methylpropyl)-N-[(3S, 5R)-5-(morpholin-4-ylcarbonyl)piperidin-3-yl]-1H-benzimidazole-2-carboxamide dihydrochloride

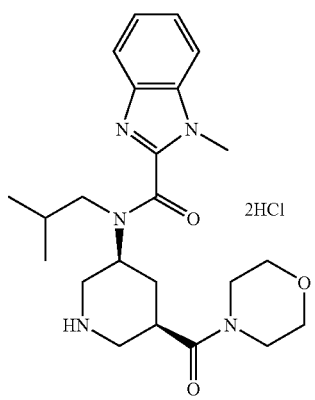 [SMILES: CC(C)CN(C(=O)c1nc2ccccc2n1C)[C@@H]1CNC[C@H](C(=O)N2CCOCC2)C1 ; "2HCl"]

MS (ESI+, m/e) 428 (M+1)

Reference Example 190 tert-butyl(3S, 5R)-3-[({1-[2-(3-methyl-1,2,4-oxadiazol-5-yl)ethyl]-1H-benzimidazol-2-yl}carbonyl)(2-methylpropyl)amino]-5-(morpholin-4-ylcarbonyl)piperidine-1-carboxylate

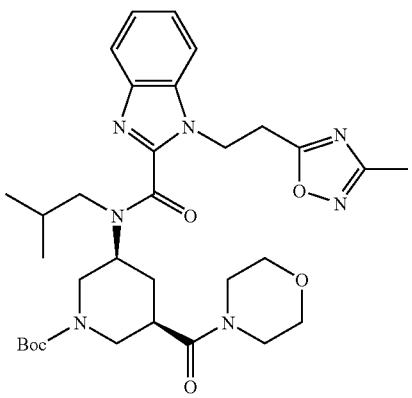 [SMILES: Cc1noc(CCn2c(C(=O)N(CC(C)C)[C@H]3C[C@@H](C(=O)N4CCOCC4)CN(C(=O)OC(C)(C)C)C3)nc3ccccc32)n1]

251

To a solution of tert-butyl(3S, 5R)-3-[{[1-(3-ethoxy-3-oxopropyl)-1H-benzimidazol-2-yl]carbonyl}(2-methylpropyl)amino]-5-(morpholin-4-ylcarbonyl)piperidine-1-carboxylate (260 mg) in ethanol (5 ml) was added 2M aqueous sodium hydroxide solution (1.06 ml), and the mixture was stirred at room temperature for 3 days. The reaction mixture was adjusted to pH 7 with 1M hydrochloric acid, and extracted with ethyl acetate. The extract was washed with saturated brine, and dried over anhydrous sodium sulfate. The solvent was evaporated under reduced pressure. The residue, N-hydroxy acetamidine (47 mg), 1H-benzotriazol-1-ol (79 mg) and N,N-diisopropylethylamine (217 μl) were dissolved in DMF (5 ml), WSC.HCl (121 mg) was added and the mixture was stirred at 60° C. for 2 hr. The reaction mixture was concentrated under reduced pressure, and the residue was diluted with aqueous sodium bicarbonate and extracted with ethyl acetate. The extract was washed with saturated brine, and dried over anhydrous magnesium sulfate. The solvent was evaporated under reduced pressure. The residue was dissolved in toluene (15 ml), and the mixture was refluxed under heating for 15 hr. The reaction mixture was cooled to room temperature, and concentrated under reduced pressure. The residue was subjected to basic silica gel column chromatography, and a fraction eluted with ethyl acetate-hexane (7:3) was concentrated under reduced pressure to give the object product (191 mg).

MS (ESI+, m/e) 624 (M+1)

In the same manner as in Example 12, the following compound (Example 106) was obtained.

Example 106

1-[2-(3-methyl-1,2,4-oxadiazol-5-yl)ethyl]-N-(2-methylpropyl)-N-[(3S, 5R)-5-(morpholin-4-ylcarbonyl)piperidin-3-yl]-1H-benzimidazole-2-carboxamide dihydrochloride

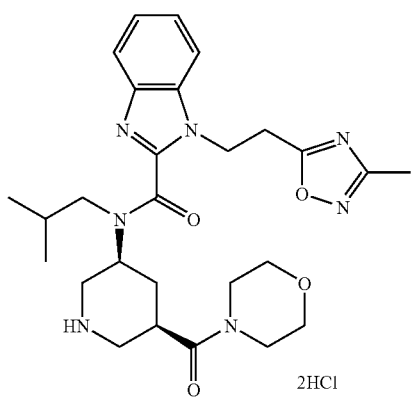 [SMILES: Cc1noc(CCn2c(C(=O)N(CC(C)C)[C@@H]3CNC[C@H](C(=O)N4CCOCC4)C3)nc3ccccc32)n1 ; "2HCl"]

MS (ESI+, m/e) 524 (M+1)

In the same manner as in Reference Example 69, the following compound (Reference Example 191) was obtained.
Reference Example 191

252

1-tert-butyl 3-methyl(3R, 5S)-5-[{[1-(2,2-difluoroethyl)-1H-benzimidazol-2-yl]carbonyl}(2-methylpropyl)amino]piperidine-1,3-dicarboxylate

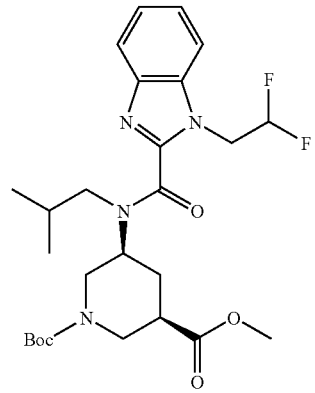 [SMILES: COC(=O)[C@@H]1C[C@H](N(CC(C)C)C(=O)c2nc3ccccc3n2CC(F)F)CN(C(=O)OC(C)(C)C)C1]

MS (ESI+, m/e) 523 (M+1)

In the same manner as in Reference Example 172, the following compound (Reference Example 192) was obtained.

Reference Example 192

(3R, 5S)-1-(tert-butoxycarbonyl)-5-[{[1-(2,2-difluoroethyl)-1H-benzimidazol-2-yl]carbonyl}(2-methylpropyl)amino]piperidine-3-carboxylic acid

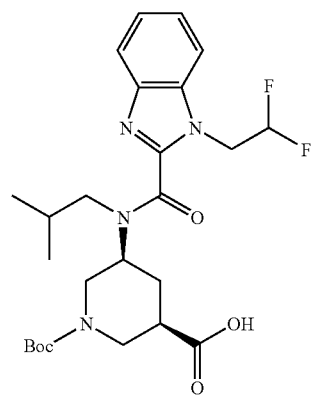 [SMILES: CC(C)CN(C(=O)c1nc2ccccc2n1CC(F)F)[C@H]1C[C@@H](C(=O)O)CN(C(=O)OC(C)(C)C)C1]

MS (ESI+, m/e) 509 (M+1)

In the same manner as in Reference Example 39, the following compounds (Reference Examples 193-194) were obtained.

Reference Example 193 tert-butyl(3S, 5R)-3-[{[1-(2,2-difluoroethyl)-1H-benzimidazol-2-yl]carbonyl}(2-methylpropyl)amino]-5-(morpholin-4-ylcarbonyl)piperidine-1-carboxylate

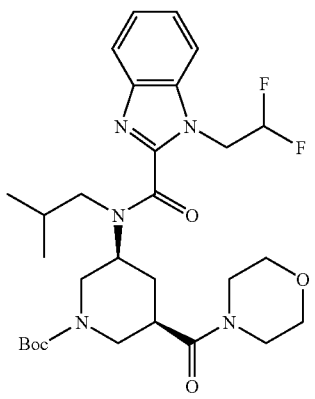

MS (ESI+, m/e) 578 (M+1)

Reference Example 194 tert-butyl(3S, 5R)-3-[{[1-(2,2-difluoroethyl)-1H-benzimidazol-2-yl]carbonyl}(2-methylpropyl)amino]-5-(piperidin-1-ylcarbonyl)piperidine-1-carboxylate

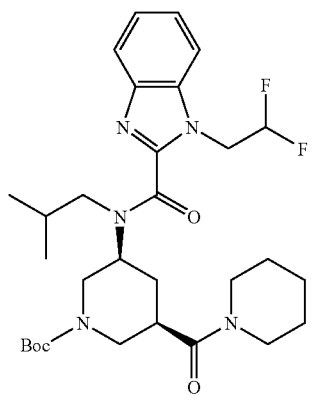 [SMILES: CC(C)CN(C(=O)c1nc2ccccc2n1CC(F)F)[C@H]1C[C@@H](C(=O)N2CCCCC2)CN(C(=O)OC(C)(C)C)C1]

MS (ESI+, m/e) 576 (M+1)

In the same manner as in Example 12, the following compounds (Examples 107-108) were obtained.

Example 107

1-(2,2-difluoroethyl)-N-(2-methylpropyl)-N-[(3S,5R)-5-(morpholin-4-ylcarbonyl)piperidin-3-yl]-1H-benzimidazole-2-carboxamide dihydrochloride

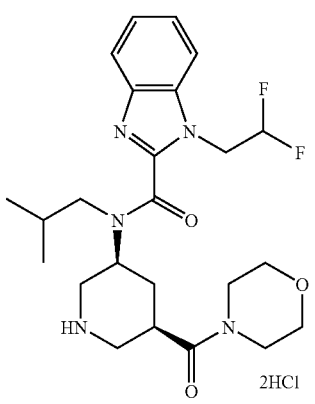 [SMILES: CC(C)CN(C(=O)c1nc2ccccc2n1CC(F)F)[C@@H]1CNC[C@H](C(=O)N2CCOCC2)C1 ; "2HCl"]

MS (ESI+, m/e) 478 (M+1)

Example 108

1-(2,2-difluoroethyl)-N-(2-methylpropyl)-N-[(3S,5R)-5-(piperidin-1-ylcarbonyl)piperidin-3-yl]-1H-benzimidazole-2-carboxamide dihydrochloride

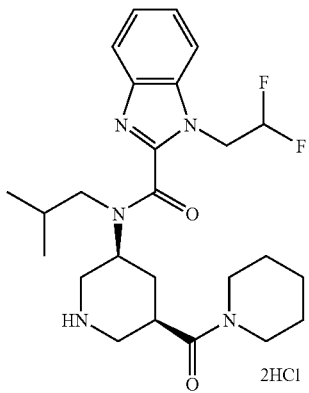 [SMILES: CC(C)CN(C(=O)c1nc2ccccc2n1CC(F)F)[C@@H]1CNC[C@H](C(=O)N2CCCCC2)C1 ; "2HCl"]

MS (ESI+, m/e) 476 (M+1)

In the same manner as in Reference Example 60, the following compound (Reference Example 195) was obtained.

Reference Example 195 tert-butyl(3S, 5R)-3-[{[1-(2,2-difluoroethyl)-1H-benzimidazol-2-yl]carbonyl}(2-methylpropyl)amino]-5-(hydroxymethyl)piperidine-1-carboxylate

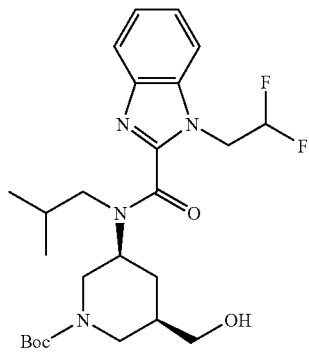 [SMILES: CC(C)CN(C(=O)c1nc2ccccc2n1CC(F)F)[C@H]1C[C@@H](CO)CN(C(=O)OC(C)(C)C)C1]

MS (ESI+, m/e) 495 (M+1)

In the same manner as in Example 24, the following compound (Example 109) was obtained.

Example 109

1-(2,2-difluoroethyl)-N-[(3S, 5R)-5-(hydroxymethyl)piperidin-3-yl]-N-(2-methylpropyl)-1H-benzimidazole-2-carboxamide dihydrochloride

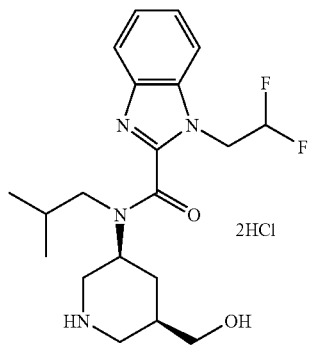 [SMILES: CC(C)CN(C(=O)c1nc2ccccc2n1CC(F)F)[C@@H]1CNC[C@H](CO)C1 ; "2HCl"]

MS (ESI+, m/e) 395 (M+1)

In the same manner as in Reference Example 69, the following compounds (Reference Examples 196-197) were obtained.

Reference Example 196

1-tert-butyl 3-methyl(3R, 5S)-5-[{[1-(1-methylethyl)-1H-benzimidazol-2-yl]carbonyl}(2-methylpropyl)amino]piperidine-1,3-dicarboxylate

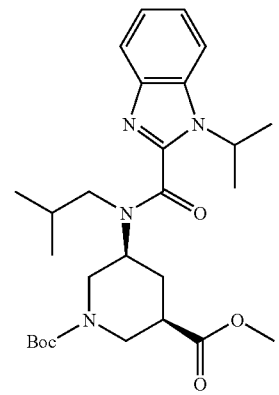 [SMILES: COC(=O)[C@@H]1C[C@H](N(CC(C)C)C(=O)c2nc3ccccc3n2C(C)C)CN(C(=O)OC(C)(C)C)C1]

MS (ESI+, m/e) 501 (M+1)

Reference Example 197

1-tert-butyl 3-methyl(3R, 5S)-5-{(2-methylpropyl)[(1-propyl-1H-benzimidazol-2-yl)carbonyl]amino}piperidine-1,3-dicarboxylate

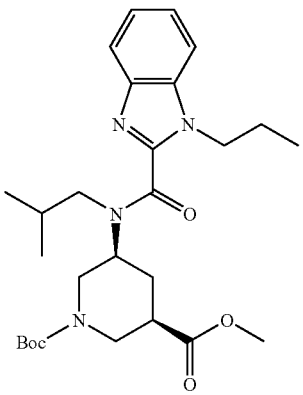 [SMILES: CCCn1c(C(=O)N(CC(C)C)[C@H]2C[C@@H](C(=O)OC)CN(C(=O)OC(C)(C)C)C2)nc2ccccc21]

MS (ESI+, m/e) 501 (M+1)

In the same manner as in Reference Example 189, the following compound (Reference Example 198) was obtained.

Reference Example 198

1-tert-butyl 3-methyl(3R, 5S)-5-[(2-methylpropyl){[1-(2,2,2-trifluoroethyl)-1H-benzimidazol-2-yl]carbonyl}amino]piperidine-1,3-dicarboxylate

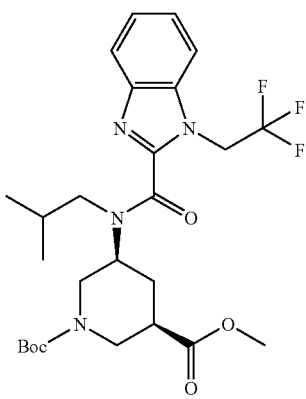 [SMILES: COC(=O)[C@@H]1C[C@H](N(CC(C)C)C(=O)c2nc3ccccc3n2CC(F)(F)F)CN(C(=O)OC(C)(C)C)C1]

MS (ESI+, m/e) 541 (M+1)

In the same manner as in Reference Example 172, the following compounds (Reference Examples 199-201) were obtained.

Reference Example 199

(3R, 5S)-1-(tert-butoxycarbonyl)-5-[{[1-(1-methylethyl)-1H-benzimidazol-2-yl]carbonyl}(2-methylpropyl)amino]piperidine-3-carboxylic acid

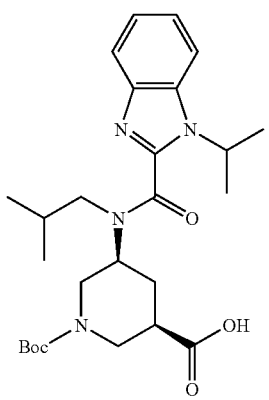 [SMILES: CC(C)CN(C(=O)c1nc2ccccc2n1C(C)C)[C@H]1C[C@@H](C(=O)O)CN(C(=O)OC(C)(C)C)C1]

MS (ESI+, m/e) 487 (M+1)

Reference Example 200

(3R, 5S)-1-(tert-butoxycarbonyl)-5-{(2-methylpropyl)[(1-propyl-1H-benzimidazol-2-yl)carbonyl]amino}piperidine-3-carboxylic acid

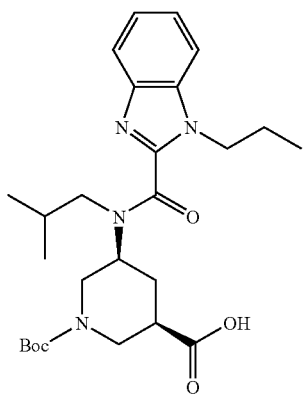 [SMILES: CCCn1c(C(=O)N(CC(C)C)[C@H]2C[C@@H](C(=O)O)CN(C(=O)OC(C)(C)C)C2)nc2ccccc21]

MS (ESI+, m/e) 487 (M+1)

Reference Example 201

(3R, 5S)-1-(tert-butoxycarbonyl)-5-[(2-methylpropyl){[1-(2,2,2-trifluoroethyl)-1H-benzimidazol-2-yl]carbonyl}amino]piperidine-3-carboxylic acid

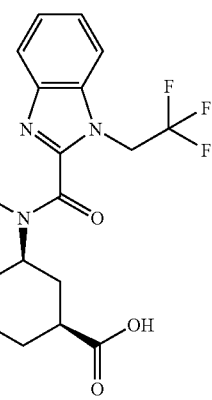

MS (ESI+, m/e) 527 (M+1)

In the same manner as in Reference Example 39, the following compounds (Reference Examples 202-204) were obtained.

Reference Example 202 tert-butyl(3S, 5R)-3-[{[1-(1-methylethyl)-1H-benz-imidazol-2-yl]carbonyl}(2-methylpropyl)amino]-5-(morpholin-4-ylcarbonyl)piperidine-1-carboxylate

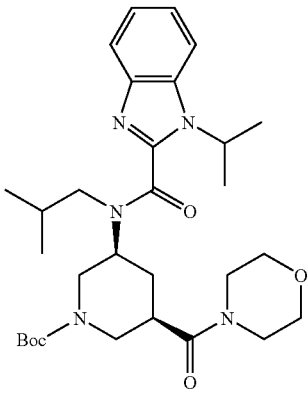 [SMILES: CC(C)CN(C(=O)c1nc2ccccc2n1C(C)C)[C@H]1C[C@@H](C(=O)N2CCOCC2)CN(C(=O)OC(C)(C)C)C1]

MS (ESI+, m/e) 556 (M+1)

Reference Example 203 tert-butyl(3S, 5R)-3-{(2-methylpropyl)[(1-propyl-1H-benzimidazol-2-yl)carbonyl]amino}-5-(morpholin-4-ylcarbonyl)piperidine-1-carboxylate

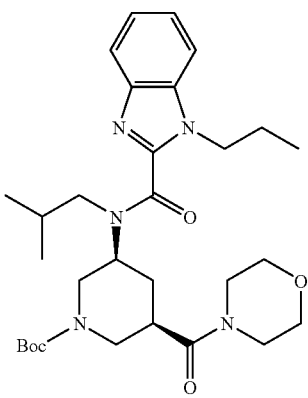 [SMILES: CCCn1c(C(=O)N(CC(C)C)[C@H]2C[C@@H](C(=O)N3CCOCC3)CN(C(=O)OC(C)(C)C)C2)nc2ccccc21]

MS (ESI+, m/e) 556 (M+1)

Reference Example 204 tert-butyl(3S, 5R)-3-[(2-methylpropyl){[1-(2,2,2-trifluoroethyl)-1H-benzimidazol-2-yl]carbonyl}amino]-5-(morpholin-4-ylcarbonyl)piperidine-1-carboxylate

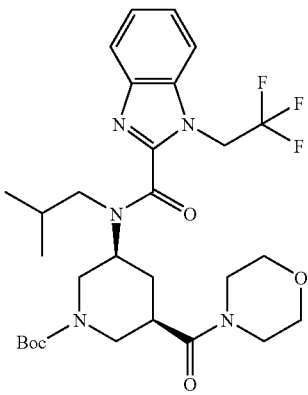 [SMILES: CC(C)CN(C(=O)c1nc2ccccc2n1CC(F)(F)F)[C@H]1C[C@@H](C(=O)N2CCOCC2)CN(C(=O)OC(C)(C)C)C1]

MS (ESI+, m/e) 596 (M+1)

In the same manner as in Example 12, the following compounds (Examples 110-112) were obtained.

Example 110

1-(1-methylethyl)-N-(2-methylpropyl)-N-[(3S, 5R)-5-(morpholin-4-ylcarbonyl)piperidin-3-yl]-1H-benzimidazole-2-carboxamide dihydrochloride

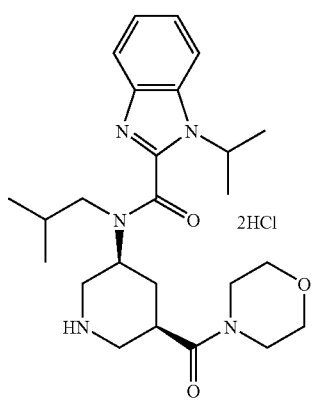 [SMILES: CC(C)CN(C(=O)c1nc2ccccc2n1C(C)C)[C@@H]1CNC[C@H](C(=O)N2CCOCC2)C1 ; "2HCl"]

MS (ESI+, m/e) 456 (M+1)

Example 111

N-(2-methylpropyl)-N-[(3S, 5R)-5-(morpholin-4-ylcarbonyl)piperidin-3-yl]-1-propyl-1H-benzimidazole-2-carboxamide dihydrochloride

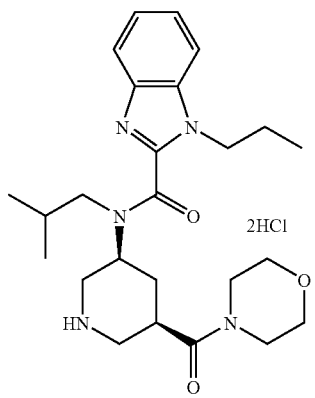 [SMILES: CCCn1c(C(=O)N(CC(C)C)[C@@H]2CNC[C@H](C(=O)N3CCOCC3)C2)nc2ccccc21 ; "2HCl"]

MS (ESI+, m/e) 456 (M+1)

Example 112

N-(2-methylpropyl)-N-[(3S, 5R)-5-(morpholin-4-ylcarbonyl)piperidin-3-yl]-1-(2,2,2-trifluoroethyl)-1H-benzimidazole-2-carboxamide dihydrochloride

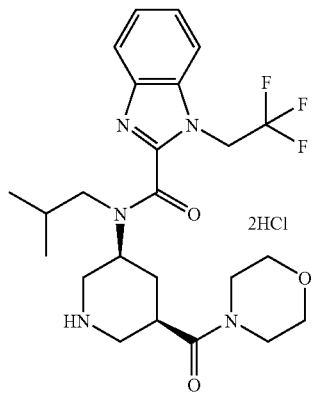 [SMILES: CC(C)CN(C(=O)c1nc2ccccc2n1CC(F)(F)F)[C@@H]1CNC[C@H](C(=O)N2CCOCC2)C1 ; "2HCl"]

MS (ESI+, m/e) 496 (M+1)

In the same manner as in Reference Example 60, the following compounds (Reference Examples 205-206) were obtained.

Reference Example 205 tert-butyl(3R, 5S)-3-(hydroxymethyl)-5-{(2-methylpropyl)[(1-propyl-1H-benzimidazol-2-yl)carbonyl]amino}piperidine-1-carboxylate


MS (ESI+, m/e) 473 (M+1)

Reference Example 206 tert-butyl(3R, 5S)-3-(hydroxymethyl)-5-[(2-methylpropyl){[1-(2,2,2-trifluoroethyl)-1H-benzimidazol-2-yl]carbonyl}amino]piperidine-1-carboxylate

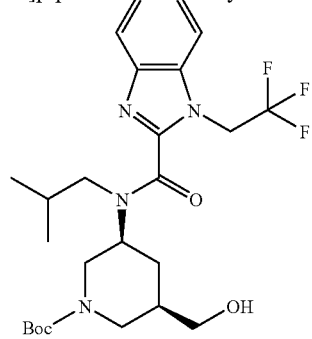

MS (ESI+, m/e) 513 (M+1)

In the same manner as in Example 24, the following compounds (Examples 113-114) were obtained.

Example 113

N-[3S, 5R)-5-(hydroxymethyl)piperidin-3-yl]-N-(2-methylpropyl)-1-propyl-1H-benzimidazole-2-carboxamide s dihydrochloride

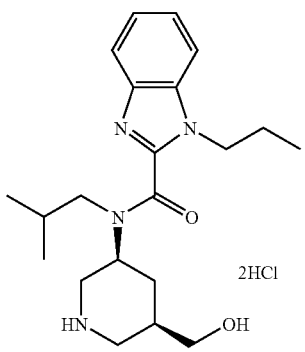 [SMILES: CCCn1c(C(=O)N(CC(C)C)[C@@H]2CNC[C@H](CO)C2)nc2ccccc21 ; "2HCl"]

MS (ESI+, m/e) 373 (M+1)

Example 114

N-[(3S, 5R)-5-(hydroxymethyl)piperidin-3-yl]-N-(2-methylpropyl)-1-(2,2,2-trifluoroethyl)-1H-benzimidazole-2-carboxamide dihydrochloride

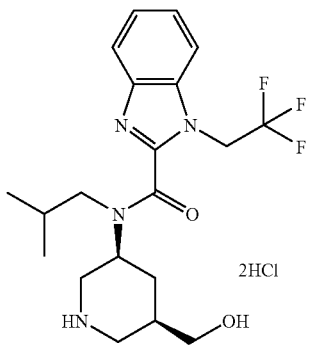 [SMILES: CC(C)CN(C(=O)c1nc2ccccc2n1CC(F)(F)F)[C@@H]1CNC[C@H](CO)C1 ; "2HCl"]

MS (ESI+, m/e) 413 (M+1)

In the same manner as in Reference Example 35, the following compound (Reference Example 207) was obtained.

Reference Example 207

1-cyclopropyl-2-(trichloromethyl)-1H-benzimidazole

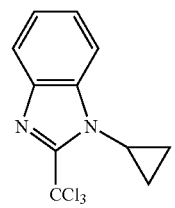

$^1$H-NMR (CDCl$_3$) δ 1.33-1.42 (2H, m), 1.44-1.54 (2H, m), 3.51-3.61 (1H, m), 7.29-7.43 (2H, m), 7.62-7.68 (1H, m), 7.83-7.90 (1H, m).

In the same manner as in Reference Example 37, the following compound (Reference Example 208) was obtained.

Reference Example 208

1-tert-butyl 3-methyl(3R, 5S)-5-{[(1-cyclopropyl-1H-benzimidazol-2-yl)carbonyl](2-methylpropyl)amino}piperidine-1,3-dicarboxylate

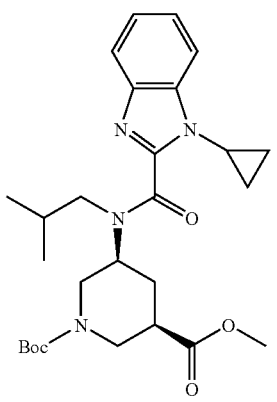 [SMILES: COC(=O)[C@@H]1C[C@H](N(CC(C)C)C(=O)c2nc3ccccc3n2C2CC2)CN(C(=O)OC(C)(C)C)C1]

MS (ESI+, m/e) 499 (M+1)

In the same manner as in Reference Example 172, the following compound (Reference Example 209) was obtained.

Reference Example 209

(3R, 5S)-1-(tert-butoxycarbonyl)-5-{[(1-cyclopropyl-1H-benzimidazol-2-yl)carbonyl](2-methylpropyl)amino}piperidine-3-carboxylic acid

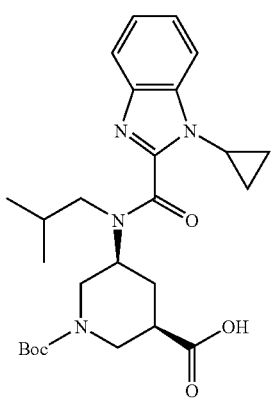 [SMILES: CC(C)CN(C(=O)c1nc2ccccc2n1C1CC1)[C@H]1C[C@@H](C(=O)O)CN(C(=O)OC(C)(C)C)C1]

MS (ESI+, m/e) 485 (M+1)

In the same manner as in Reference Example 39, the following compound (Reference Example 210) was obtained.

Reference Example 210 tert-butyl(3S, 5R)-3-{[(1-cyclopropyl-1H-benzimidazol-2-yl)carbonyl](2-methylpropyl)amino}-5-(morpholin-4-ylcarbonyl)piperidine-1-carboxylate

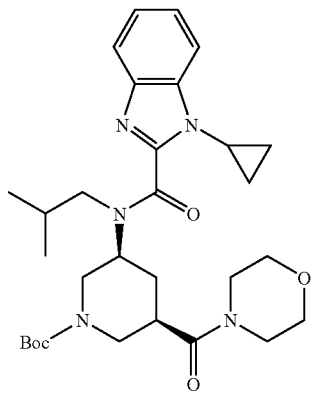 [SMILES: CC(C)CN(C(=O)c1nc2ccccc2n1C1CC1)[C@H]1C[C@@H](C(=O)N2CCOCC2)CN(C(=O)OC(C)(C)C)C1]

MS (ESI+, m/e) 554 (M+1)

In the same manner as in Example 12, the following compound (Example 115) was obtained.

Example 115

1-cyclopropyl-N-(2-methylpropyl)-N-[(3S, 5R)-5-(morpholin-4-ylcarbonyl)piperidin-3-yl]-1H-benzimidazole-2-carboxamide dihydrochloride

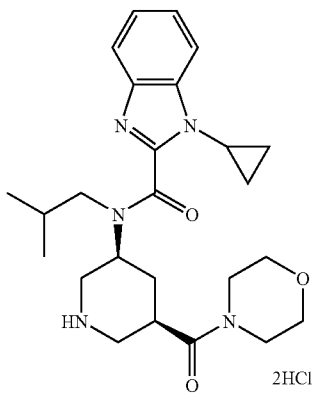 [SMILES: CC(C)CN(C(=O)c1nc2ccccc2n1C1CC1)[C@@H]1CNC[C@H](C(=O)N2CCOCC2)C1 ; "2HCl"]

MS (ESI+, m/e) 454 (M+1)

Reference Example 211 ethyl 3-(2-phenylethyl)imidazo[1,2-a]pyridine-2-carboxylate

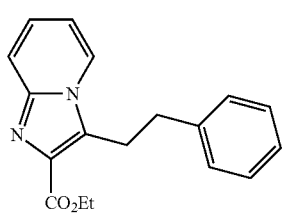 [SMILES: CCOC(=O)c1nc2ccccn2c1CCc1ccccc1]

To a solution of ethyl 3-bromo-2-oxo-5-phenylpentanoate (1.9 g) in THF (10 ml) was added 2-aminopyridine (600 mg) at room temperature, and the reaction mixture was heated under reflux for 15 hr. The precipitated crystals were collected by filtration, washed with THF to give 2-amino-1-[3-ethoxy-2,3-dioxo-1-(2-phenylethyl)propyl]pyridinium bromide (1.36 g). 2-Amino-1-[3-ethoxy-2,3-dioxo-1-(2-phenylethyl)propyl]pyridinium bromide (1.36 g) was dissolved in ethanol (10 ml), and the mixture was refluxed under heating for 3 hr. The reaction mixture was concentrated, and dissolved in dichloromethane. The solution was washed successively with aqueous sodium bicarbonate and saturated brine, and dried over anhydrous sodium sulfate. The solvent was evaporated under reduced pressure. The residue was recrystallized from ethyl acetate-diethyl ether to give the object product (950 mg).

$^1$H-NMR (CDCl$_3$) δ 1.47(3H, t), 3.00 (2H, t), 3.57 (2H, t), 4.47 (2H, q), 6.73 (1H, t), 7.12-7.13 (2H, m), 7.16-7.27 (4H, m), 7.65-7.67 (2H, m).

Reference Example 212 ethyl 3-(hydroxymethyl)imidazo[1,2-a]pyridine-2-carboxylate

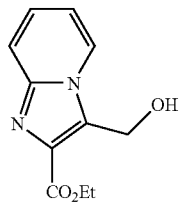 [SMILES: CCOC(=O)c1nc2ccccn2c1CO]

To a solution of ethyl imidazo[1,2-a]pyridine-2-carboxylate (5.0 g) in acetic acid (30 ml) were added 37% m formaldehyde (14 ml) and sodium acetate (8.0 g) at room temperature, and the reaction mixture was heated under reflux for 15 hr. The reaction mixture was cooled to room temperature and dissolved in dichloromethane. The mixture was adjusted to pH 8 with 10% aqueous sodium hydroxide solution at 0° C. The organic layer was separated, washed with water and dried over anhydrous sodium sulfate. The solvent was evaporated under reduced pressure. The residue was subjected to silica gel column chromatography, and a fraction eluted with dichloromethane-methanol (15:1) was concentrated under reduced pressure to give the object product (2.1 g).

$^1$H-NMR (CDCl$_3$) δ 1.43 (3H, t), 4.42 (2H, t), 5.30 (2H, s), 7.06 (1H, t), 7.45 (1H, t), 7.60 (1H, d), 8.50 (1H, d).

Reference Example 213 ethyl 3-(chloromethyl)imidazo[1,2-a]pyridine-2-carboxylate hydrochloride

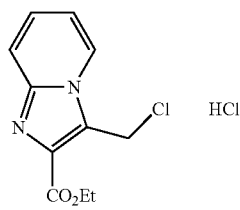 [SMILES: CCOC(=O)c1nc2ccccn2c1CCl ; Cl]

To a solution of ethyl 3-(hydroxymethyl)imidazo[1,2-a]pyridine-2-carboxylate (2.85 g) in chloroform (40 ml) was added thionyl chloride (8.0 ml) at room temperature, and the mixture was heated under reflux for 12 hr. The reaction solution was cooled to room temperature, and concentrated under reduced pressure. The precipitated crystals were collected by filtration, washed with diethyl ether to give the object product (3.50 g).

$^1$H-NMR (CDCl$_3$) δ 8.37 (3H, t), 4.40 (2H, t), 5.57 (2H, s), 7.34 (1H, t), 7.67 (1H, t), 7.82 (1H, m), 8.71 (1H, d).

Reference Example 214 ethyl 3-(phenoxymethyl)imidazo[1,2-a]pyridine-2-carboxylate

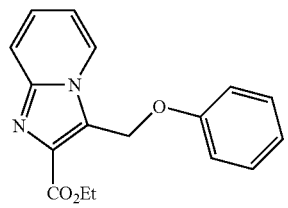 [SMILES: CCOC(=O)c1nc2ccccn2c1COc1ccccc1]

A solution of a mixture of phenol (2.20 g) and sodium hydride (95 wt %, 500 mg) in DMF (40 ml) was added dropwise to a solution of ethyl 3-(chloromethyl)imidazo[1,2-a]pyridine-2-carboxylate hydrochloride (3.5 g) in DMF (50 ml) at 0° C. Triethylamine (2.7 ml) was added at the same temperature over 30 min. The reaction mixture was stirred at 50° C. for 3 hr, and the reaction mixture was diluted with water and extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (6:1) was concentrated under reduced pressure to give the object product (1.5 g).

$^1$H-NMR (CDCl$_3$) δ 8.31 (3H, t), 4.34 (2H, t), 5.80 (2H, s), 6.97 (1H, t), 7.06-7.08 (2H, m), 7.12 (1H, t), 7.29-7.33 (2H, m), 7.44-7.48 (1H, m), 7.70 (1H, d), 8.54 (1H, d).

Reference Example 215 ethyl 3-[(1E)-4-methoxybut-1-en-1-yl]imidazo[1,2-a]pyridine-2-carboxylate

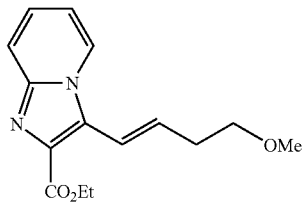 [SMILES: CCOC(=O)c1nc2ccccn2c1/C=C/CCOC]

To a suspension of (3-methoxypropyl)(triphenyl)phosphonium bromide (3.56 g) in THF (50 ml) was added potassium tert-butoxide (0.38 g) at −78° C., and the mixture was stirred at the same temperature for 30 min. Ethyl 3-formylimidazo[1,2-a]pyridine-2-carboxylate (1.7 g) was added to the reaction mixture, and the mixture was stirred at room temperature for 12 hr. Water was added to the reaction mixture, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate was concentrated under reduced pressure to give the object product (256 mg).

MS (ESI+, m/e) 275 (M+1)

Reference Example 216 ethyl 3-(4-methoxybutyl)imidazo[1,2-a]pyridine-2-carboxylate

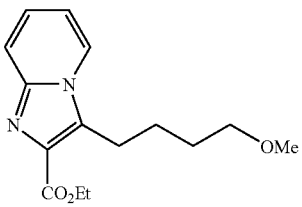 [SMILES: CCOC(=O)c1nc2ccccn2c1CCCCOC]

Ethyl 3-[(1E)-4-methoxybut-1-en-1-yl]imidazo[1,2-a]pyridine-2-carboxylate (530 mg) and diphenyl sulfide (3.6 mg) were dissolved in ethyl acetate (13 ml), 10% palladium carbon (50% in water) (53 mg) was added and the mixture was stirred in a hydrogen stream at ambient temperature and normal pressure for 2.5 hr. The catalyst was filtered off, and the to filtrate was concentrated under reduced pressure. The residue was subjected to silica gel column chromatography, and a fraction eluted with ethyl acetate was concentrated under reduced pressure to give the object product (260 mg).

$^1$H-NMR (CDCl$_3$) δ 8.46 (3H, t), 1.67-1.78 (4H, m), 3.32-3.34 (2H, m), 3.33 (3H, s), 3.42 (2H, t), 4.46 (2H, q), 6.88 (1H, t), 7.22 (1H, dd), 7.67 (1H, d), 7.99 (1H, d).

Reference Example 217 ethyl 3-(4-methoxybutyl)-5,6,7,8-tetrahydroimidazo[1,2-a]pyridine-2-carboxylate

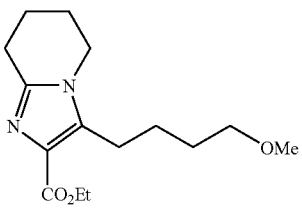 [SMILES: CCOC(=O)c1nc2n(c1CCCCOC)CCCC2]

Ethyl 3-[(1E)-4-methoxybut-1-en-1-yl]imidazo[1,2-a]pyridine-2-carboxylate (1.40 g) was dissolved in ethyl acetate (30 ml), 10% palladium carbon (50% in water) (510 mg) was added and the mixture was stirred in a hydrogen stream at ambient temperature and normal pressure for 12 hr. The catalyst was filtered off, and the filtrate was concentrated under reduced pressure. The residue was subjected to silica gel column chromatography, and a fraction eluted with ethyl acetate-methanol (5:1) was concentrated under reduced pressure to give the object product (1.14 g).

$^1$H-NMR (CDCl$_3$) δ 1.39 (3H, t), 1.62-1.67 (4H, m), 1.89-1.92 (2H, m), 1.99-2.01 (2H, m), 2.89 (2H, t), 2.92-2.96 (2H, m), 3.32 (3H, s), 3.38-3.41 (2H, m), 3.82-3.85 (2H, m), 4.35 (2H, q).

Reference Example 218 tert-butyl(3S, 5R)-3-[(2-methylpropyl){[3-(2-phenylethyl)imidazo[1,2-a]pyridin-2-yl]carbonyl}amino]-5-(morpholin-4-ylcarbonyl)piperidine-1-carboxylate

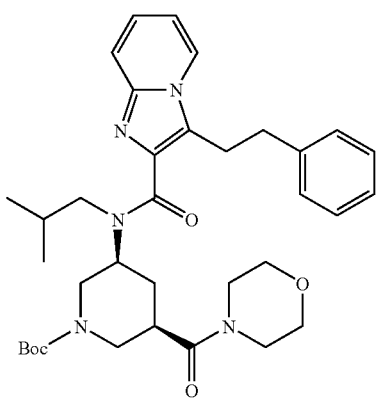

Ethyl 3-(2-phenylethyl)imidazo[1,2-a]pyridine-2-carboxylate (883 mg) was dissolved in ethanol (50 ml), 2N aqueous sodium hydroxide solution (3 ml) was added, and the mixture was stirred at room temperature for 15 hr. The reaction mixture was concentrated under reduced pressure, neutralized with 1N hydrochloric acid, subjected to DIAION HP-20 (manufactured by Mitsubishi Chemical), and washed with water. The fraction eluted with acetone was concentrated under reduced pressure to give 3-(2-phenylethyl)imidazo[1,2-a]pyridine-2-carboxylic acid (1.03 g). The obtained 3-(2-phenylethyl)imidazo[1,2-a]pyridine-2-carboxylic acid (341 mg), tert-butyl(3S, 5R)-3-[(2-methylpropyl)amino]-5-(morpholin-4-ylcarbonyl)piperidine-1-carboxylate (370 mg) and N,N-diisopropylethylamine (862 μl) were dissolved in acetonitrile (20 ml), chloro-N,N,N',N'-tetramethylformamidinium hexafluorophosphate (561 mg) was added and the mixture was stirred at room temperature for 15 hr. The reaction mixture was concentrated, and the residue was diluted with aqueous sodium bicarbonate. The mixture was extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate-hexane (9:1) was concentrated under reduced pressure to give the object product (522 mg).

MS (ESI+, m/e) 618 (M+1)

Reference Example 219 tert-butyl(3S, 5R)-3-[(2-methylpropyl){[3-(phenoxymethyl)imidazo[1,2-a]pyridin-2-yl]carbonyl}amino]-5-(morpholin-4-ylcarbonyl)piperidine-1-carboxylate

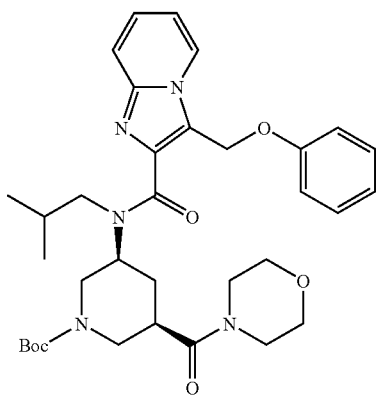 [SMILES: CC(C)CN(C(=O)c1nc2ccccn2c1COc1ccccc1)[C@H]1C[C@@H](C(=O)N2CCOCC2)CN(C(=O)OC(C)(C)C)C1]

Ethyl 3-(phenoxymethyl)imidazo[1,2-a]pyridine-2-carboxylate (889 mg) was dissolved in ethanol (50 ml), 2N aqueous sodium hydroxide solution (3 ml) was added, and the mixture was stirred at room temperature for 15 hr. The precipitated crystals were collected by filtration, and washed with ethanol to give sodium 3-(phenoxymethyl)imidazo[1,2-a]pyridine-2-carboxylate (680 g). The obtained sodium 3-(phenoxymethyl)imidazo[1,2-a]pyridine-2-carboxylate (290 mg), tert-butyl(3S, 5R)-3-[(2-methylpropyl)amino]-5-(morpholin-4-ylcarbonyl)piperidine-1-carboxylate (370 mg) and N,N-diisopropylethylamine (862 μl) were dissolved in acetonitrile (20 ml), chloro-N,N,N',N'-tetramethylformamidinium hexafluorophosphate (561 mg) was added and the mixture was stirred at room temperature for 15 hr. The reaction mixture was concentrated, and the residue was diluted with aqueous sodium bicarbonate, and extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate-hexane (9:1) was concentrated under reduced pressure to give the object product (563 mg).

$^1$H-NMR (CDCl$_3$) δ 0.65-1.06 (6H, m), 1.15-1.54 (9H, m), 1.72-2.53 (4H, m), 2.57-3.01 (2H, m), 3.16-5.00 (12H, m), 5.51-5.73 (2H, m), 6.86-7.07 (4H, m), 7.23-7.35 (4H, m), 7.45-7.66 (1H, m), 8.27 (1H, t).

MS (ESI+, m/e) 620 (M+1)

In the same manner as in Example 12, the following compound (Example 116) was obtained.

Example 116

N-(2-methylpropyl)-N-[(3S, 5R)-5-(morpholin-4-ylcarbonyl)piperidin-3-yl]-3-(2-phenylethyl)imidazo[1,2-a]pyridine-2-carboxamide dihydrochloride

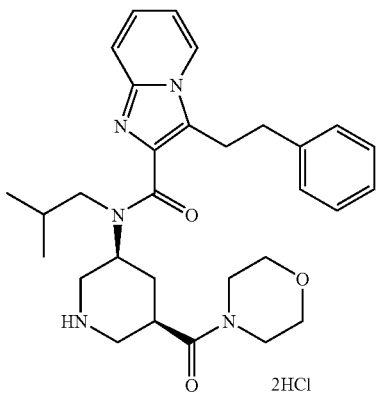 [SMILES: CC(C)CN(C(=O)c1nc2ccccn2c1CCc1ccccc1)[C@@H]1CNC[C@H](C(=O)N2CCOCC2)C1 ; "2HCl"]

MS (ESI+, m/e) 518 (M+1)

Example 117

N-(2-methylpropyl)-N-[(3S, 5R)-5-(morpholin-4-ylcarbonyl)piperidin-3-yl]-3-(phenoxymethyl)imidazo[1,2-a]pyridine-2-carboxamide dihydrochloride

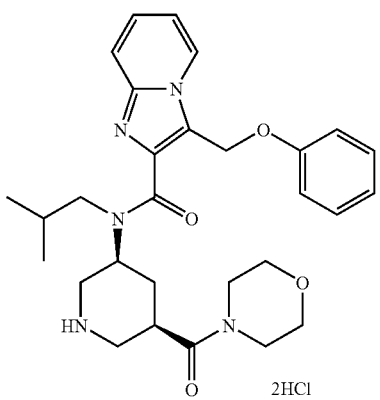 [SMILES: CC(C)CN(C(=O)c1nc2ccccn2c1COc1ccccc1)[C@@H]1CNC[C@H](C(=O)N2CCOCC2)C1 ; "2HCl"]

tert-Butyl(3S, 5R)-3-[(2-methylpropyl){[3-(phenoxymethyl)imidazo[1,2-a]pyridin-2-yl]carbonyl}amino]-5-(morpholin-4-ylcarbonyl)piperidine-1-carboxylate (290 mg) was dissolved in 4M hydrogen chloride-ethyl acetate (5 ml), and the mixture was stirred at room temperature for 3 hr. The reaction mixture was concentrated to give the object product (278 mg).

$^1$H-NMR (DMSO-d$_6$) δ 0.63-0.97 (6H, m), 1.74-2.45 (3H, m), 2.81-4.66 (17H, m), 5.51-5.61 (2H, m), 6.95-7.11 (3H, m), 7.19-7.38 (3H, m), 7.56-7.81 (2H, m), 8.57-8.69 (1H, m), 9.07-9.69 (2H, m).

MS (ESI+, m/e) 520 (M+1)

Reference Example 220 tert-butyl(3S, 5R)-3-[{[3-(4-methoxybutyl)-5,6,7,8-tetrahydroimidazo[1,2-a]pyridin-2-yl]carbonyl}(2-methylpropyl)amino]-5-(morpholin-4-ylcarbonyl)piperidine-1-carboxylate

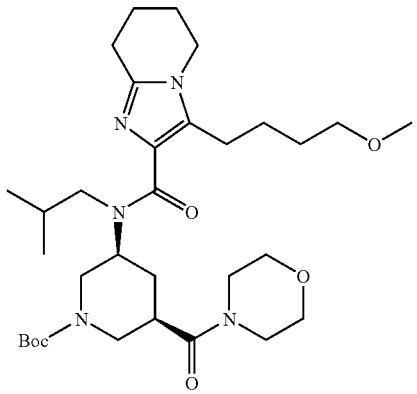 [SMILES: COCCCCc1c(C(=O)N(CC(C)C)[C@H]2C[C@@H](C(=O)N3CCOCC3)CN(C(=O)OC(C)(C)C)C2)nc2n1CCCC2]

Ethyl 3-(4-methoxybutyl)-5,6,7,8-tetrahydroimidazo[1,2-a]pyridine-2-carboxylate (56 mg) was dissolved in ethanol (5 ml), lithium hydroxide monohydrate (42 mg) was added and the mixture was stirred at 50° C. for 6 hr. 8N Aqueous sodium hydroxide solution (0.1 ml) was added to the reaction mixture, and the mixture was stirred at 60° C. for 15 hr, and concentrated under reduced pressure. The residue was dissolved in acetonitrile (5 ml), tert-butyl(3S, 5R)-3-[(2-methylpropyl)amino]-5-(morpholin-4-ylcarbonyl)piperidine-1-carboxylate (74 mg), N,N-diisopropylethylamine (172 μl) and chloro-N,N,N',N'-tetramethylformamidinium hexafluorophosphate (112 mg) were added and the mixture was stirred at room 15 temperature for 5 hr. The reaction mixture was concentrated, and the residue was diluted with aqueous sodium bicarbonate, and extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate was concentrated under reduced pressure to give the object product (26 mg).

MS (ESI+, m/e) 604 (M+1)

In the same manner as in Example 12, the following compound (Example 118) was obtained.

Example 118

3-(4-methoxybutyl)-N-(2-methylpropyl)-N-[(3S, 5R)-5-(morpholin-4-ylcarbonyl)piperidin-3-yl]-5,6,7,8-tetrahydroimidazo[1,2-a]pyridine-2-carboxamide dihydrochloride

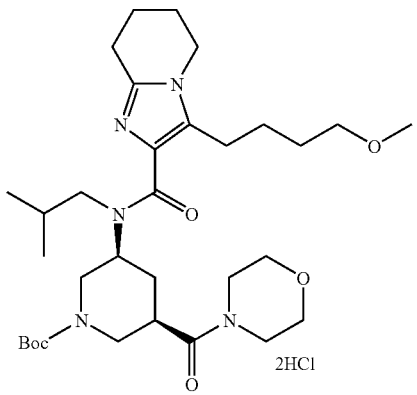 [SMILES: COCCCCc1c(C(=O)N(CC(C)C)[C@H]2C[C@@H](C(=O)N3CCOCC3)CN(C(=O)OC(C)(C)C)C2)nc2n1CCCC2 ; "2HCl"]

MS (ESI+, m/e) 504 (M+1)

Reference Example 221

1-tert-butyl 3-methyl(3R, 5S)-5-[{[3-(4-methoxybutyl)imidazo[1,2-a]pyridin-2-yl]carbonyl}(2-methylpropyl)amino]piperidine-1,3-dicarboxylate

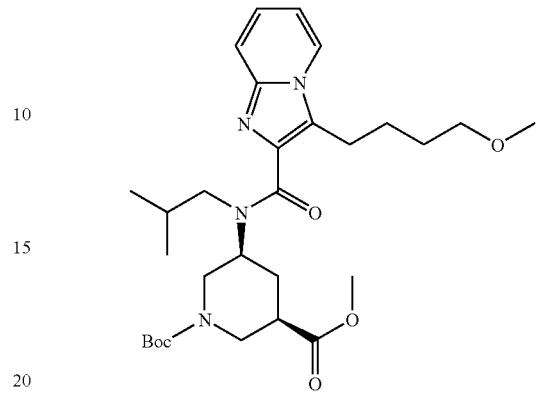

Ethyl 3-(4-methoxybutyl)imidazo[1,2-a]pyridine-2-carboxylate (183 mg) was dissolved in ethanol (5 ml), lithium hydroxide monohydrate (139 mg) was added and the mixture was stirred at 60° C. for 15 hr. The reaction mixture was concentrated under reduced pressure, and the residue was dissolved in acetonitrile (5 ml). 1-tert-Butyl 3-methyl(3R, 5S)-5-[(2-methylpropyl)amino]piperidine-1,3-dicarboxylate (208 mg), N,N-diisopropylethylamine (570 μl) and chloro-N,N,N',N'-tetramethylformamidinium hexafluorophosphate (370 mg) were added and the mixture was stirred at room temperature for 15 hr. The reaction mixture was concentrated, and the residue was diluted with aqueous sodium bicarbonate, and extracted with ethyl acetate. The extract was washed with saturated brine, and dried over anhydrous sodium sulfate. The solvent was evaporated under reduced pressure. The residue was subjected to basic silica gel column chromatography, and a fraction eluted with ethyl acetate was concentrated under reduced pressure to give the object product (224 mg).

MS (ESI+, m/e) 545 (M+1)

In the same manner as in Reference Example 172, the following compound (Reference Example 222) was obtained.

Reference Example 222

(3R, 5S)-1-(tert-butoxycarbonyl)-5-[{[3-(4-methoxybutyl)imidazo[1,2-a]pyridin-2-yl]carbonyl}(2-methylpropyl)amino]piperidine-3-carboxylic acid

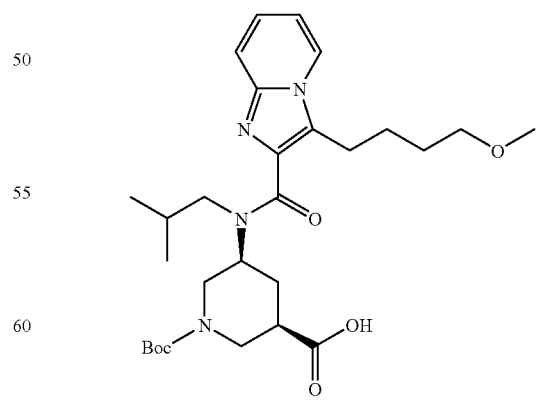

MS (ESI+, m/e) 531 (M+1)

In the same manner as in Reference Example 39, the following compounds (Reference Examples 223-224) were obtained.

Reference Example 223 tert-butyl(3S, 5R)-3-[{[3-(4-methoxybutyl)imidazo[1,2-a]pyridin-2-yl]carbonyl}(2-methylpropyl)amino]-5-(morpholin-4-ylcarbonyl)piperidine-1-carboxylate

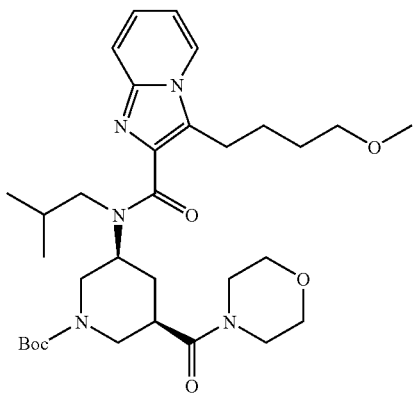 [SMILES: COCCCCc1c(C(=O)N(CC(C)C)[C@H]2C[C@@H](C(=O)N3CCOCC3)CN(C(=O)OC(C)(C)C)C2)nc2ccccn12]

MS (ESI+, m/e) 600 (M+1)

Reference Example 224 tert-butyl(3S, 5R)-3-[{[3-(4-methoxybutyl)imidazo[1,2-a]pyridin-2-yl]carbonyl}(2-methylpropyl)amino]-5-(pyrrolidin-1-ylcarbonyl)piperidine-1-carboxylate

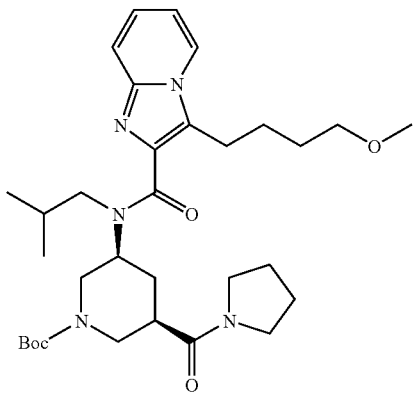 [SMILES: COCCCCc1c(C(=O)N(CC(C)C)[C@H]2C[C@@H](C(=O)N3CCCC3)CN(C(=O)OC(C)(C)C)C2)nc2ccccn12]

MS (ESI+, m/e) 584 (M+1)

In the same manner as in Example 12, the following compounds (Examples 119-120) were obtained.

Example 119

3-(4-methoxybutyl)-N-(2-methylpropyl)-N-[(3S, 5R)-5-(morpholin-4-ylcarbonyl)piperidin-3-yl]imidazo[1,2-a]pyridine-2-carboxamide dihydrochloride

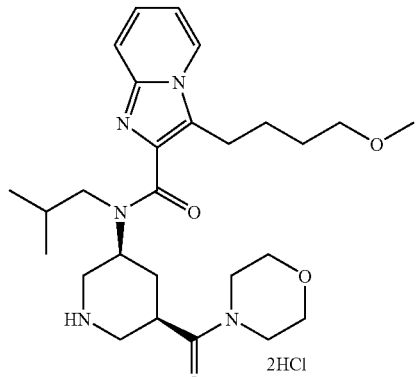

MS (ESI+, m/e) 500 (M+1)

Example 120

3-(4-methoxybutyl)-N-(2-methylpropyl)-N-[(3S, 5R)-5-(pyrrolidin-1-ylcarbonyl)piperidin-3-yl]imidazo[1,2-a]pyridine-2-carboxamide dihydrochloride

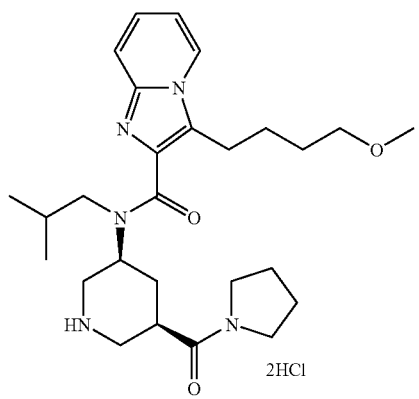 [SMILES: COCCCCc1c(C(=O)N(CC(C)C)[C@@H]2CNC[C@H](C(=O)N3CCCC3)C2)nc2ccccn12 ; "2HCl"]

MS (ESI+, m/e) 484 (M+1)

Example 121

N-(2-methylpropyl)-N-[(3S, 5R)-5-(morpholin-4-ylcarbonyl)piperidin-3-yl]quinoline-2-carboxamide 2 TFA Salt

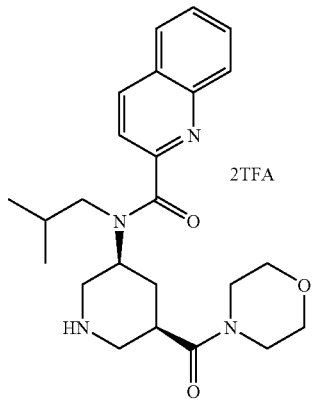

A 0.08M solution (1000 μL, 80 μmol) of tert-butyl (3S, 5R)-3-[(2-methylpropyl)amino]-5-(morpholin-4-ylcarbonyl)piperidine-1-carboxylate in DMF and quinoline-2-carboxylic acid (15.2 mg, 88 μmol) were mixed, a 0.32M solution (500 μL, 160 μmol) of chloro-N,N,N',N'-tetramethylformamidinium hexafluorophosphate and N,N-diisopropylethylamine in DMF was added at room temperature and the mixture was stirred for 16 hr. After completion of the reaction, 2% aqueous sodium hydrogen carbonate solution (1.0 ml) was added, and extracted with ethyl acetate (3.5 ml). The organic layer was separated by upper layer Phase Septube (manufactured by Wako Pure Chemical Industries, Ltd.). The solvent was evaporated under reduced pressure, and the residue was dissolved in DMSO-methanol (1:1) (1 ml), purified by preparative HPLC, and the object fraction was concentrated to give a protected title compound. 1M MSA acetonitrile solution (3 ml) was added to the obtained protected compound, and the mixture was stirred at room temperature for 16 hr. After completion of the reaction, 1M DIEA acetonitrile solution (3.5 ml) was added, and the reaction mixture was directly developed by preparative HPLC to give the object product (12.3 mg).

MS(ESI+):425(M+H)

In the same manner as in Example 121, the following compounds (Examples 122-124) were obtained.

Example 122

N-(2-methylpropyl)-N-[(3S, 5R)-5-(morpholin-4-ylcarbonyl)piperidin-3-yl]isoquinoline-3-carboxamide 2TFA Salt

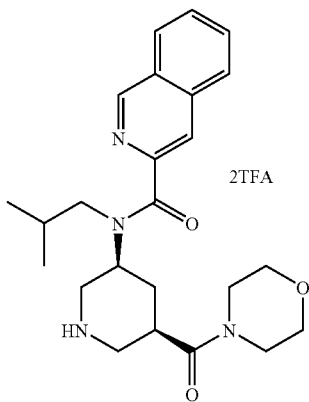

MS (ESI+):425 (M+H)

Example 123

5-fluoro-N-(2-methylpropyl)-N-[(3S, 5R)-5-(morpholin-4-ylcarbonyl)piperidin-3-yl]-1H-benzimidazole-2-carboxamide TFA Salt

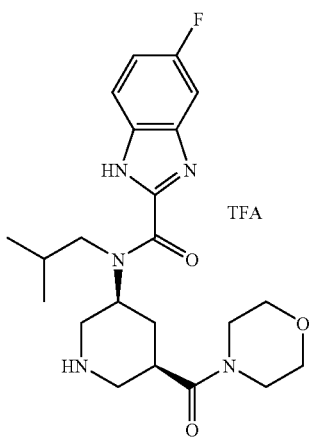 [SMILES: "TFA" ; CC(C)CN(C(=O)c1nc2cc(F)ccc2[nH]1)[C@@H]1CNC[C@H](C(=O)N2CCOCC2)C1]

MS (ESI+):432 (M+H)

Example 124

5-chloro-N-(2-methylpropyl)-N-[(3S, 5R)-5-(morpholin-4-ylcarbonyl)piperidin-3-yl]-1H-benzimidazole-2-carboxamide TFA salt

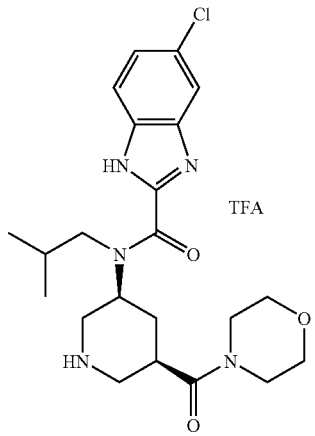 [SMILES: "TFA" ; CC(C)CN(C(=O)c1nc2cc(Cl)ccc2[nH]1)[C@@H]1CNC[C@H](C(=O)N2CCOCC2)C1]

MS (ESI+):448 (M+H)

Example 125

N-{(3S, 5R)-5-[(1R)-1-hydroxy-2-methoxyethyl]piperidin-3-yl}-1-(4-methoxybutyl)-N-(2-methylpropyl)-1H-benzimidazole-2-carboxamide dihydrochloride (Example 125-1) and N-{(3S, 5R)-5-[(1S)-1-hydroxy-2-methoxyethyl]piperidin-3-yl}-1-(4-methoxybutyl)-N-(2-methylpropyl)-1H-benzimidazole-2-carboxamide dihydrochloride (Example 125-2)

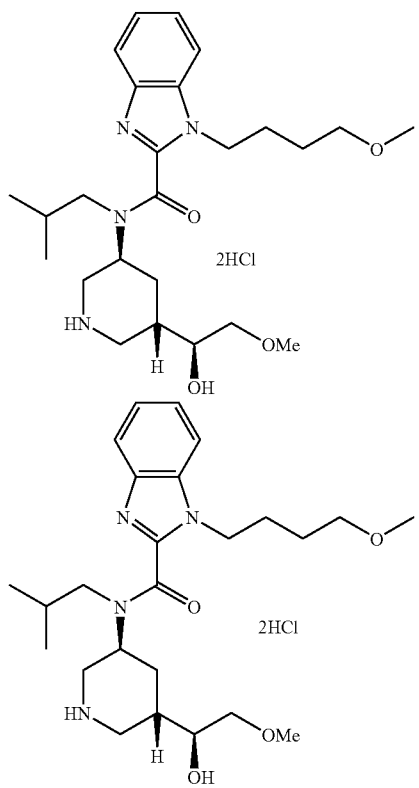

tert-Butyl(3R, 5S)-3-(1-hydroxy-2-methoxyethyl)-5-[{[1-(4-methoxybutyl)-1H-benzimidazol-2-yl]carbonyl}(2-methylpropyl)amino]piperidine-1-carboxylate (7.3 g) and vinyl acetate (146 ml) were dissolved in isopropanol (292 ml), lipase (Toyobo, LIP-301, 20 g) was added at room temperature, and the mixture was stirred at room temperature for 24 hr. The completion of the reaction was confirmed by HPLC, and the reaction mixture was filtered. The filtrate was concentrated under reduced pressure, and the residue was subjected to silica gel column chromatography, and a fraction eluted with ethyl acetate-hexane (1:9-1:0) was concentrated under reduced pressure to give a first elution component (3.76 g) and a second elution component (3.15 g). It was confirmed that the first elution component was a compound of Example 73-1 wherein the hydroxyl group was acetylated, and the second elution component (99.9%de) was the same as the compound of Example 73-2.

The obtained first elution component (100 mg) was dissolved in methanol (1 ml), 1M aqueous sodium hydroxide solution (1 ml) was added and the mixture was stirred at room temperature for 1 hr. 1M Hydrochloric acid (1 ml) was added to the reaction mixture for neutralization and methanol was evaporated under reduced pressure. The concentrate was diluted with water, and the mixture was extracted with ethyl acetate. The extract was washed with saturated brine, dried over anhydrous sodium sulfate, and concentrated under reduced pressure. The residue was dissolved in ethanol (1 ml), 12M hydrochloric acid (0.50 ml) was added and the mixture was stirred at room temperature for 1 hr. The reaction mixture was concentrated under reduced pressure, the residue was dissolved in ethanol, and ethanol was evaporated under reduced pressure. This operation was repeated twice to give the object product (52 mg) of Example compound 125-1.

Example 125-1

Spectrum Data $^1$H-NMR (CDCl$_3$) δ 0.71 (2 H, dd), 0.95 (4 H, dd), 1.38-1.63 (2 H, m), 1.66-1.86 (3 H, m), 1.86-2.04 (1 H, m), 2.12 (2 H, dd), 2.59-2.91 (1 H, m), 3.02 (1 H, d), 3.09-3.22 (4 H, m), 3.24-3.39 (9 H, m), 3.50 (2 H, br s), 3.62 (1 H, br s), 4.15 (2 H, br s), 4.21-4.39 (2 H, m), 7.15-7.53 (2 H, m), 7.55-7.87 (2 H, m), 8.33-9.18 (1 H, m), 9.43 (1 H, br s)
MS (ESI+, m/e) 461 (M+1)

The obtained second elution component (447 mg) was dissolved in ethanol (1 ml), 12M hydrochloric acid (0.70 ml) was added and the mixture was stirred at room temperature for 1 hr. The reaction mixture was concentrated under reduced pressure, the residue was dissolved in ethanol, and ethanol was evaporated under reduced pressure. This operation was repeated twice to give the object product (365 mg) of Example compound 125-2.

Example 125-2

Spectrum Data $^1$H-NMR (CDCl$_3$) δ 0.71 (2 H, dd), 0.81-1.12 (4 H, m), 1.31-1.61 (2 H, m), 1.62-1.98 (5 H, m), 1.98-2.23 (2 H, m), 2.57-2.87 (1 H, m), 3.14 (1 H, d), 3.18-3.23 (3 H, m), 3.23-3.39 (10 H, m), 3.39-3.63 (3 H, m), 4.23-4.38 (3 H, m), 7.16-7.51 (2 H, m), 7.55-7.86 (2 H, m), 8.29-9.11 (1 H, m), 9.38 (1 H, br s)
MS (ESI+, m/e) 461 (M+1)

Example 126

N-{(3S, 5R)-5-[(1S)-1-hydroxyethyl]piperidin-5-yl}-1-(4-methoxybutyl)-N-(2-methylpropyl)-1H-benzimidazole-2-carboxamide dihydrochloride (Example 126-1) and N-{(3S, 5R)-5-[(1R)-1-hydroxyethyl]piperidin-5-yl}-1-(4-methoxybutyl)-N-(2-methylpropyl)-1H-benzimidazole-2-carboxamide dihydrochloride (Example 126-2)

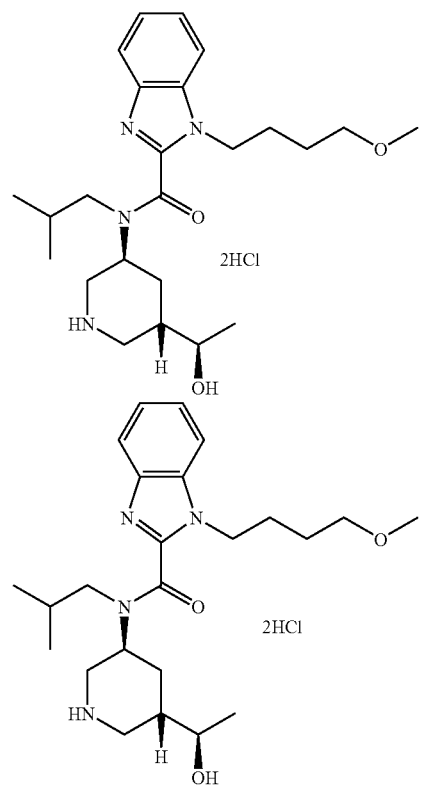

tert-Butyl(3R, 5S)-3-(1-hydroxyethyl)-5-[{[1-(4-methoxybutyl)-1H-benzimidazol-2-yl]carbonyl}(2-methylpropyl)amino]piperidine-1-carboxylate (39.95 g) and vinyl acetate (789 ml) were dissolved in isopropanol (1.6 l), lipase (Toyobo, LIP-301, 120 g) was added at room temperature, and the mixture was stirred at room temperature for 15 hr. The completion of the reaction was confirmed by HPLC, and the reaction mixture was filtered. The filtrate was concentrated under reduced pressure, and the residue was subjected to silica gel column chromatography, and a fraction eluted with ethyl acetate-hexane (1:9-1:0) was concentrated under reduced pressure to give a first elution component (23.3 g) and a second elution component (18.3 g). It was confirmed that the first elution component was a compound of Example 74-1 wherein the hydroxyl group was acetylated, and the second elution component (99.8% de) was the same as the compound of Example 74-2.

The obtained first elution component (100 mg) was dissolved in methanol (1 ml), 1M aqueous sodium hydroxide solution (1 ml) was added and the mixture was stirred at room temperature for 1 hr. 1M Hydrochloric acid (1 ml) was added to the reaction mixture for neutralization and methanol was evaporated under reduced pressure. The concentrate was diluted with water, and the mixture was extracted with ethyl acetate. The extract was washed with saturated brine, dried over anhydrous sodium sulfate, and concentrated under reduced pressure. The residue was dissolved in ethanol (1 ml), 12M hydrochloric acid (0.50 ml) was added and the mixture was stirred at room temperature for 1 hr. The reaction mixture was concentrated under reduced pressure, the residue was dissolved in ethanol, and ethanol was evaporated under reduced pressure. This operation was repeated twice to give the object product (75 mg) of Example compound 126-1.

Example 126-1

Spectrum Data $^1$H-NMR (CDCl$_3$) δ 0.72 (3 H, dd), 0.84-1.18 (7 H, m), 1.45-1.66 (3 H, m), 1.67-1.98 (3 H, m), 2.00-2.19 (2 H, m), 2.54-2.81 (1 H, m), 2.92-3.23 (5 H, m), 3.25-3.40 (4 H, m), 3.40-3.70 (3 H, m), 4.07-4.47 (3 H, m), 7.23-7.51 (2 H, m), 7.54-7.91 (2 H, m), 8.56-9.55 (1 H, m), 9.86 (1 H, d)

MS (ESI+, m/e) 431 (M+1)

The obtained second elution component (1.0 g) was dissolved in 10% hydrogen chloride containing methanol solution (40 ml), and the mixture was stirred at room temperature for 15 hr. The reaction mixture was concentrated under reduced pressure, the residue was dissolved in ethanol, and ethanol was evaporated under reduced pressure. This operation was repeated twice to give the object product (0.86 g) of Example compound 126-2.

Example 126-2

Spectrum Data $^1$H-NMR (CDCl$_3$) δ 0.71 (3 H, dd), 0.94 (3 H, d), 1.09 (3 H, dd), 1.27-1.64 (3 H, m), 1.70 (1 H, s), 1.74-2.00 (4 H, m), 2.00-2.29 (1 H, m), 2.54-2.76 (1 H, m), 3.11 (1 H, d), 3.20 (4 H, d), 3.24-3.62 (7 H, m), 4.32 (3 H, d), 7.16-7.54 (2 H, m), 7.72 (2 H, q), 8.27-9.22 (1 H, m), 9.36-9.56 (1 H, m)

MS (ESI+, m/e) 431 (M+1)

Example 127

N-{(3S, 5R)-5-[(1S)-1-hydroxypropyl]piperidin-5-yl}-1-(4-methoxybutyl)-N-(2-methylpropyl)-1H-benzimidazole-2-carboxamide dihydrochloride (Example 127-1) and N-{(3S, 5R)-5-[(1R)-1-hydroxypropyl]piperidin-5-yl}-1-(4-methoxybutyl)-N-(2-methylpropyl)-1H-benzimidazole-2-carboxamide dihydrochloride (Example 127-2)

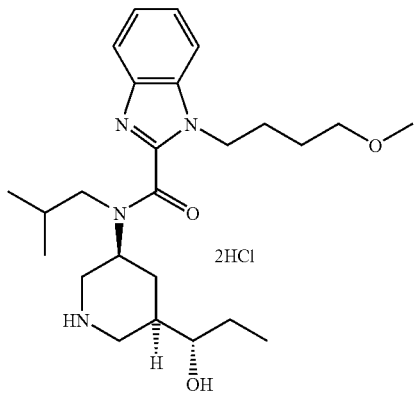

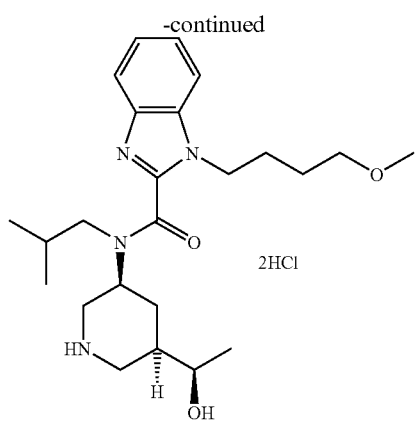

tert-Butyl(3R, 5S)-3-(1-hydroxypropyl)-5-[{[1-(4-methoxybutyl)-1H-benzimidazol-2-yl]carbonyl}(2-methylpropyl)amino]piperidine-1-carboxylate (16.4 g) and vinyl acetate (328 ml) were dissolved in isopropanol (656 ml), lipase (Toyobo, LIP-301, 65.6 g) and molecular sieves 4A (65.6 g) were added at room temperature, and the mixture was stirred at room temperature for 77 hr. Lipase (Toyobo, LIP-301, 8.2 g) was added to the reaction mixture, and the mixture was stirred at room temperature for 118 hr. Lipase (Toyobo, LIP-301, 16.4 g) was again added to the reaction mixture, and the mixture was stirred at room temperature for 140 hr. Lipase (Toyobo, LIP-301, 16.4 g) was further added to the reaction mixture, and the mixture was stirred at room temperature for 333 hr. The completion of the reaction was confirmed by HPLC, and the reaction mixture was filtered. The filtrate was concentrated under reduced pressure, and the residue was subjected to silica gel column chromatography, and a fraction eluted with ethyl acetate-hexane (1:9-3:2) was concentrated under reduced pressure to give a first elution component (9.5 g) and a second elution component (8.0 g). It was confirmed that the first elution component was a compound of Example 75-1 wherein the hydroxyl group was acetylated, and the second elution component (99.7%de) was the same as the compound of Example 75-2.

The obtained first elution component (100 mg) was dissolved in methanol (1 ml), 1M aqueous sodium hydroxide solution (1 ml) was added and the mixture was stirred at room temperature for 1 hr. 1M Hydrochloric acid (1 ml) was added to the reaction mixture for neutralization and methanol was evaporated under reduced pressure. The concentrate was diluted with water, and the mixture was extracted with ethyl acetate. The extract was washed with saturated brine, dried over anhydrous sodium sulfate, and concentrated under reduced pressure. The residue was dissolved in ethanol (1 ml), 12M hydrochloric acid (0.50 ml) was added and the mixture was stirred at room temperature for 1 hr. The reaction mixture was concentrated under reduced pressure, the residue was dissolved in ethanol, and ethanol was evaporated under reduced pressure. This operation was repeated twice to give the object product (62 mg) of Example compound 127-1.

Example 127-1

Spectrum Data $^1$H-NMR (CDCl$_3$) δ 0.71 (2 H, dd), 0.79-1.11 (7 H, m), 1.32-1.58 (4 H, m), 1.60-1.68 (1 H, m), 1.70-1.85 (3 H, m), 1.87-2.20 (2 H, m), 2.59-2.87 (1 H, m), 3.00 (1 H, d), 3.08-3.23 (4 H, m), 3.23-3.41 (6 H, m), 3.49 (1 H, d), 3.89-4.23 (2

H, m), 4.23-4.55 (2 H, m), 7.16-7.52 (2 H, m), 7.55-7.86 (2 H, m), 8.24-9.18 (1 H, m), 9.21-9.57 (1 H, m)

MS (ESI+, m/e) 445 (M+1)

The obtained second elution component (0.85 g) was dissolved in ethanol (2 ml), 12M hydrochloric acid (1.5 ml) was added, and the mixture was stirred at room temperature for 1 hr. The reaction mixture was concentrated under reduced pressure, the residue was dissolved in ethanol, and ethanol was evaporated under reduced pressure. This operation was repeated twice to give the object product (0.64 g) of Example compound 127-2.

Example 127-2

Spectrum Data $^1$H-NMR (CDCl$_3$) δ 0.71 (2 H, dd), 0.78-1.01 (7 H, m), 1.26-1.66 (4 H, m), 1.66-1.86 (4 H, m), 1.93 (1 H, d), 2.02-2.23 (1 H, m), 2.53-2.84 (1 H, m), 3.03-3.24 (5 H, m), 3.31 (5 H, q), 3.37-3.56 (2 H, m), 4.16 (2 H, br s), 4.22-4.44 (2 H, m), 7.16-7.54 (2 H, m), 7.54-7.87 (2 H, m), 8.16-9.27 (1 H, m), 9.36-9.84 (1 H, m)

MS (ESI+, m/e) 445 (M+1)

In the same manner as in Reference Example 82, the following compound (Reference Example 225) was obtained.

Reference Example 225 tert-butyl(3S, 5R)-3-[{[1-(4-methoxybutyl)-1H-benzimidazol-2-yl]carbonyl}(2-methylpropyl)amino]-5-[(4-methoxypiperidin-1-yl)carbonyl]piperidine-1-carboxylate

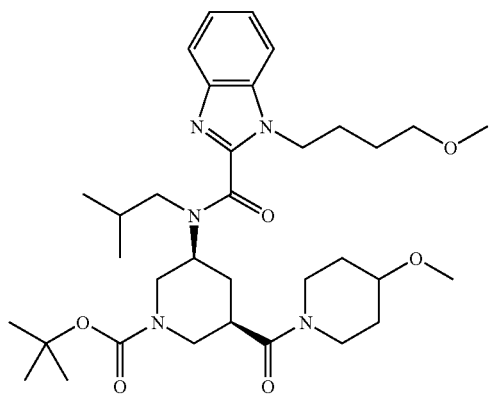 [SMILES: COCCCCn1c(C(=O)N(CC(C)C)[C@H]2C[C@@H](C(=O)N3CCC(OC)CC3)CN(C(=O)OC(C)(C)C)C2)nc2ccccc21]

MS (ESI+, m/e) 628 (M+1)

In the same manner as in Example 25, the following compound (Example 128) was obtained.

Example 128

1-(4-methoxybutyl)-N-{(3S, 5R)-5-[(4-methoxypiperidin-1-yl)carbonyl]piperidin-3-yl}-N-(2-methylpropyl)-1H-benzimidazole-2-carboxamide dihydrochloride

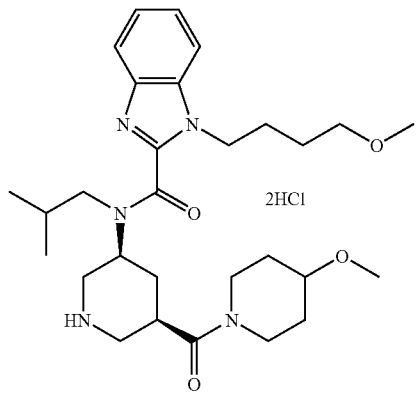 [SMILES: COCCCCn1c(C(=O)N(CC(C)C)[C@@H]2CNC[C@H](C(=O)N3CCC(OC)CC3)C2)nc2ccccc21 ; "2HCl"]

MS (ESI+, m/e) 528 (M+1)

Example 129

1-(3-ethoxypropyl)-N-(2-methylpropyl)-N-[(3S, 5R)-5-(morpholin-4-ylcarbonyl)piperidin-3-yl]-1H-benzimidazole-2-carboxamide trifluoroacetate

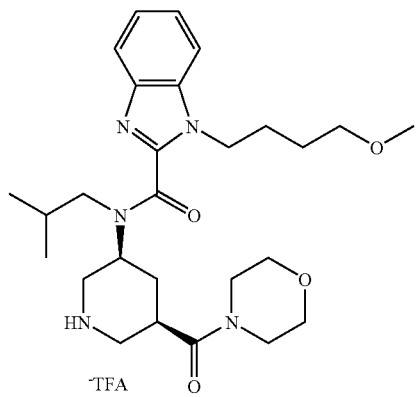 [SMILES: COCCCCn1c(C(=O)N(CC(C)C)[C@@H]2CNC[C@H](C(=O)N3CCOCC3)C2)nc2ccccc21]

A 0.16M solution (500 μL, 80 μmol) of tert-butyl(3S, 5R)-3-[(2-methylpropyl)amino]-5-(morpholin-4-ylcarbonyl)piperidine-1-carboxylate in toluene, a 0.32M solution (500 μL, 160 μmol) of triphenylphosphine in toluene, and a 0.32M solution (500 μL, 160 μmol) of 3-ethoxypropan-1-ol in toluene were mixed, diisopropyl azodicarboxylate (30 μL, 160 μmol) was added at room temperature and the mixture was stirred for 16 hr. 4N Hydrochloric acid-ethyl acetate solution (2.0 ml) was added to the reaction mixture, and the mixture was further stirred at room temperature for 5 hr. 4N Aqueous sodium hydroxide solution (2.0 ml) was added, and the mixture was neutralized and extracted. The organic layer was separated by upper layer Phase Septube (manufactured by Wako Pure Chemical Industries, Ltd.). The solvent was evaporated under reduced pressure, and the residue was dissolved in DMSO-methanol (1:1) (1 ml) and purified by preparative HPLC. The object fraction was concentrated, and the residue was diluted with aqueous calcium carbonate solution and extracted with ethyl acetate. The extract was washed with saturated brine, and dried over anhydrous magnesium sulfate. The solvent was evaporated under reduced pressure to give the title compound (38.4 mg).

MS (ESI+):500 (M+H)

In the same manner as in Example 129, the following compounds (Examples 130-146) were obtained.

Example 130

1-(4-methoxybutyl)-N-(2-methylpropyl)-N-[(3S, 5R)-5-(morpholin-4-ylcarbonyl)piperidin-3-yl]-1H-benzimidazole-2-carboxamide trifluoroacetate

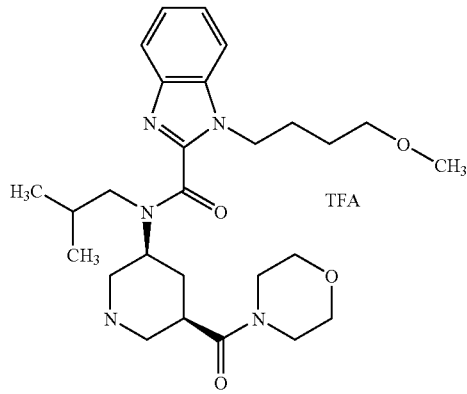 [SMILES: COCCCCn1c(C(=O)N(CC(C)C)[C@@H]2CNC[C@H](C(=O)N3CCOCC3)C2)nc2ccccc21]

MS (ESI+, m/e) 500 (M+1)

Example 131

1-(3-methoxypropyl)-N-(2-methylpropyl)-N-[(3S, 5R)-5-(morpholin-4-ylcarbonyl)piperidin-3-yl]-1H-benzimidazole-2-carboxamide trifluoroacetate

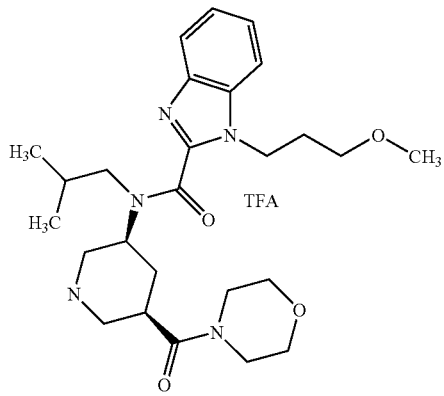 [SMILES: "TFA" ; COCCCn1c(C(=O)N(CC(C)C)[C@@H]2CNC[C@H](C(=O)N3CCOCC3)C2)nc2ccccc21]

MS (ESI+, m/e) 486 (M+1)

Example 132

N-(2-methylpropyl)-1-[3-(methylsulfanyl)propyl]-N-[(3S, 5R)-5-(morpholin-4-ylcarbonyl)piperidin-3-yl]-1H-benzimidazole-2-carboxamide trifluoroacetate

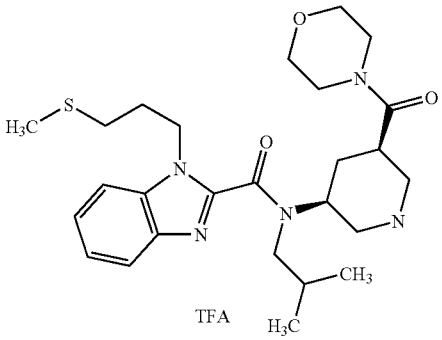 [SMILES: "TFA" ; CSCCCn1c(C(=O)N(CC(C)C)[C@@H]2CNC[C@H](C(=O)N3CCOCC3)C2)nc2ccccc21]

MS (ESI+, m/e) 502 (M+1)

Example 133

N-(2-methylpropyl)-1-[2-(methylsulfanyl)ethyl]-N-[(3S, 5R)-5-(morpholin-4-ylcarbonyl)piperidin-3-yl]-1H-benzimidazole-2-carboxamide trifluoroacetate

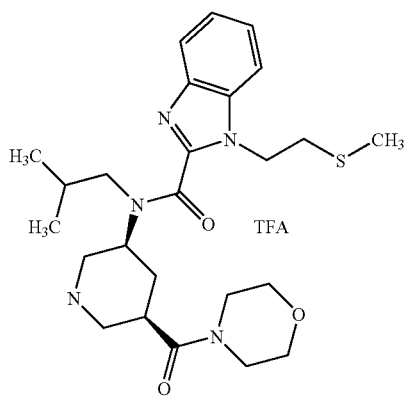 [SMILES: "TFA" ; CSCCn1c(C(=O)N(CC(C)C)[C@@H]2CNC[C@H](C(=O)N3CCOCC3)C2)nc2ccccc21]

MS (ESI+, m/e) 488 (M+1)

Example 134

1-ethyl-N-(2-methylpropyl)-N-[(3R, 5S)-5-(morpholin-4-ylcarbonyl)piperidin-3-yl]-1H-benzimidazole-2-carboxamide trifluoroacetate

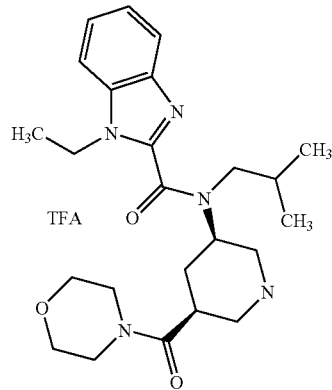 [SMILES: "TFA" ; CCn1c(C(=O)N(CC(C)C)[C@H]2CNC[C@@H](C(=O)N3CCOCC3)C2)nc2ccccc21]

MS (ESI+, m/e) 442 (M+1)

Example 135

1-(1-methylethyl)-N-(2-methylpropyl)-N-[(3S, 5R)-5-(morpholin-4-ylcarbonyl)piperidin-3-yl]-1H-benzimidazole-2-carboxamide trifluoroacetate

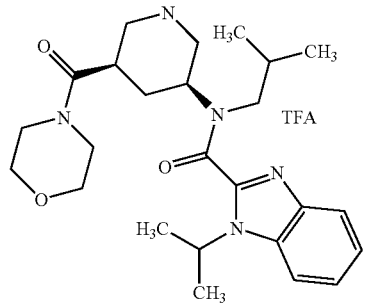 [SMILES: CC(C)CN(C(=O)c1nc2ccccc2n1C(C)C)[C@@H]1CNC[C@H](C(=O)N2CCOCC2)C1]

MS (ESI+, m/e) 456 (M+1)

Example 136

N-(2-methylpropyl)-N-[(3S, 5R)-5-(morpholin-4-ylcarbonyl)piperidin-3-yl]-1-propyl-1H-benzimidazole-2-carboxamide trifluoroacetate

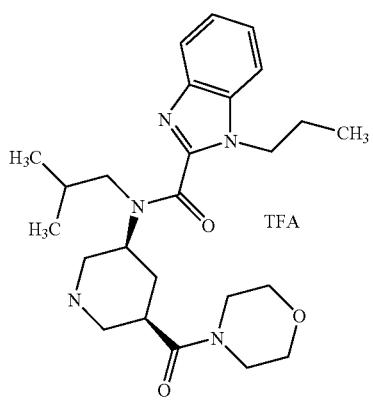 [SMILES: CCCn1c(C(=O)N(CC(C)C)[C@@H]2CNC[C@H](C(=O)N3CCOCC3)C2)nc2ccccc21]

MS (ESI+, m/e) 456 (M+1)

Example 137

1-butyl-N-(2-methylpropyl)-N-[(3S, 5R)-5-(morpholin-4-ylcarbonyl)piperidin-3-yl]-1H-benzimidazole-2-carboxamide trifluoroacetate

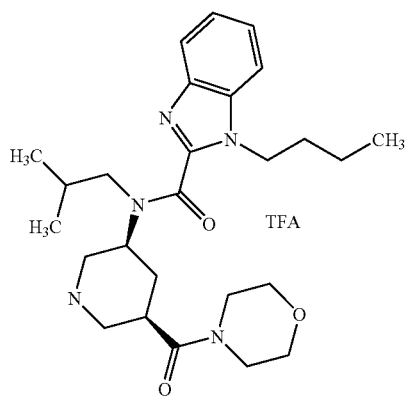 [SMILES: CCCCn1c(C(=O)N(CC(C)C)[C@@H]2CNC[C@H](C(=O)N3CCOCC3)C2)nc2ccccc21]

MS (ESI+, m/e) 470 (M+1)

Example 138

N-(2-methylpropyl)-N-[(3S, 5R)-5-(morpholin-4-ylcarbonyl)piperidin-3-yl]-1-(pent-3-yn-1-yl)-1H-benzimidazole-2-carboxamide trifluoroacetate

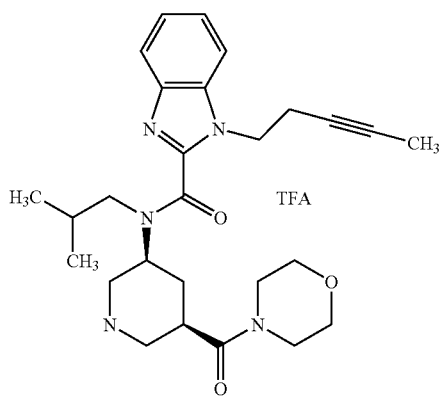 [SMILES: CC#CCCn1c(C(=O)N(CC(C)C)[C@@H]2CNC[C@H](C(=O)N3CCOCC3)C2)nc2ccccc21]

MS (ESI+, m/e) 480 (M+1)

Example 139

1-[(2-methylcyclopropyl)methyl]-N-(2-methylpropyl)-N-[(3S, 5R)-5-(morpholin-4-ylcarbonyl)piperidin-3-yl]-1H-benzimidazole-2-carboxamide trifluoroacetate

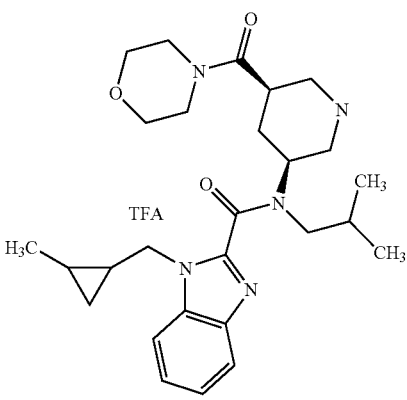 [SMILES: CC(C)CN(C(=O)c1nc2ccccc2n1CC1CC1C)[C@@H]1CNC[C@H](C(=O)N2CCOCC2)C1]

MS (ESI+, m/e) 482 (M+1)

Example 140

1-(2,2-difluoroethyl)-N-(2-methylpropyl)-N-[(3S, 5R)-5-(morpholin-4-ylcarbonyl)piperidin-3-yl]-1H-benzimidazole-2-carboxamide trifluoroacetate

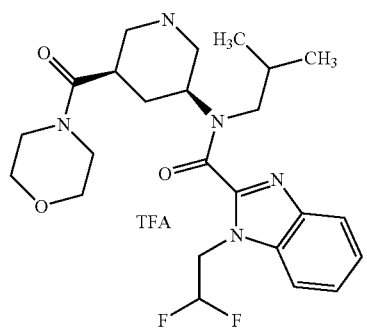 [SMILES: CC(C)CN(C(=O)c1nc2ccccc2n1CC(F)F)[C@@H]1CNC[C@H](C(=O)N2CCOCC2)C1]

MS (ESI+, m/e) 478 (M+1)

Example 141

N-(2-methylpropyl)-N-[(3S, 5R)-5-(morpholin-4-ylcarbonyl)piperidin-3-yl]-1-(3,3,3-trifluoropropyl)-1H-benzimidazole-2-carboxamide trifluoroacetate

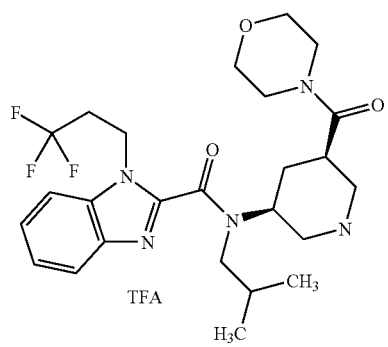 [SMILES: CC(C)CN(C(=O)c1nc2ccccc2n1CCC(F)(F)F)[C@@H]1CNC[C@H](C(=O)N2CCOCC2)C1]

MS (ESI+, m/e) 510 (M+1)

Example 142

N-(2-methylpropyl)-N-[(3S, 5R)-5-(morpholin-4-ylcarbonyl)piperidin-3-yl]-1-(4,4,4-trifluorobutyl)-1H-benzimidazole-2-carboxamide trifluoroacetate

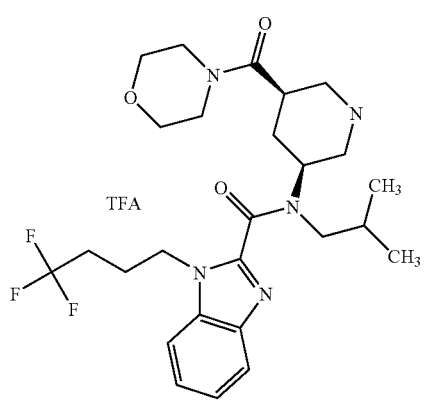 [SMILES: CC(C)CN(C(=O)c1nc2ccccc2n1CCCC(F)(F)F)[C@@H]1CNC[C@H](C(=O)N2CCOCC2)C1]

MS (ESI+, m/e) 524 (M+1)

Example 143

N-(2-methylpropyl)-N-[(3S, 5R)-5-(morpholin-4-ylcarbonyl)piperidin-3-yl]-1-(4-oxopentyl)-1H-benzimidazole-2-carboxamide trifluoroacetate

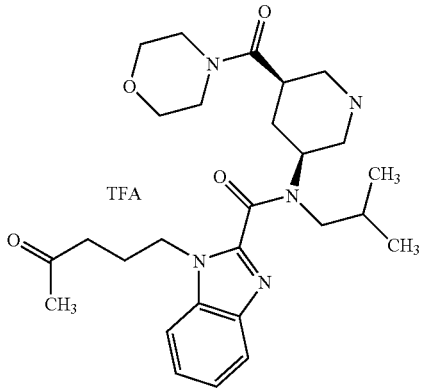 [SMILES: CC(=O)CCCn1c(C(=O)N(CC(C)C)[C@@H]2CNC[C@H](C(=O)N3CCOCC3)C2)nc2ccccc21]

MS (ESI+, m/e) 498 (M+1)

Example 144

N-(2-methylpropyl)-N-[(3S, 5R)-5-(morpholin-4-ylcarbonyl)piperidin-3-yl]-1-(2-(pyridin-2-yl)ethyl)-1H-benzimidazole-2-carboxamide ditrifluoroacetate

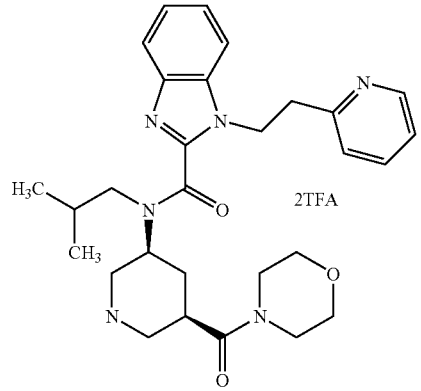 [SMILES: CC(C)CN(C(=O)c1nc2ccccc2n1CCc1ccccn1)[C@@H]1CNC[C@H](C(=O)N2CCOCC2)C1 ; "2TFA"]

MS (ESI+, m/e) 519 (M+1)

Example 145

N-(2-methylpropyl)-N-[(3S, 5R)-5-(morpholin-4-ylcarbonyl)piperidin-3-yl]-1-(2-(pyridin-3-yl)ethyl)-1H-benzimidazole-2-carboxamide ditrifluoroacetate

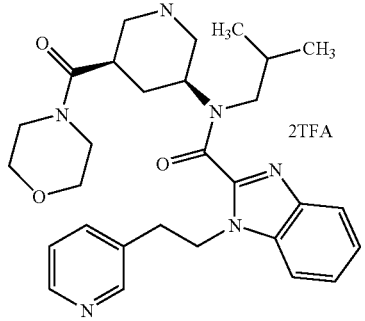 [SMILES: CC(C)CN(C(=O)c1nc2ccccc2n1CCc1cccnc1)[C@@H]1CNC[C@H](C(=O)N2CCOCC2)C1 ; "2TFA"]

MS (ESI+, m/e) 519 (M+1)

Example 146

N-(2-methylpropyl)-1-[2-(4-methyl-1,3-thiazol-5-yl)ethyl]-N-[(3S, 5R)-5-(morpholin-4-ylcarbonyl)piperidin-3-yl]-1H-benzimidazole-2-carboxamide trifluoroacetate

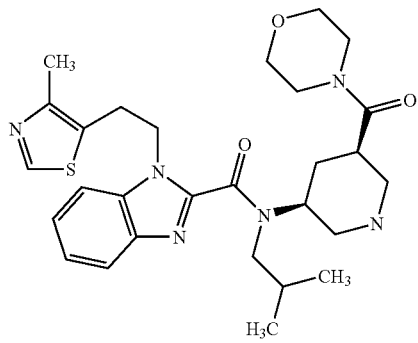 [SMILES: Cc1ncsc1CCn1c(C(=O)N(CC(C)C)[C@@H]2CNC[C@H](C(=O)N3CCOCC3)C2)nc2ccccc21]

MS (ESI+, m/e) 539 (M+1)

Reference Example 225 ethyl 2-tert-butyl-6-oxo-1,6-dihydropyrimidine-5-carboxylate

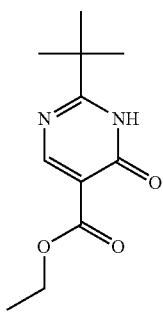 [SMILES: CCOC(=O)c1cnc(C(C)(C)C)[nH]c1=O]

To a solution of diethyl 2,2-dimethylpropanimidamide m hydrochloride (1.36 g) and (ethoxymethylene)malonate (2.16 g) in ethanol (100 ml) was added 20% sodium ethoxide-ethanol solution (6.8 g) under ice-cooling, and the mixture was stirred at 80° C. for 5 hr. The reaction mixture was concentrated under reduced pressure, 1M hydrochloric acid (10 ml) was added under ice-cooling, and the mixture was extracted with ethyl acetate. The extract was concentrated under reduced pressure, hexane was added to the residue, and the precipitate was collected by filtration to give the object product(1.65 g) as a powder.

MS (ESI+, m/e) 225 (M+1)

$^1$H-NMR (CDCl$_3$) δ 8.33-1.41 (3H, m), 1.43 (9H, s), 4.32-4.41 (2H, m), 8.72 (1H, s).

Reference Example 226

2-tert-butyl-6-oxo-1,6-dihydropyrimidine-5-carboxylic acid

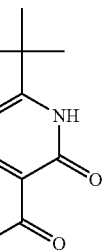

Ethyl 2-tert-butyl-6-oxo-1,6-dihydropyrimidine-5-carboxylate (43.9 g) was dissolved in ethanol (200 ml), 2M aqueous sodium hydroxide solution (330 ml) was added and the mixture was stirred at room temperature for 40 hr. The reaction mixture was concentrated under reduced pressure, and aqueous layer of the mixture was adjusted to pH 8 with 6M hydrochloric acid. The mixture was concentrated under reduced pressure and azeotroped with 2-propanol. The residue was suspended in acetone, and insoluble powder was collected by filtration. The obtained powder was suspended in 1M hydrochloric acid and the mixture was adjusted to pH 3, and concentrated under reduced pressure. The residue was azeotroped with 2-propanol, and the insoluble material was suspended in acetone and filtered off. The filtrate was concentrated under reduced pressure to give the object product (32.8 g) as a powder.

$^1$H-NMR (DMSO-d$_6$) δ 8.45 (9H, s), 8.99 (1H, s), 10.59 (1H, br s), 12.47 (1H, br s).

Reference Example 227

1-tert-butyl 3-methyl(3R, 5S)-5-{[(2-tert-butyl-4-chloropyrimidin-5-yl)carbonyl](isobutyl)amino}piperidine-1,3-dicarboxylate

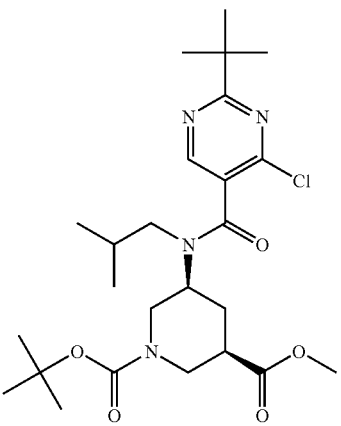 [SMILES: COC(=O)[C@@H]1C[C@H](N(CC(C)C)C(=O)c2cnc(C(C)(C)C)nc2Cl)CN(C(=O)OC(C)(C)C)C1]

2-tert-Butyl-6-oxo-1,6-dihydropyrimidine-5-carboxylic acid (3.25 g) was dissolved in THF (60 ml), thionyl chloride (4.3 ml) and DMF (5 drops) were added and the mixture was heated under reflux with stirring for 2.5 hr. The reaction mixture was cooled to room temperature, concentrated under reduced pressure, and the residue was azeotroped with toluene. The obtained residue was suspended in THF (50 ml), and the suspension was added to a solution of 1-tert-butyl 3-methyl (3R,5S)-5-(isobutylamino)piperidine-1,3-dicarboxylate (4.13 g) and diisopropylethylamine (9.15 µl) in THF (50 ml) and the mixture was stirred at room temperature for 8 hr. The reaction mixture was concentrated under reduced pressure, diluted with water, and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (1:19-2:3) was concentrated under reduced pressure to give the object product (6.29 g).

MS (ESI+, m/e) 511 (M+1)

Reference Example 228

1-tert-butyl 3-methyl(3R,5S)-5-{[(2-tert-butyl-4-(hex-1-yn-1-yl)pyrimidin-5-yl)carbonyl](2-methylpropyl)amino}piperidine-1,3-dicarboxylate

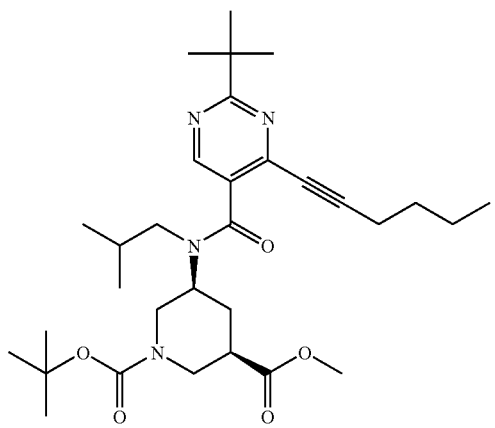 [SMILES: CCCCC#Cc1nc(C(C)(C)C)ncc1C(=O)N(CC(C)C)[C@H]1C[C@@H](C(=O)OC)CN(C(=O)OC(C)(C)C)C1]

1-tert-Butyl 3-methyl(3R,5S)-5-{[(2-tert-butyl-4-chloropyrimidin-5-yl)carbonyl](isobutyl)amino}piperidine-1,3-dicarboxylate (300 mg), dichloro[bis(triphenylphosphine)]palladium (412 mg), copper iodide (112 mg) and N,N-diisopropylethylamine (0.51 µL) were dissolved in DMF (8 ml), and the mixture was stirred at room temperature for 15 min. 1-Hexyne (0.08 ml) was added and the mixture was stirred at room temperature 2 hr, and further at 70° C. for 8 hr. The mixture was cooled to room temperature, adsorbed to silica gel (10 g), and a fraction eluted with ethyl acetate was concentrated under reduced pressure. The residue was subjected to silica gel column chromatography, and a fraction eluted with hexane-ethyl acetate (95:5-30:70) was concentrated under reduced pressure to give the object product (218 mg).

MS (ESI+, m/e) 557 (M+1)

Reference Example 229

1-tert-butyl 3-methyl(3R,5S)-5-{[(2-tert-butyl-4-hexylpyrimidin-5-yl)carbonyl](2-methylpropyl)amino}piperidine-1,3-dicarboxylate

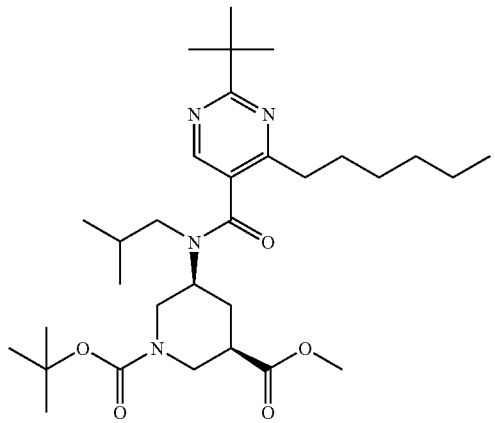 [SMILES: CCCCCCc1nc(C(C)(C)C)ncc1C(=O)N(CC(C)C)[C@H]1C[C@@H](C(=O)OC)CN(C(=O)OC(C)(C)C)C1]

1-tert-Butyl 3-methyl(3R,5S)-5-{[(2-tert-butyl-4-(hex-1-yn-1-yl)pyrimidin-5-yl)carbonyl](2-methylpropyl)amino}piperidine-1,3-dicarboxylate (218 mg) and palladium-carbon (20 mg) were suspended in methanol and the mixture was stirred under a hydrogen atmosphere (1 atom) at room temperature for 16 hr. The palladium catalyst was filtered off, and the filtrate was concentrated under reduced pressure to give the object product (219 mg) as a solid.

MS (ESI+, m/e) 561 (M+1)

Reference Example 230 tert-butyl(3S,5R)-3-{[(2-tert-butyl-4-hexylpyrimidin-5-yl)carbonyl](2-methylpropyl)amino}-5-(morpholin-4-ylcarbonyl)piperidine-1-carboxylate

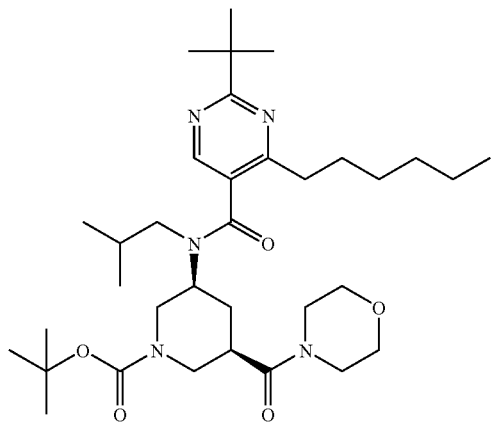 [SMILES: CCCCCCc1nc(C(C)(C)C)ncc1C(=O)N(CC(C)C)[C@H]1C[C@@H](C(=O)N2CCOCC2)CN(C(=O)OC(C)(C)C)C1]

1-tert-Butyl 3-methyl(3R,5S)-5-{[(2-tert-butyl-4-hexylpyrimidin-5-yl)carbonyl](2-methylpropyl)amino}piperidine-1,3-dicarboxylate (219 mg) was dissolved in methanol (3 ml) and THF (2 ml), 1M aqueous sodium hydroxide solution (2 ml) was added and the mixture was stirred at room temperature for 2 hr. The reaction mixture was concentrated under reduced pressure, and the aqueous layer of the mixture was adjusted to pH 5-6 with saturated aqueous ammonium chloride solution, and the mixture was extracted with ethyl acetate. The extract was washed with saturated brine, and dried over anhydrous magnesium sulfate. The solvent was evaporated under reduced pressure. The obtained residue, morpholine (41 µl), 1H-benzotriazol-1-ol (30 mg) and triethylamine (140 µl) were to dissolved in 1,2-dichloroethane (4 ml), WSC.HCl (115 mg) was added and the mixture was stirred at room temperature for 3 days. The reaction mixture was poured into water, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-80:20) was concentrated under reduced pressure to give the object product (88 mg).

MS (ESI+, m/e) 616 (M+1)

Reference Example 231

4-chloro-1-(4-methoxybutyl)-2-phenyl-1H-imidazole-5-carbaldehyde

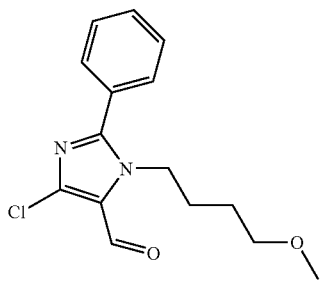 [SMILES: COCCCCn1c(-c2ccccc2)nc(Cl)c1C=O]

To a solution of 4-chloro-2-phenyl-1H-imidazole-5-carbaldehyde (500 mg) and 4-methoxybutyl methanesulfonate (660 mg) in N,N-dimethylacetamide (10 ml) was added cesium carbonate (2.4 g), and the mixture was stirred at 90° C. for 7 hr. After cooling to room temperature, the reaction mixture was diluted with water and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-3:7) was concentrated under reduced pressure to give the object product (702 mg).

$^1$H-NMR (CDCl$_3$) δ: 1.43-1.58 (2H, m), 1.76-1.88 (2H, m), 3.27 (3H, s), 3.30 (2H, t), 4.31-4.40 (2H, m), 7.52 (2H, d), 7.41-7.56 (1H, m), 7.56-7.69 (2H, m), 9.85 (1H, s).

MS (ESI+, m/e) 293 (M+1)

In the same manner as in the method shown in Reference Example 231, the following compound (Reference Example 232) was obtained.

Reference Example 232

2-butyl-4-chloro-1-(4-methoxybutyl)-1H-imidazole-5-carbaldehyde

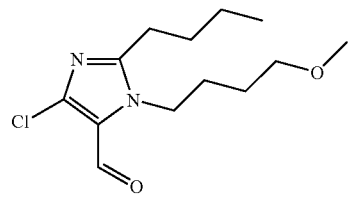 [SMILES: CCCCc1nc(Cl)c(C=O)n1CCCCOC]

$^1$H-NMR (CDCl$_3$) δ: 0.96 (3H, t), 1.33-1.49 (2H, m), 1.60 (2H, d), 1.68-1.85 (2H, m), 1.76 (2H, quin), 2.67 (1H, d), 2.67 (1H, s), 3.33 (3H, s), 3.41 (2H, t), 4.27 (1H, s), 4.23 (1H, d), 9.72 (1H, s).

MS (ESI+, m/e) 273 (M+1)

Reference Example 233

4-chloro-1-(4-methoxybutyl)-2-phenyl-1H-imidazole-5-carboxylic acid

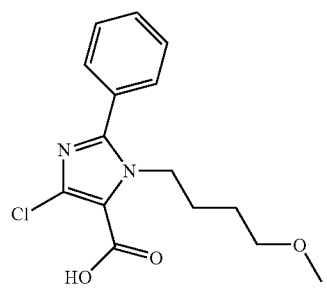 [SMILES: COCCCCn1c(-c2ccccc2)nc(Cl)c1C(=O)O]

To a solution of 4-chloro-1-(4-methoxybutyl)-2-phenyl-1H-imidazole-5-carbaldehyde (790 mg) in tert-butanol (15 ml) and 2-methyl-2-butene (1.5 ml) was added aqueous solution (4 ml) of sodium chlorite (300 mg) and sodium dihydrogen phosphate (400 mg), and the mixture was stirred at room temperature for 12 hr. 1M Hydrochloric acid was added, and the mixture was adjusted to pH 3, and extracted with ethyl acetate. The extract was washed with saturated brine, and dried over anhydrous magnesium sulfate. The solvent was evaporated under reduced pressure to give the object product (730 mg).

MS (ESI+, m/e) 309 (M+1)

In the same manner as in the method shown in Reference Example 233, the following compound (Reference Example 234) was obtained.

Reference Example 234

2-butyl-4-chloro-1-(4-methoxybutyl)-1H-imidazole-5-carboxylic acid

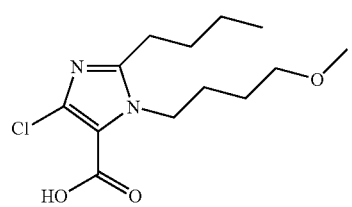 [SMILES: CCCCc1nc(Cl)c(C(=O)O)n1CCCCOC]

MS (ESI+, m/e) 289 (M+1)

Reference Example 235 tert-butyl(3S,5R)-3-[{[4-chloro-1-(4-methoxybutyl)-2-phenyl-1H-imidazol-5-yl]carbonyl}(2-methylpropyl)amino]-5-(morpholin-4-ylcarbonyl)piperidine-1-carboxylate

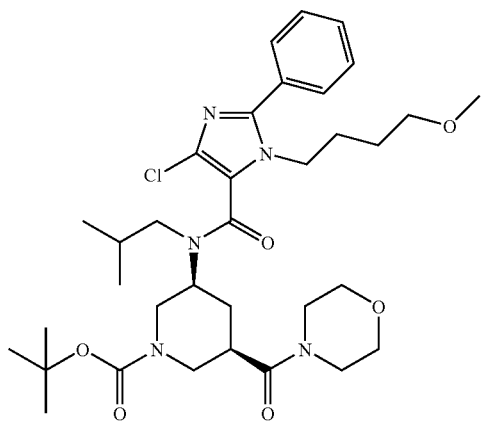 [SMILES: COCCCCn1c(-c2ccccc2)nc(Cl)c1C(=O)N(CC(C)C)[C@H]1C[C@@H](C(=O)N2CCOCC2)CN(C(=O)OC(C)(C)C)C1]

4-Chloro-1-(4-methoxybutyl)-2-phenyl-1H-imidazole-5-carboxylic acid (309 mg), tert-butyl(3S,5R)-3-[(2-methylpropyl)amino]-5-(morpholin-4-ylcarbonyl)piperidine-1-carboxylate (370 mg) obtained in Reference Example 22 and N,N-diisopropylethylamine (270 μl) were dissolved in 1,2-dichloroethane (8 ml), chloro-N,N,N',N'-tetramethylformamidinium hexafluorophosphate (340 mg) was added and the mixture was stirred at room temperature for 4 days. The reaction mixture was diluted with saturated aqueous sodium hydrogen carbonate solution and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (425 mg).

MS (ESI+, m/e) 661 (M+1)

In the same manner as in the method shown in Reference Example 235, the following compound (Reference Example 236) was obtained.

Reference Example 236 tert-butyl(3S,5R)-3-[{[2-butyl-4-chloro-1-(4-methoxybutyl)-1H-imidazol-5-yl]carbonyl}(2-methylpropyl)amino]-5-(morpholin-4-ylcarbonyl)piperidine-1-carboxylate

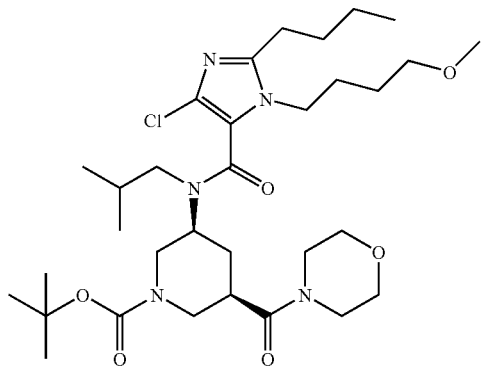 [SMILES: CCCCc1nc(Cl)c(C(=O)N(CC(C)C)[C@H]2C[C@@H](C(=O)N3CCOCC3)CN(C(=O)OC(C)(C)C)C2)n1CCCCOC]

MS (ESI+, m/e) 641 (M+1)

Reference Example 237 tert-butyl(3S,5R)-3-[{[1-(4-methoxybutyl)-2-phenyl-1H-imidazol-5-yl]carbonyl}(2-methylpropyl)amino]-5-(morpholin-4-ylcarbonyl)piperidine-1-carboxylate

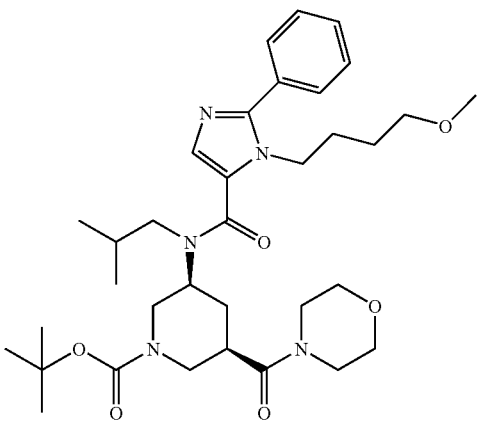 [SMILES: COCCCCn1c(C(=O)N(CC(C)C)[C@H]2C[C@@H](C(=O)N3CCOCC3)CN(C(=O)OC(C)(C)C)C2)cnc1-c1ccccc1]

tert-Butyl(3S,5R)-3-[{[4-chloro-1-(4-methoxybutyl)-2-phenyl-1H-imidazol-5-yl]carbonyl}(2-methylpropyl)amino]-5-(morpholin-4-ylcarbonyl)piperidine-1-carboxylate (200 mg), palladium(II) hydroxide-carbon (20 mg) and potassium acetate (30 mg) were suspended in methanol (10 ml), and the mixture was stirred under a hydrogen atmosphere (1 atom) at room temperature for 1 day. The palladium catalyst was filtered off and the filtrate was concentrated under reduced pressure. The residue was suspended in water, and the suspension was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-80:20) was concentrated under reduced pressure to give the object product (90 mg).

MS (ESI+, m/e) 626 (M+1)

In the same manner as in the method shown in Reference Example 237, the following compound (Reference Example 238) was obtained.

Reference Example 238 tert-butyl(3S,5R)-3-[{[2-butyl-1-(4-methoxybutyl)-1H-imidazol-5-yl]carbonyl}(2-methylpropyl)amino]-5-(morpholin-4-ylcarbonyl)piperidine-1-carboxylate

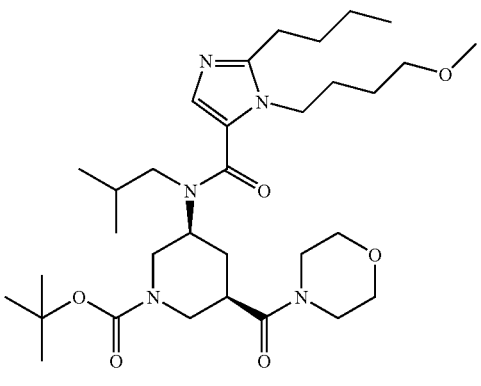 [SMILES: CCCCc1ncc(C(=O)N(CC(C)C)[C@H]2C[C@@H](C(=O)N3CCOCC3)CN(C(=O)OC(C)(C)C)C2)n1CCCCOC]

MS (ESI+, m/e) 606 (M+1)

Reference Example 239 tert-butyl N-[cyclohexyl(imino)methyl]glycinate

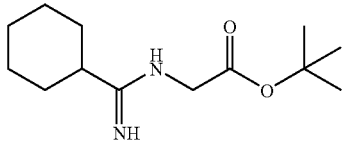 [SMILES: CC(C)(C)OC(=O)CNC(=N)C1CCCCC1]

To a solution of cyclohexanecarboximidamide hydrochloride (2.00 g) and tert-butyl glycinate hydrochloride (2.06 g) in DMF (16 ml) was added triethylamine (4.30 ml) at room temperature, and the mixture was stirred at 60° C. for 3 hr. The reaction mixture was cooled to room temperature, diluted with water, and the mixture was extracted with ethyl acetate. The extract was washed with saturated brine, and dried over anhydrous magnesium sulfate. The solvent was evaporated under reduced pressure to give the object product (0.84 g).

$^1$H-NMR (CDCl$_3$) δ: 1.26-1.34 (4H, m), 1.48 (7H, d), 1.63-1.78 (2H, m), 1.79-1.91 (1H, m), 1.84 (2H, dd), 1.97 (2H, d), 2.43 (1H, t), 3.93-4.02 (1H, m), 4.09 (2H, d).

Reference Example 240

4-chloro-2-cyclohexyl-1H-imidazole-5-carbaldehyde

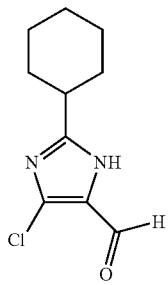 [SMILES: O=Cc1[nH]c(C2CCCCC2)nc1Cl]

tert-Butyl N-[cyclohexyl(imino)methyl]glycinate (830 mg) was dissolved in a solution (10%, 15 ml) of trifluoroacetic acid in 1,2-dichloroethane and the mixture was stirred at room temperature for 1 day. The reaction mixture was concentrated under reduced pressure. The residue was suspended in toluene, phosphorus oxychloride (3.21 ml) was added and the mixture was stirred at 80° C. for 30 min. DMF (2.67 ml) was added and the mixture was stirred at 100° C. for 5 hr. The reaction mixture was ice-cooled, basified by pouring into an aqueous sodium hydroxide solution, and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (495 mg).

$^1$H-NMR (CDCl$_3$) δ: 1.22-1.34 (1H, m), 1.39 (1H, dt), 1.57 (2H, qd), 1.74 (1H, ddd), 1.80-1.89 (1H, m), 1.83 (2H, dd), 2.02 (1H, d), 2.06 (1H, d), 2.79 (1H, tt), 9.65 (1H, s), 10.59 (1H, br s).

In the same manner as in the method shown in Reference Example 231, the following compound (Reference Example 241) was obtained.

Reference Example 241

4-chloro-2-cyclohexyl-1-(4-methoxybutyl)-1H-imidazole-5-carbaldehyde

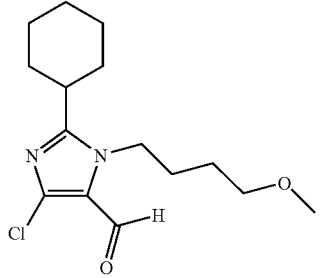 [SMILES: COCCCCn1c(C2CCCCC2)nc(Cl)c1C=O]

$^1$H-NMR (CDCl$_3$) δ: 1.27-1.43 (3H, m), 1.60-1.67 (3H, m), 1.69-1.81 (6H, m), 1.84-1.89 (2H, m), 2.65 (1H, tt), 3.29-3.46 (6H, m), 4.25 (2H, t), 9.71 (1H, s).

In the same manner as in the method shown in Reference Example 233, the following compound (Reference Example 242) was obtained.

Reference Example 242

4-chloro-2-cyclohexyl-1-(4-methoxybutyl)-1H-imidazole-5-carboxylic acid

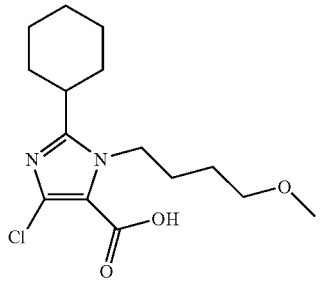 [SMILES: COCCCCn1c(C2CCCCC2)nc(Cl)c1C(=O)O]

MS (ESI+, m/e) 315 (M+1)

In the same manner as in the method shown in Reference Example 235, the following compound (Reference Example 243) was obtained.

Reference Example 243 tert-butyl(3S,5R)-3-[{[4-chloro-2-cyclohexyl-1-(4-methoxybutyl)-1H-imidazol-5-yl]carbonyl}(2-methylpropyl)amino]-5-(morpholin-4-ylcarbonyl)piperidine-1-carboxylate

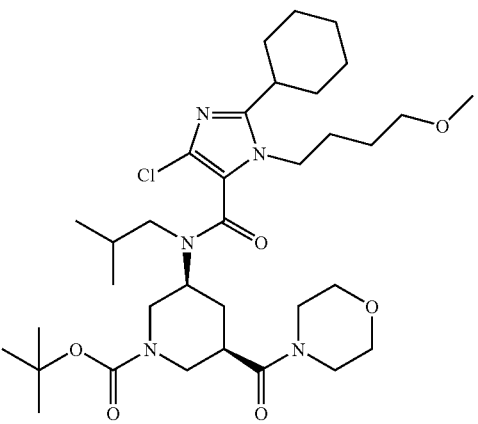 [SMILES: COCCCCn1c(C2CCCCC2)nc(Cl)c1C(=O)N(CC(C)C)[C@H]1C[C@@H](C(=O)N2CCOCC2)CN(C(=O)OC(C)(C)C)C1]

MS (ESI+, m/e) 667 (M+1)

In the same manner as in the method shown in Reference Example 237, the following compound (Reference Example 244) was obtained.

Reference Example 244 tert-butyl(3S,5R)-3-[{[2-cyclohexyl-1-(4-methoxybutyl)-1H-imidazol-5-yl]carbonyl}(2-methylpropyl)amino]-5-(morpholin-4-ylcarbonyl)piperidine-1-carboxylate

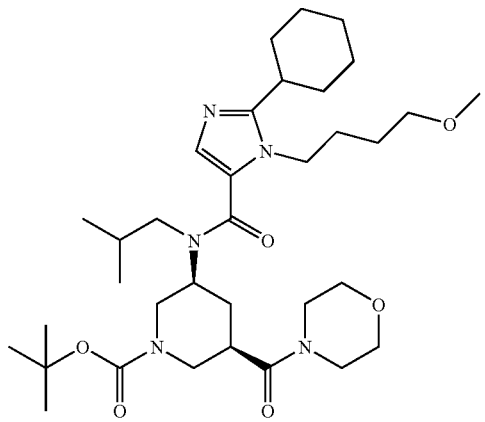 [SMILES: COCCCCn1c(C(=O)N(CC(C)C)[C@H]2C[C@@H](C(=O)N3CCOCC3)CN(C(=O)OC(C)(C)C)C2)cnc1C1CCCCC1]

MS (ESI+, m/e) 632 (M+1)

Reference Example 245 methyl 2-diazo-7-methoxy-3-oxoheptanoate

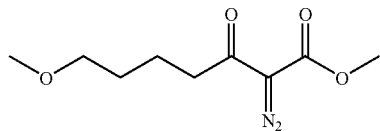

To a solution (100 ml) of methyl 7-methoxy-3-oxoheptanoate (5.00 g) and 4-(acetylamino)benzenesulfonyl azide (7.02 g) in acetonitrile was added triethylamine (11.1 ml) and the mixture was stirred at room temperature for 2 days. Insoluble material was filtered through celite, and the filtrate was concentrated under reduced pressure. The residue was suspended in diethyl ether and the insoluble material was filtered off. The filtrate was concentrated under reduced pressure to give the object product (6.93 g).

$^1$H-NMR (CDCl$_3$) δ: 1.49-1.83 (4H, m), 2.88 (2H, t), 3.32 (3H, s), 3.39 (2H, t), 3.84 (3H, s).

Reference Example 246 methyl 5-(4-methoxybutyl)-2-oxo-1-phenyl-2,3-dihydro-1H-imidazole-4-carboxylate

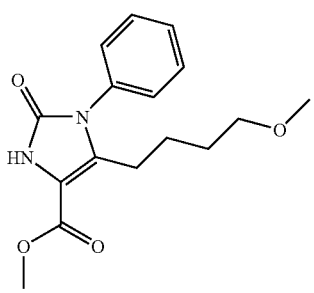 [SMILES: COCCCCc1c(C(=O)OC)[nH]c(=O)n1-c1ccccc1]

Methyl 2-diazo-7-methoxy-3-oxoheptanoate (6.93 g) and 1-phenylurea (5.41 g) were suspended in toluene (30 ml)-1,2-dichloroethane (30 ml), rhodium tetraacetate (230 mg) was added and the mixture was stirred at 80° C. for 2 hr. After cooling to room temperature, trifluoroacetic acid (7.5 ml) was added and the reaction mixture was stirred at room temperature for 1 day. The reaction mixture was concentrated under reduced pressure, and the residue was subjected to silica gel column chromatography, and a fraction eluted with ethyl acetate-hexane (15:85-100:0) was concentrated under reduced pressure to give the object product (7.40 g).

MS (ESI+, m/e) 305 (M+1)

Reference Example 247 methyl 2-chloro-5-(4-methoxybutyl)-1-phenyl-1H-imidazole-4-carboxylate

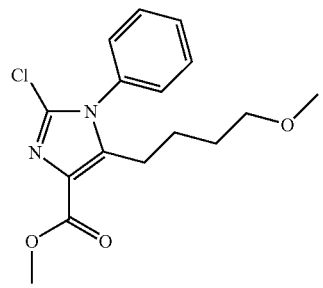 [SMILES: COCCCCc1c(C(=O)OC)nc(Cl)n1-c1ccccc1]

Methyl 5-(4-methoxybutyl)-2-oxo-1-phenyl-2,3-dihydro-1H-imidazole-4-carboxylate (1.50 g) was dissolved in phosphorus oxychloride (18 ml) and the mixture was stirred at 100° C. for 10 hr. After cooling to room temperature, the reaction mixture was concentrated under reduced pressure. The residue was diluted with saturated aqueous sodium hydrogen carbonate solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (454 mg).

$^1$H-NMR (CDCl$_3$) δ: 1.37-1.53 (4H, m), 2.72-2.88 (2H, m), 3.16-3.33 (5H, m), 3.92 (3H, s), 7.17-7.33 (2H, m), 7.51-7.57 (3H, m).

Reference Example 248

2-chloro-5-(4-methoxybutyl)-1-phenyl-1H-imidazole-4-carboxylic acid

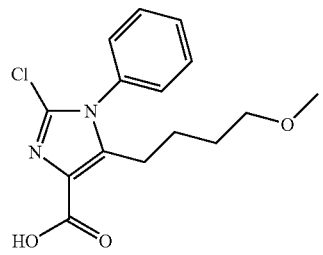 [SMILES: COCCCCc1c(C(=O)O)nc(Cl)n1-c1ccccc1]

Methyl 2-chloro-5-(4-methoxybutyl)-1-phenyl-1H-imidazole-4-carboxylate (450 mg) was dissolved in methanol (5 ml), 1M aqueous sodium hydroxide solution (4.2 ml) was added and the mixture was stirred at 80° C. for 2 hr. After cooling to room temperature, the reaction mixture was concentrated under reduced pressure. The residue was acidified with 1M hydrochloric acid and extracted with ethyl acetate. The extract was washed with saturated brine, and dried over anhydrous magnesium sulfate. The solvent was evaporated under reduced pressure to give the object product (372 mg).

MS (ESI+, m/e) 309 (M+1)

In the same manner as in the method shown in Reference Example 235, the following compound (Reference Example 249) was obtained.

Reference Example 249 tert-butyl(3S,5R)-3-[{[2-chloro-5-(4-methoxybutyl)-1-phenyl-1H-imidazol-4-yl]carbonyl}(2-methylpropyl)amino]-5-(morpholin-4-ylcarbonyl)piperidine-1-carboxylate

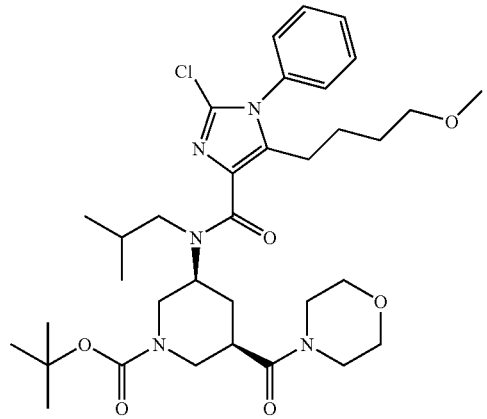 [SMILES: COCCCCc1c(C(=O)N(CC(C)C)[C@H]2C[C@@H](C(=O)N3CCOCC3)CN(C(=O)OC(C)(C)C)C2)nc(Cl)n1-c1ccccc1]

MS (ESI+, m/e) 661 (M+1)

In the same manner as in the method shown in Reference Example 237, the following compound (Reference Example 250) was obtained.

Reference Example 250 tert-butyl(3S,5R)-3-[{[5-(4-methoxybutyl)-1-phenyl-1H-imidazol-4-yl]carbonyl}(2-methylpropyl)amino]-5-(morpholin-4-ylcarbonyl)piperidine-1-carboxylate

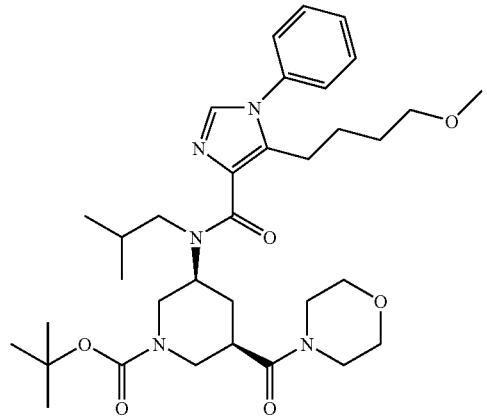 [SMILES: COCCCCc1c(C(=O)N(CC(C)C)[C@H]2C[C@@H](C(=O)N3CCOCC3)CN(C(=O)OC(C)(C)C)C2)ncn1-c1ccccc1]

MS (ESI+, m/e) 626 (M+1)

In the same manner as in the method shown in Reference Example 231, the following compound (Reference Example 251) was obtained.

Reference Example 251 ethyl 1-(4-methoxybutyl)-1H-imidazole-2-carboxylate

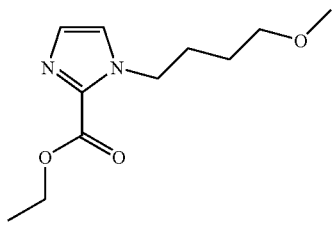 [SMILES: CCOC(=O)c1nccn1CCCCOC]

$^1$H-NMR (CDCl$_3$) δ: 1.43 (3H, t), 1.59 (2H, dd), 1.89 (2H, quin), 3.32 (3H, s), 3.39 (2H, t), 4.34-4.50 (4H, m), 7.12 (2H, d).

MS (ESI+, m/e) 227 (M+1)

Reference Example 252 ethyl 4-bromo-1-(4-methoxybutyl)-1H-imidazole-2-carboxylate

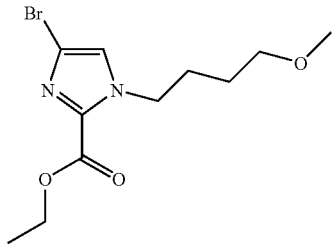 [SMILES: CCOC(=O)c1nc(Br)cn1CCCCOC]

Ethyl 1-(4-methoxybutyl)-1H-imidazole-2-carboxylate (2.18 g) was dissolved in acetonitrile (30 ml), N-bromosuccinimide (1.71 g) was added and the mixture was stirred at 60° C. for 14 hr. After cooling to room temperature, the reaction mixture was concentrated under reduced pressure. The residue was subjected to silica gel column chromatography, and a fraction eluted with ethyl acetate-hexane (10:90-70:30) was concentrated under reduced pressure to give the object product (689 mg).

$^1$H-NMR (CDCl$_3$) δ: 1.42 (3H, t), 1.60 (2H, dd), 1.89 (2H, quin), 3.33 (3H, s), 3.40 (2H, t), 4.34-4.50 (4H, m), 7.08 (1H, s).

MS (ESI+, m/e) 306 (M+1)

Reference Example 253 tert-butyl(3S,5R)-3-[{[4-bromo-1-(4-methoxybutyl)-1H-imidazol-2-yl]carbonyl}(2-methylpropyl)amino]-5-(morpholin-4-ylcarbonyl)piperidine-1-carboxylate

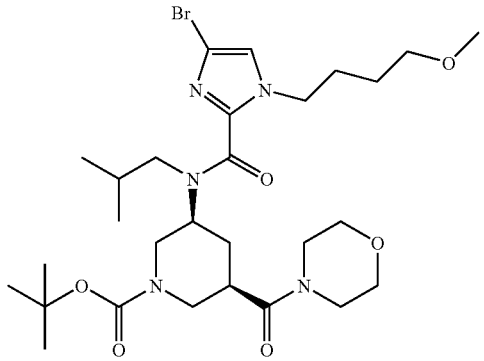 [SMILES: COCCCCn1cc(Br)nc1C(=O)N(CC(C)C)[C@H]1C[C@@H](C(=O)N2CCOCC2)CN(C(=O)OC(C)(C)C)C1]

Ethyl 4-bromo-1-(4-methoxybutyl)-1H-imidazole-2-carboxylate (290 mg) and lithium hydroxide monohydrate (60 mg) were suspended in THF (2 ml), ethanol(2 ml) and water (1 ml) and the mixture was stirred at room temperature for 2 hr. The reaction mixture was concentrated under reduced pressure. The obtained residue and tert-butyl(3S,5R)-3-[(2-methylpropyl)amino]-5-(morpholin-4-ylcarbonyl)piperidine-1-carboxylate (355 mg) obtained in Reference Example 22 were suspended in 1,2-dichloroethane (3 ml), chloro-N,N,N',N'-tetramethylformamidinium hexafluorophosphate (405 mg) was added and the mixture was stirred at room temperature for 3 days. The reaction mixture was diluted with saturated aqueous sodium hydrogen carbonate solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure. The obtained residue was purified by reversed-phase preparative HPLC, and the object fraction was concentrated under reduced pressure. The residue was basified with 3.5M aqueous potassium carbonate solution, and the mixture was extracted with ethyl acetate. The extract was washed with saturated brine, and dried over anhydrous magnesium sulfate. The solvent was evaporated under reduced pressure to give the object product (117 mg).

MS (ESI+, m/e) 629 (M+1)

Reference Example 254 methyl 2-methoxy-5-(4-methoxybutyl)-1-phenyl-1H-imidazole-4-carboxylate

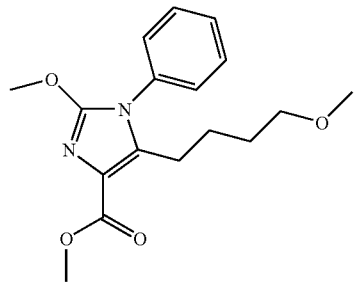

Methyl 5-(4-methoxybutyl)-2-oxo-1-phenyl-2,3-dihydro-1H-imidazole-4-carboxylate (2.00 g) was dissolved in dichloromethane (14 ml), trimethyloxonium tetrafluoroborate (2.00 g) was added and the mixture was stirred at room temperature for 16 hr. Saturated aqueous sodium hydrogen carbonate solution was added to the reaction mixture, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (585 mg).

$^1$H-NMR (CDCl$_3$) δ: 1.35-1.51 (4H, m), 2.72-2.81 (2H, m), 3.14-3.30 (5H, m), 3.90 (3H, s), 4.02 (3H, s), 7.20-7.33 (3H, m), 7.42-7.55 (2H, m).

MS (ESI+, m/e) 319 (M+1)

Reference Example 255 methyl 2-ethoxy-5-(4-methoxybutyl)-1-phenyl-1H-imidazole-4-carboxylate

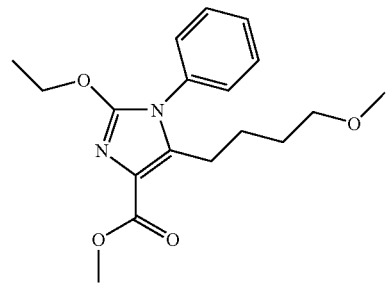 [SMILES: CCOc1nc(C(=O)OC)c(CCCCOC)n1-c1ccccc1]

Methyl 5-(4-methoxybutyl)-2-oxo-1-phenyl-2,3-dihydro-1H-imidazole-4-carboxylate (740 mg) was dissolved in acetonitrile (8 ml), a 1M solution (6.1 ml) of trimethyloxonium tetrafluoroborate in dichloromethane was added and the reaction mixture was stirred at room temperature for 3 days. Saturated aqueous sodium hydrogen carbonate solution was added to the reaction mixture, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-80:20) was concentrated under reduced pressure to give the object product (79 mg).

MS (ESI+, m/e) 333 (M+1)

In the same manner as in the method shown in Reference Example 248, the following compounds (Reference Examples 256-257) were obtained.

Reference Example 256

2-methoxy-5-(4-methoxybutyl)-1-phenyl-1H-imidazole-4-carboxylic acid

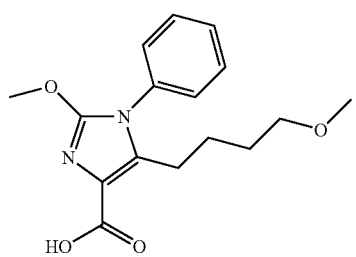

MS (ESI+, m/e) 305 (M+1)

Reference Example 257

2-ethoxy-5-(4-methoxybutyl)-1-phenyl-1H-imidazole-4-carboxylic acid

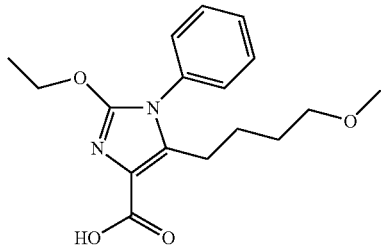 [SMILES: CCOc1nc(C(=O)O)c(CCCCOC)n1-c1ccccc1]

MS (ESI+, m/e) 319 (M+1)

In the same manner as in the method shown in Reference Example 235, the following compounds (Reference Examples 258-259) were obtained.

Reference Example 258 tert-butyl(3S,5R)-3-[{[2-methoxy-5-(4-methoxybutyl)-1-phenyl-1H-imidazol-4-yl]carbonyl}(2-methylpropyl)amino]-5-(morpholin-4-ylcarbonyl)piperidine-1-carboxylate

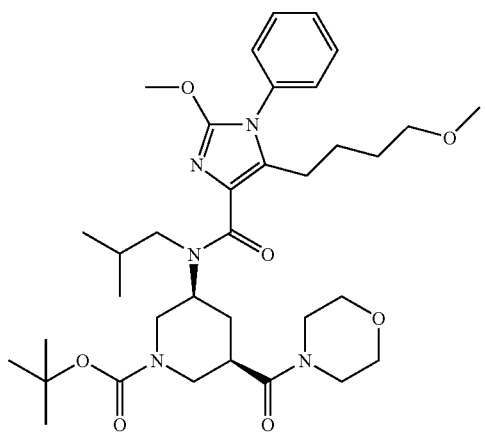 [SMILES: COCCCCc1c(C(=O)N(CC(C)C)[C@H]2C[C@@H](C(=O)N3CCOCC3)CN(C(=O)OC(C)(C)C)C2)nc(OC)n1-c1ccccc1]

MS (ESI+, m/e) 656 (M+1)

Reference Example 259 tert-butyl(3S,5R)-3-[{[2-ethoxy-5-(4-methoxybutyl)-1-phenyl-1H-imidazol-4-yl]carbonyl}(2-methylpropyl)amino]-5-(morpholin-4-ylcarbonyl)piperidine-1-carboxylate

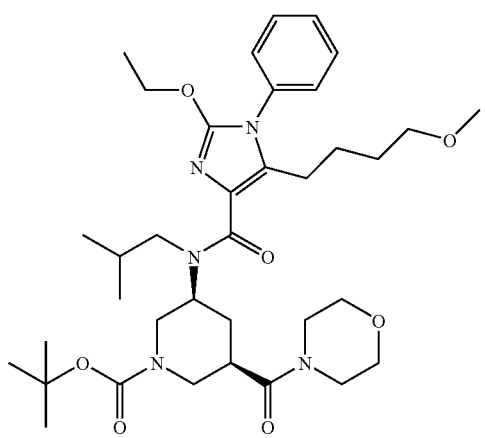 [SMILES: CCOc1nc(C(=O)N(CC(C)C)[C@H]2C[C@@H](C(=O)N3CCOCC3)CN(C(=O)OC(C)(C)C)C2)c(CCCCOC)n1-c1ccccc1]

MS (ESI+, m/e) 670 (M+1)

Reference Example 260 methyl 2-(hydroxyimino)-7-methoxy-3-oxoheptanoate

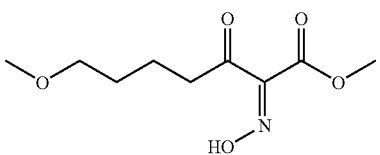

To an aqueous solution (20 ml) of sodium nitrite (2.20 g) was added dropwise a solution of methyl 7-methoxy-3-oxoheptanoate (5.00 g) obtained in Reference Example 359 in acetic acid (5 ml) under ice-cooling, and the reaction mixture was stirred at room temperature for 3 hr. The reaction mixture was diluted with water, and the mixture was extracted with ethyl acetate. The extract was washed with saturated brine, and dried over anhydrous magnesium sulfate. The solvent was evaporated under reduced pressure to give the object product (5.91 g).

$^1$H-NMR (CDCl$_3$) δ: 1.60-1.79 (4H, m), 2.82 (2H, t), 3.38 (3H, s), 3.46 (2H, t), 3.90 (3H, s).

Reference Example 261 methyl 2-(acetylamino)-7-methoxy-3-oxoheptanoate

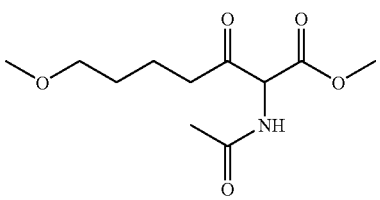

Methyl 2-(hydroxyimino)-7-methoxy-3-oxoheptanoate (5.70 g) and palladium-carbon (900 mg) were suspended in acetic acid (60 ml)-acetic anhydride (25 ml) and the mixture was stirred under a hydrogen atmosphere (1 atom) at room temperature for 14 hr. The palladium catalyst was filtered off, and the filtrate was concentrated under reduced pressure to give the object product (5.48 g).

$^1$H-NMR (CDCl$_3$) δ: 1.54-1.62 (2H, m), 1.65-1.75 (2H, m), 2.07 (3H, s), 2.75 (2H, q), 3.26-3.43 (5H, m), 3.81 (3H, s), 5.26 (1H, d), 6.65 (1H, br s).

Reference Example 262 methyl 5-(4-methoxybutyl)-2-methyl-1-phenyl-1H-imidazole-4-carboxylate

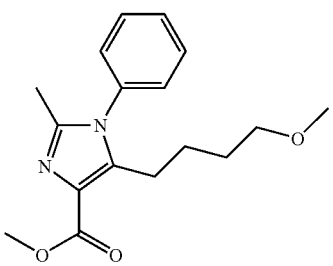

Methyl 2-(acetylamino)-7-methoxy-3-oxoheptanoate (5.45 g), 5 aniline (3.01 ml) and trifluoroacetic acid (2.48 ml) were dissolved in butyronitrile (30 ml), and the reaction mixture was heated under reflux for 2 hr. The reaction mixture was cooled to room temperature and concentrated under reduced pressure. 3.6M Aqueous potassium carbonate solution was added to the obtained residue and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (3.88 g).

$^1$H-NMR (CDCl$_3$) δ: 1.36-1.53 (4H, m), 1.71 (2H, td), 2.21 (3H, s), 2.76 (2H, t), 3.13-3.30 (3H, m), 3.91 (3H, s), 7.16-7.25 (2H, m), 7.47-7.61 (3H, m).

MS (ESI+, m/e) 303 (M+1)

Reference Example 263

5-(4-methoxybutyl)-2-methyl-1-phenyl-1H-imidazole-4-carboxylic acid

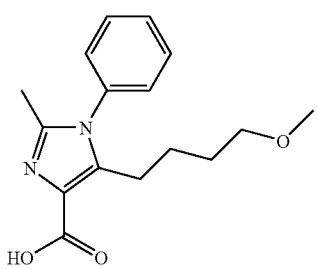

Methyl 5-(4-methoxybutyl)-2-methyl-1-phenyl-1H-imidazole-4-carboxylate (3.85 g) was dissolved in methanol (26 ml)-water (24 ml), lithium hydroxide monohydrate (800 mg) was added and the mixture was heated under reflux for 2 hr. After cooling to room temperature, the reaction mixture was concentrated under reduced pressure. The residue was adjusted to pH=7 with 1M hydrochloric acid, subjected to DIAION HP-20 (manufactured by Mitsubishi Chemical), washed with water and a fraction eluted with acetone was concentrated under reduced pressure to give the object product (1.08 g).

$^1$H-NMR (DMSO-d$_6$) δ: 1.28 (5H, br s), 2.07 (3H, s), 2.50 (1H, br s), 2.69 (2H, br s), 3.08 (3H, s), 7.41 (2H, d), 7.51-7.67 (3H, m).

MS (ESI+, m/e) 289 (M+1)

In the same manner as in the method shown in Reference Example 235, the following compound (Reference Example 264) was obtained.

Reference Example 264 tert-butyl(3S,5R)-3-[{[5-(4-methoxybutyl)-2-methyl-1-phenyl-1H-imidazol-4-yl]carbonyl}(2-methylpropyl)amino]-5-(morpholin-4-ylcarbonyl)piperidine-1-carboxylate

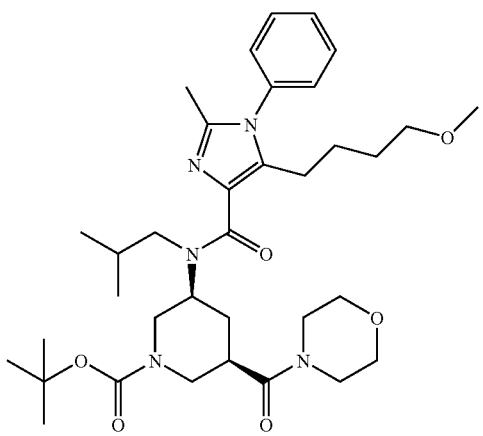 [SMILES: COCCCCc1c(C(=O)N(CC(C)C)[C@H]2C[C@@H](C(=O)N3CCOCC3)CN(C(=O)OC(C)(C)C)C2)nc(C)n1-c1ccccc1]

$^1$H-NMR (CDCl$_3$) δ: 0.94 (6H, br s), 1.35-1.52 (4H, m), 1.45 (9H, d), 1.83 (3H, br s), 2.02-2.19 (4H, m), 2.62 (2H, d), 2.72-2.85 (3H, m), 3.11-3.27 (6H, m), 3.49 (2H, br s), 3.58-3.75 (2H, m), 3.69 (5H, dd), 4.06-4.21 (2H, m), 7.17-7.33 (2H, m), 7.45-7.62 (3H, m).

MS (ESI+, m/e) 640 (M+1)

Reference Example 265

5-[(benzyloxy)methyl]-1-phenyl-1H-1,2,3-triazole-4-carboxylic acid

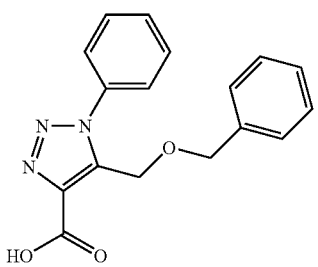 [SMILES: O=C(O)c1nnn(-c2ccccc2)c1COCc1ccccc1]

Methyl 4-(benzyloxy)-3-oxobutanoate (5.00 g) and azidobenzene (2.68 g) were dissolved in methanol (30 ml), sodium methanolate (28% methanol solution, 6.5 g) was added and the mixture was stirred at room temperature for 2 hr, and then heated under reflux for 18 hr. 1M Aqueous sodium hydroxide solution (10 ml) was added and the mixture was heated under reflux for 2 hr. The reaction mixture was cooled to room temperature and concentrated under reduced pressure. The residue was dissolved in water and washed with ethyl acetate-hexane (1:1, v/v). The obtained aqueous solution was acidified with 1M hydrochloric acid, and the mixture was extracted with ethyl acetate. The extract was washed with saturated brine, and dried over anhydrous magnesium sulfate. The solvent was evaporated under reduced pressure to give the object product (6.03 g).

$^1$H-NMR (CDCl$_3$) δ: 4.62 (2H, s), 4.88 (2H, s), 7.22-7.39 (5H, m), 7.47-7.62 (3H, m), 7.68 (2H, dd).

MS (ESI+, m/e) 310 (M+1)

Reference Example 266

1-tert-butyl 3-methyl(3R,5S)-5-[({5-[(benzyloxy)methyl]-1-phenyl-1H-1,2,3-triazol-4-yl}carbonyl)(2-methylpropyl)amino]piperidine-1,3-dicarboxylate

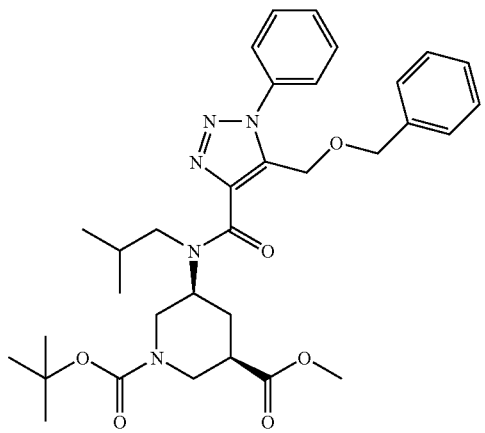 [SMILES: COC(=O)[C@@H]1C[C@H](N(CC(C)C)C(=O)c2nnn(-c3ccccc3)c2COCc2ccccc2)CN(C(=O)OC(C)(C)C)C1]

5-[(Benzyloxy)methyl]-1-phenyl-1H-1,2,3-triazole-4-carboxylic acid (6.00 g) was dissolved in THF (50 ml), thionyl chloride (2.15 ml) and DMF (5 drops) were added and the mixture was heated under reflux with stirring for 2 hr. The reaction mixture was cooled to room temperature, concentrated under reduced pressure, and the residue was azeotroped with toluene. The obtained residue was suspended in THF (20 ml), and the suspension was added to a solution of 1-tert-butyl 3-methyl(3R,5S)-5-(isobutylamino)piperidine-1,3-dicarboxylate (6.10 g) and diisopropylethylamine (10.0 μl) in THF (30 ml) and the mixture was stirred at room temperature for 14 hr. The reaction mixture was concentrated under reduced pressure, diluted with water, and extracted with ethyl acetate. The extract was washed successively with 1M hydrochloric acid and saturated brine, and dried over anhydrous magnesium sulfate. The solvent was evaporated under reduced pressure. The residue was subjected to silica gel column chromatography, and a fraction eluted with ethyl acetate-hexane (5:95-70:30) was concentrated under reduced pressure to give the object product (7.70 g).

$^1$H-NMR (CDCl$_3$) δ: 0.77-1.06 (6H, m), 1.36-1.53 (9H, m), 1.57 (2H, br s), 1.80-2.00 (1H, m), 2.14-2.33 (1H, m), 2.63 (2H, br s), 2.82 (1H, br s), 3.30 (1H, d), 3.56 (1H, br s), 3.71 (3H, s), 4.21-4.37 (2H, m), 4.54 (2H, s), 4.76 (2H, d), 7.17-7.22 (2H, m), 7.24-7.36 (3H, m), 7.46-7.57 (3H, m), 7.59-7.68 (2H, m).

MS (ESI+, m/e) 606 (M+1)

Reference Example 267

1-tert-butyl 3-methyl(3R,5S)-5-[{[5-(hydroxymethyl)-1-phenyl-1H-1,2,3-triazol-4-yl]carbonyl}(2-methylpropyl)amino]piperidine-1,3-dicarboxylate

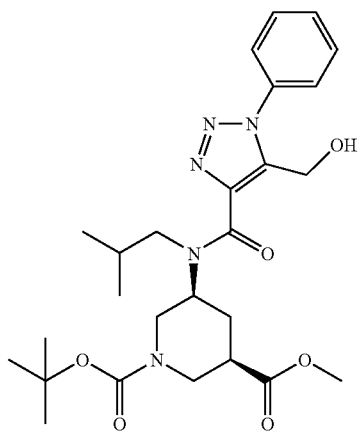 [SMILES: COC(=O)[C@@H]1C[C@H](N(CC(C)C)C(=O)c2nnn(-c3ccccc3)c2CO)CN(C(=O)OC(C)(C)C)C1]

1-tert-Butyl 3-methyl(3R,5S)-5-[({5-[(benzyloxy)methyl]-1-phenyl-1H-1,2,3-triazol-4-yl}carbonyl)(2-methylpropyl)amino]piperidine-1,3-dicarboxylate (2.92 g) and palladium(II) hydroxide-carbon (500 mg) were suspended in methanol, and the mixture was stirred under a hydrogen atmosphere (5 atom) at room temperature for 10 hr. The palladium catalyst was filtered off, and the filtrate was concentrated under reduced pressure to give the object product (2.39 g) as a solid.

$^1$H-NMR (CDCl$_3$) δ: 0.96 (6H, dd), 1.46 (9H, d), 1.60-1.95 (1H, m), 2.19 (1H, dt), 2.60 (1H, d), 2.68-2.93 (2H, m), 3.28 (1H, br s), 3.54 (1H, br s), 3.72 (3H, s), 4.32 (2H, br s), 4.65 (2H, d), 4.82-4.98 (2H, m), 7.57 (5H, s).

MS (ESI+, m/e) 516 (M+1)

Reference Example 268

(3R,5S)-1-(tert-butoxycarbonyl)-5[{[M5-(hydroxymethyl)-1-phenyl-1H-1,2,3-triazol-4-yl]carbonyl}(2-methylpropyl)amino]piperidine-3-carboxylic acid

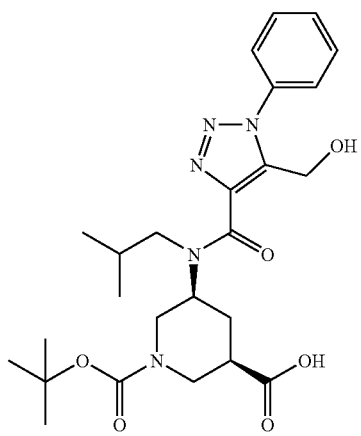 [SMILES: CC(C)CN(C(=O)c1nnn(-c2ccccc2)c1CO)[C@H]1C[C@@H](C(=O)O)CN(C(=O)OC(C)(C)C)C1]

311

1-tert-Butyl 3-methyl(3R,5S)-5-[{[5-(hydroxymethyl)-1-phenyl-1H-1,2,3-triazol-4-yl]carbonyl}(2-methylpropyl)amino]piperidine-1,3-dicarboxylate (2.25 g) was dissolved in THF (10 ml)-methanol (10 ml)-water (8 ml), 8M aqueous sodium hydroxide solution (1.5 ml) was added and the reaction mixture was stirred at room temperature for 3 hr. The reaction mixture was neutralized with saturated aqueous ammonium chloride solution, acidified with 1M hydrochloric acid and extracted with ethyl acetate. The extract was washed with saturated brine, and dried over anhydrous magnesium sulfate. The solvent was evaporated under reduced pressure to give the object product (2.18 g).

MS (ESI+, m/e) 502 (M+1)

Reference Example 269 tert-butyl(3S,5R)-3-[{[5-(hydroxymethyl)-1-phenyl-1H-1,2,3-triazol-4-yl]carbonyl}(2-methylpropyl)amino]-5-(morpholin-4-ylcarbonyl)piperidine-1-carboxylate

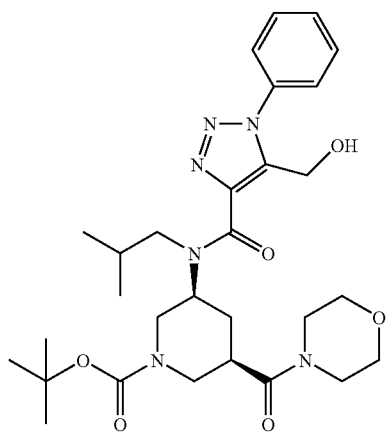 [SMILES: CC(C)CN(C(=O)c1nnn(-c2ccccc2)c1CO)[C@H]1C[C@@H](C(=O)N2CCOCC2)CN(C(=O)OC(C)(C)C)C1]

(3R,5S)-1-(tert-Butoxycarbonyl)-5-[{[5-(hydroxymethyl)-1-phenyl-1H-1,2,3-triazol-4-yl]carbonyl}(2-methylpropyl)amino]piperidine-3-carboxylic acid (2.18 g), 5 morpholine (0.46 ml), 1H-benzotriazol-1-ol (330 mg) and triethylamine (1.5 ml) were dissolved in acetonitrile (20 ml), WSC.HCl (1.25 g) was added and the mixture was stirred at room temperature for 3 days. The reaction mixture was poured into water, and the mixture was extracted with ethyl acetate. The extract was washed successively with saturated aqueous sodium hydrogen carbonate solution and saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (2.35 g).

$^1$H-NMR (CDCl$_3$) δ: 0.92 (2H, d), 0.98 (4H, dd), 1.42 (6H, s), 1.49 (3H, s), 2.04 (2H, s), 2.56 (1H, br s), 2.87 (3H, br s), 3.26 (1H, dd), 3.45 (2H, dd), 3.60-3.76 (2H, m), 3.68 (4H, t), 4.14-4.38 (2H, m), 4.52-4.80 (2H, m), 4.65 (1H, d), 4.90 (1H, dd), 7.49-7.65 (5H, m).

MS (ESI+, m/e) 571 (M+1)

312

Reference Example 270 tert-butyl(3S,5R)-3-[({5-[(2-methoxyethoxy)methyl]-1-phenyl-1H-1,2,3-triazol-4-yl}carbonyl)(2-methylpropyl)amino]-5-(morpholin-4-ylcarbonyl)piperidine-1-carboxylate

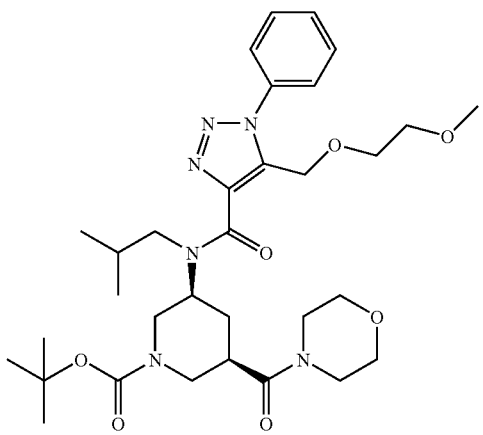 [SMILES: COCCOCc1c(C(=O)N(CC(C)C)[C@H]2C[C@@H](C(=O)N3CCOCC3)CN(C(=O)OC(C)(C)C)C2)nnn1-c1ccccc1]

tert-Butyl(3S,5R)-3-[{[5-(hydroxymethyl)-1-phenyl-1H-1,2,3-triazol-4-yl]carbonyl}(2-methylpropyl)amino]-5-(morpholin-4-ylcarbonyl)piperidine-1-carboxylate (215 mg) was dissolved in DMF (3 ml), sodium hydride (50% in oil, 30 mg) was added under ice-cooling. The reaction mixture was stirred at room temperature for 30 min, 1-bromo-2-methoxyethane (55 µl) was added under ice-cooling, and the mixture was further stirred at room temperature for 14 hr. The reaction mixture was diluted with saturated aqueous sodium hydrogen carbonate solution, and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (149 mg).

MS (ESI+, m/e) 629 (M+1)

Reference Example 271 tert-butyl(3S,5R)-3-[(2-methylpropyl){[5-(phenoxymethyl)-1-phenyl-1H-1,2,3-triazol-4-yl]carbonyl}amino]-5-(morpholin-4-ylcarbonyl)piperidine-1-carboxylate

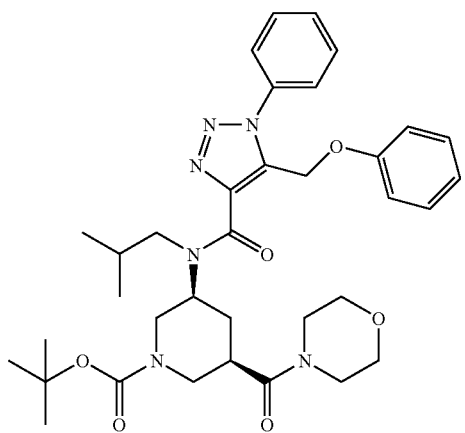 [SMILES: CC(C)CN(C(=O)c1nnn(-c2ccccc2)c1COc1ccccc1)[C@H]1C[C@@H](C(=O)N2CCOCC2)CN(C(=O)OC(C)(C)C)C1]

tert-Butyl(3S,5R)-3-[{[5-(hydroxymethyl)-1-phenyl-1H-1,2,3-triazol-4-yl]carbonyl}(2-methylpropyl)amino]-5-(morpholin-4-ylcarbonyl)piperidine-1-carboxylate (205 mg), phenol (70 mg) and triphenylphosphine (190 mg) were dissolved in toluene (5 ml), diisopropyl azodicarboxylate (40% toluene solution, 365 mg) was added, and the mixture was stirred at room temperature for 12 hr. The reaction mixture was poured into saturated brine, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted to with ethyl acetate-hexane (10:90-100:0) was concentrated under reduced pressure to give the object product (344 mg).

MS (ESI+, m/e) 647 (M+1)

In the same manner as in the method shown in Reference Example 271, the following compounds (Reference Examples 272-273) were obtained.

Reference Example 272 tert-butyl(3S,5R)-3-[({5-[(3-methoxyphenoxy)methyl]-1-phenyl-1H-1,2,3-triazol-4-yl}carbonyl)(2-methylpropyl)amino]-5-(morpholin-4-ylcarbonyl)piperidine-1-carboxylate

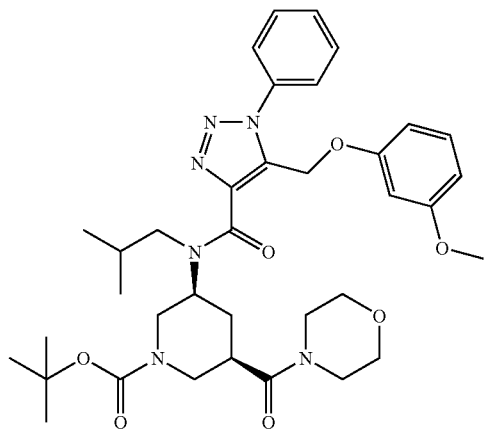 [SMILES: COc1cccc(OCc2c(C(=O)N(CC(C)C)[C@H]3C[C@@H](C(=O)N4CCOCC4)CN(C(=O)OC(C)(C)C)C3)nnn2-c2ccccc2)c1]

MS (ESI+, m/e) 677 (M+1)

Reference Example 273 tert-butyl(3S,5R)-3-[({5-[(4-methoxyphenoxy)methyl]-1-phenyl-1H-1,2,3-triazol-4-yl}carbonyl)(2-methylpropyl)amino]-5-(morpholin-4-ylcarbonyl)piperidine-1-carboxylate

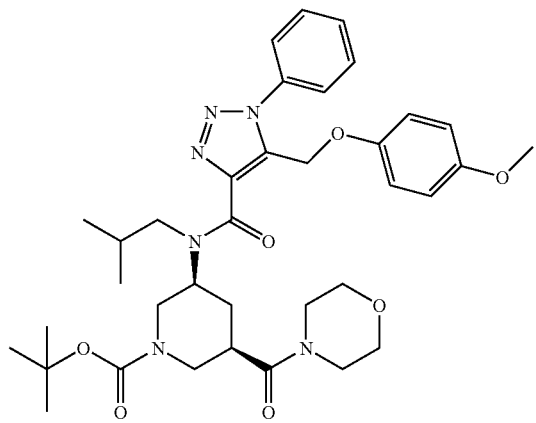 [SMILES: COc1ccc(OCc2c(C(=O)N(CC(C)C)[C@H]3C[C@@H](C(=O)N4CCOCC4)CN(C(=O)OC(C)(C)C)C3)nnn2-c2ccccc2)cc1]

MS (ESI+, m/e) 677 (M+1)

Example 147

2-tert-butyl-4-hexyl-N-(2-methylpropyl)-N-[(3S,5R)-5-(morpholin-4-ylcarbonyl)piperidin-3-yl]pyrimidine-5-carboxamide dihydrochloride

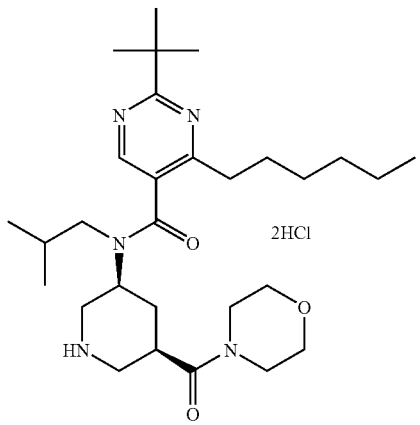 [SMILES: CCCCCCc1nc(C(C)(C)C)ncc1C(=O)N(CC(C)C)[C@@H]1CNC[C@H](C(=O)N2CCOCC2)C1 ; "2HCl"]

tert-Butyl(3S,5R)-3-{[(2-tert-butyl-4-hexylpyrimidin-5-yl)carbonyl](2-methylpropyl)amino}-5-(morpholin-4-ylcarbonyl)piperidine-1-carboxylate (88.4 mg) was dissolved in 1M hydrogen chloride-ethyl acetate (3 ml), and the mixture was stirred at room temperature for 1.5 hr. The reaction mixture was concentrated to give the object product (62.7 mg).

MS (ESI+, m/e) 516 (M+1)

In the same manner as in the method shown in the above-mentioned Example 147, the compounds described in the following Examples 148-159 were obtained.

Example 148

4-chloro-1-(4-methoxybutyl)-N-(2-methylpropyl)-N-[(3S,5R)-5-(morpholin-4-ylcarbonyl)piperidin-3-yl]-2-phenyl-1H-imidazole-5-carboxamide dihydrochloride

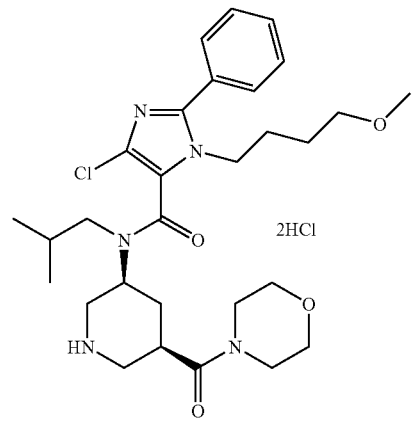 [SMILES: COCCCCn1c(-c2ccccc2)nc(Cl)c1C(=O)N(CC(C)C)[C@@H]1CNC[C@H](C(=O)N2CCOCC2)C1 ; "2HCl"]

MS (ESI+, m/e) 561 (M+1)

Example 149

1-(4-methoxybutyl)-N-(2-methylpropyl)-N-[(3S,5R)-5-(morpholin-4-ylcarbonyl)piperidin-3-yl]-2-phenyl-1H-imidazole-5-carboxamide dihydrochloride

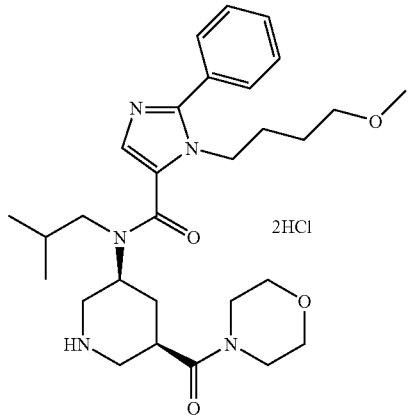 [SMILES: COCCCCn1c(C(=O)N(CC(C)C)[C@@H]2CNC[C@H](C(=O)N3CCOCC3)C2)cnc1-c1ccccc1 ; "2HCl"]

MS (ESI+, m/e) 526 (M+1)

Example 150

2-butyl-4-chloro-1-(4-methoxybutyl)-N-(2-methylpropyl)-N-[(3S,5R)-5-(morpholin-4-ylcarbonyl)piperidin-3-yl]-1H-imidazole-5-carboxamide dihydrochloride

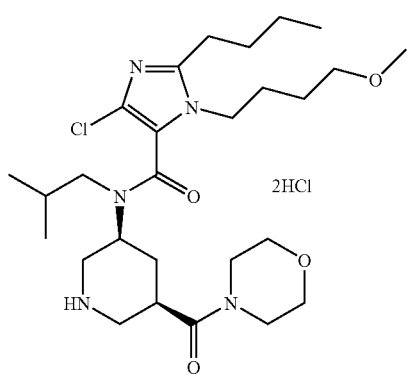 [SMILES: CCCCc1nc(Cl)c(C(=O)N(CC(C)C)[C@@H]2CNC[C@H](C(=O)N3CCOCC3)C2)n1CCCCOC ; "2HCl"]

MS (ESI+, m/e) 541 (M+1)

Example 151

2-butyl-1-(4-methoxybutyl)-N-(2-methylpropyl)-N-[(3S,5R)-5-(morpholin-4-ylcarbonyl)piperidin-3-yl]-1H-imidazole-5-carboxamide dihydrochloride

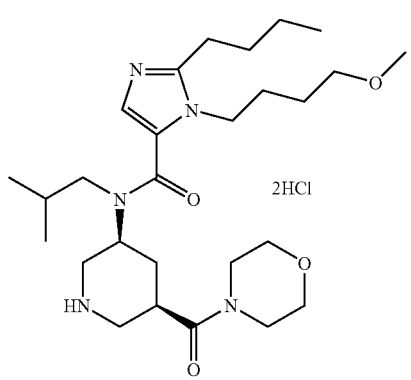 [SMILES: CCCCc1ncc(C(=O)N(CC(C)C)[C@@H]2CNC[C@H](C(=O)N3CCOCC3)C2)n1CCCCOC ; "2HCl"]

MS (ESI+, m/e) 506 (M+1)

Example 152

4-chloro-2-cyclohexyl-1-(4-methoxybutyl)-N-(2-methylpropyl)-N-[(3S,5R)-5-(morpholin-4-ylcarbonyl)piperidin-3-yl]-1H-imidazole-5-carboxamide dihydrochloride

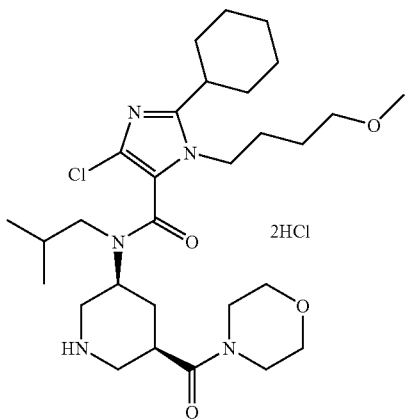 [SMILES: COCCCCn1c(C2CCCCC2)nc(Cl)c1C(=O)N(CC(C)C)[C@@H]1CNC[C@H](C(=O)N2CCOCC2)C1 ; "2HCl"]

MS (ESI+, m/e) 567 (M+1)

Example 153

2-cyclohexyl-1-(4-methoxybutyl)-N-(2-methylpropyl)-N-[(3S,5R)-5-(morpholin-4-ylcarbonyl)piperidin-3-yl]-1H-imidazole-5-carboxamide dihydrochloride

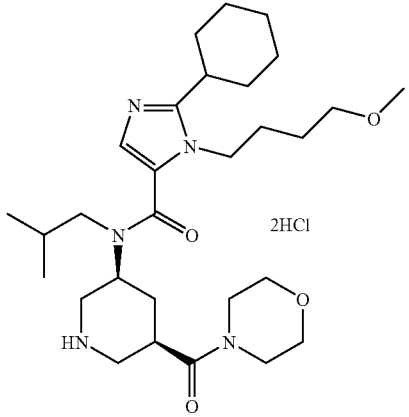 [SMILES: COCCCCn1c(C(=O)N(CC(C)C)[C@@H]2CNC[C@H](C(=O)N3CCOCC3)C2)cnc1C1CCCCC1 ; "2HCl"]

MS (ESI+, m/e) 532 (M+1)

Example 154

4-bromo-1-(4-methoxybutyl)-N-(2-methylpropyl)-N-[(3S,5R)-5-(morpholin-4-ylcarbonyl)piperidin-3-yl]-1H-imidazole-2-carboxamide dihydrochloride

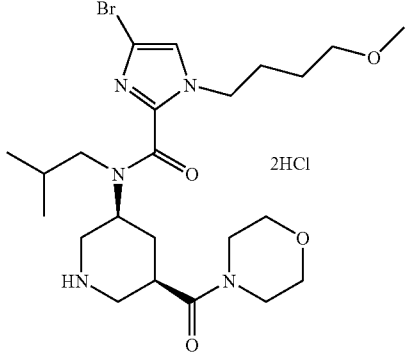 [SMILES: COCCCCn1cc(Br)nc1C(=O)N(CC(C)C)[C@@H]1CNC[C@H](C(=O)N2CCOCC2)C1 ; "2HCl"]

MS (ESI+, m/e) 529 (M+1)

317

Example 155

2-chloro-5-(4-methoxybutyl)-N-(2-methylpropyl)-N-[(3S,5R)-5-(morpholin-4-ylcarbonyl)piperidin-3-yl]-1-phenyl-1H-imidazole-4-carboxamide dihydrochloride

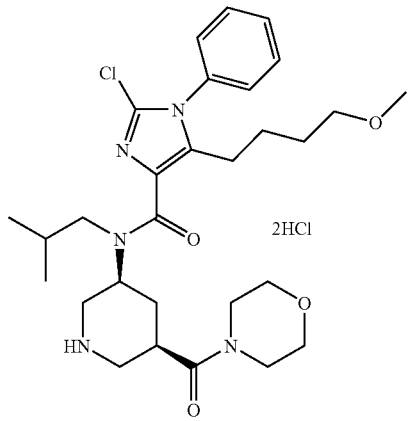 [SMILES: COCCCCc1c(C(=O)N(CC(C)C)[C@@H]2CNC[C@H](C(=O)N3CCOCC3)C2)nc(Cl)n1-c1ccccc1 ; "2HCl"]

MS (ESI+, m/e) 561 (M+1)

Example 156

5-(4-methoxybutyl)-N-(2-methylpropyl)-N-[(3S,5R)-5-(morpholin-4-ylcarbonyl)piperidin-3-yl]-1-phenyl-1H-imidazole-4-carboxamide dihydrochloride

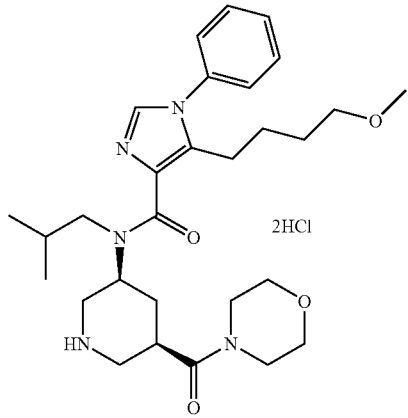 [SMILES: COCCCCc1c(C(=O)N(CC(C)C)[C@@H]2CNC[C@H](C(=O)N3CCOCC3)C2)ncn1-c1ccccc1 ; "2HCl"]

MS (ESI+, m/e) 526 (M+1)

318

Example 157

N-(2-methylpropyl)-N-[(3S,5R)-5-(morpholin-4-ylcarbonyl)piperidin-3-yl]-5-(phenoxymethyl)-1-phenyl-1H-1,2,3-triazole-4-carboxamide hydrochloride

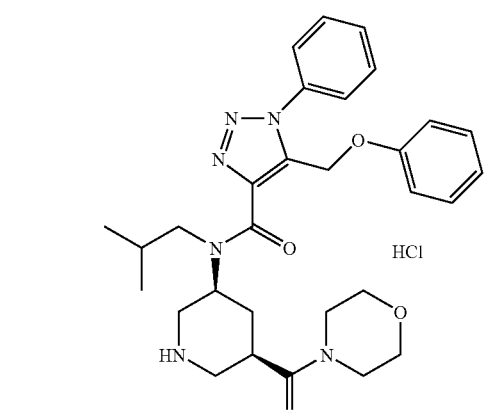

MS (ESI+, m/e) 547 (M+1)

Example 158

5-[(2-methoxyethoxy)methyl]-N-(2-methylpropyl)-N-[(3S,5R)-5-(morpholin-4-ylcarbonyl)piperidin-3-yl]-1-phenyl-1H-1,2,3-triazole-4-carboxamide hydrochloride

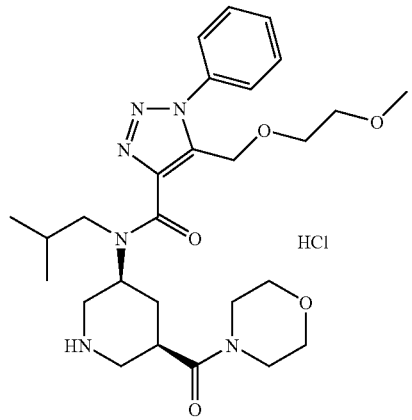 [SMILES: COCCOCc1c(C(=O)N(CC(C)C)[C@@H]2CNC[C@H](C(=O)N3CCOCC3)C2)nnn1-c1ccccc1 ; Cl]

MS (ESI+, m/e) 529 (M+1)

Example 159

5-[(3-methoxyphenoxy)methyl]-N-(2-methylpropyl)-N-[(3S,5R)-5-(morpholin-4-ylcarbonyl)piperidin-3-yl]-1-phenyl-1H-1,2,3-triazole-4-carboxamide hydrochloride

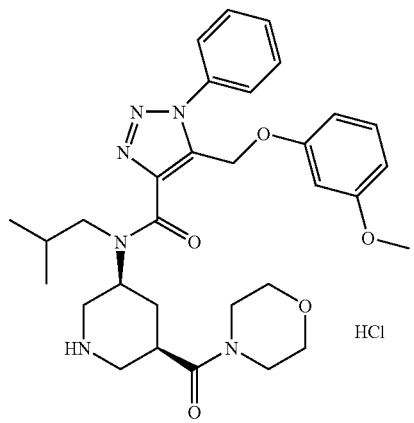 [SMILES: COc1cccc(OCc2c(C(=O)N(CC(C)C)[C@@H]3CNC[C@H](C(=O)N4CCOCC4)C3)nnn2-c2ccccc2)c1 ; Cl]

MS (ESI+, m/e) 577 (M+1)

Example 160

5-(4-methoxybutyl)-N-(2-methylpropyl)-N-[(3S,5R)-5-(morpholin-4-ylcarbonyl)piperidin-3-yl]-2-oxo-1-phenyl-2,3-dihydro-1H-imidazole-4-carboxamide hydrochloride

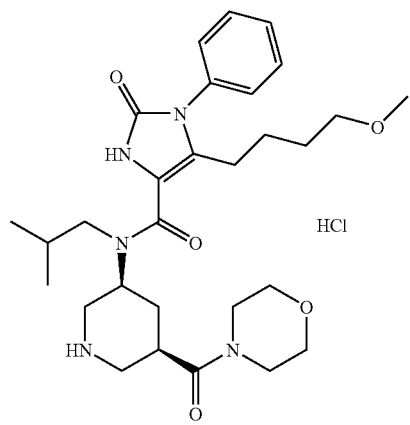 [SMILES: COCCCCc1c(C(=O)N(CC(C)C)[C@@H]2CNC[C@H](C(=O)N3CCOCC3)C2)[nH]c(=O)n1-c1ccccc1 ; Cl]

tert-Butyl(3S,5R)-3-[{[2-methoxy-5-(4-methoxybutyl)-1-phenyl-1H-imidazol-4-yl]carbonyl}(2-methylpropyl)amino]-5-(morpholin-4-ylcarbonyl)piperidine-1-carboxylate (94 mg) was dissolved in methanol (4 ml)-water (2 ml)-6M hydrochloric acid (2 ml), and the mixture was stirred at room temperature for 2 hr and then heated under reflux for 6 hr. The reaction mixture was concentrated under reduced pressure, and the residue was basified with 8M aqueous sodium hydroxide solution under ice-cooling and extracted with ethyl acetate. The extract was washed with saturated brine, and dried over anhydrous magnesium sulfate. The solvent was evaporated under reduced pressure. The residue was dissolved in 1M hydrogen chloride-ethyl acetate (3 ml), and the mixture was stirred at room temperature for 10 min. The reaction mixture was concentrated to give the object product (28 mg).

MS (ESI+, m/e) 542 (M+1)

Example 161

2-methoxy-5-(4-methoxybutyl)-N-(2-methylpropyl)-N-[(3S,5R)-5-(morpholin-4-ylcarbonyl)piperidin-3-yl]-1-phenyl-1H-imidazole-4-carboxamide fumarate

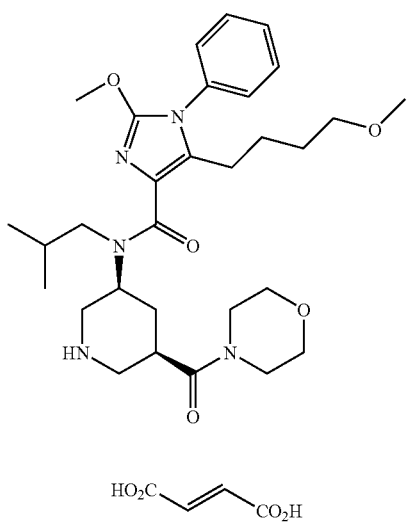

tert-Butyl(3S,5R)-3-[{[2-methoxy-5-(4-methoxybutyl)-1-phenyl-1H-imidazol-4-yl]carbonyl}(2-methylpropyl)amino]-5-(morpholin-4-ylcarbonyl)piperidine-1-carboxylate (110 mg) was dissolved in trifluoroacetic acid (25% toluene solution, 4 ml), and the mixture was stirred at room temperature for 4 hr. The reaction mixture was basified with saturated aqueous potassium carbonate solution, and extracted with ethyl acetate. The m extract was washed with saturated brine, and dried over anhydrous magnesium sulfate. The solvent was evaporated under reduced pressure. The residue was subjected to silica gel column chromatography, and a fraction eluted with ethyl acetate-hexane-methanol (50:50:0-100:0:0-85:0:15) was Is concentrated under reduced pressure. The residue was dissolved in methanol (2 ml), fumaric acid (15 mg) was added and the mixture was stirred at room temperature for 1 hr. The reaction mixture was concentrated under reduced pressure to give the object product (86 mg).

MS (ESI+, m/e) 556 (M+1)

In the same manner as in the method shown in the above-mentioned Example 161, the compounds described in the following Examples 162-163 were obtained.

Example 162

5-(4-methoxybutyl)-2-methyl-N-(2-methylpropyl)-N-[(3S,5R)-5-(morpholin-4-ylcarbonyl)piperidin-3-yl]-1-phenyl-1H-imidazole-4-carboxamide fumarate

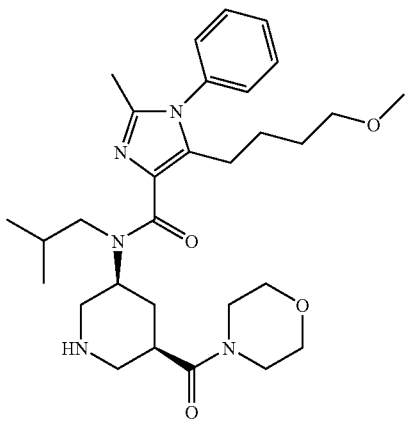

MS (ESI+, m/e) 540 (M+1)

Example 163

2-ethoxy-5-(4-methoxybutyl)-N-(2-methylpropyl)-N-[(3S,5R)-5-(morpholin-4-ylcarbonyl)piperidin-3-yl]-1-phenyl-1H-imidazole-4-carboxamide fumarate

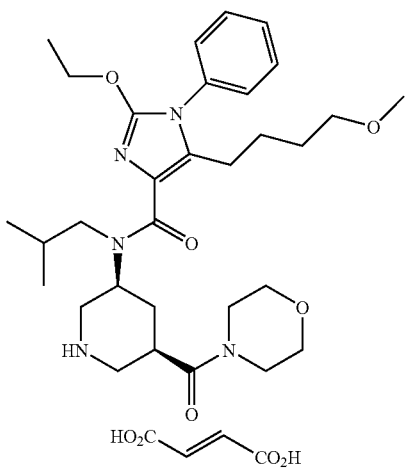

MS (ESI+, m/e) 570 (M+1)

In the same manner as in the method shown in Reference Example 265, the following compounds (Reference Examples 274-275) were obtained.

Reference Example 274

5-[(benzyloxy)methyl]-1-(2-fluorophenyl)-1H-1,2,3-triazole-4-carboxylic acid

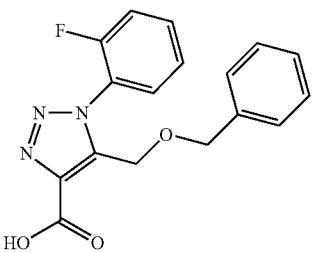 [SMILES: Cc1ccccc1-n1nnc(C(=O)O)c1COCc1ccccc1]

$^1$H-NMR (CDCl$_3$) δ: 4.45 (2H, s), 4.65-4.78 (2H, m), 7.06 (1H, dd), 7.25-7.39 (8H, m).
MS (ESI+, m/e) 328 (M+1)

Reference Example 275

5-[(benzyloxy)methyl]-1-(2-methylphenyl)-1H-1,2,3-triazole-4-carboxylic acid

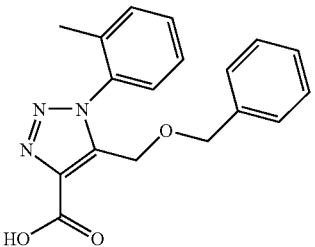

$^1$H-NMR (CDCl$_3$) δ: 2.05 (3H, s), 4.45 (2H, s), 4.65-4.78 (2H, m), 7.06 (1H, dd), 7.25-7.39 (8H, m).
MS (ESI+, m/e) 324 (M+1)

In the same manner as in the method shown in Reference Example 266, the following compounds (Reference Examples 276-277) were obtained.

Reference Example 276

1-tert-butyl 3-methyl(3R,5S)-5-[({5-[(benzyloxy)methyl]-1-(2-fluorophenyl)-1H-1,2,3-triazol-4-yl}carbonyl)(2-methylpropyl)amino]piperidine-1,3-dicarboxylate

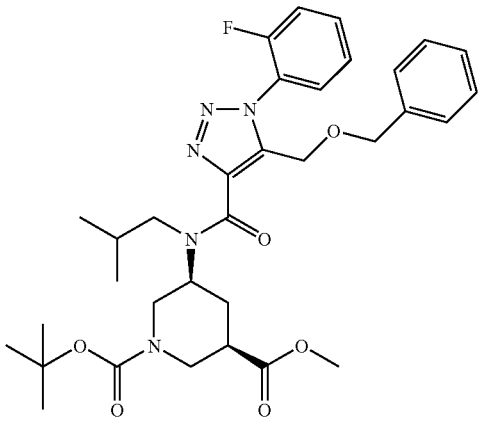 [SMILES: COC(=O)[C@@H]1C[C@H](N(CC(C)C)C(=O)c2nnn(-c3ccccc3C)c2COCc2ccccc2)CN(C(=O)OC(C)(C)C)C1]

323

$^1$H-NMR (CDCl$_3$) δ: 0.89 (3H, d), 0.97 (3H, d), 1.45 (6H, d), 1.46 (3H, s), 1.93-2.06 (3H, m), 2.16-2.32 (1H, m), 2.44-2.93 (3H, m), 3.29 (1H, br s), 3.40-3.94 (2H, m), 3.70 (3H, s), 4.29-4.46 (3H, m), 4.82 (2H, d), 6.99 (2H, dd), 7.20-7.36 (5H, m), 7.43-7.59 (2H, m).

MS (ESI+, m/e) 624 (M+1)

Reference Example 277

1-tert-butyl 3-methyl(3R,5S)-5-[({5-[(benzyloxy)methyl]-1-(2-methylphenyl)-1H-1,2,3-triazol-4-yl}carbonyl)(2-methylpropyl)amino]piperidine-1,3-dicarboxylate

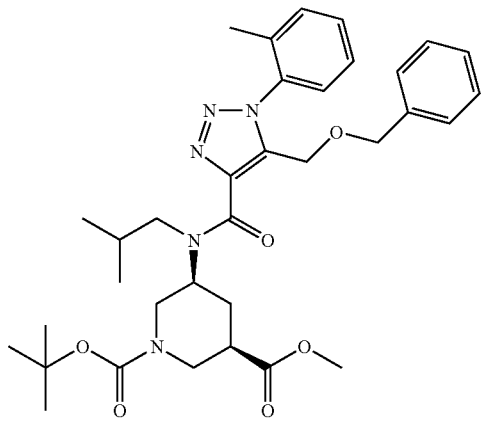

$^1$H-NMR (CDCl$_3$) δ: 0.88 (4H, t), 0.98 (2H, d), 1.44 (5H, d), 1.48 (4H, s), 1.94-2.07 (4H, m), 2.16-2.32 (1H, m), 2.46-2.62 (1H, m), 2.62-2.78 (2H, m), 2.83 (1H, br s), 3.29 (1H, d), 3.49-3.64 (2H, m), 3.70 (3H, s), 4.25 (1H, br s), 4.32-4.48 (3H, m), 4.57-4.73 (2H, m), 6.96-7.10 (1H, m), 7.03 (1H, d), 7.21-7.33 (6H, m), 7.43-7.50 (1H, m).

MS (ESI+, m/e) 620 (M+1)

In the same manner as in the method shown in Reference Example 267, the following compounds (Reference Examples 278-279) were obtained.

Reference Example 278

1-tert-butyl 3-methyl(3R,5S)-5-[{[1-(2-fluorophenyl)-5-(hydroxymethyl)-1H-1,2,3-triazol-4-yl]carbonyl}(2-methylpropyl)amino]piperidine-1,3-dicarboxylate

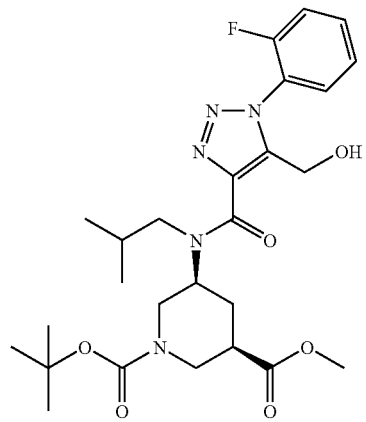

$^1$H-NMR (CDCl$_3$) δ: 0.96 (6H, dd), 1.35-1.52 (9H, m), 1.67 (1H, d), 2.00-2.10 (1H, m), 2.60 (1H, d), 2.75 (2H, br s), 3.28 (1H, br s), 3.57 (1H, br s), 3.61-3.77 (3H, m), 4.06-4.65 (4H, m), 4.45 (1H, d), 5.16 (1H, br s), 7.19-7.31 (1H, m), 7.34-7.44 (2H, m), 7.47 (1H, d).

MS (ESI+, m/e) 534 (M+1)

Reference Example 279

1-tert-butyl 3-methyl(3R,5S)-5-[{[5-(hydroxymethyl)-1-(2-methylphenyl)-1H-1,2,3-triazol-4-yl]carbonyl}(2-methylpropyl)amino]piperidine-1,3-dicarboxylate

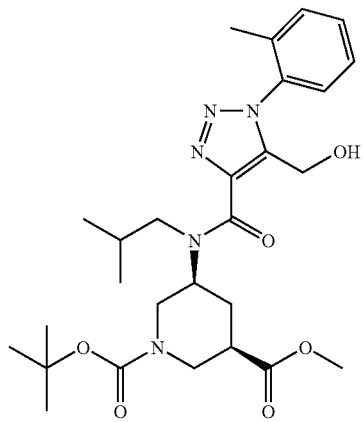 [SMILES: COC(=O)[C@@H]1C[C@H](N(CC(C)C)C(=O)c2nnn(-c3ccccc3C)c2CO)CN(C(=O)OC(C)(C)C)C1]

$^1$H-NMR (CDCl$_3$) δ: 0.96 (6H, dd), 1.35-1.52 (9H, m), 1.67 (1H, d), 2.02-2.15 (4H, m), 2.60 (1H, d), 2.75 (2H, br s), 3.28 (1H, br s), 3.57 (1H, br s), 3.61-3.77 (3H, m), 4.06-4.65 (4H, m), 4.45 (1H, d), 5.16 (1H, br s), 7.19-7.31 (1H, m), 7.34-7.44 (2H, m), 7.47 (1H, d).

MS (ESI+, m/e) 530 (M+1)

In the same manner as in the method shown in Reference Example 271, the following compounds (Reference Examples 280-281) were obtained.

Reference Example 280

1-tert-butyl 3-methyl(3R,5S)-5-[{[1-(2-fluorophenyl)-5-(phenoxymethyl)-1H-1,2,3-triazol-4-yl]carbonyl}(2-methylpropyl)amino]piperidine-1,3-dicarboxylate

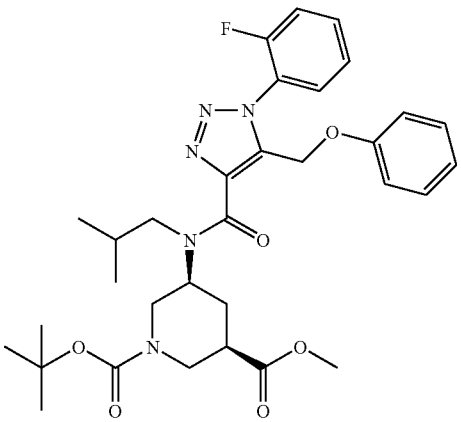

¹H-NMR (CDCl₃) δ: 0.86-1.02 (6H, m), 1.37-1.54 (9H, m), 2.14-2.35 (1H, m), 2.47-2.63 (1H, m), 2.67 (1H, br s), 2.84 (1H, br s), 3.54 (1H, t), 3.71 (3H, s), 4.35 (1H, br s), 4.91-5.07 (2H, m), 5.40 (2H, d), 6.36 (2H, br s), 6.64 (2H, d), 6.91 (1H, t), 7.18 (2H, t), 7.23-7.33 (3H, m), 7.42-7.58 (2H, m).

MS (ESI+, m/e) 610 (M+1)

Reference Example 281

1-tert-butyl 3-methyl(3R,5S)-5-[{[1-(2-methylphenyl)-5-(phenoxymethyl)-1H-1,2,3-triazol-4-yl]carbonyl}(2-methylpropyl)amino]piperidine-1,3-dicarboxylate

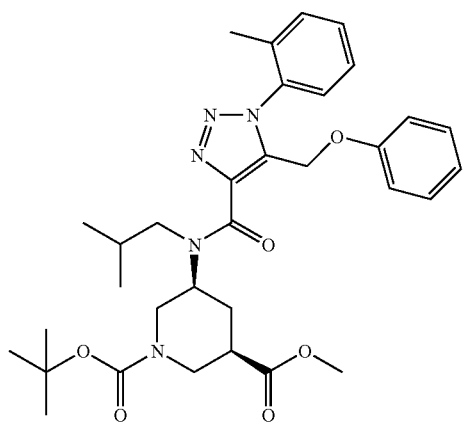 [SMILES: COC(=O)[C@@H]1C[C@H](N(CC(C)C)C(=O)c2nnn(-c3ccccc3F)c2COc2ccccc2)CN(C(=O)OC(C)(C)C)C1]

MS (ESI+, m/e) 606 (M+1)

Reference Example 282 tert-butyl(3S,5R)-3-[{[1-(2-fluorophenyl)-5-(phenoxymethyl)-1H-1,2,3-triazol-4-yl]carbonyl}(2-methylpropyl)amino]-5-(hydroxymethyl)piperidine-1-carboxylate

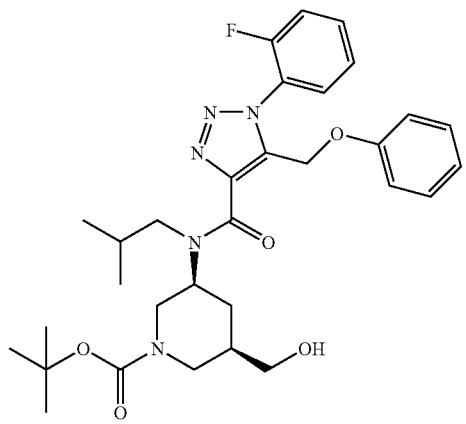 [SMILES: CC(C)CN(C(=O)c1nnn(-c2ccccc2F)c1COc1ccccc1)[C@H]1C[C@@H](CO)CN(C(=O)OC(C)(C)C)C1]

Calcium(II) chloride (200 mg) was dissolved in ethanol (5 ml), sodium tetrahydroborate (140 mg) was added under ice-cooling and the mixture was stirred at 0° C. for 30 min. A solution (8 ml) of 1-tert-butyl 3-methyl(3R,5S)-5-[{[1-(2-fluorophenyl)-5-(phenoxymethyl)-1H-1,2,3-triazol-4-yl]carbonyl}(2-methylpropyl)amino]piperidine-1,3-dicarboxylate (760 mg) in ethanol was added to the reaction mixture under ice-cooling, and the mixture was stirred at room temperature for 13 hr. The reaction mixture was diluted with saturated aqueous sodium hydrogen carbonate solution and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-75:25) was concentrated under reduced pressure to give the object product (447 mg).

¹H-NMR (CDCl₃) δ: 0.85-1.01 (6H, m), 1.45 (9H, d), 1.84 (1H, br s), 2.01 (1H, br s), 2.17 (1H, s), 2.44 (1H, br s), 2.72-3.38 (1H, m), 3.23-3.39 (1H, m), 3.57 (3H, br s), 3.89 (1H, br s), 4.16 (1H, s), 4.33 (1H, br s), 4.28-4.86 (1H, m), 5.39 (2H, d), 6.64 (2H, d), 6.91 (1H, t), 7.18 (2H, t), 7.23-7.33 (2H, m), 7.42-7.58 (2H, m).

MS (ESI+, m/e) 582 (M+1)

In the same manner as in the method shown in Reference Example 282, the following compounds (Reference Examples 283-285) were obtained.

Reference Example 283 tert-butyl(3S,5R)-3-[{[1-(2-fluorophenyl)-5-(4-methoxybutyl)-1H-1,2,3-triazol-4-yl]carbonyl}(2-methylpropyl)amino]-5-(hydroxymethyl)piperidine-1-carboxylate

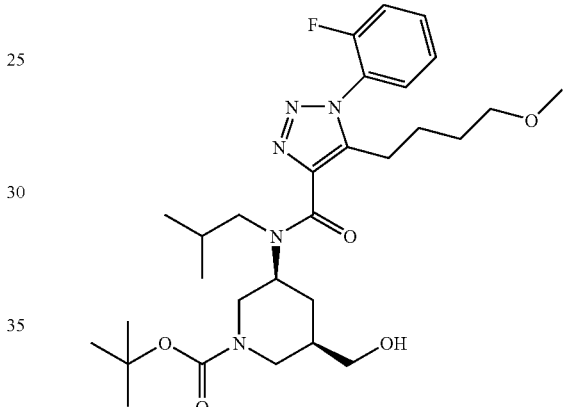

MS (ESI+, m/e) 562 (M+1)

Reference Example 284 tert-butyl(3S,5R)-3-[{[1-(2,3-difluorophenyl)-5-(4-methoxybutyl)-1H-1,2,3-triazol-4-yl]carbonyl}(2-methylpropyl)amino]-5-(hydroxymethyl)piperidine-1-carboxylate

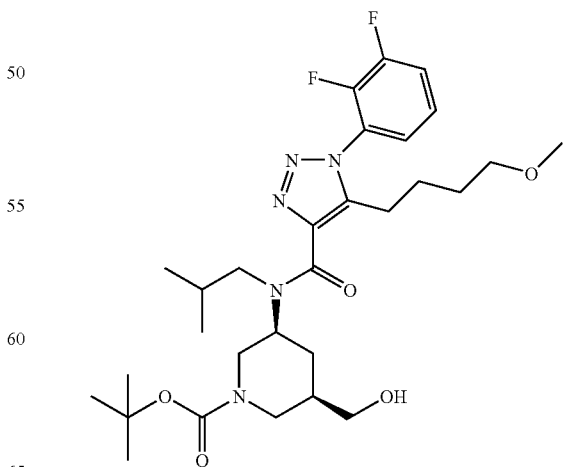

MS (ESI+, m/e) 580 (M+1)

Reference Example 285 tert-butyl(3S,5R)-3-[{[1-(2,6-difluorophenyl)-5-(4-methoxybutyl)-1H-1,2,3-triazol-4-yl]carbonyl}(2-methylpropyl)amino]-5-(hydroxymethyl)piperidine-1-carboxylate

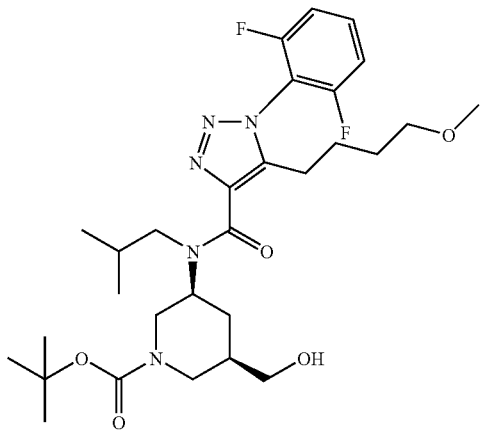 [SMILES: COCCCCc1c(C(=O)N(CC(C)C)[C@H]2C[C@@H](CO)CN(C(=O)OC(C)(C)C)C2)nnn1-c1c(F)cccc1F]

MS (ESI+, m/e) 580 (M+1)

In the same manner as in the method shown in Reference Example 270, the following compound (Reference Example 286) was obtained.

Reference Example 286

(3R,5S)-1-(tert-butoxycarbonyl)-5-[({5-[(2-methoxyethoxy)methyl]-1-(2-methylphenyl)-1H-1,2,3-triazol-4-yl}carbonyl)(2-methylpropyl)amino]piperidine-3-carboxylic acid

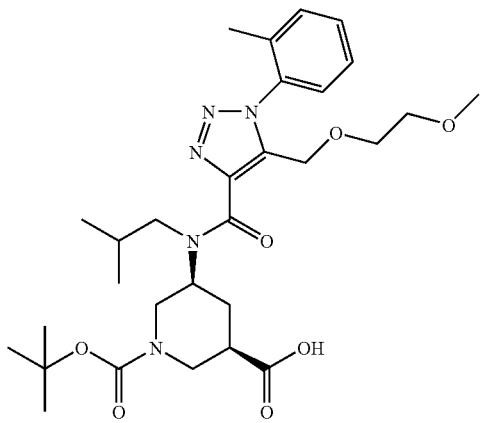 [SMILES: COCCOCc1c(C(=O)N(CC(C)C)[C@H]2C[C@@H](C(=O)O)CN(C(=O)OC(C)(C)C)C2)nnn1-c1ccccc1C]

MS (ESI+, m/e) 588 (M+1)

Reference Example 287 tert-butyl(3R,5S)-3-(hydroxymethyl)-5-[({5-[(2-methoxyethoxy)methyl]-1-(2-methylphenyl)-1H-1,2,3-triazol-4-yl}carbonyl)(2-methylpropyl)amino]piperidine-1-carboxylate

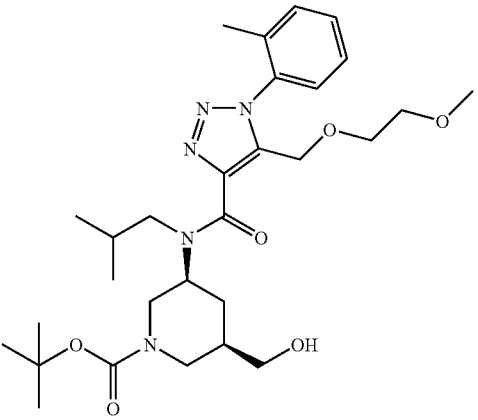 [SMILES: COCCOCc1c(C(=O)N(CC(C)C)[C@H]2C[C@@H](CO)CN(C(=O)OC(C)(C)C)C2)nnn1-c1ccccc1C]

(3R,5S)-1-(tert-Butoxycarbonyl)-5-[({5-[(2-methoxyethoxy)methyl]-1-(2-methylphenyl)-1H-1,2,3-triazol-4-yl}carbonyl)(2-methylpropyl)amino]piperidine-3-carboxylic acid (900 mg) and 1-methylmorpholine (274 μl) were dissolved in THF (5 ml), ethyl chlorocarbonate (230 μl) was added under ice-cooling and the mixture was stirred at 0° C. for 1 hr. Sodium tetrahydroborate (200 mg) and methanol (2 ml) were added to the reaction mixture, and the mixture was further stirred at room temperature for 14 hr. The reaction mixture was diluted with saturated aqueous sodium hydrogen carbonate solution and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-90:10) was concentrated under reduced pressure to give the object product (704 mg).

$^1$H-NMR (CDCl$_3$) δ: 0.88 (3H, d), 0.98 (3H, d), 1.40-1.53 (9H, m), 1.67 (1H, s), 1.83 (1H, br s), 1.96-2.13 (5H, m), 2.13-2.87 (2H, m), 3.25 (3H, s), 3.29-3.42 (2H, m), 3.48 (2H, d), 3.46 (2H, br s), 3.57 (3H, br s), 4.26 (2H, br s), 4.62 (2H, d), 7.26-7.40 (3H, m), 7.42-7.49 (1H, m).

MS (ESI+, m/e) 560 (M+1)

Reference Example 288 tert-butyl(3R,5S)-3-formyl-5-[({5-[(2-methoxyethoxy)methyl]-1-(2-methylphenyl)-1H-1,2,3-triazol-4-yl}carbonyl)(2-methylpropyl)amino]piperidine-1-carboxylate

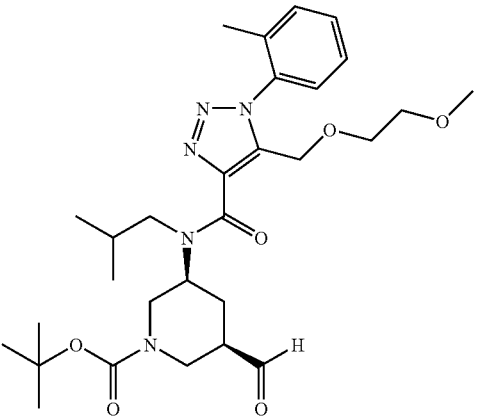 [SMILES: COCCOCc1c(C(=O)N(CC(C)C)[C@H]2C[C@@H](C=O)CN(C(=O)OC(C)(C)C)C2)nnn1-c1ccccc1C]

tert-Butyl(3R,5S)-3-(hydroxymethyl)-5-[({5-[(2-methoxyethoxy)methyl]-1-(2-methylphenyl)-1H-1,2,3-triazol-4-yl}carbonyl)(2-methylpropyl)amino]piperidine-1-carboxylate (534 mg) and triethylamine (1.1 ml) were dissolved in DMSO, sulfur trioxide-pyridine complex (610 mg) was added and the mixture was stirred at room temperature for 1 day. The reaction mixture was diluted with ethyl acetate and washed with saturated brine. The organic layer was washed successively with 1M hydrochloric acid and saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (377 mg).

$^1$H-NMR (CDCl$_3$) δ: 0.86-1.03 (6H, m), 1.37-1.53 (9H, m), 1.62 (2H, br s), 1.97-2.14 (4H, m), 2.35-2.93 (3H, m), 3.13-3.29 (4H, m), 3.34 (2H, d), 3.35 (1H, br s), 3.47 (2H, d), 3.75 (1H, br s), 4.24-4.50 (1H, m), 4.57-4.73 (3H, m), 7.27-7.40 (3H, m), 7.42-7.49 (1H, m), 9.57-9.87 (1H, m).

MS (ESI+, m/e) 558 (M+1)

In the same manner as in the method shown in Reference Example 288, the following compounds (Reference Examples 289-291) were obtained.

Reference Example 289 tert-butyl(3S,5R)-3-[{[1-(2-fluorophenyl)-5-(4-methoxybutyl)-1H-1,2,3-triazol-4-yl]carbonyl}(2-methylpropyl)amino]-5-formylpiperidine-1-carboxylate

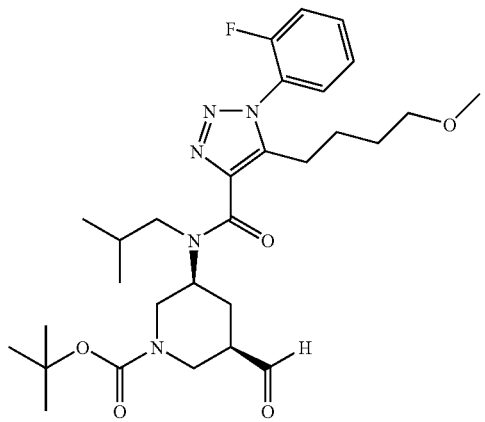 [SMILES: COCCCCc1c(C(=O)N(CC(C)C)[C@H]2C[C@@H](C=O)CN(C(=O)OC(C)(C)C)C2)nnn1-c1ccccc1F]

MS (ESI+, m/e) 560 (M+1)

Reference Example 290 tert-butyl(3S,5R)-3-[{[1-(2,3-difluorophenyl)-5-(4-methoxybutyl)-1H-1,2,3-triazol-4-yl]carbonyl}(2-methylpropyl)amino]-5-formylpiperidine-1-carboxylate

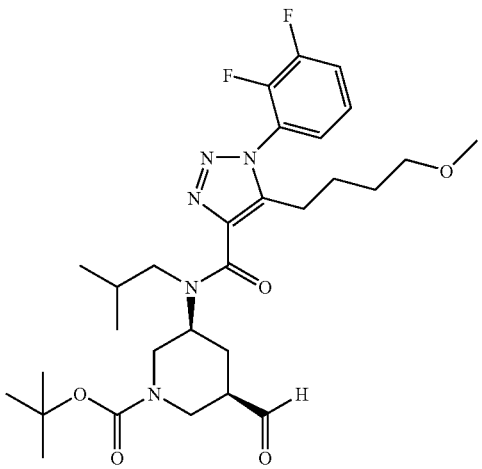 [SMILES: COCCCCc1c(C(=O)N(CC(C)C)[C@H]2C[C@@H](C=O)CN(C(=O)OC(C)(C)C)C2)nnn1-c1cccc(F)c1F]

MS (ESI+, m/e) 578 (M+1)

Reference Example 291 tert-butyl(3S,5R)-3-[{[1-(2,6-difluorophenyl)-5-(4-methoxybutyl)-1H-1,2,3-triazol-4-yl]carbonyl}(2-methylpropyl)amino]-5-formylpiperidine-1-carboxylate

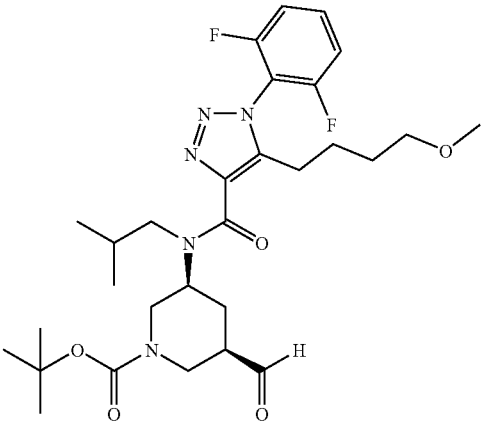 [SMILES: COCCCCc1c(C(=O)N(CC(C)C)[C@H]2C[C@@H](C=O)CN(C(=O)OC(C)(C)C)C2)nnn1-c1c(F)cccc1F]

MS (ESI+, m/e) 578 (M+1)

Reference Example 292 tert-butyl(3R,5S)-3-(1-hydroxyethyl)-5-[({5-[(2-methoxyethoxy)methyl]-1-(2-methylphenyl)-1H-1,2,3-triazol-4-yl}carbonyl)(2-methylpropyl)amino]piperidine-1-carboxylate

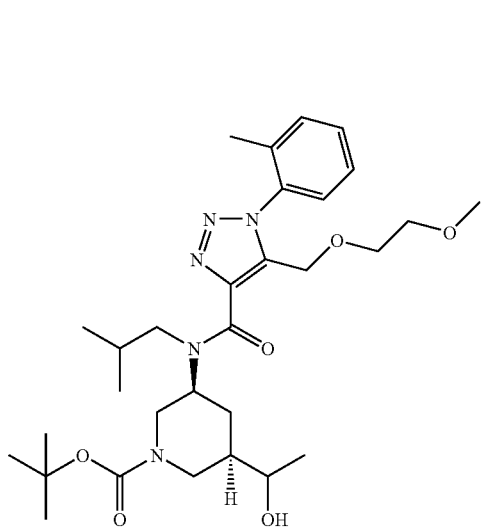 [SMILES: COCCOCc1c(C(=O)N(CC(C)C)[C@H]2C[C@@H](C(C)O)CN(C(=O)OC(C)(C)C)C2)nnn1-c1ccccc1C]

tert-Butyl(3R,5S)-3-formyl-5-[({5-[(2-methoxyethoxy)methyl]-1-(2-methylphenyl)-1H-1,2,3-triazol-4-yl}carbonyl)(2-methylpropyl)amino]piperidine-1-carboxylate (360 mg) was dissolved in THF (4 ml), a solution (1M, 1.95 ml) of methyl magnesium bromide in THF was added under ice-cooling and the mixture was stirred for 3 hr. The reaction mixture was poured into saturated aqueous ammonium chloride solution, and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (325 mg).

$^1$H-NMR (CDCl$_3$) δ 0.90 (3H, br s), 0.99 (3H, d), 1.32 (1H, d), 1.26 (3H, t), 1.37-1.54 (9H, m), 1.60-1.76 (3H, m), 1.97-2.12 (4H, m), 2.15-2.32 (1H, m), 2.35-3.04 (2H, m), 3.25 (3H, s), 3.35 (2H, br s), 3.44-3.61 (3H, m), 3.68 (1H, br s), 4.31 (2H, br s), 4.54-4.70 (2H, m), 7.29-7.41 (3H, m), 7.42-7.49 (1H, m).

MS (ESI+, m/e) 574 (M+1)

In the same manner as in the method shown in Reference Example 292, the following compounds (Reference Examples 293-299) were obtained.

Reference Example 293 tert-butyl(3S,5R)-3-[{[1-(2-fluorophenyl)-5-(4-methoxybutyl)-1H-1,2,3-triazol-4-yl]carbonyl}(2-methylpropyl)amino]-5-(1-hydroxypropyl)piperidine-1-carboxylate

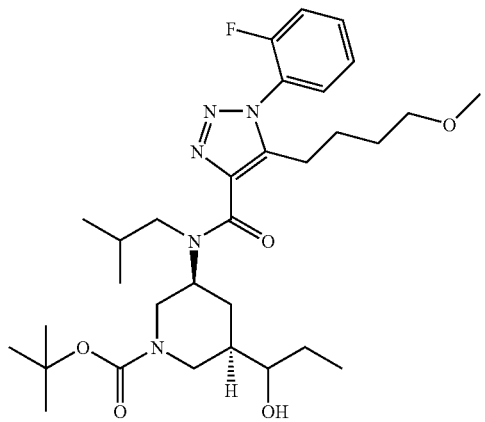 [SMILES: CCC(O)[C@@H]1C[C@H](N(CC(C)C)C(=O)c2nnn(-c3ccccc3F)c2CCCCOC)CN(C(=O)OC(C)(C)C)C1]

MS (ESI+, m/e) 590 (M+1)

Reference Example 294 tert-butyl(3S,5R)-3-[{[1-(2-fluorophenyl)-5-(4-methoxybutyl)-1H-1,2,3-triazol-4-yl]carbonyl}(2-methylpropyl)amino]-5-(1-hydroxybutyl)piperidine-1-carboxylate

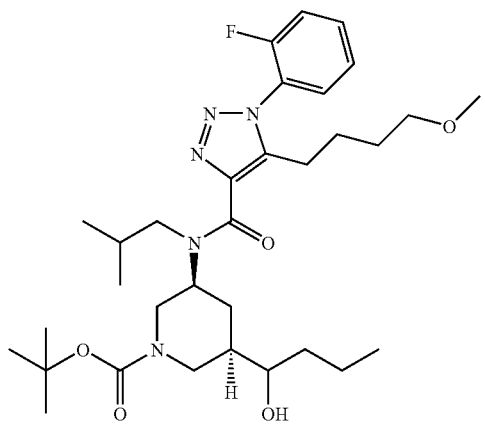 [SMILES: CCCC(O)[C@@H]1C[C@H](N(CC(C)C)C(=O)c2nnn(-c3ccccc3F)c2CCCCOC)CN(C(=O)OC(C)(C)C)C1]

MS (ESI+, m/e) 604 (M+1)

Reference Example 295 tert-butyl(3S,5R)-3-[{[1-(2-fluorophenyl)-5-(4-methoxybutyl)-1H-1,2,3-triazol-4-yl]carbonyl}(2-methylpropyl)amino]-5-(1-hydroxy-2-methylpropyl)piperidine-1-carboxylate

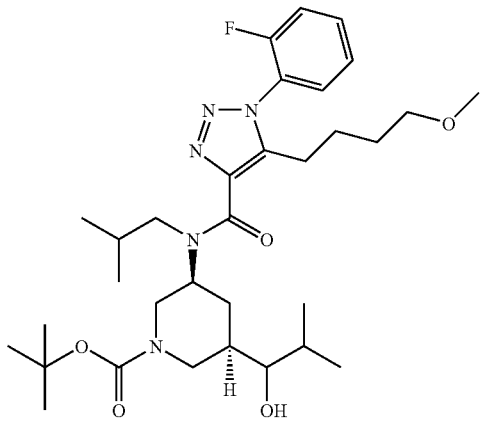 [SMILES: COCCCCc1c(C(=O)N(CC(C)C)[C@H]2C[C@@H](C(O)C(C)C)CN(C(=O)OC(C)(C)C)C2)nnn1-c1ccccc1F]

MS (ESI+, m/e) 604 (M+1)

Reference Example 296 tert-butyl(3R,5S)-3-[cyclopropyl(hydroxy)methyl]-5-[{[1-(2-fluorophenyl)-5-(4-methoxybutyl)-1H-1,2,3-triazol-4-yl]carbonyl}(2-methylpropyl)amino]piperidine-1-carboxylate

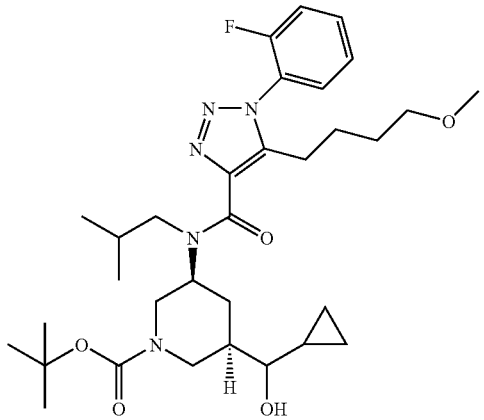 [SMILES: COCCCCc1c(C(=O)N(CC(C)C)[C@H]2C[C@@H](C(O)C3CC3)CN(C(=O)OC(C)(C)C)C2)nnn1-c1ccccc1F]

MS (ESI+, m/e) 602 (M+1)

Reference Example 297 tert-butyl(3S,5R)-3-[{[1-(2-fluorophenyl)-5-(4-methoxybutyl)-1H-1,2,3-triazol-4-yl]carbonyl}(2-methylpropyl)amino]-5-(1-hydroxypentyl)piperidine-1-carboxylate

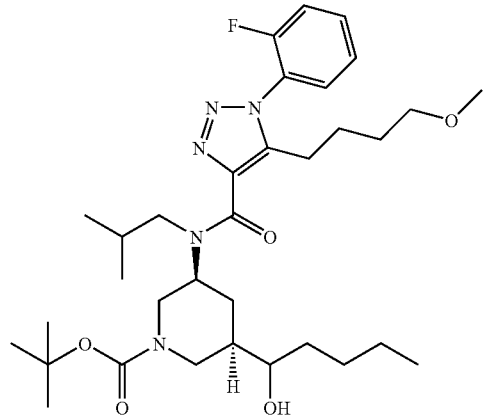 [SMILES: CCCCC(O)[C@@H]1C[C@H](N(CC(C)C)C(=O)c2nnn(-c3ccccc3F)c2CCCCOC)CN(C(=O)OC(C)(C)C)C1]

MS (ESI+, m/e) 618 (M+1)

Reference Example 298 tert-butyl(3S,5R)-3-[{[1-(2,3-difluorophenyl)-5-(4-methoxybutyl)-1H-1,2,3-triazol-4-yl]carbonyl}(2-methylpropyl)amino]-5-(1-hydroxyethyl)piperidine-1-carboxylate

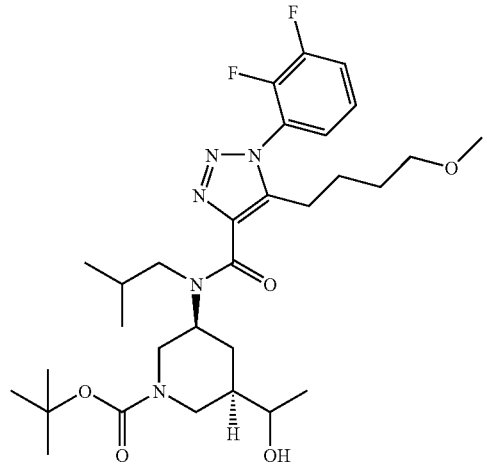 [SMILES: COCCCCc1c(C(=O)N(CC(C)C)[C@H]2C[C@@H](C(C)O)CN(C(=O)OC(C)(C)C)C2)nnn1-c1cccc(F)c1F]

MS (ESI+, m/e) 594 (M+1)

Reference Example 299 tert-butyl(3S,5R)-3-[{[1-(2,6-difluorophenyl)-5-(4-methoxybutyl)-1H-1,2,3-triazol-4-yl]carbonyl}(2-methylpropyl)amino]-5-(1-hydroxyethyl)piperidine-1-carboxylate

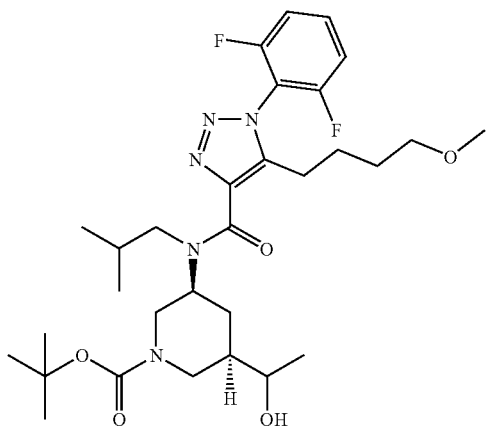 [SMILES: COCCCCc1c(C(=O)N(CC(C)C)[C@H]2C[C@@H](C(C)O)CN(C(=O)OC(C)(C)C)C2)nnn1-c1c(F)cccc1F]

MS (ESI+, m/e) 594 (M+1)

Reference Example 300 tert-butyl(3S,5R)-3-[{[1-(2-fluorophenyl)-5-(hydroxymethyl)-1H-1,2,3-triazol-4-yl]carbonyl}(2-methylpropyl)amino]-5-(morpholin-4-ylcarbonyl)piperidine-1-carboxylate

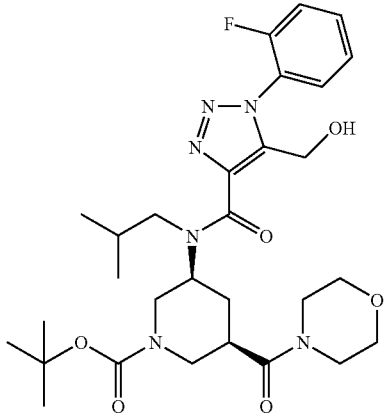 [SMILES: CC(C)CN(C(=O)c1nnn(-c2ccccc2F)c1CO)[C@H]1C[C@@H](C(=O)N2CCOCC2)CN(C(=O)OC(C)(C)C)C1]

1-tert-Butyl 3-methyl(3R,5S)-5-[{[1-(2-fluorophenyl)-5-(hydroxymethyl)-1H-1,2,3-triazol-4-yl]carbonyl}(2-methylpropyl)amino]piperidine-1,3-dicarboxylate (1.05 g) was dissolved in THF (10 ml)-methanol (8 ml)-water (8 ml), 8M aqueous sodium hydroxide solution (600 μl) was added and the mixture was stirred at 70° C. for 1.5 hr. The reaction mixture was cooled to room temperature and concentrated under reduced pressure. The residue was diluted with water, neutralized with saturated aqueous ammonium chloride solution and extracted with ethyl acetate. The extract was washed with saturated brine, and dried over anhydrous magnesium sulfate. The solvent was evaporated under reduced pressure. The residue, morpholine, 1-hydroxybenzotriazole (150 mg) and triethylamine (700 μl) were dissolved in acetonitrile (20 ml), WSC·HCL (555 mg) was added and the mixture was stirred at room temperature for 8 hr. The reaction mixture was concentrated under reduced pressure, diluted with ethyl acetate and washed with water. The organic layer was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (764 mg).

$^1$H-NMR (CDCl$_3$) δ 0.98 (5H, dd), 0.85-1.02 (1H, m), 1.42 (6H, s), 1.49 (3H, s), 2.16 (1H, d), 2.56 (1H, br s), 2.87 (2H, br s), 3.25 (1H, dd), 3.47 (1H, dd), 3.53 (1H, br s), 3.59-3.76 (5H, m), 3.64 (3H, br s), 4.10-4.37 (3H, m), 4.45-4.62 (2H, m), 5.14-5.30 (1H, m), 7.29-7.45 (2H, m), 7.49-7.65 (2H, m).

MS (ESI+, m/e) 589 (M+1)

In the same manner as in the method shown in Reference Example 271, the following compound (Reference Example 301) was obtained.

Reference Example 301 tert-butyl(3S,5R)-3-[{[1-(2-fluorophenyl)-5-(phenoxymethyl)-1H-1,2,3-triazol-4-yl]carbonyl}(2-methylpropyl)amino]-5-(morpholin-4-ylcarbonyl)piperidine-1-carboxylate

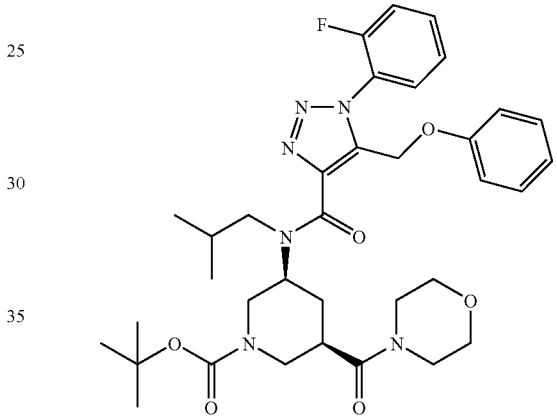

MS (ESI+, m/e) 665 (M+1)

Reference Example 302 tert-butyl(3S,5R)-3-[{[5-(bromomethyl)-1-(2-fluorophenyl)-1H-1,2,3-triazol-4-yl]carbonyl}(2-methylpropyl)amino]-5-(morpholin-4-ylcarbonyl)piperidine-1-carboxylate

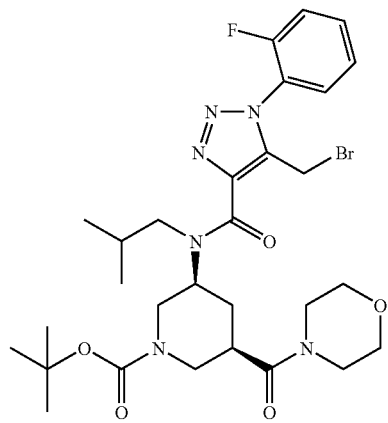 [SMILES: CC(C)CN(C(=O)c1nnn(-c2ccccc2F)c1CBr)[C@H]1C[C@@H](C(=O)N2CCOCC2)CN(C(=O)OC(C)(C)C)C1]

To a solution (4 ml) of tert-butyl(3S,5R)-3-[{[1-(2-fluorophenyl)-5-(hydroxymethyl)-1H-1,2,3-triazol-4-yl]carbonyl}(2-methylpropyl)amino]-5-(morpholin-4-ylcarbonyl)piperidine-1-carboxylate (410 mg) and triphenylphosphine (275 mg) in dichloromethane was added under ice-cooling carbon tetrabromide (350 mg), and the mixture was stirred at room temperature for 1 hr. The reaction mixture was concentrated under reduced pressure, and the residue was subjected to silica gel column chromatography, and a fraction eluted with ethyl acetate-hexane (10:90-100:0) was concentrated under reduced pressure to give the object product (442 mg).

MS (ESI+, m/e) 652 (M+1)

Reference Example 303 tert-butyl(3S,5R)-3-[({5-[(diethoxyphosphoryl)methyl]-1-(2-fluorophenyl)-1H-1,2,3-triazol-4-yl}carbonyl)(2-methylpropyl)amino]-5-(morpholin-4-ylcarbonyl)piperidine-1-carboxylate

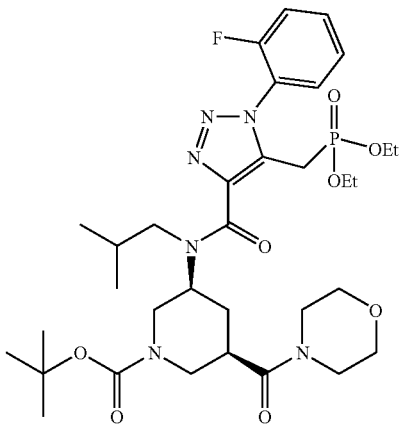 [SMILES: CCOP(=O)(Cc1c(C(=O)N(CC(C)C)[C@H]2C[C@@H](C(=O)N3CCOCC3)CN(C(=O)OC(C)(C)C)C2)nnn1-c1ccccc1F)OCC]

tert-Butyl(3S,5R)-3-[{[5-(bromomethyl)-1-(2-fluorophenyl)-1H-1,2,3-triazol-4-yl]carbonyl}(2-methylpropyl)amino]-5-(morpholin-4-ylcarbonyl)piperidine-1-carboxylate (440 mg) was dissolved in DMF (4 ml), triethyl phosphate (295 μl) was added and the mixture was stirred at 110° C. for 12 hr. After cooling to room temperature, the reaction mixture was diluted with ethyl acetate and washed with saturated brine. The organic layer was dried over anhydrous magnesium sulfate, and the solvent was evaporated under reduced pressure to give the object product (473 mg).

MS (ESI+, m/e) 709 (M+1)

Reference Example 304 tert-butyl(3S,5R)-3-[({1-(2-fluorophenyl)-5-[(E)-2-(1,3-thiazol-2-yl)ethenyl]-1H-1,2,3-triazol-4-yl}carbonyl)(2-methylpropyl)amino]-5-(morpholin-4-ylcarbonyl)piperidine-1-carboxylate

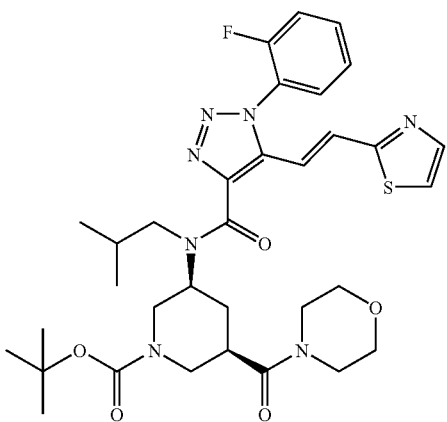 [SMILES: CC(C)CN(C(=O)c1nnn(-c2ccccc2F)c1/C=C/c1nccs1)[C@H]1C[C@@H](C(=O)N2CCOCC2)CN(C(=O)OC(C)(C)C)C1]

tert-Butyl(3S,5R)-3-[({5-[(diethoxyphosphoryl)methyl]-1-(2-fluorophenyl)-1H-1,2,3-triazol-4-yl}carbonyl)(2-methylpropyl)amino]-5-(morpholin-4-ylcarbonyl)piperidine-1-carboxylate (470 mg) and 1,3-thiazole-2-carbaldehyde (90 mg) were dissolved in THF (4 ml), sodium hydride (50% in oil, 50 mg) was added under ice-cooling and the mixture was stirred at room temperature for 12 hr. The reaction mixture was diluted with saturated aqueous sodium hydrogen carbonate solution and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (327 mg).

MS (ESI+, m/e) 668 (M+1)

Reference Example 305 tert-butyl(3S,5R)-3-[({1-(2-fluorophenyl)-5-[2-(1,3-thiazol-2-yl)ethyl]-1H-1,2,3-triazol-4-yl}carbonyl)(2-methylpropyl)amino]-5-(morpholin-4-ylcarbonyl)piperidine-1-carboxylate

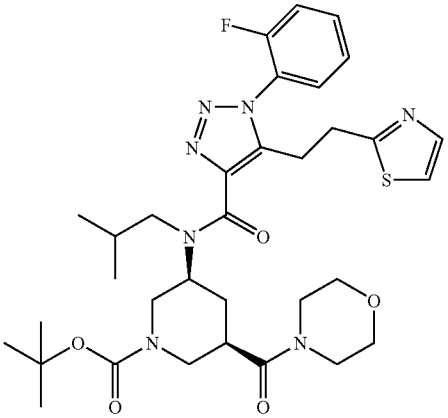 [SMILES: CC(C)CN(C(=O)c1nnn(-c2ccccc2F)c1CCc1nccs1)[C@H]1C[C@@H](C(=O)N2CCOCC2)CN(C(=O)OC(C)(C)C)C1]

tert-Butyl(3S,5R)-3-[({1-(2-fluorophenyl)-5-[(E)-2-(1,3-thiazol-2-yl)ethenyl]-1H-1,2,3-triazol-4-yl}carbonyl)(2-methylpropyl)amino]-5-(morpholin-4-ylcarbonyl)piperidine-1-carboxylate (200 mg) and 5% palladium-carbon (20 mg) were suspended in methanol (4 ml), and the mixture was stirred at room temperature under a hydrogen atmosphere (1 atom) for 3 days. Insoluble material was filtered off, and the filtrate was concentrated under reduced pressure to give the object product (200 mg).

MS (ESI+, m/e) 670 (M+1)

Reference Example 306 tert-butyl(3S,5R)-3-[{[1-(2-fluorophenyl)-5-(4-methoxybutyl)-1H-1,2,3-triazol-4-yl]carbonyl}(2-methylpropyl)amino]-5-(oxirane-2-yl)piperidine-1-carboxylate

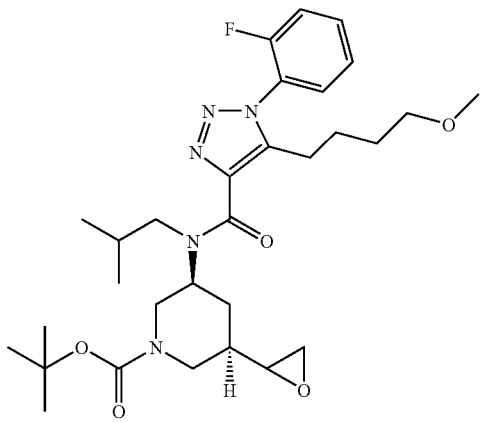 [SMILES: COCCCCc1c(C(=O)N(CC(C)C)[C@H]2C[C@@H](C3CO3)CN(C(=O)OC(C)(C)C)C2)nnn1-c1ccccc1F]

Trimethylsulfoxonium iodide (390 mg) was dissolved in DMSO (5 ml), sodium hydride (50% in oil, 85 mg) was added, and the mixture was stirred at room temperature for 1 hr. A solution (10 ml) of tert-butyl(3S,5R)-3-[{[1-(2-fluorophenyl)-5-(4-methoxybutyl)-1H-1,2,3-triazol-4-yl]carbonyl}(2-methylpropyl)amino]-5-formylpiperidine-1-carboxylate (656 mg) in DMSO was added to the reaction mixture, and the mixture was further stirred at room temperature for 1 hr. The reaction mixture was diluted with saturated aqueous sodium hydrogen carbonate solution and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (372 mg).

MS (ESI+, m/e) 574 (M+1)

Reference Example 307 tert-butyl(3S,5R)-3-[{[1-(2-fluorophenyl)-5-(4-methoxybutyl)-1H-1,2,3-triazol-4-yl]carbonyl}(2-methylpropyl)amino]-5-(1-hydroxy-2-methoxyethyl)piperidine-1-carboxylate

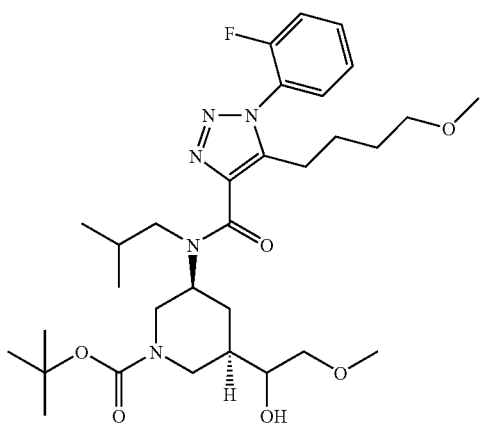 [SMILES: COCCCCc1c(C(=O)N(CC(C)C)[C@H]2C[C@@H](C(O)COC)CN(C(=O)OC(C)(C)C)C2)nnn1-c1ccccc1F]

tert-Butyl(3S,5R)-3-[{[1-(2-fluorophenyl)-5-(4-methoxybutyl)-1H-1,2,3-triazol-4-yl]carbonyl}(2-methylpropyl)amino]-5-(oxirane-2-yl)piperidine-1-carboxylate (190 mg) was dissolved in methanol (5 ml), sodium methoxide (28% methanol solution, 320 mg) was added and the mixture was stirred at 70° C. for 8 hr. The reaction mixture was cooled to room temperature, diluted with water and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (167 mg).

MS (ESI+, m/e) 606 (M+1)

In the same manner as in the method shown in Reference Example 307, the following compound (Reference Example 308) was obtained.

Reference Example 308 tert-butyl(3R,5S)-3-(2-ethoxy-1-hydroxyethyl)-5-[{[1-(2-fluorophenyl)-5-(4-methoxybutyl)-1H-1,2,3-triazol-4-yl]carbonyl}(2-methylpropyl)amino]piperidine-1-carboxylate

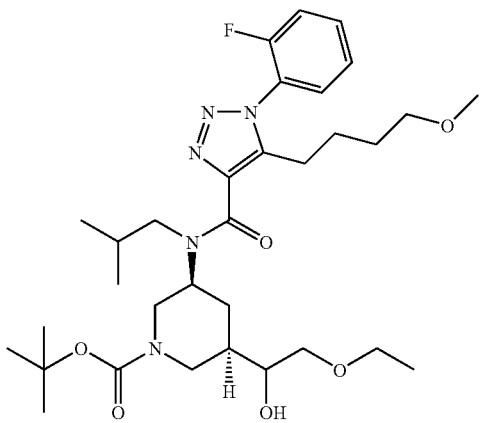 [SMILES: CCOCC(O)[C@@H]1C[C@H](N(CC(C)C)C(=O)c2nnn(-c3ccccc3F)c2CCCCOC)CN(C(=O)OC(C)(C)C)C1]

MS (ESI+, m/e) 620 (M+1)

Reference Example 309 tert-butyl(3S,5R)-3-[{[1-(2-fluorophenyl)-5-(4-methoxybutyl)-1H-1,2,3-triazol-4-yl]carbonyl}(2-methylpropyl)amino]-5-(methoxymethyl)piperidine-1-carboxylate

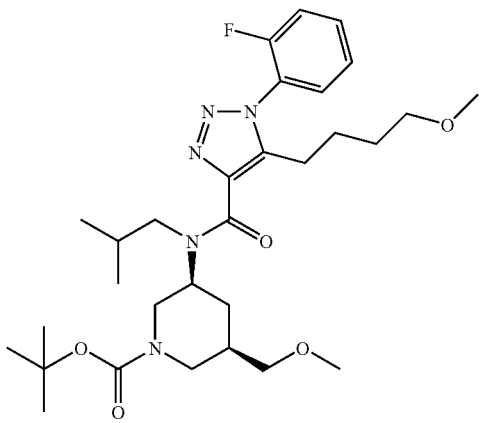 [SMILES: COCCCCc1c(C(=O)N(CC(C)C)[C@H]2C[C@@H](COC)CN(C(=O)OC(C)(C)C)C2)nnn1-c1ccccc1F]

tert-Butyl(3S,5R)-3-[{[1-(2-fluorophenyl)-5-(4-methoxybutyl)-1H-1,2,3-triazol-4-yl]carbonyl}(2-methylpropyl)amino]-5-(hydroxymethyl)piperidine-1-carboxylate (165 mg) and triethylamine (215 μl) were dissolved in THF (4 ml), and methanesulfonyl chloride (60 μl) was added under ice-cooling. The mixture was stirred at 0° C. for 2 hr, and sodium methoxide (28% methanol solution, 600 mg) and methanol (2 ml) were added, and the mixture was further stirred at 75° C. for 3 hr. The mixture was cooled to room temperature and diluted with water and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-80:20) was concentrated under reduced pressure to give the object product (142 mg).

MS (ESI+, m/e) 576 (M+1)

Reference Example 310 tert-butyl(3R,5S)-3-(difluoromethyl)-5-[{[1-(2-fluorophenyl)-5-(4-methoxybutyl)-1H-1,2,3-triazol-4-yl]carbonyl}(2-methylpropyl)amino]piperidine-1-carboxylate

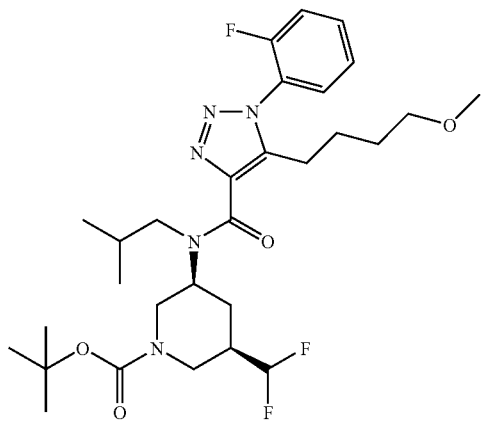 [SMILES: COCCCCc1c(C(=O)N(CC(C)C)[C@H]2C[C@@H](C(F)F)CN(C(=O)OC(C)(C)C)C2)nnn1-c1ccccc1F]

tert-Butyl(3S,5R)-3-[{[1-(2-fluorophenyl)-5-(4-methoxybutyl)-1H-1,2,3-triazol-4-yl]carbonyl}(2-methylpropyl)amino]-5-formylpiperidine-1-carboxylate (200 mg) was dissolved in toluene (4 ml), and diethylaminosulfur trifluoride (240 μl) was added under ice-cooling. The mixture was stirred at room temperature for 3 days and diluted with saturated aqueous ammonium chloride solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-80:20) was concentrated under reduced pressure to give the object product (45 mg).

MS (ESI+, m/e) 582 (M+1)

In the same manner as in the method shown in Reference Example 271, the following compound (Reference Example 311) was obtained.

Reference Example 311 tert-butyl(3S,5R)-3-[({5-[(4-fluorophenoxy)methyl]-1-phenyl-1H-1,2,3-triazol-4-yl}carbonyl)(2-methylpropyl)amino]-5-(morpholin-4-ylcarbonyl)piperidine-1-carboxylate

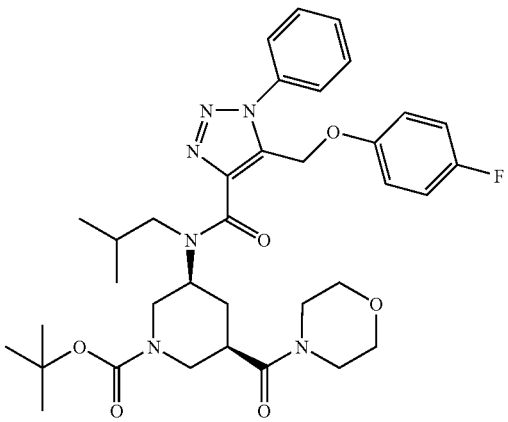 [SMILES: CC(C)CN(C(=O)c1nnn(-c2ccccc2)c1COc1ccc(F)cc1)[C@H]1C[C@@H](C(=O)N2CCOCC2)CN(C(=O)OC(C)(C)C)C1]

MS (ESI+, m/e) 665 (M+1)

In the same manner as in the method shown in Reference Example 265, the following compounds (Reference Examples 312-318) were obtained.

Reference Example 312

1-(2-fluorophenyl)-5-methyl-1H-1,2,3-triazole-4-carboxylic acid

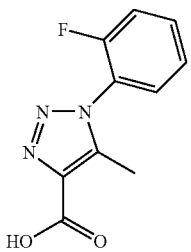 [SMILES: Cc1c(C(=O)O)nnn1-c1ccccc1F]

$^1$H-NMR (CDCl$_3$) δ 3.13 (3H, s), 7.29-7.43 (2H, m), 7.43-7.55 (1H, m), 7.56-7.70 (1H, m).
MS (ESI+, m/e) 222 (M+1)

Reference Example 313

5-ethyl-1-(2-fluorophenyl)-1H-1,2,3-triazole-4-carboxylic acid

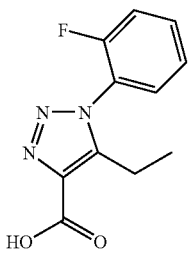 [SMILES: CCc1c(C(=O)O)nnn1-c1ccccc1F]

$^1$H-NMR (CDCl$_3$) δ 1.16 (3H, t), 2.96 (2H, q), 7.29-7.43 (2H, m), 7.43-7.55 (1H, m), 7.56-7.70 (1H, m).
MS (ESI+, m/e) 236 (M+1)

Reference Example 314

1-(2-fluorophenyl)-5-propyl-1H-1,2,3-triazole-4-carboxylic acid

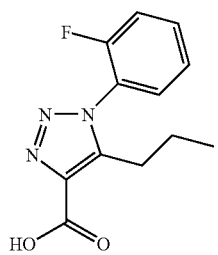 [SMILES: CCCc1c(C(=O)O)nnn1-c1ccccc1F]

$^1$H-NMR (CDCl$_3$) δ 0.84 (3H, t), 1.44-1.67 (2H, m), 2.84-3.09 (2H, m), 7.29-7.54 (3H, m), 7.56-7.70 (1H, m).
MS (ESI+, m/e) 250 (M+1)

Reference Example 315

1-(2-fluorophenyl)-5-(1-methylethyl)-1H-1,2,3-triazole-4-carboxylic acid

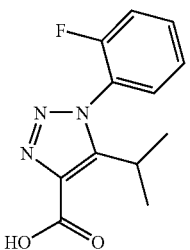 [SMILES: CC(C)c1c(C(=O)O)nnn1-c1ccccc1F]

$^1$H-NMR (CDCl$_3$) δ 1.11-1.49 (6H, m), 3.14-3.39 (1H, m), 7.27-7.54 (3H, m), 7.54-7.71 (1H, m).
MS (ESI+, m/e) 250 (M+1)

Reference Example 316

5-butyl-1-(2-fluorophenyl)-1H-1,2,3-triazole-4-carboxylic acid

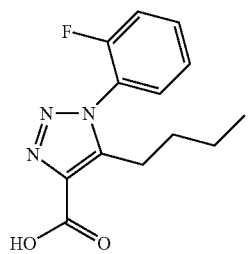 [SMILES: CCCCc1c(C(=O)O)nnn1-c1ccccc1F]

$^1$H-NMR (CDCl$_3$) δ 1.10 (3H, t), 1.23-1.90 (4H, m), 2.89-3.00 (2H, m), 7.29-7.43 (2H, m), 7.43-7.55 (1H, m), 7.56-7.70 (1H, m).
MS (ESI+, m/e) 264 (M+1)

Reference Example 317

1-(2-fluorophenyl)-5-[(methylsulfanyl)methyl]-1H-1,2,3-triazole-4-carboxylic acid

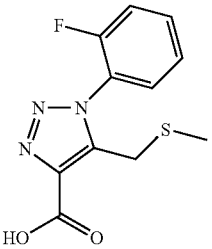 [SMILES: CSCc1c(C(=O)O)nnn1-c1ccccc1F]

$^1$H-NMR (CDCl$_3$) δ 2.01 (3H, s), 4.06 (2H, s), 7.28-7.45 (2H, m), 7.52-7.68 (2H, m).
MS (ESI+, m/e) 268 (M+1)

Reference Example 318

1-(2-fluorophenyl)-5-(3,3,3-trifluoropropyl)-1H-1,2,3-triazole-4-carboxylic acid

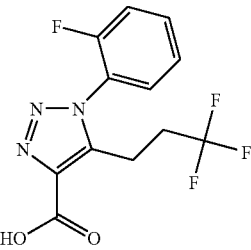 [SMILES: O=C(O)c1nnn(-c2ccccc2F)c1CCC(F)(F)F]

$^1$H-NMR (CDCl$_3$) δ 2.50 (2H, dt), 3.11-3.21 (2H, m), 7.32-7.47 (2H, m), 7.47-7.58 (1H, m), 7.59-7.74 (1H, m).
MS (ESI+, m/e) 304 (M+1)

In the same manner as in the method shown in Reference Example 235, the following compounds (Reference Examples 319-323) were obtained.

Reference Example 319 tert-butyl(3S,5R)-3-[{[1-(2-fluorophenyl)-5-methyl-1H-1,2,3-triazol-4-yl]carbonyl}(2-methylpropyl)amino]-5-(morpholin-4-ylcarbonyl)piperidine-1-carboxylate

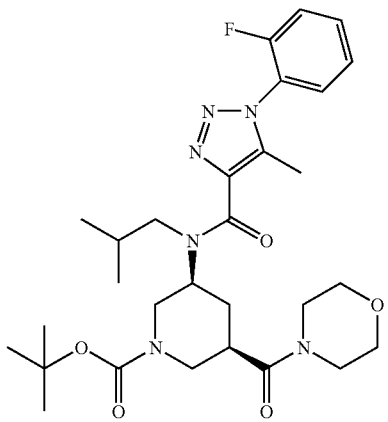 [SMILES: Cc1c(C(=O)N(CC(C)C)[C@H]2C[C@@H](C(=O)N3CCOCC3)CN(C(=O)OC(C)(C)C)C2)nnn1-c1ccccc1F]

MS (ESI+, m/e) 573 (M+1)

Reference Example 320 tert-butyl(3S,5R)-3-[{[5-ethyl-1-(2-fluorophenyl)-1H-1,2,3-triazol-4-yl]carbonyl}(2-methylpropyl)amino]-5-(morpholin-4-ylcarbonyl)piperidine-1-carboxylate

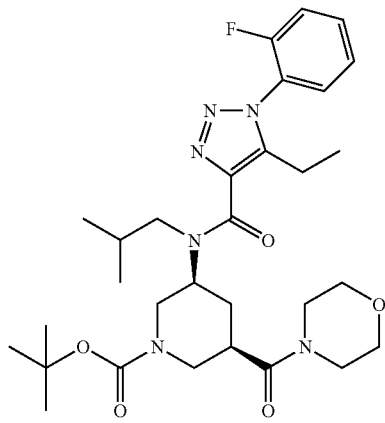 [SMILES: CCc1c(C(=O)N(CC(C)C)[C@H]2C[C@@H](C(=O)N3CCOCC3)CN(C(=O)OC(C)(C)C)C2)nnn1-c1ccccc1F]

$^1$H-NMR (CDCl$_3$) δ 0.85 (2H, br s), 0.98 (4H, dd), 1.03-1.18 (3H, m), 1.41 (6H, s), 1.48 (3H, br s), 1.85-2.25 (2H, m), 2.46 (1H, br s), 2.65-2.89 (6H, m), 2.96 (1H, br s), 3.23 (1H, br s), 3.40 (1H, br s), 3.68 (6H, br s), 4.06-4.34 (2H, m), 4.66 (1H, br s), 7.28-7.51 (3H, m), 7.60 (1H, d).

MS (ESI+, m/e) 587 (M+1)

Reference Example 321 tert-butyl(3S,5R)-3-[{[1-(2-fluorophenyl)-5-propyl-1H-1,2,3-triazol-4-yl]carbonyl}(2-methylpropyl)amino]-5-(morpholin-4-ylcarbonyl)piperidine-1-carboxylate

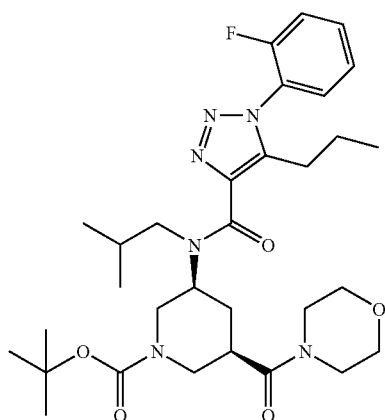 [SMILES: CCCc1c(C(=O)N(CC(C)C)[C@H]2C[C@@H](C(=O)N3CCOCC3)CN(C(=O)OC(C)(C)C)C2)nnn1-c1ccccc1F]

$^1$H-NMR (CDCl$_3$) δ 0.69-0.92 (5H, m), 0.97 (4H, dd), 1.32-1.55 (11H, m), 1.79-2.11 (2H, m), 2.18 (1H, br s), 2.44 (1H, br s), 2.64-3.03 (5H, m), 3.23 (1H, br s), 3.39 (1H, d), 3.68 (8H, br s), 4.06-4.31 (1H, m), 4.63 (1H, br s), 7.28-7.51 (3H, m), 7.61 (1H, br s).

MS (ESI+, m/e) 601 (M+1)

Reference Example 322 tert-butyl(3S,5R)-3-[{[1-(2-fluorophenyl)-5-(1-methylethyl)-1H-1,2,3-triazol-4-yl]carbonyl}(2-methylpropyl)amino]-5-(morpholin-4-ylcarbonyl)piperidine-1-carboxylate

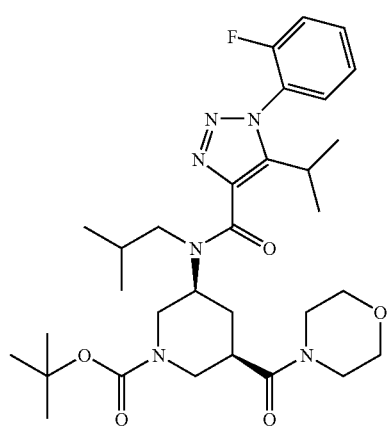 [SMILES: CC(C)CN(C(=O)c1nnn(-c2ccccc2F)c1C(C)C)[C@H]1C[C@@H](C(=O)N2CCOCC2)CN(C(=O)OC(C)(C)C)C1]

$^1$H-NMR (CDCl$_3$) δ 0.72-0.93 (2H, m), 0.99 (4H, dd), 1.16-1.35 (6H, m), 1.35-1.56 (9H, m), 1.93-2.13 (2H, m), 2.23 (1H, d), 2.45 (1H, br s), 2.61-2.95 (6H, m), 2.95-3.22 (1H, m), 3.34 (2H, br s), 3.51-3.87 (6H, m), 4.12 (1H, br s), 7.28-7.51 (3H, m), 7.54-7.67 (1H, m).

MS (ESI+, m/e) 601 (M+1)

Reference Example 323 tert-butyl(3S,5R)-3-[{[5-butyl-1-(2-fluorophenyl)-1H-1,2,3-triazol-4-yl]carbonyl}(2-methylpropyl)amino]-5-(morpholin-4-ylcarbonyl)piperidine-1-carboxylate

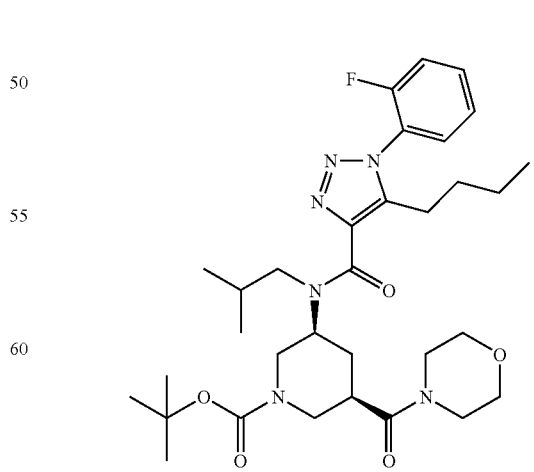

MS (ESI+, m/e) 615 (M+1)

Reference Example 324

1-tert-butyl 3-methyl(3R,5S)-5-[({1-(2-fluorophenyl)-5-[(methylsulfanyl)methyl]-1H-1,2,3-triazol-4-yl}carbonyl)(2-methylpropyl)amino]piperidine-1,3-dicarboxylate

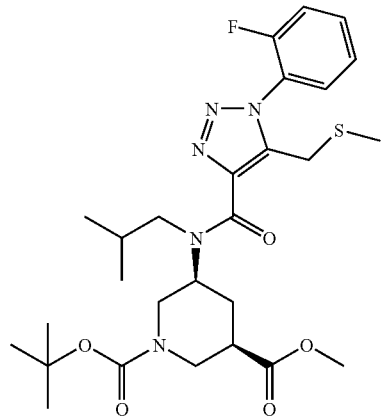 [SMILES: COC(=O)[C@@H]1C[C@H](N(CC(C)C)C(=O)c2nnn(-c3ccccc3F)c2CSC)CN(C(=O)OC(C)(C)C)C1]

1-(2-Fluorophenyl)-5-[(methylsulfanyl)methyl]-1H-1,2,3-triazole-4-carboxylic acid (960 mg), 1-tert-butyl 3-methyl (3R,5S)-5-(isobutylamino)piperidine-1,3-dicarboxylate (1.15 g) and N,N-diisopropylethylamine (1.6 µl) were dissolved in 1,2-dichloroethane (10 ml), chloro-N,N,N',N'-tetramethylformamidinium hexafluorophosphate (1.50 g) was added and the mixture was stirred at room temperature for 3 days. The reaction mixture was diluted with saturated aqueous sodium hydrogen carbonate solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (1.60 g).

$^1$H-NMR (CDCl$_3$) δ 0.95 (6H, dd), 1.36-1.53 (9H, m), 1.90-2.05 (5H, m), 2.14-2.31 (1H, m), 2.40-2.95 (3H, m), 3.30 (1H, d), 3.46-3.62 (1H, m), 3.71 (3H, s), 3.88-4.02 (2H, m), 4.17-4.82 (2H, m), 4.30 (1H, br s), 7.25-7.41 (2H, m), 7.48-7.65 (2H, m).

MS (ESI+, m/e) 564 (M+1)

In the same manner as in the method shown in Reference Example 324, the following compound (Reference Example 325) was obtained.

Reference Example 325

1-tert-butyl 3-methyl(3R,5S)-5-[{[1-(2-fluorophenyl)-5-(3,3,3-trifluoropropyl)-1H-1,2,3-triazol-4-yl]carbonyl}(2-methylpropyl)amino]piperidine-1,3-dicarboxylate

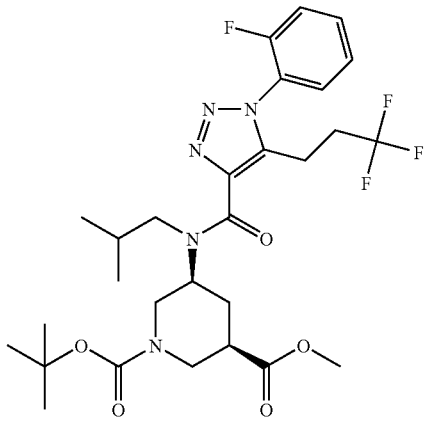 [SMILES: COC(=O)[C@@H]1C[C@H](N(CC(C)C)C(=O)c2nnn(-c3ccccc3F)c2CCC(F)(F)F)CN(C(=O)OC(C)(C)C)C1]

$^1$H-NMR (CDCl$_3$) δ 0.85-1.02 (6H, m), 1.46 (7H, d), 1.46 (2H, br s), 1.78-2.02 (1H, m), 2.09-2.76 (5H, m), 2.85 (1H, d), 2.97-3.11 (2H, m), 3.21-3.37 (1H, m), 3.39-3.66 (1H, m), 3.71 (3H, s), 3.76-4.02 (1H, m), 4.16-4.94 (2H, m), 4.25 (1H, br s), 7.39 (2H, t), 7.47 (1H, t), 7.62 (1H, ddd).

MS (ESI+, m/e) 600 (M+1)

In the same manner as in the method shown in Reference Example 300, the following compounds (Reference Examples 326-327) were obtained.

Reference Example 326 tert-butyl(3S,5R)-3-[({1-(2-fluorophenyl)-5-[(methylsulfanyl)methyl]-1H-1,2,3-triazol-4-yl}carbonyl)(2-methylpropyl)amino]-5-(morpholin-4-ylcarbonyl)piperidine-1-carboxylate

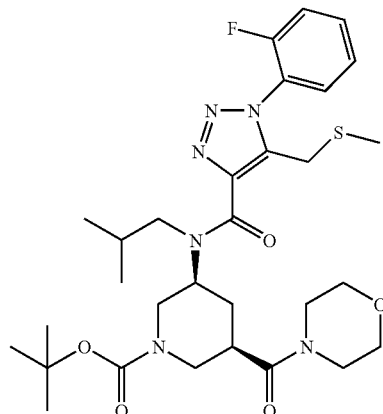

$^1$H-NMR (CDCl$_3$) δ 0.85-1.01 (6H, m), 1.48 (1H, br s), 1.42 (8H, s), 1.99 (3H, s), 2.16 (1H, d), 2.47 (1H, br s), 2.78-2.94 (3H, m), 3.18-3.32 (1H, m), 3.32-3.44 (1H, m), 3.59-3.75 (9H, m), 3.93 (2H, d), 3.87 (1H, br s), 4.19-4.32 (1H, m), 4.71 (1H, br s), 7.37 (2H, t), 7.56 (2H, ddd).

MS (ESI+, m/e) 619 (M+1)

Reference Example 327 tert-butyl(3S,5R)-3-[{[1-(2-fluorophenyl)-5-(3,3,3-trifluoropropyl)-1H-1,2,3-triazol-4-yl]carbonyl}(2-methylpropyl)amino]-5-(morpholin-4-ylcarbonyl)piperidine-1-carboxylate

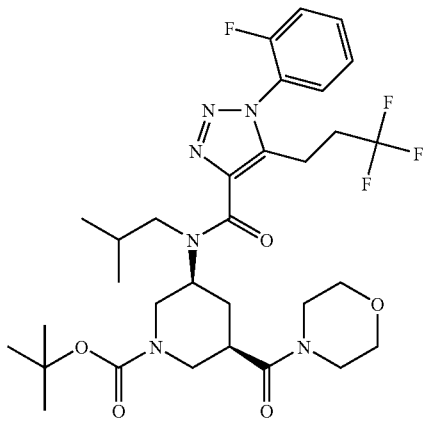 [SMILES: CC(C)CN(C(=O)c1nnn(-c2ccccc2F)c1CCC(F)(F)F)[C@H]1C[C@@H](C(=O)N2CCOCC2)CN(C(=O)OC(C)(C)C)C1]

$^1$H-NMR (CDCl$_3$) δ 0.87 (2H, d), 0.97 (4H, d), 1.37-1.53 (9H, m), 2.03-2.19 (2H, m), 2.36 (1H, br s), 2.45 (2H, br s), 2.82 (3H, br s), 3.06 (1H, d), 3.03 (1H, br s), 3.19-3.35 (1H, m), 3.43 (1H, dd), 3.59-3.76 (5H, m), 3.64 (3H, br s), 3.90-4.20 (2H, m), 4.74 (1H, br s), 7.33-7.50 (3H, m), 7.55-7.72 (1H, m).

MS (ESI+, m/e) 655 (M+1)

Reference Example 328 ethyl 1-(2-fluorophenyl)-1H-1,2,3-triazole-4-carboxylate

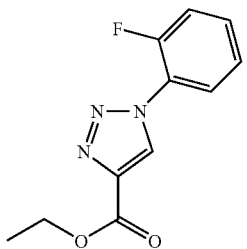 [SMILES: CCOC(=O)c1cn(-c2ccccc2F)nn1]

1-Azido-2-fluorobenzene (1.0 g) and ethyl propiolate (2.2 g) were dissolved in toluene (12 ml) and the mixture was stirred at 100° C. for 13 hr. After cooling to room temperature, the reaction mixture was concentrated under reduced pressure. The residue was subjected to silica gel column chromatography, and a fraction eluted with ethyl acetate-hexane (10:90-80:20) was concentrated under reduced pressure to give the object product (111 mg).

MS (ESI+, m/e) 235 (M+1)

Reference Example 329

1-(2-fluorophenyl)-1H-1,2,3-triazole-4-carboxylic acid

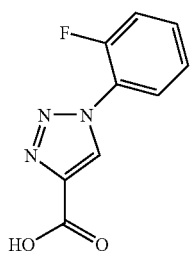 [SMILES: O=C(O)c1cn(-c2ccccc2F)nn1]

Ethyl 1-(2-fluorophenyl)-1H-1,2,3-triazole-4-carboxylate (110 mg) was dissolved in ethanol (3 ml)-water (2 ml)-1M aqueous sodium hydroxide solution (1 ml) and the mixture was stirred at 60° C. for 12 hr. After cooling to room temperature, the reaction mixture was concentrated under reduced pressure. The residue was diluted with water, neutralized (pH:2) with 1M hydrochloric acid, and the mixture was extracted with ethyl acetate. The extract was washed with saturated brine, and dried over anhydrous magnesium sulfate. The solvent was evaporated under reduced pressure to give the object product (92 mg).

MS (ESI+, m/e) 208 (M+1)

In the same manner as in the method shown in Reference Example 235, the following compound (Reference Example 330) was obtained.

Reference Example 330 tert-butyl(3S,5R)-3-[{[1-(2-fluorophenyl)-1H-1,2,3-triazol-4-yl]carbonyl}(2-methylpropyl)amino]-5-(morpholin-4-ylcarbonyl)piperidine-1-carboxylate

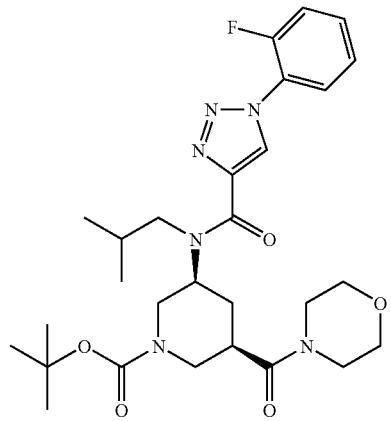 [SMILES: CC(C)CN(C(=O)c1cn(-c2ccccc2F)nn1)[C@H]1C[C@@H](C(=O)N2CCOCC2)CN(C(=O)OC(C)(C)C)C1]

$^1$H-NMR (CDCl$_3$) δ 0.86-1.02 (6H, m), 1.40 (6H, br s), 1.48 (3H, br s), 2.01-2.18 (2H, m), 2.77-2.94 (6H, m), 3.13-3.51 (1H, m), 3.58-3.74 (6H, m), 3.88-5.22 (4H, m), 7.28-7.42 (2H, m), 7.42-7.56 (1H, m), 7.77-8.05 (1H, m), 8.59 (1H, br s).

MS (ESI+, m/e) 559 (M+1)

Reference Example 331 tert-butyl(3S,5R)-3-[{[1-(2-fluorophenyl)-5-(methoxymethyl)-1H-1,2,3-triazol-4-yl]carbonyl}(2-methylpropyl)amino]-5-(morpholin-4-ylcarbonyl)piperidine-1-carboxylate

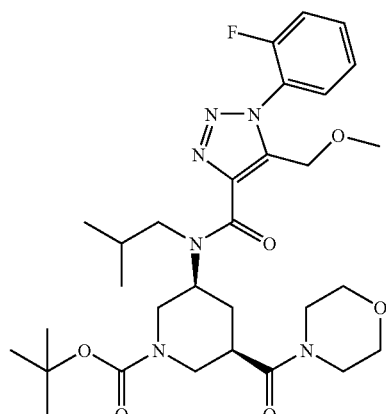

tert-Butyl(3S,5R)-3-[{[1-(2-fluorophenyl)-5-(hydroxymethyl)-1H-1,2,3-triazol-4-yl]carbonyl}(2-methylpropyl)amino]-5-(morpholin-4-ylcarbonyl)piperidine-1-carboxylate (210 mg) and triethylamine (150 μl) were dissolved in THF (4 ml), and methanesulfonyl chloride (45 μl) was added under ice-cooling. The mixture was stirred at 0° C. for 4 hr, sodium methoxide (28% methanol solution, 350 mg) and methanol (4 ml) were added and the mixture was stirred at room temperature for 2 hr. The reaction mixture was diluted with water and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (195 mg).

$^1$H-NMR (CDCl$_3$) δ 0.86 (2H, d), 0.97 (4H, dd), 1.42 (6H, s), 1.48 (3H, s), 2.17 (2H, br s), 2.67-3.06 (3H, m), 3.16-3.25 (4H, m), 3.29 (1H, br s), 3.33-3.56 (2H, m), 3.72 (4H, s), 3.68 (4H, s), 4.19-4.33 (1H, m), 4.51-4.81 (3H, m), 7.28-7.44 (2H, m), 7.47-7.65 (2H, m).

MS (ESI+, m/e) 603 (M+1)

Reference Example 332 tert-butyl(3S,5R)-3-[({1-(2-fluorophenyl)-5-[(2-methoxyethoxy)methyl]-1H-1,2,3-triazol-4-yl}carbonyl)(2-methylpropyl)amino]-5-(morpholin-4-ylcarbonyl)piperidine-1-carboxylate

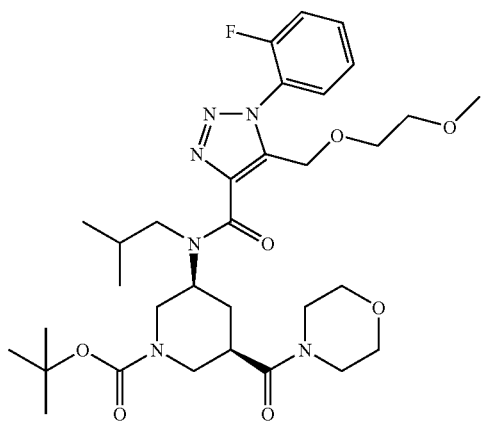 [SMILES: COCCOCc1c(C(=O)N(CC(C)C)[C@H]2C[C@@H](C(=O)N3CCOCC3)CN(C(=O)OC(C)(C)C)C2)nnn1-c1ccccc1F]

tert-Butyl(3S,5R)-3-[{[1-(2-fluorophenyl)-5-(hydroxymethyl)-1H-1,2,3-triazol-4-yl]carbonyl}(2-methylpropyl)amino]-5-(morpholin-4-ylcarbonyl)piperidine-1-carboxylate (510 mg) and triethylamine (365 μl) were dissolved in THF (8 ml), and methanesulfonyl chloride (110 μl) was added under ice-cooling. The mixture was stirred at 0° C. for 3 hr, 2-methoxyethanol (200 mg) was added and the mixture was stirred at room temperature for 14 hr. The reaction mixture was diluted with water and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (491 mg).

$^1$H-NMR (CDCl$_3$) δ 0.87 (2H, d), 0.97 (4H, dd), 1.33-1.54 (9H, m), 1.85-2.22 (2H, m), 2.49 (1H, br s), 2.80 (2H, br s), 2.99 (1H, br s), 3.13-3.41 (6H, m), 3.41-3.58 (3H, m), 3.58-3.90 (8H, m), 4.10-4.22 (1H, m), 4.28 (1H, br s), 4.64 (1H, br s), 4.76-4.96 (2H, m), 7.28-7.40 (2H, m), 7.47-7.63 (2H, m).

MS (ESI+, m/e) 647 (M+1)

In the same manner as in the method shown in Reference Example 270, the following compound (Reference Example 333) was obtained.

Reference Example 333 tert-butyl(3S,5R)-3-[({5-[(2,2-difluoroethoxy)methyl]-1-phenyl-1H-1,2,3-triazol-4-yl}carbonyl)(2-methylpropyl)amino]-5-(morpholin-4-ylcarbonyl)piperidine-1-carboxylate

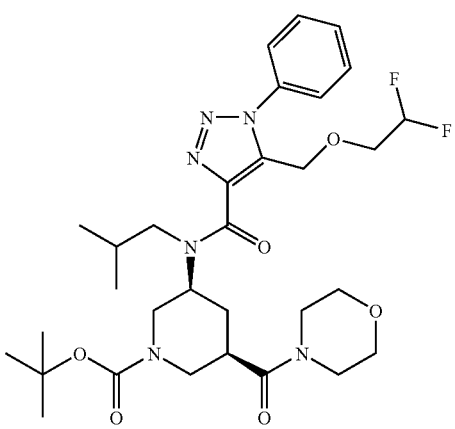 [SMILES: CC(C)CN(C(=O)c1nnn(-c2ccccc2)c1COCC(F)F)[C@H]1C[C@@H](C(=O)N2CCOCC2)CN(C(=O)OC(C)(C)C)C1]

MS (ESI+, m/e) 635 (M+1)

In the same manner as in the method shown in Reference Example 235, the following compound (Reference Example 334) was obtained.

Reference Example 334 tert-butyl(3S,5R)-3-{[(5-cyclopropyl-1-phenyl-1H-1,2,3-triazol-4-yl)carbonyl](2-methylpropyl)amino}-5-(morpholin-4-ylcarbonyl)piperidine-1-carboxylate

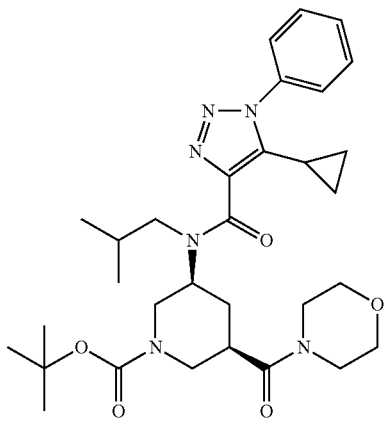 [SMILES: CC(C)CN(C(=O)c1nnn(-c2ccccc2)c1C1CC1)[C@H]1C[C@@H](C(=O)N2CCOCC2)CN(C(=O)OC(C)(C)C)C1]

MS (ESI+, m/e) 581 (M+1)

Reference Example 335 tert-butyl(3S,5R)-3-[{[1-(2-fluorophenyl)-5-(4-methoxybutyl)-1H-1,2,3-triazol-4-yl]carbonyl}(2-methylpropyl)amino]-5-(1,3-oxazol-5-yl)piperidine-1-carboxylate

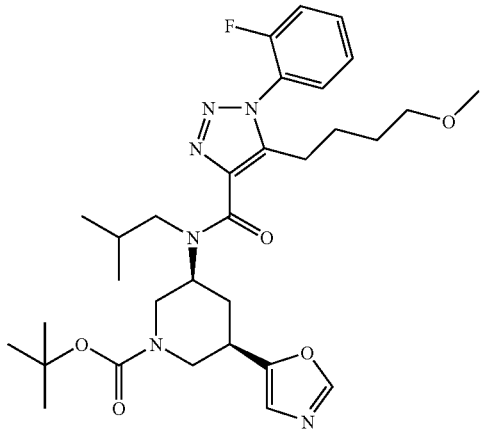 [SMILES: COCCCCc1c(C(=O)N(CC(C)C)[C@H]2C[C@@H](c3cnco3)CN(C(=O)OC(C)(C)C)C2)nnn1-c1ccccc1F]

tert-Butyl(3S,5R)-3-[{[1-(2-fluorophenyl)-5-(4-methoxybutyl)-1H-1,2,3-triazol-4-yl]carbonyl}(2-methylpropyl)amino]-5-formylpiperidine-1-carboxylate (235 mg) and tosylmethyl isocyanide (125 mg) were dissolved in methanol (4 ml), sodium methoxide (28% methanol solution, 325 mg) was added and the mixture was heated under reflux with stirring for 2 hr. The mixture was cooled to room temperature, diluted with water and extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (5:95-100:0) was concentrated under reduced pressure to give the object product (98.5 mg).

$^1$H-NMR (CDCl$_3$) δ 0.90 (3H, br s), 0.99 (3H, d), 1.40-1.57 (13H, m), 1.71 (2H, br s), 1.92-2.07 (1H, m), 2.13-2.37 (1H, m), 2.68 (2H, d), 2.83 (2H, d), 2.90-3.07 (1H, m), 3.17-3.31 (5H, m), 3.48-4.05 (2H, m), 4.13-4.91 (2H, m), 6.86 (1H, s), 7.36 (2H, t), 7.47 (1H, t), 7.58 (1H, td), 7.81 (1H, s).

MS (ESI+, m/e) 599 (M+1)

In the same manner as in the method shown in Reference Example 335, the following compound (Reference Example 336) was obtained.

Reference Example 336 tert-butyl(3S)-3-[{[1-(2-fluorophenyl)-5-(4-methoxybutyl)-1H-1,2,3-triazol-4-yl]carbonyl}(2-methylpropyl)amino]-5-(1,3-oxazol-5-yl)piperidine-1-carboxylate

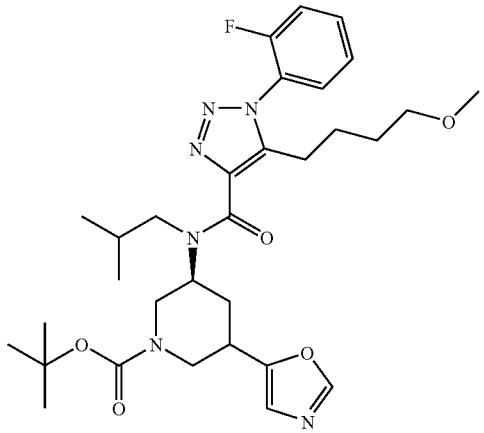 [SMILES: COCCCCc1c(C(=O)N(CC(C)C)[C@H]2CC(c3cnco3)CN(C(=O)OC(C)(C)C)C2)nnn1-c1ccccc1F]

MS (ESI+, m/e) 599 (M+1)

In the same manner as in the method shown in Example 147, the compounds described in the following Examples 164-168 were obtained.

Example 164

1-(2-fluorophenyl)-5-[(2-methoxyethoxy)methyl]-N-(2-methylpropyl)-N-[3S,5R)-5-(morpholin-4-ylcarbonyl)piperidin-3-yl]-1H-1,2,3-triazole-4-carboxamide hydrochloride

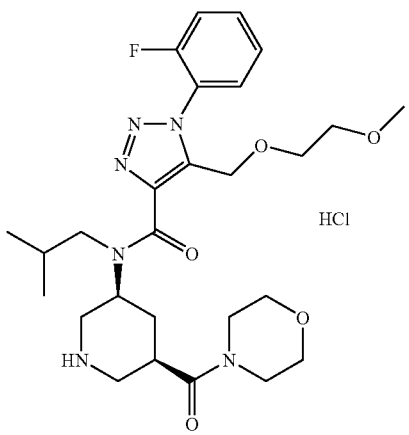 [SMILES: COCCOCc1c(C(=O)N(CC(C)C)[C@@H]2CNC[C@H](C(=O)N3CCOCC3)C2)nnn1-c1ccccc1F ; Cl]

MS (ESI+, m/e) 547 (M+1)

Example 165

1-(2-fluorophenyl)-5-(4-methoxybutyl)-N-[(3S,5R)-5-(methoxymethyl)piperidin-3-yl]-N-(2-methylpropyl)-1H-1,2,3-triazole-4-carboxamide hydrochloride

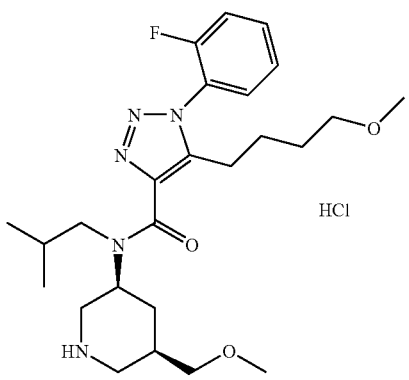 [SMILES: COCCCCc1c(C(=O)N(CC(C)C)[C@@H]2CNC[C@H](COC)C2)nnn1-c1ccccc1F ; Cl]

MS (ESI+, m/e) 476 (M+1)

Example 166

1-(2-fluorophenyl)-5-(4-methoxybutyl)-N-(2-methylpropyl)-N-[(3S,5R)-5-(1,3-oxazol-5-yl)piperidin-3-yl]-1H-1,2,3-triazole-4-carboxamide hydrochloride

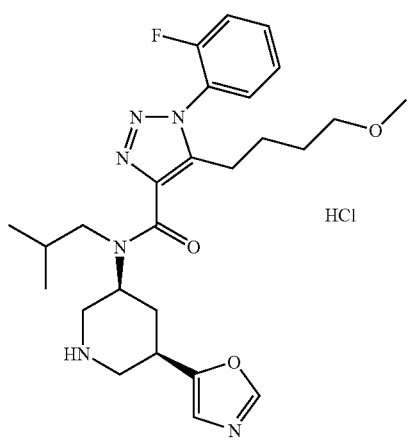 [SMILES: COCCCCc1c(C(=O)N(CC(C)C)[C@@H]2CNC[C@H](c3cnco3)C2)nnn1-c1ccccc1F ; Cl]

MS (ESI+, m/e) 499 (M+1)

Example 167

1-(2-fluorophenyl)-5-(4-methoxybutyl)-N-(2-methylpropyl)-N-[(3S)-5-(1,3-oxazol-5-yl)piperidin-3-yl]-1H-1,2,3-triazole-4-carboxamide hydrochloride

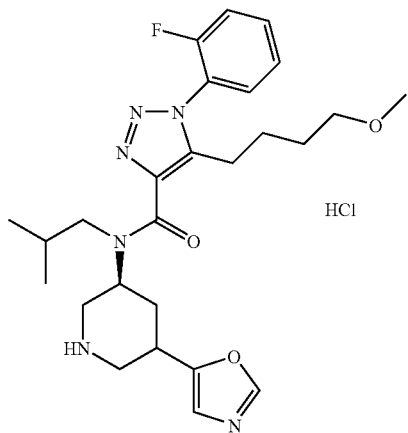 [SMILES: COCCCCc1c(C(=O)N(CC(C)C)[C@@H]2CNCC(c3cnco3)C2)nnn1-c1ccccc1F ; Cl]

MS (ESI+, m/e) 499 (M+1)

Example 168

5-cyclopropyl-N-(2-methylpropyl)-N-[(3S,5R)-5-(morpholin-4-ylcarbonyl)piperidin-3-yl]-1-phenyl-1H-1,2,3-triazole-4-carboxamide hydrochloride

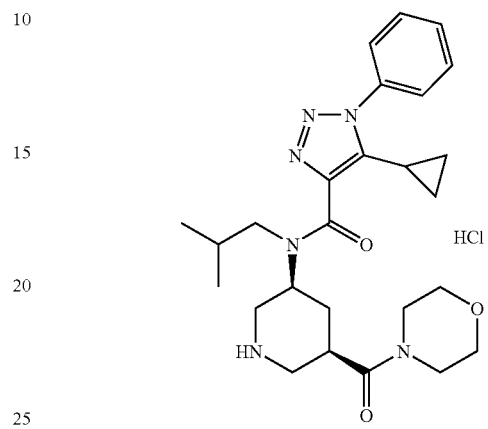

MS (ESI+, m/e) 481 (M+1)

In the same manner as in the method shown in Example 161, the compound described in the following Example 169 was obtained.

Example 169

N-[3S,5R)-5-(difluoromethyl)piperidin-3-yl]-1-(2-fluorophenyl)-5-(4-methoxybutyl)-N-(2-methylpropyl)-1H-1,2,3-triazole-4-carboxamide ½ fumarate

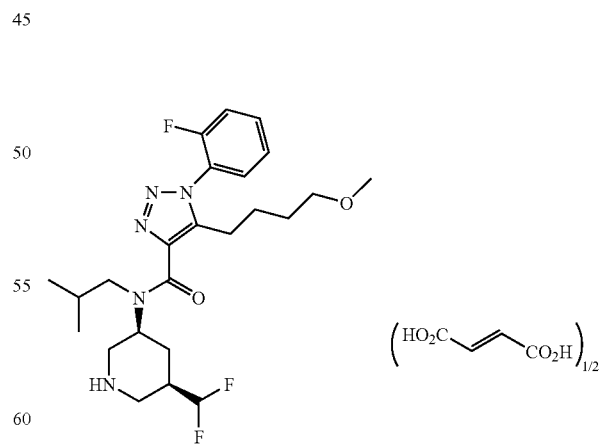

MS (ESI+, m/e) 482 (M+1)

Example 170

1-(2-fluorophenyl)-N-[3S,5R)-5-(hydroxymethyl)piperidin-3-yl]-5-(4-methoxybutyl)-N-(2-methylpropyl)-1H-1,2,3-triazole-4-carboxamide hydrochloride

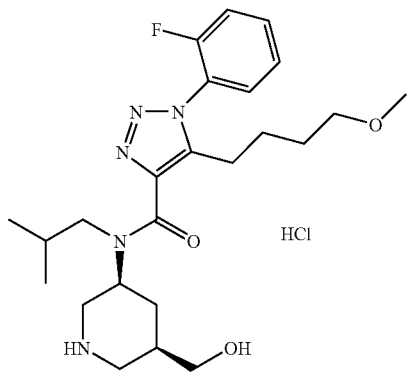 [SMILES: COCCCCc1c(C(=O)N(CC(C)C)[C@@H]2CNC[C@H](CO)C2)nnn1-c1ccccc1F ; Cl]

tert-Butyl(3S,5R)-3-[{[1-(2-fluorophenyl)-5-(4-methoxybutyl)-1H-1,2,3-triazol-4-yl]carbonyl}(2-methylpropyl)amino]-5-(hydroxymethyl)piperidine-1-carboxylate (400 mg) was dissolved in 10% hydrogen chloride-methanol (4 ml), and the mixture was stirred at room temperature for 18 hr. The reaction mixture was concentrated to give the object product (334 mg).

MS (ESI+, m/e) 462 (M+1)

In the same manner as in the method shown in Example 170, the compounds described in the following Examples 171-173 were obtained.

Example 171

1-(2-fluorophenyl)-N-[(3S,5R)-5-(hydroxymethyl)piperidin-3-yl]-N-(2-methylpropyl)-5-(phenoxymethyl)-1H-1,2,3-triazole-4-carboxamide hydrochloride

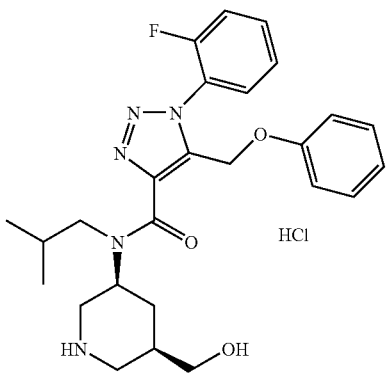 [SMILES: CC(C)CN(C(=O)c1nnn(-c2ccccc2F)c1COc1ccccc1)[C@@H]1CNC[C@H](CO)C1 ; Cl]

MS (ESI+, m/e) 482 (M+1)

Example 172

1-(2,3-difluorophenyl)-N-[(3S,5R)-5-(hydroxymethyl)piperidin-3-yl]-5-(4-methoxybutyl)-N-(2-methylpropyl)-1H-1,2,3-triazole-4-carboxamide hydrochloride

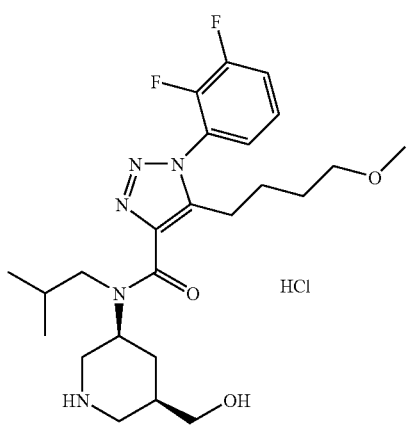 [SMILES: COCCCCc1c(C(=O)N(CC(C)C)[C@@H]2CNC[C@H](CO)C2)nnn1-c1cccc(F)c1F ; Cl]

MS (ESI+, m/e) 480 (M+1)

Example 173

1-(2,6-difluorophenyl)-N-[(3S,5R)-5-(hydroxymethyl)piperidin-3-yl]-5-(4-methoxybutyl)-N-(2-methylpropyl)-1H-1,2,3-triazole-4-carboxamide hydrochloride

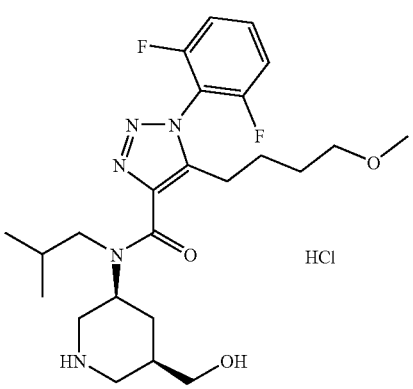 [SMILES: COCCCCc1c(C(=O)N(CC(C)C)[C@@H]2CNC[C@H](CO)C2)nnn1-c1c(F)cccc1F ; Cl]

MS (ESI+, m/e) 480 (M+1)

Example 174

N-[(3S,5R)-5-(1-hydroxyethyl)piperidin-3-yl]-5-[(2-methoxyethoxy)methyl]-1-(2-methylphenyl)-N-(2-methylpropyl)-1H-1,2,3-triazole-4-carboxamide ½ fumarate

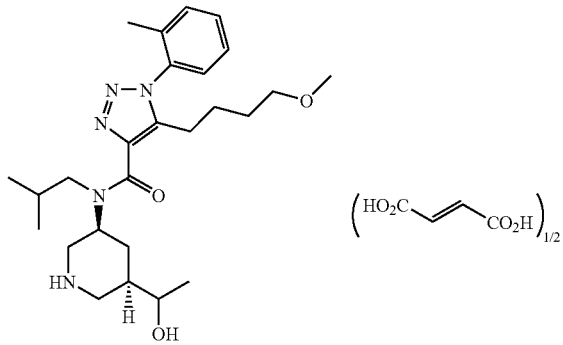

tert-Butyl(3R,5S)-3-(1-hydroxyethyl)-5-[({5-[(2-methoxyethoxy)methyl]-1-(2-methylphenyl)-1H-1,2,3-triazol-4-yl}carbonyl)(2-methylpropyl)amino]piperidine-1-carboxylate (319 mg) was dissolved in 10% hydrogen chloride-methanol (4 ml), and the mixture was stirred at room temperature for 13 hr. The reaction mixture was concentrated under reduced pressure, and the residue was subjected to reversed-phase preparative HPLC and the eluted fraction was concentrated under reduced pressure. The residual aqueous layer was neutralized with 3.5M aqueous potassium carbonate solution and extracted with ethyl acetate. The extract was dried over anhydrous magnesium sulfate, and the solvent was concentrated under reduced pressure. The residue and fumaric acid (27.9 mg) were dissolved in methanol (2 ml), and the solvent was evaporated under reduced pressure to give the object product (254 mg).

MS (ESI+, m/e) 474 (M+1)

In the same manner as in the method shown in Example 174, the compounds described in the following Examples 175-184 were obtained.

Example 175

1-(2-fluorophenyl)-5-(hydroxymethyl)-N-(2-methylpropyl)-N-[(3S,5R)-5-(morpholin-4-ylcarbonyl)piperidin-3-yl]-1H-1,2,3-triazole-4-carboxamide ½ fumarate

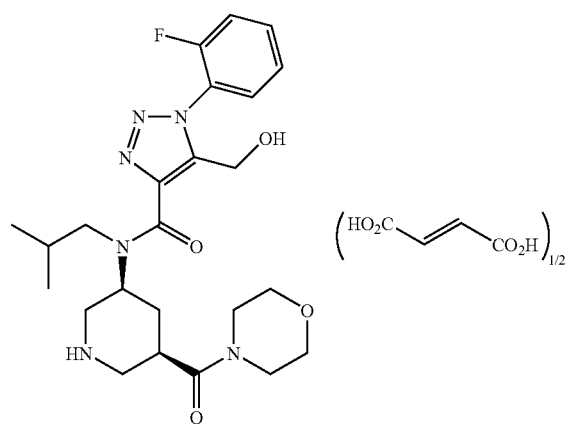

MS (ESI+, m/e) 489 (M+1)

Example 176

1-(2-fluorophenyl)-N-[(3S,5R)-5-(1-hydroxy-2-methoxyethyl)piperidin-3-yl]-5-(4-methoxybutyl)-N-(2-methylpropyl)-1H-1,2,3-triazole-4-carboxamide ½ fumarate

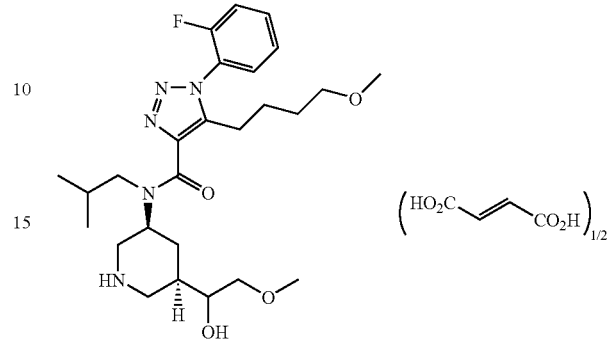

MS (ESI+, m/e) 506 (M+1)

Example 177

N-[(3S,5R)-5-(2-ethoxy-1-hydroxyethyl)piperidin-3-yl]-1-(2-fluorophenyl)-5-(4-methoxybutyl)-N-(2-methylpropyl)-1H-1,2,3-triazole-4-carboxamide ½ fumarate

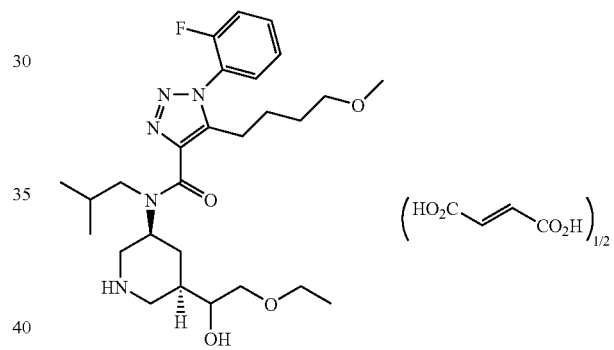

MS (ESI+, m/e) 520 (M+1)

Example 178

1-(2,3-difluorophenyl)-N-[(3S,5R)-5-(1-hydroxyethyl)piperidin-3-yl]-5-(4-methoxybutyl)-N-(2-methylpropyl)-1H-1,2,3-triazole-4-carboxamide ½ fumarate

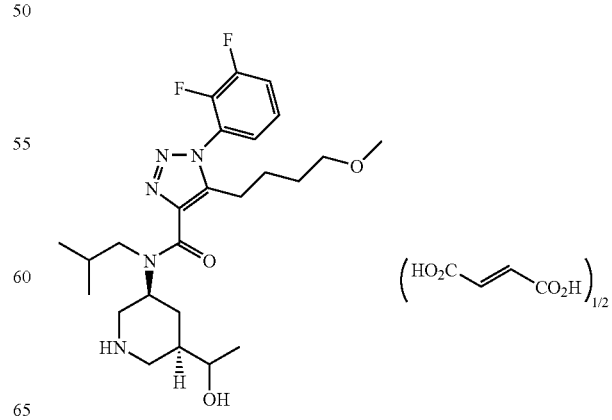

MS (ESI+, m/e) 494 (M+1)

Example 179

1-(2,6-difluorophenyl)-N-[(3S,5R)-5-(1-hydroxyethyl)piperidin-3-yl]-5-(4-methoxybutyl)-N-(2-methylpropyl)-1H-1,2,3-triazole-4-carboxamide ½ fumarate

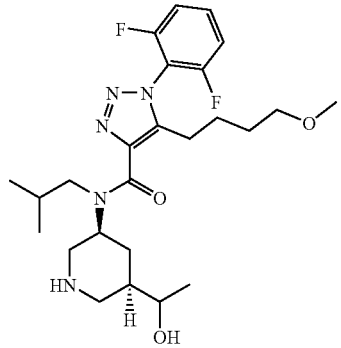

MS (ESI+, m/e) 494 (M+1)

Example 180

N-{(3S,5R)-5-[cyclopropyl(hydroxy)methyl]piperidin-3-yl}-1-(2-fluorophenyl)-5-(4-methoxybutyl)-N-(2-methylpropyl)-1H-1,2,3-triazole-4-carboxamide ½ fumarate

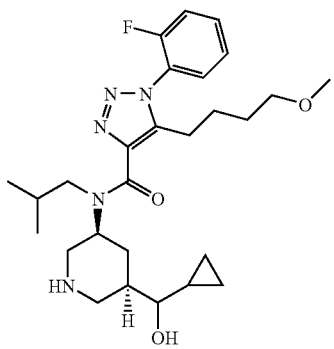

MS (ESI+, m/e) 502 (M+1)

Example 181

1-(2-fluorophenyl)-N-[3S,5R)-5-(1-hydroxypropyl)piperidin-3-yl]-5-(4-methoxybutyl)-N-(2-methylpropyl)-1H-1,2,3-triazole-4-carboxamide ½ fumarate

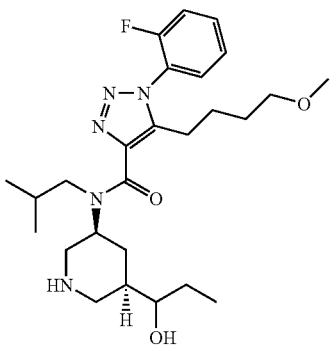

MS (ESI+, m/e) 490 (M+1)

Example 182

1-(2-fluorophenyl)-N-[(3S,5R)-5-(1-hydroxybutyl)piperidin-3-yl]-5-(4-methoxybutyl)-N-(2-methylpropyl)-1H-1,2,3-triazole-4-carboxamide ½ fumarate

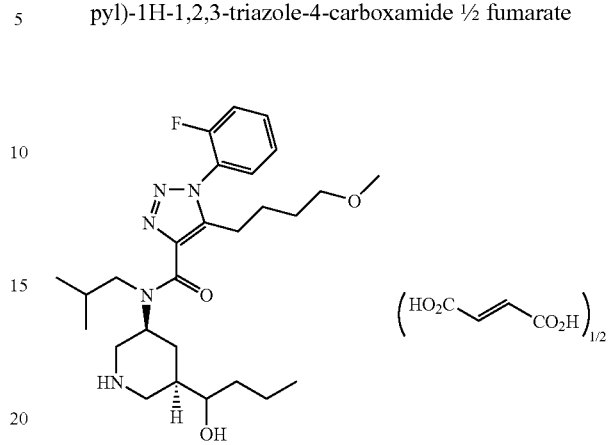

MS (ESI+, m/e) 504 (M+1)

Example 183

1-(2-fluorophenyl)-N-[(3S,5R)-5-(1-hydroxy-2-methylpropyl)piperidin-3-yl]-5-(4-methoxybutyl)-N-(2-methylpropyl)-1H-1,2,3-triazole-4-carboxamide ½ fumarate

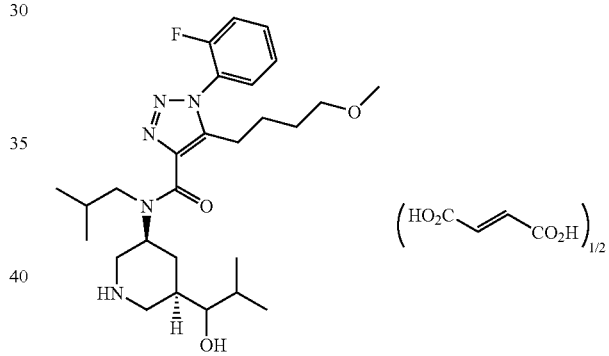

MS (ESI+, m/e) 504 (M+1)

Example 184

1-(2-fluorophenyl)-N-[(3S,5R)-5-(1-hydroxypentyl)piperidin-3-yl]-5-(4-methoxybutyl)-N-(2-methylpropyl)-1H-1,2,3-triazole-4-carboxamide ½ fumarate

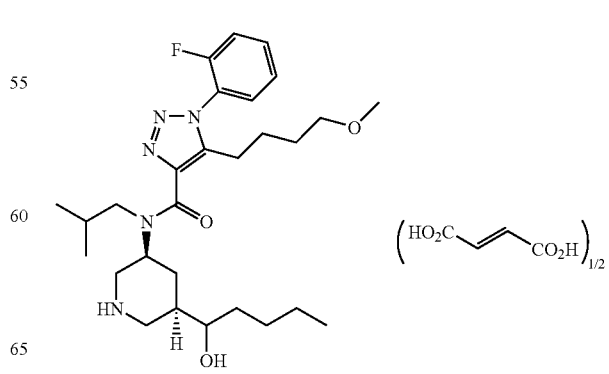

MS (ESI+, m/e) 518 (M+1)

Example 185

1-(2-fluorophenyl)-N-(2-methylpropyl)-N-[(3S, 5R)-5-(morpholin-4-ylcarbonyl)piperidin-3-yl]-5-(phenoxymethyl)-1H-1,2,3-triazole-4-carboxamide ½ fumarate

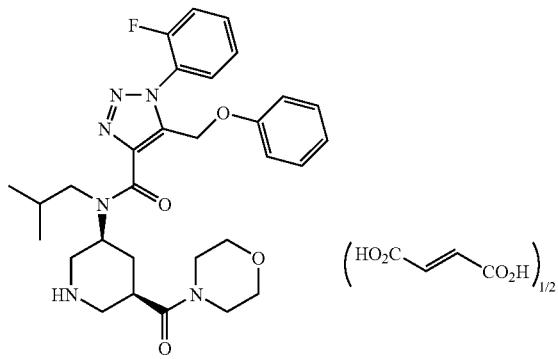

tert-Butyl(3S,5R)-3-[{[1-(2-fluorophenyl)-5-(phenoxymethyl)-1H-1,2,3-triazol-4-yl]carbonyl}(2-methylpropyl)amino]-5-(morpholin-4-ylcarbonyl)piperidine-1-carboxylate (119 mg) was dissolved in 1M hydrogen chloride-ethyl acetate (4 ml), and the mixture was stirred at room temperature for 13 hr and concentrated under reduced pressure. The residue was diluted with ethyl acetate, washed successively with 3.5M aqueous potassium carbonate solution and saturated brine, and dried over anhydrous magnesium sulfate. The solvent was evaporated under reduced pressure. The residue was subjected to basic silica gel column chromatography, and a fraction eluted with ethyl acetate-hexane-methanol (10:90:0-100:0:0-85:0:15) was concentrated under reduced pressure. The residue was dissolved in methanol (2 ml), fumaric acid (7.9 mg) was added and the mixture was stirred at room temperature for 1 hr. The reaction mixture was concentrated under reduced pressure to give the object product (87 mg).

MS (ESI+, m/e) 565 (M+1)

In the same manner as in the method shown in Example 185, the compounds described in the following Examples 186-197 were obtained.

Example 186

1-(2-fluorophenyl)-5-[(2-methoxyethoxy)methyl]-N-(2-methylpropyl)-N-[(3S,5R)-5-(morpholin-4-ylcarbonyl)piperidin-3-yl]-1H-1,2,3-triazole-4-carboxamide ½ fumarate

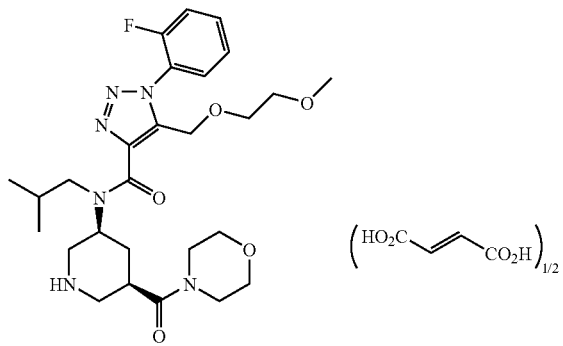

MS (ESI+, m/e) 547 (M+1)

Example 187

1-(2-fluorophenyl)-N-(2-methylpropyl)-N-[(3S,5R)-5-(morpholin-4-ylcarbonyl)piperidin-3-yl]-5-[2-(1,3-thiazol-2-yl)ethyl]-1H-1,2,3-triazole-4-carboxamide ½ fumarate

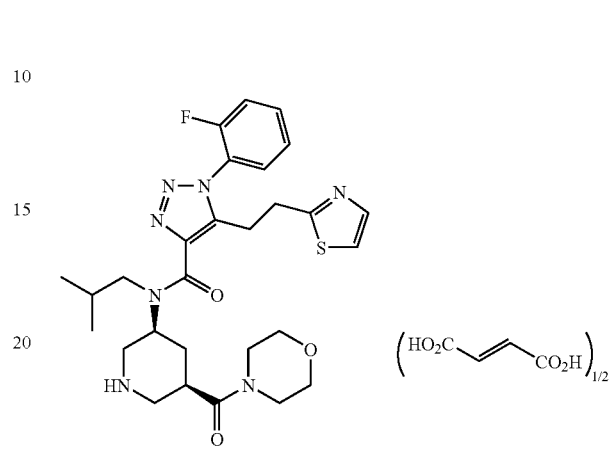

MS (ESI+, m/e) 570 (M+1)

Example 188

5-[(4-fluorophenoxy)methyl]-N-(2-methylpropyl)-N-[(3S,5R)-5-(morpholin-4-ylcarbonyl)piperidin-3-yl]-1-phenyl-1H-1,2,3-triazole-4-carboxamide ½ fumarate

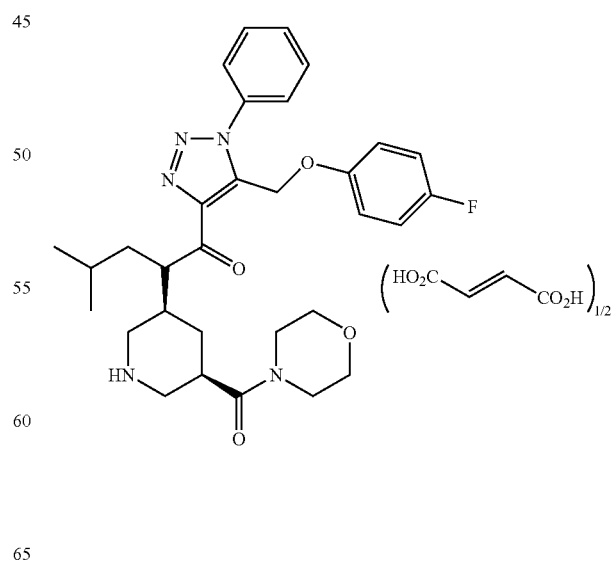

MS (ESI+, m/e) 565 (M+1)

365

Example 189

1-(2-fluorophenyl)-N-(2-methylpropyl)-N-[(3S,5R)-5-(morpholin-4-ylcarbonyl)piperidin-3-yl]-1H-1,2,3-triazole-4-carboxamide 1/2 fumarate

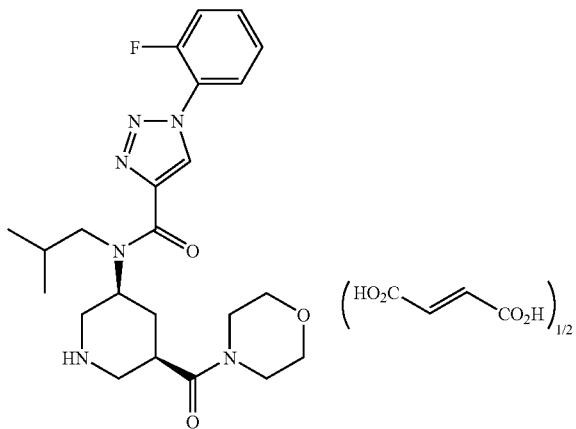

MS (ESI+, m/e) 459 (M+1)

Example 190

1-(2-fluorophenyl)-5-methyl-N-(2-methylpropyl)-N-[(3S,5R)-5-(morpholin-4-ylcarbonyl)piperidin-3-yl]-1H-1,2,3-triazole-4-carboxamide 1/2 fumarate

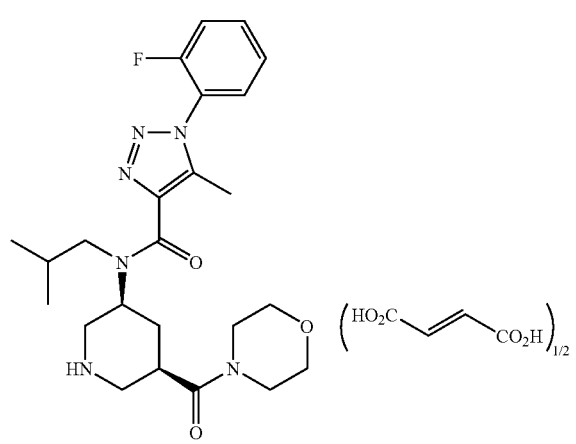

MS (ESI+, m/e) 473 (M+1)

366

Example 191

5-ethyl-1-(2-fluorophenyl)-N-(2-methylpropyl)-N-[(3S,5R)-5-(morpholin-4-ylcarbonyl)piperidin-3-yl]-1H-1,2,3-triazole-4-carboxamide 1/2 fumarate

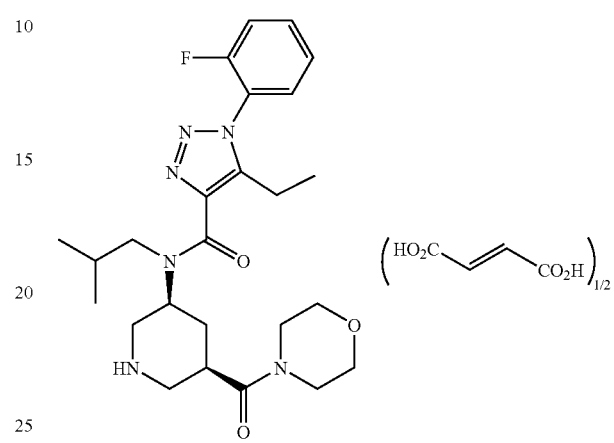

MS (ESI+, m/e) 487 (M+1)

Example 192

1-(2-fluorophenyl)-N-(2-methylpropyl)-N-[(3S,5R)-5-(morpholin-4-ylcarbonyl)piperidin-3-yl]-5-propyl-1H-1,2,3-triazole-4-carboxamide 1/2 fumarate

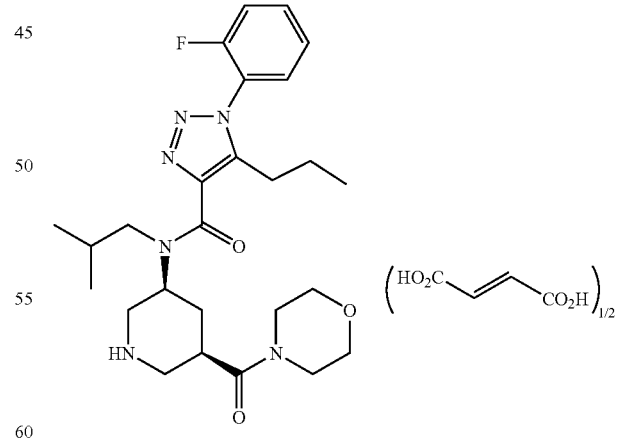

MS (ESI+, m/e) 501 (M+1)

Example 193

5-butyl-1-(2-fluorophenyl)-N-(2-methylpropyl)-N-[(3S,5R)-5-(morpholin-4-ylcarbonyl)piperidin-3-yl]-1H-1,2,3-triazole-4-carboxamide 1/2 fumarate

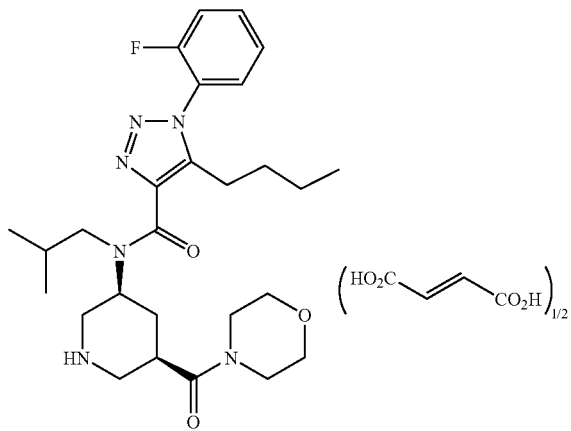

MS (ESI+, m/e) 515 (M+1)

Example 194

1-(2-fluorophenyl)-N-(2-methylpropyl)-N-[(3S,5R)-5-(morpholin-4-ylcarbonyl)piperidin-3-yl]-5-(3,3,3-trifluoropropyl)-1H-1,2,3-triazole-4-carboxamide ½ fumarate

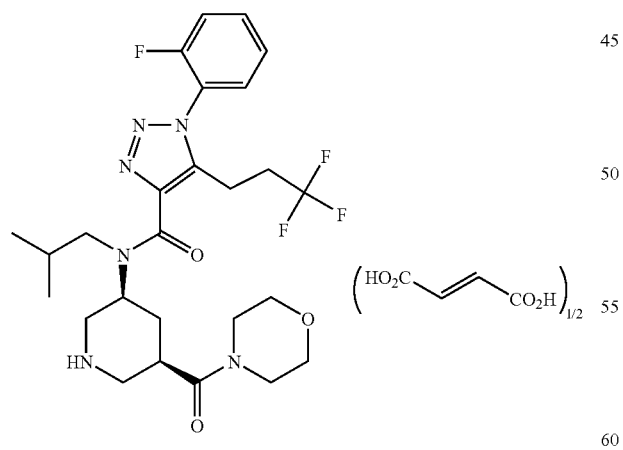

MS (ESI+, m/e) 555 (M+1)

Example 195

1-(2-fluorophenyl)-N-(2-methylpropyl)-5-[(methylsulfanyl)methyl]-N-[(3S,5R)-5-(morpholin-4-ylcarbonyl)piperidin-3-yl]-1H-1,2,3-triazole-4-carboxamide 1/2 fumarate

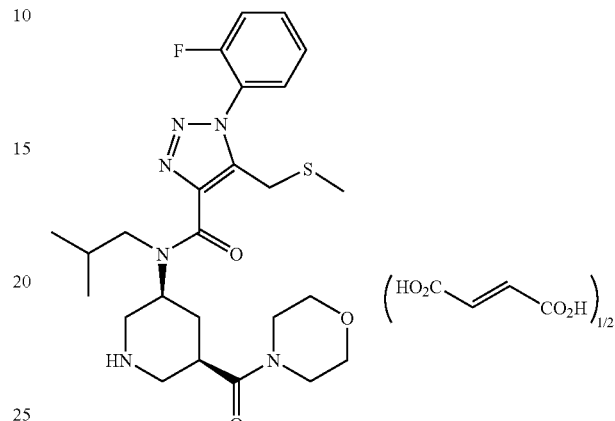

MS (ESI+, m/e) 519 (M+1)

Example 196

1-(2-fluorophenyl)-5-(methoxymethyl)-N-(2-methylpropyl)-N-[(3S,5R)-5-(morpholin-4-ylcarbonyl)piperidin-3-yl]-1H-1,2,3-triazole-4-carboxamide ½ fumarate

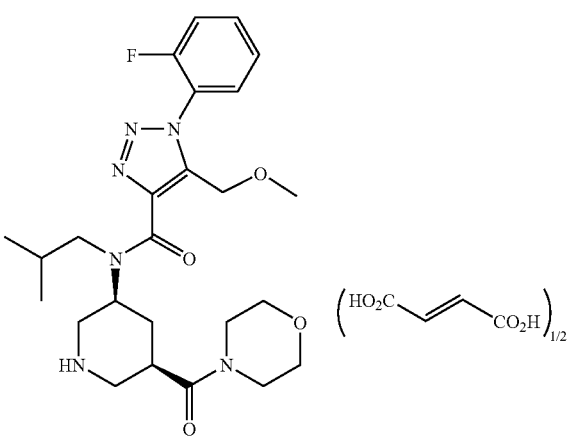

MS (ESI+, m/e) 503 (M+1)

Example 197

1-(2-fluorophenyl)-5-(1-methylethyl)-N-(2-methylpropyl)-N-[(3S,5R)-5-(morpholin-4-ylcarbonyl)piperidin-3-yl]-1H-1,2,3-triazole-4-carboxamide 1/2 fumarate

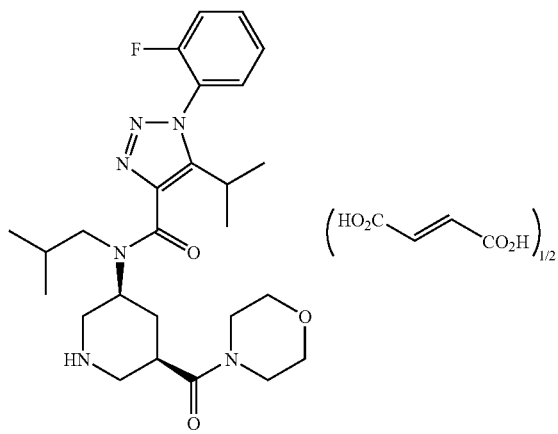

MS (ESI+, m/e) 501 (M+1)

Example 198

5-[(2,2-difluoroethoxy)methyl]-N-(2-methylpropyl)-N-[(3S,5R)-5-(morpholin-4-ylcarbonyl)piperidin-3-yl]-1-phenyl-1H-1,2,3-triazole-4-carboxamide

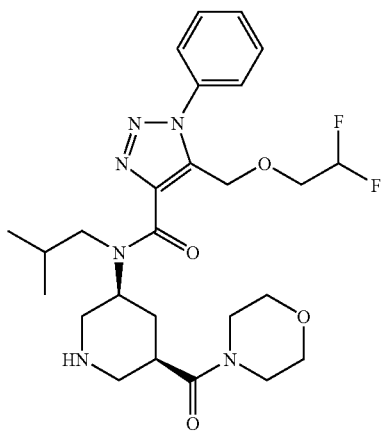 [SMILES: CC(C)CN(C(=O)c1nnn(-c2ccccc2)c1COCC(F)F)[C@@H]1CNC[C@H](C(=O)N2CCOCC2)C1]

tert-Butyl(3S,5R)-3-[({5-[(2,2-difluoroethoxy)methyl]-1-phenyl-1H-1,2,3-triazol-4-yl}carbonyl)(2-methylpropyl)amino]-5-(morpholin-4-ylcarbonyl)piperidine-1-carboxylate (15.0 mg) was dissolved in 1M hydrogen chloride-ethyl acetate (3 ml), and the mixture was stirred at room temperature for 3 hr. The reaction mixture was concentrated under reduced pressure, the residue was subjected to reversed-phase preparative HPLC and the eluted fraction was concentrated under reduced pressure. The residual aqueous layer was neutralized with 3.5M aqueous potassium carbonate solution and extracted with ethyl acetate. The extract was dried over anhydrous magnesium sulfate, and the solvent was evaporated under reduced pressure to give the object product (3.6 mg).

MS (ESI+, m/e) 535 (M+1)

Reference Example 337 methyl 5-(2-methoxyphenyl)-1H-pyrrole-2-carboxylate

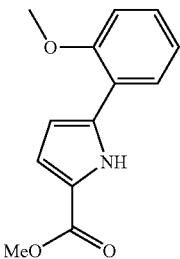 [SMILES: COC(=O)c1ccc(-c2ccccc2OC)[nH]1]

28%-Sodium metholate-methanol solution (4.4 ml) was diluted with methanol (5 ml), and cooled to −20° C. A solution of (2E)-3-(2-methoxyphenyl)prop-2-enal (2.4 g) and ethyl azidoacetate (7.5 g) in methanol (8 ml) was added over 30 min, and the mixture was stirred at −10° C. for 1 hr and at room temperature for 2 hr. The reaction mixture was poured into water and extracted with ether. The extract was washed with brine, and dried over anhydrous sodium sulfate. The solvent was evaporated under reduced pressure. The residue was subjected to silica gel column chromatography, and a fraction eluted with ethyl acetate-hexane (1:4) was concentrated under reduced pressure to give methyl(2Z,4E)-2-azido-5-(2-methoxyphenyl)penta-2,4-dienoate (3.6 g). A part (3.5 g) thereof was dissolved in chloroform (10 ml), zinc iodide (214 mg) was added and the mixture was stirred at room temperature for 12 hr. The reaction mixture was poured into water, and extracted with 1,2-dichloroethane. The extract was dried over anhydrous sodium sulfate and the solvent was evaporated under reduced pressure. The residue was subjected to silica gel column chromatography, and a fraction eluted with ethyl acetate-hexane (1:4) was concentrated under reduced pressure to give the object product (3.26 g).

$^1$H-NMR (CDCl$_3$) δ 3.88 (3H, s), 4.00 (3H, s), 6.57-6.66 (1H, m), 6.90-7.06 (3H, m), 7.20-7.29 (1H, m), 7.68 (1H, d), 10.41 (1H, br s)

Reference Example 338 ethyl 1-(4-methoxybutyl)-5-phenyl-1H-pyrrole-2-carboxylate

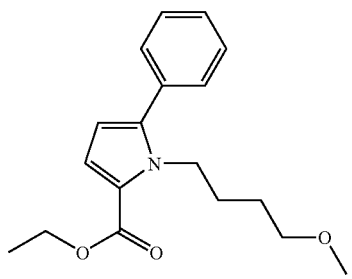 [SMILES: CCOC(=O)c1ccc(-c2ccccc2)n1CCCCOC]

Ethyl 5-phenyl-1H-pyrrole-2-carboxylate (400 mg) and 4-methoxybutyl methanesulfonate (440 mg) were dissolved in DMF (10 ml), cesium carbonate (780 mg) was added and the mixture was stirred at 60° C. for 12 hr. The reaction mixture was poured into water and the mixture was extracted with ethyl acetate. The extract was washed with brine, and dried over anhydrous sodium sulfate. The solvent was evaporated under reduced pressure. The residue was subjected to silica gel column chromatography, and a fraction eluted with ethyl acetate-hexane (1:9-1:4) was concentrated under reduced pressure to give the object product (430 mg).

$^1$H-NMR (CDCl$_3$) δ 1.31-1.47 (2H, m), 1.61-1.76 (2H, m), 3.21 (2H, t), 3.22-3.23 (3H, m), 3.83 (3H, s), 6.15 (1H, d), 7.03 (1H, d), 7.34-7.48 (5H, m).

In the same manner as in Reference Example 338, the following compounds (Reference Examples 340-343) were synthesized.

Reference Example 339 ethyl 1-(4-methoxybutyl)-5-(1-methylethyl)-1H-pyrrole-2-carboxylate

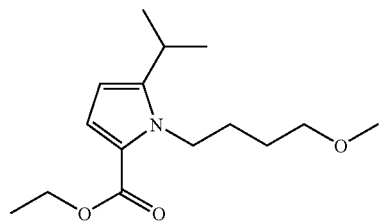 [SMILES: CCOC(=O)c1ccc(C(C)C)n1CCCCOC]

$^1$H-NMR (CDCl$_3$) δ 1.18-1.41 (9H, m), 1.55-1.83 (4H, m), 1.56-1.85 (3H, m), 2.95 (1H, dt), 3.28-3.47 (5H, m), 4.18-4.39 (4H, m), 5.99 (1H, t), 6.95 (1H, d).

Reference Example 340 methyl 1-(4-methoxybutyl)-5-(thiophen-2-yl)-1H-pyrrole-2-carboxylate

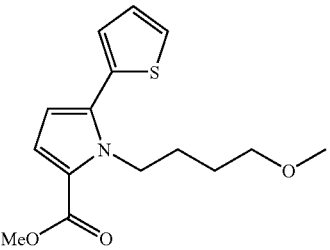 [SMILES: COCCCCn1c(C(=O)OC)ccc1-c1cccs1]

$^1$H-NMR (CDCl$_3$) δ 1.48-1.63 (2H, m), 1.81 (1H, m), 3.25-3.38 (3H, m), 3.27-3.35 (5H, m), 3.84 (3H, s), 4.46 (2H, d), 6.28 (1H, d), 7.00 (1H, d), 7.08-7.13 (2H, m), 7.39 (1H, dd)

Reference Example 341 methyl 1-(4-methoxybutyl)-5-(2-methoxyphenyl)-1H-pyrrole-2-carboxylate

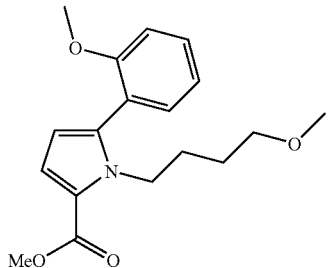 [SMILES: COCCCCn1c(C(=O)OC)ccc1-c1ccccc1OC]

$^1$H-NMR (CDCl$_3$) δ 1.21-1.44 (2H, m), 1.54-1.69 (2H, m), 3.20 (3H, s), 3.16 (1H, t), 3.80 (3H, s), 3.83 (3H, s), 4.18 (2H, t), 4.25-4.41 (2H, m), 6.09 (1H, d), 6.93-7.13 (3H, m), 7.20-7.49 (2H, m)

Reference Example 342 methyl 1-(4-methoxybutyl)-1H-pyrrole-2-carboxylate

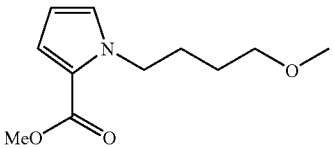

$^1$H-NMR (CDCl$_3$) δ 1.57 (2H, dd), 1.77-1.91 (2H, m), 3.32 (3H, s), 3.38 (2H, t), 3.81 (3H, s), 4.34 (2H, t), 6.09-6.14 (1H, m), 6.83-6.87 (1H, m), 6.95 (1H, dd)

Reference Example 343 methyl 5-formyl-1-(4-methoxybutyl)-1H-pyrrole-2-carboxylate

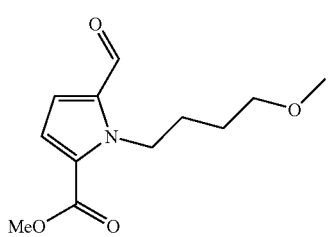 [SMILES: COCCCCn1c(C=O)ccc1C(=O)OC]

$^1$H-NMR (CDCl$_3$) δ 1.54-1.69 (2H, m), 1.70-1.90 (2H, m), 3.33 (3H, s), 3.40 (2H, t), 3.88 (3H, s), 4.84 (2H, d), 6.86-6.96 (2H, m), 9.71 (1H, s)

Reference Example 344 methyl 5-bromo-1H-pyrrole-2-carboxylate

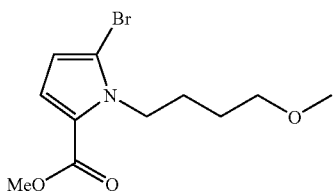 [SMILES: COCCCCn1c(Br)ccc1C(=O)OC]

Methyl 1-(4-methoxybutyl)-1H-pyrrole-2-carboxylate (4.5 g) was dissolved in dichloromethane (30 ml), N-bromosuccinimide (4.0 g) was added and the mixture was stirred for 1 hr. The reaction mixture was washed successively with water and brine, and dried over anhydrous sodium sulfate. The solvent was evaporated under reduced pressure. The residue was subjected to silica gel column chromatography, and a fraction eluted with ethyl acetate-hexane (1:4) was concentrated under reduced pressure to give the object product (2.2 g).

$^1$H-NMR (CDCl$_3$) δ 1.62 (2H, dd), 1.70-1.85 (2H, m), 3.33 (3H, s), 3.39 (2H, t), 3.80 (3H, s), 4.38-4.50 (2H, m), 6.19 (1H, d), 6.94 (1H, d)

Reference Example 345

1-(4-methoxybutyl)-5-phenyl-1H-pyrrole-2-carboxylic acid

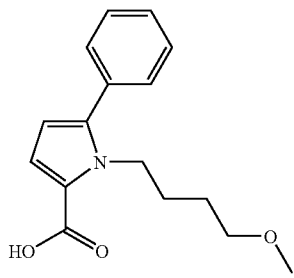 [SMILES: COCCCCn1c(C(=O)O)ccc1-c1ccccc1]

Ethyl 1-(4-methoxybutyl)-5-phenyl-1H-pyrrole-2-carboxylate (430 mg) was dissolved in methanol (2 ml), 2M aqueous sodium hydroxide solution (4 ml) was added and the mixture was stirred at 60° C. for 12 hr. The reaction mixture was concentrated under reduced pressure, and the aqueous layer of the mixture was adjusted to pH 3 with 6M hydrochloric acid, and the mixture was extracted with ethyl acetate. The extract was washed with brine, and dried over anhydrous sodium sulfate. The solvent was evaporated under reduced pressure to give the object product (420 mg).

$^1$H-NMR (DMSO-d$_6$) δ: 1.11-1.27 (2H, m), 1.44-1.60 (2H, m), 3.01-3.13 (5H, m), 4.31 (2H, t), 6.15 (1H, d), 6.91 (1H, d), 7.34-7.50 (5H, m), 12.15 (1H, s)

In the same manner as in Reference Example 345, the following compounds (Reference Examples 346-349) were synthesized.

Reference Example 346

1-(4-methoxybutyl)-5-(1-methylethyl)-1H-pyrrole-2-carboxylic acid

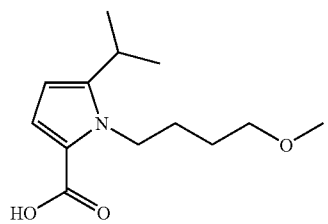 [SMILES: COCCCCn1c(C(=O)O)ccc1C(C)C]

$^1$H-NMR (CDCl$_3$) δ 1.53-1.83 (4H, m), 2.94 (1H, m), 3.25-3.46 (5H, m), 4.27 (2H, dd), 5.88-6.10 (1H, m), 6.95 (1H, t), 8.9(1H, br)

Reference Example 347

1-(4-methoxybutyl)-5-(thiophen-2-yl)-1H-pyrrole-2-carboxylic acid

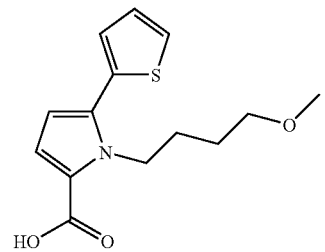 [SMILES: COCCCCn1c(C(=O)O)ccc1-c1cccs1]

$^1$H-NMR (CDCl$_3$) δ 1.55 (2H, d), 1.73-1.88 (3H, m), 3.22-3.39 (3H, m), 4.42 (2H, d), 6.29 (1H, d), 7.11 (3H, d), 7.39 (1H, dd)

Reference Example 348

1-(4-methoxybutyl)-5-(2-methoxyphenyl)-1H-pyrrole-2-carboxylic acid

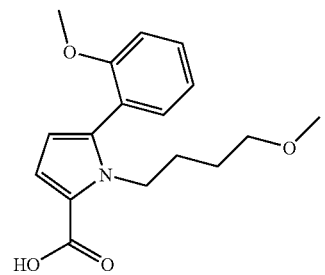 [SMILES: COCCCCn1c(C(=O)O)ccc1-c1ccccc1OC]

¹H-NMR (CDCl₃) δ 1.21-1.42 (2H, m), 1.57-1.72 (1H, m), 3.18 (5H, t), 3.81 (3H, s), 4.20 (2H, t), 6.13 (1H, d), 6.94-7.09 (2H, m), 7.20-7.30 (2H, m), 7.42 (1H, dd)

Reference Example 349

5-bromo-1-(4-methoxybutyl)-1H-pyrrole-2-carboxylic acid

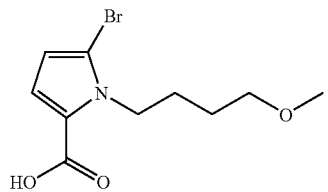

¹H-NMR (CDCl₃) δ 1.56-1.70 (2H, m), 1.72-1.88 (2H, m), 3.34 (3H, s), 3.41 (2H, t), 4.38-4.55 (2H, m), 6.25 (1H, d), 7.10 (1H, d)

Reference Example 350 tert-butyl(3S,5R)-3-[{[1-(4-methoxybutyl)-5-phenyl-1H-pyrrol-2-yl]carbonyl}(2-methylpropyl) amino]-5-(morpholin-4-ylcarbonyl)piperidine-1-carboxylate

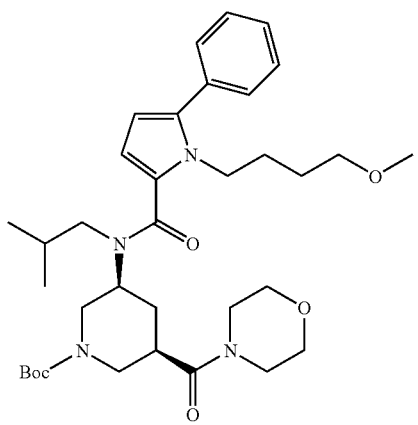 [SMILES: COCCCCn1c(C(=O)N(CC(C)C)[C@H]2C[C@@H](C(=O)N3CCOCC3)CN(C(=O)OC(C)(C)C)C2)ccc1-c1ccccc1]

To a mixture of 1-(4-methoxybutyl)-5-phenyl-1H-pyrrole-2-carboxylic acid (137 mg), 1-tert-butyl 3-methyl (3R,5S)-5-(isobutylamino)piperidine-1,3-dicarboxylate (134 mg), chloro-N,N,N',N'-tetramethylformamidinium hexafluorophosphate (168 mg) and 1,2-dichloroethane (5 ml) was added diisopropylethylamine (0.449 ml) and the mixture was stirred at room temperature for 12 hr. The reaction mixture was concentrated under reduced pressure, diluted with water, and partitioned. The aqueous layer was extracted with ethyl acetate, the organic layers were combined and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (150 mg).

MS (ESI+, m/e) 625 (M+1)

In the same manner as in Reference Example 350, the following compounds (Reference Examples 351-354) were synthesized.

Reference Example 351 tert-butyl(3S,5R)-3-[{[1-(4-methoxybutyl)-5-(1-methylethyl)-1H-pyrrol-2-yl]carbonyl}(2-methylpropyl)amino]-5-(morpholin-4-ylcarbonyl)piperidine-1-carboxylate

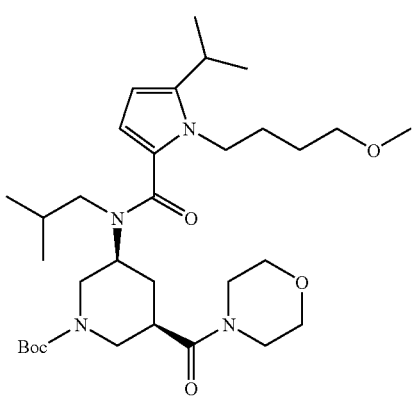 [SMILES: COCCCCn1c(C(=O)N(CC(C)C)[C@H]2C[C@@H](C(=O)N3CCOCC3)CN(C(=O)OC(C)(C)C)C2)ccc1C(C)C]

MS (ESI+, m/e) 592 (M+1)

Reference Example 352 tert-butyl(3S,5R)-3-[{[1-(4-methoxybutyl)-5-(thiophen-2-yl)-1H-pyrrol-2-yl]carbonyl}(2-methylpropyl)amino]-5-(morpholin-4-ylcarbonyl)piperidine-1-carboxylate

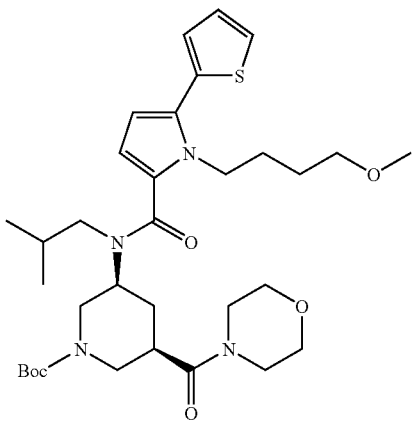 [SMILES: COCCCCn1c(C(=O)N(CC(C)C)[C@H]2C[C@@H](C(=O)N3CCOCC3)CN(C(=O)OC(C)(C)C)C2)ccc1-c1cccs1]

MS (ESI+, m/e) 631 (M+1)

Reference Example 353 tert-butyl(3S,5R)-3-[{[1-(4-methoxybutyl)-5-(2-methoxyphenyl)-1H-pyrrol-2-yl]carbonyl}(2-methylpropyl)amino]-5-(morpholin-4-ylcarbonyl)piperidine-1-carboxylate

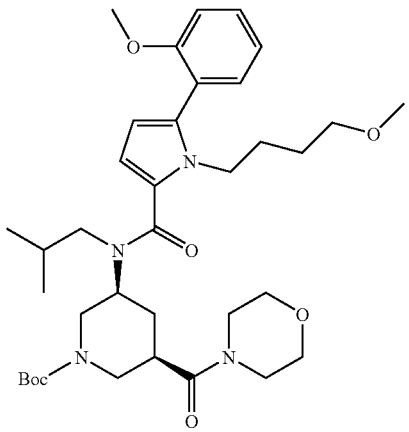 [SMILES: COCCCCn1c(C(=O)N(CC(C)C)[C@H]2C[C@@H](C(=O)N3CCOCC3)CN(C(=O)OC(C)(C)C)C2)ccc1-c1ccccc1OC]

MS (ESI+, m/e) 655 (M+1)

Reference Example 354 tert-butyl(3S,5R)-3-[{[5-bromo-1-(4-methoxybutyl)-1H-pyrrol-2-yl]carbonyl}(2-methylpropyl)amino]-5-(morpholin-4-ylcarbonyl)piperidine-1-carboxylate

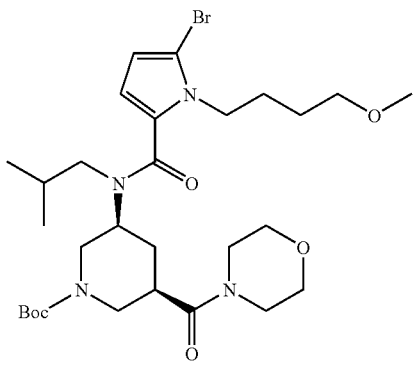 [SMILES: COCCCCn1c(Br)ccc1C(=O)N(CC(C)C)[C@H]1C[C@@H](C(=O)N2CCOCC2)CN(C(=O)OC(C)(C)C)C1]

MS (ESI+, m/e) 628 (M+1)

Reference Example 355 tert-butyl(3S,5R)-3-[{[1-(4-methoxybutyl)-5-(pyridin-3-yl)-1H-pyrrol-2-yl]carbonyl}(2-methylpropyl)amino]-5-(morpholin-4-ylcarbonyl)piperidine-1-carboxylate

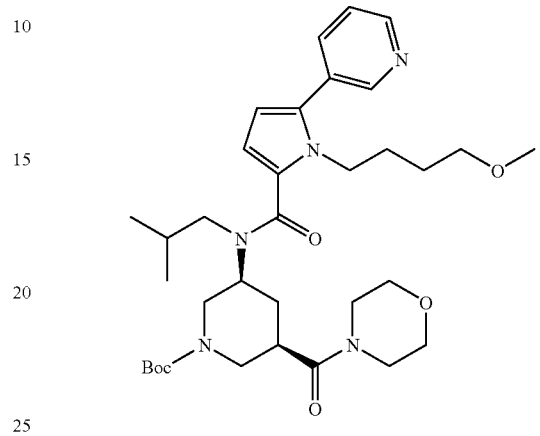

A mixture of tert-butyl(3S,5R)-3-[{[5-bromo-1-(4-methoxybutyl)-1H-pyrrol-2-yl]carbonyl}(2-methylpropyl)amino]-5-(morpholin-4-ylcarbonyl)piperidine-1-carboxylate (188 mg), pyridin-3-ylboronic acid (41 mg), tetrakis(triphenylphosphine)palladium(0) (35 mg), sodium carbonate (371 mg), ethanol (2 ml), toluene (2 ml) and water (2 ml) was heated under reflux for 12 hr. The reaction mixture was concentrated under reduced pressure, and the residue was suspended in ethyl acetate and washed with water. The organic layer was dried over anhydrous sodium sulfate and the solvent was evaporated under reduced pressure. The residue was subjected to silica gel column chromatography, and a fraction eluted with ethyl acetate-hexane (1:1-1:0) was concentrated under reduced pressure, and crystals were collected by filtration to give the object product (200 mg).

MS (ESI+, m/e) 626 (M+1)

Reference Example 356 tert-butyl(3S,5R)-3-[{[1-(4-methoxybutyl)-1H-pyrrol-2-yl]carbonyl}(2-methylpropyl)amino]-5-(morpholin-4-ylcarbonyl)piperidine-1-carboxylate

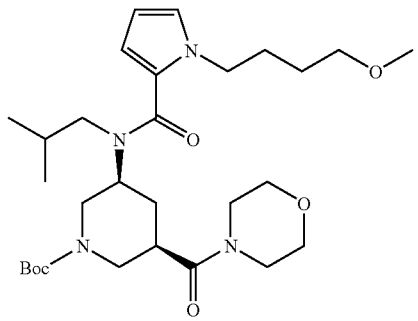 [SMILES: COCCCCn1cccc1C(=O)N(CC(C)C)[C@H]1C[C@@H](C(=O)N2CCOCC2)CN(C(=O)OC(C)(C)C)C1]

A mixture of tert-butyl(3S,5R)-3-[{[5-bromo-1-(4-methoxybutyl)-1H-pyrrol-2-yl]carbonyl}(2-methylpropyl)amino]-5-(morpholin-4-ylcarbonyl)piperidine-1-carboxylate (220 mg), pyridin-2-ylboronic acid (65 mg), sodium carbonate (370 mg), tetrakis(triphenylphosphine)palladium (40 mg), ethanol (2 ml), toluene (2 ml) and water (2 ml) was stirred at 80° C. for 12 hr. The solvent was evaporated under reduced pressure. The residue was dissolved in ethyl acetate-water, and the organic layer was washed with saturated brine, and dried over anhydrous sodium sulfate. The solvent was evaporated under reduced pressure. The residue was subjected to silica gel column chromatography, and a fraction eluted with ethyl acetate-hexane (1:1-1:0) was concentrated under reduced pressure to give the object product (240 mg).

MS (ESI+, m/e) 549 (M+1)

Example 199

1-(4-methoxybutyl)-N-(2-methylpropyl)-N-[(3S,5R)-5-(morpholin-4-ylcarbonyl)piperidin-3-yl]-5-phenyl-1H-pyrrole-2-carboxamide hydrochloride

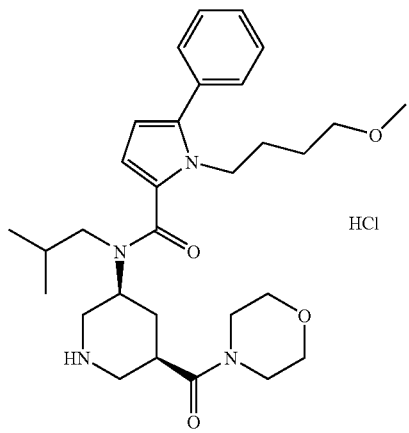 [SMILES: COCCCCn1c(C(=O)N(CC(C)C)[C@@H]2CNC[C@H](C(=O)N3CCOCC3)C2)ccc1-c1ccccc1 ; Cl]

tert-Butyl(3S,5R)-3-[{[1-(4-methoxybutyl)-5-phenyl-1H-pyrrol-2-yl]carbonyl}(2-methylpropyl)amino]-5-(morpholin-4-ylcarbonyl)piperidine-1-carboxylate (150 mg) was dissolved in ethyl acetate (5 ml), 4N hydrogen chloride-ethyl acetate(5 ml) was added and the mixture was stirred for 1 hr. The solvent was evaporated under reduced pressure to give the object product (110 mg).

MS (ESI+, m/e) 525 (M+1)

In the same manner as in Example 199, the following compound was synthesized.

Example 200

1-(4-methoxybutyl)-N-(2-methylpropyl)-N-[(3S,5R)-5-(morpholin-4-ylcarbonyl)piperidin-3-yl]-5-(pyridin-3-yl)-1H-pyrrole-2-carboxamide dihydrochloride

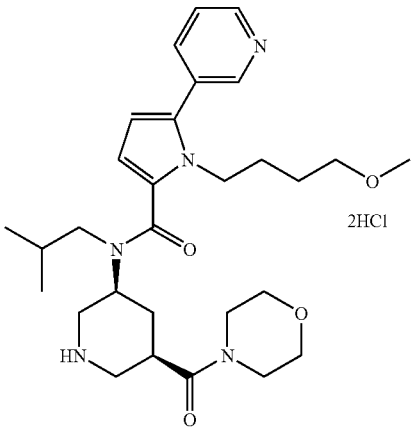 [SMILES: COCCCCn1c(C(=O)N(CC(C)C)[C@@H]2CNC[C@H](C(=O)N3CCOCC3)C2)ccc1-c1cccnc1 ; "2HCl"]

MS (ESI+, m/e) 526 (M+1)

Example 201

1-(4-methoxybutyl)-N-(2-methylpropyl)-N-[(3S,5R)-5-(morpholin-4-ylcarbonyl)piperidin-3-yl]-5-(thiophen-2-yl)-1H-pyrrole-2-carboxamide

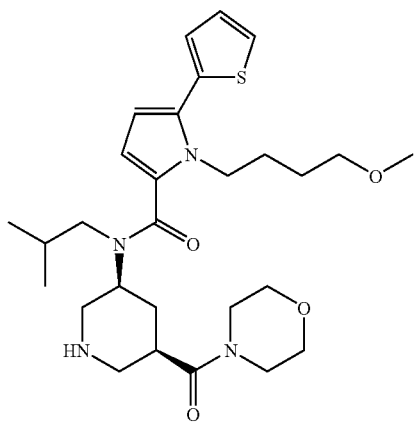 [SMILES: COCCCCn1c(C(=O)N(CC(C)C)[C@@H]2CNC[C@H](C(=O)N3CCOCC3)C2)ccc1-c1cccs1]

tert-Butyl(3S,5R)-3-[{[1-(4-methoxybutyl)-5-(thiophen-2-yl)-1H-pyrrol-2-yl]carbonyl}(2-methylpropyl)amino]-5-(morpholin-4-ylcarbonyl)piperidine-1-carboxylate (65 mg) was dissolved in ethyl acetate (2 ml), 4N hydrogen chloride-ethyl acetate (5 ml) was added and the mixture was stirred for 1 hr. The solvent was evaporated under reduced pressure, and the residue was subjected to reversed-phase preparative HPLC and the eluted fraction was concentrated under reduced pressure. The residual aqueous layer was neutralized with saturated aqueous sodium hydrogen carbonate and extracted with ethyl acetate. The extract was dried over anhydrous sodium sulfate and the solvent was evaporated under reduced pressure to give the object product (20 mg).

MS (ESI+, m/e) 531 (M+1)

In the same manner as in Example 201, the following compound was synthesized.

Example 202

1-(4-methoxybutyl)-5-(2-methoxyphenyl)-N-(2-methylpropyl)-n-[(3S,5R)-5-(morpholin-4-ylcarbonyl)piperidin-3-yl]-1H-pyrrole-2-carboxamide

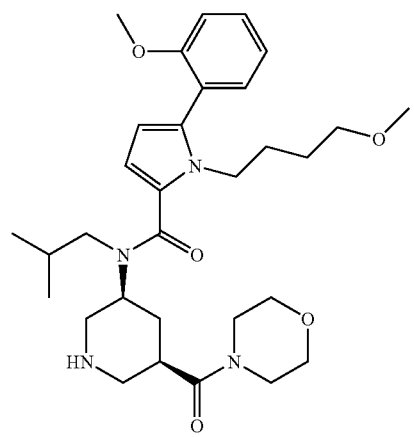 [SMILES: COCCCCn1c(C(=O)N(CC(C)C)[C@@H]2CNC[C@H](C(=O)N3CCOCC3)C2)ccc1-c1ccccc1OC]

MS (ESI+, m/e) 531 (M+1)

Example 203

1-(4-methoxybutyl)-5-(1-methylethyl)-N-(2-methylpropyl)-N-[(3S,5R)-5-(morpholin-4-ylcarbonyl)piperidin-3-yl]-1H-pyrrole-2-carboxamide

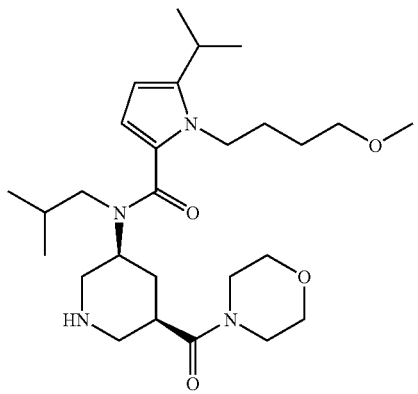 [SMILES: COCCCCn1c(C(=O)N(CC(C)C)[C@@H]2CNC[C@H](C(=O)N3CCOCC3)C2)ccc1C(C)C]

MS (ESI+, m/e) 492 (M+1)

Example 204

1-(4-methoxybutyl)-N-(2-methylpropyl)-N-[(3S,5R)-5-(morpholin-4-ylcarbonyl)piperidin-3-yl]-1H-pyrrole-2-carboxamide

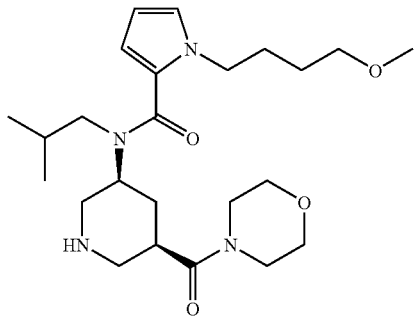 [SMILES: COCCCCn1cccc1C(=O)N(CC(C)C)[C@@H]1CNC[C@H](C(=O)N2CCOCC2)C1]

MS (ESI+, m/e) 450 (M+1)

Example 205

Methyl 1-(4-methoxybutyl)-5-{(2-methylpropyl)[(3S,5R)-5-(morpholin-4-ylcarbonyl)piperidin-3-yl]carbamoyl}-1H-pyrrole-2-carboxylate

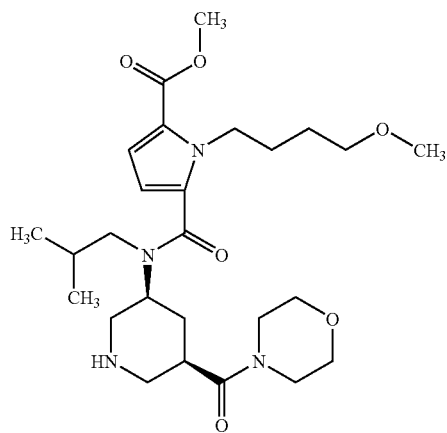 [SMILES: COCCCCn1c(C(=O)OC)ccc1C(=O)N(CC(C)C)[C@@H]1CNC[C@H](C(=O)N2CCOCC2)C1]

5-(Methoxycarbonyl)-1H-pyrrole-2-carboxylic acid (160 mg), tert-butyl(3S,5R)-3-[(2-methylpropyl)amino]-5-(morpholin-4-ylcarbonyl)piperidine-1-carboxylate (250 mg) obtained in Reference Example 22 and N,N-diisopropylethylamine (630 μl) were dissolved in 1,2-dichloroethane (10 ml), chloro-N,N,N',N'-tetramethylformamidinium hexafluorophosphate (410 mg) was added and the mixture was stirred at room temperature for 3 hr. The reaction mixture was concentrated, diluted with aqueous calcium carbonate solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (0:10-10:0) was concentrated under reduced pressure. The residue was dissolved in DMA (10 ml), cesium carbonate (790 mg) and 4-methoxybutyl methanesulfonate (230 mg) were added, and the mixture was stirred at 70° C. overnight. The reaction mixture was concentrated under reduced pressure, the residue was diluted with water, and the mixture was extracted with ethyl acetate. The extract was washed with saturated brine, and dried over anhydrous magnesium sulfate and concentrated under reduced pressure. The residue was dissolved in TFA (1.0 ml), and the mixture was stirred at room temperature for 30 min, and concentrated under reduced pressure. This was purified by HPCL, and the object fraction was concentrated, the residue was diluted with aqueous calcium carbonate solution and the mixture was extracted with ethyl acetate. The extract was washed with saturated brine, and dried over anhydrous magnesium sulfate. The solvent was evaporated under reduced pressure to give the object product (62.9 mg).

MS (ESI+, m/e) 507 (M+1)

In the same manner as in the method shown in Example 7, the following compound (Example 206) was obtained.

Example 206

(5-methyl-2-oxo-1,3-dioxol-4-yl)methyl(3R,5S)-5-[{[5-(4-methoxybutyl)-1-phenyl-1H-1,2,3-triazol-4-yl]carbonyl}(2-methylpropyl)amino]piperidine-3-carboxylate hydrochloride

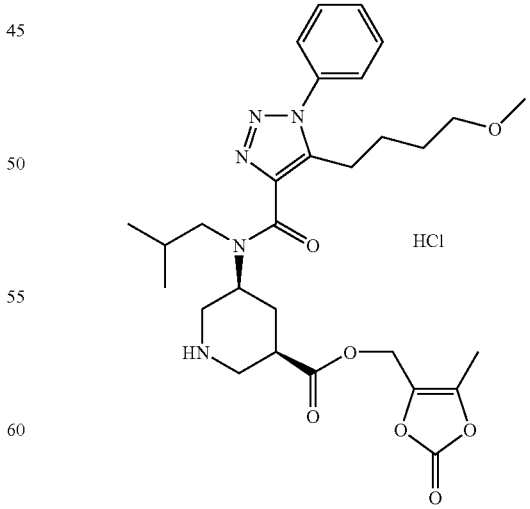

MS (ESI+, m/e) 570 (M+1)

In the same manner as in Reference Example 362, the following compound (Reference Example 357) was obtained.

Reference Example 357 methyl 5-acetyl-1-(4-methoxybutyl)-1H-pyrrole-2-carboxylate

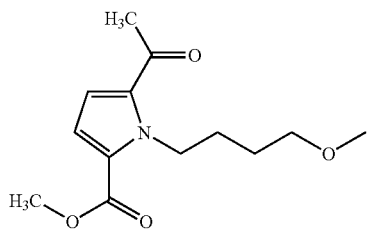

MS (ESI+, m/e) 254 (M+1)
$^1$H-NMR (CDCl$_3$) δ 1.57-1.82 (4H, m), 2.49 (3H, s), 3.32 (3H, s), 3.40 (2H, t), 3.85 (3H, s), 4.84 (2H, t), 6.88 (2H, s).

In the same manner as in Reference Example 11, the following compound (Reference Example 358) was obtained.

Reference Example 358

5-acetyl-1-(4-methoxybutyl)-1H-pyrrole-2-carboxylic acid

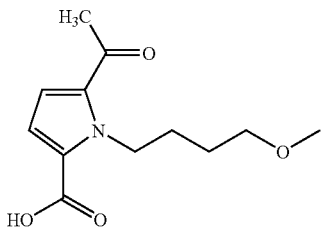

MS (ESI+, m/e) 240 (M+1)
$^1$H-NMR (CDCl$_3$) δ 1.58-1.68 (2H, m), 1.74-1.84 (2H, m), 2.52 (3H, s), 3.34 (3H, s), 3.42 (2H, t), 4.85 (2H, t), 6.92 (1H, d), 7.04 (1H, d), 8.66 (1H, br).

Reference Example 359 methyl 7-methoxy-3-oxoheptanoate

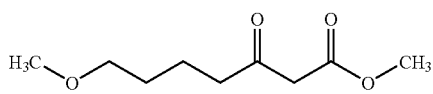

A solution of 5-methoxypentanic acid (26.4 g) in THF (250 ml) was cooled 0° C.-5° C., and oxalyl chloride (50.8 g) was added dropwise over 30 min. The mixture was stirred at room temperature for 2 hr. The solvent was concentrated under reduced pressure.

A solution of 2,2-dimethyl-1,3-dioxane-4,6-dione (28.8 g) in dichloromethane (300 ml) was cooled to 0° C.-5° C., pyridine (31.6 g) was added, and 5-methoxypentanoyl chloride/dichloromethane solution (20 ml) was added dropwise over 30 min. The mixture was stirred at 0° C.-5° C. for 1 hr.

The reaction mixture was poured into 0.5N hydrochloric acid (300 ml), washed with water, and dried over anhydrous magnesium sulfate. The solvent was evaporated under reduced pressure. The residue was dissolved in methanol (450 ml) and the mixture was stirred under reflux for 15 hr. The solvent was concentrated under reduced pressure, and the residue was distilled under reduced pressure. The fraction distilled under reduced pressure of 0.3 mmHg at 90° C.-92° C. was collected to give the object product (27.4 g) as an oil.

MS (ESI+, m/e) 189 (M+1)
$^1$H-NMR (CDCl$_3$) δ 1.55-1.72 (4H, m), 2.57 (2H, t), 3.31 (3H, t), 3.37 (3H, t), 3.45 (2H, s), 3.73 (3H, s).

Reference Example 360

5-(4-methoxybutyl)-1-phenyl-1H-1,2,3-triazole-4-carboxylic acid

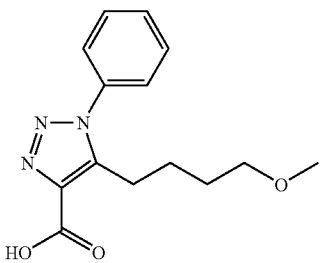 [SMILES: COCCCCc1c(C(=O)O)nnn1-c1ccccc1]

A solution of sodium hydride (60% in oil, 2 g) in DMF (50 ml) was cooled to 0° C.-5° C., methyl 7-methoxy-3-oxoheptanoate (9.4 g) was added, and the mixture was stirred at 0° C.-5° C. for 30 min. Phenyl azide (6 g) was added, and the mixture was stirred at room temperature for 15 hr. The solvent was concentrated under reduced pressure, and methanol (100 ml) was added to the residue and 4N aqueous sodium hydroxide solution (20 ml) was further added. The mixture was stirred at 60° C. for 1 hr. The solvent was evaporated under reduced pressure and water (100 ml) was added to the residue. 6N Hydrochloric acid was added for neutralization and the mixture was extracted with ethyl acetate (100 ml×2). The extract was dried over anhydrous sodium sulfate and the solvent was evaporated under reduced pressure. The residue was subjected to silica gel column chromatography, and a fraction eluted with ethyl acetate was concentrated under reduced pressure to give the object product (7.2 g) as a white powder.

MS (ESI+, m/e) 276 (M+1)
$^1$H-NMR (CDCl$_3$) δ 1.49-1.70 (4H, m), 3.04 (2H, t), 3.27 (3H, s), 3.31 (2H, t), 7.44-7.49 (2H, m), 7.58-7.61 (3H, m), 8.76 (1H, br).

Reference Example 361

5-(4-methoxybutyl)-1-(2-methylphenyl)-1H-1,2,3-triazole-4-carboxylic acid

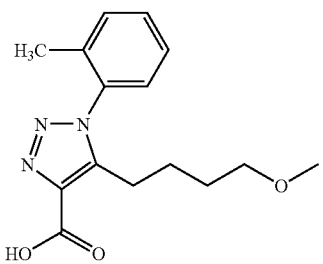 [SMILES: COCCCCc1c(C(=O)O)nnn1-c1ccccc1C]

A solution of sodium hydride (60% in oil, 280 mg) in DMF (10 ml) was cooled to 0° C.-5° C., methyl 7-methoxy-3-oxoheptanoate (1.32 g) was added, and the mixture was stirred at 0° C.-5° C. for 30 min. Then, 1-azido-2-methylbenzene (932 mg) was added, and the mixture was stirred at room temperature for 15 hr. The solvent was concentrated under reduced pressure, methanol (10 ml) was added to the residue, and 4N aqueous sodium hydroxide solution (5 ml) was added and the mixture was stirred at 60° C. for 1 hr. The solvent was evaporated under reduced pressure and water (20 ml) was added to the residue. 6N Hydrochloric acid was added for neutralization and the mixture was extracted with ethyl acetate (20 ml×2). The extract was dried over anhydrous sodium sulfate and the solvent was evaporated under reduced pressure. The residue was subjected to silica gel column chromatography, and a fraction eluted with ethyl acetate was concentrated under reduced pressure to give the object product (930 mg) as an oil.

MS (ESI+, m/e) 290 (M+1)
$^1$H-NMR (CDCl$_3$) δ 1.48-1.62 (4H, m), 2.06 (3H, s), 2.88 (2H, t), 3.24 (3H, s), 3.27 (2H, t), 7.24-7.28 (1H, m), 7.38-7.54 (3H, m), 8.61 (1H, br).

In the same manner as in Reference Example 361, the following compounds (Reference Examples 362-372) were obtained.

Reference Example 362

5-(4-methoxybutyl)-1-(3-methylphenyl)-1H-1,2,3-triazole-4-carboxylic acid

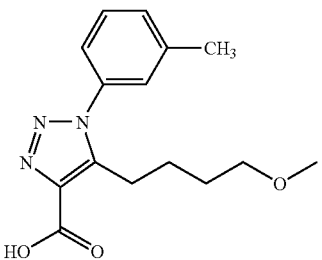

MS (ESI+, m/e) 290 (M+1)
$^1$H-NMR (CDCl$_3$) δ 1.50-1.70 (4H, m), 2.47 (3H, s), 3.03 (2H, t), 3.27 (3H, s), 3.31 (2H, t), 7.24 (2H, t), 7.40 (1H, d), 7.47 (1H, t), 9.69 (1H, br).

Reference Example 363

5-(4-methoxybutyl)-1-(4-methylphenyl)-1H-1,2,3-triazole-4-carboxylic acid

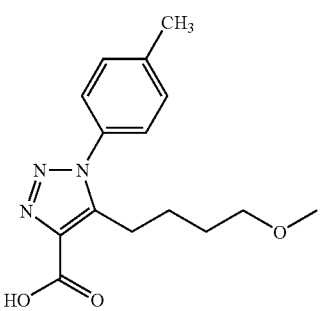 [SMILES: COCCCCc1c(C(=O)O)nnn1-c1ccc(C)cc1]

MS (ESI+, m/e) 290 (M+1)
$^1$H-NMR (CDCl$_3$) δ 1.49-1.69 (4H, m), 2.48 (3H, s), 3.02 (2H, t), 3.28 (3H, s), 3.31 (2H, t), 7.36 (4H, q), 10.71 (1H, br).

Reference Example 364

5-(4-methoxybutyl)-1-(2-methoxyphenyl)-1H-1,2,3-triazole-4- carboxylic acid

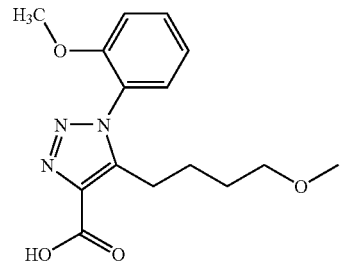

MS (ESI+, m/e) 306 (M+1)
$^1$H-NMR (CDCl$_3$) δ 1.43-1.63 (4H, m), 2.88 (2H, br s), 3.25 (3H, s), 3.27 (2H, t), 3.80 (3H, s), 7.09-7.16 (2H, m), 7.35 (1H, dd), 7.56 (1H, dt), 10.23 (1H, br).

Reference Example 365

5-(4-methoxybutyl)-1-(3-methoxyphenyl)-1H-1,2,3-triazole-4-carboxylic acid

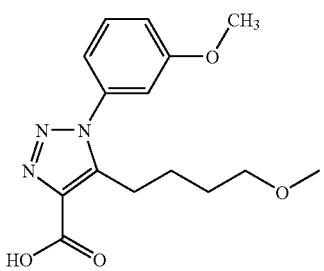

MS (ESI+, m/e) 306 (M+1)
$^1$H-NMR (CDCl$_3$) δ 1.51-1.71 (4H, m), 3.05 (2H, t), 3.28 (3H, s), 3.32 (2H, t), 3.88 (3H, s), 6.98-7.03 (2H, m), 7.12 (1H, dd), 7.48 (1H, t), 10.43 (1H, br).

Reference Example 366

5-(4-methoxybutyl)-1-(4-methoxyphenyl)-1H-1,2,3-triazole-4-carboxylic acid

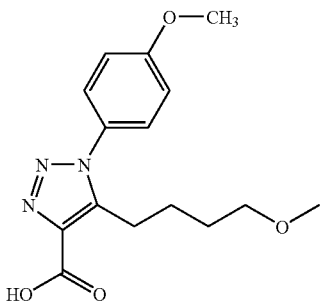 [SMILES: COCCCCc1c(C(=O)O)nnn1-c1ccc(OC)cc1]

MS (ESI+, m/e) 306 (M+1)
$^1$H-NMR (CDCl$_3$) δ 1.52-1.66 (4H, m), 3.00 (2H, t), 3.28 (3H, s), 3.31 (2H, t), 3.90 (3H, s), 7.07 (2H, d), 7.36 (2H, d), 9.85 (1H, br).

Reference Example 367

1-(3-chlorophenyl)-5-(4-methoxybutyl)-1H-1,2,3-triazole-4-carboxylic acid

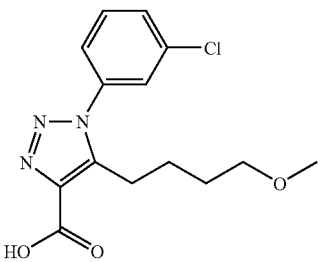 [SMILES: COCCCCc1c(C(=O)O)nnn1-c1cccc(Cl)c1]

MS (ESI+, m/e) 310 (M+1)
$^1$H-NMR (CDCl$_3$) δ 1.52-1.71 (4H, m), 3.06 (2H, t), 3.29 (3H, s), 3.34 (2H, t), 7.37-7.43 (1H, m), 7.51-7.61 (3H, m), 9.31 (1H, br).

Reference Example 368

1-(4-chlorophenyl)-5-(4-methoxybutyl)-1H-1,2,3-triazole-4-carboxylic acid

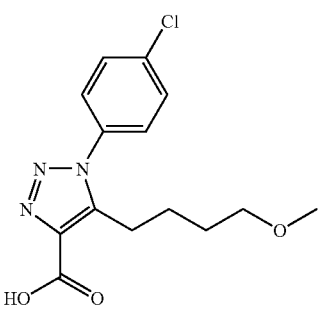

MS (ESI+, m/e) 310 (M+1)
$^1$H-NMR (CDCl$_3$) δ 1.50-1.70 (4H, m), 3.03 (2H, t), 3.28 (3H, s), 3.32 (2H, t), 7.42 (2H, d), 7.59 (2H, d), 7.83 (1H, br).

Reference Example 369

1-(3-fluorophenyl)-5-(4-methoxybutyl)-1H-1,2,3-triazole-4-carboxylic acid

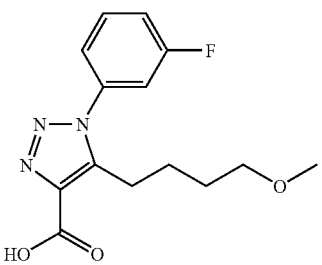 [SMILES: COCCCCc1c(C(=O)O)nnn1-c1cccc(F)c1]

MS (ESI+, m/e) 294 (M+1)
$^1$H-NMR (CDCl$_3$) δ 1.52-1.72 (4H, m), 3.07 (2H, t), 3.29 (3H, s), 3.34 (2H, t), 7.23-7.35 (3H, m), 7.56-7.63 (1H, m), 9.06 (1H, br).

Reference Example 370

1-(4-fluorophenyl)-5-(4-methoxybutyl)-1H-1,2,3-triazole-4-carboxylic acid

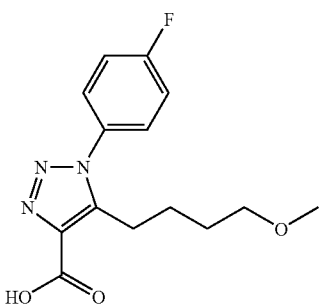 [SMILES: COCCCCc1c(C(=O)O)nnn1-c1ccc(F)cc1]

MS (ESI+, m/e) 294 (M+1)
$^1$H-NMR (CDCl$_3$) δ 1.51-1.69 (4H, m), 3.02 (2H, t), 3.28 (3H, s), 3.33 (2H, t), 7.26-7.32 (2H, m), 7.44-7.49 (2H, m), 10.15 (1H, br).

Reference Example 371

5-(4-methoxybutyl)-1-[3-(trifluoromethyl)phenyl]-1H-1,2,3-triazole-4-carboxylic acid

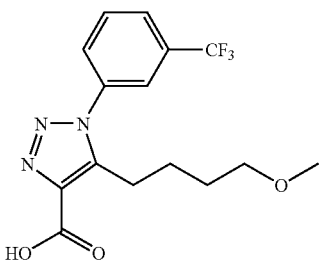 [SMILES: COCCCCc1c(C(=O)O)nnn1-c1cccc(C(F)(F)F)c1]

MS (ESI+, m/e) 344 (M+1)
$^1$H-NMR (CDCl$_3$) δ 1.53-1.73 (4H, m), 3.07 (2H, t), 3.27 (3H, s), 3.33 (2H, t), 7.70 (1H, d), 7.78 (2H, t), 7.89 (1H, d), 10.18 (1H, br).

Reference Example 372

1-(3,4-difluorophenyl)-5-(4-methoxybutyl)-1H-1,2,3-triazole-4-carboxylic acid

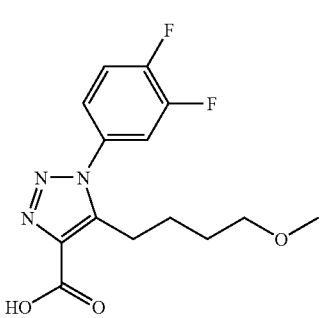 [SMILES: COCCCCc1c(C(=O)O)nnn1-c1ccc(F)c(F)c1]

MS (ESI+, m/e) 312 (M+1)
$^1$H-NMR (CDCl$_3$) δ 1.53-1.71 (4H, m), 3.05 (2H, t), 3.30 (3H, s), 3.35 (2H, t), 7.25-7.30 (1H, m), 7.37-7.44 (2H, m), 9.61 (1H, br).

Reference Example 373

1-(2-fluorophenyl)-5-(4-methoxybutyl)-1H-1,2,3-triazole-4-carboxylic acid

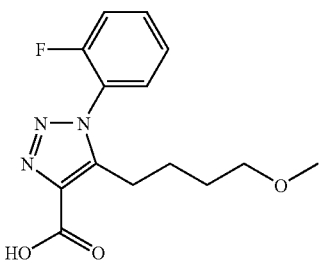 [SMILES: COCCCCc1c(C(=O)O)nnn1-c1ccccc1F]

A solution of methyl 7-methoxy-3-oxoheptanoate (2.0 g) in methanol (70 ml) was cooled to 0° C.-5° C., 1-azido-2-fluorobenzene (960 mg) and 28% sodium methoxide methanol solution (2 g) were added and the mixture was stirred at 60° C. for 3 hr. Then, 1N sodium hydroxide (14 ml) was added, and the mixture was stirred at 60° C. for 1 hr. The solvent was evaporated under reduced pressure and water (20 ml) was added to the residue. 1N Hydrochloric acid was added for neutralization and the mixture was extracted with ethyl acetate (50 ml×2). The extract was dried over anhydrous sodium sulfate and the solvent was evaporated under reduced pressure. The residue was subjected to silica gel column chromatography, and a fraction eluted with ethyl acetate was concentrated under reduced pressure to give the object product (1.61 g) as an oil.

MS (ESI+, m/e) 294 (M+1)
$^1$H-NMR (CDCl$_3$) δ 1.45-1.64 (4H, m), 2.97 (2H, t), 3.25 (3H, s), 3.29 (2H, t), 7.33-7.41 (2H, m), 7.46-7.51 (1H, m), 7.59-7.66 (1H, m), 9.27 (1H, br).

Reference Example 374

1-(2-chlorophenyl)-5-(4-methoxybutyl)-1H-1,2,3-triazole-4-carboxylic acid

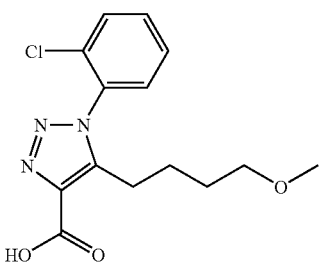 [SMILES: COCCCCc1c(C(=O)O)nnn1-c1ccccc1Cl]

A solution of methyl 7-methoxy-3-oxoheptanoate (2.0 g) in methanol (70 ml) was cooled to 0° C.-5° C., 1-azido-2-chlorobenzene (1.08 g) and 28% sodium methoxide methanol solution (2 g) were added and the mixture was stirred at 60° C. for 3 hr. Then, 1N sodium hydroxide (14 ml) was added, and the mixture was stirred at 60° C. for 1 hr. The solvent was evaporated under reduced pressure and water (20 ml) was added to the residue. 1N Hydrochloric acid was added for neutralization and the mixture was extracted with ethyl acetate (50 ml×2). The extract was dried over anhydrous sodium sulfate and the solvent was evaporated under reduced pressure. The residue was subjected to silica gel column chromatography, and a fraction eluted with ethyl acetate was concentrated under reduced pressure to give the object product (1.26 g) as a powder.

MS (ESI+, m/e) 310 (M+1)
$^1$H-NMR (CDCl$_3$) δ 1.46-1.59 (4H, m), 2.92 (2H, t), 3.25 (3H, s), 3.29 (2H, t), 7.44-7.67 (4H, m), 9.43 (1H, br).

In the same manner as in Reference Example 374, the following compounds (Reference Examples 375-377) were obtained.

Reference Example 375

1-(2,3-difluorophenyl)-5-(4-methoxybutyl)-1H-1,2,3-triazole-4-carboxylic acid

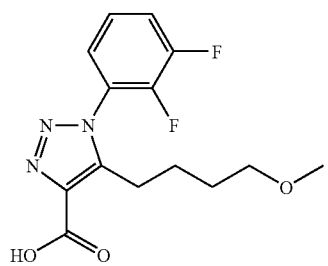 [SMILES: COCCCCc1c(C(=O)O)nnn1-c1cccc(F)c1F]

MS (ESI+, m/e) 312 (M+1)
$^1$H-NMR (CDCl$_3$) δ 1.48-1.67 (4H, m), 3.00 (2H, t), 3.26 (3H, s), 3.31 (2H, t), 7.28-7.40 (2H, m), 7.44-7.52 (1H, m), 8.88 (1H, br).

Reference Example 376

1-(2,6-difluorophenyl)-5-(4-methoxybutyl)-1H-1,2,3-triazole-4-carboxylic acid

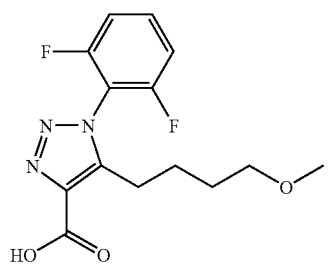 [SMILES: COCCCCc1c(C(=O)O)nnn1-c1c(F)cccc1F]

MS (ESI+, m/e) 312 (M+1)
$^1$H-NMR (CDCl$_3$) δ 1.48-1.67 (4H, m), 2.95 (2H, t), 3.26 (3H, s), 3.31 (2H, t), 7.20 (2H, t), 7.57-7.67 (1H, m), 8.69 (1H, br).

Reference Example 377

1-(3,5-difluorophenyl)-5-(4-methoxybutyl)-1H-1,2,3-triazole-4-carboxylic acid

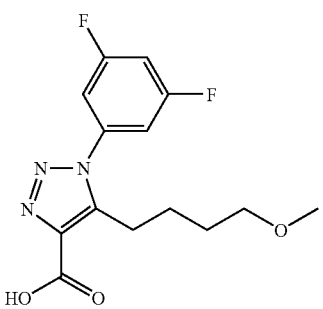 [SMILES: COCCCCc1c(C(=O)O)nnn1-c1cc(F)cc(F)c1]

MS (ESI+, m/e) 312 (M+1)

¹H-NMR (CDCl₃) δ 1.55-1.73 (4H, m), 3.10 (2H, t), 3.30 (3H, s), 3.36 (2H, t), 7.05-7.15 (3H, m), 9.78 (1H, br).

Reference Example 378

1-phenyl-5-(2-phenylethyl)-1H-1,2,3-triazole-4-carboxylic acid

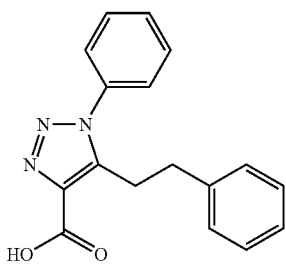 [SMILES: O=C(O)c1nnn(-c2ccccc2)c1CCc1ccccc1]

A solution of ethyl 3-oxo-5-phenylpentanoate (1.1 g) in methanol (50 ml) was cooled to 0° C.-5° C., azidobenzene (600 mg) and 28% sodium methoxide methanol solution (965 mg) were added and the mixture was stirred at 60° C. for 3 hr. Then, 1N sodium hydroxide (10 ml) was added and the mixture was stirred at 60° C. for 1 hr. The solvent was evaporated under reduced pressure and water (20 ml) was added. 1N Hydrochloric acid was added for neutralization and the mixture was extracted with ethyl acetate (30 ml×2). The extract was dried over anhydrous sodium sulfate and the solvent was evaporated under reduced pressure. The residue was subjected to silica gel column chromatography, and a fraction eluted with ethyl acetate was concentrated under reduced pressure to give the object product (480 mg) as a powder.

MS (ESI+, m/e) 294 (M+1)

¹H-NMR (CDCl₃) δ 2.93 (2H, t), 3.31 (2H, t), 6.93-6.96 (2H, m), 7.14-7.21 (5H, m), 7.48-7.60 (3H, m), 9.23 (1H, br).

Reference Example 379 tert-butyl(3S,5R)-3-[{[5-(4-methoxybutyl)-1-phenyl-1H-1,2,3-triazol-4-yl]carbonyl}(2-methylpropyl)amino]-5-(morpholin-4-ylcarbonyl)piperidine-1-carboxylate

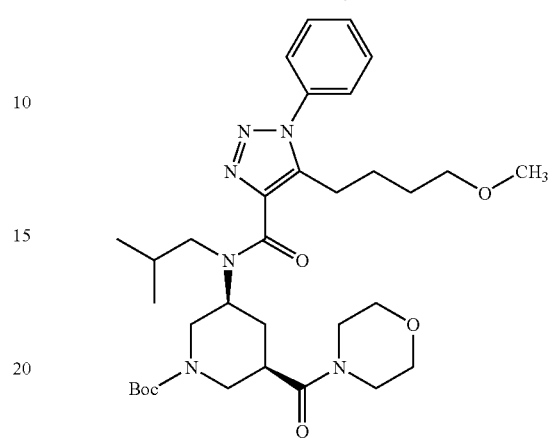

5-(4-Methoxybutyl)-1-phenyl-1H-1,2,3-triazole-4-carboxylic acid (138 mg), tert-butyl(3S,5R)-3-[(2-methylpropyl)amino]-5-(morpholin-4-ylcarbonyl)piperidine-1-carboxylate (185 mg) and N,N-diisopropylethylamine (345 μl) were dissolved in 1,2-dichloroethane (5 ml), chloro-N,N,N',N'-tetramethylformamidinium hexafluorophosphate (154 mg) was added and the mixture was stirred at room temperature for 15 hr. The reaction mixture was diluted with saturated aqueous sodium hydrogen carbonate solution and the mixture was extracted with ethyl acetate. The extract was washed with saturated brine, and dried over anhydrous magnesium sulfate. The solvent was evaporated under reduced pressure. The residue was subjected to silica gel column chromatography, and a fraction eluted with ethyl acetate-hexane (10:90-100:0) was concentrated under reduced pressure to give the object product (235 mg) as an amorphous compound.

MS (ESI+, m/e) 627 (M+1)

In the same manner as in Reference Example 379, the following compounds (Reference Examples 380-381) were obtained.

Reference Example 380 tert-butyl(3S,5R)-3-[{[5-acetyl-1-(4-methoxybutyl)-1H-pyrrol-2-yl]carbonyl}(2-methylpropyl)amino]-5-(morpholin-4-ylcarbonyl)piperidine-1-carboxylate

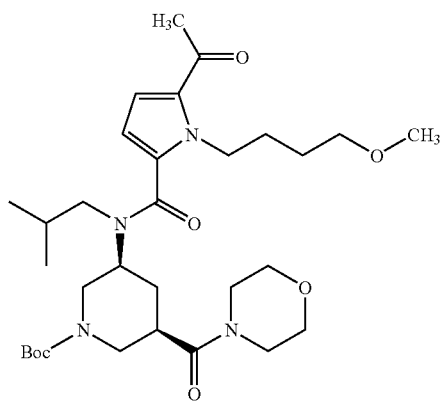 [SMILES: COCCCCn1c(C(C)=O)ccc1C(=O)N(CC(C)C)[C@H]1C[C@@H](C(=O)N2CCOCC2)CN(C(=O)OC(C)(C)C)C1]

MS (ESI+, m/e) 591 (M+1)

Reference Example 381 tert-butyl 4-[{[5-(4-methoxybutyl)-1-phenyl-1H-1,2,3-triazol-4-yl]carbonyl}(2-methylpropyl)amino]octahydroisoquinoline-2(1H)-carboxylate

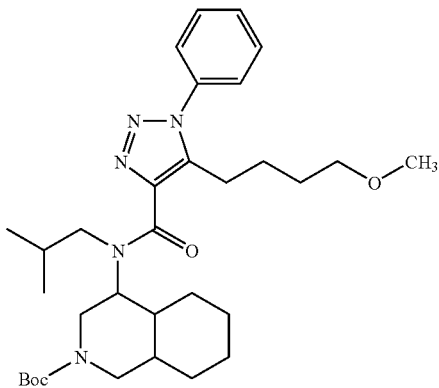 [SMILES: COCCCCc1c(C(=O)N(CC(C)C)C2CN(C(=O)OC(C)(C)C)CC3CCCCC32)nnn1-c1ccccc1]

MS (ESI+, m/e) 568 (M+1)

Reference Example 382

1-tert-butyl 3-methyl(3R,5S)-5-[{[5-(4-methoxybutyl)-1-phenyl-1H-1,2,3-triazol-4-yl]carbonyl}(2-methylpropyl)amino]piperidine-1,3-dicarboxylate

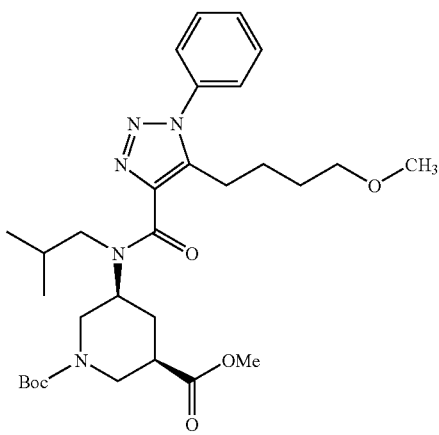 [SMILES: COCCCCc1c(C(=O)N(CC(C)C)[C@H]2C[C@@H](C(=O)OC)CN(C(=O)OC(C)(C)C)C2)nnn1-c1ccccc1]

To a solution of 5-(4-methoxybutyl)-1-phenyl-1H-1,2,3-triazole-4-carboxylic acid (2.75 g) in THF (50 ml) were added thionyl chloride (0.876 ml) and DMF (5 drops), and the mixture was heated under reflux with stirring for 2 hr. The reaction mixture was cooled to room temperature, concentrated under reduced pressure, and the residue was azeotroped with toluene (25 ml). The obtained residue was dissolved in THF (10 ml), added to a solution of 1-tert-butyl 3-methyl(3R,5S)-5-[(2-methylpropyl)amino]piperidine-1,3-dicarboxylate (3.14 g) and diisopropylethylamine (5.2 g) in THF (50 ml) and the mixture was stirred at room temperature for 2 hr. The reaction mixture was concentrated under reduced pressure, diluted with water, and extracted with ethyl acetate (50 ml). The extract was washed successively with 1M hydrochloric acid and saturated brine, and dried over anhydrous magnesium sulfate. The solvent was evaporated under reduced pressure. The residue was subjected to silica gel column chromatography, and a fraction eluted with ethyl acetate-hexane (5:95-50:50) was concentrated under reduced pressure to give the object product (4.32 g).

MS (ESI+, m/e) 572 (M+1)

Reference Example 383 tert-butyl(3R,5S)-3-(1-hydroxy-1-methylethyl)-5-[{[5-(4-methoxybutyl)-1-phenyl-1H-1,2,3-triazol-4-yl]carbonyl}(2-methylpropyl)amino]piperidine-1-carboxylate

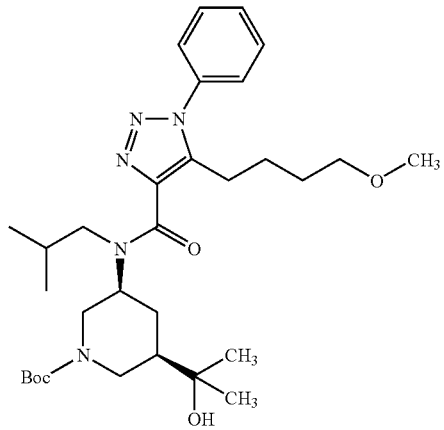 [SMILES: COCCCCc1c(C(=O)N(CC(C)C)[C@H]2C[C@@H](C(C)(C)O)CN(C(=O)OC(C)(C)C)C2)nnn1-c1ccccc1]

A solution of 1-tert-butyl 3-methyl(3R,5S)-5-[{[5-(4-methoxybutyl)-1-phenyl-1H-1,2,3-triazol-4-yl]carbonyl}(2-methylpropyl)amino]piperidine-1,3-dicarboxylate (286 mg) in THF (5 ml) was cooled to −40° C. Methylmagnesium bromide (3M-diethyl ether solution, 1 ml) was added thereto and the mixture was stirred at the same temperature for 30 min. Saturated aqueous ammonium chloride solution was added to the reaction mixture, and the mixture was extracted with ethyl acetate (10 ml×2). The extract was washed with saturated brine, and dried over anhydrous sodium sulfate. The solvent was evaporated under reduced pressure. The residue was purified by silica gel column chromatography [eluent: n-hexane-ethyl acetate (7:3→3:7)] to give the object product (180 mg) as an amorphous compound.

MS (ESI+, m/e) 572 (M+1)

Reference Example 384

(3R,5S)-1-(tert-butoxycarbonyl)-5-[{[5-(4-methoxybutyl)-1-phenyl-1H-1,2,3-triazol-4-yl]carbonyl}(2-methylpropyl)amino]piperidine-3-carboxylic acid

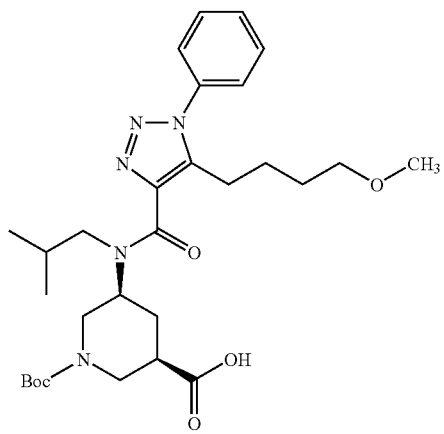 [SMILES: COCCCCc1c(C(=O)N(CC(C)C)[C@H]2C[C@@H](C(=O)O)CN(C(=O)OC(C)(C)C)C2)nnn1-c1ccccc1]

To a solution of 1-tert-butyl 3-methyl(3R,5S)-5-[{[5-(4-methoxybutyl)-1-phenyl-1H-1,2,3-triazol-4-yl]carbonyl}(2-methylpropyl)amino]piperidine-1,3-dicarboxylate (1.715 g) in methanol (10 ml) was added 4N aqueous sodium hydroxide solution (10 ml), and the mixture was stirred at 65° C. for 30 min. The solvent was concentrated under reduced pressure, and the residue was neutralized with 10% aqueous citric acid solution. The mixture was extracted with ethyl acetate (20 ml×2) and the extract was dried over anhydrous sodium sulfate. The solvent was evaporated under reduced pressure to give the object product (1.56 g) as an amorphous compound.

MS (ESI+, m/e) 558 (M+1)

Reference Example 385 tert-butyl(3S,5R)-3-[{[5-(4-methoxybutyl)-1-phenyl-1H-1,2,3-triazol-4-yl]carbonyl}(2-methylpropyl)amino]-5-(pyrrolidin-1-ylcarbonyl)piperidine-1-carboxylate

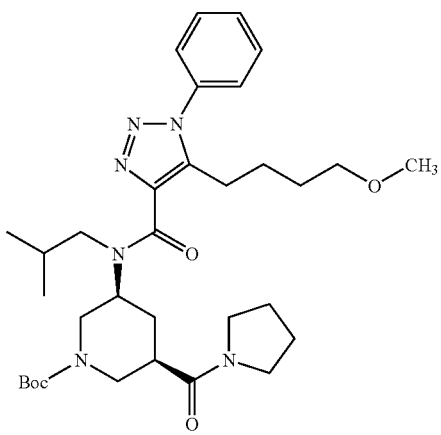 [SMILES: COCCCCc1c(C(=O)N(CC(C)C)[C@H]2C[C@@H](C(=O)N3CCCC3)CN(C(=O)OC(C)(C)C)C2)nnn1-c1ccccc1]

A solution of (3R,5S)-1-(tert-butoxycarbonyl)-5-[{[5-(4-methoxybutyl)-1-phenyl-1H-1,2,3-triazol-4-yl]carbonyl}(2-methylpropyl)amino]piperidine-3-carboxylic acid (279 mg), pyrrolidine (42 μl), WSC•HCl (144 mg), HOBt (107 mg), diisopropylethylamine (255 μl) and DMF (3 ml) was stirred at room temperature for 15 hr. The reaction mixture was poured into saturated aqueous sodium hydrogen carbonate, and the liberated oil was extracted with ethyl acetate (20 ml). The extract was washed successively with water and saturated brine, and dried over anhydrous magnesium sulfate. The solvent was evaporated under reduced pressure. The residue was subjected to silica gel column chromatography, and a fraction eluted with ethyl acetate was concentrated under reduced pressure to give the object product (245 mg) as an amorphous compound.

MS (ESI+, m/e) 611 (M+1)

In the same manner as in Reference Example 385, the following compounds (Reference Examples 386-387) were obtained.

Reference Example 386 tert-butyl(3S,5R)-3-[{[5-(4-methoxybutyl)-1-phenyl-1H-1,2,3-triazol-4-yl]carbonyl}(2-methylpropyl)amino]-5-(piperidin-1-ylcarbonyl)piperidine-1-carboxylate

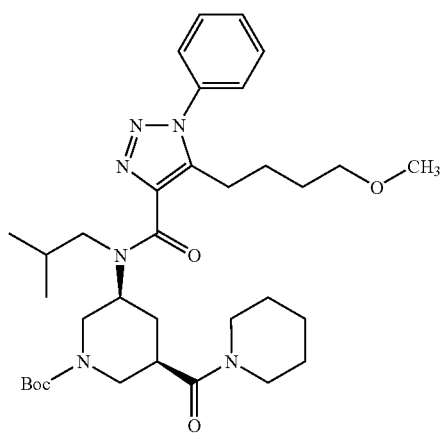 [SMILES: COCCCCc1c(C(=O)N(CC(C)C)[C@H]2C[C@@H](C(=O)N3CCCCC3)CN(C(=O)OC(C)(C)C)C2)nnn1-c1ccccc1]

MS (ESI+, m/e) 625 (M+1)

Reference Example 387 tert-butyl(3R,5S)-3-(7-azabicyclo[2.2.1]hept-7-ylcarbonyl)-5-[{[5-(4-methoxybutyl)-1-phenyl-1H-1,2,3-triazol-4-yl]carbonyl}(2-methylpropyl)amino]piperidine-1-carboxylate

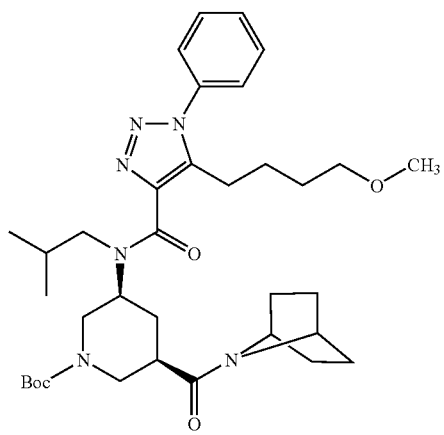 [SMILES: COCCCCc1c(C(=O)N(CC(C)C)[C@H]2C[C@@H](C(=O)N3C4CCC3CC4)CN(C(=O)OC(C)(C)C)C2)nnn1-c1ccccc1]

MS (ESI+, m/e) 637 (M+1)

Reference Example 388 tert-butyl(3S,5R)-3-[{[1-(2-chlorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

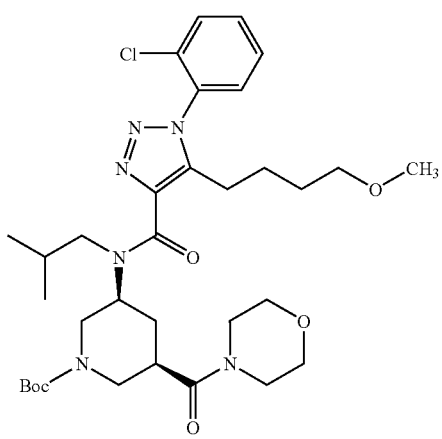 [SMILES: COCCCCc1c(C(=O)N(CC(C)C)[C@H]2C[C@@H](C(=O)N3CCOCC3)CN(C(=O)OC(C)(C)C)C2)nnn1-c1ccccc1Cl]

To a solution of 1-(2-chlorophenyl)-5-(4-methoxybutyl)-1H-1,2,3-triazole-4-carboxylic acid (155 mg) in THF (5 ml) were added thionyl chloride (0.11 ml) and DMF (1 drop), and the mixture was heated under reflux with stirring for 2 hr. The reaction mixture was cooled to room temperature, concentrated under reduced pressure, and the residue was azeotroped with toluene (5 ml). The obtained residue was dissolved in THF (5 ml), added to a solution of tert-butyl (3S,5R)-3-[(2-methylpropyl)amino]-5-(morpholin-4-ylcarbonyl)piperidine-1-carboxylate (185 mg) and diisopropylethylamine (0.345 ml) in THF (5 ml) and the mixture was stirred at room temperature for 2 hr. The reaction mixture was concentrated under reduced pressure, diluted with water, and extracted with ethyl acetate (10 ml). The extract was washed successively with 1M hydrochloric acid and saturated brine, and dried over anhydrous magnesium sulfate. The solvent was evaporated under reduced pressure. The residue was subjected to silica gel column chromatography, and a fraction eluted with hexane-ethyl acetate (5:95-30:70) was concentrated under reduced pressure to give the object product (280 mg).

$^1$H-NMR (CDCl$_3$) δ 0.83-1.00 (6H, m), 1.43 (9H, s), 1.49-1.55 (4H, m), 1.90-2.16 (2H, m), 2.47 (1H, br.s), 2.76-2.97 (5H, m), 3.21-3.25 (6H m), 3.36-3.44 (1H, m), 3.61-3.73 (8H, m), 4.23-4.28 (2H, m), 4.68 (1H, br.s), 7.42-7.65 (4H, m).

MS (ESI+, m/e) 662 (M+1)

Reference Example 389 tert-butyl(3S,5R)-3-[{[1-(2-fluorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

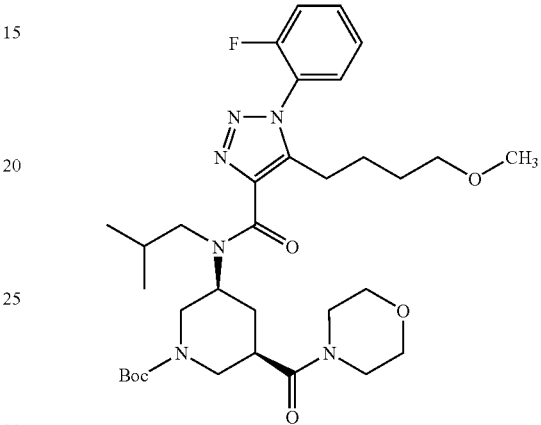

To a solution of 1-(2-fluorophenyl)-5-(4-methoxybutyl)-1H-1,2,3-triazole-4-carboxylic acid (1.61 g) in THF (20 ml) were added thionyl chloride (1.2 ml) and DMF (5 drops), and the mixture was heated under reflux with stirring for 2 hr. The reaction mixture was cooled to room temperature, concentrated under reduced pressure, and the residue was azeotroped with toluene (20 ml). The obtained residue was dissolved in THF (5 ml), added to a solution of tert-butyl (3S,5R)-3-[(2-methylpropyl)amino]-5-(morpholin-4-ylcarbonyl)piperidine-1-carboxylate (2.03 g) and diisopropylethylamine (3.9 ml) in THF (30 ml) and the mixture was stirred at room temperature for 2 hr. The reaction mixture was concentrated under reduced pressure, diluted with water, and extracted with ethyl acetate (50 ml). The extract was washed successively with 1M hydrochloric acid and saturated brine, and dried over anhydrous magnesium sulfate. The solvent was evaporated under reduced pressure. The residue was subjected to silica gel column chromatography, and a fraction eluted with hexane-ethyl acetate (5:95-30:70) was concentrated under reduced pressure to give the object product (2.64 g).

$^1$H-NMR (CDCl$_3$) δ 0.84-0.99 (6H, m), 1.41 (9H, s), 1.48-1.55 (4H, m), 1.90-2.16 (2H, m), 2.44 (1H, br.s), 2.61-2.99 (5H, m), 3.20-3.28 (6H m), 3.36-3.44 (1H, m), 3.61-3.76 (8H, m), 4.23 (2H, br.s), 4.66 (1H, br.s), 7.31-7.39 (2H, m), 7.42-7.46 (1H, m), 7.56-7.63 (1H, m).

MS (ESI+, m/e) 645 (M+1)

In the same manner as in Reference Example 389, the following compounds (Reference Examples 390-399) were obtained.

399

Reference Example 390 tert-butyl(3S,5R)-3-[{[1-(3-chlorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

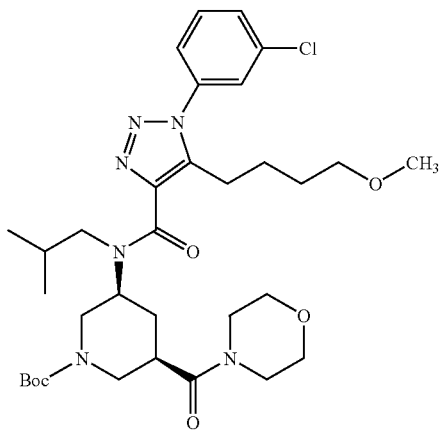

MS (ESI+, m/e) 662 (M+1)

Reference Example 391 tert-butyl (3S,5R)-3-[({5-(4-methoxybutyl)-1-[3-(trifluoromethyl)phenyl]-1H-1,2,3-triazol-4-yl}carbonyl)(2-methylpropyl)amino]-5-(morpholin-4-ylcarbonyl)piperidine-1-carboxylate

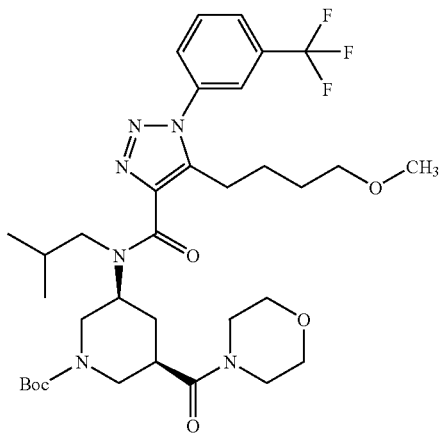 [SMILES: COCCCCc1c(C(=O)N(CC(C)C)[C@H]2C[C@@H](C(=O)N3CCOCC3)CN(C(=O)OC(C)(C)C)C2)nnn1-c1cccc(C(F)(F)F)c1]

MS (ESI+, m/e) 695 (M+1)

400

Reference Example 392 tert-butyl (3S,5R)-3-[{[1-(4-fluorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

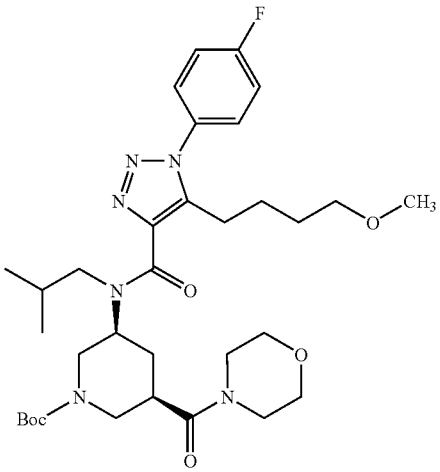

MS (ESI+, m/e) 645 (M+1)

Reference Example 393 tert-butyl (3S,5R)-3-[{[1-(4-chlorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

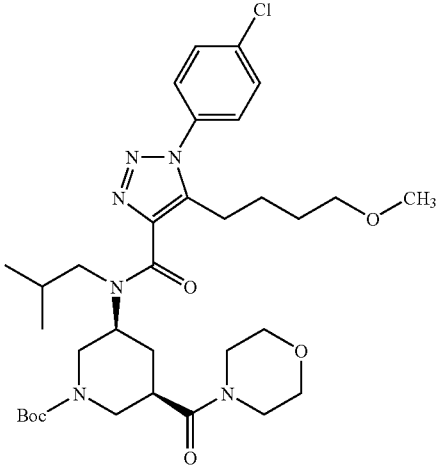 [SMILES: COCCCCc1c(C(=O)N(CC(C)C)[C@H]2C[C@@H](C(=O)N3CCOCC3)CN(C(=O)OC(C)(C)C)C2)nnn1-c1ccc(Cl)cc1]

MS (ESI+, m/e) 662 (M+1)

401

Reference Example 394 tert-butyl (3S,5R)-3-[{[1-(3-fluorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

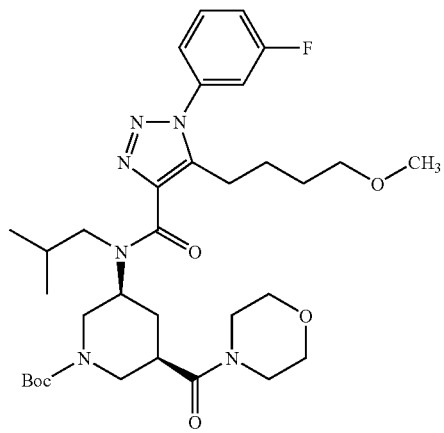 [SMILES: COCCCCc1c(C(=O)N(CC(C)C)[C@H]2C[C@@H](C(=O)N3CCOCC3)CN(C(=O)OC(C)(C)C)C2)nnn1-c1cccc(F)c1]

MS (ESI+, m/e) 645 (M+1)

Reference Example 395 tert-butyl (3S,5R)-3-[{[1-(3,4-difluorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

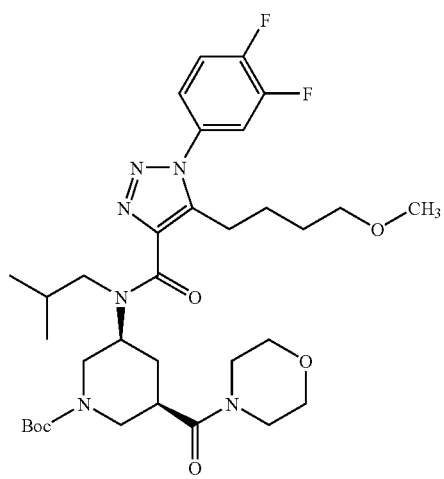 [SMILES: COCCCCc1c(C(=O)N(CC(C)C)[C@H]2C[C@@H](C(=O)N3CCOCC3)CN(C(=O)OC(C)(C)C)C2)nnn1-c1ccc(F)c(F)c1]

MS (ESI+, m/e) 663 (M+1)

402

Reference Example 396 tert-butyl (3S,5R)-3-[{[1-(2,3-difluorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

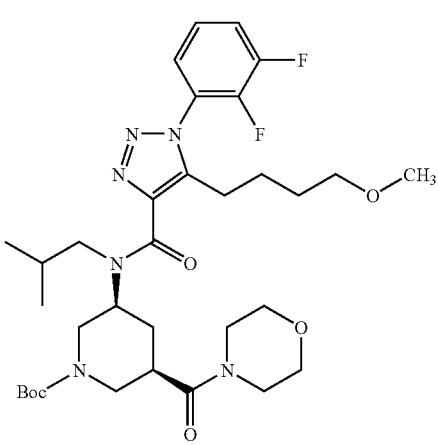 [SMILES: COCCCCc1c(C(=O)N(CC(C)C)[C@H]2C[C@@H](C(=O)N3CCOCC3)CN(C(=O)OC(C)(C)C)C2)nnn1-c1cccc(F)c1F]

MS (ESI+, m/e) 663 (M+1)

Reference Example 397 tert-butyl (3S,5R)-3-[{[1-(2,6-difluorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

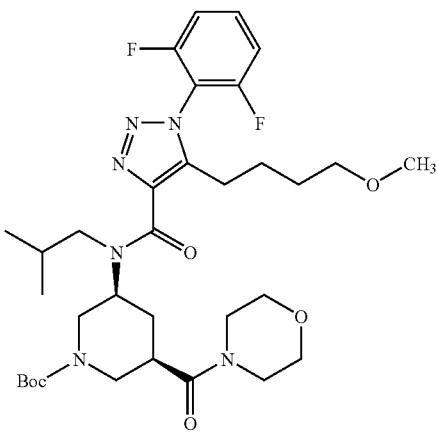 [SMILES: COCCCCc1c(C(=O)N(CC(C)C)[C@H]2C[C@@H](C(=O)N3CCOCC3)CN(C(=O)OC(C)(C)C)C2)nnn1-c1c(F)cccc1F]

MS (ESI+, m/e) 663 (M+1)

Reference Example 398 tert-butyl (3S,5R)-3-[{[1-(3,5-difluorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate

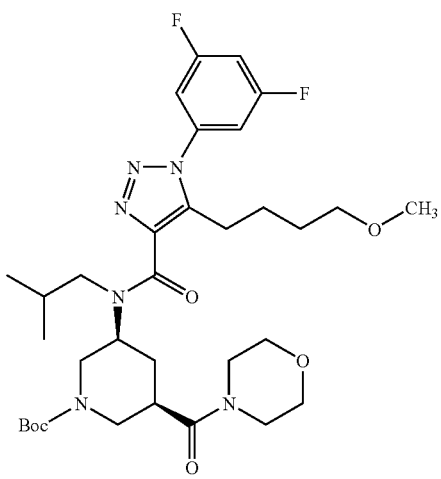 [SMILES: COCCCCc1c(C(=O)N(CC(C)C)[C@H]2C[C@@H](C(=O)N3CCOCC3)CN(C(=O)OC(C)(C)C)C2)nnn1-c1cc(F)cc(F)c1]

MS (ESI+, m/e) 663 (M+1)

Reference Example 399 tert-butyl (3S,5R)-3-[(2-methylpropyl){[1-phenyl-5-(2-phenylethyl)-1H-1,2,3-triazol-4-yl]carbonyl}amino]-5-(morpholin-4-ylcarbonyl)piperidine-1-carboxylate

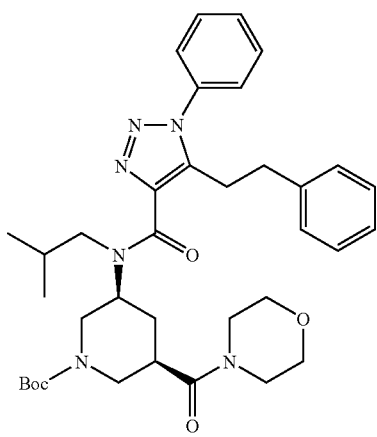 [SMILES: CC(C)CN(C(=O)c1nnn(-c2ccccc2)c1CCc1ccccc1)[C@H]1C[C@@H](C(=O)N2CCOCC2)CN(C(=O)OC(C)(C)C)C1]

MS (ESI+, m/e) 645 (M+1)

Reference Example 400

1-tert-butyl 3-methyl (3R,5S)-5-[{[5-(4-methoxybutyl)-1-(2-methylphenyl)-1H-1,2,3-triazol-4-yl]carbonyl}(2-methylpropyl)amino]piperidine-1,3-dicarboxylate

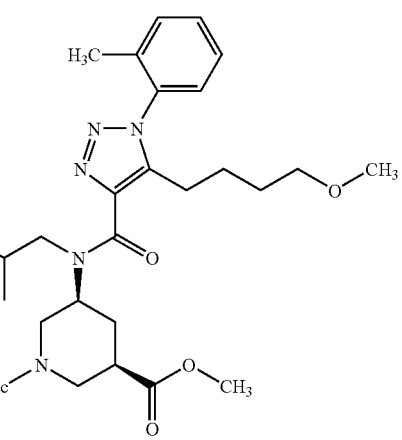

To a solution of 5-(4-methoxybutyl)-1-(2-methylphenyl)-1H-1,2,3-triazole-4-carboxylic acid (930 mg) in THF (10 ml) were added thionyl chloride (0.7 ml) and DMF (1 drop), and the mixture was heated under reflux with stirring for 2 hr. The reaction mixture was cooled to room temperature, concentrated under reduced pressure, and the residue was azeotroped with toluene (5 ml). The obtained residue was dissolved in THF (1 ml), added to a solution of 1-tert-butyl 3-methyl (3R,5S)-5-[(2-methylpropyl)amino]piperidine-1,3-dicarboxylate (1.0 g) and diisopropylethylamine (2.2 ml) in THF (10 ml) and the mixture was stirred at room temperature for 2 hr. The reaction mixture was concentrated under reduced pressure, diluted with water, and extracted with ethyl acetate (20 ml). The extract was washed successively with 1M hydrochloric acid and saturated brine, and dried over anhydrous magnesium sulfate. The solvent was evaporated under reduced pressure. The residue was subjected to silica gel column chromatography, and a fraction eluted with ethyl acetate-hexane (5:95-50:50) was concentrated under reduced pressure to give the object product (1.47 g) as an oil.

MS (ESI+, m/e) 586 (M+1)

In the same manner as in Reference Example 400, the following compounds (Reference Examples 401-405) were obtained.

Reference Example 401

1-tert-butyl 3-methyl (3R,5S)-5-[{[5-(4-methoxybutyl)-1-(3-methylphenyl)-1H-1,2,3-triazol-4-yl]carbonyl}(2-methylpropyl)amino]piperidine-1,3-dicarboxylate

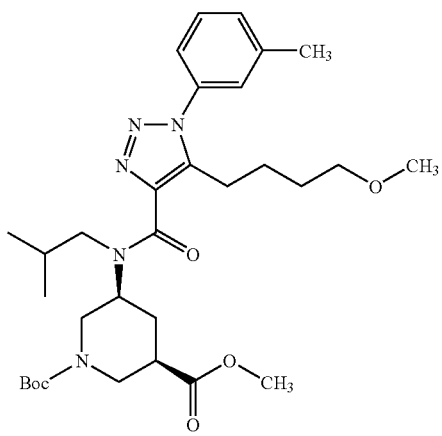 [SMILES: COCCCCc1c(C(=O)N(CC(C)C)[C@H]2C[C@@H](C(=O)OC)CN(C(=O)OC(C)(C)C)C2)nnn1-c1cccc(C)c1]

MS (ESI+, m/e) 586 (M+1)

Reference Example 402

1-tert-butyl 3-methyl (3R,5S)-5-[{[5-(4-methoxybutyl)-1-(4-methylphenyl)-1H-1,2,3-triazol-4-yl]carbonyl}(2-methylpropyl)amino]piperidine-1,3-dicarboxylate

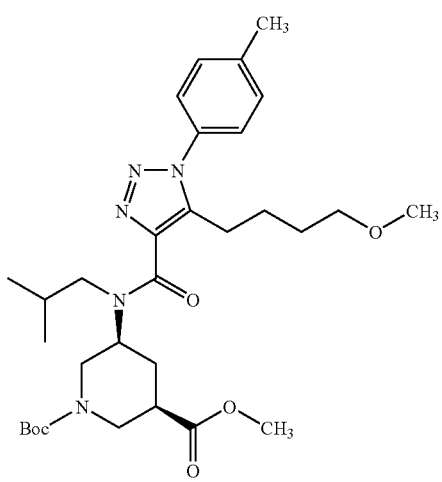 [SMILES: COCCCCc1c(C(=O)N(CC(C)C)[C@H]2C[C@@H](C(=O)OC)CN(C(=O)OC(C)(C)C)C2)nnn1-c1ccc(C)cc1]

MS (ESI+, m/e) 586 (M+1)

Reference Example 403

1-tert-butyl 3-methyl (3R,5S)-5-[{[5-(4-methoxybutyl)-1-(2-methoxyphenyl)-1H-1,2,3-triazol-4-yl]carbonyl}(2-methylpropyl)amino]piperidine-1,3-dicarboxylate

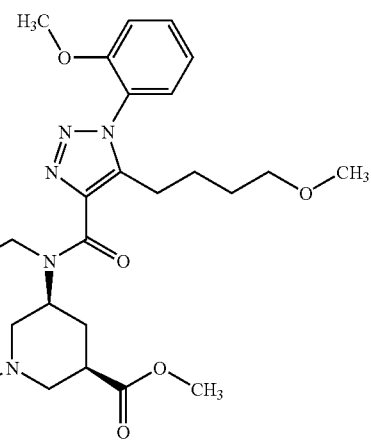

MS (ESI+, m/e) 602 (M+1)

Reference Example 404

1-tert-butyl 3-methyl (3R,5S)-5-[{[5-(4-methoxybutyl)-1-(3-methoxyphenyl)-1H-1,2,3-triazol-4-yl]carbonyl}(2-methylpropyl)amino]piperidine-1,3-dicarboxylate

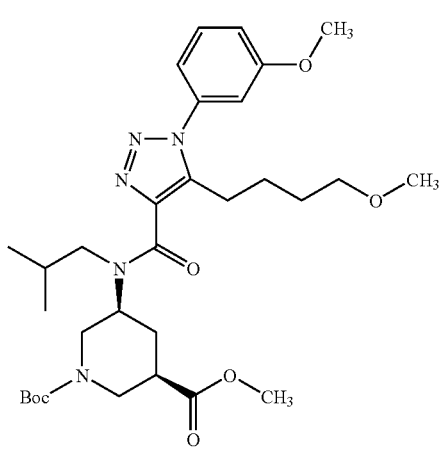 [SMILES: COCCCCc1c(C(=O)N(CC(C)C)[C@H]2C[C@@H](C(=O)OC)CN(C(=O)OC(C)(C)C)C2)nnn1-c1cccc(OC)c1]

MS (ESI+, m/e) 602 (M+1)

Reference Example 405

1-tert-butyl 3-methyl (3R,5S)-5-[{[5-(4-methoxybutyl)-1-(4-methoxyphenyl)-1H-1,2,3-triazol-4-yl]carbonyl}(2-methylpropyl)amino]piperidine-1,3-dicarboxylate

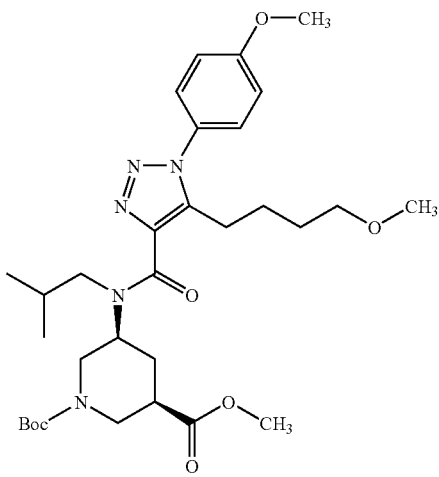 [SMILES: COCCCCc1c(C(=O)N(CC(C)C)[C@H]2C[C@@H](C(=O)OC)CN(C(=O)OC(C)(C)C)C2)nnn1-c1ccc(OC)cc1]

MS (ESI+, m/e) 602 (M+1)

Reference Example 406

(3R,5S)-1-(tert-butoxycarbonyl)-5-[{[5-(4-methoxybutyl)-1-(2-methylphenyl)-1H-1,2,3-triazol-4-yl]carbonyl}(2-methylpropyl)amino]piperidine-3-carboxylic acid

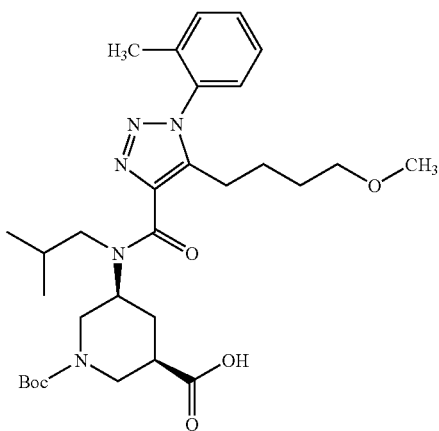 [SMILES: COCCCCc1c(C(=O)N(CC(C)C)[C@H]2C[C@@H](C(=O)O)CN(C(=O)OC(C)(C)C)C2)nnn1-c1ccccc1C]

To a solution of 1-tert-butyl 3-methyl (3R,5S)-5-[{[5-(4-methoxybutyl)-1-(2-methylphenyl)-1H-1,2,3-triazol-4-yl]carbonyl}(2-methylpropyl)amino]piperidine-1,3-dicarboxylate (1.47 g) in methanol (10 ml) was added 4N aqueous sodium hydroxide solution (5 ml), and the mixture was stirred at 50° C. for 30 min. The solvent was concentrated under reduced pressure, and the residue was neutralized with 10% aqueous citric acid solution, extracted with ethyl acetate (30 ml×2) and the extract was dried over anhydrous sodium sulfate. The solvent was evaporated under reduced pressure to give the object product (1.3 g) as an amorphous compound.

MS (ESI+, m/e) 572 (M+1)

In the same manner as in Reference Example 406, the following compounds (Reference Examples 407-411) were obtained.

Reference Example 407

(3R,5S)-1-(tert-butoxycarbonyl)-5-[{[5-(4-methoxybutyl)-1-(3-methylphenyl)-1H-1,2,3-triazol-4-yl]carbonyl}(2-methylpropyl)amino]piperidine-3-carboxylic acid

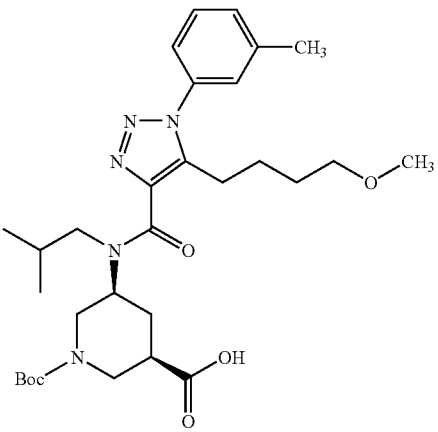 [SMILES: COCCCCc1c(C(=O)N(CC(C)C)[C@H]2C[C@@H](C(=O)O)CN(C(=O)OC(C)(C)C)C2)nnn1-c1cccc(C)c1]

MS (ESI+, m/e) 572 (M+1)

Reference Example 408

(3R,5S)-1-(tert-butoxycarbonyl)-5-[{[5-(4-methoxybutyl)-1-(4-methylphenyl)-1H-1,2,3-triazol-4-yl]carbonyl}(2-methylpropyl)amino]piperidine-3-carboxylic acid

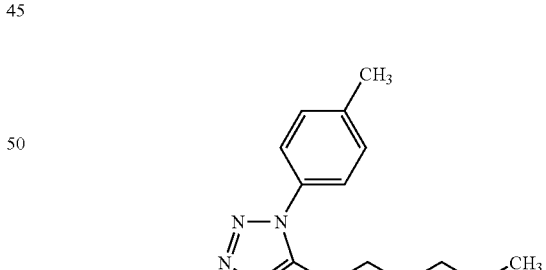
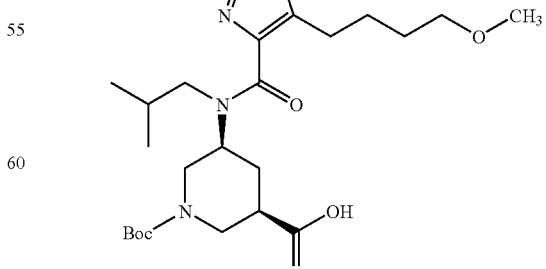

MS (ESI+, m/e) 572 (M+1)

Reference Example 409

(3R,5S)-1-(tert-butoxycarbonyl)-5-[{[5-(4-methoxy-butyl)-1-(2-methoxyphenyl)-1H-1,2,3-triazol-4-yl]carbonyl}(2-methylpropyl)amino]piperidine-3-carboxylic acid

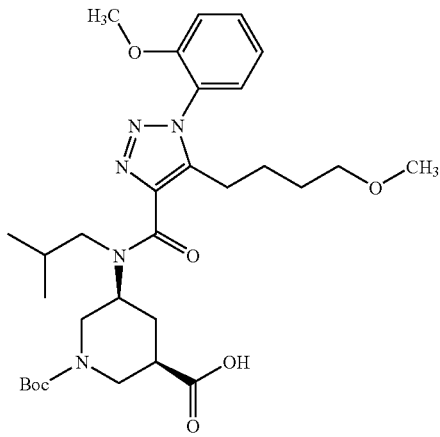 [SMILES: COCCCCc1c(C(=O)N(CC(C)C)[C@H]2C[C@@H](C(=O)O)CN(C(=O)OC(C)(C)C)C2)nnn1-c1ccccc1OC]

MS (ESI+, m/e) 588 (M+1)

Reference Example 410

(3R,5S)-1-(tert-butoxycarbonyl)-5-[{[5-(4-methoxy-butyl)-1-(3-methoxyphenyl)-1H-1,2,3-triazol-4-yl]carbonyl}(2-methylpropyl)amino]piperidine-3-carboxylic acid

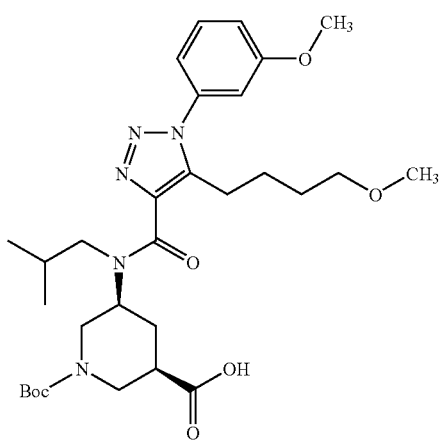 [SMILES: COCCCCc1c(C(=O)N(CC(C)C)[C@H]2C[C@@H](C(=O)O)CN(C(=O)OC(C)(C)C)C2)nnn1-c1cccc(OC)c1]

MS (ESI+, m/e) 588 (M+1)

Reference Example 411

(3R,5S)-1-(tert-butoxycarbonyl)-5-[{[5-(4-methoxy-butyl)-1-(4-methoxyphenyl)-1H-1,2,3-triazol-4-yl]carbonyl}(2-methylpropyl)amino]piperidine-3-carboxylic acid

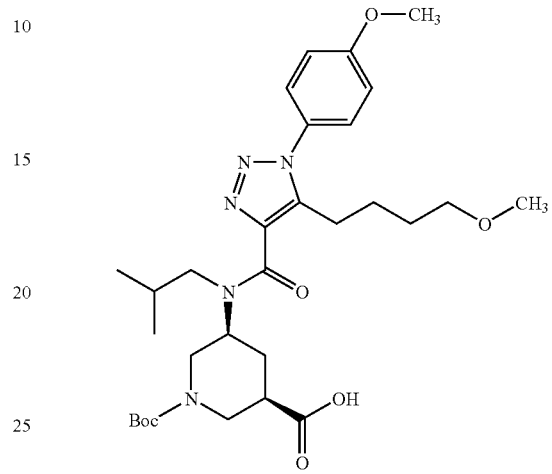

MS (ESI+, m/e) 588 (M+1)

Reference Example 412 tert-butyl (3S,5R)-3-[{[5-(4-methoxybutyl)-1-(2-methylphenyl)-1H-1,2,3-triazol-4-yl]carbonyl}(2-methylpropyl)amino]-5-(morpholin-4-ylcarbonyl)piperidine-1-carboxylate

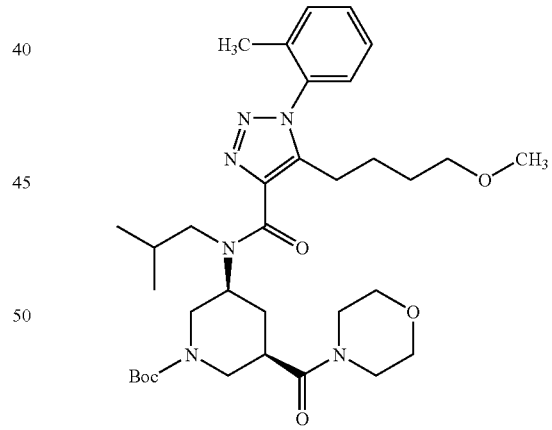

A solution of (3R,5S)-1-(tert-butoxycarbonyl)-5-[{[5-(4-methoxybutyl)-1-(2-methylphenyl)-1H-1,2,3-triazol-4-yl]carbonyl}(2-methylpropyl)amino]piperidine-3-carboxylic acid (286 mg), morpholine (44 µl), WSC.HCl (144 mg), HOBt (107 mg), diisopropylethylamine (255 µl) and DMF (3 ml) was stirred at room temperature for 15 hr. The reaction mixture was poured into saturated aqueous sodium hydrogen carbonate, and the liberated oil was extracted with ethyl acetate (20 ml). The extract was washed successively with water and saturated brine, and dried over anhydrous magnesium sulfate. The solvent was evaporated under reduced pressure. The residue was subjected to silica gel column chroma-

Reference Example 413 tert-butyl (3S,5R)-3-[{[5-(4-methoxybutyl)-1-(3-methylphenyl)-1H-1,2,3-triazol-4-yl]carbonyl}(3-methylpropyl)amino]-5-(morpholin-4-ylcarbonyl)piperidine-1-carboxylate

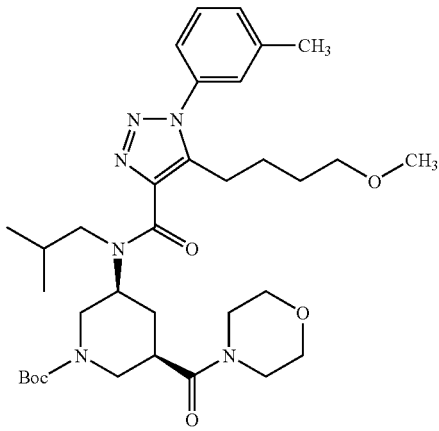

MS (ESI+, m/e) 641 (M+1)

Reference Example 414 tert-butyl (3S,5R)-3-[{[5-(4-methoxybutyl)-1-(4-methylphenyl)-1H-1,2,3-triazol-4-yl]carbonyl}(4-methylpropyl)amino]-5-(morpholin-4-ylcarbonyl)piperidine-1-carboxylate

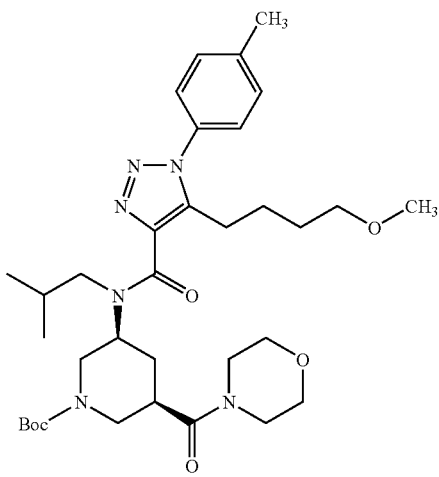

MS (ESI+, m/e) 641 (M+1)

Reference Example 415 tert-butyl (3S,5R)-3-[{[5-(4-methoxybutyl)-1-(2-methoxyphenyl)-1H-1,2,3-triazol-4-yl]carbonyl}(2-methylpropyl)amino]-5-(morpholin-4-ylcarbonyl)piperidine-1-carboxylate

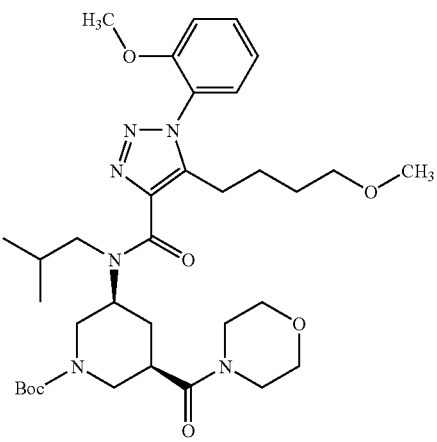 [SMILES: COCCCCc1c(C(=O)N(CC(C)C)[C@H]2C[C@@H](C(=O)N3CCOCC3)CN(C(=O)OC(C)(C)C)C2)nnn1-c1ccccc1OC]

MS (ESI+, m/e) 657 (M+1)

Reference Example 416 tert-butyl (3S,5R)-3-[{[5-(4-methoxybutyl)-1-(3-methoxyphenyl)-1H-1,2,3-triazol-4-yl]carbonyl}(2-methylpropyl)amino]-5-(morpholin-4-ylcarbonyl)piperidine-1-carboxylate

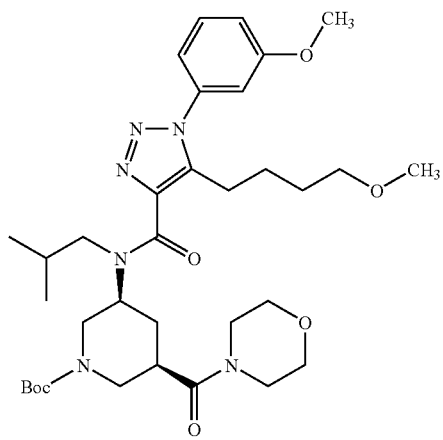 [SMILES: COCCCCc1c(C(=O)N(CC(C)C)[C@H]2C[C@@H](C(=O)N3CCOCC3)CN(C(=O)OC(C)(C)C)C2)nnn1-c1cccc(OC)c1]

MS (ESI+, m/e) 657 (M+1)

tography, and a fraction eluted with ethyl acetate was concentrated under reduced pressure to give the object product (255 mg) as an amorphous compound.

MS (ESI+, m/e) 641 (M+1)

In the same manner as in Reference Example 412, the following compounds (Reference Examples 413-417) were obtained.

Reference Example 417 tert-butyl (3S,5R)-3-[{[5-(4-methoxybutyl)-1-(4-methoxyphenyl)-1H-1,2,3-triazol-4-yl]carbonyl}(2-methylpropyl)amino]-5-(morpholin-4-ylcarbonyl)piperidine-1-carboxylate

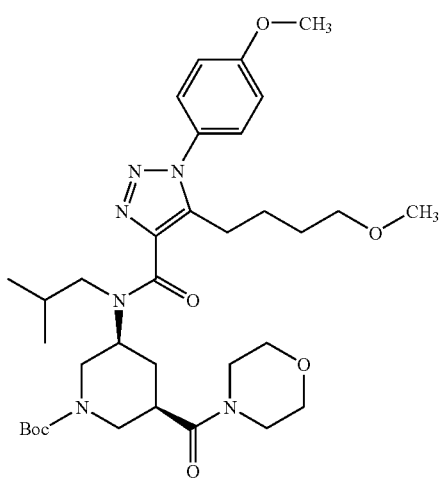 [SMILES: COCCCCc1c(C(=O)N(CC(C)C)[C@H]2C[C@@H](C(=O)N3CCOCC3)CN(C(=O)OC(C)(C)C)C2)nnn1-c1ccc(OC)cc1]

MS (ESI+, m/e) 657 (M+1)

Reference Example 418

1-tert-butyl 3-[(5-methyl-2-oxo-1,3-dioxol-4-yl)methyl](3R,5S)-5-[{[5-(4-methoxybutyl)-1-(2-methylphenyl)-1H-1,2,3-triazol-4-yl]carbonyl}(2-methylpropyl)amino]piperidine-1,3-dicarboxylate

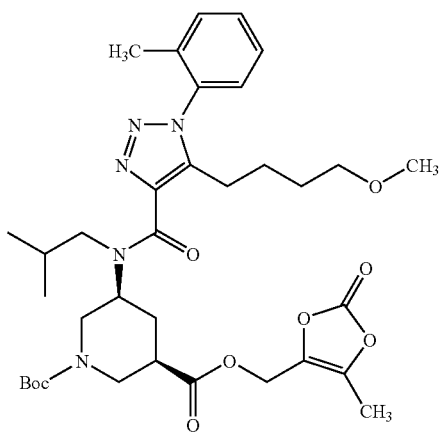 [SMILES: COCCCCc1c(C(=O)N(CC(C)C)[C@H]2C[C@@H](C(=O)OCc3oc(=O)oc3C)CN(C(=O)OC(C)(C)C)C2)nnn1-c1ccccc1C]

To a solution of (3R,5S)-1-(tert-butoxycarbonyl)-5-[{[5-(4-methoxybutyl)-1-(2-methylphenyl)-1H-1,2,3-triazol-4-yl]carbonyl}(2-methylpropyl)amino]piperidine-3-carboxylic acid (286 mg) and 4-(hydroxymethyl)-5-methyl-1,3-dioxol-2-one (78 mg) in DMA (5 ml) were added toluenesulfonyl chloride (64 mg), DMAP (12 mg) and potassium carbonate (90 mg) under ice-cooling, and the mixture was stirred at 0° C. for 6 hr and at room temperature for 15 hr. The reaction mixture was poured into ice-cooled 5% aqueous citric acid (10 ml), and the liberated oil was extracted with ethyl acetate (20 ml). The extract was washed with brine, and dried over anhydrous sodium sulfate. The solvent was evaporated under reduced pressure. The residue was subjected to silica gel column chromatography, and a fraction eluted with hexane-ethyl acetate (50:50) was concentrated under reduced pressure to give the object product (210 mg) as an amorphous compound.

MS (ESI+, m/e) 684 (M+1)

In the same manner as in Example 2, the following compounds (Examples 207-230) were obtained.

Example 207

5-acetyl-1-(4-methoxybutyl)-N-(2-methylpropyl)-N-[(3S,5R)-5-(morpholin-4-ylcarbonyl)piperidin-3-yl]-1H-pyrrole-2-carboxamide hydrochloride

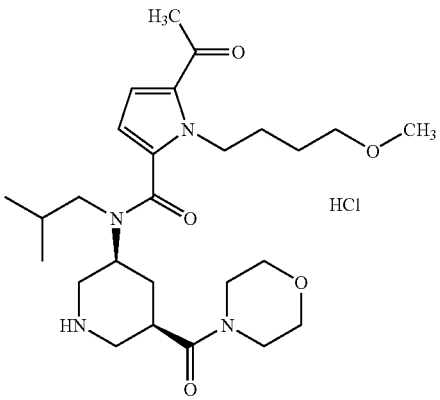 [SMILES: COCCCCn1c(C(C)=O)ccc1C(=O)N(CC(C)C)[C@@H]1CNC[C@H](C(=O)N2CCOCC2)C1 ; Cl]

MS (ESI+, m/e) 517 (M+1)

Example 208

N-(decahydroisoquinolin-4-yl)-5-(4-methoxybutyl)-N-(2-methylpropyl)-1-phenyl-1H-1,2,3-triazole-4-carboxamide hydrochloride

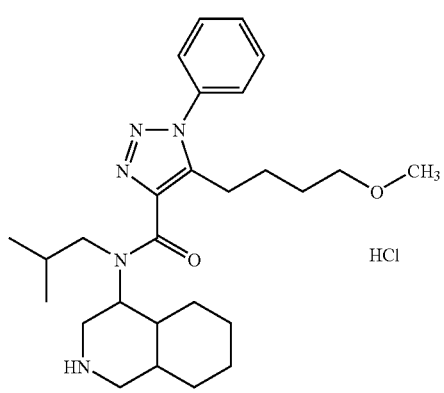 [SMILES: COCCCCc1c(C(=O)N(CC(C)C)C2CNCC3CCCCC32)nnn1-c1ccccc1 ; Cl]

MS (ESI+, m/e) 468 (M+1)

Example 209 methyl (3R,5S)-5-[{[5-(4-methoxybutyl)-1-phenyl-1H-1,2,3-triazol-4-yl]carbonyl}(2-methylpropyl)amino]piperidine-3-carboxylate hydrochloride

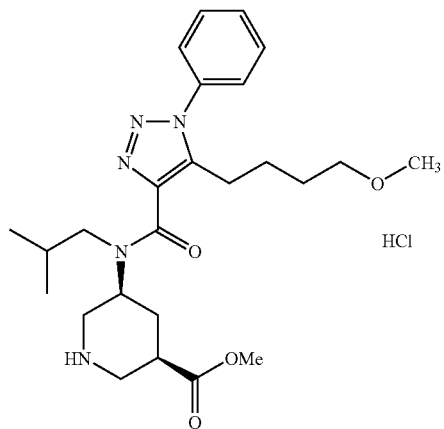 [SMILES: COCCCCc1c(C(=O)N(CC(C)C)[C@@H]2CNC[C@H](C(=O)OC)C2)nnn1-c1ccccc1 ; Cl]

MS (ESI+, m/e) 472 (M+1)

Example 210

N-[(3S,5R)-5-(1-hydroxy-1-methylethyl)piperidin-3-yl]-5-(4-methoxybutyl)-N-(2-methylpropyl)-1-phenyl-1H-1,2,3-triazole-4-carboxamide hydrochloride

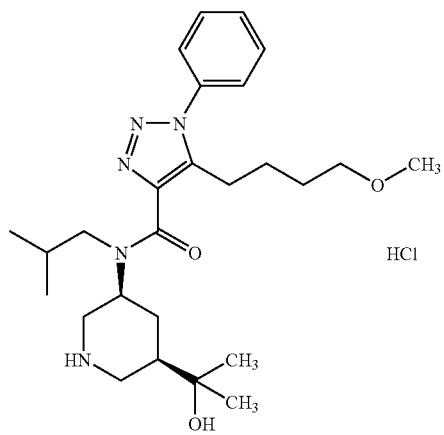 [SMILES: COCCCCc1c(C(=O)N(CC(C)C)[C@@H]2CNC[C@H](C(C)(C)O)C2)nnn1-c1ccccc1 ; Cl]

MS (ESI+, m/e) 472 (M+1)

Example 211

5-(4-methoxybutyl)-N-(2-methylpropyl)-1-phenyl-N-[(3S,5R)-5-(piperidin-1-ylcarbonyl)piperidin-3-yl]-1H-1,2,3-triazole-4-carboxamide hydrochloride

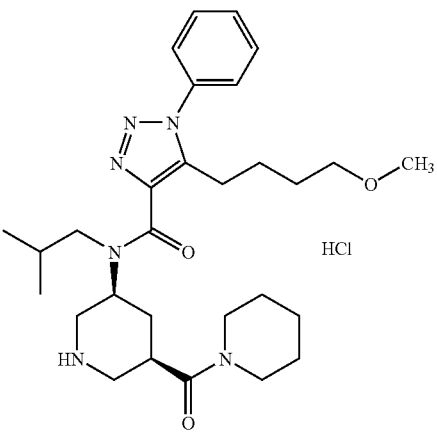 [SMILES: COCCCCc1c(C(=O)N(CC(C)C)[C@@H]2CNC[C@H](C(=O)N3CCCCC3)C2)nnn1-c1ccccc1 ; Cl]

MS (ESI+, m/e) 525 (M+1)

Example 212

N-[(3S,5R)-5-(7-azabicyclo[2.2.1]hept-7-ylcarbonyl)piperidin-3-yl]-5-(4-methoxybutyl)-N-(2-methylpropyl)-1-phenyl-1H-1,2,3-triazole-4-carboxamide hydrochloride

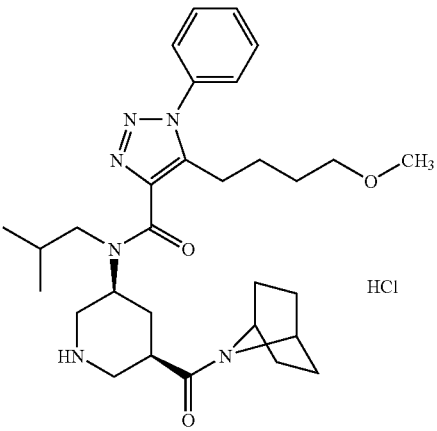 [SMILES: COCCCCc1c(C(=O)N(CC(C)C)[C@@H]2CNC[C@H](C(=O)N3C4CCC3CC4)C2)nnn1-c1ccccc1 ; Cl]

MS (ESI+, m/e) 537 (M+1)

Example 213

1-(3-chlorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

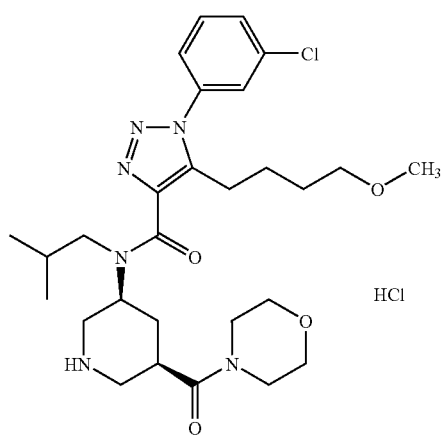 [SMILES: COCCCCc1c(C(=O)N(CC(C)C)[C@@H]2CNC[C@H](C(=O)N3CCOCC3)C2)nnn1-c1cccc(Cl)c1 ; Cl]

MS (ESI+, m/e) 562 (M+1)

Example 214

5-(4-methoxybutyl)-N-(2-methylpropyl)-N-[(3S,5R)-5-(morpholin-4-ylcarbonyl)piperidin-3-yl]-1-[3-(trifluoromethyl)phenyl]-1H-1,2,3-triazole-4-carboxamide hydrochloride

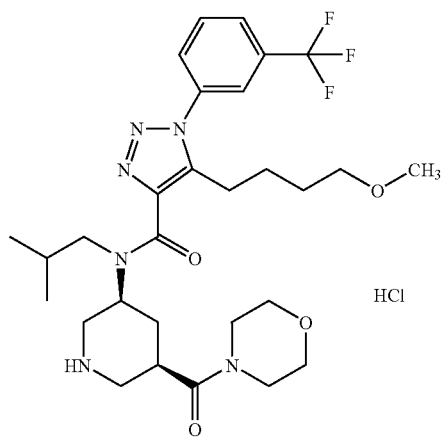 [SMILES: COCCCCc1c(C(=O)N(CC(C)C)[C@@H]2CNC[C@H](C(=O)N3CCOCC3)C2)nnn1-c1cccc(C(F)(F)F)c1 ; Cl]

MS (ESI+, m/e) 595 (M+1)

Example 215

1-(4-fluorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

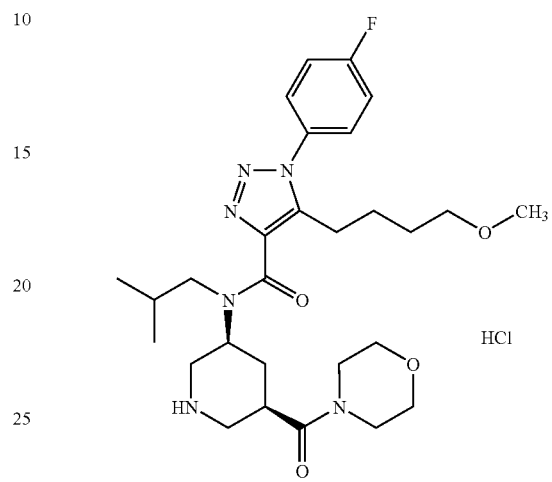

MS (ESI+, m/e) 595 (M+1)

Example 216

1-(4-chlorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

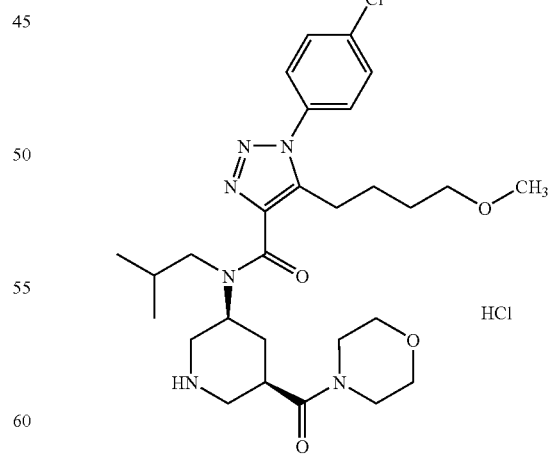

MS (ESI+, m/e) 562 (M+1)

Example 217

1-(3-fluorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

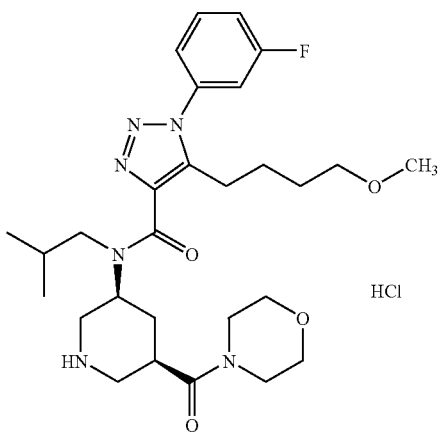

MS (ESI+, m/e) 545 (M+1)

Example 218

1-(3,4-difluorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

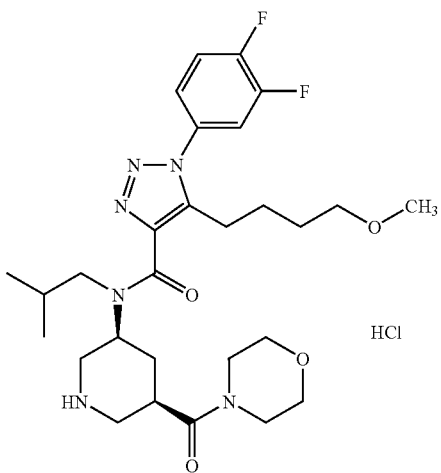 [SMILES: COCCCCc1c(C(=O)N(CC(C)C)[C@@H]2CNC[C@H](C(=O)N3CCOCC3)C2)nnn1-c1ccc(F)c(F)c1 ; Cl]

MS (ESI+, m/e) 563 (M+1)

Example 219

(3R,5S)-5-[{[5-(4-methoxybutyl)-1-phenyl-1H-1,2,3-triazol-4-yl]carbonyl}(2-methylpropyl)amino]piperidine-3-carboxylic acid hydrochloride

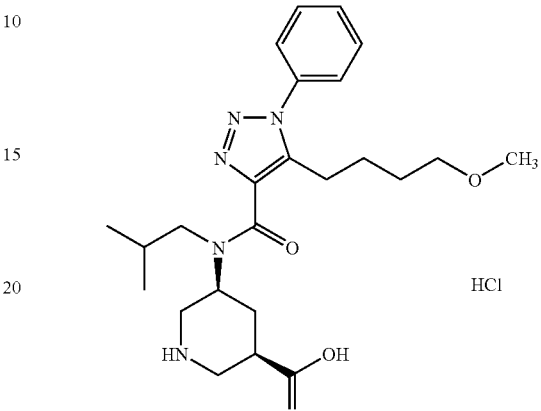

MS (ESI+, m/e) 458 (M+1)

Example 220

5-(4-methoxybutyl)-1-(3-methylphenyl)-N-(2-methylpropyl)-N-[(3S,5R)-5-(morpholin-4-ylcarbonyl)piperidin-3-yl]-1H-1,2,3-triazole-4-carboxamide hydrochloride

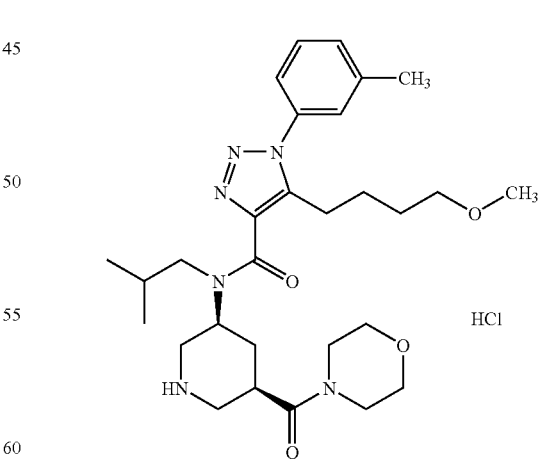

MS (ESI+, m/e) 541 (M+1)

Example 221

5-(4-methoxybutyl)-1-(4-methylphenyl)-N-(2-methylpropyl)-N-[(3S,5R)-5-(morpholin-4-ylcarbonyl)piperidin-3-yl]-1H-1,2,3-triazole-4-carboxamide hydrochloride

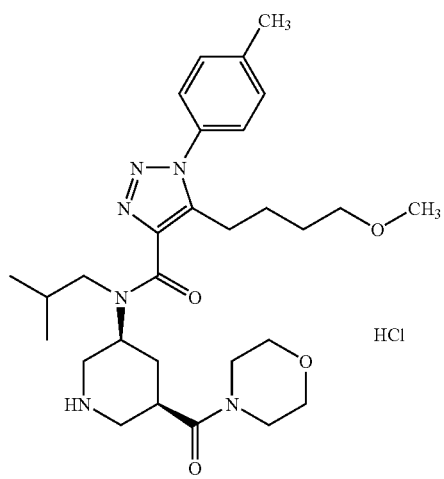 [SMILES: COCCCCc1c(C(=O)N(CC(C)C)[C@@H]2CNC[C@H](C(=O)N3CCOCC3)C2)nnn1-c1ccc(C)cc1 ; Cl]

MS (ESI+, m/e) 541 (M+1)

Example 222

5-(4-methoxybutyl)-1-(2-methoxyphenyl)-N-(2-methylpropyl)-N-[(3S,5R)-5-(morpholin-4-ylcarbonyl)piperidin-3-yl]-1H-1,2,3-triazole-4-carboxamide hydrochloride

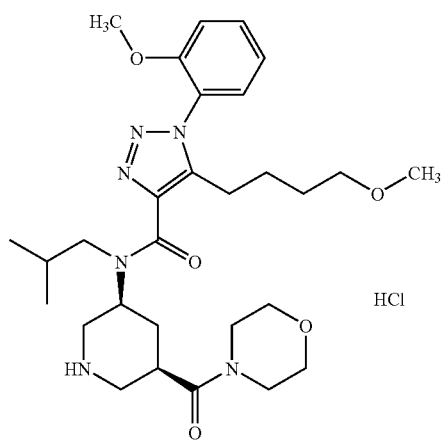 [SMILES: COCCCCc1c(C(=O)N(CC(C)C)[C@@H]2CNC[C@H](C(=O)N3CCOCC3)C2)nnn1-c1ccccc1OC ; Cl]

MS (ESI+, m/e) 557 (M+1)

Example 223

5-(4-methoxybutyl)-1-(3-methoxyphenyl)-N-(2-methylpropyl)-N-[(3S,5R)-5-(morpholin-4-ylcarbonyl)piperidin-3-yl]-1H-1,2,3-triazole-4-carboxamide hydrochloride

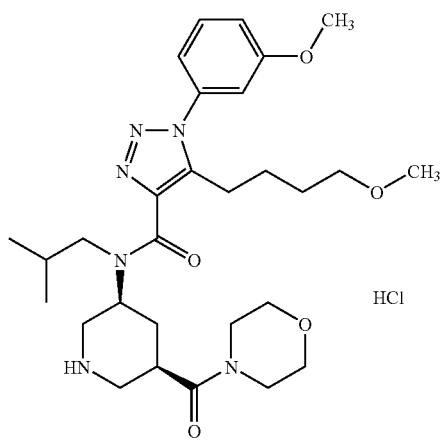 [SMILES: COCCCCc1c(C(=O)N(CC(C)C)[C@@H]2CNC[C@H](C(=O)N3CCOCC3)C2)nnn1-c1cccc(OC)c1 ; Cl]

MS (ESI+, m/e) 557 (M+1)

Example 224

5-(4-methoxybutyl)-1-(4-methoxyphenyl)-N-(2-methylpropyl)-N-[(3S,5R)-5-(morpholin-4-ylcarbonyl)piperidin-3-yl]-1H-1,2,3-triazole-4-carboxamide hydrochloride

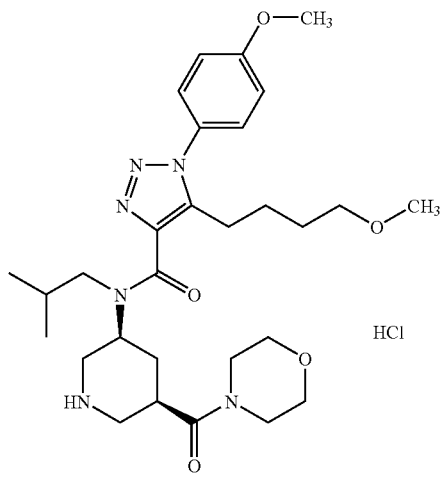 [SMILES: COCCCCc1c(C(=O)N(CC(C)C)[C@@H]2CNC[C@H](C(=O)N3CCOCC3)C2)nnn1-c1ccc(OC)cc1 ; Cl]

MS (ESI+, m/e) 557 (M+1)

Example 225

1-(2,3-difluorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

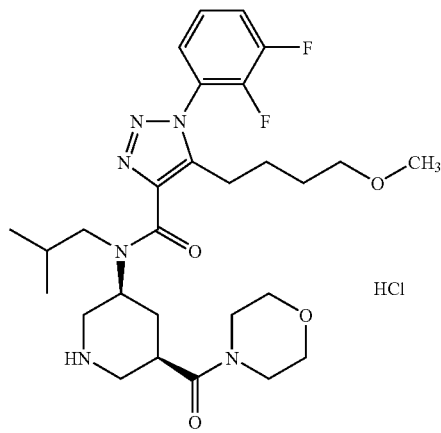 [SMILES: COCCCCc1c(C(=O)N(CC(C)C)[C@@H]2CNC[C@H](C(=O)N3CCOCC3)C2)nnn1-c1cccc(F)c1F ; Cl]

MS (ESI+, m/e) 563 (M+1)

Example 226

1-(2,6-difluorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

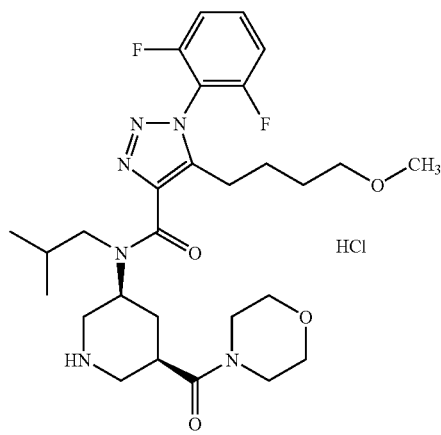 [SMILES: COCCCCc1c(C(=O)N(CC(C)C)[C@@H]2CNC[C@H](C(=O)N3CCOCC3)C2)nnn1-c1c(F)cccc1F ; Cl]

MS (ESI+, m/e) 563 (M+1)

Example 227

1-(3,5-difluorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

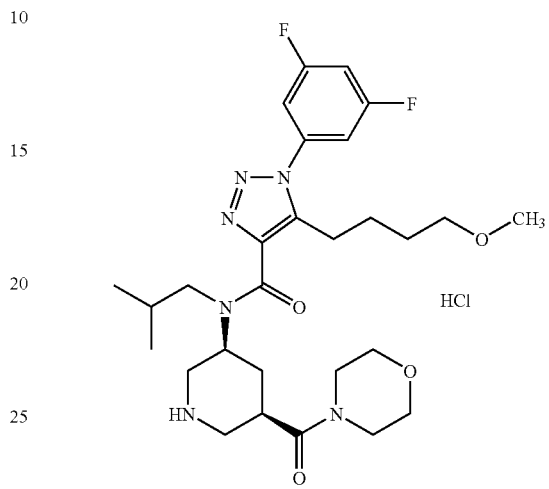

MS (ESI+, m/e) 563 (M+1)

Example 228

N-(2-methylpropyl)-N-[(3S,5R)-5-(morpholin-4-ylcarbonyl)piperidin-3-yl]-1-phenyl-5-(2-phenylethyl)-1H-1,2,3-triazole-4-carboxamide hydrochloride

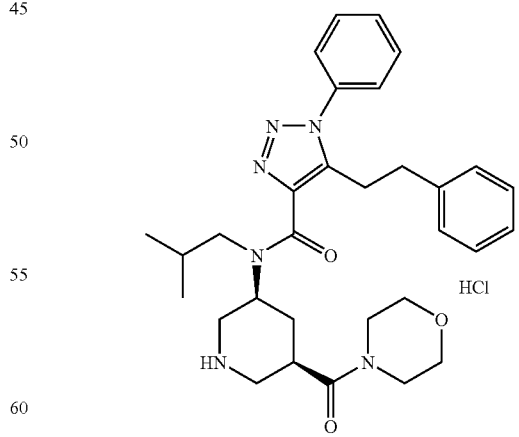

MS (ESI+, m/e) 545 (M+1)

Example 229

(3R,5S)-5-[{[5-(4-methoxybutyl)-1-(2-methylphenyl)-1H-1,2,3-triazol-4-yl]carbonyl}(2-methylpropyl)amino]piperidine-3-carboxylic acid hydrochloride

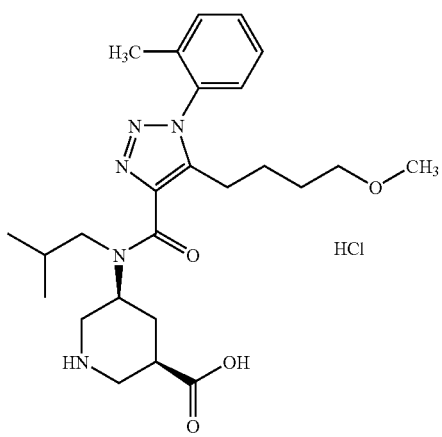 [SMILES: COCCCCc1c(C(=O)N(CC(C)C)[C@@H]2CNC[C@H](C(=O)O)C2)nnn1-c1ccccc1C ; Cl]

MS (ESI+, m/e) 472 (M+1)

Example 230

(5-methyl-2-oxo-1,3-dioxol-4-yl)methyl (3R,5S)-5-[{[5-(4-methoxybutyl)-1-(2-methylphenyl)-1H-1,2,3-triazol-4-yl]carbonyl}(2-methylpropyl)amino]piperidine-3-carboxylate hydrochloride

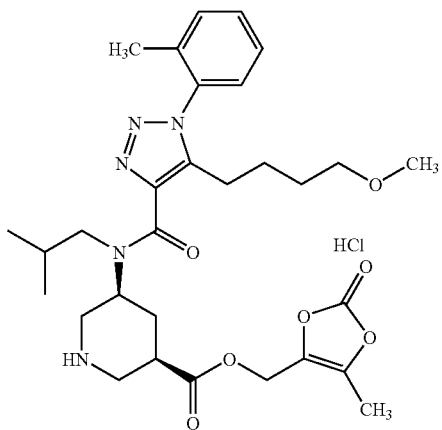 [SMILES: COCCCCc1c(C(=O)N(CC(C)C)[C@@H]2CNC[C@H](C(=O)OCc3oc(=O)oc3C)C2)nnn1-c1ccccc1C ; Cl]

MS (ESI+, m/e) 584 (M+1)

Example 231

5-(4-methoxybutyl)-N-(2-methylpropyl)-N-[(3S,5R)-5-(morpholin-4-ylcarbonyl)piperidin-3-yl]-1-phenyl-1H-1,2,3-triazole-4-carboxamide hydrochloride

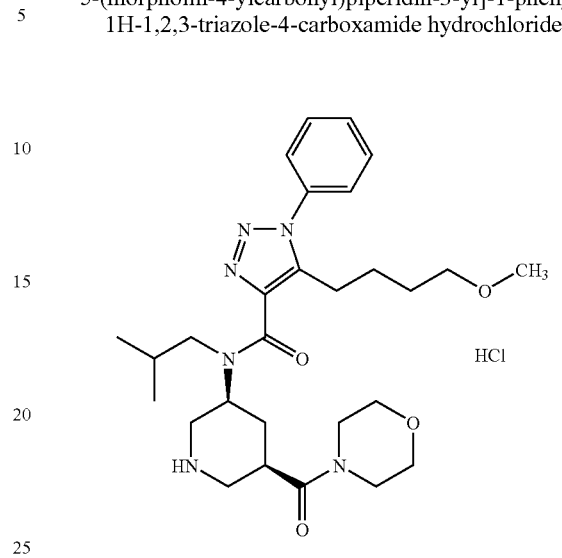

tert-Butyl (3S,5R)-3-[{[5-(4-methoxybutyl)-1-phenyl-1H-1,2,3-triazol-4-yl]carbonyl}(2-methylpropyl)amino]-5-(morpholin-4-ylcarbonyl)piperidine-1-carboxylate (235 mg) was dissolved in ethyl acetate (0.5 ml), 4N hydrogen chloride-ethyl acetate solution (0.5 ml) was added, and the mixture was stirred at room temperature for 1 hr. The solvent was evaporated under reduced pressure, and the residue was dried under reduced pressure to give the object product (200 mg).

MS (ESI+, m/e) 527 (M+1)

$^1$H-NMR (DMSO-d$_6$) δ 0.80-0.85 (3H, m), 0.90-0.95 (3H, m), 1.36 (4H, br s), 1.98-2.48 (3H, m), 2.79-3.08 (1H, t), 3.10 (3H, s), 3.10-3.15 (2H, m), 3.24-3.37 (6H, m), 3.52-3.62 (8H, m), 4.19-4.66 (1H, m), 7.61-7.66 (5H, m), 9.69 (2H, br s).

Example 232

5-(4-methoxybutyl)-N-(2-methylpropyl)-1-phenyl-N-[(3S,5R)-5-(pyrrolidin-1-ylcarbonyl)piperidin-3-yl]-1H-1,2,3-triazole-4-carboxamide hydrochloride

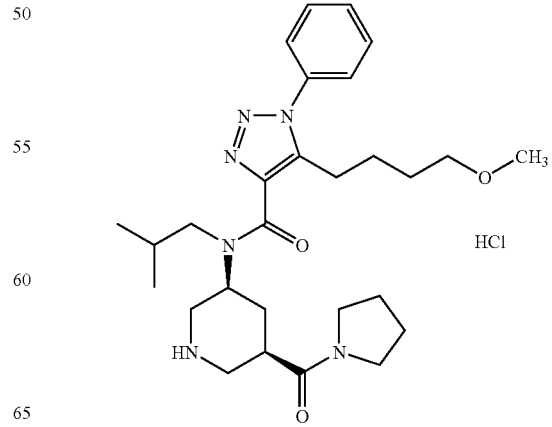

tert-Butyl (3S,5R)-3-[{[5-(4-methoxybutyl)-1-phenyl-1H-1,2,3-triazol-4-yl]carbonyl}(2-methylpropyl)amino]-5-(pyrrolidin-1-ylcarbonyl)piperidine-1-carboxylate (245 mg) was dissolved in ethyl acetate (0.5 ml), 4N hydrogen chloride-ethyl acetate solution (0.5 ml) was added, and the mixture was stirred at room temperature for 1 hr. The solvent was evaporated under reduced pressure, and the residue was dried under reduced pressure to give the object product (205 mg).

MS (ESI+, m/e) 527 (M+1)

$^1$H-NMR (DMSO-$d_6$) δ 0.80-0.85 (3H, m), 0.90-0.95 (3H, m), 1.36 (4H, br s), 1.76-1.82 (2H, m), 1.87-1.98 (4H, m), 2.02-2.13 (2H, m), 2.79-2.84 (2H, m), 2.90-2.97 (1H, m), 3.10 (3H, s), 3.13 (2H, t), 3.27-3.34 (6H, m), 3.47-3.66 (3H, m), 4.20-4.63 (1H, m), 7.61-7.66 (5H, m), 9.69 (2H, br s).

Example 233

1-(2-fluorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

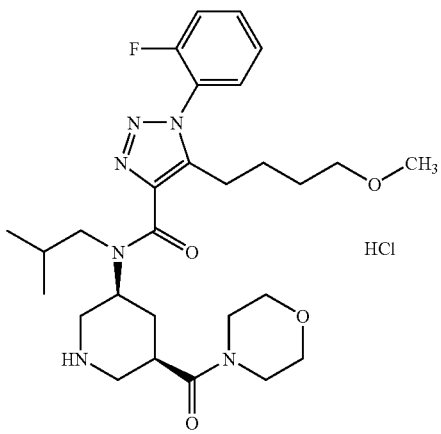 [SMILES: COCCCCc1c(C(=O)N(CC(C)C)[C@@H]2CNC[C@H](C(=O)N3CCOCC3)C2)nnn1-c1ccccc1F ; Cl]

tert-Butyl (3S,5R)-3-[{[1-(2-fluorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate (85 mg) was dissolved in ethyl acetate (0.5 ml), 4N hydrogen chloride-ethyl acetate solution (0.5 ml) was added, and the mixture was stirred at room temperature for 1 hr. The solvent was evaporated under reduced pressure, and the residue was dried under reduced pressure to give the object product (70 mg).

MS (ESI+, m/e) 545 (M+1)

$^1$H-NMR (DMSO-$d_6$) δ 0.78-0.85 (3H, m), 0.90-0.95 (3H, m), 1.36 (4H, br s), 1.99-2.46 (3H, m), 2.71 (2H, br s), 2.95 (1H, t), 3.09-3.13 (5H, m), 3.23-3.33 (6H, m), 3.51-3.65 (8H, m), 4.20-4.63 (1H, m), 7.51 (1H, t), 7.63 (1H, t), 7.73-7.87 (2H, m), 9.62 (2H, br s).

Example 234

5-(4-methoxybutyl)-1-(2-methylphenyl)-N-(2-methylpropyl)-N-[(3S,5R)-5-(morpholin-4-ylcarbonyl)piperidin-3-yl]-1H-1,2,3-triazole-4-carboxamide hydrochloride

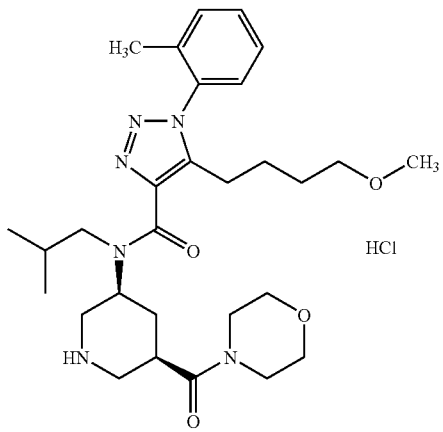 [SMILES: COCCCCc1c(C(=O)N(CC(C)C)[C@@H]2CNC[C@H](C(=O)N3CCOCC3)C2)nnn1-c1ccccc1C ; Cl]

tert-Butyl (3S,5R)-3-[{[5-(4-methoxybutyl)-1-(2-methylphenyl)-1H-1,2,3-triazol-4-yl]carbonyl}(2-methylpropyl)amino]-5-(morpholin-4-ylcarbonyl)piperidine-1-carboxylate (255 mg) was dissolved in ethyl acetate (0.5 ml), 4N hydrogen chloride-ethyl acetate solution (0.5 ml) was added, and the mixture was stirred at room temperature for 1 hr. The solvent was evaporated under reduced pressure, and the residue was dried under reduced pressure to give the object product (220 mg).

MS (ESI+, m/e) 541 (M+1)

$^1$H-NMR (DMSO-$d_6$) δ 0.79-0.85 (3H, m), 0.90-0.95 (3H, m), 1.33 (4H, br s), 1.93-2.14 (6H, m), 2.62 (2H, br s), 2.88-3.03 (1H, m), 3.08-3.12 (5H, m), 3.22-3.45 (6H, m), 3.50-3.67 (8H, m), 4.22-4.66 (1H, m), 7.44-7.58 (4H, m), 9.76 (2H, br s).

Example 235

1-(2-chlorophenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

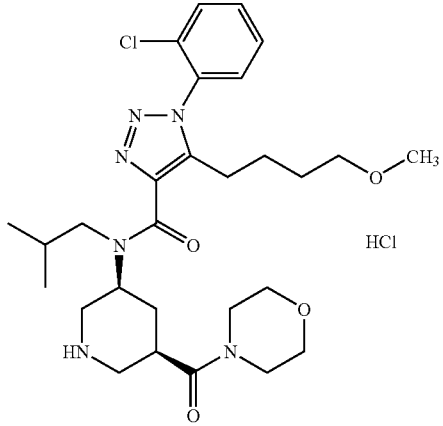 [SMILES: COCCCCc1c(C(=O)N(CC(C)C)[C@@H]2CNC[C@H](C(=O)N3CCOCC3)C2)nnn1-c1ccccc1Cl ; Cl]

tert-Butyl (3S,5R)-3-[{[1-(2-chlorophenyl)-5-(4-methoxybutyl)-1H-1,2,3-triazol-4-yl]carbonyl}(2-methylpropyl)amino]-5-(morpholin-4-ylcarbonyl)piperidine-1-carboxylate (280 mg) was dissolved in ethyl acetate (0.5 ml), 4N hydrogen chloride-ethyl acetate solution (0.5 ml) was added, and the mixture was stirred at room temperature for 1 hr. The solvent was evaporated under reduced pressure, and the residue was dried under reduced pressure to give the object product (245 mg).

MS (ESI+, m/e) 562 (M+1)

$^1$H-NMR (DMSO-$d_6$) δ 0.82-0.85 (3H, m), 0.90-0.97 (3H, m), 1.41 (4H, br s), 1.98-2.17 (3H, m), 2.68 (2H, br s), 2.95-3.07 (1H, m), 3.13 (3H, s), 3.16 (2H, t), 3.27-3.43 (6H, m), 3.55-3.64 (8H, m), 4.28-4.71 (1H, m), 7.69 (1H, t), 7.75-7.82 (2H, m), 7.87 (1H, d), 9.67 (2H, br s).

In the same manner as in the method shown in Reference Example 149, the following compound (Reference Example 419) was obtained.

Reference Example 419 tert-butyl (3S,5R)-3-[{[5-(4-methoxybutyl)-1-phenyl-1H-1,2,3-triazol-4-yl]carbonyl}(2-methylpropyl)amino]-5-[methoxy(methyl)carbamoyl]piperidine-1-carboxylate

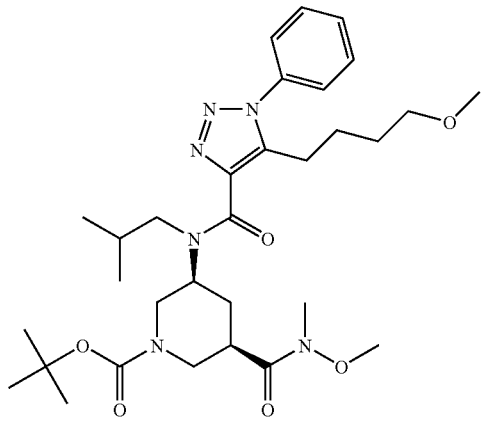 [SMILES: COCCCCc1c(C(=O)N(CC(C)C)[C@H]2C[C@@H](C(=O)N(C)OC)CN(C(=O)OC(C)(C)C)C2)nnn1-c1ccccc1]

MS (ESI+, m/e) 601 (M+1)

Reference Example 420 tert-butyl (3R,5S)-3-amino-5-[{[5-(4-methoxybutyl)-1-phenyl-1H-1,2,3-triazol-4-yl]carbonyl}(2-methylpropyl)amino]piperidine-1-carboxylate

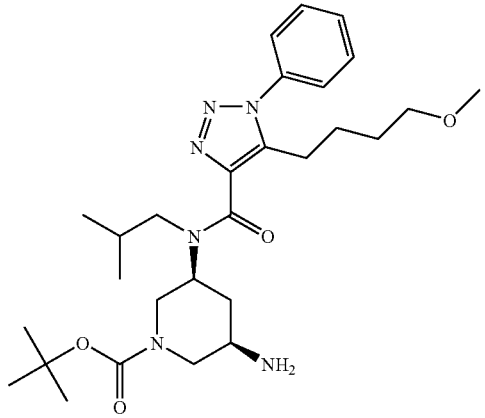 [SMILES: COCCCCc1c(C(=O)N(CC(C)C)[C@H]2C[C@@H](N)CN(C(=O)OC(C)(C)C)C2)nnn1-c1ccccc1]

(3R,5S)-1-(tert-Butoxycarbonyl)-5-[{[5-(4-methoxybutyl)-1-phenyl-1H-1,2,3-triazol-4-yl]carbonyl}(2-methylpropyl)amino]piperidine-3-carboxylic acid (250 mg) was dissolved in toluene (5 ml), diphenylphosphoryl azide (0.15 ml) and triethylamine (94 μl) were added and the mixture was stirred at 100° C. for 2 hr. The reaction mixture was cooled to room temperature, 8M aqueous sodium hydroxide solution (0.56 ml) was added and the mixture was stirred at room temperature for 1 hr. The reaction mixture was diluted with saturated aqueous sodium hydrogen carbonate and the mixture was extracted twice with ethyl acetate. The extract was dried over anhydrous sodium sulfate and the solvent was evaporated under reduced pressure. The residue was subjected to basic silica gel column chromatography, and a fraction eluted with ethyl acetate-hexane (1:1-1:0) and ethyl acetate-methanol (10:1) was concentrated under reduced pressure to give the object product (155 mg).

MS (ESI+, m/e) 529 (M+1)

Example 236

5-(4-methoxybutyl)-N-[(3S,5R)-5-(5-methyl-1,3,4-oxadiazol-2-yl)piperidin-3-yl]-N-(2-methylpropyl)-1-phenyl-1H-1,2,3-triazole-4-carboxamide 0.5 fumarate

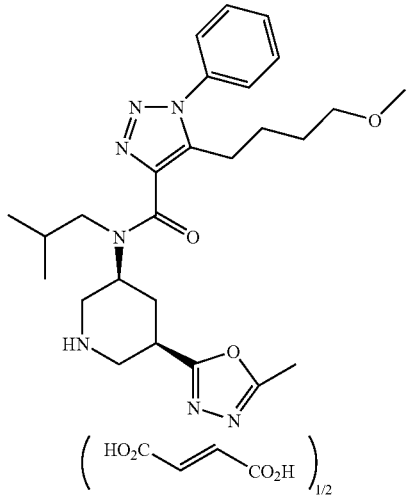

(3R,5S)-1-(tert-Butoxycarbonyl)-5-[{[5-(4-methoxybutyl)-1-phenyl-1H-1,2,3-triazol-4-yl]carbonyl}(2-methylpropyl)amino]piperidine-3-carboxylic acid (200 mg) was dissolved in toluene (5 ml), 5-methyl-1H-tetrazole (36 mg) and N,N'-dicyclohexylcarbodiimide (96 mg) were added and the mixture was stirred at 80° C. for 15 hr. Water was added to the reaction mixture, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (1:3-1:1) was concentrated under reduced pressure. The residue was dissolved in toluene (1 ml), trifluoroacetic acid (1 ml) was added and the mixture was stirred at room temperature for 1 hr. The reaction mixture was concentrated under reduced pressure, basified with saturated aqueous sodium hydrogen carbonate, and the mixture was extracted twice with ethyl acetate. The extract was dried over anhydrous sodium sulfate and the solvent was evaporated under reduced pressure. The residue was dissolved in methanol (1 ml), fumaric acid (12 mg) was added and the mixture was concentrated under reduced pressure to give the object product (85 mg).

MS (ESI+, m/e) 496 (M+1)

Reference Example 421 tert-butyl (3R,5S)-3-acetyl-5-[{[5-(4-methoxybutyl)-1-phenyl-1H-1,2,3-triazol-4-yl]carbonyl}(2-methylpropyl)amino]piperidine-1-carboxylate

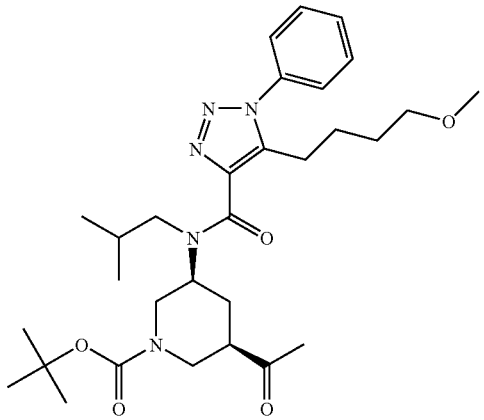 [SMILES: COCCCCc1c(C(=O)N(CC(C)C)[C@H]2C[C@@H](C(C)=O)CN(C(=O)OC(C)(C)C)C2)nnn1-c1ccccc1]

tert-Butyl (3S,5R)-3-[{[5-(4-methoxybutyl)-1-phenyl-1H-1,2,3-triazol-4-yl]carbonyl}(2-methylpropyl)amino]-5-[methoxy(methyl)carbamoyl]piperidine-1-carboxylate (230 mg) was dissolved in THF (5 ml), a 1M solution (1.9 ml) of methylmagnesium bromide in THF was added at 0° C., and the mixture was stirred at room temperature for 2 hr. Saturated aqueous ammonium chloride solution was added to the reaction mixture, and the mixture was extracted with ethyl acetate. The extract was washed with water and saturated brine, and dried over anhydrous sodium sulfate. The solvent was evaporated under reduced pressure. The residue was subjected to silica gel column chromatography, and a fraction eluted with ethyl acetate-hexane (1:5-1:2) was concentrated under reduced pressure to give the object product (177 mg).

MS (ESI+, m/e) 556 (M+1)

In the same manner as in the method shown in Example 60, the following compound (Example 237) was obtained.

Example 237

N-[(3S,5R)-5-acetylpiperidin-3-yl]-5-(4-methoxybutyl)-N-(2-methylpropyl)-1-phenyl-1H-1,2,3-triazole-4-carboxamide hydrochloride

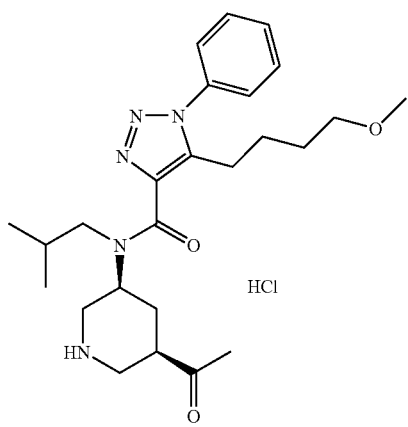 [SMILES: COCCCCc1c(C(=O)N(CC(C)C)[C@@H]2CNC[C@H](C(C)=O)C2)nnn1-c1ccccc1 ; Cl]

MS (ESI+, m/e) 456 (M+1)

Reference Example 422 tert-butyl (3'R,5'S)-5'-[{[5-(4-methoxybutyl)-1-phenyl-1H-1,2,3-triazol-4-yl]carbonyl}(2-methylpropyl)amino]-2-oxo-1,3'-bipiperidine-1'-carboxylate

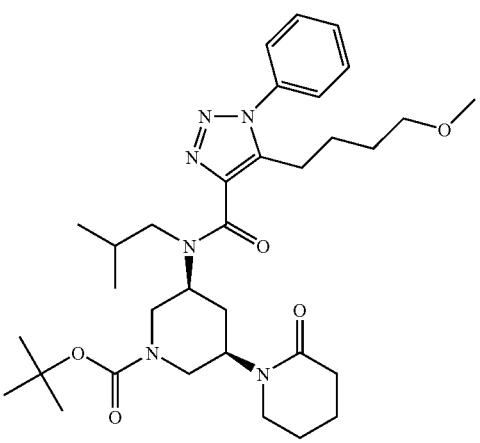 [SMILES: COCCCCc1c(C(=O)N(CC(C)C)[C@H]2C[C@@H](N3CCCCC3=O)CN(C(=O)OC(C)(C)C)C2)nnn1-c1ccccc1]

tert-Butyl (3R,5S)-3-amino-5-[{[5-(4-methoxybutyl)-1-phenyl-1H-1,2,3-triazol-4-yl]carbonyl}(2-methylpropyl)amino]piperidine-1-carboxylate (150 mg) was dissolved in THF (3 ml), diisopropylethylamine (74 μl) and 5-bromovaleryl chloride (42 μl) were added at 0° C. and the mixture was stirred at 0° C. for 1 hr. The reaction mixture was diluted with water, and the mixture was extracted with ethyl acetate. The extract was washed with saturated brine, dried over anhydrous sodium sulfate, and concentrated under reduced pressure. The residue was dissolved in THF (10 ml), potassium tert-butoxide (96 mg) was added at 0° C. and the mixture was stirred at room temperature for 1 hr. The reaction mixture was concentrated under reduced pressure, the residue was diluted with water, and the mixture was extracted with ethyl acetate. The extract was washed with saturated brine, dried over anhydrous sodium sulfate, and concentrated under reduced pressure. The obtained residue was subjected to silica gel chromatography, and a fraction eluted with ethyl acetate-hexane (1:3-1:0) was concentrated under reduced pressure to give the object product (150 mg).

MS (ESI+, m/e) 611 (M+1)

In the same manner as in the method shown in Reference Example 422, the following compounds (Reference Examples 423-424) were obtained.

433

Reference Example 423 tert-butyl (3S,5R)-3-[{[5-(4-methoxybutyl)-1-phenyl-1H-1,2,3-triazol-4-yl]carbonyl}(2-methylpropyl)amino]-5-(2-oxopyrrolidin-1-yl)piperidine-1-carboxylate

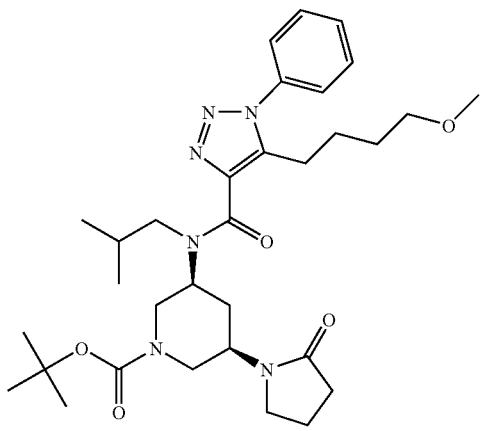 [SMILES: COCCCCc1c(C(=O)N(CC(C)C)[C@H]2C[C@@H](N3CCCC3=O)CN(C(=O)OC(C)(C)C)C2)nnn1-c1ccccc1]

MS (ESI+, m/e) 597 (M+1)

Reference Example 424 tert-butyl (3S,5R)-3-[{[5-(4-methoxybutyl)-1-phenyl-1H-1,2,3-triazol-4-yl]carbonyl}(2-methylpropyl)amino]-5-(2-oxotetrahydropyrimidin-1(2H)-yl)piperidine-1-carboxylate

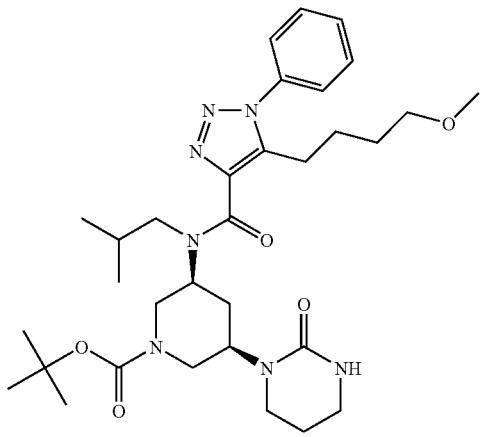 [SMILES: COCCCCc1c(C(=O)N(CC(C)C)[C@H]2C[C@@H](N3CCCNC3=O)CN(C(=O)OC(C)(C)C)C2)nnn1-c1ccccc1]

MS (ESI+, m/e) 612 (M+1)

In the same manner as in Example 60, the following compounds (Examples 238-240) were obtained.

434

Example 238

5-(4-methoxybutyl)-N-(2-methylpropyl)-N-[(3'R,5'S)-2-oxo-1,3'-bipiperidin-5'-yl]-1-phenyl-1H-1,2,3-triazole-4-carboxamide hydrochloride

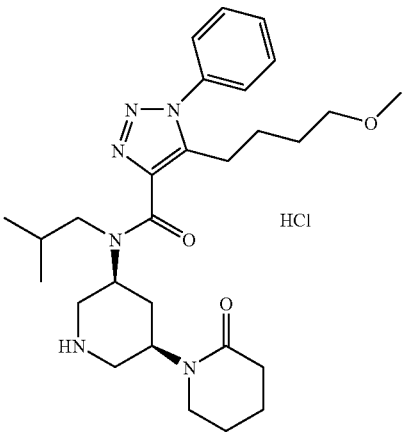 [SMILES: COCCCCc1c(C(=O)N(CC(C)C)[C@@H]2CNC[C@H](N3CCCCC3=O)C2)nnn1-c1ccccc1 ; Cl]

MS (ESI+, m/e) 511 (M+1)

Example 239

5-(4-methoxybutyl)-N-(2-methylpropyl)-N-[(3S,5R)-5-(2-oxopyrrolidin-1-yl)piperidin-3-yl]-1-phenyl-1H-1,2,3-triazole-4-carboxamide hydrochloride

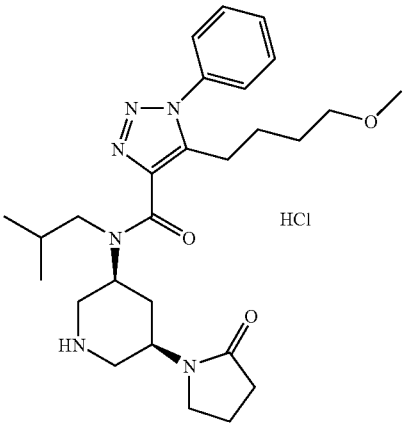 [SMILES: COCCCCc1c(C(=O)N(CC(C)C)[C@@H]2CNC[C@H](N3CCCC3=O)C2)nnn1-c1ccccc1 ; Cl]

MS (ESI+, m/e) 497 (M+1)

Example 240

5-(4-methoxybutyl)-N-(2-methylpropyl)-N-[(3S,5R)-5-(2-oxotetrahydropyrimidin-1(2H)-yl)piperidin-3-yl]-1-phenyl-1H-1,2,3-triazole-4-carboxamide hydrochloride

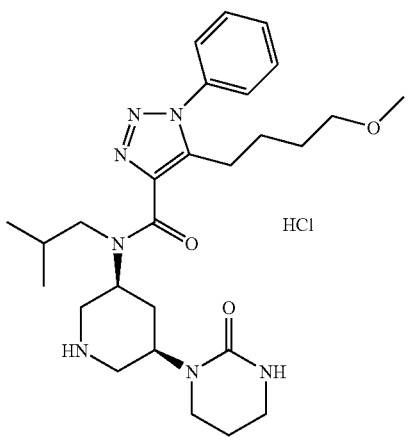 [SMILES: COCCCCc1c(C(=O)N(CC(C)C)[C@@H]2CNC[C@H](N3CCCNC3=O)C2)nnn1-c1ccccc1 ; Cl]

MS (ESI+, m/e) 512 (M+1)

Reference Example 425 methyl 5-(4-methoxybutyl)-1-phenyl-1H-pyrazole-4-carboxylate

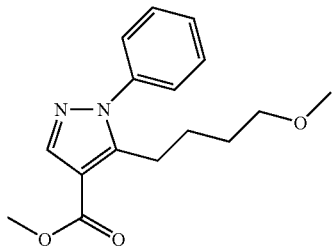

A solution of methyl 7-methoxy-3-oxoheptanoate (526 mg) and N,N-dimethylformamide dimethylacetal (0.45 ml) in toluene (5 ml) was stirred at 80° C. for 5 hr. The reaction mixture was concentrated under reduced pressure, and the residue was dissolved in ethanol (5 ml). Phenylhydrazine (0.41 ml) was added and the mixture was stirred at 80° C. for 15 hr. The reaction mixture was concentrated under reduced pressure, water was added to the residue, and the mixture was extracted with ethyl acetate. The extract was washed with saturated brine, and dried over anhydrous magnesium sulfate and concentrated under reduced pressure. The obtained residue was subjected to silica gel chromatography, and a fraction eluted with hexane-ethyl acetate-hexane (1:9-1:3) was concentrated under reduced pressure to give the object product (620 mg) as an oil.

MS (ESI+, m/e) 289 (M+1)

In the same manner as in Reference Example 74, the following compound (Reference Example 426) was obtained.

Reference Example 426

5-(4-methoxybutyl)-1-phenyl-1H-pyrazole-4-carboxylic acid

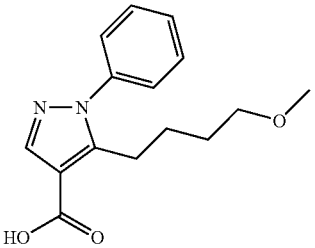 [SMILES: COCCCCc1c(C(=O)O)cnn1-c1ccccc1]

MS (ESI+, m/e) 275 (M+1)

In the same manner as in Reference Example 163, the following compounds (Reference Examples 427-428) were obtained.

Reference Example 427 tert-butyl (3S,5R)-3-[{[5-(4-methoxybutyl)-1-phenyl-1H-pyrazol-4-yl]carbonyl}(2-methylpropyl)amino]-5-(morpholin-4-ylcarbonyl)piperidine-1-carboxylate

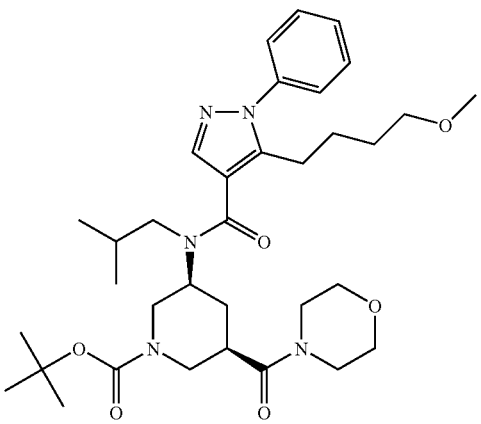 [SMILES: COCCCCc1c(C(=O)N(CC(C)C)[C@H]2C[C@@H](C(=O)N3CCOCC3)CN(C(=O)OC(C)(C)C)C2)cnn1-c1ccccc1]

MS (ESI+, m/e) 626 (M+1)

Reference Example 428 tert-butyl (3S)-3-[{[5-(4-methoxybutyl)-1-phenyl-1H-1,2,3-triazol-4-yl]carbonyl}(2-methylpropyl)amino]piperidine-1-carboxylate

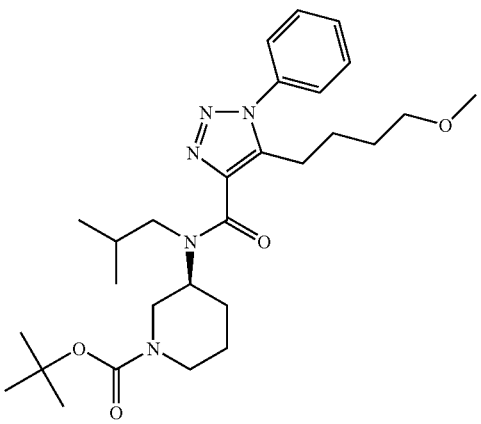 [SMILES: COCCCCc1c(C(=O)N(CC(C)C)[C@H]2CCCN(C(=O)OC(C)(C)C)C2)nnn1-c1ccccc1]

MS (ESI+, m/e) 514 (M+1)

In the same manner as in Example 60, the following compounds (Examples 241-242) were obtained.

Example 241

5-(4-methoxybutyl)-N-(2-methylpropyl)-N-[(3S,5R)-5-(morpholin-4-ylcarbonyl)piperidin-3-yl]-1-phenyl-1H-pyrazole-4-carboxamide dihydrochloride

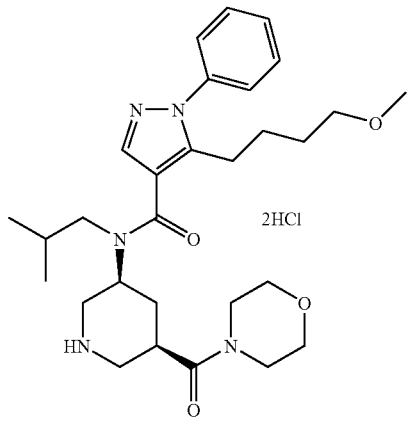 [SMILES: COCCCCc1c(C(=O)N(CC(C)C)[C@@H]2CNC[C@H](C(=O)N3CCOCC3)C2)cnn1-c1ccccc1 ; "2HCl"]

MS (ESI+, m/e) 526 (M+1)

Example 242

5-(4-methoxybutyl)-N-(2-methylpropyl)-1-phenyl-N-[(3S)-piperidin-3-yl]-1H-1,2,3-triazole-4-carboxamide hydrochloride

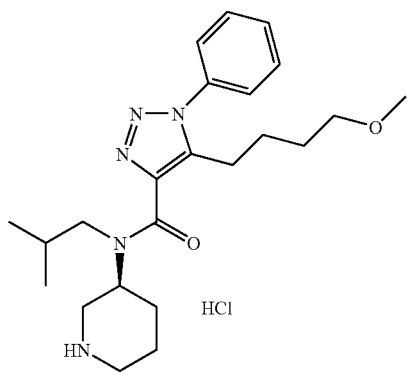 [SMILES: COCCCCc1c(C(=O)N(CC(C)C)[C@H]2CCCNC2)nnn1-c1ccccc1 ; Cl]

MS (ESI+, m/e) 414 (M+1)

In the same manner as in Reference Examples 360 and 361, the following compounds (Reference Examples 429-430) were obtained.

Reference Example 429

1-(2,3-dihydro-1H-inden-5-yl)-5-(4-methoxybutyl)-1H-1,2,3-triazole-4-carboxylic acid

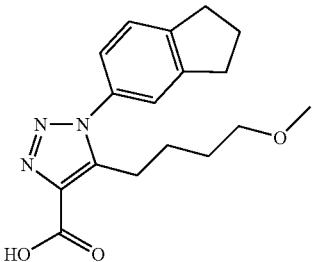 [SMILES: COCCCCc1c(C(=O)O)nnn1-c1ccc2c(c1)CCC2]

MS (ESI+, m/e) 316 (M+1)

Reference Example 430

1-(4-fluoro-3-methylphenyl)-5-(4-methoxybutyl)-1H-1,2,3-triazole-4-carboxylic acid

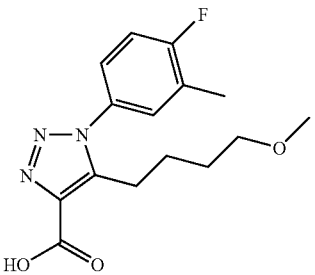 [SMILES: COCCCCc1c(C(=O)O)nnn1-c1ccc(F)c(C)c1]

MS (ESI+, m/e) 308 (M+1)

In the same manner as in Reference Example 163, the following compounds (Reference Examples 431-432) were obtained.

Reference Example 431

1-tert-butyl 3-methyl (3R,5S)-5-[{[1-(2,3-dihydro-1H-inden-5-yl)-5-(4-methoxybutyl)-1H-1,2,3-triazol-4-yl]carbonyl}(2-methylpropyl)amino]piperidine-1,3-dicarboxylate

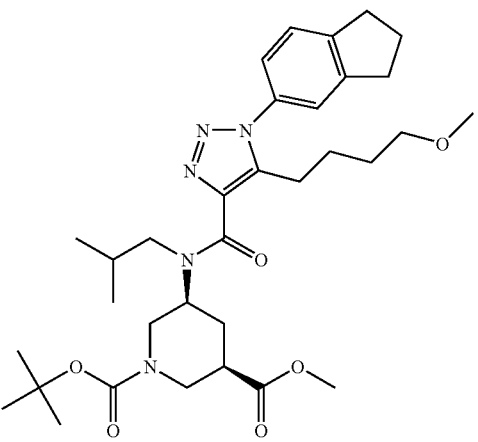 [SMILES: COCCCCc1c(C(=O)N(CC(C)C)[C@H]2C[C@@H](C(=O)OC)CN(C(=O)OC(C)(C)C)C2)nnn1-c1ccc2c(c1)CCC2]

MS (ESI+, m/e) 612 (M+1)

Reference Example 432

1-tert-butyl 3-methyl (3R,5S)-5-[{[1-(4-fluoro-3-methylphenyl)-5-(4-methoxybutyl)-1H-1,2,3-triazol-4-yl]carbonyl}(2-methylpropyl)amino]piperidine-1,3-dicarboxylate

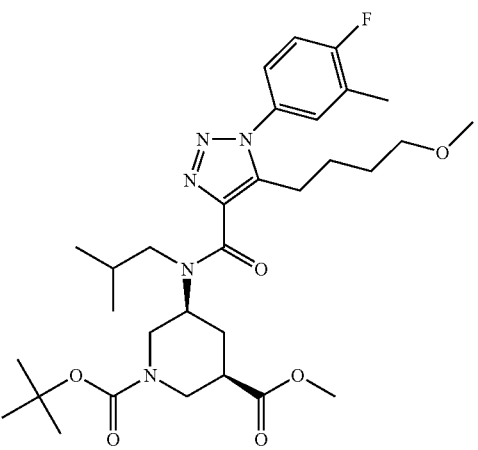 [SMILES: COCCCCc1c(C(=O)N(CC(C)C)[C@H]2C[C@@H](C(=O)OC)CN(C(=O)OC(C)(C)C)C2)nnn1-c1ccc(F)c(C)c1]

MS (ESI+, m/e) 604 (M+1)

In the same manner as in Reference Example 74, the following compounds (Reference Examples 433-434) were obtained.

Reference Example 433

(3R,5S)-1-(tert-butoxycarbonyl)-5-[{[1-(2,3-dihydro-1H-inden-5-yl)-5-(4-methoxybutyl)-1H-1,2,3-triazol-4-yl]carbonyl}(2-methylpropyl)amino]piperidine-3-carboxylic acid

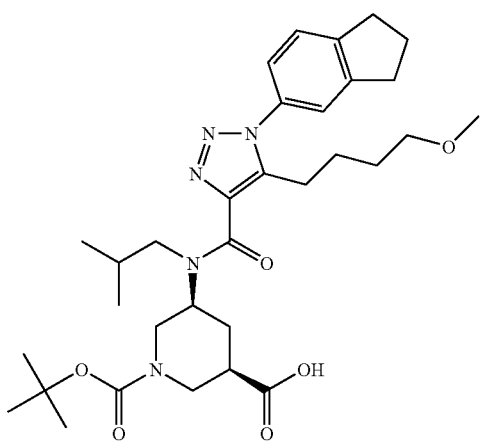 [SMILES: COCCCCc1c(C(=O)N(CC(C)C)[C@H]2C[C@@H](C(=O)O)CN(C(=O)OC(C)(C)C)C2)nnn1-c1ccc2c(c1)CCC2]

MS (ESI+, m/e) 598 (M+1)

Reference Example 434

(3R,5S)-1-(tert-butoxycarbonyl)-5-[{[1-(4-fluoro-3-methylphenyl)-5-(4-methoxybutyl)-1H-1,2,3-triazol-4-yl]carbonyl}(2-methylpropyl)amino]piperidine-3-carboxylic acid

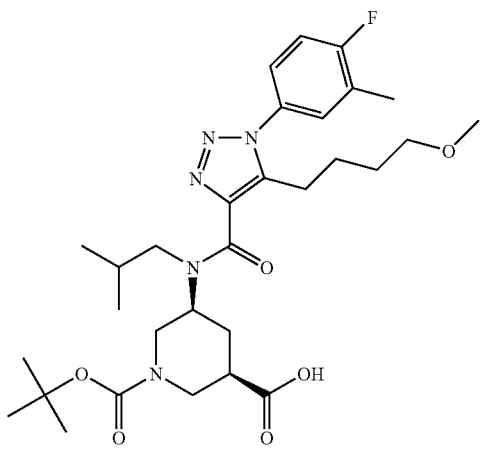 [SMILES: COCCCCc1c(C(=O)N(CC(C)C)[C@H]2C[C@@H](C(=O)O)CN(C(=O)OC(C)(C)C)C2)nnn1-c1ccc(F)c(C)c1]

MS (ESI+, m/e) 590 (M+1)

In the same manner as in Reference Example 385, the following compounds (Reference Examples 435-436) were obtained.

Reference Example 435 tert-butyl (3S,5R)-3-[{[1-(2,3-dihydro-1H-inden-5-yl)-5-(4-methoxybutyl)-1H-1,2,3-triazol-4-yl]carbonyl}(2-methylpropyl)amino]-5-(morpholin-4-ylcarbonyl)piperidine-1-carboxylate

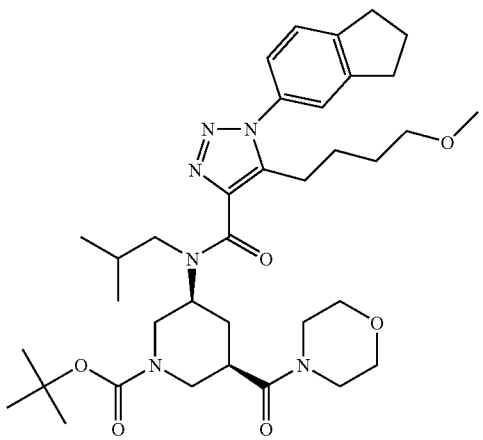 [SMILES: COCCCCc1c(C(=O)N(CC(C)C)[C@H]2C[C@@H](C(=O)N3CCOCC3)CN(C(=O)OC(C)(C)C)C2)nnn1-c1ccc2c(c1)CCC2]

MS (ESI+, m/e) 667 (M+1)

Reference Example 436 tert-butyl (3S,5R)-3-[{[1-(4-fluoro-3-methylphenyl)-5-(4-methoxybutyl)-1H-1,2,3-triazol-4-yl]carbonyl}(2-methylpropyl)amino]-5-(morpholin-4-ylcarbonyl)piperidine-1-carboxylate

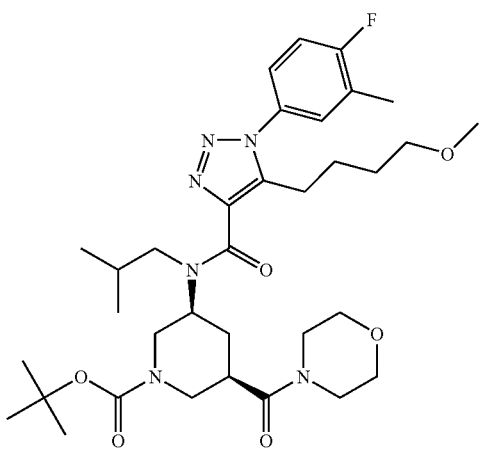 [SMILES: COCCCCc1c(C(=O)N(CC(C)C)[C@H]2C[C@@H](C(=O)N3CCOCC3)CN(C(=O)OC(C)(C)C)C2)nnn1-c1ccc(F)c(C)c1]

MS (ESI+, m/e) 659 (M+1)

In the same manner as in Reference Example 80, the following compounds (Reference Examples 437-438) were obtained.

Reference Example 437 tert-butyl (3R,5S)-3-carbamoyl-5-[{[1-(2,3-dihydro-1H-inden-5-yl)-5-(4-methoxybutyl)-1H-1,2,3-triazol-4-yl]carbonyl}(2-methylpropyl)amino]piperidine-1-carboxylate

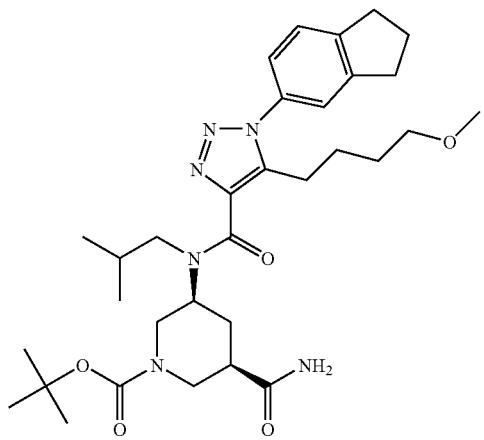

MS (ESI+, m/e) 597 (M+1)

Reference Example 438 tert-butyl (3R,5S)-3-carbamoyl-5-[{[1-(4-fluoro-3-methylphenyl)-5-(4-methoxybutyl)-1H-1,2,3-triazol-4-yl]carbonyl}(2-methylpropyl)amino]piperidine-1-carboxylate

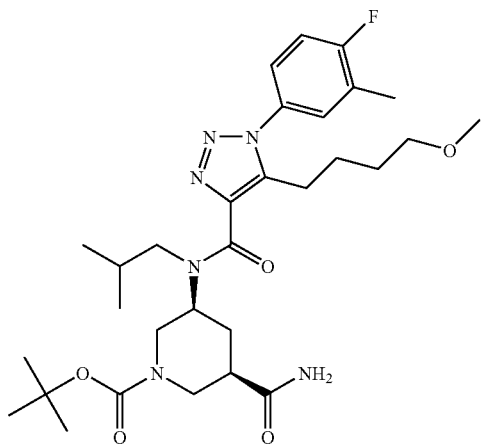 [SMILES: COCCCCc1c(C(=O)N(CC(C)C)[C@H]2C[C@@H](C(N)=O)CN(C(=O)OC(C)(C)C)C2)nnn1-c1ccc(F)c(C)c1]

MS (ESI+, m/e) 589 (M+1)

In the same manner as in Example 60, the following compounds (Examples 243-246) were obtained.

Example 243

1-(2,3-dihydro-1H-inden-5-yl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

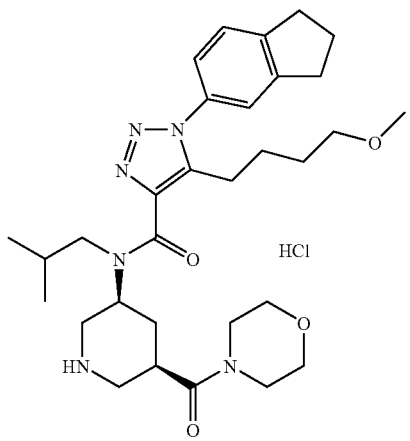 [SMILES: COCCCCc1c(C(=O)N(CC(C)C)[C@@H]2CNC[C@H](C(=O)N3CCOCC3)C2)nnn1-c1ccc2c(c1)CCC2 ; Cl]

MS (ESI+, m/e) 567 (M+1)

Example 244

1-(4-fluoro-3-methylphenyl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

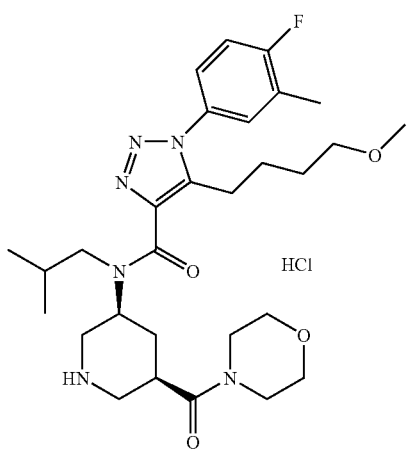 [SMILES: COCCCCc1c(C(=O)N(CC(C)C)[C@@H]2CNC[C@H](C(=O)N3CCOCC3)C2)nnn1-c1ccc(F)c(C)c1 ; Cl]

MS (ESI+, m/e) 559 (M+1)

Example 245

(3R,5S)-5-[{[1-(2,3-dihydro-1H-inden-5-yl)-5-(4-methoxybutyl)-1H-1,2,3-triazol-4-yl]carbonyl}(2-methylpropyl)amino]piperidine-3-carboxamide hydrochloride

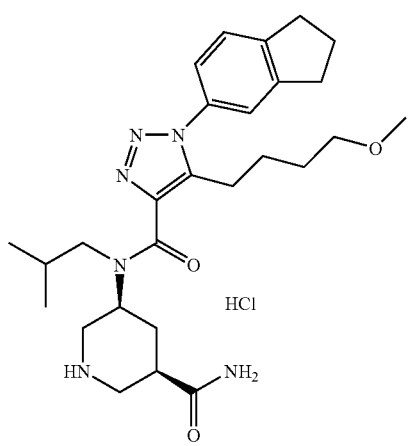 [SMILES: COCCCCc1c(C(=O)N(CC(C)C)[C@@H]2CNC[C@H](C(N)=O)C2)nnn1-c1ccc2c(c1)CCC2 ; Cl]

MS (ESI+, m/e) 497 (M+1)

Example 246

(3R,5S)-5-[{[1-(4-fluoro-3-methylphenyl)-5-(4-methoxybutyl)-1H-1,2,3-triazol-4-yl]carbonyl}(2-methylpropyl)amino]piperidine-3-carboxamide hydrochloride

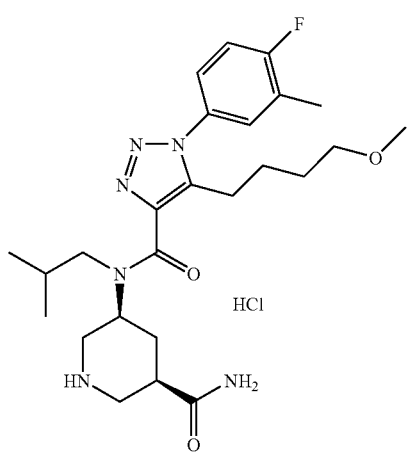 [SMILES: COCCCCc1c(C(=O)N(CC(C)C)[C@@H]2CNC[C@H](C(N)=O)C2)nnn1-c1ccc(F)c(C)c1 ; Cl]

MS (ESI+, m/e) 489 (M+1)

In the same manner as in Reference Examples 360 and 361, the following compound (Reference Example 439) was obtained.

Reference Example 439

1-(2,3-dihydro-1H-inden-4-yl)-5-(4-methoxybutyl)-1H-1,2,3-triazole-4-carboxylic acid

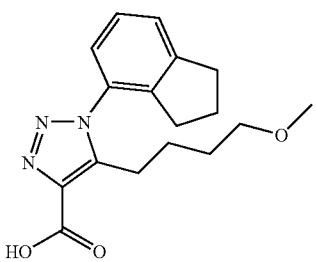 [SMILES: COCCCCc1c(C(=O)O)nnn1-c1cccc2c1CCC2]

MS (ESI+, m/e) 316 (M+1)

In the same manner as in Reference Example 163, the following compound (Reference Example 440) was obtained.

Reference Example 440

1-tert-butyl 3-methyl (3R,5S)-5-[{[1-(2,3-dihydro-1H-inden-4-yl)-5-(4-methoxybutyl)-1H-1,2,3-triazol-4-yl]carbonyl}(2-methylpropyl)amino]piperidine-1,3-dicarboxylate

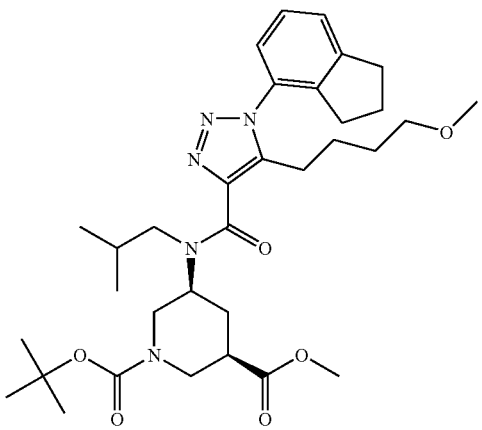 [SMILES: COCCCCc1c(C(=O)N(CC(C)C)[C@H]2C[C@@H](C(=O)OC)CN(C(=O)OC(C)(C)C)C2)nnn1-c1cccc2c1CCC2]

MS (ESI+, m/e) 612 (M+1)

In the same manner as in Reference Example 74, the following compound (Reference Example 441) was obtained.

Reference Example 441

(3R,5S)-1-(tert-butoxycarbonyl)-5-[{[1-(2,3-dihydro-1H-inden-4-yl)-5-(4-methoxybutyl)-1H-1,2,3-triazol-4-yl]carbonyl}(2-methylpropyl)amino]piperidine-3-carboxylic acid

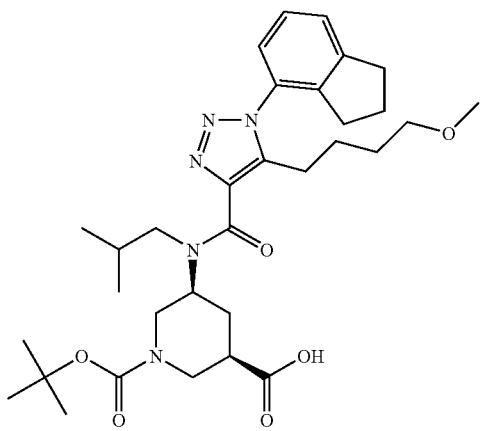 [SMILES: COCCCCc1c(C(=O)N(CC(C)C)[C@H]2C[C@@H](C(=O)O)CN(C(=O)OC(C)(C)C)C2)nnn1-c1cccc2c1CCC2]

MS (ESI+, m/e) 597 (M+1)

In the same manner as in Reference Example 385, the following compound (Reference Example 442) was obtained.

Reference Example 442 tert-butyl (3S,5R)-3-[{[1-(2,3-dihydro-1H-inden-4-yl)-5-(4-methoxybutyl)-1H-1,2,3-triazol-4-yl]carbonyl}(2-methylpropyl)amino]-5-(morpholin-4-ylcarbonyl)piperidine-1-carboxylate

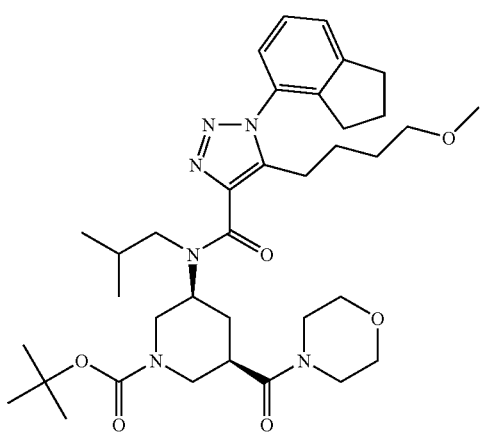 [SMILES: COCCCCc1c(C(=O)N(CC(C)C)[C@H]2C[C@@H](C(=O)N3CCOCC3)CN(C(=O)OC(C)(C)C)C2)nnn1-c1cccc2c1CCC2]

MS (ESI+, m/e) 667 (M+1)

In the same manner as in Example 60, the following compound (Example 247) was obtained.

Example 247

1-(2,3-dihydro-1H-inden-4-yl)-5-(4-methoxybutyl)-N-(2-methylpropyl)-N-[(3S,5R)-5-(morpholin-4-ylcarbonyl)piperidin-3-yl]-1H-1,2,3-triazole-4-carboxamide hydrochloride

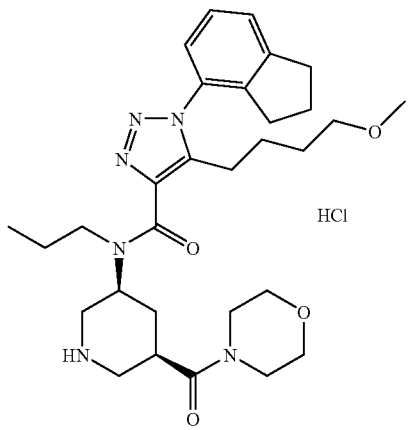 [SMILES: CCCN(C(=O)c1nnn(-c2cccc3c2CCC3)c1CCCCOC)[C@@H]1CNC[C@H](C(=O)N2CCOCC2)C1 ; Cl]

MS (ESI+, m/e) 567 (M+1)

In the same manner as in Reference Example 385, the following compounds (Reference Examples 443-444) were obtained.

Reference Example 443 tert-butyl (3S,5R)-3-[{[5-(4-methoxybutyl)-1-(2-methylphenyl)-1H-1,2,3-triazol-4-yl]carbonyl}(2-methylpropyl)amino]-5-(pyrrolidin-1-ylcarbonyl)piperidine-1-carboxylate

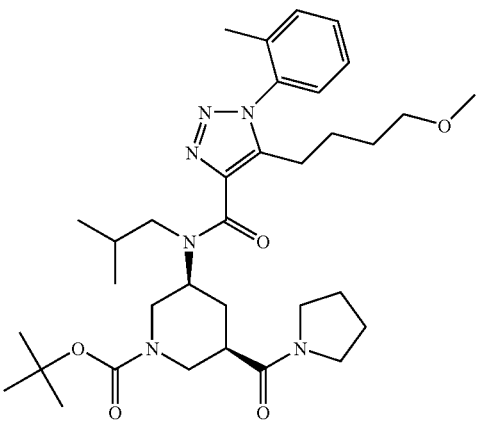 [SMILES: COCCCCc1c(C(=O)N(CC(C)C)[C@H]2C[C@@H](C(=O)N3CCCC3)CN(C(=O)OC(C)(C)C)C2)nnn1-c1ccccc1C]

MS (ESI+, m/e) 625 (M+1)

Reference Example 444 tert-butyl (3S,5R)-3-[{[5-(4-methoxybutyl)-1-(4-methylphenyl)-1H-1,2,3-triazol-4-yl]carbonyl}(2-methylpropyl)amino]-5-(pyrrolidin-1-ylcarbonyl)piperidine-1-carboxylate

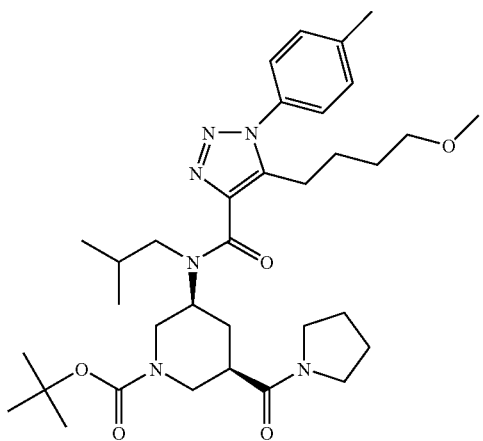 [SMILES: COCCCCc1c(C(=O)N(CC(C)C)[C@H]2C[C@@H](C(=O)N3CCCC3)CN(C(=O)OC(C)(C)C)C2)nnn1-c1ccc(C)cc1]

MS (ESI+, m/e) 625 (M+1)

In the same manner as in Example 60, the following compounds (Examples 248-249) were obtained.

Example 248

5-(4-methoxybutyl)-1-(2-methylphenyl)-N-(2-methylpropyl)-N-[(3S,5R)-5-(pyrrolidin-1-ylcarbonyl)piperidin-3-yl]-1H-1,2,3-triazole-4-carboxamide hydrochloride

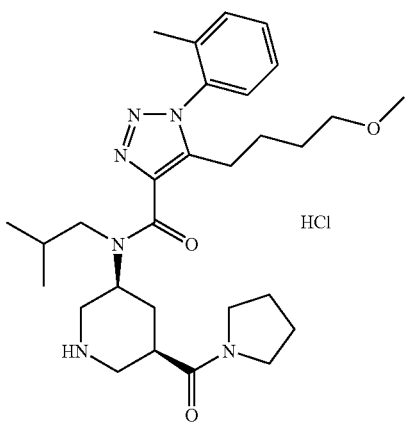 [SMILES: COCCCCc1c(C(=O)N(CC(C)C)[C@@H]2CNC[C@H](C(=O)N3CCCC3)C2)nnn1-c1ccccc1C ; Cl]

MS (ESI+, m/e) 525 (M+1)

Example 249

5-(4-methoxybutyl)-1-(4-methylphenyl)-N-(2-methylpropyl)-N-[(3S,5R)-5-(pyrrolidin-1-ylcarbonyl)piperidin-3-yl]-1H-1,2,3-triazole-4-carboxamide hydrochloride

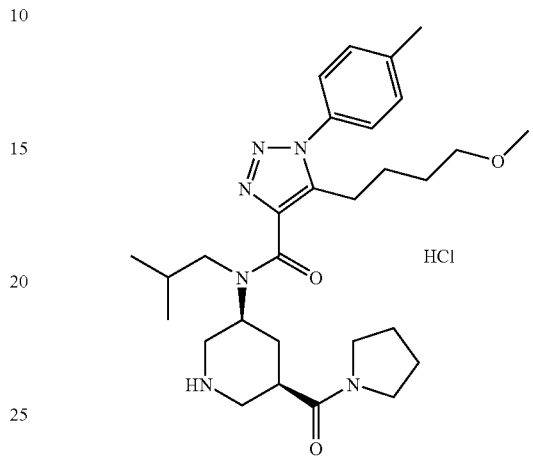

MS (ESI+, m/e) 525 (M+1)

Reference Example 445 ethyl [(4-methoxybutyl)amino](thioxo)acetate

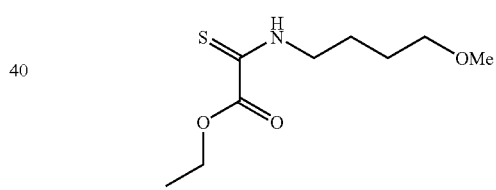

To a solution of 4-methoxybutane-1-amine hydrochloride (1.40 g) and triethylamine (4.18 ml) in DMA (100 ml) was added dropwise ethyl chloroglyoxylate (1.12 ml) at 0° C. The reaction mixture was stirred at room temperature for 2 hr. Water was added to the reaction mixture, and the mixture was extracted with ethyl acetate. The extract was washed successively with 1M hydrochloric acid, aqueous sodium bicarbonate and saturated brine, and dried over anhydrous sodium sulfate. The solvent was evaporated under reduced pressure. The residue was dissolved in toluene (100 ml), Lawesson's reagent (6.07 g) was added, and the mixture was stirred at 90° C. for 2 hr. The reaction mixture was cooled to room temperature, aqueous sodium bicarbonate was added, and the mixture was stirred for 30 min and extracted with ethyl acetate. The extract was washed with saturated brine, dried over anhydrous sodium sulfate, and subjected to basic silica gel column chromatography. The fraction eluted with ethyl acetate was concentrated under reduced pressure to give the object product (1.2 g).

MS (ESI+, m/e) 220 (M+1)

Reference Example 446 butyl 4-(4-methoxybutyl)-5-phenyl-4H-1,2,4-triazole-3-carboxylate

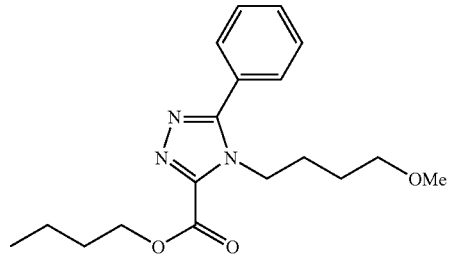 [SMILES: CCCCOC(=O)c1nnc(-c2ccccc2)n1CCCCOC]

Ethyl [(4-methoxybutyl)amino](thioxo)acetate (1.2 g) and benzohydrazide (745 mg) were dissolved in 1-butanol (10 ml), and the mixture was stirred at 140° C. for 15 hr. The reaction mixture was cooled to room temperature, 10% aqueous citric acid solution was added, and the mixture was extracted with ethyl acetate. The extract was washed with saturated brine, and dried over anhydrous sodium sulfate. The solvent was evaporated under reduced pressure. The residue was subjected to silica gel column chromatography, and a fraction eluted with ethyl acetate-hexane (8:2) was concentrated under reduced pressure to give the object product (80 mg).

MS (ESI+, m/e) 332 (M+1)

In the same manner as in the method shown in Reference Example 54, the following compound (Reference Example 447) was obtained.

Reference Example 447 tert-butyl (3S,5R)-3-[{[4-(4-methoxybutyl)-5-phenyl-4H-1,2,4-triazol-3-yl]carbonyl}(2-methylpropyl)amino]-5-(morpholin-4-ylcarbonyl)piperidine-1-carboxylate

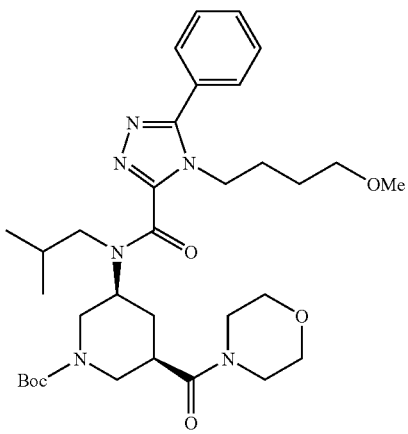 [SMILES: COCCCCn1c(C(=O)N(CC(C)C)[C@H]2C[C@@H](C(=O)N3CCOCC3)CN(C(=O)OC(C)(C)C)C2)nnc1-c1ccccc1]

MS (ESI+, m/e) 627 (M+1)

In the same manner as in the method shown in Example 11, the following compound (Example 250) was obtained.

Example 250

4-(4-methoxybutyl)-N-(2-methylpropyl)-N-[(3S,5R)-5-(morpholin-4-ylcarbonyl)piperidin-3-yl]-5-phenyl-4H-1,2,4-triazole-3-carboxamide hydrochloride

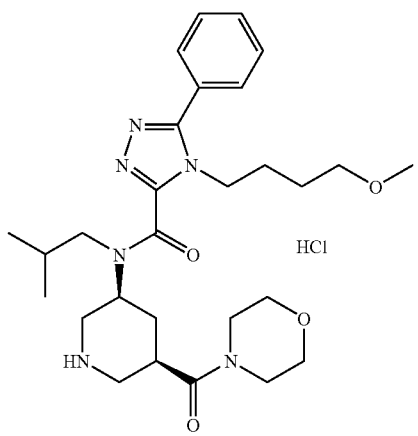 [SMILES: COCCCCn1c(C(=O)N(CC(C)C)[C@@H]2CNC[C@H](C(=O)N3CCOCC3)C2)nnc1-c1ccccc1 ; Cl]

MS (ESI+, m/e) 527 (M+1)

In the same manner as in Example 121, the following compound (Example 251) was obtained.

Example 251

N-(2-methylpropyl)-N-[(3S,5R)-5-(morpholin-4-ylcarbonyl)piperidin-3-yl]-1-phenyl-5-propyl-1H-pyrazole-4-carboxamide trifluoroacetate

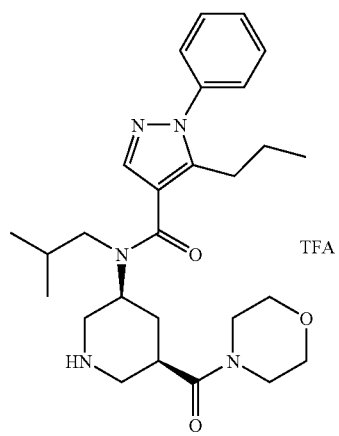 [SMILES: "TFA" ; CCCc1c(C(=O)N(CC(C)C)[C@@H]2CNC[C@H](C(=O)N3CCOCC3)C2)cnn1-c1ccccc1]

MS (ESI+): 482 (M+H)

Example 252

1-(4-methoxybutyl)-N-(2-methylpropyl)-N-[(3S,5R)-5-(morpholin-4-ylcarbonyl)piperidin-3-yl]-1H-benzimidazole-2-carboxamide methanesulfonate

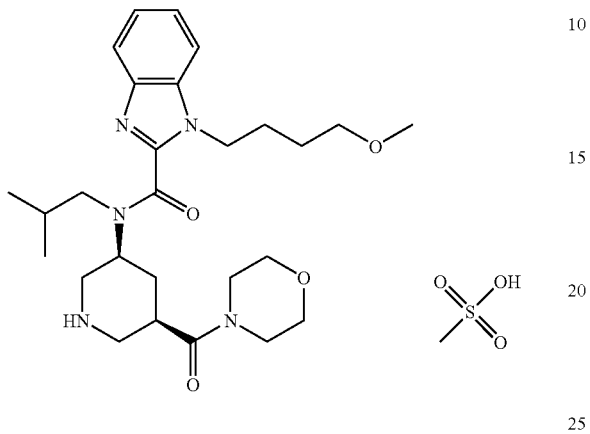

1-(4-Methoxybutyl)-N-(2-methylpropyl)-N-[(3S,5R)-5-(morpholin-4-ylcarbonyl)piperidin-3-yl]-1H-benzimidazole-2-carboxamide (208 mg) was dissolved in ethyl acetate (2 ml), a solution of methanesulfonic acid (40 µl) in ethyl acetate (1 ml) was added at 75° C., hexane (1 ml) was added, and the mixture was heated under reflux and stood at room temperature overnight. The precipitated crystals were collected by filtration, and dried at 70° C. for 3 hr to give the object product (158 mg).

MS (ESI+, m/e) 500 (M+1)

melting point: 144.4° C.

In the same manner as in Reference Example 22, the compound of Reference Example 448 was obtained.

Reference Example 448 tert-butyl (3S,5R)-3-[(cyclopropylmethyl)amino]-5-(morpholin-4-ylcarbonyl)piperidine-1-carboxylate

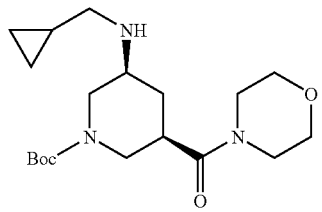 [SMILES: CC(C)(C)OC(=O)N1C[C@@H](NCC2CC2)C[C@@H](C(=O)N2CCOCC2)C1]

MS (ESI+, m/e) 368 (M+1)

In the same manner as in Reference Example 64, the compound of Reference Example 449 was obtained.

Reference Example 449 tert-butyl (3S,5R)-3-[(1H-benzimidazol-2-ylcarbonyl)(cyclopropylmethyl)amino]-5-(morpholin-4-ylcarbonyl)piperidine-1-carboxylate

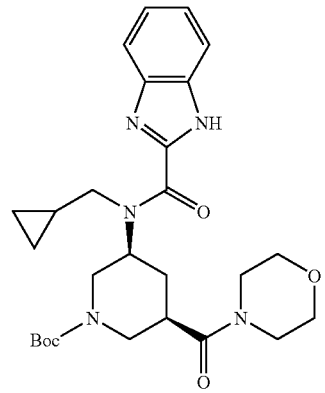 [SMILES: CC(C)(C)OC(=O)N1C[C@H](C(=O)N2CCOCC2)C[C@H](N(CC2CC2)C(=O)c2nc3ccccc3[nH]2)C1]

MS (ESI+, m/e) 512 (M+1)

In the same manner as in Reference Example 69, the compounds of Reference Example 450 and Reference Example 451 were obtained.

Reference Example 450 tert-butyl (3S,5R)-3-[(cyclopropylmethyl){[1-(4-methoxybutyl)-1H-benzimidazol-2-yl]carbonyl}amino]-5-(morpholin-4-ylcarbonyl)piperidine-1-carboxylate

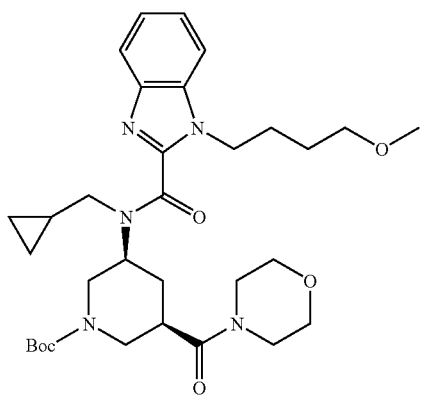 [SMILES: COCCCCn1c(C(=O)N(CC2CC2)[C@H]2C[C@@H](C(=O)N3CCOCC3)CN(C(=O)OC(C)(C)C)C2)nc2ccccc21]

MS (ESI+, m/e) 598 (M+1)

Reference Example 451 tert-butyl (3S,5R)-3-[(cyclopropylmethyl){[1-(3-methoxypropyl)-1H-benzimidazol-2-yl]carbonyl}amino]-5-(morpholin-4-ylcarbonyl)piperidine-1-carboxylate

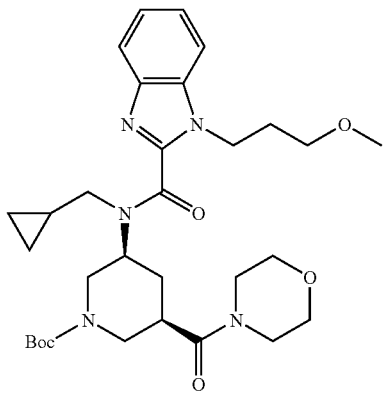 [SMILES: COCCCn1c(C(=O)N(CC2CC2)[C@H]2C[C@@H](C(=O)N3CCOCC3)CN(C(=O)OC(C)(C)C)C2)nc2ccccc21]

MS (ESI+, m/e) 584 (M+1)

In the same manner as in Example 12, the compounds of Example 253 and Example 254 were obtained.

Example 253

N-(cyclopropylmethyl)-1-(4-methoxybutyl)-N-[(3S,5R)-5-(morpholin-4-ylcarbonyl)piperidin-3-yl]-1H-benzimidazole-2-carboxamide dihydrochloride

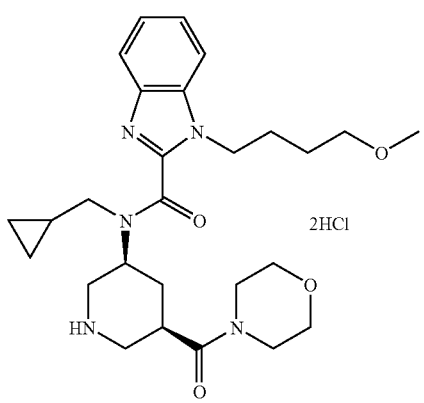 [SMILES: COCCCCn1c(C(=O)N(CC2CC2)[C@@H]2CNC[C@H](C(=O)N3CCOCC3)C2)nc2ccccc21 ; "2HCl"]

MS (ESI+, m/e) 498 (M+1)

Example 254

N-(cyclopropylmethyl)-1-(3-methoxypropyl)-N-[(3S,5R)-5-(morpholin-4-ylcarbonyl)piperidin-3-yl]-1H-benzimidazole-2-carboxamide dihydrochloride

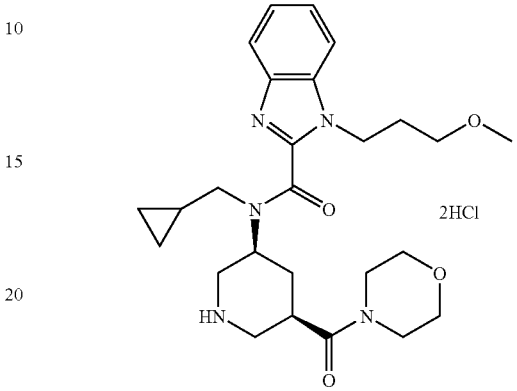

MS (ESI+, m/e) 484 (M+1)

Reference Example 452 tert-butyl (3S,5R)-3-amino-5-(morpholin-4-ylcarbonyl)piperidine-1-carboxylate

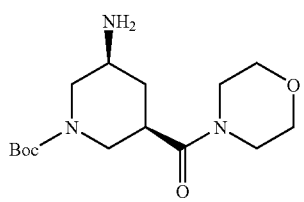 [SMILES: CC(C)(C)OC(=O)N1C[C@@H](N)C[C@@H](C(=O)N2CCOCC2)C1]

tert-Butyl (3S,5R)-3-{[(benzyloxy)carbonyl]amino}-5-(morpholin-4-ylcarbonyl)piperidine-1-carboxylate (39 g) and palladium(II) hydroxide-carbon (4 g) were suspended in methanol (500 ml) and the mixture was stirred under a hydrogen atmosphere (1 atom) at room temperature for 15 hr. The palladium catalyst was filtered off, and the filtrate was concentrated under reduced pressure to give tert-butyl (3S,5R)-3-amino-5-(morpholin-4-ylcarbonyl)piperidine-1-carboxylate (28 g).

$^1$H-NMR (CDCl$_3$) δ 1.41-1.52 (9H, m), 1.53-1.66 (3H, m), 2.03 (1H, d), 2.36 (1H, d), 2.59-2.83 (3H, m), 3.45-3.76 (8H, m), 3.97-4.30 (2H, m).

MS (ESI+, m/e) 314 (M+1)

Reference Example 453 tert-butyl (3R,5S)-3-(morpholin-4-ylcarbonyl)-5-{[(2-nitrophenyl)sulfonyl]amino}piperidine-1-carboxylate

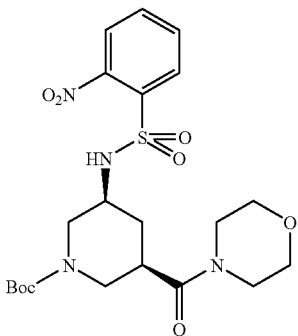 [SMILES: CC(C)(C)OC(=O)N1C[C@@H](NS(=O)(=O)c2ccccc2[N+](=O)[O-])C[C@@H](C(=O)N2CCOCC2)C1]

tert-Butyl (3S,5R)-3-amino-5-(morpholin-4-ylcarbonyl)piperidine-1-carboxylate (3.13 g) and triethylamine (2.1 ml) were dissolved in THF (30 ml), 2-nitrobenzenesulfonyl chloride (2.44 g) was added at room temperature, and the mixture was stirred at room temperature for 15 hr. Water was added to the reaction mixture, and the mixture was extracted with ethyl acetate. The extract was washed with saturated brine, and dried over anhydrous sodium sulfate. The solvent was evaporated under reduced pressure to give the object product (4.68 g).

$^1$H-NMR (CDCl$_3$) δ 1.43 (9H, s), 1.80-2.14 (2H, m), 2.55-2.98 (3H, m), 3.36-3.77 (9H, m), 3.89-4.18 (2H, m), 6.16 (1H, br. s.), 7.70-7.79 (2H, m), 7.81-7.89 (1H, m), 8.13-8.21 (1H, m).

MS (ESI+, m/e) 499 (M+1)

Reference Example 454 tert-butyl (3R,5S)-3-(morpholin-4-ylcarbonyl)-5-{[(2-nitrophenyl)sulfonyl](propyl)amino}piperidine-1-carboxylate

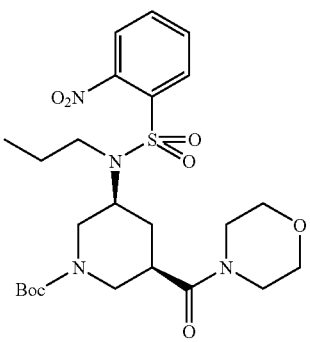 [SMILES: CCCN([C@H]1C[C@@H](C(=O)N2CCOCC2)CN(C(=O)OC(C)(C)C)C1)S(=O)(=O)c1ccccc1[N+](=O)[O-]]

tert-Butyl (3R,5S)-3-(morpholin-4-ylcarbonyl)-5-{[(2-nitrophenyl)sulfonyl]amino}piperidine-1-carboxylate (4.68 g) was dissolved in DMA (20 ml), cesium carbonate (9.18 g) and 1-iodopropane (1.83 ml) were added, and the mixture was stirred at 60° C. for 4 hr. The reaction mixture was diluted with water, and extracted with ethyl acetate. The extract was washed with saturated brine, dried over anhydrous magnesium sulfate and concentrated under reduced pressure. The residue was subjected to silica gel column chromatography, and a fraction eluted with ethyl acetate-hexane (3:7-10:0) was concentrated under reduced pressure to give the object product (4.02 g).

$^1$H-NMR (CDCl$_3$) δ 0.87 (3H, t), 1.45 (9H, s), 1.49-1.73 (1H, m), 1.85-2.03 (2H, m), 2.61-2.90 (3H, m), 3.19 (2H, t), 3.47-3.74 (9H, m), 3.79-3.95 (1H, m), 4.04-4.23 (2H, m), 7.58-7.66 (1H, m), 7.66-7.75 (2H, m), 8.02-8.10 (1H, m).

MS (ESI+, m/e) 541 (M+1)

Reference Example 455 tert-butyl (3R,5S)-3-(morpholin-4-ylcarbonyl)-5-(propylamino)piperidine-1-carboxylate

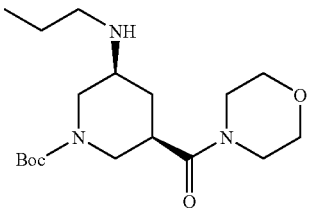 [SMILES: CCCN[C@H]1C[C@@H](C(=O)N2CCOCC2)CN(C(=O)OC(C)(C)C)C1]

tert-Butyl (3R,5S)-3-(morpholin-4-ylcarbonyl)-5-{[(2-nitrophenyl)sulfonyl](propyl)amino}piperidine-1-carboxylate (4.02 g) and lithium hydroxide monohydrate (1.56 g) were dissolved in DMF (20 ml), thioglycol acid (1.3 ml) was added at room temperature, and the mixture was stirred for 2 days at room temperature. The reaction mixture was diluted with aqueous sodium bicarbonate, and the mixture was extracted with ethyl acetate. The extract was washed with saturated brine, and dried over anhydrous magnesium sulfate. The solvent was evaporated under reduced pressure. The residue was subjected to basic silica gel column chromatography, and a fraction eluted with ethyl acetate-hexane (1:9-10:0) was concentrated under reduced pressure. The residue was diluted with 10% aqueous citric acid solution, and washed with ethyl acetate. The aqueous layer was neutralized with aqueous sodium bicarbonate and extracted with ethyl acetate. The extract was washed with saturated brine, and dried over anhydrous magnesium sulfate. The solvent was evaporated under reduced pressure to give the object product (1.89 g).

$^1$H-NMR (CDCl$_3$) δ 0.92 (3H, t), 1.36-1.71 (13H, m), 2.05 (1H, d), 2.26-2.95 (6H, m), 3.50-3.75 (8H, m), 3.96-4.46 (2H, m).

MS (ESI+, m/e) 356 (M+1)

Reference Example 456 tert-butyl (3S,5R)-3-[(1H-benzimidazol-2-ylcarbonyl)(propyl)amino]-5-(morpholin-4-ylcarbonyl)piperidine-1-carboxylate

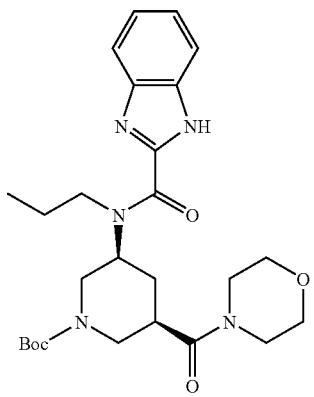 [SMILES: CCCN(C(=O)c1nc2ccccc2[nH]1)[C@H]1C[C@@H](C(=O)N2CCOCC2)CN(C(=O)OC(C)(C)C)C1]

2-(Trichloromethyl)-1H-benzimidazole (1.09 g) and tert-butyl (3R,5S)-3-(morpholin-4-ylcarbonyl)-5-(propylamino)piperidine-1-carboxylate (1.49 g) were dissolved in THF (120 ml), sodium hydrogen carbonate (3.52 g) and water (60 ml) were added and the mixture was stirred at room temperature for 2 hr. The reaction mixture was diluted with aqueous sodium bicarbonate, and extracted with ethyl acetate. The extract was washed with saturated brine, and dried over anhydrous magnesium sulfate. The solvent was evaporated under reduced pressure. The residue was subjected to basic silica gel column chromatography, and a fraction eluted with ethyl acetate-hexane (2:8-10:0) was concentrated under reduced pressure to give the object product (1.97 g).

$^1$H-NMR (CDCl$_3$) δ 0.88-1.06 (3H, m), 1.30-1.54 (9H, m), 1.59-1.91 (3H, m), 1.92-2.48 (2H, m), 2.68-3.21 (3H, m), 3.26-4.00 (9H, m), 4.01-4.56 (3H, m), 7.28-7.45 (2H, m), 7.47-7.61 (1H, m), 7.60-7.89 (1H, m), 10.43-11.17 (1H, m).

MS (ESI+, m/e) 500 (M+1)

Reference Example 457 tert-butyl (3S,5R)-3-[{[1-(4-methoxybutyl)-1H-benzimidazol-2-yl]carbonyl}(propyl)amino]-5-(morpholin-4-ylcarbonyl)piperidine-1-carboxylate

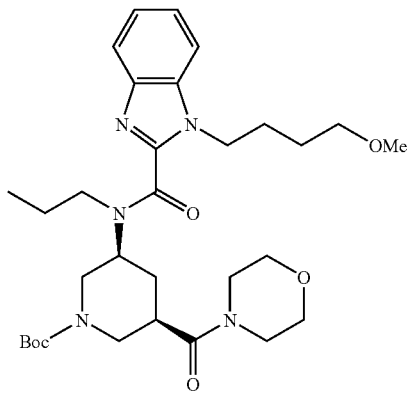 [SMILES: CCCN(C(=O)c1nc2ccccc2n1CCCCOC)[C@H]1C[C@@H](C(=O)N2CCOCC2)CN(C(=O)OC(C)(C)C)C1]

tert-Butyl (3S,5R)-3-[(1H-benzimidazol-2-ylcarbonyl)(propyl)amino]-5-(morpholin-4-ylcarbonyl)piperidine-1-carboxylate (1.97 g) and 4-methoxybutyl methanesulfonate (754 mg) were dissolved in DMA (50 ml), cesium carbonate (1.93 g) was added and the mixture was stirred at 60° C. for 15 hr. The reaction mixture was diluted with water, and the mixture was extracted with ethyl acetate. The extract was washed with brine, and dried over anhydrous sodium sulfate. The solvent was evaporated under reduced pressure. The residue was subjected to basic silica gel column chromatography, and a fraction eluted with ethyl acetate-hexane (0:10-5:5) was concentrated under reduced pressure to give the object product (2.19 g).

$^1$H-NMR (CDCl3) δ 0.64-1.08 (3H, m), 1.29-1.53 (9H, m), 1.54-1.72 (3H, m), 1.75-2.40 (5H, m), 2.49-3.21 (5H, m), 3.22-3.90 (14H, m), 4.00-4.52 (4H, m), 7.27-7.40 (2H, m), 7.45 (1H, t), 7.54-7.84 (1H, m).

MS (ESI+, m/e) 586 (M+1)

Example 255

1-(4-methoxybutyl)-N-[(3S,5R)-5-(morpholin-4-ylcarbonyl)piperidin-3-yl]-N-propyl-1H-benzimidazole-2-carboxamide dihydrochloride

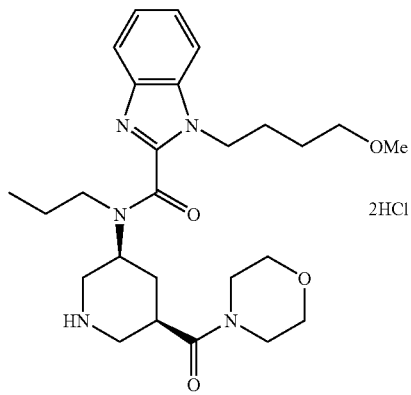 [SMILES: CCCN(C(=O)c1nc2ccccc2n1CCCCOC)[C@@H]1CNC[C@H](C(=O)N2CCOCC2)C1 ; "2HCl"]

tert-Butyl (3S,5R)-3-[{[1-(4-methoxybutyl)-1H-benzimidazol-2-yl]carbonyl}(propyl)amino]-5-(morpholin-4-ylcarbonyl)piperidine-1-carboxylate (2.19 g) was dissolved in 4M hydrogen chloride-ethyl acetate (20 ml), and the mixture was stirred at room temperature for 2 hr. The reaction mixture was concentrated to give the object product (2.09 g).

$^1$H-NMR (DMSO-d$_6$) δ 0.59-1.00 (3H, m), 1.38-1.88 (6H, m), 1.92-2.11 (2H, m), 2.16-2.36 (1H, m), 2.85-3.88 (20H, m), 4.22-4.57 (3H, m), 7.24-7.44 (2H, m), 7.59-7.82 (2H, m), 8.46-9.94 (2H, m).

In the same manner as in Reference Example 22, the compound of Reference Example 458 was obtained.

Reference Example 458 tert-butyl (3S,5R)-3-[(1-methylethyl)amino]-5-(morpholin-4-ylcarbonyl)piperidine-1-carboxylate

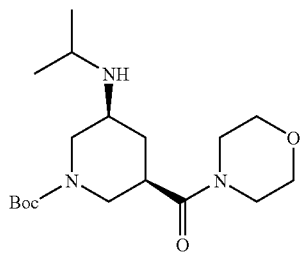 [SMILES: CC(C)N[C@H]1C[C@@H](C(=O)N2CCOCC2)CN(C(=O)OC(C)(C)C)C1]

MS (ESI+, m/e) 356 (M+1)

In the same manner as in Reference Example 379, the compound of Reference Example 459 was obtained.

Reference Example 459 tert-butyl (3S,5R)-3-[{[1-(2-fluorophenyl)-5-(4-methoxybutyl)-1H-1,2,3-triazol-4-yl]carbonyl}(1-methylethyl)amino]-5-(morpholin-4-ylcarbonyl)piperidine-1-carboxylate

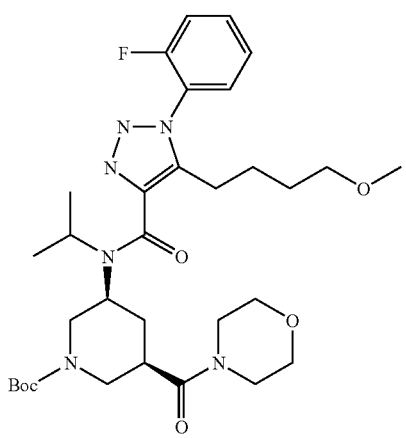 [SMILES: COCCCCC1=C(C(=O)N(C(C)C)[C@H]2C[C@@H](C(=O)N3CCOCC3)CN(C(=O)OC(C)(C)C)C2)NNN1c1ccccc1F]

MS (ESI+, m/e) 631 (M+1)

In the same manner as in Reference Example 219, the compound of Reference Example 460 was obtained.

Reference Example 460 tert-butyl (3S,5R)-3-[(1-methylethyl){[3-(phenoxymethyl)imidazo[1,2-a]pyridin-2-yl]carbonyl}amino]-5-(morpholin-4-ylcarbonyl)piperidine-1-carboxylate

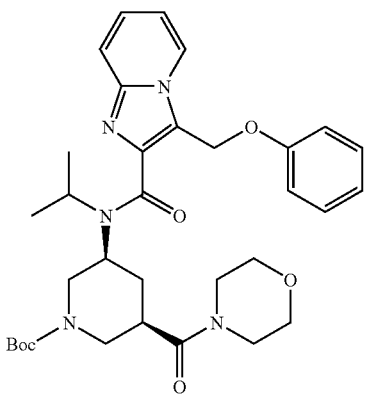 [SMILES: CC(C)N(C(=O)c1nc2ccccn2c1COc1ccccc1)[C@H]1C[C@@H](C(=O)N2CCOCC2)CN(C(=O)OC(C)(C)C)C1]

MS (ESI+, m/e) 606 (M+1)

In the same manner as in Example 101, the compounds of Example 256 and Example 257 were obtained.

Example 256

1-(2-fluorophenyl)-5-(4-methoxybutyl)-N-(1-methylethyl)-N-[(3S,5R)-5-(morpholin-4-ylcarbonyl)piperidin-3-yl]-1H-1,2,3-triazole-4-carboxamide hydrochloride

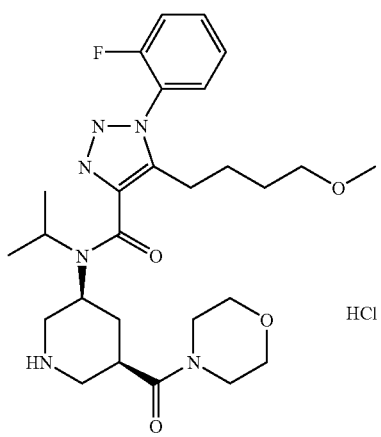 [SMILES: COCCCCC1=C(C(=O)N(C(C)C)[C@@H]2CNC[C@H](C(=O)N3CCOCC3)C2)NNN1c1ccccc1F ; Cl]

MS (ESI+, m/e) 531 (M+1)

Example 257

N-(1-methylethyl)-N-[(3S,5R)-5-(morpholin-4-ylcarbonyl)piperidin-3-yl]-3-(phenoxymethyl)imidazo[1,2-a]pyridine-2-carboxamide dihydrochloride

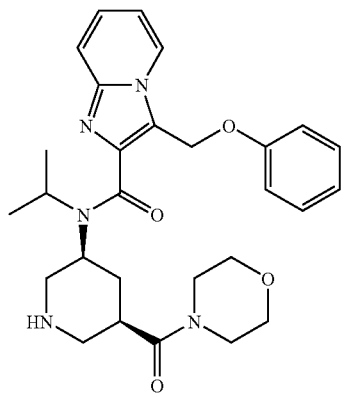 [SMILES: CC(C)N(C(=O)c1nc2ccccn2c1COc1ccccc1)[C@@H]1CNC[C@H](C(=O)N2CCOCC2)C1]

MS (ESI+, m/e) 506 (M+1)

In the same manner as in Reference Example 64, the compound of Reference Example 461 was obtained.

461
Reference Example 461 tert-butyl (3S,5R)-3-[(1H-benzimidazol-2-ylcarbonyl)(1-methylethyl)amino]-5-(morpholin-4-ylcarbonyl)piperidine-1-carboxylate

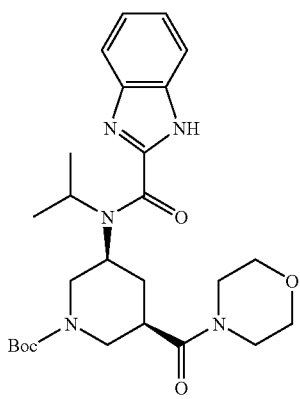 [SMILES: CC(C)N(C(=O)c1nc2ccccc2[nH]1)[C@H]1C[C@@H](C(=O)N2CCOCC2)CN(C(=O)OC(C)(C)C)C1]

MS (ESI+, m/e) 500 (M+1)

In the same manner as in Reference Example 69, the compound of Reference Example 462 was obtained.

Reference Example 462 tert-butyl (3S,5R)-3-[{[1-(4-methoxybutyl)-1H-benzimidazol-2-yl]carbonyl}(1-methylethyl)amino]-5-(morpholin-4-ylcarbonyl)piperidine-1-carboxylate

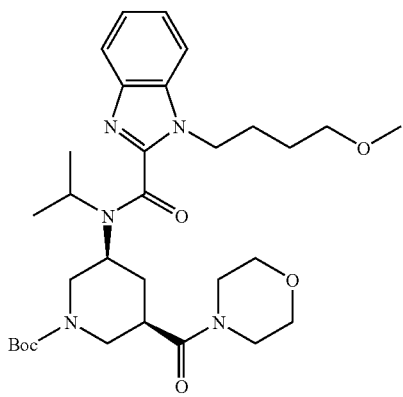 [SMILES: COCCCCn1c(C(=O)N(C(C)C)[C@H]2C[C@@H](C(=O)N3CCOCC3)CN(C(=O)OC(C)(C)C)C2)nc2ccccc21]

MS (ESI+, m/e) 586 (M+1)

In the same manner as in Example 101, the compound of Example 258 was obtained.

462
Example 258

1-(4-methoxybutyl)-N-(1-methylethyl)-N-[(3S,5R)-5-(morpholin-4-ylcarbonyl)piperidin-3-yl]-1H-benzimidazole-2-carboxamide dihydrochloride

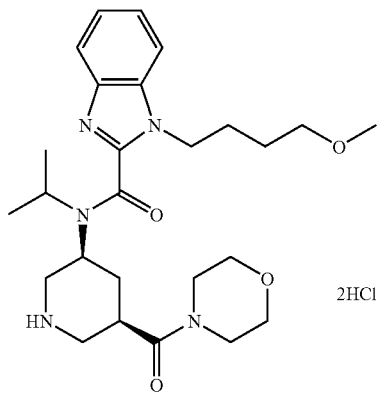 [SMILES: COCCCCn1c(C(=O)N(C(C)C)[C@@H]2CNC[C@H](C(=O)N3CCOCC3)C2)nc2ccccc21 ; "2HCl"]

MS (ESI+, m/e) 486 (M+1)

In the same manner as in Reference Example 379, the compound of Reference Example 463 was obtained.

Reference Example 463 tert-butyl (3S,5R)-3-[{[1-(2-fluorophenyl)-5-(4-methoxybutyl)-1H-1,2,3-triazol-4-yl]carbonyl}(propyl)amino]-5-(morpholin-4-ylcarbonyl)piperidine-1-carboxylate

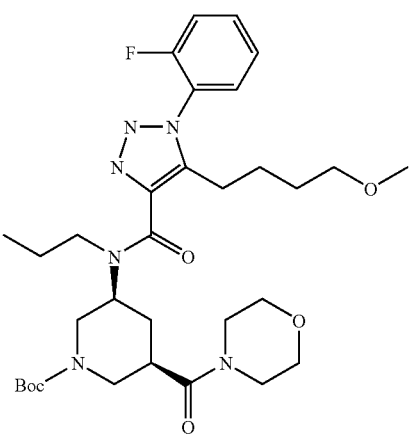 [SMILES: CCCN(C(=O)C1=C(CCCCOC)N(c2ccccc2F)NN1)[C@H]1C[C@@H](C(=O)N2CCOCC2)CN(C(=O)OC(C)(C)C)C1]

MS (ESI+, m/e) 631 (M+1)

In the same manner as in Reference Example 219, the compound of Reference Example 464 was obtained.

463

Reference Example 464 tert-butyl (3R,5S)-3-(morpholin-4-ylcarbonyl)-5-
[{[3-(phenoxymethyl)imidazo[1,2-a]pyridin-2-yl]
carbonyl}(propyl)amino]piperidine-1-carboxylate

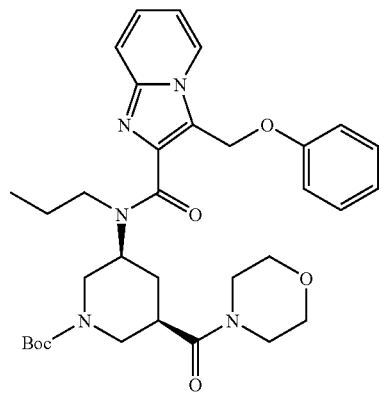 [SMILES: CCCN(C(=O)c1nc2ccccn2c1COc1ccccc1)[C@H]1C[C@@H](C(=O)N2CCOCC2)CN(C(=O)OC(C)(C)C)C1]

MS (ESI+, m/e) 606 (M+1)

In the same manner as in Example 101, the compounds of
Example 259 and Example 260 were obtained.

Example 259

1-(2-fluorophenyl)-5-(4-methoxybutyl)-N-[(3S,5R)-
5-(morpholin-4-ylcarbonyl)piperidin-3-yl]-N-propyl-
1H-1,2,3-triazole-4-carboxamide hydrochloride

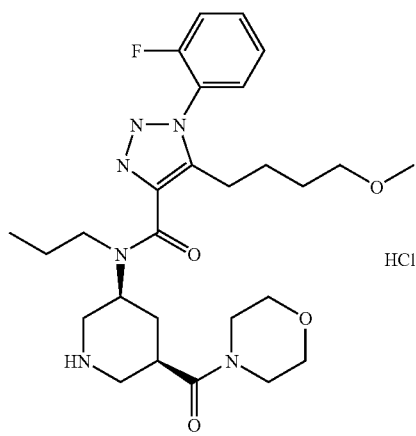 [SMILES: CCCN(C(=O)C1=C(CCCCOC)N(c2ccccc2F)NN1)[C@@H]1CNC[C@H](C(=O)N2CCOCC2)C1 ; Cl]

MS (ESI+, m/e) 531 (M+1)

464

Example 260

N-[(3S,5R)-5-(morpholin-4-ylcarbonyl)piperidin-3-
yl]-3-(phenoxymethyl)-N-propylimidazo[1,2-a]pyri-
dine-2-carboxamide dihydrochloride

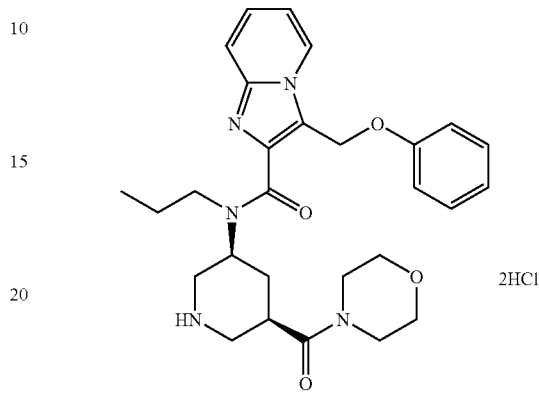

MS (ESI+, m/e) 506 (M+1)

In the same manner as in Reference Example 64, the compound of Reference Example 465 was obtained.

Reference Example 465 tert-butyl (3S,5R)-3-[(1H-benzimidazol-2-ylcarbo-
nyl)amino]-5-(morpholin-4-ylcarbonyl)piperidine-1-
carboxylate

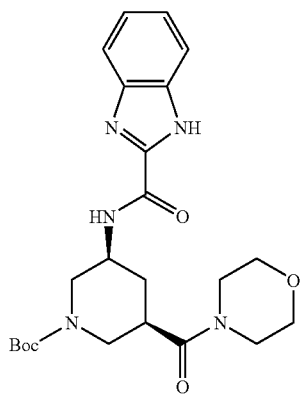

MS (ESI+, m/e) 458 (M+1)

In the same manner as in Reference Example 69, the compound of Reference Example 466 was obtained.

Reference Example 466 tert-butyl (3S,5R)-3-({[1-(4-methoxybutyl)-1H-benzimidazol-2-yl]carbonyl}amino)-5-(morpholin-4-ylcarbonyl)piperidine-1-carboxylate

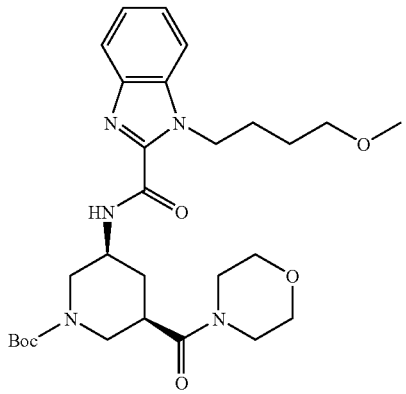 [SMILES: COCCCCn1c(C(=O)N[C@H]2C[C@@H](C(=O)N3CCOCC3)CN(C(=O)OC(C)(C)C)C2)nc2ccccc21]

MS (ESI+, m/e) 544 (M+1)

In the same manner as in Example 101, the compound of Example 261 was obtained.

Example 261

1-(4-methoxybutyl)-N-[(3S,5R)-5-(morpholin-4-ylcarbonyl)piperidin-3-yl]-1H-benzimidazole-2-carboxamide dihydrochloride

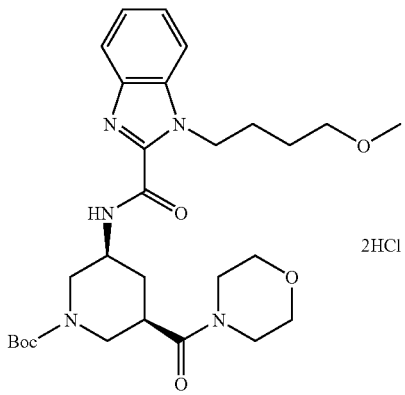 [SMILES: COCCCCn1c(C(=O)N[C@H]2C[C@@H](C(=O)N3CCOCC3)CN(C(=O)OC(C)(C)C)C2)nc2ccccc21 ; "2HCl"]

MS (ESI+, m/e) 444 (M+1)

Reference Example 467 tert-butyl (3S,5R)-3-[{[1-(4-methoxybutyl)-1H-benzimidazol-2-yl]carbonyl}(methyl)amino]-5-(morpholin-4-ylcarbonyl)piperidine-1-carboxylate

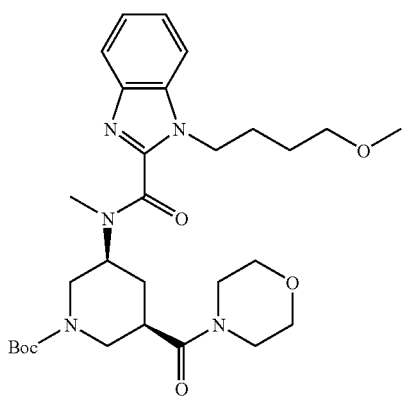 [SMILES: COCCCCn1c(C(=O)N(C)[C@H]2C[C@@H](C(=O)N3CCOCC3)CN(C(=O)OC(C)(C)C)C2)nc2ccccc21]

tert-Butyl (3S,5R)-3-({[1-(4-methoxybutyl)-1H-benzimidazol-2-yl]carbonyl}amino)-5-(morpholin-4-ylcarbonyl)piperidine-1-carboxylate (290 mg) was dissolved in DMF (5 ml), sodium hydride (60% in oil) (880 mg) was added, and the mixture was stirred at room temperature for 1 hr. Methyl iodide (98 μl) was added and the mixture was stirred at room temperature for 3 days. The reaction mixture was diluted with aqueous sodium bicarbonate, and the mixture was extracted with ethyl acetate. The extract was washed with saturated brine, and dried over anhydrous magnesium sulfate. The solvent was evaporated under reduced pressure. The residue was subjected to basic silica gel column chromatography, and a fraction eluted with ethyl acetate-hexane (1:9-7:3) was concentrated under reduced pressure to give the object product (225 mg).

MS (ESI+, m/e) 558 (M+1)

In the same manner as in Reference Example 467, the compound of Reference Example 468 was obtained.

Reference Example 468 tert-butyl (3S,5R)-3-(ethyl{[1-(4-methoxybutyl)-1H-benzimidazol-2-yl]carbonyl}amino)-5-(morpholin-4-ylcarbonyl)piperidine-1-carboxylate

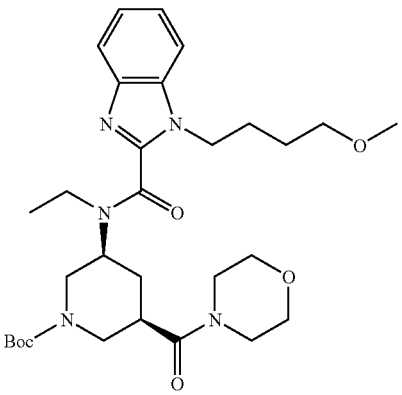 [SMILES: CCN(C(=O)c1nc2ccccc2n1CCCCOC)[C@H]1C[C@@H](C(=O)N2CCOCC2)CN(C(=O)OC(C)(C)C)C1]

MS (ESI+, m/e) 572 (M+1)

In the same manner as in Example 12, the compounds of Example 262 and Example 263 were obtained.

Example 262

1-(4-methoxybutyl)-N-methyl-N-[(3S,5R)-5-(morpholin-4-ylcarbonyl)piperidin-3-yl]-1H-benzimidazole-2-carboxamide dihydrochloride

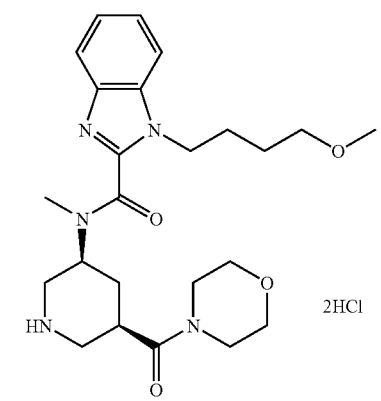 [SMILES: COCCCCn1c(C(=O)N(C)[C@@H]2CNC[C@H](C(=O)N3CCOCC3)C2)nc2ccccc21 ; "2HCl"]

MS (ESI+, m/e) 458 (M+1)

Example 263

N-ethyl-1-(4-methoxybutyl)-N-[(3S,5R)-5-(morpholin-4-ylcarbonyl)piperidin-3-yl]-1H-benzimidazole-2-carboxamide dihydrochloride

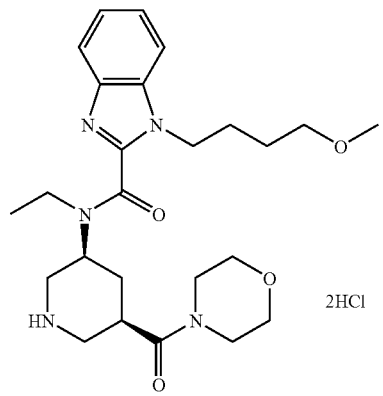 [SMILES: CCN(C(=O)c1nc2ccccc2n1CCCCOC)[C@@H]1CNC[C@H](C(=O)N2CCOCC2)C1 ; "2HCl"]

MS (ESI+, m/e) 472 (M+1)

Example 264

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride

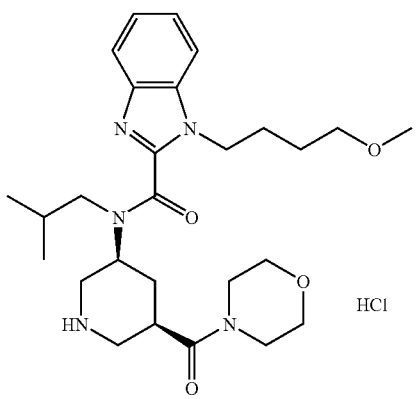 [SMILES: COCCCCn1c(C(=O)N(CC(C)C)[C@@H]2CNC[C@H](C(=O)N3CCOCC3)C2)nc2ccccc21 ; Cl]

1-(4-Methoxybutyl)-N-(2-methylpropyl)-N-[(3S,5R)-5-(morpholin-4-ylcarbonyl)piperidin-3-yl]-1H-benzimidazole-2-carboxamide (24.4 g) was dissolved in ethyl acetate (225 ml), and the mixture was heated to 45-55° C. 4M Hydrogen chloride-ethyl acetate (12.8 ml) was added dropwise, and the precipitate was dissolved at the same temperature. After confirmation of dissolution, heptane (75 ml) was added dropwise, and the mixture was cooled to 25-35° C. The seed crystal (45 mg) was added and the mixture was stirred for 30 min. The mixture was heated to 50-55° C., and heptane (150 ml) was added dropwise. The mixture was stirred at the same temperature for 1 hr, gradually cooled to 0-5° C., and stirred at the same temperature for 1 hr. The precipitated crystals were collected by filtration, washed with ethyl acetate-heptane (90 ml), and dried under reduced pressure at 40-50° C. to give the object product (15.3 g).

Example 265

1-(4-methoxybutyl)-N-(2-methylpropyl)-N-[(3S,5R)-5-(morpholin-4-ylcarbonyl)piperidin-3-yl]-1H-benzimidazole-2-carboxamide hydrochloride

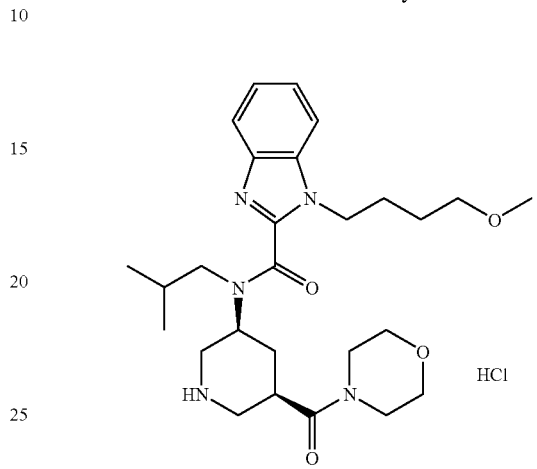

1-(4-Methoxybutyl)-N-(2-methylpropyl)-N-[(3S,5R)-5-(morpholin-4-ylcarbonyl)piperidin-3-yl]-1H-benzimidazole-2-carboxamide hydrochloride (3.0 g) was suspended in 2-propanol-ethyl acetate (25.5 ml), and dissolved by heating to 40-50° C. Heptane (10.5 ml) was added dropwise at the same temperature, and the mixture was cooled to 30-40° C., and seed crystal (3.0 mg) was added. Heptane (7 ml) was added dropwise at the same temperature, and the mixture was heated to 45-50° C. 2-Propanol-ethyl acetate-heptane (12 ml) was added dropwise, heptane (9 ml) was further added dropwise, and the mixture was heated to 50-60° C. and stirred for 1 hr. The mixture was cooled to 5° C. or lower, and stirred at the same temperature for 1 hr. The crystals were collected by filtration, washed with ethyl acetate-heptane (15 ml) cooled to 5° C. or lower, and dried under reduced pressure at 40-50° C. to give the object product (2.6 g).

MS (ESI+, m/e) 500 (M+1)

melting point: 158° C.

Preparation Example 1

| | |
|---|---:|
| (1) compound of Example 1 | 10.0 g |
| (2) Lactose | 70.0 g |
| (3) Corn starch | 50.0 g |
| (4) Soluble starch | 7.0 g |
| (5) Magnesium stearate | 3.0 g |

10.0 g of the compound of Example 1 and 3.0 g of magnesium stearate are granulated with 70 ml of an aqueous solution of soluble starch (7.0 g as soluble starch), then and the mixture is dried and mixed with 70.0 g of lactose and 50.0 g of corn starch (any of lactose, corn starch, soluble starch and magnesium stearate is products in conformity to the 14$^{th}$ revision of the Japanese Pharmacopoeia). The mixture is compressed to give tablets.

Experimental Example 1

Human renin was obtained by expressing preprorenin (1-406) in an animal cell, treating the prorenin (24-406) contained in the culture supernatant with trypsin, and taking the active type (67-406).

(1) Construction of Renin-Expressing Vector

A plasmid DNA to express human renin in HEK293 cells was prepared as follows. PCR was carried out using human renal cDNA (Clontech Laboratories, Inc., Marathon Ready cDNA) as the template and using two synthetic DNAs (5'-AAGCTTATGGATGGATGGAGA-3'; SEQ ID No.1, and 5'-GGATCCTCAGCGGGCCAAGGC-3'; SEQ ID No.2), and the obtained fragments were cloned using a TOPO TA Cloning Kit (Invitrogen Corp.). The obtained fragments were subcloned into pcDNA3.1(+) that had been cleaved by HindIII and BamHI, thus to obtain a plasmid DNA for human preprorenin expression (pcDNA3.1(+)/hREN).

(2) Construction of Angiotensinogen-Expressing Vector

A plasmid DNA to express human angiotensinogen in HEK293 cells was prepared as follows. PCR was carried out using human liver cDNA (Clontech Laboratories, Inc., Marathon Ready cDNA) as the template and using two synthetic DNAs (5'-AAGCTTATGCGGAAGCGAGCAC-CCCAGTCT-3'; SEQ ID No.3, and 5'-GGATCCTCACT-TGTCATCGTCGTCCTTGTAGTCTGCTGT-GCTCAGCGGGTTGGCCACGC-3'; SEQ ID No.4), and the obtained fragments were cloned using a TOPO TA Cloning Kit (Invitrogen Corp.). The obtained fragments were subcloned into pcDNA3.1(+) that had been cleaved by HindIII and BamHI, thereby to give a plasmid DNA for expression of human angiotensinogen having a FLAGtag on the C-terminal (pcDNA3.1(+)/hAngiotensinogen-FLAG). Then, PCR was carried out using the pcDNA3.1(+)/hAngiotensinogen-FLAG as the template and using two synthetic DNAs (5'-CCTTAAGCTTCCACCATGCGGAAGCGAG-CACCCCAGTCT-3'; SEQ ID No.5, and 5'-TTGGATCCTCATGCTGTGCTCAGCGGGT-TGGCCACGCGG-3'; SEQ ID No.6), and the obtained fragments were cloned using a TOPO TA Cloning Kit (Invitrogen Corp.). The obtained fragments were subcloned into pcDNA3.1(+) that had been cleaved by HindIII and BamHI, thus to obtain a plasmid DNA for human angiotensinogen expression (pcDNA3.1(+)/hAngiotensinogen).

(3) Expression of Preprorenin and Purification of Prorenin (24-406)

Expression of human preprorenin was conducted using FreeStyle 293 Expression System (Invitrogen Corp.). According to the manual accompanying the FreeStyle 293 Expression System, the plasmid DNA for human preprorenin expression (pcDNA3.1(+)/hREN) constructed in the above-mentioned (1) was used to conduct transient expression by FreeStyle 293-F cells. After transfection of the plasmid DNA, the cells were subjected to shaking culture under the conditions of 37° C., 8% $CO_2$ and 125 rpm for 3 days. A 600-ml aliquot of the culture medium was centrifuged at 2,000 rpm for 10 min to recover the culture supernatant containing prorenin (24-406). The culture supernatant was concentrated by ultrafiltration using a PM10 membrane (Millipore, Inc.) to a volume of about 50 ml, and then was dialyzed against 20 mM Tris-hydrochloric acid (pH 8.0). The dialyzate was fed to a 6-ml RESOURCE Q column (GE Healthcare) equilibrated with 20 mM Tris-hydrochloric acid (pH 8.0) at a flow rate of 3 ml/min to adsorb the prorenin (24-406). After washing the column with the buffer solution used in the equilibration, elution was carried out by means of a linear concentration gradient of sodium chloride from 0 M to 0.4 M. The fractions containing prorenin (24-406) were collected and concentrated using Vivaspin 20 (molecular weight cut off 10,000; Vivascience, Inc.) to a volume of about 2 ml.

The concentrated liquid was subjected to gel filtration chromatography using HiLoad 16/60 Superdex 200 pg (GE Healthcare) equilibrated with 20 mM Tris-hydrochloric acid (pH 8.0) containing 0.15 M sodium chloride, at a flow rate of 1.4 ml/min, thus to obtain 3.6 mg of purified prorenin (24-406).

(4) Purification of Active Type Renin (67-406)

To 3.6 mg of prorenin (24-406) dissolved in 5.2 ml of 0.1 M Tris-hydrochloric acid (pH 8.0), 12 µg of trypsin (Roche Diagnostics Corp.) was added, and the mixture was allowed to react at 28° C. for 55 min to carry out activation of renin. After the reaction, 0.4 ml of immobilized trypsin inhibitor (Pierce Biotechnology, Inc.) was added to remove the trypsin used in the activation by adsorption. The reaction liquid containing the active type renin was concentrated using Vivaspin 20 (molecular weight cut off 10,000, Vivascience, Inc.), and was diluted with 20 mM Tris-hydrochloric acid (pH 8.0). The diluted liquid was fed to a TSKgel DEAE-5PW column (7.5 mm I.D.×75 mm, Tosoh Corp.) equilibrated with 20 mM Tris-hydrochloric acid (pH 8.0) at a flow rate of 1 ml/min to adsorb the active type renin (67-406). The column was washed with the buffer solution used for the equilibration, and then elution was carried out by means of a sodium chloride linear concentration gradient from 0 M to 0.3 M, thus to obtain 1.5 mg of a purified product of active type renin (67-406).

(5) Purification of Angiotensinogen

Expression of human angiotensinogen was conducted using FreeStyle 293 Expression System (Invitrogen Corp.). According to the manual accompanying the FreeStyle 293 Expression System, the plasmid DNA for human angiotensinogen expression (pcDNA3.1(+)/hAngiotensinogen) constructed in the above-mentioned (2) was used to conduct transient expression by FreeStyle 293-F cells. After transfection of the plasmid DNA, the cells were subjected to shaking culture under the conditions of 37° C., 8% $CO_2$ and 125 rpm for 3 days. A 600-ml aliquot of the culture medium was centrifuged at 2,000 rpm for 10 min to recover the culture supernatant containing angiotensinogen. To the culture supernatant was added ammonium sulfate (30% saturated concentration), and the mixture was thoroughly stirred and centrifuged at 8,000 rpm for 20 min. The obtained supernatant was added to TOYO Pearl butyl 650M (2×5 cm, Tosoh Corporation) equilibrated with 50 mM tris-hydrochloric acid (pH 8.0) containing 30% saturated ammonium sulfate, at a flow rate of 25 ml/min to allow adsorption. After washing with equilibration buffer, angiotensinogen was eluted by linear concentration gradient from the buffer used for equilibration to 20 mM tris-hydrochloric acid (pH 8.0). The eluate containing angiotensinogen was applied to repeated concentration and dilution using Vivaspin 20 (molecular weight cut off 10,000, Vivascience, Inc.), and the buffer was changed to 20 mM tris-hydrochloric acid (pH 8.0). The eluate was fed to a 6-ml RESOURCE Q column (Amersham Biosciences, Inc.) equilibrated with 20 mM Tris-hydrochloric acid (pH 8.0) containing 50 mM sodium chloride at a flow rate of 6 ml/min to adsorb the angiotensinogen. After washing the column with the buffer solution used in the equilibration, elution was carried out by means of a linear concentration gradient of sodium chloride from 50 mM to 400 mM. The fractions containing angiotensinogen were collected and concentrated using Vivaspin 20 (molecular weight cut off 10,000, Vivascience, Inc.) to a volume of about 2 ml. The concentrated liquid was subjected to gel filtration chromatography using HiLoad 26/60 Superdex 200 pg (GE Healthcare) equilibrated with 20 mM Tris-hydrochloric acid (pH 8.0) containing 0.15 M sodium chloride, at a flow rate of 2.0 ml/min, thus to obtain 7.0 mg of purified angiotensinogen.

(6) Measurement of Renin Inhibition Value

As a substrate for renin activity measurement, the angiotensinogen mentioned in (5) above was used. 1 µl each of the test compound (containing 100% DMSO) was added to each well of a 384-well plate (ABgene). Renin was diluted with a buffer solution for reaction (20 mM sodium phosphate (pH 7.4)) to a concentration of 57 pM, and 14 µl each of the dilution was added to each well. The dilution was left to stand at 37° C. for 10 min, and then 5 µl of each of a 6 µM solution of substrate angiotensinogen was added to each well to initiate the reaction. The reaction mixture was left to stand at 37° C. for 30 min, and then 20 µl each of a reaction terminating solution [20 mM Tris-hydrochloric acid (pH 7.4), 150 mM sodium chloride, 0.1% BSA, 0.05% Tween 20 and 1 µM CGP-29287] was added to each well to terminate the reaction, thus an enzyme reaction solution was obtained. The amount of angiotensin I produced by an enzyme reaction was quantified by Enzyme Immuno Assay (EIA) described below.

Anti-angiotensin I antibody (Peninsula Laboratories Inc.) diluted 5,000-fold with PBS was added to each well of a 384 well black plate (Nalge Nunc International Co., Ltd.) by 25 µl, and left standing overnight at 4° C. to immobilize the antibody in the plate. The antibody solution was removed, PBS solution (100 µl) containing 1% BSA was added to each well, and the mixture was left standing at room temperature for 2 hr for blocking. The blocking solution was removed, and each well was washed 5 times with 100 µl of 0.05% Tween20-PBS. An angiotensin I standard solution (Wako Pure Chemical Industries, Ltd.) prepared to 0.156-10 nM with an enzyme reaction solution or buffer [20 mM tris-hydrochloric acid (pH 7.4), 150 mM sodium chloride, 0.1% BSA, 0.05% Tween20] was dispensed to each well by 10 µl. Then, a biotinated angiotensin I solution (AnaSpec, 15 µl) prepared to 1.6 nM with a buffer [20 mM tris-hydrochloric acid (pH 7.4), 150 mM sodium chloride, 0.01% BSA, 0.05% Tween20] was added to each well, mixed with a plate mixer and left standing at room temperature for 1 hr. The solutions were removed from each well, and each well was washed 5 times with 100 µl of 0.05% Tween20-PBS. Horseradish peroxydase Streptavidin (PIERCE Biotechnology inc., 25 µl) diluted to 100 ng/ml with a buffer [20 mM tris-hydrochloric acid (pH 7.4), 150 mM sodium chloride, 0.1% BSA, 0.05% Tween 20] was added to each well and the mixture was left standing at room temperature for 30 min. The solutions were removed from each well, and each well was washed 5 times with 100 µl of 0.05% Tween20-PBS. SuperSignal ELISA femto Maximum Sensitivity Substrate (PIERCE Biotechnology Inc.) was added by 25 µl and luminescence intensity was measured by EnVision (Perkin Elmer Inc.). An analytical curve was drawn from the luminescence intensity of wells containing an angiotensin I standard solution, and the amount of angiotensin I produced by an enzyme reaction was calculated and used as an index of renin activity.

While the reaction rate of the well where 100% DMSO only was added was taken as 0% inhibition rate, and the reaction rate of the well where angiotensin I was not contained was taken as 100% inhibition rate, the renin inhibitory activity of the wells where the test compound (containing 100% DMSO) was added was calculated.

(7) Results

The results measured according to the above-mentioned method (6) are shown in Table 1.

TABLE 1

| Human renin inhibitory activity | |
|---|---|
| Example No. | inhibitory activity (%) at 0.1 µM |
| 3 | 96 |
| 4 | 96 |
| 10 | 97 |
| 12 | 97 |
| 25 | 98 |
| 38 | 98 |
| 40 | 97 |
| 48 | 97 |
| 49 | 97 |
| 73-1 | 96 |
| 73-2 | 96 |
| 74-1 | 94 |
| 74-2 | 96 |
| 75-1 | 95 |
| 75-2 | 90 |
| 85 | 97 |
| 117 | 98 |
| 233 | 97 |
| 235 | 97 |

From the results of Table 1, it is clear that compounds (I) and (II) of the present invention have a superior renin inhibitory activity.

Experimental Example 2

(1) Ex Vivo Renin Inhibitory Activity Test Using *Macaca Fascicularis*

Male *macaca fascicularis* was used. The blood samples were collected from femoral vein at the time points of before drug administration and 4 hr after drug administration (EDTA-2Na$^+$ at final concentration of 7.5 mmol/L was used as an anticoagulant). The collected blood was centrifuged using a cooling centrifuge (centrifuge 5415R: Eppendorf Co., Ltd.) at 4° C., 10000 rpm for 10 min, and the obtained plasma was preserved at −20° C. until a parameter measurement. The drug was dissolved in 0.5% methylcellulose and orally administered at 1 mg/kg. The plasma renin activity (PRA) was measured using RIA kit (renin activity "PRA": SRL Inc.). PRA was calculated by the following formula.

$$PRA_{(ng/mL/h)} = \frac{(X_{37° C.} - X_{4° C.})}{\text{incubation time } (h)}$$

$X_{37° C.}$: angiotensin I concentration for incubation at 37° C.

$X_{4° C.}$: angiotensin I concentration for incubation at 4° C.

PRA at each time point after drug administration was calculated as percentage relative to the value before administration and taken as $PRA_{\%}$. The renin inhibitory activity of the drug administration group was calculated as an inhibitory rate by amending the $PRA_{\%}$ at each time point after drug administration with $PRA_{\%}$ of the vehicle group.

(2) Results

The results measured according to the above-mentioned method (1) are shown in Table 2.

TABLE 2

*Macaca fascicularis* plasma renin activity

| Example | PPA inhibitory activity (%, n = 3-7) |
|---|---|
| Example 7 | 93 |
| Example 10 | 72 |
| Example 11 | 89 |
| Example 18 | 89 |
| Example 21 | 85 |
| Example 25 | 79 |
| Example 33 | 77 |
| Example 40 | 75 |
| Example 42 | 70 |
| Example 48 | 78 |
| Example 60 | 85 |
| Example 62 | 75 |
| Example 73-1 | 77 |
| Example 73-2 | 90 |
| Example 74-1 | 90 |
| Example 74-2 | 54 |
| Example 75-1 | 86 |
| Example 75-2 | 71 |
| Example 76 | 79 |
| Example 233 | 67 |
| Example 235 | 62 |

TABLE 2-continued

*Macaca fascicularis* plasma renin activity

| Example | PPA inhibitory activity (%, n = 3-7) |
|---|---|
| Example 253 | 77 |
| Example 255 | 84 |

From the results of Table 2, it is clear that compounds (I) and (II) of the present invention show a sustained and superior renin inhibitory activity in the plasma of *Macaca fascicularis* that received drug administration.

[Sequence Listing Free Text]
[SEQ ID NO: 1] primer
[SEQ ID NO: 2] primer
[SEQ ID NO: 3] primer
[SEQ ID NO: 4] primer
[SEQ ID NO: 5] primer
[SEQ ID NO: 6] primer
[SEQ ID NO: 7] partial sequence of human angiotensinogen
[SEQ ID NO: 8] substrate peptide of renin

INDUSTRIAL APPLICABILITY

Compound (I) and compound (II) have superior renin inhibitory activity and thus are useful as agents for the prophylaxis or treatment of hypertension, various organ damages attributable to hypertension, and the like.

This application is based on patent application Nos. 161049/2008 and 004882/2009 filed in Japan, the contents of which are hereby incorporated by reference.

The invention claimed is:
1. 1-(4-Methoxybutyl)-N-(2-methylpropyl)-N-[(3S,5R)-5-(morpholin-4-ylcarbonyl)piperidin-3-yl]-1H-benzimidazole-2-carboxamide or a salt thereof.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial
<220> FEATURE:
<223> OTHER INFORMATION: synthetic construct; primer

<400> SEQUENCE: 1
aagcttatgg atggatggag a                                              21

<210> SEQ ID NO 2
<211> LENGTH: 21
<212> TYPE: DNA
<213> ORGANISM: Artificial
<220> FEATURE:
<223> OTHER INFORMATION: synthetic construct; primer

<400> SEQUENCE: 2
ggatcctcag cgggccaagg c                                              21

<210> SEQ ID NO 3
<211> LENGTH: 30
<212> TYPE: DNA
<213> ORGANISM: Artificial
<220> FEATURE:
<223> OTHER INFORMATION: synthetic construct; primer

<400> SEQUENCE: 3
aagcttatgc ggaagcgagc accccagtct                                     30
```

```
<210> SEQ ID NO 4
<211> LENGTH: 59
<212> TYPE: DNA
<213> ORGANISM: Artificial
<220> FEATURE:
<223> OTHER INFORMATION: synthetic construct; primer

<400> SEQUENCE: 4
ggatcctcac ttgtcatcgt cgtccttgta gtctgctgtg ctcagcgggt tggccacgc      59

<210> SEQ ID NO 5
<211> LENGTH: 39
<212> TYPE: DNA
<213> ORGANISM: Artificial
<220> FEATURE:
<223> OTHER INFORMATION: synthetic construct; primer

<400> SEQUENCE: 5
ccttaagctt ccaccatgcg gaagcgagca ccccagtct                             39

<210> SEQ ID NO 6
<211> LENGTH: 39
<212> TYPE: DNA
<213> ORGANISM: Artificial
<220> FEATURE:
<223> OTHER INFORMATION: synthetic construct; primer

<400> SEQUENCE: 6
ttggatcctc atgctgtgct cagcgggttg gccacgcgg                             39

<210> SEQ ID NO 7
<211> LENGTH: 15
<212> TYPE: PRT
<213> ORGANISM: Artificial
<220> FEATURE:
<223> OTHER INFORMATION: synthetic construct; partial sequence of human
      angiotensinogen
<220> FEATURE:
<221> NAME/KEY: MOD_RES
<222> LOCATION: (15)..(15)
<223> OTHER INFORMATION: AMIDATION

<400> SEQUENCE: 7

Asp Arg Val Tyr Ile His Pro Phe His Leu Val Ile His Asn Glu
1               5                   10                  15

<210> SEQ ID NO 8
<211> LENGTH: 16
<212> TYPE: PRT
<213> ORGANISM: Artificial
<220> FEATURE:
<223> OTHER INFORMATION: synthetic construct; substrate peptide for
      renin
<220> FEATURE:
<221> NAME/KEY: MISC_FEATURE
<222> LOCATION: (1)..(1)
<223> OTHER INFORMATION: FITC-labeled 6-aminocaproic acid
<220> FEATURE:
<221> NAME/KEY: MOD_RES
<222> LOCATION: (16)..(16)
<223> OTHER INFORMATION: AMIDATION

<400> SEQUENCE: 8

Xaa Asp Arg Val Tyr Ile His Pro Phe His Leu Val Ile His Gln Arg
1               5                   10                  15
```